United States Patent
Jalagam et al.

(10) Patent No.: US 11,267,811 B2
(45) Date of Patent: Mar. 8, 2022

(54) SMALL MOLECULE INHIBITORS OF GALECTIN-3

(71) Applicant: BRISTOL-MYERS SQUIBB COMPANY, Princeton, NJ (US)

(72) Inventors: Prasada Rao Jalagam, Bangalore (IN); Satheesh Kesavan Nair, Bangalore (IN); Manoranjan Panda, Bangalore (IN); Ramakanth Sarabu, Towaco, NJ (US); Jacob Swidorski, Doylestown, PA (US); Brett R. Beno, Yardley, PA (US); Alicia Regueiro-Ren, New Hope, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 68 days.

(21) Appl. No.: 16/650,403

(22) PCT Filed: Sep. 27, 2018

(86) PCT No.: PCT/US2018/053094
§ 371 (c)(1),
(2) Date: Mar. 25, 2020

(87) PCT Pub. No.: WO2019/067702
PCT Pub. Date: Apr. 4, 2019

(65) Prior Publication Data
US 2021/0147408 A1 May 20, 2021

Related U.S. Application Data

(60) Provisional application No. 62/563,732, filed on Sep. 27, 2017.

(51) Int. Cl.
*C07D 417/14* (2006.01)
*C07D 405/14* (2006.01)
(52) U.S. Cl.
CPC ......... *C07D 417/14* (2013.01); *C07D 405/14* (2013.01)
(58) Field of Classification Search
CPC ................ C07D 417/14; C07D 405/14
USPC ........................................ 514/310
See application file for complete search history.

(56) References Cited

U.S. PATENT DOCUMENTS

2014/0099319 A1   4/2014   Traber

FOREIGN PATENT DOCUMENTS

| WO | WO2005113568 A1 | 12/2005 |
| WO | WO2005113569 A1 | 12/2005 |
| WO | WO2014067986 A1 | 5/2014 |
| WO | WO2016120403 A1 | 8/2016 |
| WO | WO2017080973 A1 | 5/2017 |

OTHER PUBLICATIONS

DeBoer, et al., "Galectin-3 in Cardiac Remodeling and Heart", Curr Heart Fail Rep (2010) 7:1-8.
Guigure, et al. "Inhibitory potential of chemical substitutions at bioinspired sites of b-D-galactopyranose on neoglycoprotein/cell surface binding of two classes of medically relevant lectins", Bioorganic & Medicinal Chemistry vol. 19, 3280-3287, (2011).
Henderson et al., "Galectin-3 Expression and Secretion LinksMacrophages to the Promotion of Renal Fibrosis", American Journal of Pathology, vol. 172(2), pp. 288-298 (2008).
Henderson et al., "Galectin-3 regulates myofibroblast activationand hepatic fibrosis", PNAS, vol. 103(13) pp. 5060-5065 (2006).
Jarvis, et al., "Galectin-3C: Human Lectin for Treatment of Cancer" ACS Symposium Series, vol. 1115. Chapter 12, pp. 195-23 (2012).
MacKinnon, et al., "Regulation of Transforming Growth Factor-b1—driven Lung Fibrosis by Galectin-3", Am J Respir Crit Care Med vol. 185, Iss. 5, pp. 537-546 (2012).
U.S. Appl. No. 16/754,381, filed Apr. 8, 2020, Jalagam et al.

*Primary Examiner* — Kahsay Habte
(74) *Attorney, Agent, or Firm* — Jing G. Sun

(57) ABSTRACT

The present disclosure relates to compounds of formula I, which inhibit Gal-3, and include pharmaceutically acceptable salts, compositions comprising such compounds, and methods using and making such compounds and compositions.

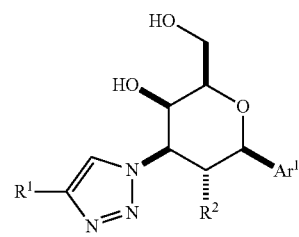

I

20 Claims, No Drawings

SMALL MOLECULE INHIBITORS OF GALECTIN-3

CROSS REFERENCE TO RELATED APPLICATION

This application is a 371 of International Application No. PCT/US2018/053094 filed on Sep. 27, 2018, which claims the benefit of U.S. Provisional Application 62/563,732 filed Sep. 27, 2017, the entire content of which is incorporated herein by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involment of Gal-3 in the development of fibrotic process in multiple organs such as lung (Am J. Respir. Crit. Care Med. 185: 537-546), liver (PNAS 103:5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319 and WO2014067986.

DESCRIPTION OF THE INVENTION

The present disclosure relates to compounds of formula I, which inhibit Gal-3, and include pharmaceutically acceptable salts, compositions comprising such compounds, and methods using and making such compounds and compositions.

One aspect of the invention is a compound of formula I

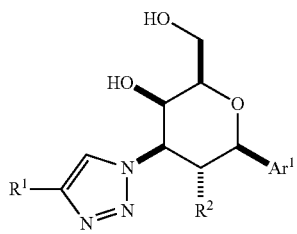

I where:
$R^1$ is $((R^3)(R^4)N)$carbonyl or $Ar^2$;
$R^2$ is hydrogen, halo, hydroxy, alkoxy, alkenyloxy, (halo)alkenyloxy, $((alkyl)_2(O)P)$alkenyloxy ($Ph_2(O)P$)alkenyloxy, haloalkoxy, (hydroxy)alkoxy, (alkoxy)alkoxy, (alkoxycarbonyl)alkoxy, (carboxy)alkoxy, $((alkylSO_2)N(H)C(O))$alkoxy, $((Ar^4SO_2)N(H)C(O))$alkoxy, (tetrazolyl)alkoxy, (carboxy)alkyl, $(R^5)(R^6)NC(O)$alkyl, or (carboxy)cycloalkyl;
$R^3$ is hydrogen, alkyl, cycloalkyl, benzyl, or halobenzyl;
$R^4$ is hydrogen or alkyl;
or $(R^3)(R^4)N$ taken together is azetidinyl, pyrrolidinyl, piperidinyl, piperazinyl, or morpholinyl, and is substituted with 0-3 substituents selected from halo, alkyl, and alkylcarbonyl;
$R^5$ is hydrogen or alkyl;
$R^6$ is hydrogen or alkyl;
or $(R^5)(R^6)N$ taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl;
$R^7$ is hydrogen or alkyl;
$R^8$ is hydrogen or alkyl;
or $(R^7)(R^8)N$ taken together is azetidinyl, pyrrolidinyl, piperidinyl, piperazinyl, or morpholinyl, and is substituted with 0-3 substituents selected from halo, alkyl, and hydroxy;
$R^9$ is hydrogen, alkyl, alkylcarbonyl, or alkylsulfonyl;
$R^{10}$ is hydrogen or alkyl;
or $(R^9)(R^{10})N$ taken together is azetidinyl, pyrrolidinyl, piperidinyl, piperazinyl, or morpholinyl, and is substituted with 0-3 substituents selected from halo, alkyl, and alkylcarbonyl;
$R^{11}$ is cyano, halo, alkoxy, or $(R^{12})(R^{13})N$;
$R^{12}$ is hydrogen or alkyl;
$R^{13}$ is hydrogen or alkyl;
or $(R^{12})(R^{13})N$ taken together is azetidinyl, pyrrolidinyl, piperidinyl, piperazinyl, or morpholinyl;
$R^{14}$ is hydrogen, alkyl, alkylcarbonyl, alkoxycarbonyl, or alkylsulfonyl;
$R^{15}$ is hydrogen or alkyl;
or $(R^{14})(R^{15})N$ taken together is azetidinyl, pyrrolidinyl, piperidinyl, piperazinyl, or morpholinyl, and is substituted with 0-3 substituents selected from halo, alkyl, and hydroxy;
$R^{16}$ is hydrogen, alkyl, alkylcarbonyl, or alkylsulfonyl;
$R^{17}$ is hydrogen or alkyl;
or $(R^{16})(R^{17})N$ taken together is azetidinyl, pyrrolidinyl, piperidinyl, piperazinyl, or morpholinyl, and is substituted with 0-3 substituents selected from halo, alkyl, and alkylcarbonyl;
$Ar^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, phenyl, or indolyl, and is substituted with 0-3 substituents selected from alkyl, haloalkyl, hydroxyalkyl, alkoxyalkyl, (carboxy)alkyl, (alkoxycarbonyl)alkyl, $(H_2NCO)$alkyl, $(Ar^3)$alkyl, cycloalkyl, hydroxycycloalkyl, alkenyl, alkoxy, alkylthio, alkylsulfonyl, carboxy, alkoxycarbonyl, (alkylNH)carbonyl, $(((R^7)(R^8)N)$alkylNH)carbonyl, ((pyridinyl)alkylNH)carbonyl, $(R^9)(R^{10})$N, and $Ar^3$;
$Ar^2$ is phenyl, pyridinyl, naphthyl, benzoxazolyl, benzothiazolyl, quinolinyl, or quinoxalinyl, and is substituted with 0-5 substituents selected from cyano, halo, alkyl, $(R^{11})$alkyl, haloalkyl, cycloalkyl, $(R^{11})$cycloalkyl, alkoxy, cycloalkoxy, haloalkoxy, and $(R^{14})(R^{15})N$;
$Ar^3$ is phenyl, naphthalinyl, biphenyl, pyridinyl, pyridazinyl, pyrimidinyl, pyrazinyl, quinolinyl, isoquinolinyl, quinoxainyl, indolyl, indazolyl, benzimidazolyl, benzisoxazolyl, benzisothiazolyl, benzoxazolyl, benzothiazolyl, benzodioxolyl, dihydrobenzodioxinyl, dihydroquinolinonyl, or dihydrobenzothiophene-2,2-dioxide, and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{16})(R^{17})N$;

or $Ar^3$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, nitro, halo, alkyl, haloalkyl, alkoxy, haloalkoxy, alkylthio, carboxy, alkoxycarbonyl, $CONH_2$, and $(R^{16})(R^{17})N$;

or $Ar^3$ is $(alkylSO_2)$phenyl, $(alkylSO_2)$(halo)phenyl, $(aminoSO_2)$phenyl, $(dialkylaminoSO_2)$phenyl, $((alkylNHSO_2)$alkyl)phenyl, (pyrrolyl)phenyl, (imidazolyl)phenyl, (oxazolyl)phenyl, (tetrazolyl)phenyl, ((pyridinyl)methyl)phenyl, phenoxyphenyl, (benzyloxy)phenyl, ((methyl)thiazolyl)phenyl, (thiazolyl)benzenesulfamido, ((methyl)thiadiazolyl)benzenesulfamido, (methyl)benzothiazolonyl, or fluoropyrazolopyrimidinyl; and $Ar^4$ is phenyl substituted with 0-5 substituents selected from cyano, halo, alkyl, haloalkyl, alkoxy, and haloalkoxy; or a pharmaceutically acceptable salt thereof.

Another aspect of the invention is a compound of formula I where $R^1$ is $Ar^2$; $R^2$ is hydroxy; $Ar^1$ is triazolyl substituted with 0-3 substituents selected from alkyl, haloalkyl, hydroxyalkyl, alkoxyalkyl, (carboxy)alkyl, (alkoxycarbonyl)alkyl, $(H_2NCO)$alkyl, $(Ar^3)$alkyl, cycloalkyl, hydroxycycloalkyl, alkenyl, alkoxy, alkylthio, alkylsulfonyl, carboxy, alkoxycarbonyl, (alkylNH)carbonyl, $(((R^7)(R^8)N)$alkylNH)carbonyl, ((pyridinyl)alkylNH)carbonyl, $(R^9)(R^{10})N$, and $Ar^3$; $Ar^2$ is phenyl or pyridinyl and is substituted with 0-5 substituents selected from cyano, halo, alkyl, $(R^{11})$alkyl, haloalkyl, cycloalkyl, $(R^{11})$cycloalkyl, alkoxy, cycloalkoxy, haloalkoxy, and $(R^{14})(R^{15})N$; and $Ar^3$ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, CONH2, and $(R^{16})(R^{17})N$; or a pharmaceutically acceptable salt thereof.

Another aspect of the invention is a compound of formula I where $R^1$ is $Ar^2$; $R^2$ is hydroxy; $Ar^1$ is triazolyl substituted with 0-2 substituents selected from alkyl, haloalkyl, and $Ar^3$; $Ar^2$ is phenyl substituted with 0-5 halo substituents; and $Ar^3$ is phenyl or benzothiazolyl and is substituted with 0-5 substituents selected from halo, alkyl, haloalkyl, cycloalkyl, alkoxy, and haloalkoxy; or a pharmaceutically acceptable salt thereof.

Another aspect of the invention is a compound of formula I where $R^1$ is $Ar^2$.

Another aspect of the invention is a compound of formula I where $R^2$ is hydroxy.

Another aspect of the invention is a compound of formula I where $Ar^1$ is pyrazolyl, isoxazolyl, thiazolyl, or triazolyl, and is substituted with 0-1 alkyl substituents and 1 $Ar^3$ substituent.

Another aspect of the invention is a compound of formula I where $Ar^1$ is 1,2,4-triazol-2-yl.

Another aspect of the invention is a compound of formula I where $Ar^1$ is triazolyl substituted with 0-3 substituents selected from alkyl, haloalkyl, hydroxyalkyl, alkoxyalkyl, (carboxy)alkyl, (alkoxycarbonyl)alkyl, $(H_2NCO)$alkyl, $(Ar^3)$alkyl, cycloalkyl, hydroxycycloalkyl, alkenyl, alkoxy, alkylthio, alkylsulfonyl, carboxy, alkoxycarbonyl, (alkylNH)carbonyl, $(((R^7)(R^8)N)$alkylNH)carbonyl, ((pyridinyl)alkylNH)carbonyl, $(R^9)(R^{10})N$, and $Ar^3$.

Another aspect of the invention is a compound of formula I where. $Ar^1$ is triazolyl substituted with 0-2 substituents selected from alkyl, haloalkyl, and $Ar^3$.

Another aspect of the invention is a compound of formula I where $Ar^2$ is phenyl or pyridinyl and is substituted with 0-5 substituents selected from cyano, halo, alkyl, $(R^{11})$alkyl, haloalkyl, cycloalkyl, $(R^{11})$cycloalkyl, alkoxy, cycloalkoxy, haloalkoxy, and $(R^{14})(R^{15})N$.

Another aspect of the invention is a compound of formula I where $Ar^2$ is phenyl substituted with 0-5 halo substituents.

Another aspect of the invention is a compound of formula I where $Ar^3$ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, $CONH_2$, and $(R^{16})(R^{17})N$; or a pharmaceutically acceptable salt thereof.

Another aspect of the invention is a compound of formula I where $Ar^3$ is phenyl or benzothiazolyl and is substituted with 0-5 substituents selected from halo, alkyl, haloalkyl, cycloalkyl, alkoxy, and haloalkoxy.

Another aspect of the invention is a compound of formula I selected from the group consisting of

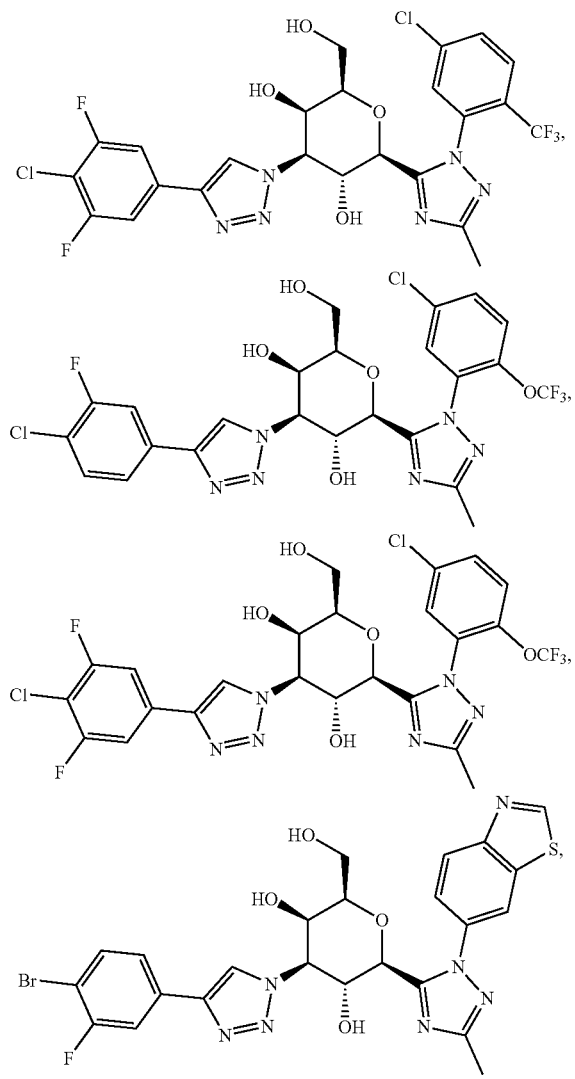

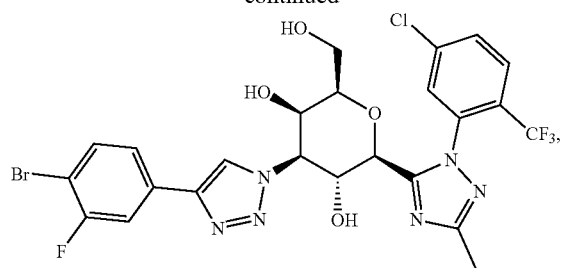
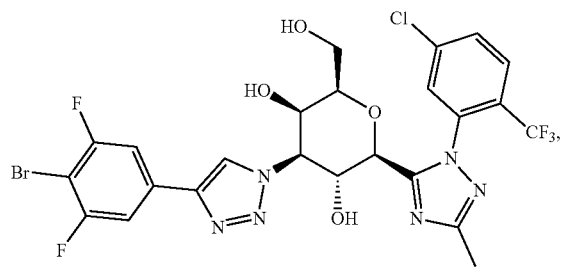
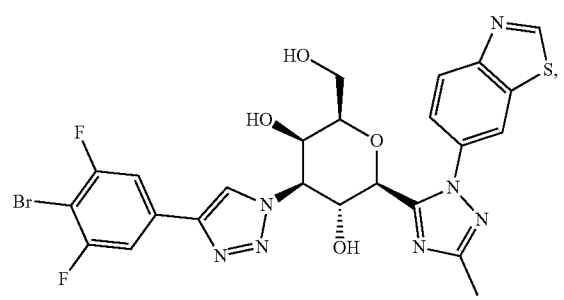
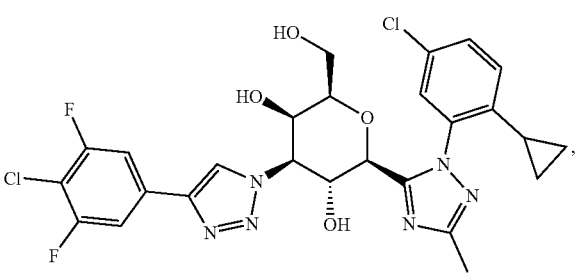
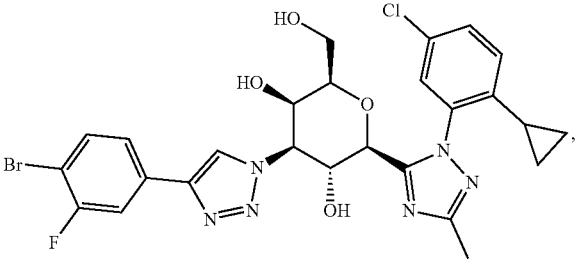
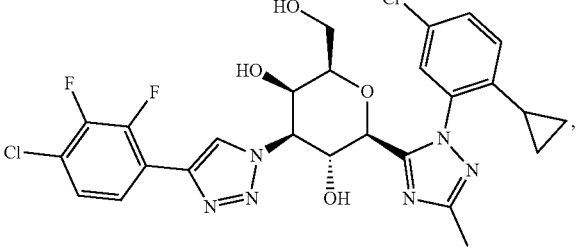
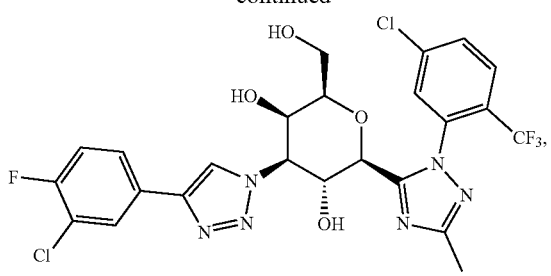
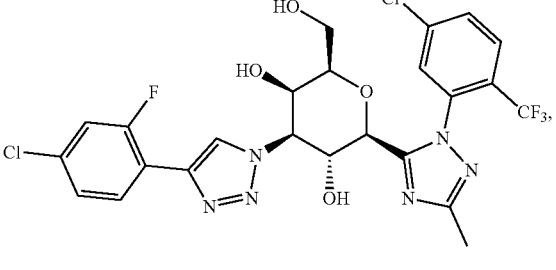
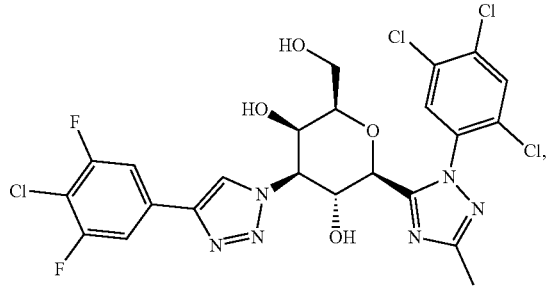
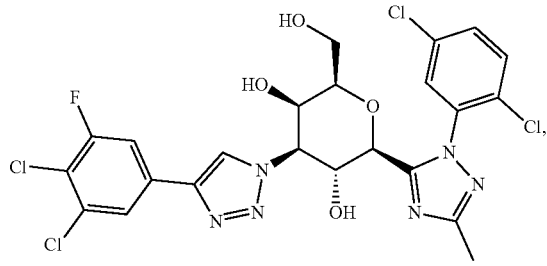
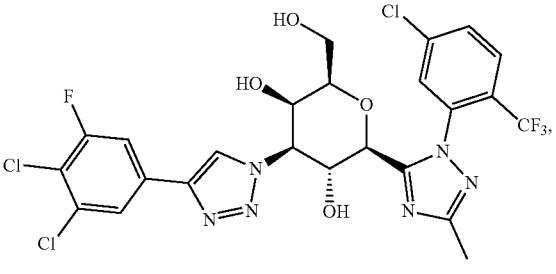
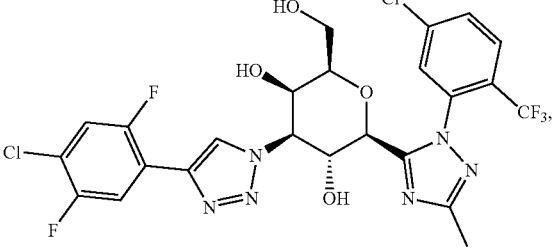

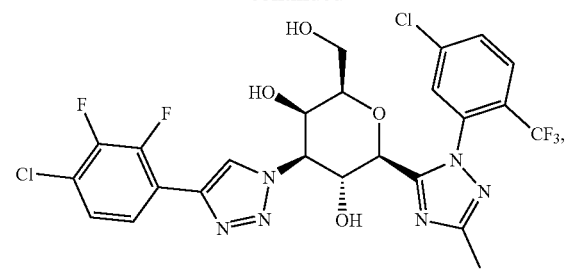
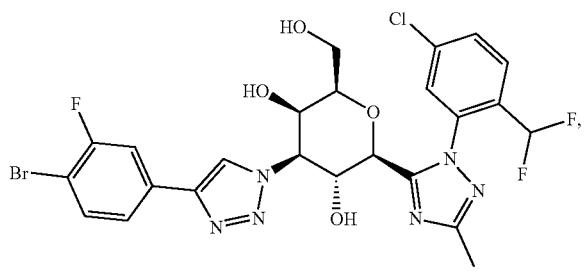
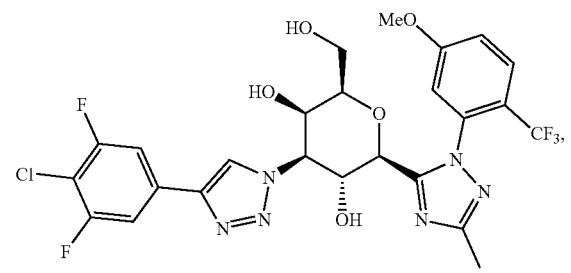
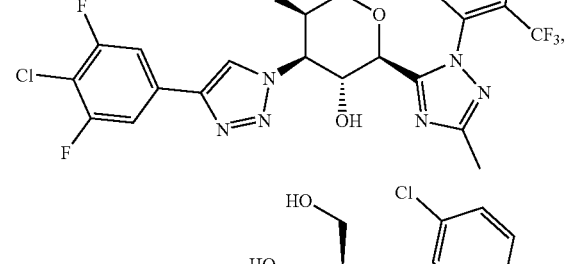
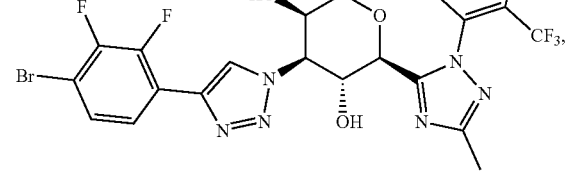
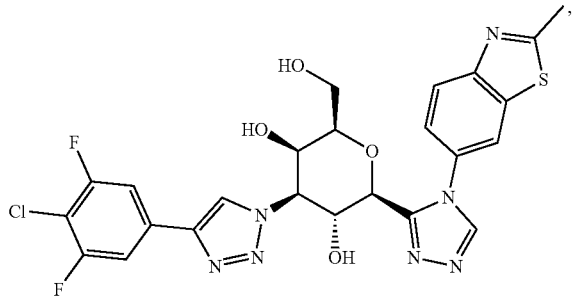
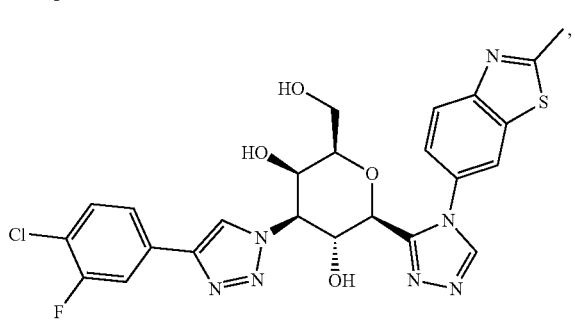
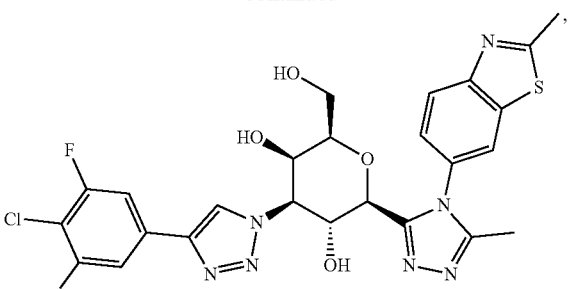
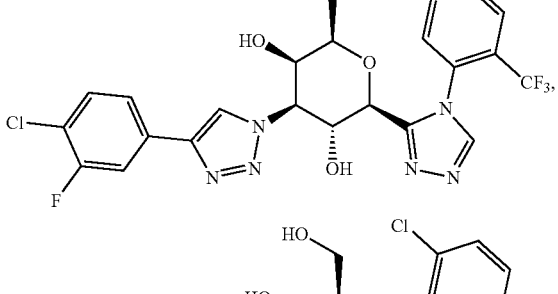
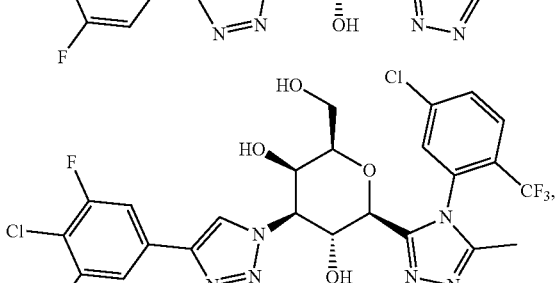
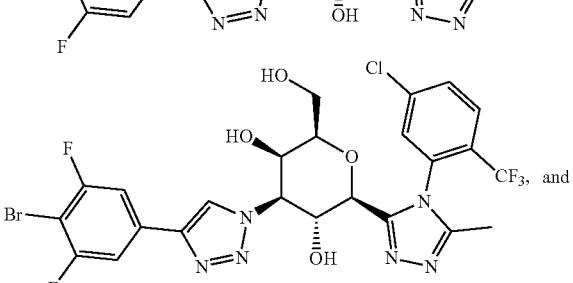
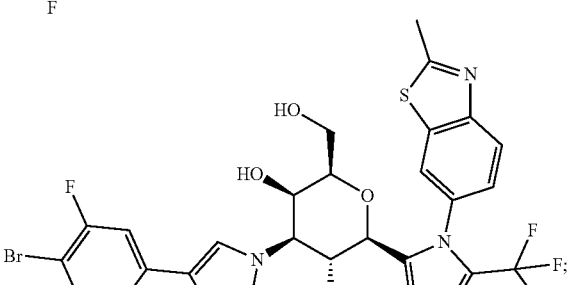
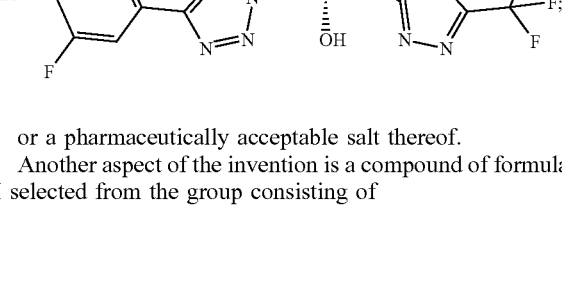
or a pharmaceutically acceptable salt thereof.
Another aspect of the invention is a compound of formula I selected from the group consisting of

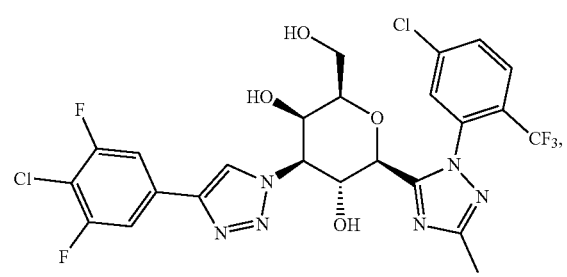
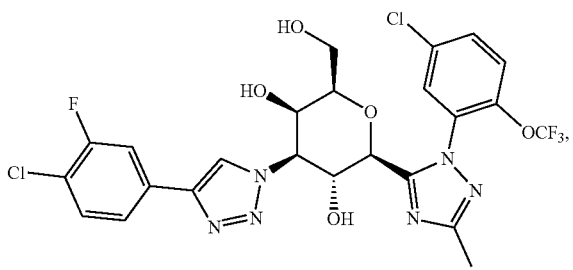
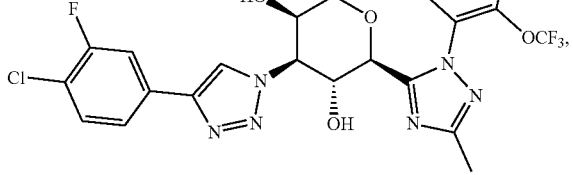
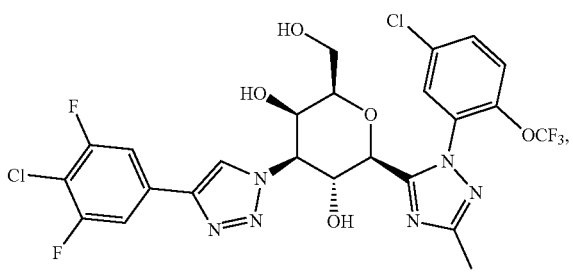
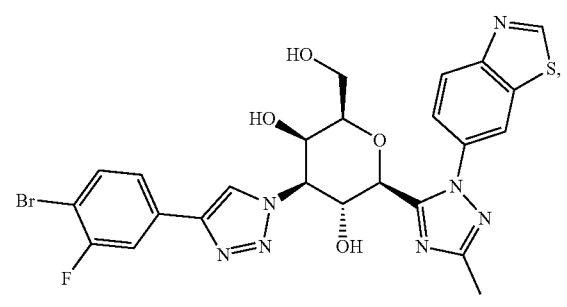
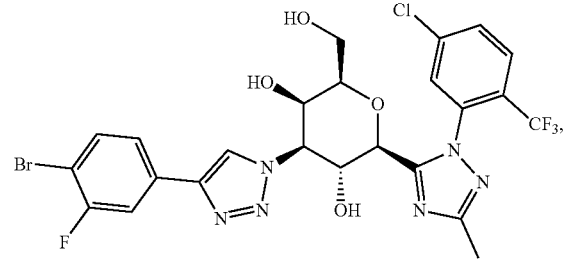
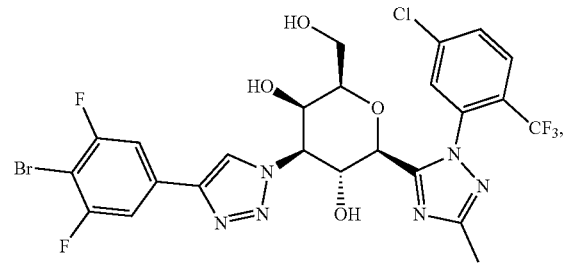
-continued
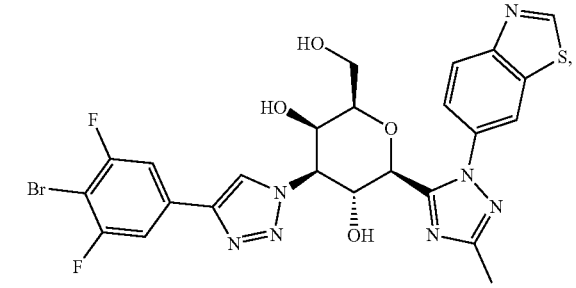
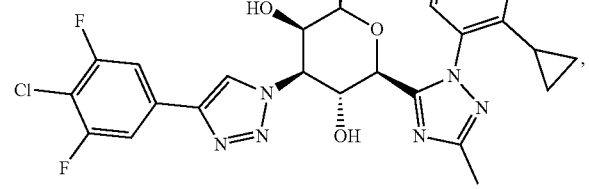
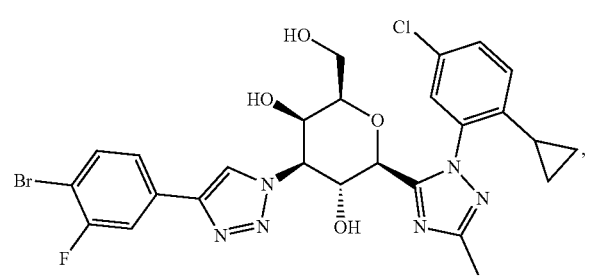
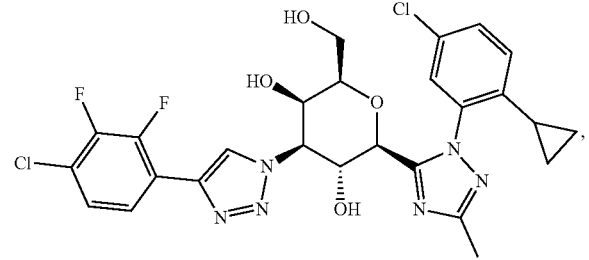
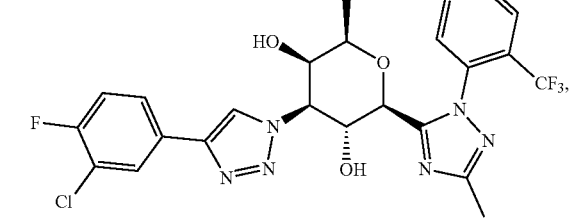
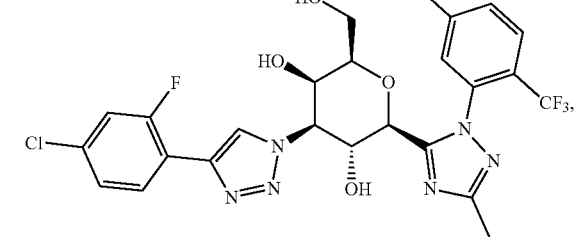

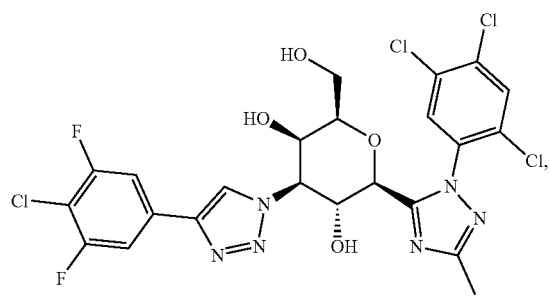
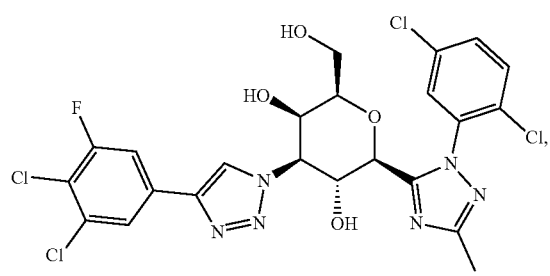
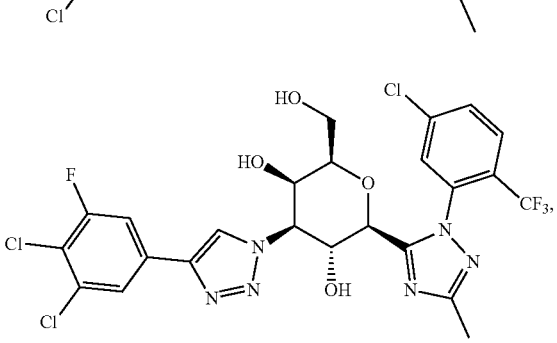
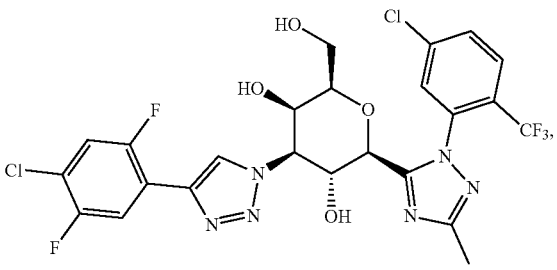
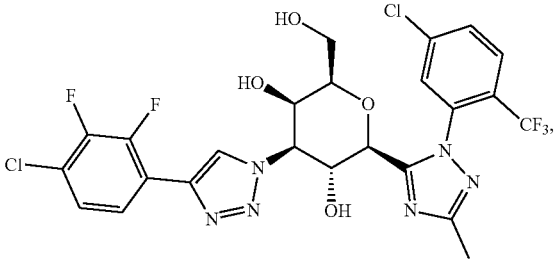
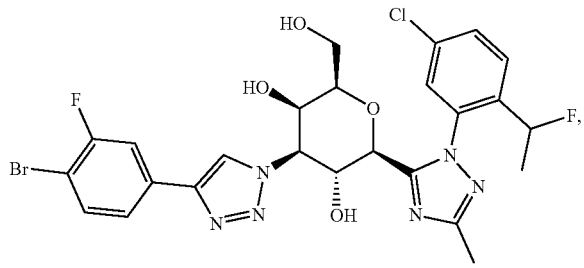
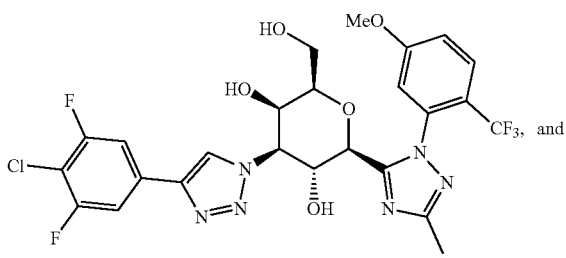
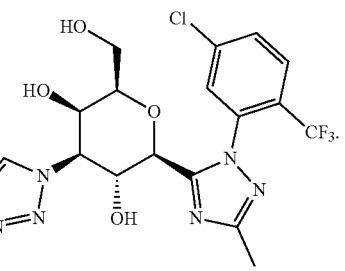
Another aspect of the invention is a compound of formula I selected from the group consisting of
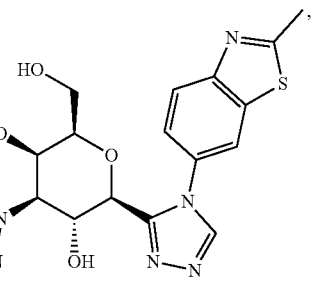
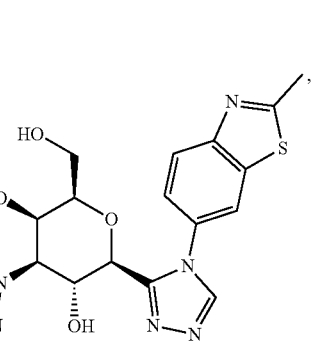
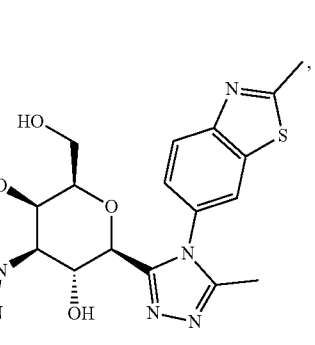

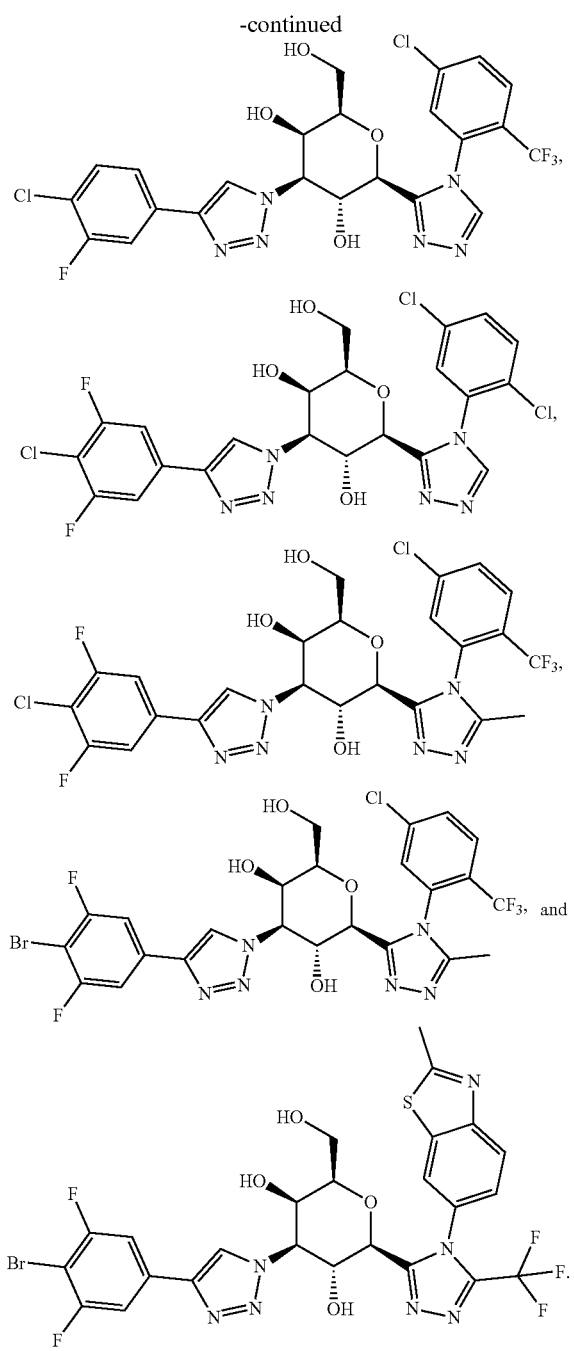

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $Ar^1$, $Ar^2$, $Ar^3$, and $Ar^4$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

BIOLOGICAL METHODS

ASSAY BUFFER Composition: 25 mM HEPES, 100 mM NaCl, 0.005% Tween 20, 0.05% BSA prepared in sterile water (all reagents from Sigma)

Controls:

Positive Control: 100% DMSO (1 μl)+His-tagged hGal-3 (20 μL)+B-ASF (20 μl)+Anti-His Terbium Antibody (5 μl)+Strep d2 Antibody (5 μl).

Negative Control: 100% DMSO (1 μl)+His-tagged hGal-3(20 μL)+Anti His Terbium Antibody (5 μl)+Strep d2 Aantibody (5 μl).

Stocks Preparation:

|  | Stock Conc. | Intermediate Conc. | Final Assay Conc. | Volume |
|---|---|---|---|---|
| His-tagged hGal-3 | 49.82 μM or can vary batch to batch | 2.525X | 15 nM | 20 μl |
| B-ASF | 25 μM | 2.525X | 15 nM | 20 μl |
| Compounds | 20 mM in 100% DMSO | Various concentration 100% DMSO | Various concentration 2% DMSO | 1 μl |
| Anti-His Tb Ab | 5.75 μM | (10X) 10 nM | 1 nM | 5 μl |
| Strep d2 | 16.67 μM | (10X) 200 nM | 20 nM | 5 μl |
| Total Assay volume |  |  |  | 51 μl |

PROTOCOL: The Gal-3 assays were performed in 384 white Opti plates in three replicates at room temperature with gentle shaking at 250-300 rpmFrom the original stocks, 2.525× working stock concentrations of His-tagged recombinant human Gal-3 (hGal-3) and that of B-ASF were prepared. From the working stock, 20 μl of hGal-3 (15 nM) and 20 μl B-ASF (15 nM) were added to the plates. In Negative Control, only hGal-3 was added. A concentration range of 50× working stocks were prepared for the compounds in 100% DMSO. Aliquots of 1 uL of the compounds were added to the wells and pre-incubated with 20 μl hGal-3 per well for 30 minutes Then 20 μl B-ASF wereadded and incubated for another 1 hour. To detect the signal, 5 μL (final conc. of 1.0 nM) terbium labelled Anti-His antibody was added and incubated for 30 min followed by adding 5 μL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in μM).

Pharmaceutical Compostion and Methods of Use

The compounds of this invention inhibit Gal-3. Accordingly, another aspect of the invention is a pharmaceutical composition comprising a therapeutically effective amount of a compound of Formula I, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of formula I or Ia.

Another aspect of the invention is a method of treating renal fibrosis, pulmonary fibrosis, hepatic fibrosis, arterial fibrosis and systemic sclerosis comprising administering to a compound of formula I or Ia to a patient.

Another aspect of the invention is a method for treating fibrosis of organs (including liver, kidney, lung, heart and skin) comprising administering to a compound of formula I or Ia to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of formula I or Ia to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of formula I or Ia to a patient.

Another aspect of the invention is a method for treating inflammatory diseases and conditions (including psoriasis, nephropathy, and pneumonia) comprising administering to a compound of formula I or Ia to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of formula I or Ia to a patient.

Another aspect of the invention is a method for treating renal diseases and conditions comprising administering to a compound of formula I or Ia to a patient.

nother aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of formula I or Ia to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of formula I or Ia to a patient.

Another aspect of the invention is a method for treating pancreatic diseases and conditions comprising administering to a compound of formula I or Ia to a patient.

Another aspect of the invention is a method for treating abnormal angiogenesis-associated diseases and conditions (including arterial obstruction) comprising administering to a compound of formula I or Ia to a patient.

Another aspect of the invention is a method for treating brain-associated diseases and conditions (including cerebral infarction and cerebral hemorrhage) comprising administering to a compound of formula I or Ia to a patient.

Another aspect of the invention is a method for treating neuropathic pain and peripheral neuropathy comprising administering to a compound of formula I or Ia to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of formula I or Ia to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

CHEMICAL METHODS

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

Section 1

Analytical LC-MS/HPLC retention time reported for each example and intermediate uses one of the following general analytical LC-MS/HPLC conditions:

LCMS Conditions:

Method A: Column: XBridge BEH XP C18 (2.1×50 mm), 2.5 μm; Mobile phase A: 10 mM $NH_4OAc$, Acetonitrile (95:5); Mobile phase B: 10 mM $NH_4OAc$: Acetonitrile (5:95); Gradient=0-100% B over 3 minutes; Temperature: 50° C.; Flow rate: 1.1 mL/min; Detection: UV at 220 nm.

Method B: Column: XBridge BEH XP C18 (2.1×50 mm); 2.5 μm; Mobile phase A: 0.1% TFA in water, Acetonitrile (95:5); Mobile phase B: 0.1% TFA in water, Acetonitrile (5:95); Gradient=0-100% B over 3 minutes; Temperature: 50° C.; Flow rate: 1.1 mL/min; Detection: UV at 220 nm.

Method C: Column-KINETEX-XB-C18 (75×3 mm-2.6 μm); M.phase A: 10 mM NH4COOH IN WATER:ACN(98:02); Mobile phase B: 10 mM NH4COOH IN WATER:ACN (02:98); Gradient=20-100% B over 4 minutes; Flow rate: 1.1 mL/min; Detection: UV at 254 nm.

Method D: Column: Waters Acquity UPLC BEH C18 (2.1×50 mm), 1.7μ; Mobile phase A: 0.1% TFA in water; Mobile phase B: 0.1% TFA in Acetonitrile; Gradient=20-90% B over 1.1 minute, then a 0.6 minute hold at 90% B; Temperature: 50° C.; Flow rate: 0.7 mL/min; Detection: UV at 220 nm.

Method E: Column: Waters Acquity UPLC BEH C18 (2.1×50 mm) 1.7μ, Mobile phase A: 10 mM $NH_4OAc$, Acetonitrile (95:5); Mobile phase B: 10 mM $NH_4OAc$: Acetonitrile (5:95), Gradient=20-90% B over 1.1 minute, then a 0.6 minute hold at 90% B; Temperature: 50° C.; Flow rate: 0.7 mL/min; Detection: UV at 220 nm.

Method F: Column: Waters Acquity UPLC BEH C18 (2.1×50 mm), 1.7μ; Mobile phase A: 0.05% TFA in water; Mobile phase B: 0.05% TFA in Acetonitrile; Gradient=2-98% B over 1.0 minute, then a 0.5 minute hold at 98% B; Temperature: 50° C.; Flow rate: 0.8 mL/min; Detection: UV at 220 nm.

Method G: Column: BEH C18 2.1×50 mm; Mobile phase A: 10% ACN—90% Water—0.1% TFA; Mobile phase B:

90% ACN—10% Water—0.1% TFA; Gradient=2-98% B over 1.0 minute; Flow Rate: 0.8 ml/min. Detection: UV at 254 nm.

Method H: Column: XBridge C18 2.1×50 mm, 1.7 μM; Mobile phase A: 5% ACN—95% Water—10 mM ammonium acetate; Mobile phase B: 95% ACN—5% Water—10 mM ammonium acetate; Gradient=0-100 B over 30 minutes; Flow Rate: 1 ml/min. Temperature: 50° C.; Detection: UV at 224 nm.

Prep-HPLC Conditions:

Method A: Column: Waters XBridge C18, 19×150 mm, 5 μm particles; Mobile Phase A: 10-mM ammonium acetate; Mobile Phase B: acetonitrile; Gradient: 15-50% B over 20 minutes, then a 5-minute hold at 100% B; Flow: 15 mL/min.

Method B: Column: Inertsil ODS(19×250 mm)-5 μm particles; Mobile Phase A: 0.1% TFA IN H2O; Mobile Phase B: ACN; Gradient: 0-70% B over 20 minutes, then a 5-minute hold at 100% B; Flow: 17 mL/min.

Method C: Column: XBridge phenyl C18 (19×250 mm), 5 μm particles; Mobile Phase A: 10-mM ammonium acetate; Mobile Phase B: acetonitrile; Gradient: 0-75% B over 20 minutes, then a 5-minute hold at 100% B; Flow: 17 mL/min.

Method D: Column: Inertsil ODS(19×250 mm) 5 μm particles; Mobile Phase A: 10-mM ammonium acetate; Mobile Phase B: ACN; Gradient: 0-90% B over 25 minutes, then a 5-minute hold at 100% B; Flow: 17 mL/min.

Method E: Column: Xbridge C18 (19×200 mm), 5-μm particles; Mobile Phase A: 10-mM ammonium acetate: acetonitrile (95:5); Mobile Phase B: acetonitrile: 10-mM ammonium acetate (95:5); Gradient: 10-50% B over 20 minutes, then a 5-minute hold at 100% B; Flow: 20 mL/min.

Method F: Column: Xbridge C18 (19×200 mm), 5-μm particles; Mobile Phase A: 0.1% TFA water:acetonitrile (95:5); Mobile Phase B: acetonitrile: water, (95:5) 0.1% TFA; Gradient: 0-40% B over 20 minutes, then a 5-minute hold at 100% B; Flow: 20 mL/min.

Method G: Column: Xbridge C18 (19×200 mm), 5-μm particles; Mobile Phase A: 10-mM ammonium acetate: acetonitrile (95:5); Mobile Phase B: acetonitrile: 10-mM ammonium acetate (95:5); Gradient: 5-45% B over 20 minutes, then a 5-minute hold at 100% B; Flow: 20 mL/min.

Method H: Column: Xbridge C18 (19×200 mm), 5-μm particles; Mobile Phase A: 10-mM ammonium acetate: acetonitrile (95:5); Mobile Phase B: acetonitrile: 10-mM ammonium acetate (95:5); Gradient: 2-42% B over 15 minutes, then a 5-minute hold at 100% B; Flow: 20 mL/min.

Method I: Column: Xbridge C18 (19×200 mm), 5-μm particles; Mobile Phase A: 0.1% TFA water:acetonitrile (95:5); Mobile Phase B: acetonitrile: water, (95:5) 0.1% TFA; Gradient: 5-45% B over 20 minutes, then a 5-minute hold at 100% B; Flow: 20 mL/min.

Method J: Column: Xbridge C18 (19×200 mm), 5-μm particles; Mobile Phase A: 0.1% TFA water:acetonitrile (95:5); Mobile Phase B: acetonitrile: water, (95:5) 0.1% TFA; Gradient: 10-50% B over 20 minutes, then a 4-minute hold at 100% B; Flow: 20 mL/min.

Method K: Column: Xbridge C18 (19×200 mm), 5-pm particles; Mobile Phase A: 10-mM ammonium acetate: acetonitrile (95:5); Mobile Phase B: acetonitrile: 10-mM ammonium acetate (95:5); Gradient: 25-65% B over 22 minutes, then a 5-minute hold at 100% B; Flow: 20 mL/min.

Method L: Column: Xbridge C18 (19×200 mm), 5-μm particles; Mobile Phase A: 10-mM ammonium acetate: acetonitrile (95:5); Mobile Phase B: acetonitrile: 10-mM ammonium acetate (95:5); Gradient: 20-60% B over 20 minutes, then a 5-minute hold at 100% B; Flow: 20 mL/min.

Method M: Column: Phenomenex Luna (30×100 mm), S10; Mobile Phase A: 0.1% TFA water: acetonitrile (90:10); Mobile Phase B: acetonitrile: water, (90:10) 0.1% TFA; Gradient: 15-80% B over 15 minutes, then a 5-minute hold at 100% B; Flow: 40 mL/min.

Method N: Column: Xbridge C18 (19×200 mm), 5-μm particles; Mobile Phase A: 10-mM ammonium acetate: acetonitrile (95:5); Mobile Phase B: acetonitrile: 10-mM ammonium acetate (95:5); Gradient: 8-48% B over 20 minutes, then a 5-minute hold at 100% B; Flow: 20 mL/min.

Method O: Column: YMC TRAIT (250×20 mm, 5 μm); Mobile phase A: 10 mM Ammonium acetate in water; Mobile phase B: Acetonitrile:Methanol (1:1); Gradient: 0-80% B over 15 minutes, then a 5-minute hold at 100% B; Flow: 20 mL/min.

Method P: Column: Sunfire C18 (150×21.2 mm, 5 μm); Mobile phase A: 10 mM Ammonium acetate in water Mobile phase B: Acetonitrile; Gradient: 0-100% B over 21 minutes, then a 5-minute hold at 100% B; Flow: 20 mL/min.

Method Q: Column: Sunfire C18 (150×21.2 mm, 5 μm); Mobile phase A: 0.1% TFA in water; Mobile phase B: Acetonitrile; Gradient: 0-100% B over 21 minutes, then a 5-minute hold at 100% B; Flow: 1 mL/min.

Method R: Column: Waters Sunfire C18, 30×100 mm, 5-μm particles; Mobile Phase A: 10% ACN—90% $H_2O$—0.1% TFA; Mobile Phase B: 90% ACN—10% $H_2O$—0.1% TFA; Gradient 20-100% B over 20 minutes, then hold at 100% B; Flow Rate: 30 mL/min.

Method S: Column: XBridge C18, 200 mm×19 mm, 5-μm particles; Mobile Phase A: 5:95 acetonitrile: $H_2O$ with 0.1% trifluoroacetic acid; Mobile Phase B: 95:5 acetonitrile: $H_2O$ with 0.1% trifluoroacetic acid; Gradient 30-70% B over 20 minutes, then hold at 100% B; Flow Rate: 20 mL/min.

Method T: Column: Waters Sunfire C18, 30×100 mm, 5-μm particles; Mobile Phase A: 10% MeOH—90% $H_2O$—0.1% TFA; Mobile Phase B: 90% MeOH—10% $H_2O$—0.1% TFA; Gradient 20-100% B over 15 minutes, then hold at 100% B; Flow Rate: 30 mL/min; Fraction collection was triggered by UV, 220 nM wavelength.

Method U: Column: XBridge C18, 200 mm×19 mm, 5-μm particles; Mobile Phase A: 5:95 acetonitrile: $H_2O$ with 10-mM ammonium acetate; Mobile Phase B: 95:5 acetonitrile: $H_2O$ with 10-mM ammonium acetate; Gradient 17-57% B over 20 minutes, then hold at 100% B; Flow Rate: 20 mL/min; Fraction collection was triggered by MS signals.

Method V: Column: Waters Sunfire C18, 30×100 mm, 5-μm particles; Mobile Phase A: 10% ACN—90% $H_2O$—0.1% TFA; Mobile Phase B: 90% ACN—10% $H_2O$—0.1% TFA; Gradient 20-100% B over 18 minutes, then hold at 100% B; Flow Rate: 30 mL/min; Fraction collection was triggered by UV, 220 nM wavelength.

Method W: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 22-62% B over 25 minutes, then hold at 100% B; Flow Rate: 20 mL/min.

Preparation of Compounds:

The non-commercially available hydrazines used in Section 1 were prepared following the methods described below.

General Procedure-1: [Representative Example]

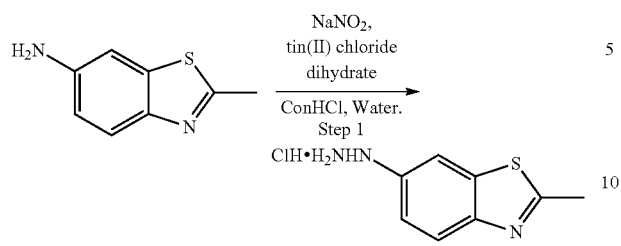

Step 1: Synthesis of 6-hydrazinyl-2-methylbenzo[d]thiazole hydrochloride: A stirred solution of 2-methylbenzo[d]thiazol-6-amine (0.47 g, 2.86 mmol) in conc. HCl (5.6 mL) was cooled to −10° C., sodium nitrite (0.197 g, 2.86 mmol) in water (1 mL) was added drop wise and stirred at −10° C. for 30 min. Then, tin(II) chloride dihydrate (2.06 g, 9.16 mmol) in con. HCl (2 mL) was added dropwise at same temperature, reaction mixture was slowly allowed to reach rt and stirred for 2 h. The reaction mixture was filtered and the residue was dried to afford 6-hydrazinyl-2-methylbenzo[d]thiazole hydrochloride (600 mg, 97%) which was as such taken for the next step without further purification. LC-MS, [M+H]$^+$=180.0 {Method E: $t_R$=0.47}. $^1$H NMR (400 MHz, DMSO-d$_6$) δ=10.28 (br s, 3H), 7.81 (d, J=8.5 Hz, 1H), 7.54 (d, J=2.5 Hz, 1H), 7.16-7.08 (m, 1H), 2.74 (s, 3H) ppm.

Preparation of 4-chloro-2-hydrazinylbenzonitrile

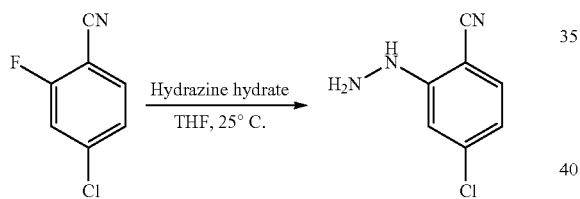

Step 1: Synthesis of 4-chloro-2-hydrazinylbenzonitrile: To a solution of 4-chloro-2-fluorobenzonitrile (0.1 g, 0.643 mmol) in tetrahydrofuran (10 mL), hydrazine (0.021 g, 0.643 mmol) was added and stirred at rt for 1 h. The reaction mixture was concentrated to give crude compound, crude was triturated with diethyl ether to give 4-chloro-2-hydrazinylbenzonitrile (100 mg, 93%) as an off-white solid. LC-MS, [M+H]$^+$=168.2, {Method C: tR=1.155}. $^1$H NMR (400 MHz, DMSO-d$_6$) δ=7.68 (s, 1H), 7.45 (d, J=8.5 Hz, 1H), 7.21 (d, J=2.5 Hz, 1H), 6.67-6.64 (m, 1H), 4.36 (br s, 2H).

Preparation of 6-fluoro-5-hydrazinylpyrazolo[1,5-a]pyrimidine

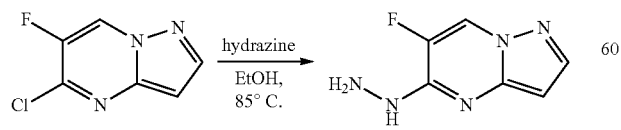

Step 1: Synthesis of 6-fluoro-5-hydrazinylpyrazolo[1,5-a]pyrimidine: To a solution of 5-chloro-6-fluoropyrazolo[1,5-a]pyrimidine (0.2 g, 1.166 mmol) in EtOH (20 mL), hydrazine hydrate (2 mL, 1.166 mmol) was added and heated at 85° C. for 16 h. The reaction mixture was concentrated. The crude compound was purified by washing with diethyl ether to give 6-fluoro-5-hydrazinylpyrazolo[1,5-a]pyrimidine (0.15 g, 77%) as an off white solid. LC-MS, [M+H]$^+$=168.0, {Method E: tR=0.44}.

Preparation of 5-(3-hydrazinylphenyl)-2-methylthiazole

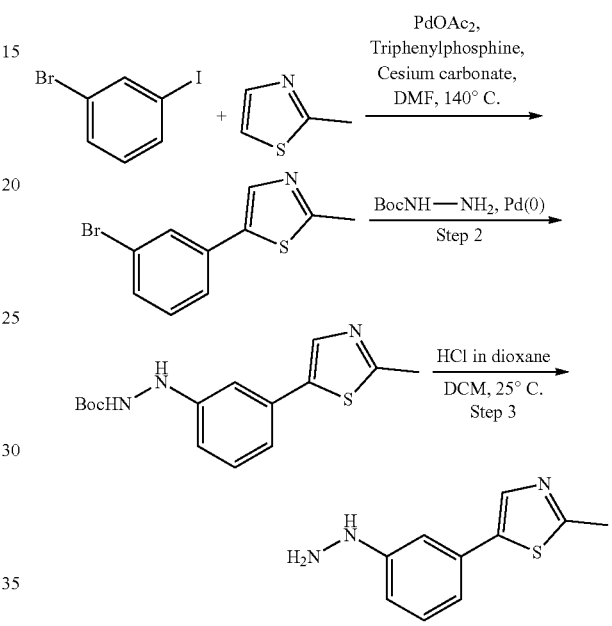

Step 1: Synthesis of 5-(3-bromophenyl)-2-methylthiazole: To a stirred solution of 2-methylthiazole (1.0 g, 10.09 mmol) in DMF (50 mL),1-bromo-3-iodobenzene (5.71 g, 20.17 mmol), triphenylphosphine (0.265 g, 1.009 mmol) and Pd(OAc)$_2$ (0.113 g, 0.504 mmol) were added and heated at 140° C. for 16 h. Then the reaction mixture was concentrated under reduced pressure to give crude residue, which was extracted with EtOAc (2×50 mL), washed with water, brine solution, dried over sodium sulphate and concentrated. The crude was purified via silica gel (0-1 chromatography 0% EtOAc in Hexane) to give 5-(3-bromophenyl)-2-methylthiazole (250 mg, 10%). LC-MS, [M+1]+=254.2, {Method E: tR: 1.76 min}.

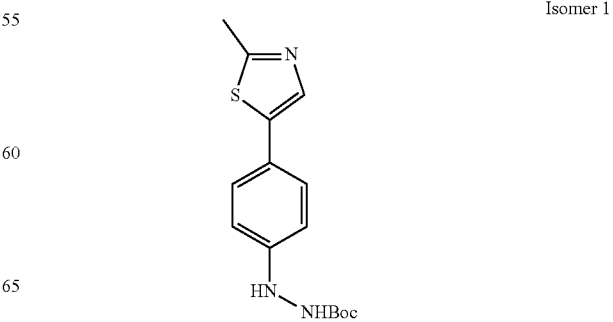

Isomer 1

Isomer 2

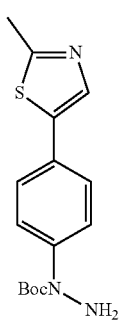

Step 2: Synthesis of tert-butyl 1-(3-(2-methylthiazol-5-yl)phenyl)hydrazine-1-carboxylate and tert-butyl 2-(3-(2-methylthiazol-5-yl)phenyl)hydrazine-1-carboxylate: A stirred suspension of 5-(3-bromophenyl)-2-methylthiazole (250 mg, 0.984 mmol), tert-butyl hydrazinecarboxylate (260 mg, 1.967 mmol) and cesium carbonate (962 mg, 2.95 mmol) in 1,4 dioxane (10 mL) was degassed with argon for 10 min. Then, 2-di-tert-butylphosphino-2',4',6'-triisopropylbiphenyl (209 mg, 0.492 mmol), tris(dibenzylideneacetone)dipalladium(0) chloroform adduct (102 mg, 0.098 mmol) were added sequentially under Argon and heated at 100° C. for 16 h. The reaction mixture was concentrated under reduced pressure to give crude residue, which was extracted with EtOAc (2×30 mL), washed with water, brine solution, dried over sodium sulphate and concentrated. The crude was purified via silica gel chromatography (0-10% EtOAc in Hexane) to give mixture of isomers which was further purified by prep-HPLC (Method F) to give tert-butyl 1-(3-(2-methylthiazol-5-yl)phenyl)hydrazine-1-carboxylate (120 mg, 40%, isomer-1) and tert-butyl 2-(3-(2-methylthiazol-5-yl)phenyl)hydrazine-1-carboxylate (120 mg, 40%, isomer-2)

Isomer 1:

LC-MS, [M+1]+=306.2, {Method E: tR: 1.37 min}; $^1$H NMR (400 MHz, CHLOROFORM-d) δ=7.78 (s, 1H), 7.29-7.24 (m, 3H), 7.06 (d, J=8.0 Hz, 1H), 6.80 (dd, J=1.5, 8.0 Hz, 1H), 6.41 (br s, 1H), 5.81 (br s, 1H), 2.74 (s, 3H), 1.50 (br s, 9H).

Isomer 2:

LC-MS, [M+1]+=306.2, {Method E: tR: 1.45 min}. $^1$H NMR (400 MHz, CHLOROFORM-d) δ=7.81 (s, 1H), 7.72-7.68 (m, 1H), 7.48 (br d, J=8.0 Hz, 1H), 7.37-7.29 (m, 1H), 7.28-7.25 (m, 1H), 4.48 (br s, 2H), 2.75 (s, 3H), 1.55 (s, 9H).

Step 3: Synthesis of 5-(3-hydrazinylphenyl)-2-methylthiazole: To a stirred solution of tert-butyl 2-(3-(2-methylthiazol-5-yl)phenyl)hydrazine-1-carboxylate (80 mg, 0.262 mmol) in DCM (4 mL) at 0° C., 4M HCl in 1,4-dioxane (0.393 mL, 1.572 mmol) was added. Then reaction mixture was allowed to reach room temperature and stirred for 5 h. The reaction mixture was concentrated under reduced pressure to give 5-(3-hydrazinylphenyl)-2-methylthiazole (50 mg, 93%). LC-MS, [M+H]+=206.2, {Method E: tR: 0.94 min} which was as such taken for next step without further purification.

General Synthetic Scheme for N-Linked 1,2,3-triazole Compounds:

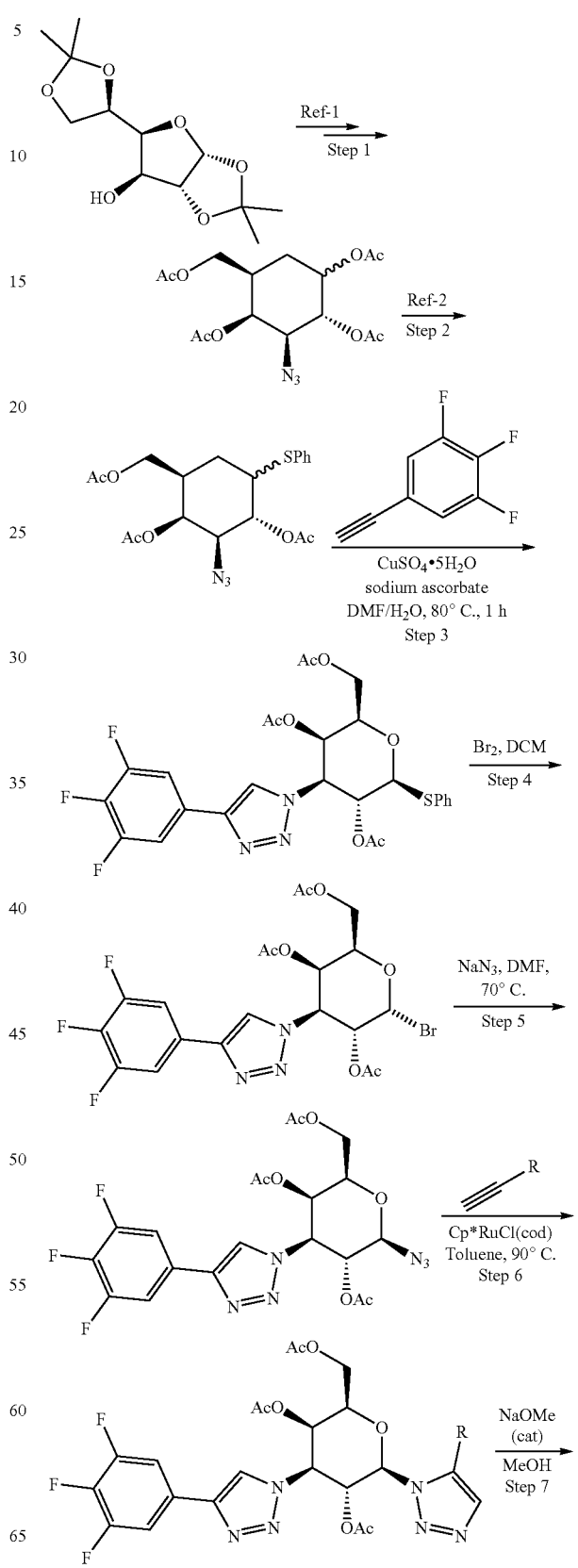

-continued

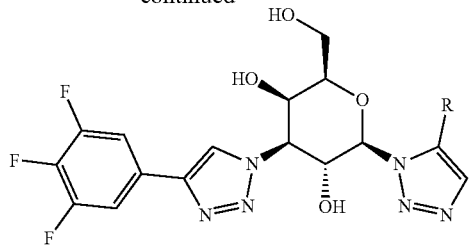

EXAMPLE 1

Preparation of (2R,3R,4S,5R,6R)-2-(5-(3-chlorophenyl)-1H-1,2,3-triazol-1-yl)-6-(hydroxymethyl)-4-(4-(3,4,5-trifluorophenyl)-1H-1,2,3-triazol-1-yl)tetrahydro-2H-pyran-3,5-diol

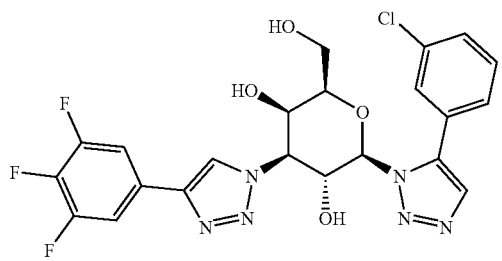 [SMILES: OC[C@H]1O[C@@H](n2nncc2-c2cccc(Cl)c2)[C@H](O)[C@@H](n2cc(-c3cc(F)c(F)c(F)c3)nn2)[C@H]1O]

Step 1: ((3R,4S,5R,6R)-6-(acetoxymethyl)-4-azidotetrahydro-2H-pyran-2,3,5-triyl triacetate from (3aR,5S,6S,6aR)-5-((R)-2,2-dimethyl-1,3-dioxolan-4-yl)-2,2-dimethyltetrahydrofuro[2,3-d][1,3]dioxol-6-ol as described in the literature. (Carbohydrate Res., 1994, 251, 33-67).

Step 2: (2R,3R,4S,5R,6S)-2-(acetoxymethyl)-4-azido-6-(phenylthio)tetrahydro-2H-pyran-3,5-diyl diacetate from ((3R,4S,5R,6R)-6-(acetoxymethyl)-4-azidotetrahydro-2H-pyran-2,3,5-triyltriacetate as described in the literature. (Chem Med Chem., 2009, 4, 1810-1815 and references cited therein).

Step 3: Synthesis of (2R,3R,4S,5R,6S)-2-(acetoxymethyl)-6-(phenylthio)-4-(4-(3,4,5-trifluorophenyl)-1H-1,2,3-triazol-1-yl)tetrahydro-2H-pyran-3,5-diyl diacetate: To a stirred solution of (2R,3R,4S,5R,6S)-2-(acetoxymethyl)-4-azido-6-(phenylthio)tetrahydro-2H-pyran-3,5-diyl diacetate (2.5 g, 5.90 mmol) in DMF (40 mL) and $H_2O$ (20 mL), 5-ethynyl-1,2,3-trifluorobenzene (1.080 mL, 8.86 mmol), sodium ascorbate (1.287 g, 6.49 mmol) and copper(II) sulfate pentahydrate (1.327 g, 5.31 mmol) were added at rt. The reaction mixture was heated at 85° C. for 1 h, cooled to rt, diluted with ice cold water (20 mL) and stirred for 15 min to get a solid. The solid was filtered, suspended in DCM (30 mL) and filtered through celite pad. The solid collected was washed with excess DCM and the filtrate was concentrated to get (2R,3R,4S,5R,6S)-2-(acetoxymethyl)-6-(phenylthio)-4-(4-(3,4,5-trifluorophenyl)-1H-1,2,3-triazol-1-yl)tetrahydro-2H-pyran-3,5-diyldiacetate (3.4 g, 5.87 mmol, 99%) as an off-white solid. LC-MS, [M+H]+=580.2, {Method C: tR: 3.12 min}. 1H NMR (400 MHz, CHLOROFORM-d): δ 7.76 (s, 1H), 7.60-7.53 (m, 2H), 7.45-7.36 (m, 5H), 5.71 (dd, J=11.0, 9.5 Hz, 1H), 5.58 (d, J=2.8 Hz, 1H), 5.19 (dd, J=11.0, 3.3 Hz, 1H), 4.89 (d, J=9.8 Hz, 1H), 4.20-4.11 (m, 3H), 2.05 (s, 3H), 2.03 (s, 3H), 1.98 (s, 3H).

Step 4: Synthesis of (2R,3R,4S,5R,6R)-2-(acetoxymethyl)-6-azido-4-(4-(3,4,5-trifluorophenyl)-1H-1,2,3-triazol-1-yl)tetrahydro-2H-pyran-3,5-diyl diacetate: To a stirred solution of (2R,3R,4S,5R,6S)-2-(acetoxymethyl)-6-(phenylthio)-4-(4-(3,4,5-trifluorophenyl)-1H-1,2,3-triazol-1-yl)tetrahydro-2H-pyran-3,5-diyl diacetate (2.8 g, 4.83 mmol) in DCM (70 mL) at −15° C., Br₂ (0.498 mL, 9.66 mmol) in DCM (2 mL) was added drop wise. The reaction mixture was quenched with cyclopentene (0.8 mL) and the solvent was removed under reduced pressure to get the crude bromo derivative which was taken as such for the next step without further purification.

Step 5: The bromo derivative from above was dissolved in DMF (15 mL) followed by the addition of sodium azide (1.477 g, 22.72 mmol) at rt under nitrogen and then heated at 70° C. for 12 h. The reaction mixture was cooled to rt, diluted with EtOAc (3×100 mL), washed with water, brine and dried over sodium sulphate. The solvent was removed under reduced pressure to get the crude residue which was purified via chromatography in silica gel (25-50% EtOAc in n-hexane) to yield (2R,3R,4S,5R,6R)-2-(acetoxymethyl)-6-azido-4-(4-(3,4,5-trifluorophenyl)-1H-1,2,3-triazol-1-yl)tetrahydro-2H-pyran-3,5-diyl diacetate (1.7 g, 3.32 mmol, 73%) as an off-white solid. LC-MS, [M+H]+=513.2, {Method C: tR: 2.92 min}. 1H NMR (400 MHz, CHLOROFORM-d): δ 7.78 (s, 1H), 7.49-7.37 (m, 2H), 5.65 (dd, J=11.2, 8.5 Hz, 1H), 5.85 (d, J=3.2 Hz, 1H), 5.16 (dd, J=11.2, 3.2 Hz, 1H), 4.82 (d, J=8.5 Hz, 1H), 4.25-4.16 (m, 3H), 2.08 (s, 3H), 2.07 (s, 3H), 1.97 (s, 3H).

Step 6: To a stirred solution of (2R,3R,4S,5R,6R)-2-(acetoxymethyl)-6-azido-4-(4-(3,4,5-trifluorophenyl)-1H-1,2,3-triazol-1-yl)tetrahydro-2H-pyran-3,5-diyl diacetate (30 mg, 0.059 mmol) in dry toluene (2 mL), 1-chloro-3-ethynylbenzene (32.0 mg, 0.234 mmol) was added at rt. The reaction mixture was degassed with argon for 5 min, followed by the addition of Cp*RuCl(cod) (0.667 mg, 1.756 μmol) and then heated at 90° C. for 14 h. The solvent was removed under reduced pressure to afford a residue containing the corresponding triazole.

Step 7: The residue from above was dissolved in MeOH (5 mL) and sodium methoxide (25% in MeOH, 0.666 mg, 3.08 μmol) was added followed by stirring at rt for 2 h. The reaction mixture was quenched with AcOH, concentrated and purified by prep-HPLC Method A to afford Example 1 (2R,3R,4S,5R,6R)-2-(5-(3-chlorophenyl)-1H-1,2,3-triazol-1-yl)-6-(hydroxymethyl)-4-(4-(3,4,5-trifluorophenyl)-1H-1,2,3-triazol-1-yl)tetrahydro-2H-pyran-3,5-diol (9.2 mg, 0.018 mmol, 57%) as off-white solid. LC-MS, [M+H]+ =523.1, {Method A: tR=1.49 min} 1H NMR (400 MHz, METHANOL-d4): δ 8.60 (s, 1H), 7.94 (s, 1H), 7.74-7.77 (m, 1H), 7.62-7.69 (m, 3H), 7.56-7.60 (m, 2H), 5.57 (d, J=8.6 Hz, 1H), 5.42 (dd, J=10.6, 9.2 Hz, 1H), 5.07 (dd, J=10.9, 3.1 Hz, 1H), 4.20 (d, J=2.7 Hz, 1H), 4.05-4.10 (m, 1H), 3.85-3.92 (m, 1H), 3.75-3.82 (m, 1H). hGal-3 $IC_{50}$=0.21 uM.

The Examples in the table below (2-11) were prepared in an analogous fashion to Example 1, substituting 1-chloro-3-ethynylbenzene with the appropriate acetylenes in the synthetic sequence.

| Ex. | hGal-3 IC$_{50}$, uM | Structure | LCMS RT | M + H | Method |
|---|---|---|---|---|---|
| 2 | 0.26 | 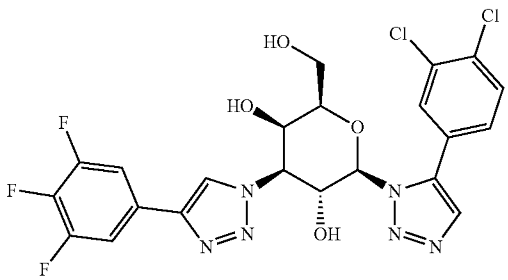 [SMILES: OC[C@H]1O[C@@H](n2nncc2-c2ccc(Cl)c(Cl)c2)[C@H](O)[C@@H](n2cc(-c3cc(F)c(F)c(F)c3)nn2)[C@H]1O] | 2.48 | 557.1 | A |
| 3 | 0.617 | 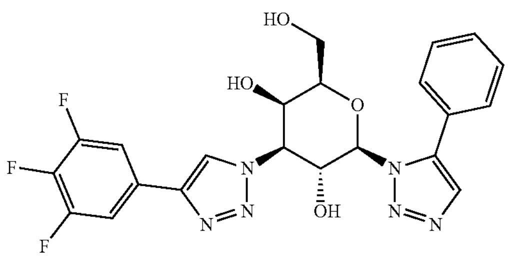 [SMILES: OC[C@H]1O[C@@H](n2nncc2-c2ccccc2)[C@H](O)[C@@H](n2cc(-c3cc(F)c(F)c(F)c3)nn2)[C@H]1O] | 1.34 | 489.2 | A |
| 4 | 0.386 | 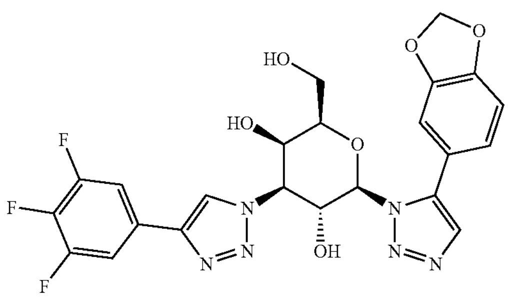 [SMILES: OC[C@H]1O[C@@H](n2nncc2-c2ccc3c(c2)OCO3)[C@H](O)[C@@H](n2cc(-c3cc(F)c(F)c(F)c3)nn2)[C@H]1O] | 1.35 | 533.2 | A |
| 5 | 0.640 | 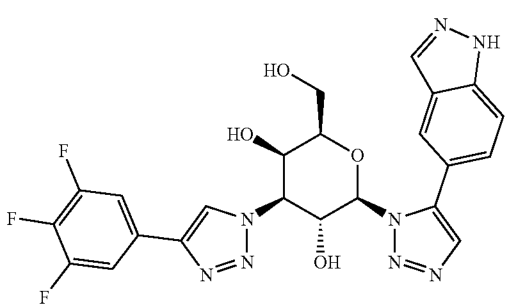 [SMILES: OC[C@H]1O[C@@H](n2nncc2-c2ccc3[nH]ncc3c2)[C@H](O)[C@@H](n2cc(-c3cc(F)c(F)c(F)c3)nn2)[C@H]1O] | 1.17 | 529.3 | A |
| 6 | 0.494 | 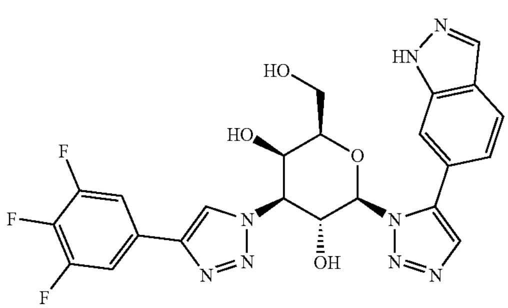 [SMILES: OC[C@H]1O[C@@H](n2nncc2-c2ccc3cn[nH]c3c2)[C@H](O)[C@@H](n2cc(-c3cc(F)c(F)c(F)c3)nn2)[C@H]1O] | 1.22 | 529.2 | A |

-continued

| Ex. | hGal-3 IC$_{50}$, uM | Structure | LCMS RT | M + H | Method |
|---|---|---|---|---|---|
| 7 | 0.329 | 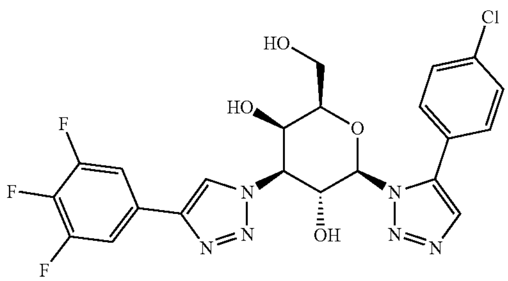 [SMILES: OC[C@H]1O[C@@H](n2nncc2-c2ccc(Cl)cc2)[C@H](O)[C@@H](n2cc(-c3cc(F)c(F)c(F)c3)nn2)[C@H]1O] | 1.48 | 523.1 | A |
| 8 | 0.158 | 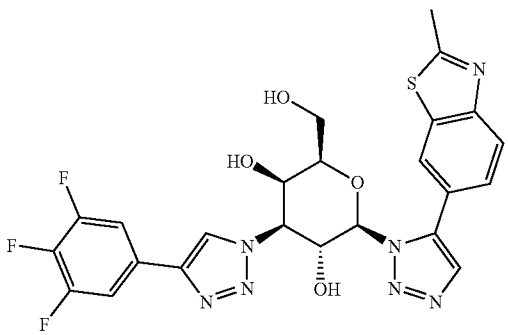 [SMILES: Cc1nc2ccc(-c3cnnn3[C@@H]3O[C@H](CO)[C@H](O)[C@H](n4cc(-c5cc(F)c(F)c(F)c5)nn4)[C@H]3O)cc2s1] | 1.36 | 560.2 | A |
| 9 | 0.158 | 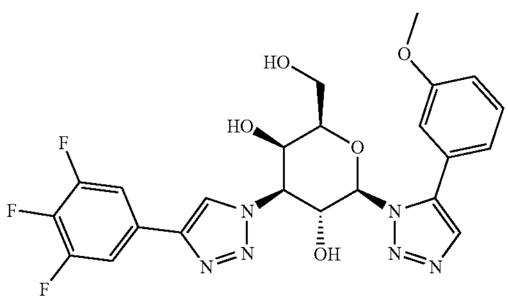 [SMILES: COc1cccc(-c2cnnn2[C@@H]2O[C@H](CO)[C@H](O)[C@H](n3cc(-c4cc(F)c(F)c(F)c4)nn3)[C@H]2O)c1] | 1.493 | 519.2 | B |
| 10 | 0.366 | 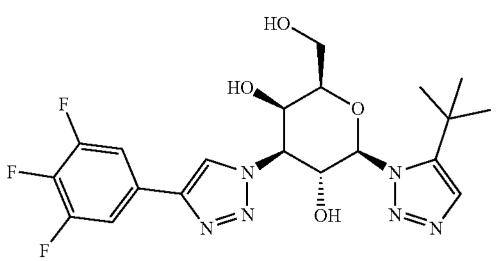 [SMILES: CC(C)(C)c1cnnn1[C@@H]1O[C@H](CO)[C@H](O)[C@H](n2cc(-c3cc(F)c(F)c(F)c3)nn2)[C@H]1O] | 1.365 | 469.2 | A |
| 11 | 0.184 | 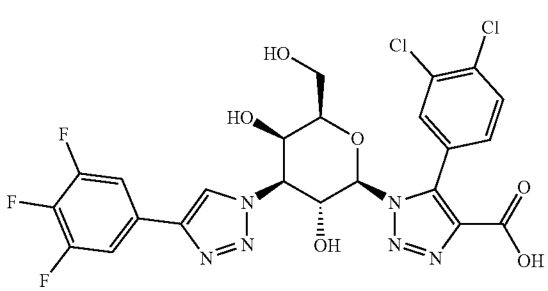 [SMILES: O=C(O)c1nnn([C@@H]2O[C@H](CO)[C@H](O)[C@H](n3cc(-c4cc(F)c(F)c(F)c4)nn3)[C@H]2O)c1-c1ccc(Cl)c(Cl)c1] | 1.136 | 601.1 | A |

General Synthetic Scheme for C2-O-alkylation on N-Linked 1,2,3-triazole Compounds:

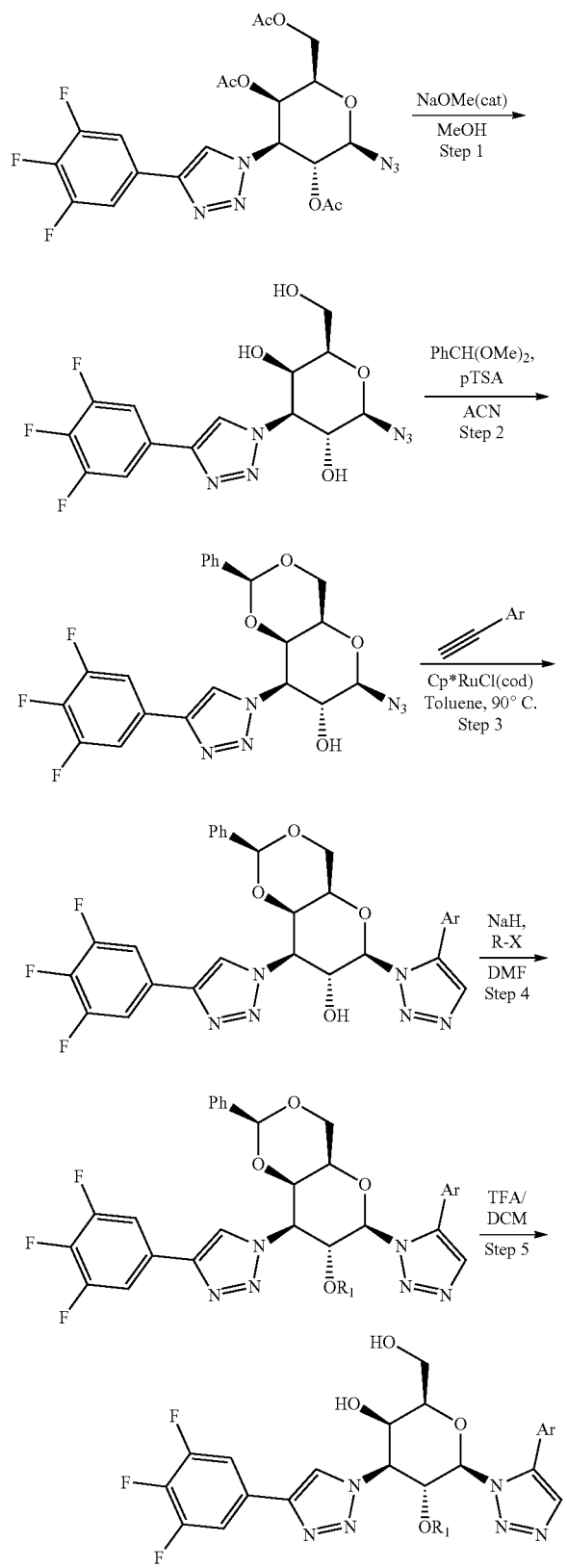

EXAMPLE 12

(2R,3R,4S,5R,6R)-6-(5-(3-chlorophenyl)-1H-1,2,3-triazol-1-yl)-5-ethoxy-2-(hydroxymethyl)-4-(4-(3,4,5-trifluorophenyl)-1H-1,2,3-triazol-1-yl)tetrahydro-2H-pyran-3-ol

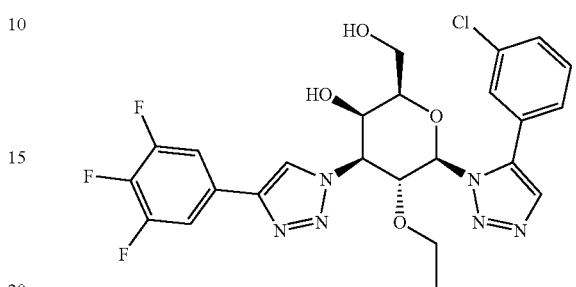

Step 1: Synthesis of (2R,3R,4S,5R,6R)-2-azido-6-(hydroxymethyl)-4-(4-(3,4,5-trifluorophenyl)-1H-1,2,3-triazol-1-yl)tetrahydro-2H-pyran-3,5-diol: To a solution of (2R,3R,4S,5R,6R)-2-(acetoxymethyl)-6-azido-4-(4-(3,4,5-trifluorophenyl)-1H-1,2,3-triazol-1-yl)tetrahydro-2H-pyran-3,5-diyl diacetate (200 mg, 0.390 mmol) in MeOH (2 mL), 25% sodium methoxide in MeOH (8.43 mg, 0.039 mmol) was added at rt and the mixture was stirred at rt for 1 h. The reaction mixture was neutralized with Amberlite IR120 (H+-resin), and concentrated to give (2R,3R,4S,5R,6R)-2-azido-6-(hydroxymethyl)-4-(4-(3,4,5-trifluorophenyl)-1H-1,2,3-triazol-1-yl)tetrahydro-2H-pyran-3,5-diol (0.14 g, 0.362 mmol, 93%) which was taken as such for next step without further purification. LC-MS, [M+H]+=387.2, {Method E: tR=0.87}.

Step 2: Synthesis of (2S,4aR,6R,7R,8R,8aR)-6-azido-2-phenyl-8-(4-(3,4,5-trifluorophenyl)-1H-1,2,3-triazol-1-yl)hexahydropyrano[3,2-d][1,3]dioxin-7-ol: To a stirred solution (2R,3R,4S,5R,6R)-2-azido-6-(hydroxymethyl)-4-(4-(3,4,5-trifluorophenyl)-1H-1,2,3-triazol-1-yl)tetrahydro-2H-pyran-3,5-diol (150 mg, 0.388 mmol) and benzaldehyde dimethyl acetal (0.146 mL, 0.971 mmol) in acetonitrile (8 mL), PTSA (7.39 mg, 0.039 mmol) was added at 0° C. The mixture was allowed to reach rt and stirred for 12 h. Then, the reaction mixture was filtered and the filtrate was diluted with EtOAc (2×50 mL), washed with water, brine solution, dried over sodium sulphate and concentrated. The residue was purified via chromatography in silica gel (5-15% EtOAc in Hexane) to give (2S,4aR,6R,7R,8R,8aR)-6-azido-2-phenyl-8-(4-(3,4,5-trifluorophenyl)-1H-1,2,3-triazol-1-yl)hexahydropyrano[3,2-d][1,3]dioxin-7-ol (0.09 g, 0.19 mmol, 50%) as off white solid. LC-MS, [M+H]+=475.1, {Method C: tR=2.94}. 1H NMR (400 MHz, CHLOROFORM-d): δ 7.94 (s, 1H), 7.42-7.27 (m, 7H), 5.51 (s, 1H), 5.02 (dd, J=10.8, 3.2 Hz, 1H), 4.90 (d, J=8.0 Hz, 1H), 4.50-4.46 (m, 2H), 4.23-4.12 (m, 1H), 3.85 (d, J=1.2 Hz, 1H), 2.40 (d, J=1.2 Hz, 1H, —OH).

Step 3: Synthesis of (2S,4aR,6R,7R,8R,8aR)-6-(5-(3-chlorophenyl)-1H-1,2,3-triazol-1-yl)-2-phenyl-8-(4-(3,4,5-trifluorophenyl)-1H-1,2,3-triazol-1-yl)hexahydropyrano[3,2-d][1,3]dioxin-7-ol: (2S,4aR,6R,7R,8R,8aR)-6-azido-2-phenyl-8-(4-(3,4,5-trifluorophenyl)-1H-1,2,3-triazol-1-yl)hexahydropyrano[3,2-d][1,3]dioxin-7-ol (60 mg, 0.126 mmol) and 1-chloro-3-ethynylbenzene (25.9 mg, 0.190 mmol) in dioxane (2 mL) were taken in a microwave vial and degassed with argon for 5 min. Then, chloro(1,5- cyclooctadiene)(pentamethylcyclopentadienyl)ruthenium (4.81 mg, 0.013 mmol) was added. The vial was sealed and heated at 100° C. for 1 h under microwave. The solvent was removed under reduced pressure and the residue was purified via chromatography in silica gel (60-80% EtOAc in n-hexane) to give (2S,4aR,6R,7R,8R,8aR)-6-(5-(3-chlorophenyl)-1H-1,2,3-triazol-1-yl)-2-phenyl-8-(4-(3,4,5-trifluorophenyl)-1H-1,2,3-triazol-1-yl)hexahydropyrano[3,2-d][1,3]dioxin-7-ol (45 mg, 0.074 mmol, 58%) as brown solid. LC-MS, [M+H]+=611.7, {Method E: tR=1.41 min}.

Step 4: Synthesis of 5-(3-chlorophenyl)-1-((4aR,6R,7R,8S,8aR)-7-ethoxy-2-phenyl-8-(4-(3,4,5-trifluorophenyl)-1H-1,2,3-triazol-1-yl)hexahydropyrano[3,2-d][1,3]dioxin-6-yl)-1H-1,2,3-triazole: To a stirred solution of (2S,4aR,6R,7R,8R,8aR)-6-(5-(3-chlorophenyl)-1H-1,2,3-triazol-1-yl)-2-phenyl-8-(4-(3,4,5-trifluorophenyl)-1H-1,2,3-triazol-1-yl)hexahydropyrano[3,2-d][1,3]dioxin-7-ol (25 mg, 0.041 mmol) in DMF (2 mL), NaH (4.91 mg, 0.123 mmol) was added at 0° C. under nitrogen and stirred for 5 min. Iodoethane (8.40 µl, 0.102 mmol) was added and the mixture was allowed to reach rt and stirred for 12 h. Then, the reaction mixture was diluted with EtOAc (2×50 mL), washed with water, brine solution, dried over sodium sulphate and concentrated. The residue was purified by via chromatography in silica gel (25-50% EtOAc in n-hexane) to give 5-(3-chlorophenyl)-1-((4aR,6R,7R,8S,8aR)-7-ethoxy-2-phenyl-8-(4-(3,4,5-trifluorophenyl)-1H-1,2,3-triazol-1-yl)hexahydropyrano[3,2-d][1,3]dioxin-6-yl)-1H-1,2,3-triazole (20 mg, 0.031 mmol, 76%) as off white solid. LC-MS, [M+H]+= 639.3, {Method E: tR=1.60 min}.

Step 5: TFA (1 mL) was added to 5-(3-chlorophenyl)-1-((4aR,6R,7R,8S,8aR)-7-ethoxy-2-phenyl-8-(4-(3,4,5-trifluorophenyl)-1H-1,2,3-triazol-1-yl)hexahydropyrano[3,2-d][1,3]dioxin-6-yl)-1H-1,2,3-triazole (14 mg, 0.022 mmol) at 0° C. and the mixture was stirred for 1 h. The TFA was removed under vacuum and the residue was purified by prep-HPLC Method B to afford Example 12 (2R,3R,4S,5R,6R)-6-(5-(3-chlorophenyl)-1H-1,2,3-triazol-1-yl)-5-ethoxy-2-(hydroxymethyl)-4-(4-(3,4,5-trifluorophenyl)-1H-1,2,3-triazol-1-yl)tetrahydro-2H-pyran-3-ol (6.5 mg, 0.012 mmol, 53%) as off white solid. LC-MS, [M+H]+=551.2, {Method A & Method B: $t_R$=1.87} 1H NMR (400 MHz, METHANOL-d4): δ 8.79 (s, 1H), 7.98 (s, 1H), 7.79-7.66 (m, 3H), 7.65-7.53 (m, 3H), 5.64 (d, J=8.6 Hz, 1H), 5.27-5.17 (m, 1H), 5.17-5.06 (m, 1H), 4.20 (d, J=2.4 Hz, 1H), 4.12-4.01 (m, 1H), 3.90 (dd, J=11.9, 7.2 Hz, 1H), 3.80 (dd, J=11.6, 4.5 Hz, 1H), 3.13-2.91 (m, 2H), 0.61 (t, J=7.1 Hz, 3H). hGal-3 $IC_{50}$=0.97 uM.

The Examples in the table below (13-14) were prepared in an analogous fashion to Example 12, substituting iodoethane with the appropriate alkyl halide in the synthetic sequence.

| Ex | hGal-3 IC50, uM | Structure | LC MS RT | M + H | Method |
|---|---|---|---|---|---|
| 13 | 0.571 | 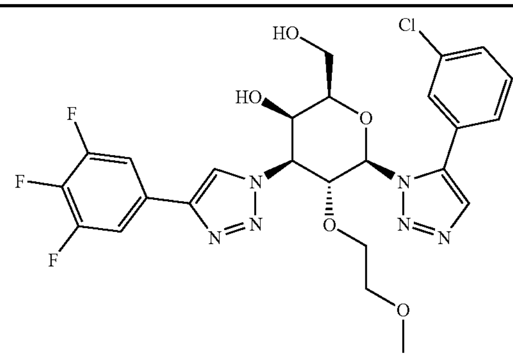 | 1.75 | 581.2 | A |
| 14 | 8.427 | 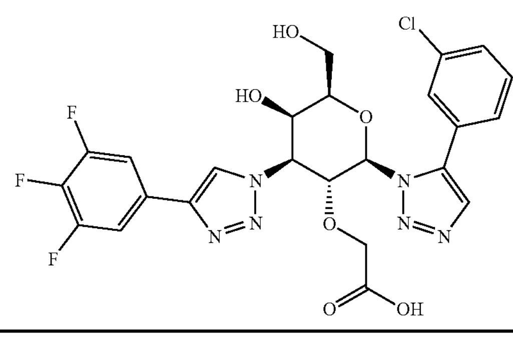 | 1.47 | 581.2 | B |

General Synthetic Scheme for C-2 Deoxy-N-Linked 1,2,3-triazole Compounds:

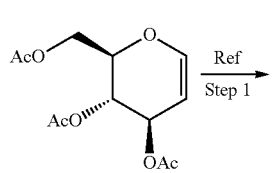

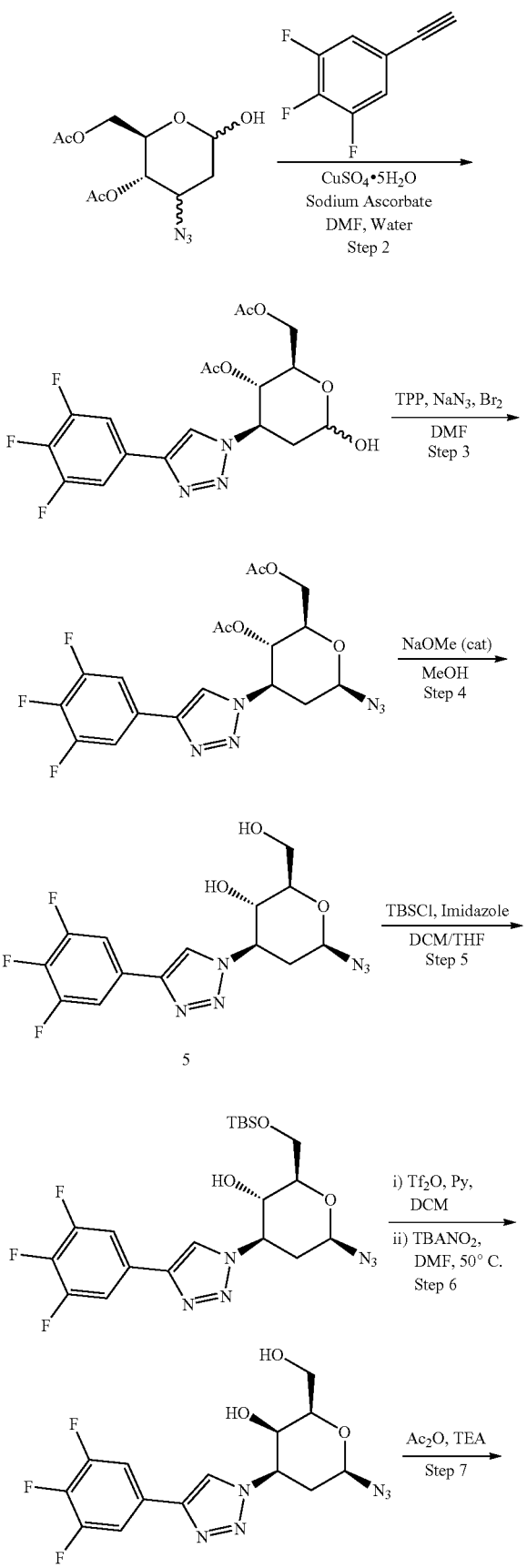
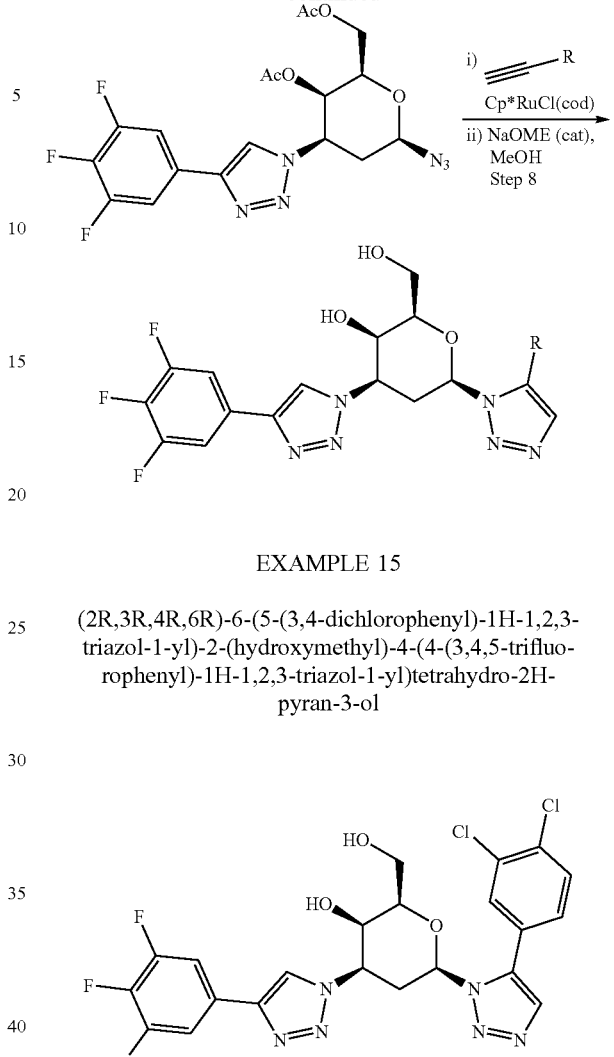

EXAMPLE 15

(2R,3R,4R,6R)-6-(5-(3,4-dichlorophenyl)-1H-1,2,3-triazol-1-yl)-2-(hydroxymethyl)-4-(4-(3,4,5-trifluorophenyl)-1H-1,2,3-triazol-1-yl)tetrahydro-2H-pyran-3-ol Step 1: ((2R,3S)-3-acetoxy-4-azido-6-hydroxytetrahydro-2H-pyran-2-yl)methyl acetate was synthesized from D-glucal triacetate as described in the literature (Tetrahedron Lett., 2010, 51, 3724-3727 and references cited therin).

Step 2: Synthesis of ((2R,3S,4R)-3-acetoxy-6-hydroxy-4-(4-(3,4,5-trifluorophenyl)-1H-1,2,3-triazol-1-yl)tetrahydro-2H-pyran-2-yl)methyl acetate: Prepared in a similar fashion as described in Example 1, step-3 using ((2R,3S,4R)-3-acetoxy-4-azido-6-hydroxytetrahydro-2H-pyran-2-yl) methyl acetate (2 g, 7.32 mmol) and 5-ethynyl-1,2,3-trifluorobenzene (1.788 mL, 14.64 mmol) as the reagents to afford ((2R,3S,4R)-3-acetoxy-6-hydroxy-4-(4-(3,4,5-trifluorophenyl)-1H-1,2,3-triazol-1-yl)tetrahydro-2H-pyran-2-yl)methyl acetate (1.5 g, 3.49 mmol, 48%) as an off-white solid {Anomeric mixture}. LC-MS, [M+H]+=430.0, {tR=2.11 & 2.23 min, Method C}.

Step 3: Synthesis of ((2R,3S,4R,6R)-3-acetoxy-6-azido-4-(4-(3,4,5-trifluorophenyl)-1H-1,2,3-triazol-1-yl)tetrahydro-2H-pyran-2-yl)methyl acetate: To a solution of ((2R,3S,4R)-3-acetoxy-6-hydroxy-4-(4-(3,4,5-trifluorophenyl)-1H-1,2,3-triazol-1-yl)tetrahydro-2H-pyran-2-yl)methyl acetate (1.5 g, 3.49 mmol) in DMF (20 mL), triphenylphosphine (1.833 g, 6.99 mmol) was added followed by sodium azide (1.136 g, 17.47 mmol) and the mixture was cooled to 0° C. Then, bromine (0.360 mL, 6.99 mmol) was added drop wise over 15 min, the mixture was allowed to warm to rt and stirred for 16 h. The reaction mixture was poured into ice cold water, extracted with EtOAc (3×50 mL), washed with brine, dried over sodium sulphate and concentrated. The residue was purified via chromatography in silica gel (0-50% EtOAc in n-hexane) to provide ((2R,3S,4R,6R)-3-acetoxy-6-azido-4-(4-(3,4,5-trifluorophenyl)-1H-1,2,3-triazol-1-yl)tetrahydro-2H-pyran-2-yl)methyl acetate (750 mg, 1.651 mmol, 47%) as an off-white solid. LC-MS, [M+H]+=455.2, {Method C: $t_R$=2.65 min}. 1H NMR (400 MHz, CHLOROFORM-d): δ 7.82 (s, 1H), 7.46 (dd, J=14.0, 6.8 Hz, 2H), 5.28 (dd, J=19.6, 9.6 Hz, 1H), 5.00-4.88 (m, 2H), 4.39 (dd, J=12.4, 4.4 Hz, 1H) 4.23 (d, J=12.4, 1H), 3.91-3.88 (m, 1H), 2.53-2.49 (m, 1H), 2.30-2.22 (m, 1H), 2.10 (s, 3H), 1.98 (s,3H).

Step 4: Synthesis of (2R,3S,4R,6R)-6-azido-2-(hydroxymethyl)-4-(4-(3,4,5-trifluorophenyl)-1H-1,2,3-triazol-1-yl)tetrahydro-2H-pyran-3-ol: To a solution of ((2R,3S,4R,6R)-3-acetoxy-6-azido-4-(4-(3,4,5-trifluorophenyl)-1H-1,2,3-triazol-1-yl)tetrahydro-2H-pyran-2-yl)methyl acetate (750 mg, 1.651 mmol) in methanol (5 mL), sodium methoxide (89 mg, 1.651 mmol) was added at rt and stirred for 1 h. Then the reaction was acidified with Amberlite IR-120 resin and filtered. The filtrate was concentrated under reduced pressure to give (2R,3S,4R,6R)-6-azido-2-(hydroxymethyl)-4-(4-(3,4,5-trifluorophenyl)-1H-1,2,3-triazol-1-yl) tetrahydro-2H-pyran-3-ol (600 mg, 1.620 mmol, 98%) as an off-white solid. LC-MS, [M+]+=370.8, {Method D: $t_R$=1.28 min}.

Step 5: Synthesis of (2R,3S,4R,6R)-6-azido-2-(((tert-butyldimethylsilyl)oxy)methyl)-4-(4-(3,4,5-trifluorophenyl)-1H-1,2,3-triazol-1-yl)tetrahydro-2H-pyran-3-ol: To a solution of (2R,3S,4R,6R)-6-azido-2-(hydroxymethyl)-4-(4-(3,4,5-trifluorophenyl)-1H-1,2,3-triazol-1-yl)tetrahydro-2H-pyran-3-ol (0.6 g, 1.620 mmol) in a mixture of DCM (10 mL) and THF (10 mL), imidazole (0.331 g, 4.86 mmol), 4-dimethylaminopyridine (0.020 g, 0.162 mmol), and TBDMS-Cl (0.293 g, 1.944 mmol) were added sequentially at 0° C. under nitrogen. Then the reaction mixture was allowed to warm to rt and stirred for 16 h. The reaction mixture was diluted with DCM (2×50 mL), washed with water (50 mL), brine solution (50 mL), dried over sodium sulphate and concentrated. The crude residue was purified by via chromatography in silica gel (0-30% EtOAc in n-hexane) to yield (2R,3S,4R,6R)-6-azido-2-(((tertbutyldimethylsilyl)oxy)methyl)-4-(4-(3,4,5-trifluorophenyl)-1H-1,2,3-triazol-1-yl)tetrahydro-2H-pyran-3-ol (0.65 g, 1.341 mmol, 83%) as a colorless liquid. LC-MS, [M+H]+=485.2, {Method C: $t_R$=3.66 min}. 1H NMR (400 MHz, CHLOROFORM-d): δ 7.89 (s, 1H), 7.46 (dd, J=8.4, 6.8 Hz, 2H), 4.91 (dd, J=10.0, 2.4 Hz, 1H), 4.51-4.46 (m, 1H), 4.13-4.07 (m, 1H) 4.03-3.87 (m, 2H), 3.63-3.59 (m, 1H), 2.49-2.40 (m, 2H), 0.93 (s, 9H), 0.13 (s, 6H).

Step 6: Synthesis of (2R,3R,4R,6R)-6-azido-2-(hydroxymethyl)-4-(4-(3,4,5-trifluorophenyl)-1H-1,2,3-triazol-1-yl)tetrahydro-2H-pyran-3-ol: To a solution of (2R,3S,4R,6R)-6-azido-2-(((tert-butyldimethylsilyl)oxy)methyl)-4-(4-(3,4,5-trifluorophenyl)-1H-1,2,3-triazol-1-yl)tetrahydro-2H-pyran-3-ol (0.65 g, 1.341 mmol) in DCM (20 mL), pyridine (0.325 mL, 4.02 mmol) was added followed by Tf$_2$O (0.340 mL, 2.012 mmol) at -15° C. and the mixture was stirred for 1 h. Then, the reaction mixture was diluted with DCM (100 mL), washed with 0.7N HCl (50 mL) followed by 10% NaHCO$_3$ (50 mL) and brine solution (50 mL). The organic layer was dried over Na$_2$SO$_4$ and concentrated to give the crude triflate (650 mg, 0.999 mmol) as a yellow liquid. This was dissolved in DMF (5 mL), treated with tetrabutylammonium nitrite (842 mg, 2.92 mmol) at rt under argon and heated at 50° C. for 16 h. The reaction mixture was quenched with ice cold water, extracted with EtOAc (2×50 mL); washed with water, brine solution, dried over sodium sulphate and concentrated. The residue was purified via chromatography in silica gel (0-100% EtOAc in n-hexane) to yield 2R,3R,4R,6R)-6-azido-2-(hydroxymethyl)-4-(4-(3,4,5-trifluorophenyl)-1H-1,2,3-triazol-1-yl) tetrahydro-2H-pyran-3-ol (300 mg, 0.803 mmol, 82%) as a pale yellow solid. LC-MS, [M+H]+=371.0, {Method C: $t_R$=1.94 min}.

Step 7: Synthesis of ((2R,3R,4R,6R)-3-acetoxy-6-azido-4-(4-(3,4,5-trifluorophenyl)-1H-1,2,3-triazol-1-yl)tetrahydro-2H-pyran-2-yl)methyl acetate: To a stirred solution of (2R,3R,4R,6R)-6-azido-2-(hydroxymethyl)-4-(4-(3,4,5-trifluorophenyl)-1H-1,2,3-triazol-1-yl)tetrahydro-2H-pyran-3-ol (300 mg, 0.810 mmol) in DCM (10 mL), TEA (0.339 mL, 2.431 mmol) was added followed by Ac$_2$O (0.115 mL, 1.215 mmol) at 0° C., allowed to warm to rt and stirred for 16 h. Then, the reaction mixture was diluted with DCM (2×50 mL), washed with water, brine solution, dried over sodium sulphate and concentrated. The residue was purified via chromatography in silica gel (0-50% EtOAc in n-hexane) to yield ((2R,3R,4R,6R)-3-acetoxy-6-azido-4-(4-(3,4,5-trifluorophenyl)-1H-1,2,3-triazol-1-yl)tetrahydro-2H-pyran-2-yl)methyl acetate (300 mg, 0.653 mmol, 81%) as an off-white solid. LC-MS, [M+H]+=455.1, {Method C: $t_R$=2.886 min} 1H NMR (400 MHz, CHLOROFORM-d): δ 7.72 (s, 1H), 7.44-7.40 (m, 2H), 5.48 (d, J=1.6 Hz, 1H), 4.99-4.91 (m, 2H), 4.21 (d, J=6.4 Hz, 2H), 4.13 (dd, J=5.6, 0.8 Hz, 1H), 2.66-2.55 (m, 1H), 2.37-2.36 (m, 1H), 2.07 (s, 3H), 2.01 (s, 3H).

Step 8: Prepared in a similar fashion as described in Example 1, step 6 using ((2R,3R,4R,6R)-3-acetoxy-6-azido-4-(4-(3,4,5-trifluorophenyl)-1H-1,2,3-triazol-1-yl)tetrahydro-2H-pyran-2-yl)methyl acetate (30 mg, 0.066 mmol) and 1,2-dichloro-4-ethynylbenzene as the reactants. The crude was purified prep-HPLC Method A to afford Example 15 (2R,3R,4R,6R)-6-(5-(3,4-dichlorophenyl)-1H-1,2,3-triazol-1-yl)-2-(hydroxymethyl)-4-(4-(3,4,5-trifluorophenyl)-1H-1,2,3-triazol-1-yl)tetrahydro-2H-pyran-3-ol (8 mg, 0.015 mmol, 24%). LC-MS, [M+H]+=541, {Method C: $t_R$=1.198 and Method D: $t_R$=1.060}. 1H NMR (400 MHz, METHANOL-d4): δ 8.62 (s, 1H), 7.99-7.97 (m, 2H), 7.75-7.66 (m, 4H), 5.87 (dd, J=11.2, 2.0 Hz, 1H), 5.24-5.20 (m, 1H), 4.17 (d, J=2.0 Hz, 1H), 4.04-4.08 (m, 1H), 3.94-3.89 (m, 1H), 3.83-3.69 (m, 2H), 2.55-2.52 (m, 1H). hGal-3 IC$_{50}$=0.88 uM.

The Examples in the table below (16-17) were prepared in an analogous fashion to Example 15, substituting 1,2-dichloro-4-ethynylbenzene with the appropriate aryl acetylenes in the synthetic sequence.

| Ex | hGal-3 IC50, uM | Structure | LC MS RT | M + H | Method |
|---|---|---|---|---|---|
| 16 | 0.609 | 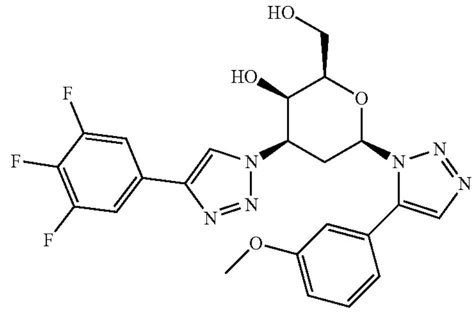 [SMILES: COc1cccc(-c2cnnn2[C@H]2C[C@@H](n3cc(-c4cc(F)c(F)c(F)c4)nn3)[C@@H](O)[C@@H](CO)O2)c1] | 1.59 | 503.2 | A |
| 17 | 0.902 | 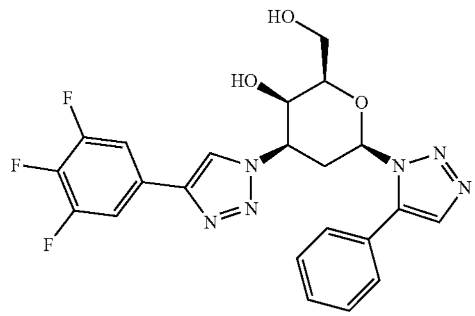 [SMILES: OC[C@H]1O[C@@H](n2nncc2-c2ccccc2)C[C@@H](n2cc(-c3cc(F)c(F)c(F)c3)nn2)[C@H]1O] | 1.54 | 473.2 | A |
General Synthetic Scheme for C2-fluoro N-Linked 1,2,3-Triazole Compounds:
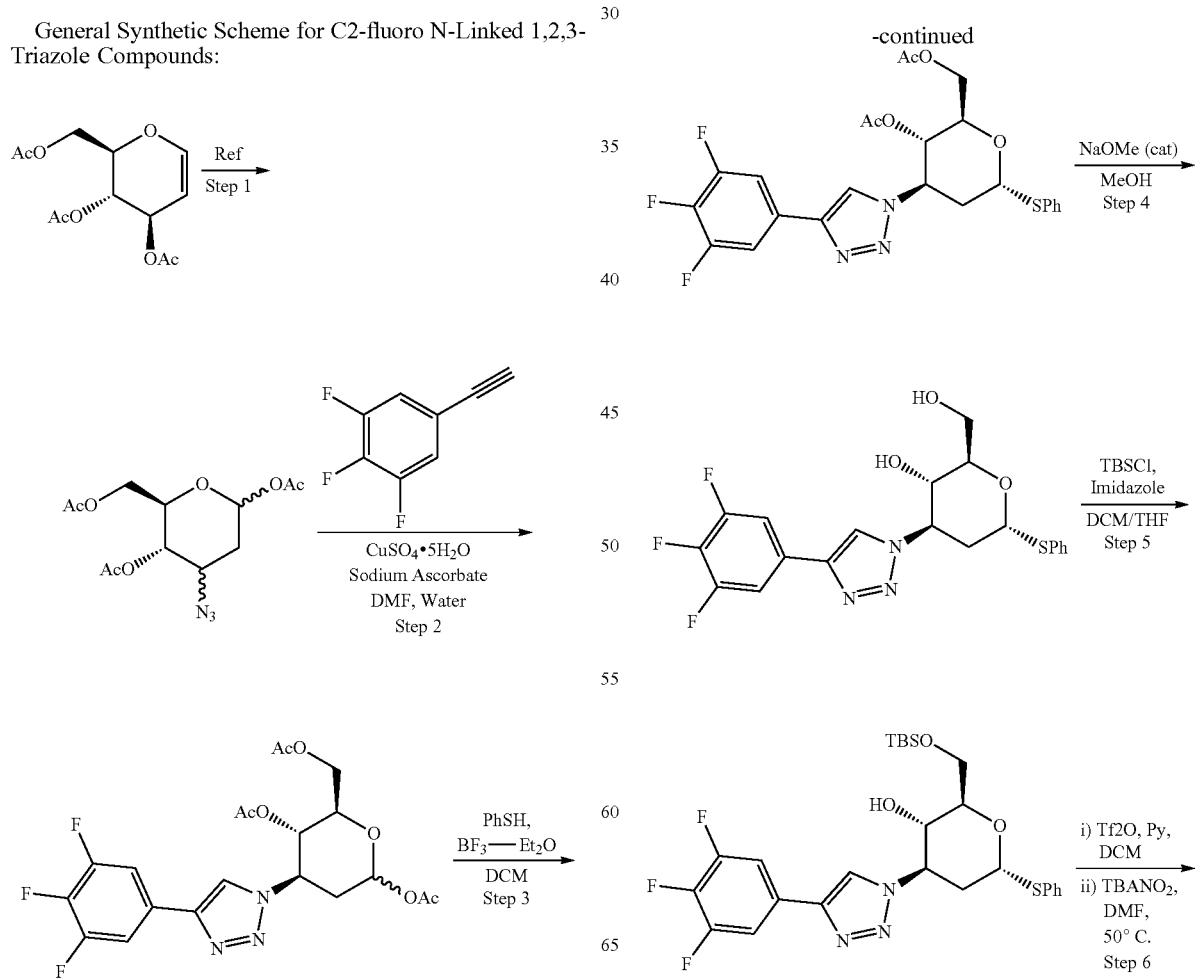

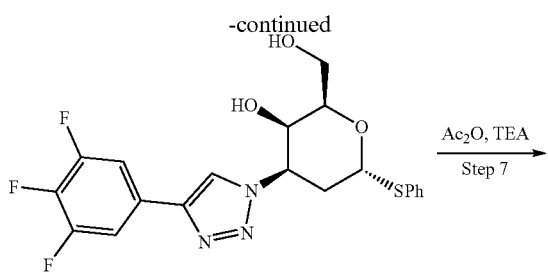

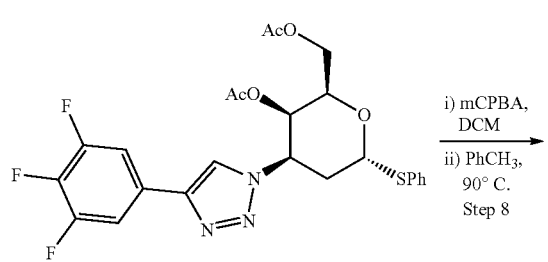

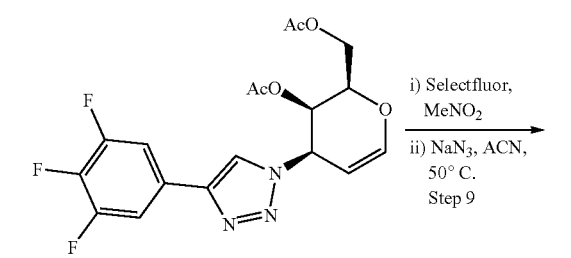

EXAMPLE 18

(2R,3R,4S,5R,6R)-6-(5-(3-chlorophenyl)-1H-1,2,3-triazol-1-yl)-5-fluoro-2-(hydroxymethyl)-4-(4-(3,4,5-trifluorophenyl)-1H-1,2,3-triazol-1-yl)tetrahydro-2H-pyran-3-ol

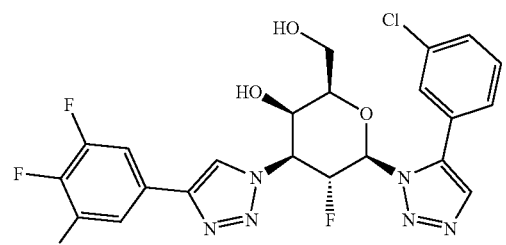

Step 1: Synthesis of (5S,6R)-6-(acetoxymethyl)-4-azido-tetrahydro-2H-pyran-2,5-diyl diacetate: Synthesized from D-glucal triacetate by following literature procedure: {Ref: Tetrahedron Lett., 2010, 51, 3724-3727 and references cited therin}.

Step 2: Synthesis of (4R,5S,6R)-6-(acetoxymethyl)-4-(4-(3,4,5-trifluorophenyl)-1H-1,2,3-triazol-1-yl)tetrahydro-2H-pyran-2,5-diyl diacetate: Prepared in a similar fashion as described in Example 1, step 3 using (4R,5S,6R)-6-(acetoxymethyl)-4-azidotetrahydro-2H-pyran-2,5-diyl diacetate (3 g, 9.52 mmol) and 5-ethynyl-1,2,3-trifluorobenzene (2.325 mL, 19.03 mmol) as the reactants to afford (4R,5S,6R)-6-(acetoxymethyl)-4-(4-(3,4,5-trifluorophenyl)-1H-1,2,3-triazol-1-yl)tetrahydro-2H-pyran-2,5-diyl diacetate (3.1 g, 6.58 mmol, 69%) as an off-white solid. {Anomeric mixture}. LC-MS, [M+H]+=472.1; {Method C: $t_R$=2.726-2.776}.

Step 3: Synthesis of ((2R,3S,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate: To a stirred solution of (4R,5S,6R)-6-(acetoxymethyl)-4-(4-(3,4,5-trifluorophenyl)-1H-1,2,3-triazol-1-yl)tetrahydro-2H-pyran-2,5-diyl diacetate (3 g, 6.36 mmol) in DCM (50 mL), $BF_3 \cdot OEt_2$ (2.419 mL, 19.09 mmol) was added followed by benzenethiol (0.912 g, 8.27 mmol) at 0° C. The reaction mixture allowed to warm to rt and stirred for 16 h. The reaction mixture was poured into ice water, extracted with DCM (3×50 mL), washed with aq. 10% $NaHCO_3$, water, brine, dried over sodium sulphate and concentrated. The residue was purified via chromatography in silica gel (0-50% EtOAc in n-hexane) to afford ((2R,3S,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (2.1 g, 4.03 mmol, 63%) as an off-white solid. LC-MS, [M+H]+= 522.1, {Method C, $t_R$=3.475 min}.

Step 4: Synthesis of (2R,3S,4R,6R)-2-(hydroxymethyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 12, step 1 using ((2R,3S,4R)-3-acetoxy-6-(phenylthio)-4-(4-(3,4,5-trifluorophenyl)-1H-1,2,3-triazol-1-yl)tetrahydro-2H-pyran-2-yl)methyl acetate (2.1 g, 4.03 mmol) as the reactant to give (2R,3S,4R)-2-(hydroxymethyl)-6-(phenylthio)-4-(4-(3,4,5-trifluorophenyl)-1H-1,2,3-triazol-1-yl)tetrahydro-2H-pyran-3-ol (1.3 g, 2.58 mmol, 64%) as off-white solid. LC-MS, [M+H]+= 438.2, {tR=2.55 min, Method C}.

Step 5: Synthesis of (2R,3S,4R,6R)-2-(((tert-butyldimethylsilyl)oxy)methyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 15, step-5 using (2R,3S,4R)-2-(hydroxymethyl)-6-(phenylthio)-4-(4-(3,4,5-trifluorophenyl)-1H-1,2,3-triazol-1-yl)tetrahydro-2H-pyran-3-ol (1.3 g, 2.97 mmol) as the reactant to give (2R,3S,4R,6R)-2-(((tertbutyldimethylsilyl)oxy)methyl)-6-(phenylthio)-4-(4-(3,4,5-trifluorophenyl)-1H-1,2,3-triazol-1-yl)tetrahydro-2H-pyran-3-ol (750 mg, 1.317 mmol, 44%) as an off-white solid. LC-MS, [M+H]+=552.2 {$t_R$=1.607 min, Method C}. $^1$H NMR (400 MHz, CHLOROFORM-d): δ 7.94 (s, 1H), 7.53-7.43 (m, 4H), 7.39-7.28 (m, 3H), 5.77 (d, J=4.8 Hz, 1H), 4.79 (ddd, J=13.3, 9.4, 4.4 Hz, 1H), 4.34 (ddd, J=9.1, 7.4, 4.5 Hz, 1H), 4.08 (td, J=9.4, 1.8 Hz, 1H), 3.98-3.91 (m, 2H), 3.84 (dd, J=10.3, 7.5 Hz, 1H), 3.00 (td, J=13.4, 5.8 Hz, 1H), 2.64 (dd, J=13.1, 4.4 Hz, 1H), 0.94 (s, 9H), 0.09 (s, 6H).

Step 6: Synthesis of (2R,3R,4R,6R)-2-(hydroxymethyl)-6-(phenylthio)-4-(4-(3,4,5-trifluorophenyl)-1H-1,2,3-triazol-1-yl)tetrahydro-2H-pyran-3-ol: Prepared in a similar fashion as described in Example 15, step 6 using (2R,3S,4R,6R)-2-(((tert-butyldimethylsilyl)oxy)methyl)-6-(phenylthio)-4-(4-(3,4,5-trifluorophenyl)-1H-1,2,3-triazol-1-yl)tetrahydro-2H-pyran-3-ol (800 mg, 1.450 mmol) as the reactant to give (2R,3R,4R,6R)-2-(hydroxymethyl)-6-(phenylthio)-4-(4-(3,4,5-trifluorophenyl)-1H-1,2,3-triazol-1-yl)tetrahydro-2Hpyran-3-ol (300 mg, 0.683 mmol, 58%) as an off-white solid. LC-MS, [M+H]+=438.2, {Method C: $t_R$=2.59 min}. 1H NMR (400 MHz, METHANOL-d4): δ 8.42 (s, 1H), 7.56-7.48 (m, 4H), 7.26-7.19 (m, 3H), 5.76 (d, J=5.2 Hz, 1H), 5.09-5.05 (m, 1H), 4.46-4.43 (m, 1H), 4.10 (s, 1H), 3.68-3.57 (m, 2H), 3.04-2.97 (m, 1H), 2.24 (dd, J=13.2, 4.0 Hz, 1H).

Step 7: Synthesis of ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate: Prepared in a similar fashion as described in Example 15, step 7 using (2R,3R,4R,6R)-2-(hydroxymethyl)-6-(phenylthio)-4-(4-(3,4,5-trifluorophenyl)-1H-1,2,3-triazol-1-yl)tetrahydro-2H-pyran-3-ol (360 mg, 0.823 mmol) as the starting material to afford to give ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (350 mg, 0.642 mmol, 78%) as a pale yellow solid. LC-MS, [M+H]+=522.2, {$t_R$=3.275 min, Method C}.

Step 8: Synthesis of ((2R,3R,4R)-3-acetoxy-4-(4-(3,4,5-trifluorophenyl)-1H-1,2,3-triazol-1-yl)-3,4-dihydro-2H-pyran-2-yl)methyl acetate: To a solution of ((2R,3R,4R,6R)-3-acetoxy-6-(phenylthio)-4-(4-(3,4,5-trifluorophenyl)-1H-1,2,3-triazol-1-yl)tetrahydro-2H-pyran-2-yl)methyl acetate (300 mg, 0.575 mmol) in DCM (20 mL), m-CPBA (142 mg, 0.575 mmol) in DCM (0.5 mL) was added at 0° C. and stirred at the same temperature for 30 min. The reaction mixture was diluted with DCM (20 mL), washed with sat NaHCO$_3$, sat NaCl, dried over sodium sulphate and concentrated to give crude residue which was taken as such for next step without further purification. The crude sulphoxide (300 mg, 0.558 mmol) thus obtained was dissolved in toluene (20 mL) and heated at 90° C. for 12 h. The solvent was removed under reduced pressure to get the crude residue which was purified via chromatography in silica gel (0-50% EtOAc in n-hexane) to afford ((2R,3R,4R)-3-acetoxy-4-(4-(3,4,5-trifluorophenyl)-1H-1,2,3-triazol-1-yl)-3,4-dihydro-2H-pyran-2-yl)methyl acetate (180 mg, 0.392 mmol, 70%) as an off-white solid. LC-MS, [M+H]+=412.0, {Method C: $t_R$=2.639 min}. 1H NMR (400 MHz, CHLOROFORM-d): δ 7.79 (s, 1H), 7.48-7.40 (m, 2H), 6.74 (dd, J=6.3, 2.3 Hz, 1H), 5.82-5.78 (m, 1H), 5.65 (d, J=5.0 Hz, 1H), 4.92 (dt, J=6.1, 1.9 Hz, 1H), 4.50 (t, J=6.5 Hz, 1H), 4.27-4.18 (m, 2H), 2.10 (s, 3H), 1.91 (s, 3H).

Step 9: Synthesis of ((2R,3R,4S,5R,6R)-3-acetoxy-6-azido-5-fluoro-4-(4-(3,4,5-trifluorophenyl)-1H-1,2,3-triazol-1-yl)tetrahydro-2H-pyran-2-yl)methyl acetate: To a solution of ((2R,3R,4R)-3-acetoxy-4-(4-(3,4,5-trifluorophenyl)-1H-1,2,3-triazol-1-yl)-3,4-dihydro-2H-pyran-2-yl) methyl acetate (80 mg, 0.194 mmol) in nitromethane (2 mL), 1-chloromethyl-4-fluoro-1,4-diazoniabicyclo[2.2.2]octane bis(tetrafluoroborate) (90 mg, 0.253 mmol) was added at rt and stirred for 12 h. The reaction mixture was diluted with EtOAc (20 mL), the solids formed were filtered and the filtrate was concentrated. The residue was taken in acetonitrile (10 mL), sodium azide (37.9 mg, 0.583 mmol) was added and the mixture was heated at 50° C. for 5 h. the reaction mixture was filtered and the filtrate was concentrated to give crude residue which was purified via chromatography in silica gel (0-50% EtOAc in n-hexane) to afford ((2R,3R,4S,5R,6R)-3-acetoxy-6-azido-5-fluoro-4-(4-(3,4,5-trifluorophenyl)-1H-1,2,3-triazol-1-yl)tetrahydro-2H-pyran-2-yl)methyl acetate (45 mg, 0.095 mmol, 49%) as an off-white solid. LC-MS, [M+45]=517.1, {Method C: $t_R$=3.009 min}. 1H NMR (400 MHz, CHLOROFORM-d): δ 7.82-7.78 (s, 1H), 7.50-7.39 (m, 2H), 5.68-5.63 (m, 1H), 5.30-5.10 (m, 1H), 5.06-4.90 (m, 2H), 4.25-4.16 (m, 3H), 2.07 (s, 3H), 2.05 (s, 3H).

Step 10: Prepared in similar fashion as described in Example 1, step 6 using ((2R,3R,4S,5R,6R)-3-acetoxy-6-azido-5-fluoro-4-(4-(3,4,5-trifluorophenyl)-1H-1,2,3-triazol-1-yl)tetrahydro-2H-pyran-2-yl)methyl acetate (18 mg, 0.038 mmol) and 1-chloro-3-ethynylbenzene (10.41 mg, 0.076 mmol) as the reactants. The crude obtained was purified by prep-HPLC Method B to afford Example 18 (2R,3R,4S,5R,6R)-6-(5-(3-chlorophenyl)-1H-1,2,3-triazol-1-yl)-5-fluoro-2-(hydroxymethyl)-4-(4-(3,4,5-trifluorophenyl)-1H-1,2,3-triazol-1-yl)tetrahydro-2H-pyran-3-ol (3 mg, 0.007 mmol, 17%). LC-MS, [M+H]+=525.2, {Method A & Method B: $t_R$=1.78}. 1H NMR (400 MHz, METHANOL-d4): δ 8.82 (s, 1H), 8.00 (s, 1H), 7.82-7.75 (m, 1H), 7.74-7.55 (m, 5H), 6.46 (dd, J=10.5, 9.0 Hz, 1H), 6.34 (dd, J=10.5, 8.5 Hz, 1H), 5.97 (dd, J=8.8, 3.3 Hz, 1H), 5.52 (td, J=10.8, 3.0 Hz, 1H), 4.33 (t, J=2.5 Hz, 1H), 4.24-4.14 (m, 1H), 4.00-3.87 (m, 1H), 3.81 (dd, J=11.5, 4.5 Hz, 1H). hGal-3 IC$_{50}$=1.04 uM General Synthetic Scheme 1 for 1,2,4-triazole Compounds:

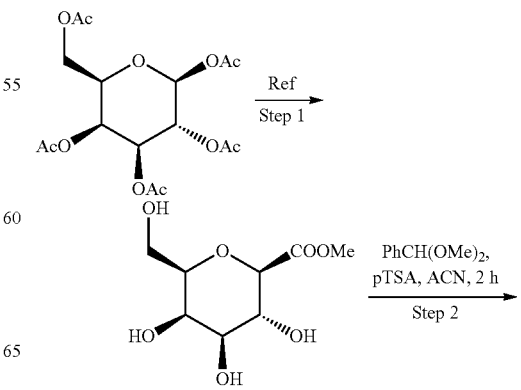

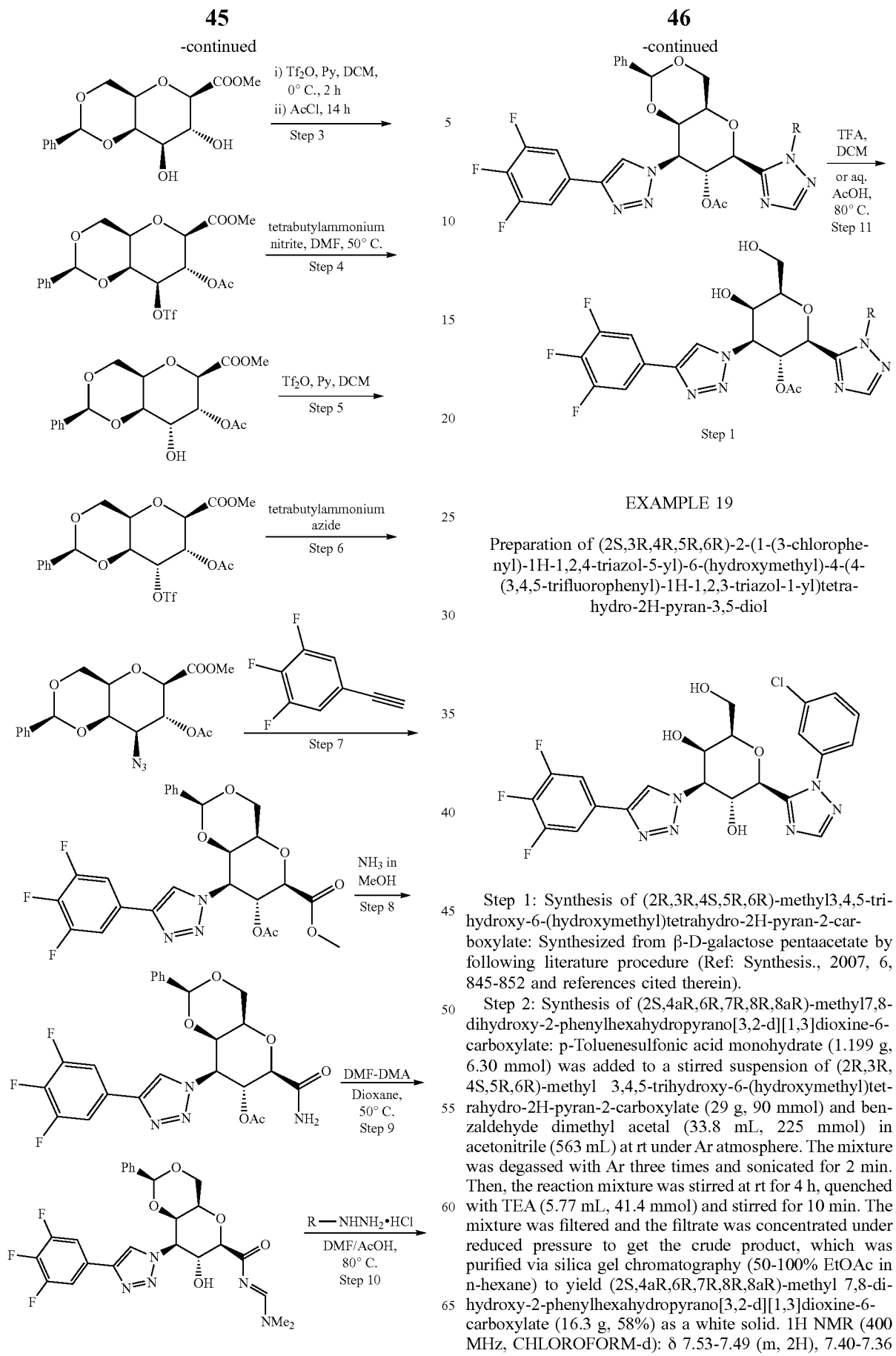

EXAMPLE 19

Preparation of (2S,3R,4R,5R,6R)-2-(1-(3-chlorophenyl)-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol Step 1: Synthesis of (2R,3R,4S,5R,6R)-methyl3,4,5-trihydroxy-6-(hydroxymethyl)tetrahydro-2H-pyran-2-carboxylate: Synthesized from β-D-galactose pentaacetate by following literature procedure (Ref: Synthesis., 2007, 6, 845-852 and references cited therein).

Step 2: Synthesis of (2S,4aR,6R,7R,8R,8aR)-methyl7,8-dihydroxy-2-phenylhexahydropyrano[3,2-d][1,3]dioxine-6-carboxylate: p-Toluenesulfonic acid monohydrate (1.199 g, 6.30 mmol) was added to a stirred suspension of (2R,3R,4S,5R,6R)-methyl 3,4,5-trihydroxy-6-(hydroxymethyl)tetrahydro-2H-pyran-2-carboxylate (29 g, 90 mmol) and benzaldehyde dimethyl acetal (33.8 mL, 225 mmol) in acetonitrile (563 mL) at rt under Ar atmosphere. The mixture was degassed with Ar three times and sonicated for 2 min. Then, the reaction mixture was stirred at rt for 4 h, quenched with TEA (5.77 mL, 41.4 mmol) and stirred for 10 min. The mixture was filtered and the filtrate was concentrated under reduced pressure to get the crude product, which was purified via silica gel chromatography (50-100% EtOAc in n-hexane) to yield (2S,4aR,6R,7R,8R,8aR)-methyl 7,8-dihydroxy-2-phenylhexahydropyrano[3,2-d][1,3]dioxine-6-carboxylate (16.3 g, 58%) as a white solid. 1H NMR (400 MHz, CHLOROFORM-d): δ 7.53-7.49 (m, 2H), 7.40-7.36

(m, 3H), 5.57 (s, 1H), 4.39 (dd, J=12.5, 1.5 Hz, 1H),4.28 (dd, J=4.0, 1.0 Hz, 1H), 4.15-4.05 (m, 2H), 3.87-3.84 (m, 4H), 3.73 (td, J=9.0, 4.0 Hz, 1H), 3.56 (q, J=1.5 Hz, 1H), 3.24 (d, J=2.5 Hz, 1H), 2.63 (d, J=8.5 Hz, 1H).

Step 3: Synthesis of (2S,4aR,6R,7S,8S,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7,8-dihydroxy-2-phenylhexahydropyrano[3,2-d][1,3]dioxine-6-carboxylate (17.3 g, 55.8 mmol) in DCM (180 mL) was added pyridine (18.04 mL, 223 mmol) at −15° C. and the mixture was stirred for 10 min. Triflic anhydride (8.48 mL, 50.2 mmol) was added dropwise over a period of 15 min under argon and the mixture was stirred for 1 h at −15° C. The reaction mixture was allowed to reach room temperature over a period of 2 h. Acetyl chloride (4.76 mL, 66.9 mmol) was added at 0° C., and the mixture was allowed to warm to rt and was stirred for 10 h. DCM (300 mL) was added, and the solution was washed with 0.7N HCl (150 mL), saturated sodium bicarbonate (2×100 mL) and brine solution. The organic layer was separated and dried over sodium sulfate. The solvent was removed under reduced pressure and purified via silica gel chromatography (30-80% EtOAc in n-hexane) to yield (2S,4aR,6R,7S,8S,8aS)-methyl-7-acetoxy-2-phenyl-8-(((trifluoromethyl)sulfonyl)oxy)hexahydropyrano[3,2-d][1,3]dioxine-6-carboxylate (14 g, 52%) as a white solid. 1H NMR (400 MHz, CHLOROFORM-d): δ 7.53 (dd, J=7.4, 2.1 Hz, 2H), 7.44-7.36 (m, 3H), 5.64 (d, J=9.9 Hz, 1H), 5.60 (s, 1H), 5.00 (dd, J=9.9, 3.6 Hz, 1H), 4.53 (d, J=3.6 Hz, 1H), 4.42 (dd, J=12.8, 1.5 Hz, 1H), 4.08 (dd, J=12.8, 1.5 Hz, 1H), 4.03 (d, J=9.9 Hz, 1H), 3.77 (s, 3H), 3.59 (d, J=1.0 Hz, 1H), 2.10 (s, 3H).

Step 4: Synthesis of (2S,4aR,6R,7R,8R,8aR)-methyl-7-acetoxy-8-hydroxy-2-phenylhexahydropyrano[3,2-d][1,3]dioxine-6-carboxylate: To a solution of (2S,4aR,6R,7S,8S,8aS)-methyl-7-acetoxy-2-phenyl-8-(((trifluoromethyl)sulfonyl)oxy)hexahydropyrano[3,2-d][1,3]dioxine-6-carboxylate (32 g, 66.1 mmol) in DMF (320 mL), was added tetrabutylammonium nitrate (50.3 g, 165 mmol) and the mixture was degased twice with argon. The mixture was heated at 50° C. for 6 h. Then the reaction mixture was diluted with EtOAc (500 mL), washed with water (4×200 mL), dried over sodium sulfate and concentrated under reduced pressure. The residue was purified via silica gel chromatography (60-100% EtOAc in n-hexane) to yield (2S,4aR,6R,7R,8R,8aR)-methyl-7-acetoxy-8-hydroxy-2-phenylhexahydropyrano[3,2-d][1,3]dioxine-6-carboxylate (15 g, 64%) as a yellow solid. 1H NMR (400 MHz, CHLOROFORM-d):δ 7.55-7.51 (m, 2H), 7.42-7.36 (m, 3H), 5.55 (s, 1H), 5.39 (dd, J=10.3, 2.8 Hz, 1H), 4.45 (d, J=10.3 Hz, 1H), 4.37 (dd, J=12.8, 1.5 Hz, 1H), 4.23 (t, J=3.1 Hz, 1H), 4.16-4.13 (m, 1H), 4.05 (dd, J=12.8, 2.0 Hz, 1H), 3.79 (d, J=1.5 Hz, 1H), 3.75 (s, 3H), 2.10 (s, 3H).

Step 5: Synthesis of (2S,4aR,6R,7S,8R,8aS)-methyl-7-acetoxy-2-phenyl-8-(((trifluoromethyl)sulfonyl)oxy)hexahydropyrano[3,2-d][1,3]dioxine-6-carboxylate: To a solution of (2S,4aR,6R,7R,8R,8aR)-methyl 7-acetoxy-8-hydroxy-2-phenylhexahydropyrano[3,2-d][1,3]dioxine-6-carboxylate (2.3 g, 6.53 mmol) in DCM (20 mL) was added pyridine (2.112 mL, 26.1 mmol) and the mixture was cooled to −15° C. Triflic anhydride (1.654 mL, 9.79 mmol) was added dropwise under argon and the mixture was stirred for 1 h at −15° C. The reaction mixture was allowed to warm to room temperature and was stirred for 2 h. The reaction mixture was diluted with DCM (200 mL), washed with aq. 0.7N HCl (50 mL), aq. NaHCO$_3$ (2×50 mL), brine solution and dried over sodium sulfate. The solvent was removed under reduced pressure and the residue was purified via silica gel chromatography (30-80% EtOAc in n-hexane) to yield (2S,4aR,6R,7S,8R,8aS)-methyl-7-acetoxy-2-phenyl-8-(((trifluoromethyl)sulfonyl)oxy)hexahydropyrano[3,2-d][1,3]dioxine-6-carboxylate (1.2 g, 38%) as a solid. 1H NMR (400 MHz, CHLOROFORM-d): δ 7.54-7.49 (m, 2H), 7.43-7.38 (m, 3H), 5.60 (s, 1H), 5.54 (dd, J=10.5, 3.0 Hz, 1H), 5.28 (t, J=3.3 Hz, 1H), 4.43-4.37 (m, 2H), 4.30 (dd, J=3.5, 1.0 Hz, 1H), 4.11 (dd, J=12.8, 1.5 Hz, 1H), 3.80 (s, 3H), 3.78 (d, J=1.5 Hz, 1H), 2.10 (s, 3H).

Step 6: Synthesis of (2S,4aR,6R,7R,8S,8aR)-methyl-7-acetoxy-8-azido-2-phenylhexahydropyrano[3,2-d][1,3]dioxine-6-carboxylate: To a solution of (2S,4aR,6R,7S,8R,8aS)-methyl-7-acetoxy-2-phenyl-8-(((trifluoromethyl)sulfonyl)oxy)hexahydropyrano[3,2-d][1,3]dioxine-6-carboxylate (1.8 g, 41.3 mmol) in DMF (18 mL) was added tetrabutyl ammonium azide (3.17 g, 11.15 mmol) in a single portion. The mixture was degased with Ar and heated at 50° C. for 5 h. The reaction mixture was diluted with EtOAc (200 mL), washed with water (3×100 mL), dried over sodium sulfate and concentrated. The residue was purified via silica gel chromatography (50-90% EtOAc in n-hexane) to yield (2S,4aR,6R,7R,8S,8aR)-methyl-7-acetoxy-8-azido-2-phenylhexahydropyrano[3,2-d][1,3]dioxine-6-carboxylate (1.2 g, 86%) as an off-white solid. LC-MS, [M+18]$^+$ =395.2, (Method C: t$_R$=2.37 min). 1H NMR (300 MHz, CHLOROFORM-d): δ 7.53 (dd, J=7.2, 2.3 Hz, 2H), 7.42-7.33 (m, 3H), 5.60 (s, 1H), 5.58-5.51 (m, 1H), 4.40-4.33 (m, 2H), 4.06 (dd, J=12.7, 1.7 Hz, 1H), 3.99 (d, J=9.8 Hz, 1H), 3.76 (s, 3H), 3.50 (s, 1H), 3.41 (dd, J=10.4, 3.2 Hz, 1H), 2.11 (s, 3H).

Step 7: Synthesis of methyl (2S,4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate: To a solution of methyl (2S,4aR,6R,7R,8S,8aR)-7-acetoxy-8-azido-2-phenylhexahydropyrano[3,2-d][1,3]dioxine-6-carboxylate (1.4 g, 3.71 mmol) in DMF (40 mL) and water (8 mL) was added sequentially 5-ethynyl-1,2,3-trifluorobenzene (1.737 g, 11.13 mmol), sodium ascorbate (0.808 g, 4.08 mmol) and copper(II) sulfate pentahydrate (0.834 g, 3.34 mmol). The reaction mixture was degassed with nitrogen for 10 min and heated at 80° C. under nitrogen for 1 h. Then the mixture was diluted with water and filtered. The solids were suspended in DCM, sonicated for 5 min and filtered. The filtrate was concentrated under reduced pressure to afford methyl (2S,4aR,6R,7R,8S,8aR)-7-acetoxy-2-phenyl-8-(4-(3,4,5-trifluorophenyl)-1H-1,2,3-triazol-1-yl) hexahydropyrano[3,2-d][1,3]dioxine-6-carboxylate (1.6 g, 80%) as a white solid. LC-MS, [M+H]$^+$=534.1, (Method C: t$_R$=3.10 min). 1H NMR (400 MHz, DMSO-d6): δ 8.82 (s, 1H), 7.71-7.93 (m, 2H), 7.29-7.47 (m, 5H), 5.65-5.74 (m, 2H), 5.61 (s, 1H), 4.58 (d, J=2.01 Hz, 1H), 4.48-4.51 (m, 1H), 4.12-4.23 (m, 2H), 4.02 (s, 1H), 3.66 (s, 3H,) 1.84 (s, 3H).

Step 8: Synthesis of (2S,4aR,6R,7R,8R,8aR)-7-hydroxy-2-phenyl-8-(4-(3,4,5-trifluorophenyl)-1H-1,2,3-triazol-1-yl) hexahydropyrano[3,2-d][1,3]dioxine-6-carboxamide: To methyl (2S,4aR,6R,7R,8S,8aR)-7-acetoxy-2-phenyl-8-(4-(3,4,5-trifluorophenyl)-1H-1,2,3-triazol-1-yl) hexahydropyrano[3,2-d][1,3]dioxine-6-carboxylate (1.6 g, 3.00 mmol) was added methanolic ammonia (7 M, 200 mL) at 0° C. The mixture was allowed to warm to rt and was stirred for 18 h. The reaction mixture was concentrated under reduced pressure to give crude residue, which was triturated with diethyl ether and filtered. The solid was washed with diethyl ether and dried to afford (2S,4aR,6R,7R,8R,8aR)-7-hydroxy-2-phenyl-8-(4-(3,4,5-trifluorophenyl)-1H-1,2,3-triazol-1-yl)

hexahydropyrano[3,2-d][1,3]dioxine-6-carboxamide (1.4 g, 97%) as a white solid. LC-MS, [M+H]⁺=477.2, (Method C: $t_R$=2.18). 1H NMR (400 MHz, METHANOL-d4) δ=8.53 (s, 1H), 7.63-7.53 (m, 2H), 7.46-7.27 (m, 6H), 5.57 (s, 1H), 5.13 (dd, J=10.5, 3.5 Hz, 1H), 4.62-4.53 (m, 2H), 4.39-4.31 (m, 1H), 4.21 (dd, J=12.5, 1.5 Hz, 1H), 4.05 (d, J=9.5 Hz, 1H), 3.93 (d, J=1.0 Hz, 1H).

Step 9: Synthesis of (2S,4aR,6R,7R,8R,8aR)-N-((E)-(dimethylamino)methylene)-7-hydroxy-2-phenyl-8-(4-(3,4,5-trifluorophenyl)-1H-1,2,3-triazol-1-yl)hexahydropyrano[3,2-d][1,3]dioxine-6-carboxamide: To a solution of (2S,4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxamide (1.4 g, 2.94 mmol) in dioxane (40 mL) was added DMF-DMA (0.590 mL, 4.41 mmol) and the mixture was heated at 50° C. for 4 h. The solvent was removed under reduced pressure. The residue was triturated with diethyl ether and filtered. The solid obtained was washed with excess diethyl ether and dried to afford (2S,4aR,6R,7R,8R,8aR)-N-((E)-(dimethylamino)methylene)-7-hydroxy-2-phenyl-8-(4-(3,4,5-trifluorophenyl)-1H-1,2,3-triazol-1-yl)hexahydropyrano[3,2-d][1,3]dioxine-6-carboxamide (1.4 g, 85%) as a white solid. LC-MS, [M+H]⁺=532.2, (Method E: $t_R$=1.23).

Step 10: Synthesis of (2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To a stirred solution of (2S,4aR,6R,7R,8R,8aR)-N-((E)-(dimethylamino)methylene)-7-hydroxy-2-phenyl-8-(4-(3,4,5-trifluorophenyl)-1H-1,2,3-triazol-1-yl)hexahydropyrano[3,2-d][1,3]dioxine-6-carboxamide (0.4 g, 0.753 mmol) in DMF (2 mL) was added (3-chlorophenyl)hydrazine hydrochloride (0.270 g, 1.505 mmol) and acetic acid (0.517 mL, 9.03 mmol) and the mixture was heated at 80° C. for 3 h. The mixture was cooled to rt, diluted with ice cold water and stirred for 10 min. The solids formed were filtered and purified via silica gel chromatography (0-3% of MeOH in chloroform) to afford (2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.2 g, 43%) as a yellow solid. LC-MS, [M+H]⁺=611.0, (Method C: $t_R$=3.0 min). 1H NMR (300 MHz, DMSO-d6): δ 8.89 (s, 1H), 8.29 (s, 1H), 7.95-7.93 (m, 1H), 7.83 (dd, J=9.3, 6.8 Hz, 2H), 7.73-7.71 (m, J=1.0 Hz, 1H), 7.67-7.62 (m, 4H), 7.39-7.32 (m, 3H), 5.64 (d, J=6.5 Hz, 1H), 5.57 (s, 1H), 5.32-5.26 (m, 1H), 5.02-5.00 (m, 1H), 4.76 (d, J=9.0 Hz, 1H), 4.50 (d, J=3.5 Hz, 1H), 4.19-4.04 (m, 3H).

Step 11: To a solution of (4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.025 g, 0.041 mmol) in DCM (1 mL) was added TFA (0.2 mL, 2.60 mmol) at 0° C. and the mixture was stirred for 1 h. Then the reaction mixture was concentrated under reduced pressure and purified by HPLC (Method A) to afford (2S,3R,4R,5R,6R)-2-(1-(3-chlorophenyl)-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol (Example 19) (15 mg, 68%) as a white solid. LC-MS, [M+H]⁺=523.1, (Method A: $t_R$=1.41 and Method B: $t_R$=1.41). 1H NMR (400 MHz, METHANOL-d4): δ 8.58 (s, 1H), 8.21 (s, 1H), 7.78-7.82 (m, 1H), 7.68-7.73 (m, 1H), 7.63-7.68 (m, 2H), 7.59-7.62 (m, 2H), 4.91-5.04 (m, 2H), 4.60 (dd, J=14.6, 8.5 Hz, 1H), 4.16 (d, J=2.0 Hz, 1H), 3.89-3.95 (m, 1H), 3.78-3.85 (m, 1H), 3.69-3.76 (m, 1H). hGal3 IC₅₀=0.12 uM.

The Examples in the table below were prepared in an analogous fashion to Example 19, substituting (3-chlorophenyl)hydrazine hydrochloride with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 20 | 0.708 | 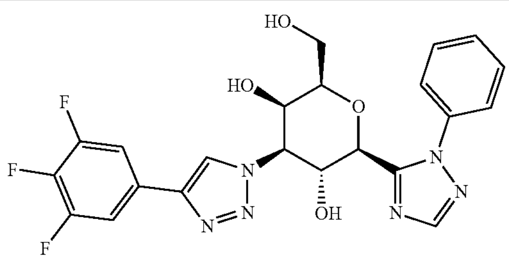 [SMILES: OC[C@H]1O[C@@H](c2ncnn2-c2ccccc2)[C@H](O)[C@@H](n2cc(-c3cc(F)c(F)c(F)c3)nn2)[C@H]1O] | 1.255 | 489.2 | A | 1H NMR (400 MHz, METHANOL-d4) δ 8.61 (s, 1H), 8.22 (s, 1H), 7.79-7.71 (m, 2H), 7.71-7.53 (m, 5H), 5.02 (dd, J = 10.5, 9.0 Hz, 1H), 4.97-4.90 (m, 1H), 4.60 (d, J = 9.0 Hz, 1H), 4.16 (d, J = 2.0 Hz, 1H), 3.94-3.87 (m, 1H), 3.86-3.77 (m, 1H), 3.73 (dd, J = 11.5, 4.5 Hz, 1H). |
| 21 | 0.079 | 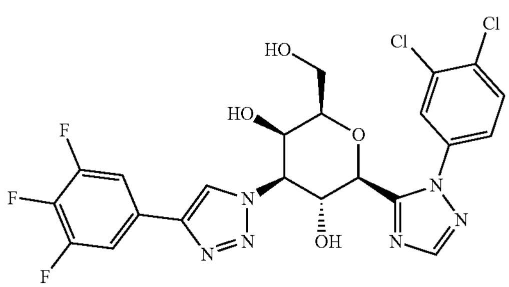 [SMILES: OC[C@H]1O[C@@H](c2ncnn2-c2ccc(Cl)c(Cl)c2)[C@H](O)[C@@H](n2cc(-c3cc(F)c(F)c(F)c3)nn2)[C@H]1O] | 2.188 | 559 | C | 1H NMR (400 MHz, METHANOL-d4) δ 8.60 (s, 1H), 8.23 (s, 1H), 7.81 (t, J = 2.3 Hz, 1H), 7.77-7.56 (m, 4H), 5.08-4.92 (m, 2H), 4.62 (d, 7 = 8.5 Hz, 1H), 4.17 (d, J = 2.0 Hz, 1H), 3.98-3.88 (m, 1H), 3.83 (dd, J = 11.5, 7.0 Hz, 1H), 3.74 (dd, J = 11.5, 4.5 Hz, 1H) |

| Ex | hGal3 IC50, uM | Structure | LCMS $t_R$ (min) | M + H | Method | 1H NMR |
|---|---|---|---|---|---|---|
| 22 | 1.110 | 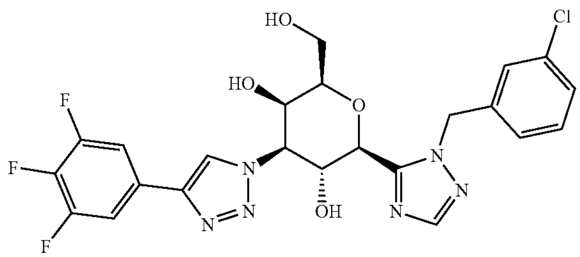 [SMILES: OC[C@H]1O[C@@H](c2ncnn2Cc2cccc(Cl)c2)[C@H](O)[C@@H](n2cc(-c3cc(F)c(F)c(F)c3)nn2)[C@H]1O] | 1.982 | 537.2 | C | 1H NMR (400 MHz, METHANOL-d4) δ 8.51 (s, 1H), 8.02 (s, 1H), 7.68-7.61 (m, 2H), 7.42 (s, 1H), 7.38-7.29 (m, 3H), 5.61 (s, 2H), 5.00 (dd, J = 10.5, 2.5 Hz, 1H), 4.87 (d, J = 9.5 Hz, 1H), 4.81-4.74 (m, 1H), 4.21 (d, J = 2.0 Hz, 1H), 4.01-3.94 (m, 1H), 3.79-3.69 (m, 2H) |
| 23 | 0.15 | 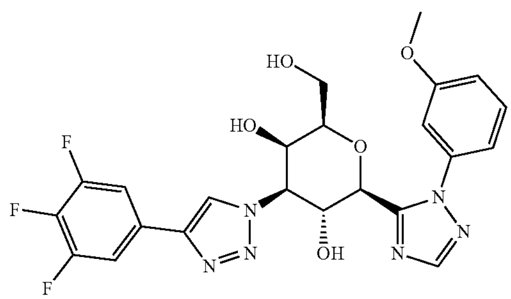 [SMILES: COc1cccc(-n2ncnc2[C@@H]2O[C@H](CO)[C@H](O)[C@H](n3cc(-c4cc(F)c(F)c(F)c4)nn3)[C@H]2O)c1] | 1.744 | 519.2 | A | 1H NMR (400 MHz, METHANOL-d4) δ 8.59 (s, 1H), 8.20 (s, 1H), 7.69-7.62 (m, 2H), 7.49-7.47 (m, 1H), 7.31-7.24 (m, 2H), 7.16-7.11 (m, 1H), 5.04-4.91 (m, 2H), 4.64 (d, J = 9.0 Hz, 1H), 4.15 (d, J = 2.0 Hz, 1H), 3.93-3.87 (m, 4H), 3.84-3.77 (m, 1H), 3.75-3.69 (m, 1H). |
| 24 | 0.48 | 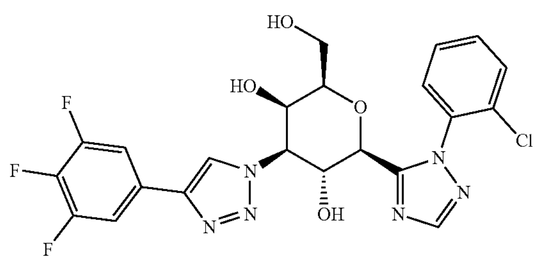 [SMILES: OC[C@H]1O[C@@H](c2ncnn2-c2ccccc2Cl)[C@H](O)[C@@H](n2cc(-c3cc(F)c(F)c(F)c3)nn2)[C@H]1O] | 1.377 | 523.1 | A | 1H NMR (400 MHz, METHANOL-d4) δ 8.58 (s, 1H), 8.27 (s, 1H), 7.74-7.62 (m, 5H), 7.59-7.54 (m, 1H), 4.94-4.88 (m, 2H), 4.45-4.36 (m, 1H), 4.13 (s, 1H), 3.82-3.64 (m, 3H) |
| 25 | 0.56 | 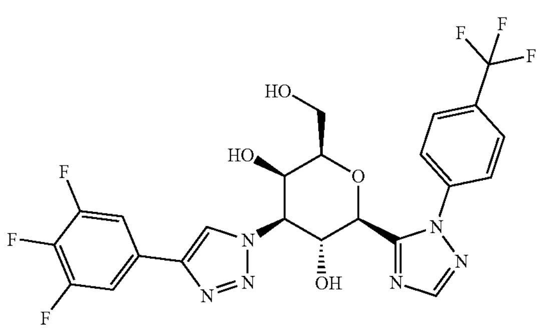 [SMILES: OC[C@H]1O[C@@H](c2ncnn2-c2ccc(C(F)(F)F)cc2)[C@H](O)[C@@H](n2cc(-c3cc(F)c(F)c(F)c3)nn2)[C@H]1O] | 1.603 | 557.2 | A | 1H NMR (400 MHz, METHANOL-d4) δ 8.50 (s, 1H), 8.15 (s, 1H), 7.92-7.82 (m, 4H), 7.56 (dd, J = 9.0, 6.6 Hz, 2H), 4.97-4.79 (m, 2H), 4.52 (d, J = 8.8 Hz, 1H), 4.05 (d, J = 2.2 Hz, 1H), 3.84 (dd, J = 7.6, 5.1 Hz, 1H), 3.72 (dd, J = 11.7, 7.6 Hz, 1H), 3.62 (dd, J = 11.6, 4.3 Hz, 1H) |
| 26 | 0.23 | 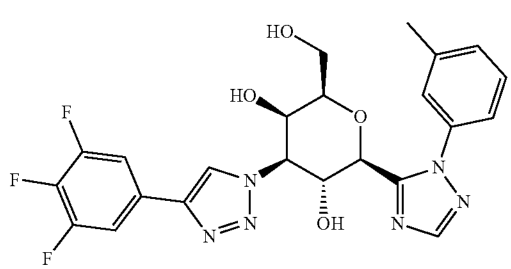 [SMILES: Cc1cccc(-n2ncnc2[C@@H]2O[C@H](CO)[C@H](O)[C@H](n3cc(-c4cc(F)c(F)c(F)c4)nn3)[C@H]2O)c1] | 1.436 | 503.2 | A | 1H NMR (400 MHz, METHANOL-d4) δ 8.48 (s, 1H), 8.09 (s, 1H), 7.56 (dd, J = 8.8, 6.8 Hz, 2H), 7.47-7.43 (m, 1H), 7.41-7.37 (m, 2H), 7.32-7.28 (m, 1H), 4.90 (dd, J = 10.5, 9.0 Hz, 1H), 4.85-4.79 (m, 1H), 4.46 (d, J = 9.0 Hz, 1H), 4.04 (d, J = 2.0 Hz, 1H), 3.81-3.76 (m, 1H), 3.72 (dd, J = 11.5, 7.5 Hz, 1H), 3.62 (dd, J = 11.5, |

-continued

| Ex | hGal3 IC50, uM | Structure | LCMS $t_R$ (min) | M + H | Method | 1H NMR |
|---|---|---|---|---|---|---|
| | | | | | | 4.5 Hz, 1H), 2.47 (s, 3H) |
| 27 | 0.18 | 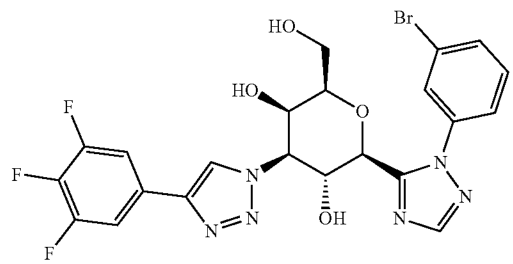 | 1.506 | 568.1 | A | 1H NMR (400 MHz, METHANOL-d4) δ 8.60 (s, 1H), 8.23 (s, 1H), 7.95 (t, J = 2.0 Hz, 1H), 7.80-7.74 (m, 2H), 7.68 (dd, J = 8.8, 6.8 Hz, 2H), 7.60-7.52 (m, 1H), 5.06-4.93 (m, 2H), 4.61 (d, J = 9.0 Hz, 1H), 4.20-4.15(m, 1H), 3.97-3.91 (m, 1H), 3.84 11.5, (dd, J = 7.0 Hz, 1H), 3.75 (dd, J = 11.8, 4.8 Hz, 1H) |
| 28 | 1.47 | 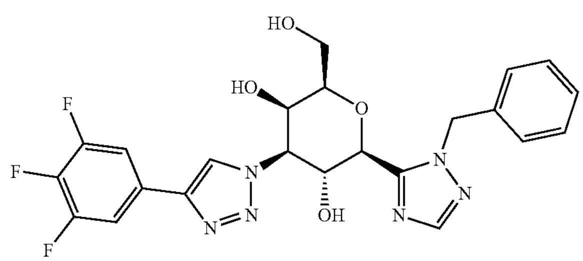 [SMILES: OC[C@H]1O[C@@H](c2ncnn2Cc2ccccc2)[C@H](O)[C@@H](n2cc(-c3cc(F)c(F)c(F)c3)nn2)[C@H]1O] | 1.531 | 503.2 | A | 1H NMR (400 MHz, METHANOL-d4) δ 8.51 (s, 1H), 8.03 (s, 1H), 7.66 (dd, J = 9.0, 6.5 Hz, 2H), 7.41-7.32 (m, 5H), 5.63 (s, 2H), 5.00 (dd, J = 10.3, 2.8 Hz, 1H), 4.87 (br. s., 2H), 4.83-4.81 (m, 1H), 4.57 (br. s., 1H), 4.21 (d, J = 3.0 Hz, 1H), 3.97 (t, J = 6.3 Hz, 1H), 3.77-3.72 (m, 2H), 3.38-3.35 (m, 1H) |
| 29 | 1.56 | 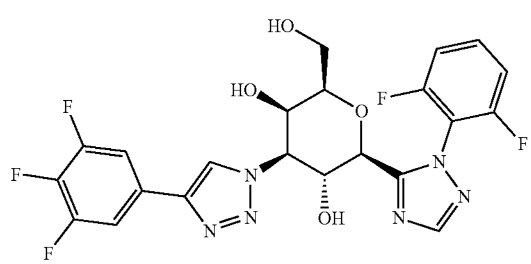 [SMILES: OC[C@H]1O[C@@H](c2ncnn2-c2c(F)cccc2F)[C@H](O)[C@@H](n2cc(-c3cc(F)c(F)c(F)c3)nn2)[C@H]1O] | 1.367 | 525.1 | A | 1H NMR (400 MHz, METHANOL-d4) δ 8.54 (s, 1H), 8.30 (s, 1H), 7.76-7.60 (m, 3H), 7.37-7.23 (m, 2H), 4.90 (dd, J = 11.0, 3.0 Hz, 1H), 4.78 (dd, J = 10.8, 9.3 Hz, 1H),4.56-4.48 (m, 1H), 4.14 (d, J = 2.5 Hz, 1H), 3.82-3.75 (m, 1H), 3.69-3.57 (m, 2H) |
| 30 | 0.59 | 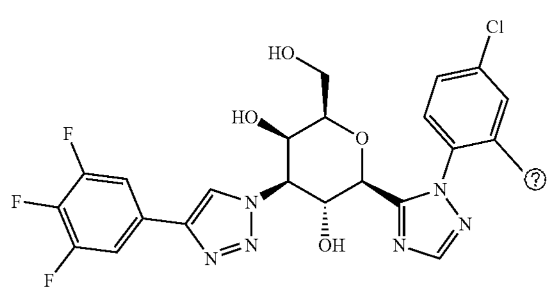 [SMILES: Cc1cc(Cl)ccc1-n1ncnc1[C@@H]1O[C@H](CO)[C@H](O)[C@H](n2cc(-c3cc(F)c(F)c(F)c3)nn2)[C@H]1O] | 1.548 | 559.1 | A | 1H NMR (400 MHz, METHANOL-d4) δ 8.45 (s, 1H), 8.15 (s, 1H), 7.70 (d J = 2.5 Hz, 1H), 7.59-7.50 (m, 3H), 7.50-7.45 (m, 1H), 4.80-4.75 (m, 1H), 4.46-4.43 (m, 1H), 4.31 (d, J = 8.5 Hz,1H), 4.01 (d, J = 1.5 Hz, 1H), 3.68-3.63 (m, 1H), 3.60-3.53 (m, 2H) |

-continued

| Ex | hGal3 IC50, uM | Structure | LCMS t_R (min) | M + H | Method | 1H NMR |
|---|---|---|---|---|---|---|
| 31 | 1.04 | 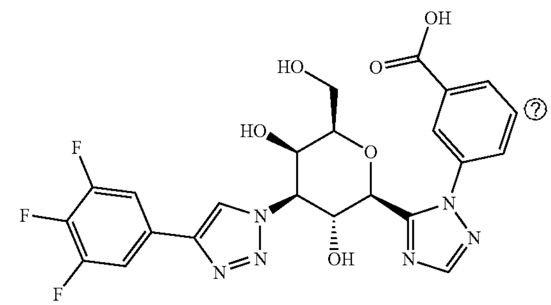 [SMILES: O=C(O)c1cccc(-n2ncnc2[C@@H]2O[C@H](CO)[C@H](O)[C@H](n3cc(-c4cc(F)c(F)c(F)c4)nn3)[C@H]2O)c1] | 0.943 | 533.2 | A | 1H NMR (400 MHz, METHANOL-d4) δ 8.49 (s, 1H), 8.23 (t, J = 1.8 Hz, 1H), 8.14-8.09 (m, 2H), 7.86 (dd, J = 7.5, 1.6 Hz, 1H), 7.66-7.52 (m, 3H), 4.95-4.80 (m, 2H), 4.51 (d, J = 9.0 Hz, 1H), 4.07 (d, J = 2.7 Hz, 1H), 3.85-3.80 (m, 1H), 3.77-3.71 (m, 1H), 3.65 (dd, J = 11.5, 5.1 Hz, 1H) |
| 32 | 0.59 | 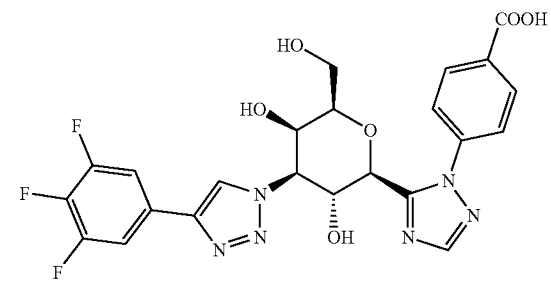 [SMILES: O=C(O)c1ccc(-n2ncnc2[C@@H]2O[C@H](CO)[C@H](O)[C@H](n3cc(-c4cc(F)c(F)c(F)c4)nn3)[C@H]2O)cc1] | 0.921 | 533.2 | A | 1H NMR (400 MHz, METHANOL-d4) δ 8.50 (s, 1H), 8.19-8.12 (m, 2H), 7.81-7.72 (m, 2H), 7.57 (dd, J = 9.0, 6.6 Hz, 2H), 4.98-4.82 (m, 2H), 4.53 (d, J = 9.0 Hz, 1H), 4.05 (d, J = 2.2 Hz, 1H), 3.83 (dd, J = 8.1, 4.4 Hz, 1H), 3.72 (dd, J = 11.7, 7.3 Hz, 1H), 3.63 (dd, J = 11.6, 4.5 Hz, 1H) |
| 33 | 0.79 | 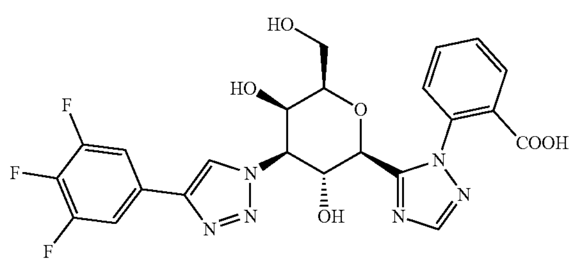 [SMILES: O=C(O)c1ccccc1-n1ncnc1[C@@H]1O[C@H](CO)[C@H](O)[C@H](n2cc(-c3cc(F)c(F)c(F)c3)nn2)[C@H]1O] | 0.921 | 533.2 | A | 1H NMR (400 MHz, METHANOL-d4) δ 8.50 (s, 1H), 8.19-8.12 (m, 2H), 7.81-7.72 (m, 2H), 7.57 (dd, J = 9.0, 6.6 Hz, 2H), 4.98-4.82 (m, 2H), 4.53 (d, J = 9.0 Hz, 1H), 4.05 (d, J = 2.2 Hz, 1H), 3.83 (dd, J = 8.1, 4.4 Hz, 1H), 3.72 (dd, J = 11.7, 7.3 Hz, 1H), 3.63 (dd, J = 11.6, 4.5 Hz, 1H) |
| 34 | 1.09 | 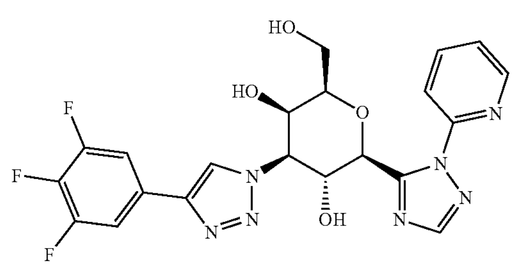 [SMILES: OC[C@H]1O[C@@H](c2ncnn2-c2ccccn2)[C@H](O)[C@@H](n2cc(-c3cc(F)c(F)c(F)c3)nn2)[C@H]1O] | 0.936 | 533.2 | A | 1H NMR (400 MHz, METHANOL-d4) δ 8.46 (s, 1H), 8.13 (s, 1H), 7.84-7.79 (m, 1H), 7.67-7.52 (m, 5H), 4.83-4.77 (m, 2H), 4.68-4.63 (m, 1H), 4.13 (d, J = 2.5 Hz, 1H), 3.88-3.78 (m, 2H), 3.75-3.69 (m, 1H) |
| 35 | 0.70 | 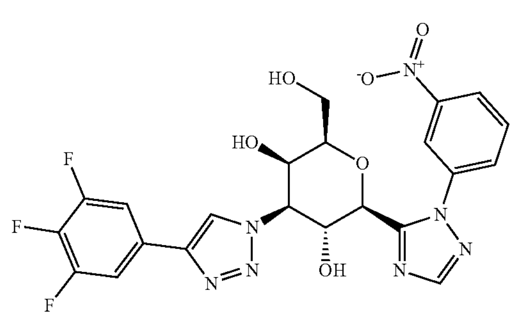 | 1.238 | 490.2 | A | 1H NMR (400 MHz, METHANOL-d4) δ 8.66-8.59 (m, 2H), 8.22 (s, 1H), 8.08 (td, J = 7.8, 2.0 Hz, 1H), 7.95-7.90 (m, 1H), 7.72-7.64 (m, 2H), 7.57-7.50 (m, 1H), 5.66 (d, J = 8.5 Hz, 1H), 5.04-4.93 (m, 2H), 4.21 (d, J = 1.5 Hz, 1H), 4.00-3.94 (m, 1H), 3.71 (d, J = 6.0 Hz, 2H) |

-continued

| Ex | hGal3 IC50, uM | Structure | LCMS t_R (min) | M + H | Method | 1H NMR |
|---|---|---|---|---|---|---|
| 36 | 0.22 | 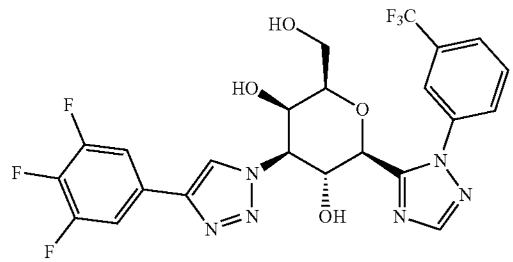 [SMILES: OC[C@H]1O[C@@H](c2ncnn2-c2cccc(C(F)(F)F)c2)[C@H](O)[C@@H](n2cc(-c3cc(F)c(F)c(F)c3)nn2)[C@H]1O] | 1.581 | 557.2 | A | 1H NMR (400 MHz, METHANOL-d4) δ 8.48 (s, 1H), 8.14 (s, 1H), 7.99-7.93 (m, 2H), 7.81 (d, J = 7.6 Hz, 1H), 7.74 (t, J = 7.7 Hz, 1H), 7.56 (dd, J = 9.0, 6.6 Hz, 2H), 4.95-4.80 (m, 2H), 4.50 (d, J = 9.0 Hz, 1H), 4.06 (d, J = 2.0 1H), 3.81 (dd, J = 6.6, 5.4 Hz, 1H), 3.71 (dd, J = 11.5, 7.1 Hz, 1H), 3.62 (dd, J = 11.6, 4.8 Hz, 1H) |
| 37 | 0.21 | 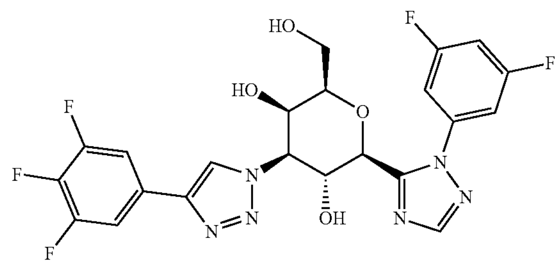 [SMILES: OC[C@H]1O[C@@H](c2ncnn2-c2cc(F)cc(F)c2)[C@H](O)[C@@H](n2cc(-c3cc(F)c(F)c(F)c3)nn2)[C@H]1O] | 1.446 | 525.1 | A | 1H NMR (400 MHz, METHANOL-d4) δ 8.49 (s, 1H), 8.11 (s, 1H), 7.59-7.52 (m, 2H), 7.38 (dd, J = 7.8, 2.3 Hz, 2H), 7.17-7.09 (m, 1H), 4.95-4.85 (m, 2H), 4.57 (d, J = 8.5 Hz, 1H), 4.06 (dd, J = 2.5, 1.0 Hz, 1H), 3.88-3.83 (m, 1H), 3.75-3.68 (m, 1H), 3.62 (dd, J = 11.5, 4.5 Hz, 1H) |
| 38 | 0.39 | 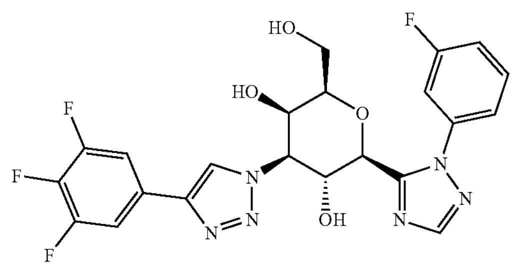 [SMILES: OC[C@H]1O[C@@H](c2ncnn2-c2cccc(F)c2)[C@H](O)[C@@H](n2cc(-c3cc(F)c(F)c(F)c3)nn2)[C@H]1O] | 1.38 | 507.1 | A | 1H NMR (400 MHz, METHANOL-d4) δ 8.49 (s, 1H), 8.11 (s, 1H), 7.61-7.43 (m, 5H), 7.29-7.21 (m, 1H), 4.95-4.81 (m, 2H), 4.52 (d, J = 9.0 Hz, 1H), 4.05 (d, J = 2.0 Hz, 1H), 3.82 (dd, J = 7.0, 4.5 Hz, 1H), 3.71 (dd, J = 11.5, 7.0 Hz, 1H), 3.62 (dd, J = 11.5, 4.5 Hz, 1H) |
| 39 | 0.55 | 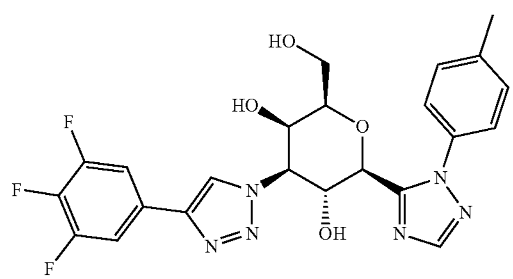 [SMILES: Cc1ccc(-n2ncnc2[C@@H]2O[C@H](CO)[C@H](O)[C@H](n3cc(-c4cc(F)c(F)c(F)c4)nn3)[C@H]2O)cc1] | 1.435 | 503.2 | A | 1H NMR (400 MHz, METHANOL-d4) δ 8.61 (s, 1H), 8.20 (s, 1H), 7.67 (dd, J = 9.0, 6.5 Hz, 2H), 7.62-7.57 (m, 2H), 7.47-7.41 (m, J = 8.0 Hz, 2H), 5.04-4.90 (m, 2H), 4.58 (d, J = 9.0 Hz, 1H), 4.16 (d, J = 2.5 Hz, 1H), 3.91-3.86 (m, 1H), 3.86-3.79 (m, 1H), 3.73 (dd, J = 11.5, 4.5 Hz, 1H), 2.48 (s, 3H) |
| 40 | 1.02 | 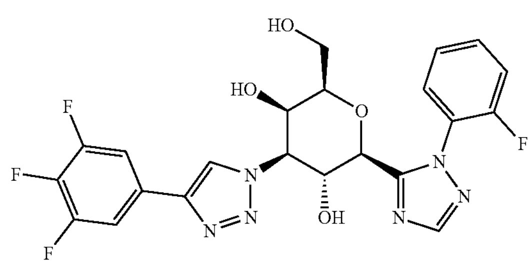 [SMILES: OC[C@H]1O[C@@H](c2ncnn2-c2ccccc2F)[C@H](O)[C@@H](n2cc(-c3cc(F)c(F)c(F)c3)nn2)[C@H]1O] | 1.329 | 507.1 | A | 1H NMR (400 MHz, METHANOL-d4) δ 8.46 (s, 1H), 8.15 (s, 1H), 7.61-7.51 (m, 4H), 7.38-7.27 (m, 2H), 4.81-4.75 (m, 2H), 4.41-4.35 (m, 1H), 4.02 (s, 1H), 3.69 (t, J = 6.0 Hz, 1H), 3.64-3.52 (m, 2H) |

| Ex | hGal3 IC50, uM | Structure | LCMS $t_R$ (min) | M + H | Method | 1H NMR |
|---|---|---|---|---|---|---|
| 41 | 0.11 | 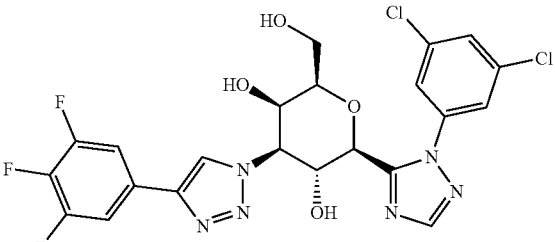 | 1.646 | 559.1 | A | 1H NMR (400 MHz, METHANOL-d4) δ 8.48 (s, 1H), 8.12 (s, 1H), 7.71(d, J = 2.0 Hz, 2H), 7.61-7.53 (m,3H), 4.92- 4.86 (m, 3H), 4.53 (d, J = 8.8 Hz, 1H), 4.06 (d, J = 1.5 Hz, 1H), 3.86 (dd, J = 6.7, 4.3 Hz, 1H), 3.72 (dd, J = 11.7, 7.1 Hz, 1H), 3.63 (dd, J = 11.7, 4.6 Hz, 1H) |
| 42 | 0.46 | 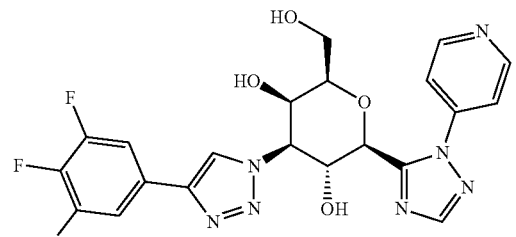 | 1.145 | 490.2 | A | 1H NMR (400 MHz, METHANOL-d4) δ 8.73-8.67 (m, 2H), 8.50 (s, 1H), 8.16 (s, 1H), 7.85-7.80 (m, 2H), 7.56 (dd, J = 9.0, 6.5 Hz, 2H), 5.02-4.86 (m, 3H), 4.62 (d, J = 9.0 Hz, 1H), 4.08 (d, J = 3.0 Hz, 1H), 3.95-3.89 (m, 1H), 3.73 (dd, J = 11.5, 7.5 Hz, 1H), 3.64 (dd, J = 11.8, 4.3 Hz, 1H) |
| 43 | 0.61 | 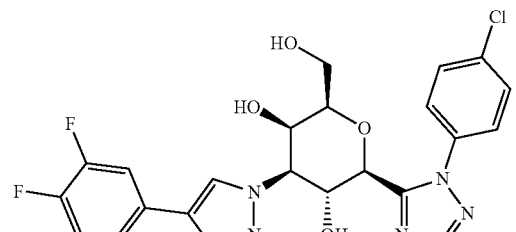 | 1.484 | 523.1 | A | 1H NMR (400 MHz, METHANOL-d4) δ 8.48 (s, 1H), 8.10 (s, 1H), 7.66-7.61 (m, 2H), 7.58-7.51 (m, 4H), 4.93-4.81 (m, 2H), 4.47 (d, J = 8.5 Hz, 1H), 4.06-4.03 (m, 1H), 3.83-3.77 (m, 1H), 3.71 (dd, J = 11.5, 7.0 Hz, 1H), 3.61 (dd, J = 12.0, 4.5 Hz, 1H) |
| 44 | 4.46 | 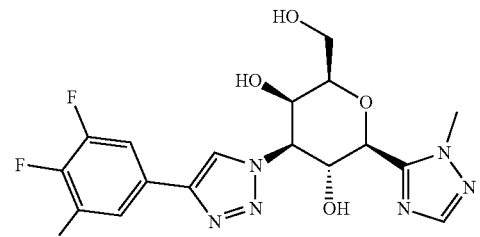 | 1.054 | 427.2 | A | 1H NMR (400 MHz, METHANOL-d4) δ 8.49 (s, 1H), 7.85 (s, 1H), 7.55 (dd, J = 9.0, 6.5 Hz, 2H), 4.91 (dd, J = 10.5, 3.0 Hz, 1H), 4.75 (br. s., 1H), 4.69-4.59 (m, 1H), 4.12-4.08 (m, 1H), 3.94 (s, 3H), 3.92-3.88 (m, 1H), 3.74-3.60 (m, 2H) |
| 45 | 0.06 | 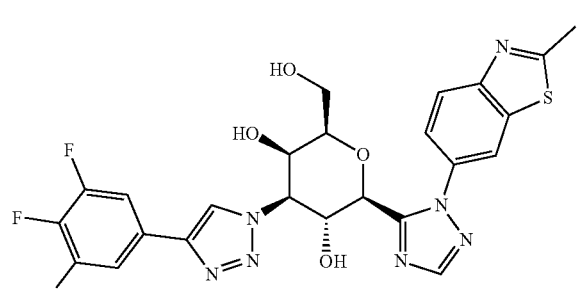 | 1.778 | 560.2 | A | 1H NMR (400 MHz, METHANOL-d4) δ 8.59 (s, 1H), 8.42 (d, J = 2.5 Hz, 1H), 8.25 (s, 1H), 8.10 (d, J = 8.5 Hz, 1H), 7.84 (dd, J = 8.8, 2.3 Hz, 1H), 7.70-7.64 (m, 2H), 5.03 (dd, J = 10.8, 9.3 Hz, 1H), 4.94 (dd, J = 10.8, 2.8 Hz, 1H), 4.62 (d, J = 9.0 Hz, 1H), 4.15 (d, J = 2.5 Hz, 1H), 3.94-3.89 (m, 1H), 3.88-3.81 (m, 1H), 3.74 (dd, J = 11.5, 4.0 Hz, 1H), 2.92 (s, 3H) |

-continued

| Ex | hGal3 IC50, uM | Structure | LCMS $t_R$ (min) | M + H | Method | 1H NMR |
|---|---|---|---|---|---|---|
| 46 | 0.04 | 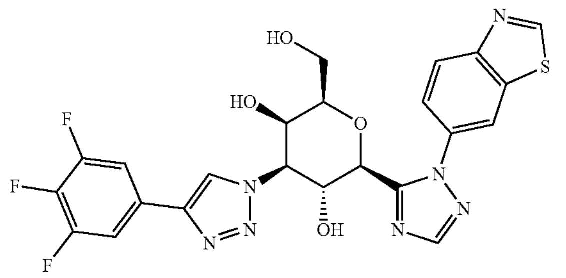 [SMILES: OC[C@H]1O[C@@H](c2ncnn2-c2ccc3ncsc3c2)[C@H](O)[C@@H](n2cc(-c3cc(F)c(F)c(F)c3)nn2)[C@H]1O] | 1.282 | 546.1 | A | 1H NMR (400 MHz, METHANOL-d4) δ 9.44 (s, 1H), 8.67-8.52 (m, 2H), 8.37-8.19 (m, 2H), 7.93 (dd, J = 8.8, 2.2 Hz, 1H), 7.68 (dd, J = 8.8, 6.6 Hz, 2H), 5.09-5.02 (m, 1H), 4.97 (d, J = 2.9 Hz, 1H), 4.62 (d, J = 2.9 Hz, 1H), 4.15 (d, J = 2.2 Hz, 1H), 3.98-3.89 (m, 1H), 3.89-3.80 (m, 1H), 3.78-3.69 (m, 1H) |
| 47 | 0.08 | 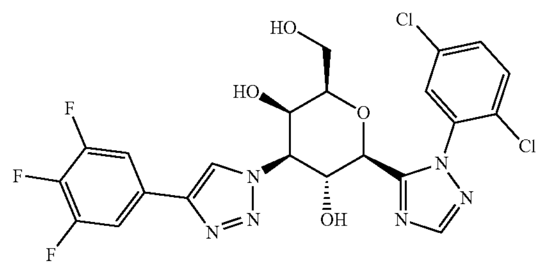 [SMILES: OC[C@H]1O[C@@H](c2ncnn2-c2cc(Cl)ccc2Cl)[C@H](O)[C@@H](n2cc(-c3cc(F)c(F)c(F)c3)nn2)[C@H]1O] | 1.525 | 559.1 | A | 1H NMR (400 MHz, METHANOL-d4) δ 8.56 (s, 1H), 8.27 (s, 1H), 7.73-7.57 (m, 4H), 4.92-4.89 (m, 1H), 4.47 (d, J = 8.8 Hz, 1H), 4.13 (s, 1H), 3.82-3.77 (m, 1H), 3.73-3.66 (m, 3H) |
| 48 | 0.11 | 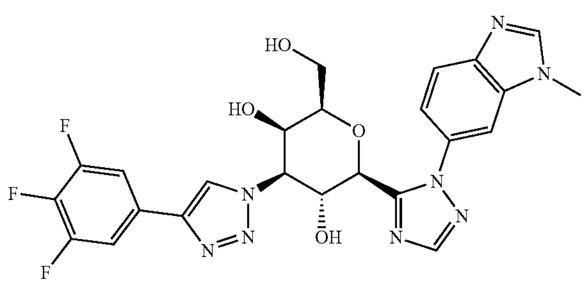 [SMILES: Cn1cnc2ccc(-n3ncnc3[C@@H]3O[C@H](CO)[C@H](O)[C@H](n4cc(-c5cc(F)c(F)c(F)c5)nn4)[C@H]3O)cc21] | 1.171 | 543.2 | A | 1H NMR (400 MHz, METHANOL-d4) δ 8.67 (s, 1H), 8.60 (s, 1H), 8.26 (s, 1H), 8.11 (d, J = 2.0 Hz, 1H), 7.95 (d, J = 8.6 Hz, 1H), 7.74 (dd, J = 8.7, 2.1 Hz, 1H), 7.67 (dd, J = 9.0, 6.6 Hz, 2H), 5.06 (dd, J = 10.8, 9.3 Hz, 1H), 4.92 (dd, J = 10.8, 2.9 Hz, 1H), 4.64 (d, J = 9.5 Hz, 1H), 4.15 (d, J = 2.2 Hz, 1H), 4.08 (s, 3H), 3.98-3.92 (m, 1H), 3.91-3.83 (m, 1H), 3.74 (dd, J = 11.5, 3.9 Hz, 1H); |
| 49 | 0.05 | 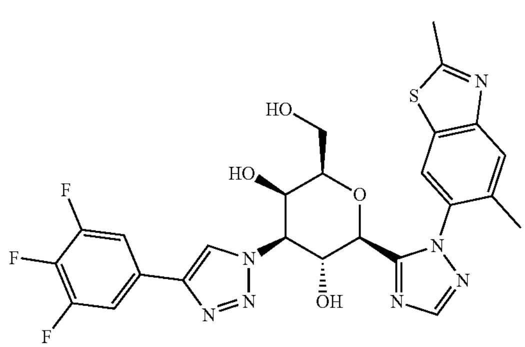 [SMILES: Cc1nc2cc(C)c(-n3ncnc3[C@@H]3O[C@H](CO)[C@H](O)[C@H](n4cc(-c5cc(F)c(F)c(F)c5)nn4)[C@H]3O)cc2s1] | 1.403 | 574.2 | A | 1H NMR (400 MHz, METHANOL-d4) δ 8.57 (s, 1H), 8.29 (s, 1H), 8.10 (s, 1H), 7.97 (s, 1H), 7.72-7.59 (m, 2H), 4.96-4.90 (m, 1H), 4.82 (br. s., 1H), 4.37 (d, J = 9.0 Hz, 1H), 4.08 (d, J = 2.7 Hz, 1H), 3.78-3.61 (m, 3H), 2.95-2.85 (s, 3H), 2.24 (s,3H) |

-continued
| Ex | hGal3 IC50, uM | Structure | LCMS $t_R$ (min) | M + H | Method | 1H NMR |
|---|---|---|---|---|---|---|
| 50 | 0.12 | 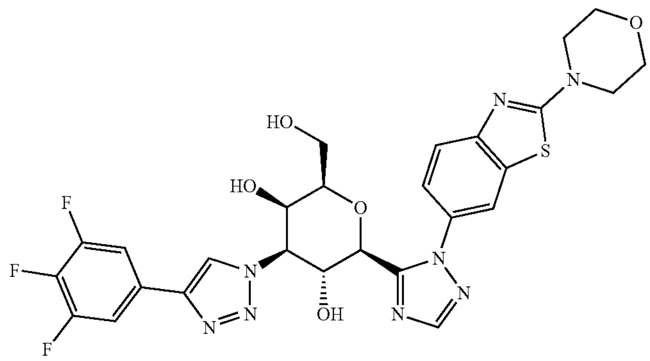 [SMILES: OC[C@H]1O[C@@H](c2ncnn2-c2ccc3nc(N4CCOCC4)sc3c2)[C@H](O)[C@@H](n2cc(-c3cc(F)c(F)c(F)c3)nn2)[C@H]1O] | 1.387 | 631.2 | A | 1H NMR (400 MHz, METHANOL-d) δ 8.59 (s, 1H), 8.21 (s, 1H), 8.11 (d, J = 1.7 Hz, 1H), 7.73-7.57 (m, 4H), 5.04-4.93 (m, 2H), 4.61 (s, 1H), 4.15 (d, J = 2.2 Hz, 1H), 3.92-3.78 (m, 6H), 3.77-3.66 (m, 5H). |
| 51 | 0.07 | 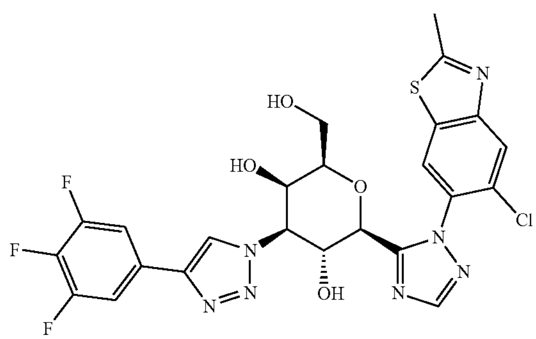 [SMILES: Cc1nc2cc(Cl)c(-n3ncnc3[C@@H]3O[C@H](CO)[C@H](O)[C@H](n4cc(-c5cc(F)c(F)c(F)c5)nn4)[C@H]3O)cc2s1] | 1.433 | 594.2 | A | 1H NMR (400 MHz, METHANOL-d4) δ 8.56 (s, 1H), 8.29 (s, 2H), 8.20 (s, 1H), 7.73-7.59 (m, 2H), 4.43 (br. s., 1H), 4.09 (s, 1H), 3.78-3.56 (m, 3H), 2.92 (s, 3H), 2.68 (s, 2H), |
| 52 | 0.30 | 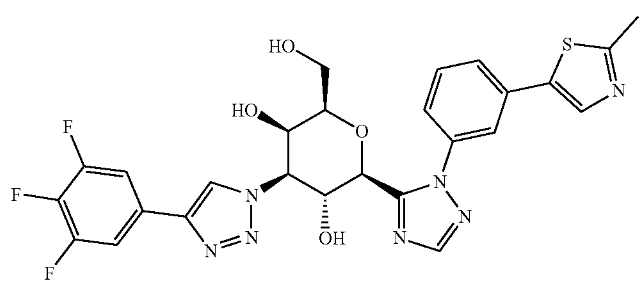 [SMILES: Cc1ncc(-c2cccc(-n3ncnc3[C@@H]3O[C@H](CO)[C@H](O)[C@H](n4cc(-c5cc(F)c(F)c(F)c5)nn4)[C@H]3O)c2)s1] | 2.088 | 586.0 | C | 1H NMR (400 MHz, METHANOL-d4) δ 8.58 (s, 1H), 8.24 (s, 1H), 8.05 (s, 1H), 7.93 (t, J = 1.8 Hz, 1H), 7.82 (dt, J = 7.3, 1.9 Hz, 1H), 7.73-7.61 (m, 4H), 5.08-4.89 (m, 2H), 4.66 (d, J = 9.0 Hz, 1H), 4.19-4.11 (m, 1H), 3.96-3.66 (m, 3H), 2.75 (s, 3H). |
General Synthetic Scheme for C2 O-alkylation of 1,2,4-triazole Compounds:
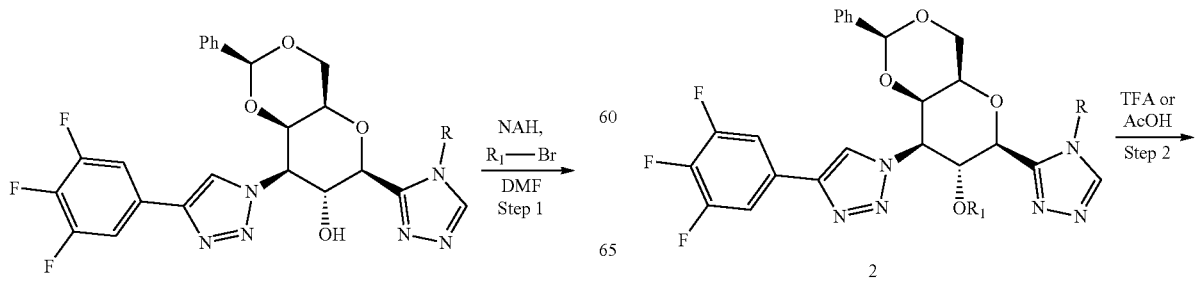

-continued

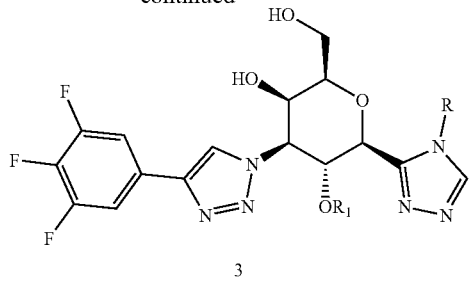

3

EXAMPLE 53

Preparation of 2-(((2S,3R,4S,5R,6R)-2-(1-(3-chlorophenyl)-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid

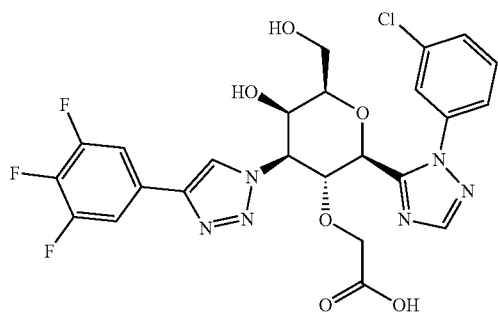 [SMILES: O=C(O)CO[C@@H]1[C@@H](n2cc(-c3cc(F)c(F)c(F)c3)nn2)[C@@H](O)[C@@H](CO)O[C@H]1c1ncnn1-c1cccc(Cl)c1]

Step 1: Synthesis of tert-butyl 2-(((2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)acetate: To a solution of (2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yOhexahydropyrano[3,2-d][1,3]dioxin-7-ol (0.03 g, 0.049 mmol) in DMF (1 mL) was added NaH (60% mineral oil) (0.014 g, 0.344 mmol) at 0° C., and the mixture was stirred for 10 min. tent-Butyl 2-bromoacetate (0.073 mL, 0.491 mmol) was then added. The mixture was slowly warmed to rt and stirred for 5 h. The reaction mixture was cooled to 0° C., quenched with ice water and filtered. The solids obtained were washed with water and dried to afford tent-butyl 2-(((2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)acetate (0.025 g, 70%) as a yellow solid, which was taken to the next step without further purification. LC-MS, [M+H]$^+$=725.4, (Method E: $t_R$=1.72).

Step 2: Synthesis of 2-(((2S,3R,4S,5R,6R)-2-(1-(3-chlorophenyl)-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid: To a solution of tent-butyl 2-(((2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)acetate (0.025 g, 0.034 mmol) in DCM (2 mL) was added TFA (0.5 mL, 6.49 mmol) at 0° C. The mixture was allowed to warm to rt and was stirred for 2 h. The solvent was removed under reduced pressure and the residue was purified by HPLC (Method C) to afford 2-(((2S,3R,4S,5R,6R)-2-(1-(3-chlorophenyl)-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy) acetic acid (Example 53) (8.5 mg, 25%) as a white solid. LC-MS, [M+H]$^+$=581.2, (Method C: $t_R$=2.38 min). 1H NMR (400 MHz, METHANOL-d$_4$): δ 8.72 (s, 1H), 8.16 (s, 1H), 7.82 (s, 1H), 7.56-7.77 (m, 5H), 5.08 (d, J=6.0 Hz, 2H), 4.61-4.73 (m, 1H), 4.16 (s, 1H), 4.01 (d, J=16.6 Hz, 1H), 3.91 (dd, J=7.3, 4.8 Hz, 1H), 3.78-3.84 (m, 1H), 3.66-3.77 (m, 2H). hGal3 IC$_{50}$=0.023 uM The Examples in the table below were prepared in an analogous fashion to Example 53, substituting tent-butyl 2-bromoacetate with the appropriate alkyl halides in the synthetic sequence.

| Ex | hGal3 IC50, uM | Structure | LCMS $t_R$ (min) | M + H | Method | 1H NMR |
|---|---|---|---|---|---|---|
| 54 | 0.083 | 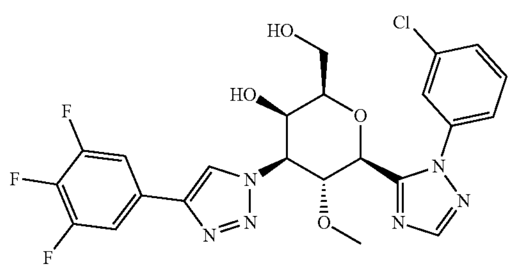 [SMILES: CO[C@@H]1[C@@H](n2cc(-c3cc(F)c(F)c(F)c3)nn2)[C@@H](O)[C@@H](CO)O[C@H]1c1ncnn1-c1cccc(Cl)c1] | 2.34 | 537.2 | C | 1H NMR (400 MHz, METHANOL-d4) δ 8.76 (s, 1H), 8.23 (s, 1H), 7.80-7.77 (m, 1H), 7.73-7.66 (m, 3H), 7.63-7.59 (m, 2H), 5.02 (dd, J = 10.5, 3.0 Hz, 1H), 4.79-4.71 (m, 1H), 4.63-4.58 (m, 1H), 4.12 (d, J = 3.0 Hz, 1H), 3.93-3.88 (m, 1H), 3.86-3.79 (m, 1H), 3.76-3.69 (m, 1H), 2.92 (s, 3H). |
| 55 | 0.157 | 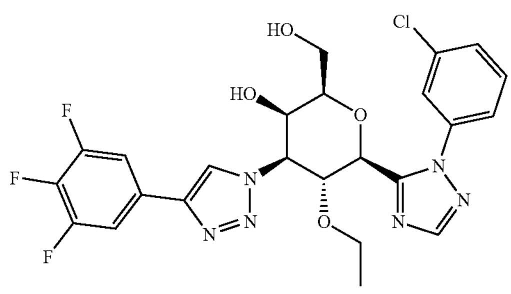 [SMILES: CCO[C@@H]1[C@@H](n2cc(-c3cc(F)c(F)c(F)c3)nn2)[C@@H](O)[C@@H](CO)O[C@H]1c1ncnn1-c1cccc(Cl)c1] | 2.53 | 551.2 | C | 1H NMR (400 MHz, METHANOL-d4) δ 8.75 (s, 1 H), 8.23 (s, 1 H),7.79-7.77 (m, 1 H), 7.71-7.65 (m, 3 H), 7.63-7.61 (m, 2 H), 5.01 (dd, J = 10.5, 3.0 Hz, 1 H), 4.77 (d, J = 10.5 Hz, 1 H), 4.64 (d, J = 9.5 Hz, 1 H), 4.14-4.12 (m, 1 H), 3.90 (dd, J = 8.0, 4.5 Hz, 1 H), 3.85-3.80 (m, 1 H), 3.76-3.70 (m, 1 H), 3.20-3.13 (m, 1 H), 2.96-2.90 (m, 1 H), 0.62 (t, J = 7.0 Hz, 3 H). |

EXAMPLE 56

Preparation of (2S,3R,4R,5R,6R)-2-(1-(3-chlorophenyl)-3-methyl-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol

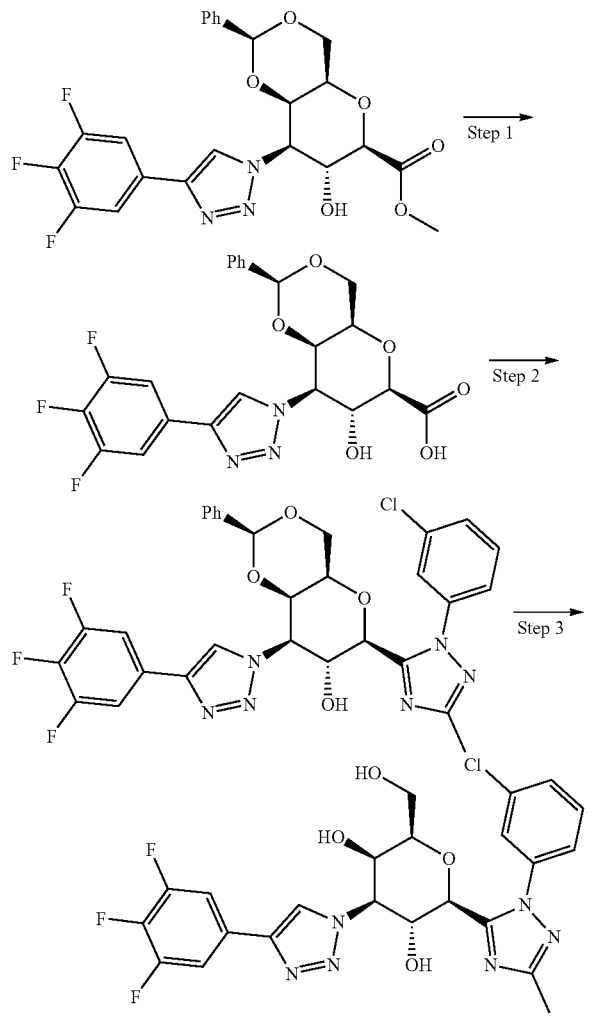

Example 56

Step 1: Synthesis of (2S,4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid: To a stirred solution of (2S,4aR,6R,7R,8S,8aR)-methyl 7-acetoxy-2-phenyl-8-(4-(3,4,5-trifluorophenyl)-1H-1,2,3-triazol-1-yl)hexahydropyrano[3,2-d][1,3]dioxine-6-carboxylate (1.6 g, 3.00 mmol) in THF (100 mL) and water (20 mL) was added lithium hydroxide (0.359 g, 15.00 mmol) and the mixture was stirred at rt for 4 h. The solvent was removed under reduced pressure, diluted with water (200 mL) and the pH was adjusted to 2-3 using 1.5N HCl solution. The solid was filtered, washed with excess water and dried to afford (2S,4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (1.38 g, 94%) as an off-white solid. LC-MS, [M+H]$^+$=478.4, (Method E: $t_R$=0.93 min).

Step 2: Synthesis of (2S,4aR,6S,7R,8R,8aR)-6-(1-(3-chlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To a solution of acetimidamide hydrochloride (0.040 g, 0.419 mmol) in DMF (2 mL) was added DIPEA (0.088 mL, 0.503 mmol) and the mixture was stirred for 5 min. (2S,4aR,6R,7R,8R,8aR)-7-Hydroxy-2-phenyl-8-(4-(3,4,5-trifluorophenyl)-1H-1,2,3-triazol-1-yl)hexahydropyrano[3,2-d][1,3]dioxine-6-carboxylic acid (0.08 g, 0.168 mmol) and HATU (0.070 g, 0.184 mmol) were added sequentially and the mixture was stirred at rt for 3 h. Next, 3-chlorophenylhydrazine hydrochloride (0.045 g, 0.251 mmol) and acetic acid (0.096 mL, 1.676 mmol) were added and the reaction mixture was heated at 80° C. for 4 h. The mixture was cooled to rt and was transferred to a separatory funnel containing aq. NaHCO$_3$. The aqueous layer was extracted with EtOAc (2×50 mL). The combined organic layers were washed with water, brine, dried over sodium sulfate and concentrated. The residue was purified by column chromatography (50-65% of EtOAc in n-hexane) to afford (4aR,6S,7R,8R,8aR)-6-(1-(3-chlorophenyl)-3-methyl-1H-1,2,4-triazol-5-yl)-2-phenyl-8-(4-(3,4,5-trifluorophenyl)-1H-1,2,3-triazol-1-yl) hexahydropyrano[3,2 d][1,3]dioxin-7-ol (0.03 g, 29%) as a liquid. LC-MS, [M+H]$^+$=625.3, (Method C: $t_R$=1.44 min).

Step 3: To a stirred solution of (2S,4aR,6S,7R,8R,8aR)-6-(1-(3-chlorophenyl)-3-methyl-1H-1,2,4-triazol-5-yl)-2-phenyl-8-(4-(3,4,5-trifluorophenyl)-1H-1,2,3-triazol-1-yl) hexahydropyrano[3,2-d][1,3]dioxin-7-ol (0.03 g, 0.048 mmol) in DCM (1 mL) was added TFA (0.2 mL, 2.60 mmol) at 0° C. and the mixture was stirred for 1 h. The reaction mixture was concentrated under reduced pressure and purified by reverse phase HPLC (Method A) to afford (2S,3R,4R,5R,6R)-2-(1-(3-chlorophenyl)-3-methyl-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol (Example 56) (3.3 mg, 13%) as an off-white solid. LC-MS, [M+H]$^+$=537.2, (Method A: $t_R$=1.47 min and Method D: $t_R$=1.47 min). 1H NMR (400 MHz, METHANOL-d4): δ 8.57 (s, 1H), 7.74-7.78 (m, 1H), 7.62-7.70 (m, 3H), 7.57-7.61 (m, 2H), 4.92-4.99 (m, 2H), 4.52-4.57 (m, 1H), 4.15 (d, J=1.5 Hz, 1H), 3.90 (dd, J=7.0, 4.0 Hz, 1H), 3.77-3.84 (m, 1H), 3.74-3.70 (m, 1H), 2.46 (s, 3H). hGal3 IC$_{50}$=0.25 uM.

General Synthetic Scheme for 3-methyl-1,2,4-triazole Compounds:

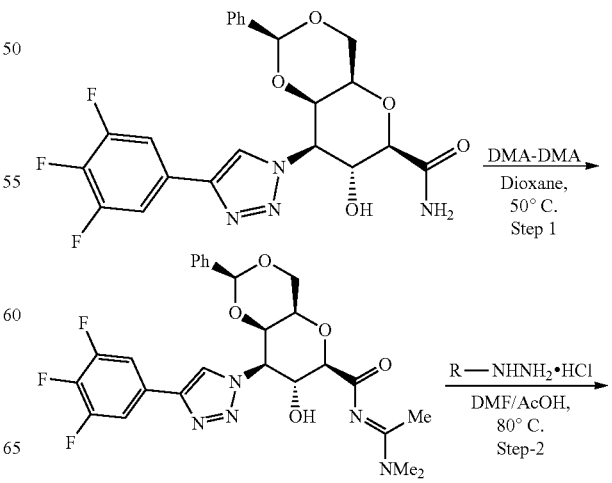

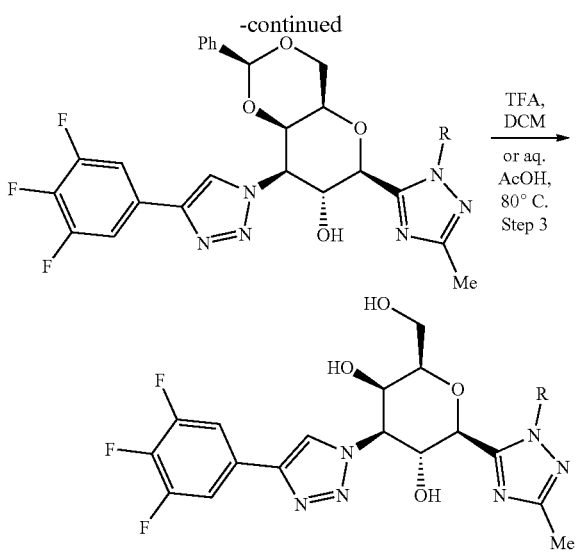

EXAMPLE 57

Preparation of (2R,3R,4R,5R,6S)-2-(hydroxymethyl)-6-(3-methyl-1-(2-methylbenzo[d]thiazol-6-yl)-1H-1,2,4-triazol-5-yl)-4-(4-(3,4,5-trifluorophenyl)-1H-1,2,3-triazol-1-yl)tetrahydro-2H-pyran-3,5-diol

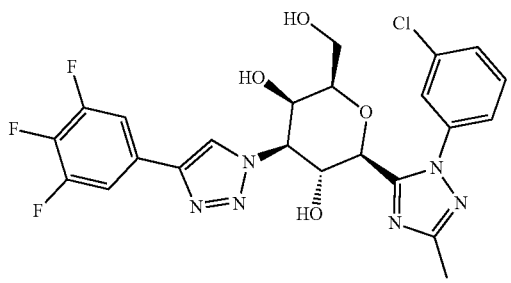 [SMILES: Cc1nc([C@@H]2O[C@H](CO)[C@H](O)[C@H](n3cc(-c4cc(F)c(F)c(F)c4)nn3)[C@H]2O)n(-c2cccc(Cl)c2)n1]

Step 1: Synthesis of (4aR,6R,7R,8R,8aR)-N-(1-(dimethylamino)ethylidene)-7-hydroxy-2-phenyl-8-(4-(3,4,5-trifluorophenyl)-1H-1,2,3-triazol-1-yl)hexahydropyrano[3,2-d][1,3]dioxine-6-carboxamide: To a stirred solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxamide (0.3 g, 0.630 mmol) in dioxane (5 mL) was added 1,1-dimethoxy-N,N-dimethylethan-1-amine (0.466 mL, 3.15 mmol) and the mixture was heated to 50° C. for 6 h. The mixture was concentrated under reduced pressure to afford a white solid, which was triturated with diethyl ether, filtered through a Buchner funnel and washed with diethyl ether. The solid was washed with diethyl ether and dried to afford (4aR,6R,7R,8R,8aR)-N-(1-(dimethylamino)ethylidene)-7-hydroxy-2-phenyl-8-(4-(3,4,5-trifluorophenyl)-1H-1,2,3-triazol-1-yl)hexahydropyrano[3,2-d][1,3]dioxine-6-carboxamide (0.3 g, 87%) as a white solid. LC-MS, [M+1]$^+$=546.5, (Method E: $t_R$=1.53 min).

Step 2: Synthesis of (4aR,6S,7R,8R,8aR)-6-(3-methyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: A mixture of (4aR,6R,7R,8R,8aR)-N-((E)-1-(dimethylamino)ethylidene)-7-hydroxy-2-phenyl-8-(4-(3,4,5-trifluorophenyl)-1H-1,2,3-triazol-1-yl)hexahydropyrano[3,2-d][1,3]dioxine-6-carboxamide (0.3 g, 0.550 mmol) and 6-hydrazinyl-2-methylbenzo[d]thiazole.HCl (0.130 g, 0.605 mmol) in acetic acid (6 mL) was stirred at rt for 2 h. Water was then added and the mixture was stirred for 5 min. The solid was filtered, washed with excess water and dried to give a solid, which was purified by silica gel chromatography (2-6% MeOH in chloroform) to give (4aR,6S,7R,8R,8aR)-6-(3-methyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.12 g, 33%) as a yellow solid. LC-MS, [M+1]$^+$=662.2, (Method C: $t_R$=2.92 min).

Step 3: Synthesis of (2R,3R,4R,5R,6S)-2-(hydroxymethyl)-6-(3-methyl-1-(2-methylbenzo[d]thiazol-6-yl)-1H-1,2,4-triazol-5-yl)-4-(4-(3,4,5-trifluorophenyl)-1H-1,2,3-triazol-1-yl)tetrahydro-2H-pyran-3,5-diol: To a stirred solution of (4aR,6S,7R,8R,8aR)-6-(3-methyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl) hexahydropyrano[3,2-d][1,3]dioxin-7-ol (0.12 g, 0.181 mmol) in DCM (5 mL) at 0° C. was added TFA (3 mL, 38.9 mmol) and the mixture was stirred at rt for 5 h. Then the reaction mixture was concentrated and purified by HPLC (Method P) to afford (2R,3R,4R,5R,6S)-2-(hydroxymethyl)-6-(3-methyl-1-(2-methylbenzo[d]thiazol-6-yl)-1H-1,2,4-triazol-5-yl)-4-(4-(3,4,5-trifluorophenyl)-1H-1,2,3-triazol-1-yl)tetrahydro-2H-pyran-3,5-diol (45 mg, 42%) as a white solid. LC-MS, [M+1]$^+$=574.2, (Method C: $t_R$=1.81 min). 1H NMR (400 MHz, METHANOL-d4) d 8.46 (s, 1H), 8.26 (d, J=2.0 Hz, 1H), 7.97 (d, J=9.0 Hz, 1H), 7.69 (dd, J=8.5, 2.0 Hz, 1H), 7.55 (dd, J=9.0, 6.5 Hz, 2H), 4.89-4.83 (m, 1H), 4.82 (d, J=2.5 Hz, 1H), 4.45 (d, J=9.0 Hz, 1H), 4.02 (d, J=2.5 Hz, 1H), 3.79-3.74 (m, 1H), 3.71 (d, J=7.5 Hz, 1H), 3.64-3.60 (m, 1H), 2.80 (s, 3H), 2.37 (s, 3H). hGal3 IC$_{50}$: 0.05 uM;

The Examples in the table below were prepared in an analogous fashion to Example 57, substituting 6-hydrazinyl-2-methylbenzo[d]thiazole, HCl with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 58 | 0.04 | 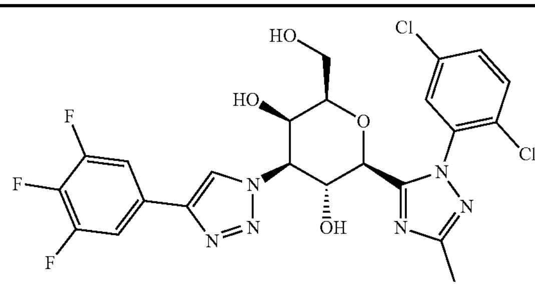 | 1.572 | 573.1 | A | 1H NMR (400 MHz, METHANOL-d4) δ 8.55 (s, 1H), 7.75-7.62 (m, 5H), 4.90 (br. s., 1H), 4.79 (br. s., 1H), 4.39 (d, J = 8.6 Hz, 1H), 4.13 (s, 1H), 3.86-3.76 (m, 1H), 3.75-3.60 (m, 2H), 2.48 (s, 3H). |

-continued

| Ex | hGal3 IC50, uM | Structure | LCMS t$_R$ (min) | M + H | Method | 1H NMR |
|---|---|---|---|---|---|---|
| 59 | 0.14 | 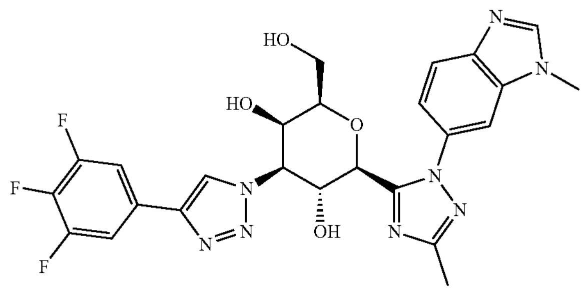 [SMILES: Cc1nc([C@@H]2O[C@H](CO)[C@H](O)[C@H](n3cc(-c4cc(F)c(F)c(F)c4)nn3)[C@H]2O)n(-c2ccc3ncn(C)c3c2)n1] | 1.209 | 557.2 | A | 1H NMR (400 MHz, METHANOL-d4) δ 8.61-8.53 (m, 1H), 8.31 (s, 1H), 7.99-7.92 (m, 1H), 7.86 (d, J = 8.6 Hz, 1H), 7.70-7.60 (m, 2H), 7.58 (dd, J = 8.7, 1.6 Hz, 1H), 5.02-4.96 (m, 1H), 4.92-4.88 (m, 1H), 4.57 (s, 1H), 4.16-4.08 (m, 1H), 3.98 (s, 3H), 3.91-3.74 (m, 3H), 2.48 (s, 3H). |
| 60 | 0.07 | 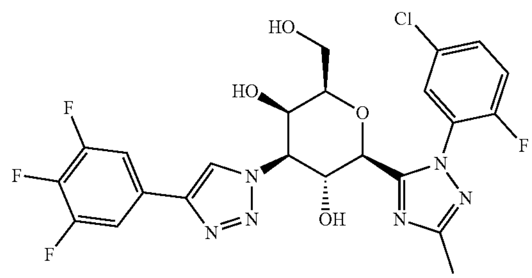 [SMILES: Cc1nc([C@@H]2O[C@H](CO)[C@H](O)[C@H](n3cc(-c4cc(F)c(F)c(F)c4)nn3)[C@H]2O)n(-c2cc(Cl)ccc2F)n1] | 1.535 | 555.1 | A | 1H NMR (400 MHz, METHANOL-d4) δ 8.56 (s, 1H), 7.75 (dd, J = 6.4, 2.7 Hz, 1H), 7.71-7.56 (m, 3H), 7.45 (t, J = 9.3 Hz, 1H), 4.94-4.90 (m, 1H), 4.82 (br. s., 1H), 4.57 (br. s., 1H), 4.49 (d, J = 9.0 Hz, 1H), 4.14 (d, J = 2.0 Hz, 1H), 3.89-3.79 (m, 1H), 3.78-3.62 (m, 2H), 2.47 (s, 3H). |
| 61 | 0.06 | 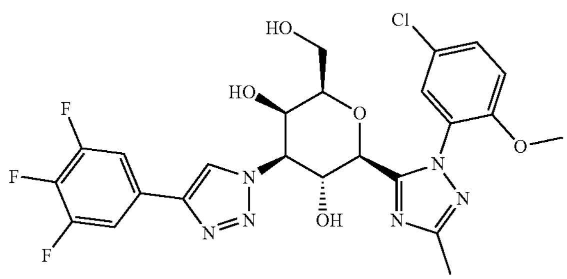 [SMILES: COc1ccc(Cl)cc1-n1nc(C)nc1[C@@H]1O[C@H](CO)[C@H](O)[C@H](n2cc(-c3cc(F)c(F)c(F)c3)nn2)[C@H]1O] | 1.534 | 567.2 | A | 1H NMR (400 MHz, METHANOL-d4) δ 8.55 (s, 1H), 7.66 (dd, J = 8.8, 6.6 Hz, 2H), 7.58 (dd, J = 8.9, 2.6 Hz, 1H), 7.50 (d, J = 2.4 Hz, 1H), 7.27 (d, J = 9.0 Hz, 1H), 4.89 (d, J = 2.9 Hz, 1H), 4.78 (d, J =10.5 Hz, 1H), 4.57 (br. s., 1H), 4.37 (d, J = 9.0 Hz, 1H), 4.12 (d, J = 2.2 Hz, 1H), 3.88 (s, 3H), 3.83-3.75 (m, 1H), 3.75-3.66 (m, 2H), 2.46 (s, 3H). |
| 62 | 0.03 | 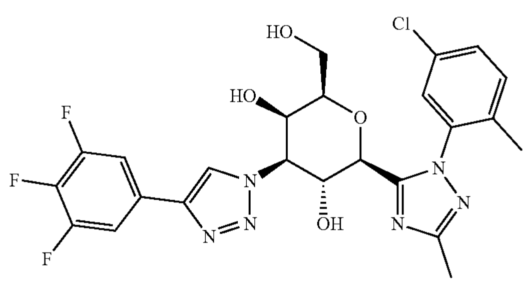 [SMILES: Cc1nc([C@@H]2O[C@H](CO)[C@H](O)[C@H](n3cc(-c4cc(F)c(F)c(F)c4)nn3)[C@H]2O)n(-c2cc(Cl)ccc2C)n1] | 1.603 | 557.2 | A | 1H NMR (400 MHz, METHANOL-d4) δ 8.50 (s, 1H), 8.15 (s, 1H), 7.92-7.82 (m, 4H), 7.56 (dd, J = 9.0, 6.6 Hz, 2H), 4.97-4.79 (m, 2H), 4.52 (d, J = 8.8 Hz, 1H), 4.05 (d, J = 2.2 Hz, 1H), 3.84 (dd, J = 7.6, 5.1 Hz, 1H), 3.72 (dd, J = 11.7, 7.6 Hz, 1H), 3.62 (dd, J = 11.6, 4.3 Hz, 1H) |
| 63 | 0.85 | 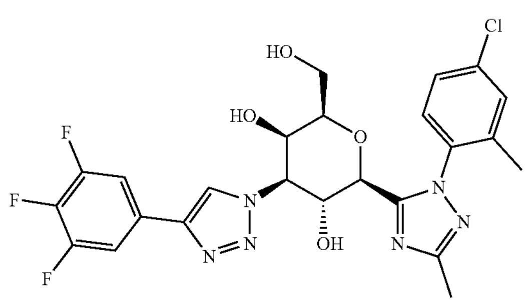 [SMILES: Cc1nc([C@@H]2O[C@H](CO)[C@H](O)[C@H](n3cc(-c4cc(F)c(F)c(F)c4)nn3)[C@H]2O)n(-c2ccc(Cl)cc2C)n1] | 1.614 | 551.2 | A | 1H NMR (400 MHz, METHANOL-d4) δ 8.57 (s, 1H), 7.67 (dd, J = 9.0, 6.6 Hz, 2H), 7.52 (d, J = 1.0 Hz, 1H), 7.47-7.36 (m, 2H), 4.33-4.24 (m, 1H), 4.11 (s, 1H), 3.79-3.62 (m, 3H), 2.47 (s, 3H), 2.14 (s, 3H). |

-continued

| Ex | hGal3 IC50, uM | Structure | LCMS t_R (min) | M + H | Method | 1H NMR |
|---|---|---|---|---|---|---|
| 64 | 0.09 | 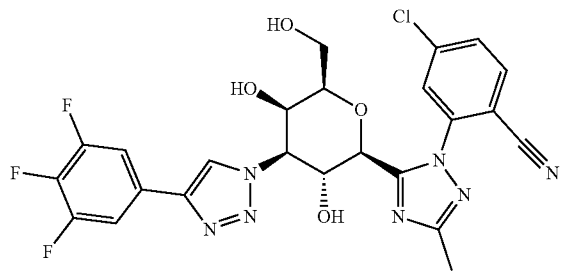 [SMILES: Cc1nc([C@@H]2O[C@H](CO)[C@H](O)[C@H](n3cc(-c4cc(F)c(F)c(F)c4)nn3)[C@H]2O)n(-c2cc(Cl)ccc2C#N)n1] | 1.509 | 562.2 | A | 1H NMR (400 MHz, METHANOL-d4) δ 8.56 (s, 1H), 8.06-7.95 (m, 2H), 7.87-7.79 (m, 1H), 7.67 (dd, J = 8.9, 6.5 Hz, 2H), 4.96-4.86 (m, 2H), 4.83 (br. s., 1H), 4.56 (d, J = 9.0 Hz, 1H), 4.14 (d, J = 2.2 Hz, 1H), 3.93-3.83 (m, 1H), 3.71 (qd, J = 11.7, 6.0 Hz, 1H), 2.50 (s, 3H). |
| 65 | 0.22 | 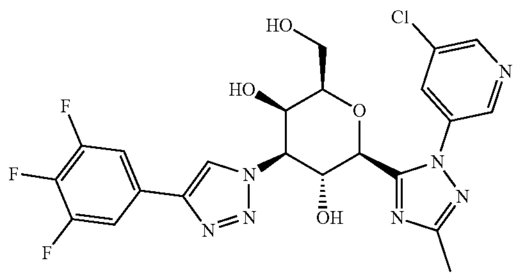 [SMILES: Cc1nc([C@@H]2O[C@H](CO)[C@H](O)[C@H](n3cc(-c4cc(F)c(F)c(F)c4)nn3)[C@H]2O)n(-c2cncc(Cl)c2)n1] | 1.287 | 538.2 | A | 1H NMR (400 MHz, METHANOL-d4) δ 8.88 (d, J = 2.2 Hz, 1H), 8.77 (d, J = 2.0 Hz, 1H), 8.62-8.53 (m, 1H), 8.33 (t, J = 2.1 Hz, 1H), 7.67 (dd, J = 8.8, 6.6 Hz, 2H), 5.00-4.91 (m, 2H), 4.64 (d, J = 8.6 Hz, 1H), 4.17 (d, J = 2.0 Hz, 1H), 3.96 (dd, J = 6.6, 5.4 Hz, 1H), 3.86-3.78 (m, 1H), 3.77-3.70 (m, 1H), 2.48 (s, 3H). |
| 66 | 3.84 | 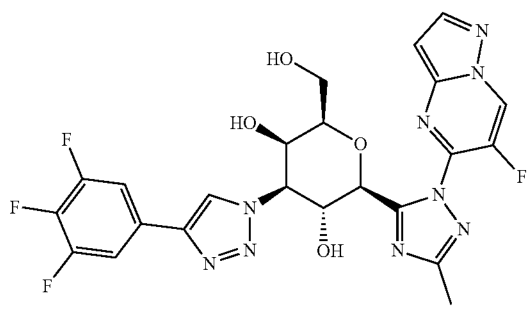 [SMILES: Cc1nc([C@@H]2O[C@H](CO)[C@H](O)[C@H](n3cc(-c4cc(F)c(F)c(F)c4)nn3)[C@H]2O)n(-c2nc3ccnn3cc2F)n1] | 1.2 | 562.2 | A | 1H NMR (400 MHz, METHANOL-d4) δ 8.83 (s, 1H), 8.70 (d, J = 4.6 Hz, 1H), 7.82 (s, 1H), 7.61-7.33 (m, 2H), 6.60 (t, J = 10.0 Hz, 1H), 6.19 (s, 1H), 5.48 (d, J =10.8 Hz, 1H), 4.98 (d, J = 9.0 Hz, 1H), 4.55 (s, 1H), 4.36 (br. s., 1H), 4.09 (d, J = 5.9 Hz, 1H), 3.97-3.73 (m, 2H), 2.30 (s, 3H). |
| 67 | 0.13 | 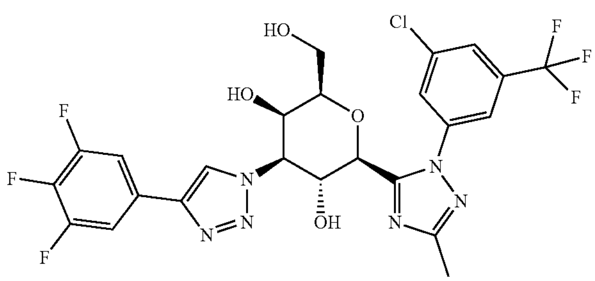 [SMILES: Cc1nc([C@@H]2O[C@H](CO)[C@H](O)[C@H](n3cc(-c4cc(F)c(F)c(F)c4)nn3)[C@H]2O)n(-c2cc(Cl)cc(C(F)(F)F)c2)n1] | 1.801 | 605.1 | B | 1H NMR (400 MHz, METHANOL-d4) δ 8.55 (s, 1H), 8.11 (s, 1H), 8.00 (s, 1H), 7.93 (s, 1H), 7.74-7.55 (m, 2H), 4.98-4.93 (m, 2H), 4.62-4.57 (m, 1H), 4.19-4.15 (m, 1H), 3.97-3.89 (m, 1H), 3.85-3.67 (m, 2H), 2.46 (s, 3H) |
| 68 | 0.02 | 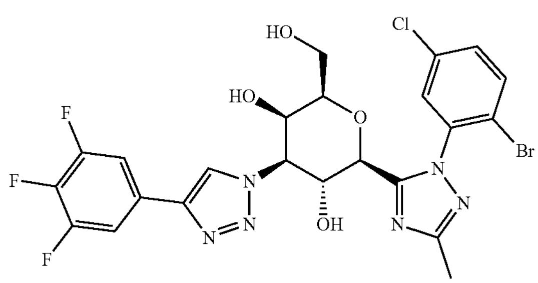 [SMILES: Cc1nc([C@@H]2O[C@H](CO)[C@H](O)[C@H](n3cc(-c4cc(F)c(F)c(F)c4)nn3)[C@H]2O)n(-c2cc(Cl)ccc2Br)n1] | 1.905 | 617.1 | A | 1H NMR (400 MHz, METHANOL-d4) δ 8.55 (s, 1H), 7.86 (d, J = 8.6 Hz, 1H), 7.77-7.61 (m, 3H), 7.58 (dd, J = 8.7, 2.6 Hz, 1H), 4.90 (d, J = 2.7 Hz, 1H), 4.38 (d, J = 8.6 Hz, 1H), 4.13 (d, J = 1.5 Hz, 1H), 3.85-3.60 (m, 3H), 3.01 (s, 1H), 2.48 (s, 3H). |

| Ex | hGal3 IC50, uM | Structure | LCMS $t_R$ (min) | M + H | Method | 1H NMR |
|---|---|---|---|---|---|---|
| 69 | 0.06 | 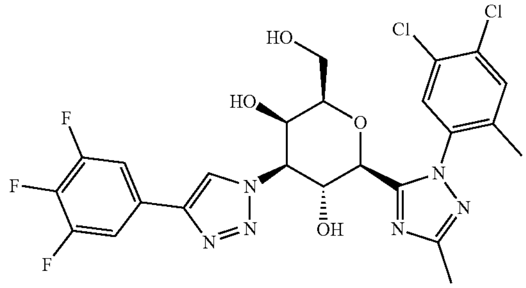 [SMILES: Cc1nc([C@@H]2O[C@H](CO)[C@H](O)[C@H](n3cc(-c4cc(F)c(F)c(F)c4)nn3)[C@H]2O)n(-c2cc(Cl)c(Cl)cc2C)n1] | 1.778 | 587.2 | A | 1H NMR (400 MHz, METHANOL-d4) δ 8.56 (s, 1H), 7.73-7.59 (m, 4H), 4.90-4.87 (m, 2H), 4.34 (d, J = 8.6 Hz, 1H), 4.11 (d, J = 1.7 Hz, 1H), 3.83-3.75 (m, 1H), 3.75-3.62 (m, 2H), 2.47 (s, 3H), 2.13 (s, 3H). |
| 70 | 0.05 | 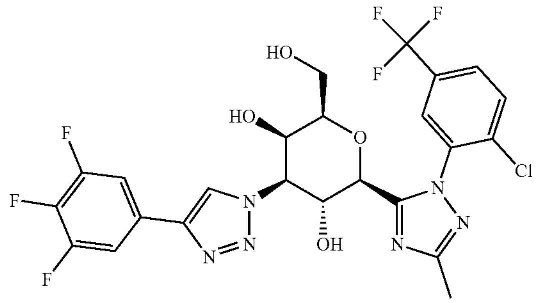 [SMILES: Cc1nc([C@@H]2O[C@H](CO)[C@H](O)[C@H](n3cc(-c4cc(F)c(F)c(F)c4)nn3)[C@H]2O)n(-c2cc(C(F)(F)F)ccc2Cl)n1] | 1.687 | 605.1 | A | 1H NMR (400 MHz, METHANOL-d4) δ 8.58-8.49 (m, 1H), 8.07-7.84 (m, 3H), 7.73-7.57 (m, 2H), 4.78 (br. s., 2H), 4.41 (d, J = 9.3 Hz, 1H), 4.11 (d, J = 1.7 Hz, 1H), 3.76 (t, J = 5.9 Hz, 1H), 3.66 (d, J = 5.9 Hz, 2H), 2.49 (s, 3H). |
| 71 | 0.09 | 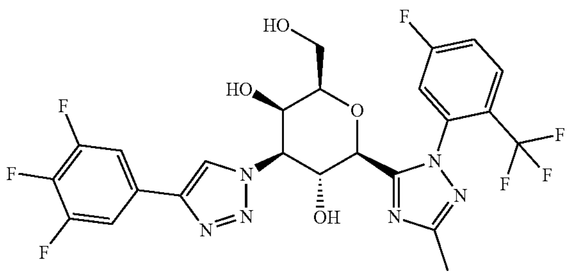 [SMILES: Cc1nc([C@@H]2O[C@H](CO)[C@H](O)[C@H](n3cc(-c4cc(F)c(F)c(F)c4)nn3)[C@H]2O)n(-c2cc(F)ccc2C(F)(F)F)n1] | 1.568 | 589.2 | A | 1H NMR (400 MHz, METHANOL-d4) δ 8.57 (s, 1H), 8.04 (dd, J = 9.0, 5.6 Hz, 1H), 7.75-7.58 (m, 3H), 7.56 (br. s., 1H), 4.37 (d, J = 9.0 Hz, 1H), 4.12 (s, 1H), 3.81 (s, 1H), 3.78-3.71 (m, 2H), 3.71-3.59 (m, 2H), 2.47 (s, 3H). |
| 72 | 0.02 | 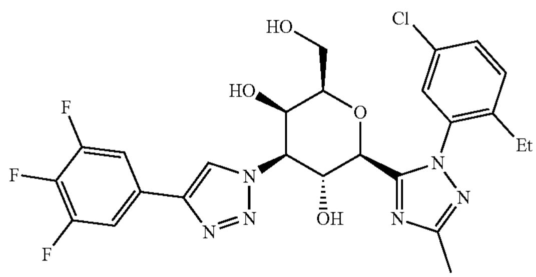 [SMILES: CCc1ccc(Cl)cc1-n1nc(C)nc1[C@@H]1O[C@H](CO)[C@H](O)[C@H](n2cc(-c3cc(F)c(F)c(F)c3)nn2)[C@H]1O] | 1.707 | 565.2 | A | 1H NMR (400 MHz, METHANOL-d4) δ 8.57 (s, 1H), 7.67 (dd, J = 8.9, 6.5 Hz, 2H), 7.61-7.55 (m, 1H), 7.51 (d, J = 8.6 Hz, 2H), 4.34-4.24 (m, 1H), 4.12 (s, 1H), 3.80-3.64 (m, 3H), 2.57-2.37 (m, 5H), 1.13 (t, J = 7.6 Hz, 3H) (2 Protons burried under solvent). |

General Synthetic Scheme 1 for 4-aryl-1,2,4-triazole Compounds:

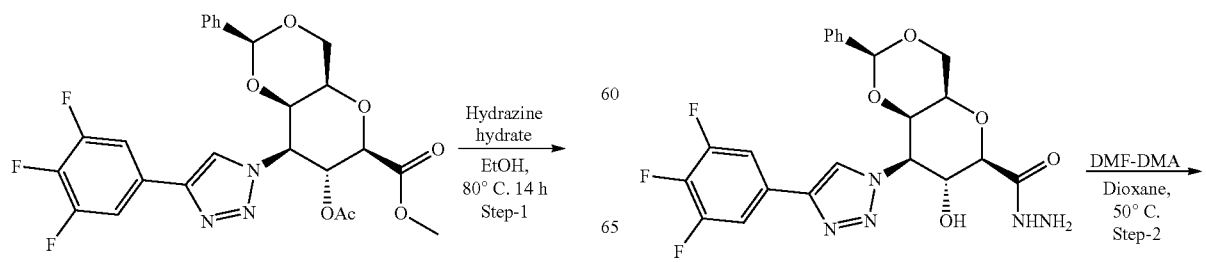

-continued

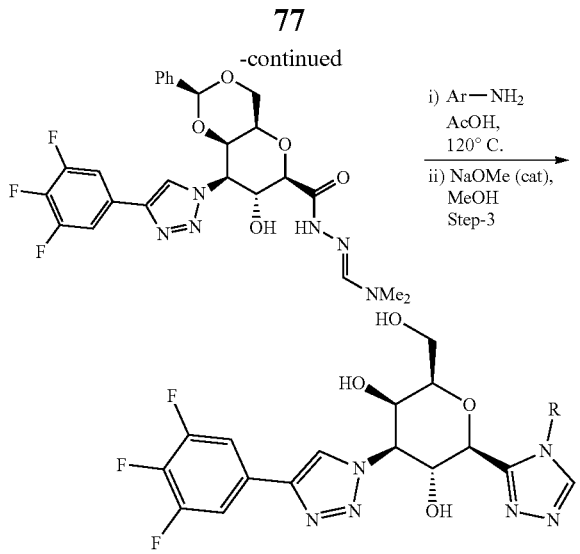

i) Ar—NH₂
AcOH,
120° C.
ii) NaOMe (cat),
MeOH
Step-3

EXAMPLE 73

Preparation of (2R,3R,4R,5R,6S)-2-(hydroxymethyl)-6-(4-phenyl-4H-1,2,4-triazol-3-yl)-4-(4-(3,4,5-trifluorophenyl)-1H-1,2,3-triazol-1-yl)tetrahydro-2H-pyran-3,5-diol

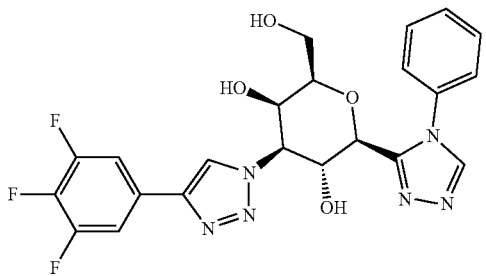 [SMILES: OC[C@H]1O[C@@H](c2nncn2-c2ccccc2)[C@H](O)[C@@H](n2cc(-c3cc(F)c(F)c(F)c3)nn2)[C@H]1O]

Step 1: Synthesis of ((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide: To a stirred solution of methyl (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate (1.5 g, 2.81 mmol) in ethanol (40 mL) was added hydrazine hydrate (1.689 g, 33.7 mmol) and the mixture was heated to 80° C. for 14 h. The reaction mixture was concentrated under reduced pressure and the residue was triturated with diethyl ether and filtered. The solid was washed with diethyl ether and dried to afford ((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (1.3 g, 88%) as a white solid. LC-MS, [M+H]⁺=492.2, (Method C: $t_R$=2.08). 1H NMR (400 MHz, DMSO-d6) δ: 9.55 (br s, 1H), 8.87 (s, 1H), 7.96-7.72 (m, 2H), 7.33-7.30 (m, 5H), 5.53 (s, 1H), 5.11 (dd, J=3.5, 11.0 Hz, 1H), 4.58 (dd, J=9.5, 10.5 Hz, 1H), 4.43 (d, J=3.0 Hz, 1H), 4.16-4.04 (m, 2H), 3.88-3.80 (m, 2H).

Step 2: Synthesis of (2S,4aR,6R,7R,8R,8aR)-N-((E)-(dimethylamino)methylene)-7-hydroxy-2-phenyl-8-(4-(3,4,5-trifluorophenyl)-1H-1,2,3-triazol-1-yl)hexahydropyrano[3,2-d][1,3]dioxine-6-carboxamide: To a solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (1.3 g, 2.65 mmol) in dioxane (30 mL), was added DMF-DMA (1.417 mL, 10.58 mmol) and the mixture was heated to 50° C. for 1 h. The solvent was removed under reduced pressure and the residue was triturated with diethyl ether and filtered. The solid obtained was washed with excess diethyl ether and dried to afford N'-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)-N,N-dimethylformohydrazonamide (1 g, 68%) as a white solid. LC-MS, [M+H]⁺= 547.2, (Method E: $t_R$=2.526).

Step 3: Synthesis of (2S,4aR,6S,7R,8R,8aR)-6-(1-(3-chlorophenyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To a stirred solution of N'-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)-N,N-dimethylformohydrazonamide (0.02 g, 0.037 mmol) in acetic acid (0.5 mL) was added aniline (3.41 mg, 0.037 mmol) and the mixture was stirred at 120° C. for 3 h. The solvent was removed under reduced pressure. The residue was dissolved in 1 mL of MeOH, cooled to 0° C. and sodium methoxide (25% in MeOH) (0.841 μl, 3.66 μmol) was added and the mixture was stirred for 1 h. The mixture was concentrated under reduced pressure and purified HPLC (Method A) to afford (2R,3R,4R,5R,6S)-2-(hydroxymethyl)-6-(4-phenyl-4H-1,2,4-triazol-3-yl)-4-(4-(3,4,5-trifluorophenyl)-1H-1,2,3-triazol-1-yl)tetrahydro-2H-pyran-3,5-diol (Example 73) (3.1 mg, 17%) as a white solid. LC-MS, [M+H]⁺=489.2, (Method C: $t_R$=1.49). 1H NMR (400 MHz, METHANOL-d4): δ 8.58 (s, 1H), 8.21 (s, 1H), 7.78-7.82 (m, 1H), 7.68-7.73 (m, 1H), 7.63-7.68 (m, 2H), 7.59-7.62 (m, 2H), 4.91-5.04 (m, 2H), 4.60 (dd, J=14.6, 8.5 Hz, 1H), 4.16 (d, J=2.0 Hz, 1H), 3.89-3.95 (m, 1H), 3.78-3.85 (m, 1H), 3.69-3.76 (m, 1H). hGal3 IC₅₀=0.21 uM.

The Examples in the table below were prepared in an analogous fashion to Example 73, substituting aniline with the appropriate aryl amine in the synthetic sequence.

| Ex | hGal3 IC50, uM | Structure | LCMS $t_R$ (min) | M + H | Method | 1H NMR |
|---|---|---|---|---|---|---|
| 74 | 0.11 | 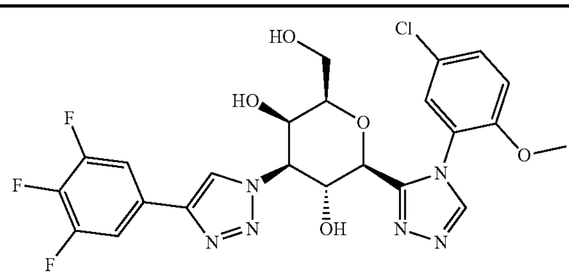 | 1.294 | 553.1 | A | ¹H NMR (400 MHz, METHANOL-d₄) δ 8.94 (s, 1H), 8.84 (s, 1H), 7.96-7.89 (m, 3H), 7.89-7.84 (m, 1H), 7.56 (d, J = 8.8 Hz, 1H), 5.24-5.14 (m, 2H), 4.69 (d, J = 8.6 Hz, 1H), 4.41-4.39 (m, 1H), 4.27 (s, 1H), 4.15 (s, 3H), 4.08-4.01 (m, 1H), 4.00-3.93 (m, 2H) |

-continued

| Ex | hGal3 IC50, uM | Structure | LCMS $t_R$ (min) | M + H | Method | 1H NMR |
|---|---|---|---|---|---|---|
| 75 | 0.33 | 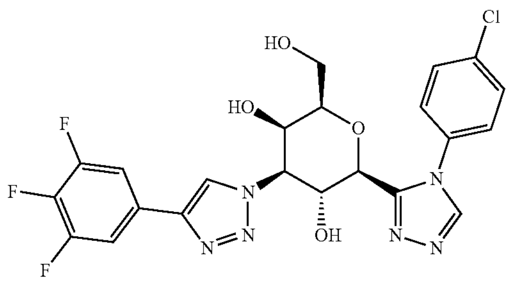 | 1.263 | 523.1 | A | ¹H NMR (400 MHz, METHANOL-d₄) δ 9.08 (s, 1H), 8.87-8.84 (m, 1H), 7.98-7.90 (m, 6H), 5.32 (dd, J = 10.8, 9.5 Hz, 1H), 5.19 (dd, J = 10.8, 2.9 Hz, 2H), 4.76 (d, J = 9.5 Hz, 1H), 4.42-4.40 (m, 1H), 4.14-4.03 (m, 2H), 4.01-3.95 (m, 1H) |
| 76 | 0.12 | 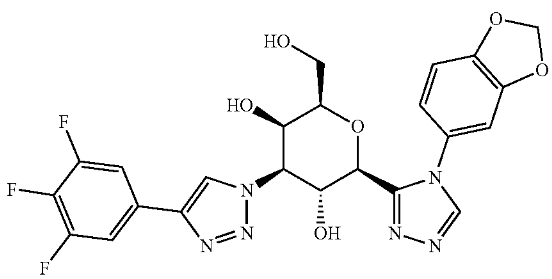 [SMILES: OC[C@H]1O[C@@H](c2nncn2-c2ccc3c(c2)OCO3)[C@H](O)[C@@H](n2cc(-c3cc(F)c(F)c(F)c3)nn2)[C@H]1O] | 1.127 | 533.1 | A | ¹H NMR (400 MHz, METHANOL-d₄) δ 8.60 (s, 1H), 8.48 (s, 1H), 7.56 (dd, J = 9.0, 6.6 Hz, 2H), 7.05 (d, J = 2.0 Hz, 1H), 7.00 (dd, J = 8.3, 2.2 Hz, 1H), 6.91 (d, J = 8.1 Hz, 1H), 6.04-5.99 (m, 2H), 4.95-4.88 (m, 1H), 4.80 (dd, J = 10.8, 2.9 Hz, 1H), 4.39 (d, J = 9.3 Hz, 1H), 4.03 (d, J = 2.4 Hz, 1H), 3.75-3.69 (m, 1H), 3.69-3.63 (m, 1H), 3.63-3.57 (m, 1H) |
| 77 | 0.14 | 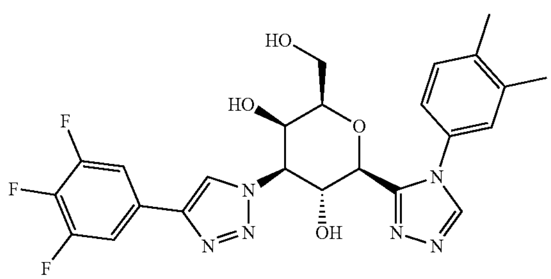 [SMILES: Cc1ccc(-n2cnnc2[C@@H]2O[C@H](CO)[C@H](O)[C@H](n3cc(-c4cc(F)c(F)c(F)c4)nn3)[C@H]2O)cc1C] | 1.324 | 517.2 | A | ¹H NMR (400 MHz, METHANOL-d₄) δ 8.62 (s, 1H), 8.48 (s, 1H), 7.56 (dd, J = 9.0, 6.6 Hz, 2H), 7.32 (d, J = 2.0 Hz, 1H), 7.29-7.21 (m, 2H), 4.94 (dd, J = 10.8, 9.5 Hz, 1H), 4.78 (dd, J = 10.8, 2.9 Hz, 2H), 4.35 (d, J = 9.3 Hz, 1H), 4.03 (d, J = 2.9 Hz, 1H), 3.73-3.66 (m, 2H), 3.64-3.57 (m, 1H), 2.30-2.26 (m, 6H) |
| 78 | 0.83 | 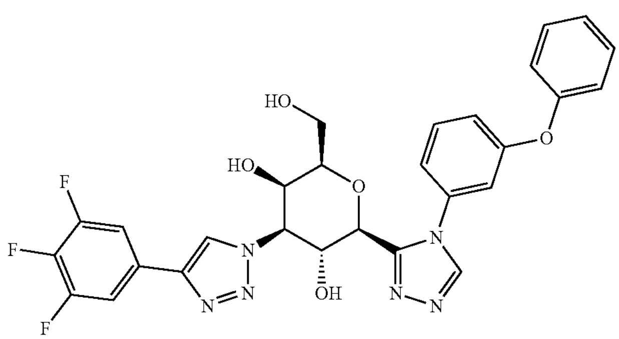 [SMILES: OC[C@H]1O[C@@H](c2nncn2-c2cccc(Oc3ccccc3)c2)[C@H](O)[C@@H](n2cc(-c3cc(F)c(F)c(F)c3)nn2)[C@H]1O] | 1.533 | 581.2 | A | ¹H NMR (400 MHz, METHANOL-d₄) δ 8.68 (s, 1H), 8.46 (s, 1H), 7.59-7.45 (m, 3H), 7.35-7.25 (m, 3H), 7.17 (t, J = 2.1 Hz, 1H), 7.12-7.06 (m, 2H), 7.04-6.99 (m, 2H), 4.89 (dd, J = 10.6, 9.4 Hz, 1H), 4.82-4.77 (m, 1H), 4.42 (s, 1H), 4.44 (s, 1H), 4.04 (d, J = 2.0 Hz, 1H), 3.72-3.66 (m, 1H), 3.64-3.52 (m, 2H) |
| 79 | 0.17 | 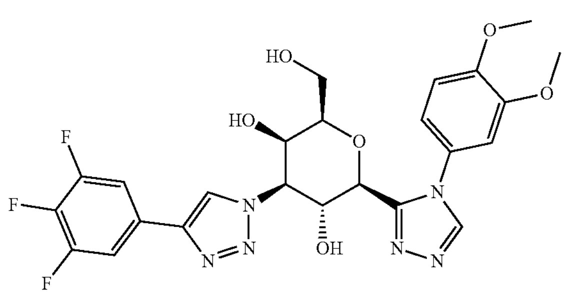 [SMILES: COc1ccc(-n2cnnc2[C@@H]2O[C@H](CO)[C@H](O)[C@H](n3cc(-c4cc(F)c(F)c(F)c4)nn3)[C@H]2O)cc1OC] | 1.125 | 549 | A | ¹H NMR (400 MHz, METHANOL-d₄) δ 8.63 (s, 1H), 8.47 (s, 1H), 7.55 (dd, J = 9.0, 6.6 Hz, 2H), 7.10 (d, J = 2.0 Hz, 1H), 7.07-7.04 (m, 2H), 4.95-4.88 (m, 1H), 4.84-4.77 (m, 1H), 4.42 (d, J = 9.3 Hz, 1H), 4.04-4.01 (m, 1H), 3.82 (s, 3H), 3.80 (s, 3H), 3.77-3.66 (m, 2H), 3.63-3.57 (m, 1H) |

-continued

| Ex | hGal3 IC50, uM | Structure | LCMS t$_R$ (min) | M + H | Method | 1H NMR |
|---|---|---|---|---|---|---|
| 80 | 0.33 | 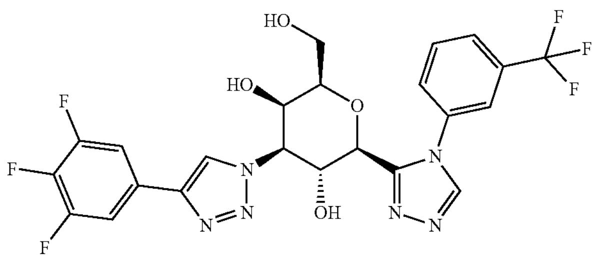 [SMILES: OC[C@H]1O[C@@H](c2nncn2-c2cccc(C(F)(F)F)c2)[C@H](O)[C@@H](n2cc(-c3cc(F)c(F)c(F)c3)nn2)[C@H]1O] | 1.354 | 557.1 | A | ¹H NMR (400 MHz, METHANOL-d$_4$) δ 8.76 (s, 1H), 8.44 (s, 1H), 7.92 (s, 1H), 7.88-7.82 (m, 2H), 7.78-7.71 (m, 1H), 7.55 (dd, J = 9.0, 6.6 Hz, 2H), 4.89 (dd, J = 10.5, 9.3 Hz, 1H), 4.83-4.78 (m, 1H), 4.41 (d, J = 9.3 Hz, 1H), 4.03 (d, J = 2.0 Hz, 1H), 3.75-3.71 (m, 1H), 3.70-3.64 (m, 1H), 3.60 (dd, J = 11.2, 4.9 Hz, 1H) |
| 81 | 5.59 | 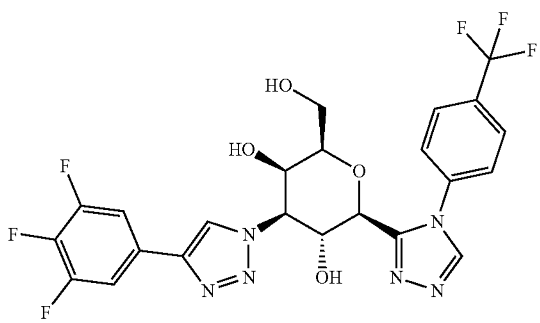 [SMILES: OC[C@H]1O[C@@H](c2nncn2-c2ccc(C(F)(F)F)cc2)[C@H](O)[C@@H](n2cc(-c3cc(F)c(F)c(F)c3)nn2)[C@H]1O] | 1.38 | 558.1 | A | ¹H NMR (400 MHz, METHANOL-d$_4$) δ 8.78 (s, 1H), 8.47 (s, 1H), 7.86 (d, J = 8.6 Hz, 2H), 7.81 (d, J = 8.1 Hz, 2H), 7.56 (dd, J = 8.9, 6.5 Hz, 2H), 4.99-4.92 (m, 1H), 4.85-4.79 (m, 1H), 4.41 (d, J = 9.3 Hz, 1H), 4.03 (d, J = 2.2 Hz, 1H), 3.78-3.74 (m, 1H), 3.72-3.66 (m, 1H), 3.60 (dd, J = 11.6, 4.3 Hz, 1H) |
| 82 | 0.58 | 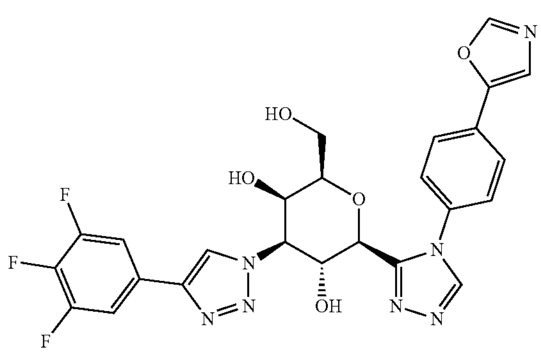 [SMILES: OC[C@H]1O[C@@H](c2nncn2-c2ccc(-c3cnco3)cc2)[C@H](O)[C@@H](n2cc(-c3cc(F)c(F)c(F)c3)nn2)[C@H]1O] | 1.093 | 556.2 | A | ¹H NMR (400 MHz, METHANOL-d$_4$) δ 8.74 (s, 1H), 8.48 (s, 1H), 8.24 (s, 1H), 7.92-7.87 (m, 2H), 7.70-7.65 (m, 2H), 7.60 (s, 1H), 7.56 (dd, J = 8.9, 6.5 Hz, 2H), 4.96 (dd, J = 10.6, 9.4 Hz, 1H), 4.81 (dd, J = 10.8, 2.9 Hz, 1H), 4.42 (d, J = 9.3 Hz, 1H), 4.03 (d, J = 2.9 Hz, 1H), 3.77-3.71 (m, 1H), 3.70-3.67 (m, 1H), 3.64-3.58 (m, 1H) |
| 83 | 0.90 | 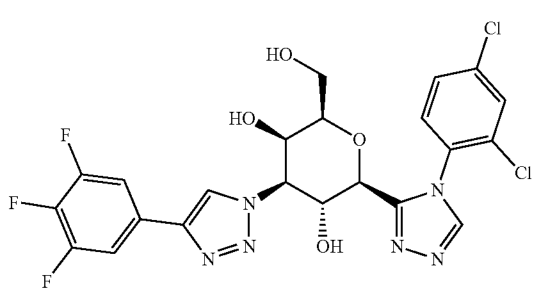 [SMILES: OC[C@H]1O[C@@H](c2nncn2-c2ccc(Cl)cc2Cl)[C@H](O)[C@@H](n2cc(-c3cc(F)c(F)c(F)c3)nn2)[C@H]1O] | 1.336 | 559.1 | A | ¹H NMR (400 MHz, METHANOL-d$_4$) δ 8.66 (s, 1H), 8.46 (s, 1H), 7.73 (d, J = 2.4 Hz, 1H), 7.56 (dd, J = 9.0, 6.6 Hz, 2H), 7.49 (dd, J = 8.6, 2.4 Hz, 2H), 4.83 (s, 1H), 4.78 (br. s., 1H), 4.28 (br. s., 1H), 4.00 (d, J = 1.7 Hz, 1H), 3.64-3.60 (m, 1H), 3.55 (d, J = 5.6 Hz, 2H) |

| Ex | hGal3 IC50, uM | Structure | LCMS t$_R$ (min) | M + H | Method | 1H NMR |
|---|---|---|---|---|---|---|
| 84 | 0.90 | 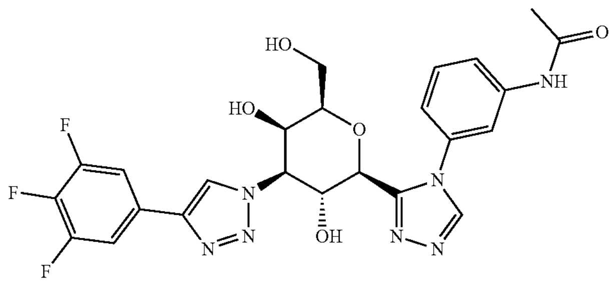 [SMILES: CC(=O)Nc1cccc(-n2cnnc2[C@@H]2O[C@H](CO)[C@H](O)[C@H](n3cc(-c4cc(F)c(F)c(F)c4)nn3)[C@H]2O)c1] | 1.007 | 546.2 | A | $^1$H NMR (400 MHz, METHANOL-d$_4$) δ 8.71 (s, 1H), 8.49 (s, 1H), 7.90 (t, J = 2.0 Hz, 1H), 7.61-7.53 (m, 3H), 7.45 (t, J = 8.1 Hz, 1H), 7.25 (ddd, J = 7.9, 2.1, 0.7 Hz, 1H), 4.98-4.91 (m, 1H), 4.84-4.78 (m, 1H), 4.44 (d, J = 9.3 Hz, 1H), 4.04 (d, J = 2.2 Hz, 1H), 3.80-3.76 (m, 1H), 3.71 (dd, J = 11.4, 7.0 Hz, 1H), 3.62 (dd, J = 11.5, 4.9 Hz, 1H), 2.07 (s, 3H) |
| 85 | 0.44 | 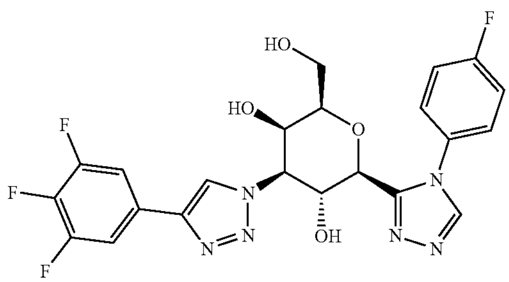 [SMILES: OC[C@H]1O[C@@H](c2nncn2-c2ccc(F)cc2)[C@H](O)[C@@H](n2cc(-c3cc(F)c(F)c(F)c3)nn2)[C@H]1O] | 1.151 | 507.1 | A | $^1$H NMR (400 MHz, METHANOL-d$_4$) δ 8.67 (s, 1H), 8.48 (s, 1H), 7.62-7.52 (m, 4H), 7.30-7.23 (m, 2H), 4.93 (dd, J = 10.6, 9.4 Hz, 1H), 4.80 (dd, J = 10.6, 2.8 Hz, 1H), 4.36 (d, J = 9.3 Hz, 1H), 4.02 (d, J = 2.4 Hz, 1H), 3.74-3.69 (m, 1H), 3.68-3.65 (m, 1H), 3.62-3.57 (m, 1H) |
| 86 | 0.38 | 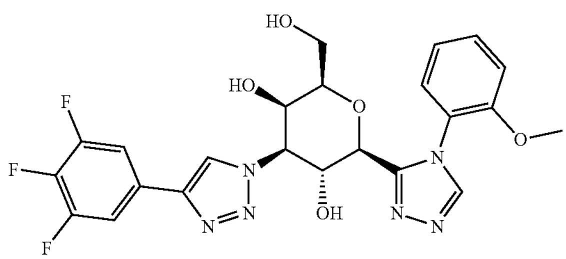 [SMILES: COc1ccccc1-n1cnnc1[C@@H]1O[C@H](CO)[C@H](O)[C@H](n2cc(-c3cc(F)c(F)c(F)c3)nn2)[C@H]1O] | 1.148 | 519.2 | A | $^1$H NMR (400 MHz, METHANOL-d$_4$) δ 8.52 (s, 1H), 8.47 (s, 1H), 7.55 (dd, J = 9.0, 6.6 Hz, 2H), 7.51-7.41 (m, 2H), 7.18 (dd, J = 8.4, 1.1 Hz, 1H), 7.05 (td, J = 7.7, 1.2 Hz, 1H), 4.89-4.82 (m, 1H), 4.76 (d, J = 2.9 Hz, 1H), 4.27 (d, J = 9.3 Hz, 1H), 4.00 (d, J = 2.9 Hz, 1H), 3.76 (s, 3H), 3.65-3.53 (m, 3H) |
| 87 | 0.10 | 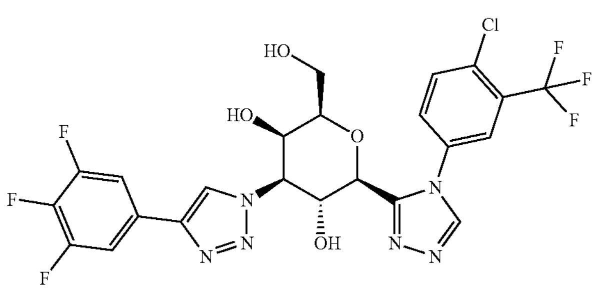 [SMILES: OC[C@H]1O[C@@H](c2nncn2-c2ccc(Cl)c(C(F)(F)F)c2)[C@H](O)[C@@H](n2cc(-c3cc(F)c(F)c(F)c3)nn2)[C@H]1O] | 1.492 | 591.1 | A | $^1$H NMR (400 MHz, METHANOL-d$_4$) δ 8.75 (s, 1H), 8.41 (s, 1H), 8.00 (d, J = 2.4 Hz, 1H), 7.85 (dd, J = 8.6, 2.7 Hz, 1H), 7.79 (d, J = 8.6 Hz, 1H), 7.54 (dd, J = 8.9, 6.7 Hz, 2H), 4.84-4.80 (m, 2H), 4.48-4.43 (m, 1H), 4.02 (d, J = 1.2 Hz, 1H), 3.77-3.72 (m, 1H), 3.66 (dd, J = 11.5, 6.8 Hz, 1H), 3.59 (dd, J = 11.5, 4.9 Hz, 1H) |
| 88 | 0.36 | 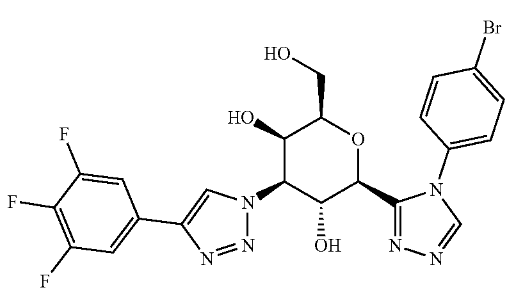 | 1.294 | 567.1 | A | $^1$H NMR (400 MHz, METHANOL-d$_4$) δ 8.70 (s, 1H), 8.48 (s, 1H), 7.71-7.67 (m, 2H), 7.56 (dd, J = 9.0, 6.6 Hz, 2H), 7.52-7.48 (m, 2H), 4.93 (dd, J = 10.8, 9.3 Hz, 1H), 4.81 (dd, J = 10.8, 2.9 Hz, 1H), 4.38 (d, J = 9.3 Hz, 1H), 4.04-4.01 (m, 1H), 3.75-3.65 (m, 2H), 3.62-3.57 (m, 1H) |

-continued

| Ex | hGal3 IC50, uM | Structure | LCMS $t_R$ (min) | M + H | Method | 1H NMR |
|---|---|---|---|---|---|---|
| 89 | 0.46 | 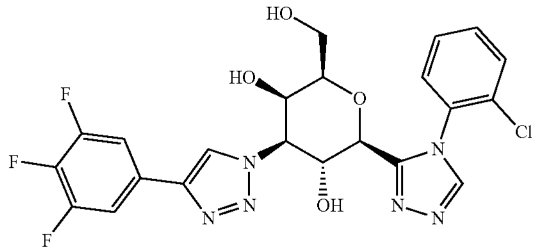 [SMILES: OC[C@H]1O[C@@H](c2nncn2-c2ccccc2Cl)[C@H](O)[C@@H](n2cc(-c3cc(F)c(F)c(F)c3)nn2)[C@H]1O] | 1.172 | 523.1 | A | ¹H NMR (400 MHz, METHANOL-d₄) δ 8.67 (br. s., 1H), 8.49-8.45 (m, 1H), 7.65-7.60 (m, 1H), 7.60-7.50 (m, 4H), 7.50-7.43 (m, 1H), 4.86-4.82 (m, 1H), 4.77 (d, J = 2.9 Hz, 1H), 4.26 (br. s., 1H), 4.00 (d, J = 2.4 Hz, 1H), 3.62-3.53 (m, 3H) |
| 90 | 0.52 | 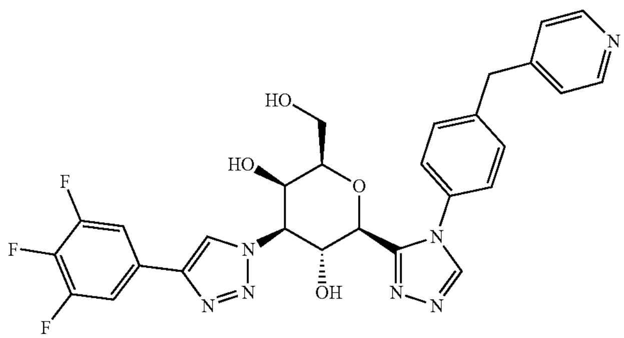 [SMILES: OC[C@H]1O[C@@H](c2nncn2-c2ccc(Cc3ccncc3)cc2)[C@H](O)[C@@H](n2cc(-c3cc(F)c(F)c(F)c3)nn2)[C@H]1O] | 1.17 | 580.2 | A | ¹H NMR (400 MHz, METHANOL-d₄) δ 8.66 (s, 1H), 8.45 (s, 1H), 8.35 (d, J = 5.6 Hz, 2H), 7.57-7.49 (m, 4H), 7.44-7.40 (m, 2H), 7.26 (d, J = 6.1 Hz, 2H), 4.95-4.88 (m, 1H), 4.84-4.77 (m, 1H), 4.46 (s, 1H), 4.39 (d, J = 9.5 Hz, 1H), 4.07 (s, 2H), 4.02 (d, J = 2.7 Hz, 1H), 3.74-3.69 (m, 1H), 3.68-3.64 (m, 1H), 3.62-3.56 (m, 1H) |
| 91 | 0.69 | 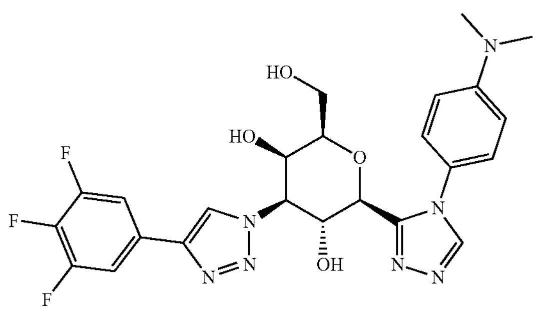 [SMILES: CN(C)c1ccc(-n2cnnc2[C@@H]2O[C@H](CO)[C@H](O)[C@H](n3cc(-c4cc(F)c(F)c(F)c4)nn3)[C@H]2O)cc1] | 1.266 | 532.2 | A | ¹H NMR (400 MHz, METHANOL-d₄) δ 8.55 (s, 1H), 8.48 (s, 1H), 7.56 (dd, J = 8.8, 6.6 Hz, 2H), 7.33-7.27 (m, 2H), 6.82-6.76 (m, 2H), 4.96-4.88 (m, 1H), 4.81-4.77 (m, 1H), 4.45 (s, 1H), 4.34 (d, J = 9.4 Hz, 1H), 4.02 (d, J = 2.7 Hz, 1H), 3.73-3.58 (m, 3H), 2.94 (s, 6H) |
| 92 | 0.36 | 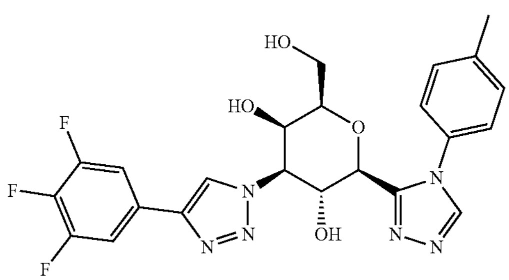 [SMILES: Cc1ccc(-n2cnnc2[C@@H]2O[C@H](CO)[C@H](O)[C@H](n3cc(-c4cc(F)c(F)c(F)c4)nn3)[C@H]2O)cc1] | 1.224 | 504.2 | A | ¹H NMR (400 MHz, METHANOL-d₄) δ 8.64 (s, 1H), 8.48 (s, 1H), 7.56 (dd, J = 9.0, 6.6 Hz, 2H), 7.44-7.39 (m, 2H), 7.36-7.31 (m, 2H), 4.98-4.91 (m, 1H), 4.78 (dd, J = 10.5, 2.9 Hz, 1H), 4.36 (d, J = 9.5 Hz, 1H), 4.02 (d, J = 2.7 Hz, 1H), 3.72-3.64 (m, 2H), 3.64-3.57 (m, 1H), 2.36 (s, 3H) |
| 93 | 0.19 | 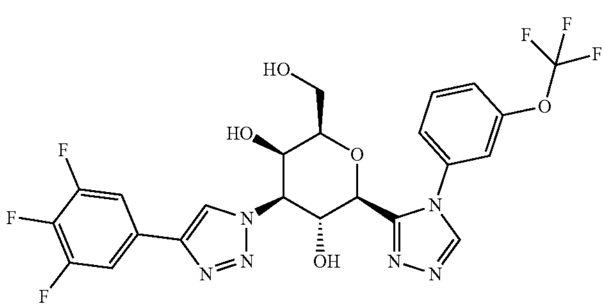 [SMILES: OC[C@H]1O[C@@H](c2nncn2-c2cccc(OC(F)(F)F)c2)[C@H](O)[C@@H](n2cc(-c3cc(F)c(F)c(F)c3)nn2)[C@H]1O] | 1.407 | 573.1 | A | ¹H NMR (400 MHz, METHANOL-d₄) δ 8.74 (s, 1H), 8.46 (s, 1H), 7.67-7.53 (m, 5H), 7.47 (ddt, J = 7.8, 2.3, 1.2 Hz, 1H), 4.92 (dd, J = 10.8, 9.3 Hz, 1H), 4.81 (dd, J = 10.8, 2.9 Hz, 1H), 4.42 (d, J = 9.3 Hz, 1H), 4.04 (dd, J = 2.9, 0.7 Hz, 1H), 3.76-3.71 (m, 1H), 3.67 (dd, J = 11.4, 7.0 Hz, 1H), 3.60 (dd, J = 11.5, 4.9 Hz, 1H) |

-continued

| Ex | hGal3 IC50, uM | Structure | LCMS $t_R$ (min) | M + H | Method | 1H NMR |
|---|---|---|---|---|---|---|
| 94 | 1.13 | 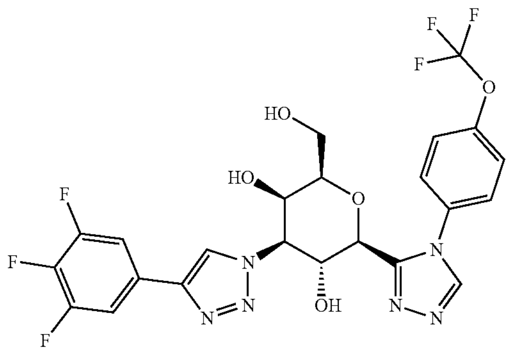 [SMILES: OC[C@H]1O[C@@H](c2nncn2-c2ccc(OC(F)(F)F)cc2)[C@H](O)[C@@H](n2cc(-c3cc(F)c(F)c(F)c3)nn2)[C@H]1O] | 1.432 | 573.1 | A | ¹H NMR (400 MHz, METHANOL-d₄) δ 8.72 (s, 1H), 8.46 (s, 1H), 7.73-7.67 (m, 2H), 7.55 (dd, J = 9.0, 6.6 Hz, 2H), 7.45 (dd, J = 9.0, 0.7 Hz, 2H), 4.92 (dd, J = 10.8, 9.3 Hz, 1H), 4.82 (dd, J = 10.8, 2.9 Hz, 1H), 4.40 (d, J = 9.3 Hz, 1H), 4.02 (dd, J = 2.9, 0.7 Hz, 1H), 3.77-3.73 (m, 1H), 3.72-3.65 (m, 1H), 3.60 (dd, J = 11.5, 4.4 Hz, 1H) |
| 95 | 0.13 | 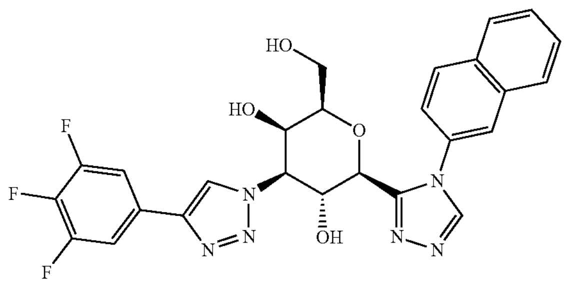 [SMILES: OC[C@H]1O[C@@H](c2nncn2-c2ccc3ccccc3c2)[C@H](O)[C@@H](n2cc(-c3cc(F)c(F)c(F)c3)nn2)[C@H]1O] | 1.362 | 539.2 | A | ¹H NMR (400 MHz, METHANOL-d₄) δ 8.80 (s, 1H), 8.45 (s, 1H), 8.16 (d, J = 1.7 Hz, 1H), 8.03 (d, J = 8.8 Hz, 1H), 8.00-7.91 (m, 2H), 7.61 (dd, J = 8.7, 2.3 Hz, 1H), 7.57-7.51 (m, 4H), 5.02-4.94 (m, 1H), 4.78 (dd, J = 10.8, 2.9 Hz, 1H), 4.44 (d, J = 9.5 Hz, 1H), 4.01 (d, J = 2.7 Hz, 1H), 3.77-3.71 (m, 2H), 3.66-3.60 (m, 1H) |
| 96 | 0.29 | 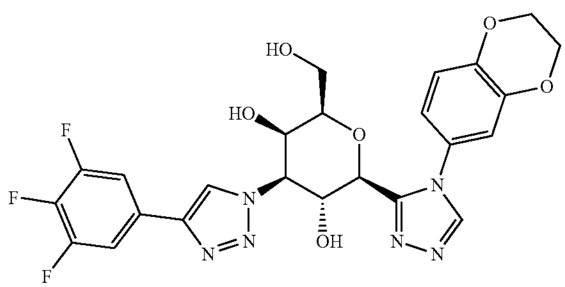 [SMILES: OC[C@H]1O[C@@H](c2nncn2-c2ccc3c(c2)OCCO3)[C@H](O)[C@@H](n2cc(-c3cc(F)c(F)c(F)c3)nn2)[C@H]1O] | 1.147 | 547.1 | A | ¹H NMR (400 MHz, METHANOL-d₄) δ 8.59 (s, 1H), 8.48 (s, 1H), 7.56 (dd, J = 8.8, 6.8 Hz, 2H), 7.04 (d, J = 2.4 Hz, 1H), 7.01-6.92 (m, 2H), 4.94-4.87 (m, 1H), 4.84-4.77 (m, 1H), 4.41-4.36 (m, 1H), 4.25-4.21 (m, 4H), 4.03 (d, J = 2.4 Hz, 1H), 3.75-3.69 (m, 1H), 3.66 (d, J = 6.6 Hz, 1H), 3.63-3.57 (m, 1H) |
| 97 | 0.35 | 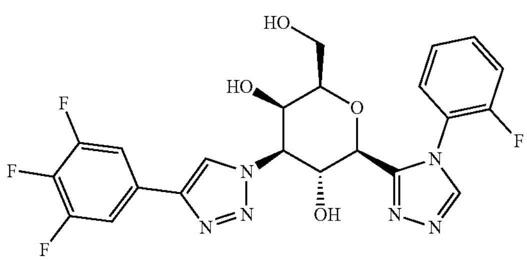 [SMILES: OC[C@H]1O[C@@H](c2nncn2-c2ccccc2F)[C@H](O)[C@@H](n2cc(-c3cc(F)c(F)c(F)c3)nn2)[C@H]1O] | 1.114 | 507.1 | A | ¹H NMR (400 MHz, METHANOL-d₄) δ 8.68 (d, J = 1.5 Hz, 1H), 8.50-8.46 (m, 1H), 7.64 (td, J = 7.9, 1.6 Hz, 1H), 7.60-7.51 (m, 3H), 7.39-7.31 (m, 2H), 4.89 (dd, J = 10.6, 9.2 Hz, 1H), 4.78 (dd, J = 10.8, 2.9 Hz, 1H), 4.36 (d, J = 9.3 Hz, 1H), 4.02 (d, J = 2.0 Hz, 1H), 3.69-3.64 (m, 1H), 3.63-3.53 (m, 2H) |
| 98 | 0.45 | 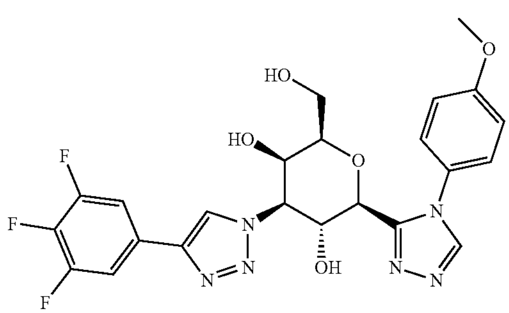 [SMILES: COc1ccc(-n2cnnc2[C@@H]2O[C@H](CO)[C@H](O)[C@H](n3cc(-c4cc(F)c(F)c(F)c4)nn3)[C@H]2O)cc1] | 1.161 | 519.2 | A | ¹H NMR (400 MHz, METHANOL-d₄) δ 8.61 (s, 1H), 8.48 (s, 1H), 7.56 (dd, J = 9.0, 6.6 Hz, 2H), 7.47-7.43 (m, 2H), 7.07-7.01 (m, 2H), 4.92 (dd, J = 10.8, 9.3 Hz, 1H), 4.79 (dd, J = 10.8, 2.9 Hz, 1H), 4.37-4.32 (m, 1H), 4.02 (d, J = 3.2 Hz, 1H), 3.79 (s, 3H), 3.73-3.65 (m, 2H), 3.64-3.58 (m, 1H) |

-continued

| Ex | hGal3 IC50, uM | Structure | LCMS $t_R$ (min) | M + H | Method | 1H NMR |
|---|---|---|---|---|---|---|
| 99 | 0.89 | 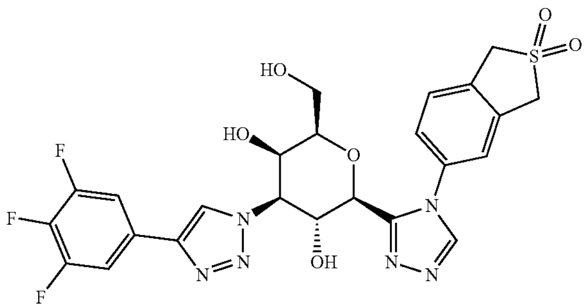 [SMILES: O=S1(=O)Cc2ccc(-n3cnnc3[C@@H]3O[C@H](CO)[C@H](O)[C@H](n4cc(-c5cc(F)c(F)c(F)c5)nn4)[C@H]3O)cc2C1] | 1.01 | 579.2 | A | ¹H NMR (400 MHz, METHANOL-d₄) δ 8.73 (s, 1H), 8.41 (s, 1H), 7.76 (s, 1H), 7.59-7.53 (m, 4H), 4.83-4.79 (m, 1H), 4.48-4.41 (m, 5H), 4.02 (d, J = 1.5 Hz, 1H), 3.78-3.68 (m, 2H), 3.61 (dd, J = 11.1, 3.8 Hz, 1H) |
| 100 | 0.47 | 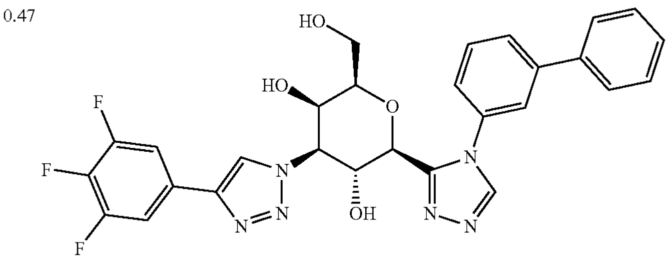 | 1.514 | 565.2 | A | ¹H NMR (400 MHz, METHANOL-d₄) δ 8.75 (s, 1H), 8.46 (s, 1H), 7.82-7.76 (m, 2H), 7.66-7.58 (m, 3H), 7.57-7.51 (m, 2H), 7.42-7.36 (m, 2H), 7.34-7.23 (m, 2H), 4.98-4.90 (m, 1H), 4.84-4.79 (m, 1H), 4.50-4.47 (m, 1H), 4.03 (d, J = 2.4 Hz, 1H), 3.77-3.72 (m, 1H), 3.68 (dd, J = 11.5, 6.8 Hz, 1H), 3.63-3.57 (m, 1H) |
| 101 | 0.08 | 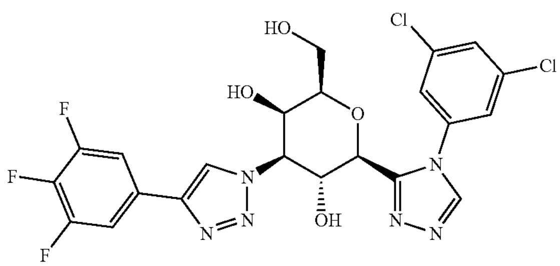 [SMILES: OC[C@H]1O[C@@H](c2nncn2-c2cc(Cl)cc(Cl)c2)[C@H](O)[C@@H](n2cc(-c3cc(F)c(F)c(F)c3)nn2)[C@H]1O] | 1.389 | 559.1 | A | ¹H NMR (400 MHz, METHANOL-d₄) δ 8.72 (s, 1H), 8.44 (s, 1H), 7.67-7.63 (m, 3H), 7.58-7.51 (m, 2H), 4.88-4.82 (m, 1H), 4.78-4.81 (m, 1H), 4.46 (d, J = 8.1 Hz, 1H), 4.04 (d, J = 2.0 Hz, 1H), 3.80-3.76 (m, 1H), 3.70 (dd, J = 11.4, 7.0 Hz, 1H), 3.64-3.58 (m, 1H) |
| 102 | 0.30 | 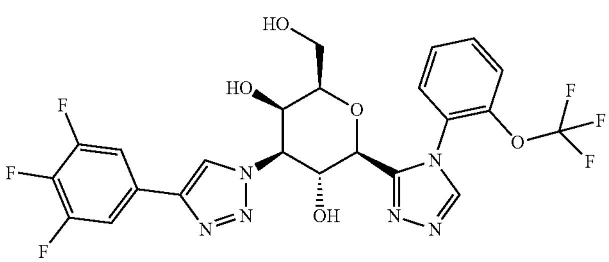 [SMILES: OC[C@H]1O[C@@H](c2nncn2-c2ccccc2OC(F)(F)F)[C@H](O)[C@@H](n2cc(-c3cc(F)c(F)c(F)c3)nn2)[C@H]1O] | 1.324 | 573.1 | A | ¹H NMR (400 MHz, METHANOL-d₄) δ 8.67 (s, 1H), 8.48 (s, 1H), 7.71 (dd, J = 7.8, 1.7 Hz, 1H), 7.68-7.61 (m, 1H), 7.59-7.49 (m, 4H), 4.95-4.88 (m, 1H), 4.78 (dd, J = 10.8, 2.9 Hz, 1H), 4.28 (d, J = 9.3 Hz, 1H), 4.02 (d, J = 2.2 Hz, 1H), 3.63 (t, J = 6.5 Hz, 1H), 3.56 (d, J = 6.1 Hz, 2H) |
| 103 | 0.70 | 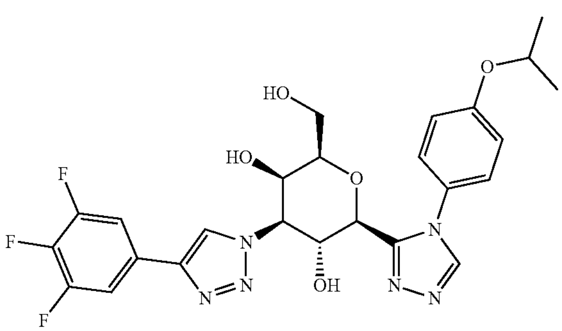 [SMILES: CC(C)Oc1ccc(-n2cnnc2[C@@H]2O[C@H](CO)[C@H](O)[C@H](n3cc(-c4cc(F)c(F)c(F)c4)nn3)[C@H]2O)cc1] | 1.395 | 547.2 | A | ¹H NMR (400 MHz, METHANOL-d₄) δ 8.61 (s, 1H), 8.47 (s, 1H), 7.56 (dd, J = 9.0, 6.6 Hz, 2H), 7.44-7.39 (m, 2H), 7.03-6.98 (m, 2H), 4.91 (dd, J = 10.6, 9.4 Hz, 1H), 4.80 (dd, J = 10.8, 2.9 Hz, 1H), 4.61 (dt, J = 12.0, 6.1 Hz, 1H), 4.36 (d, J = 9.3 Hz, 1H), 4.02 (d, J = 2.9 Hz, 1H), 3.73-3.65 (m, 2H), 3.63-3.57 (m, 1H), 1.27 (dd, J = 6.0, 1.8 Hz, 6H) |

-continued

| Ex | hGal3 IC50, uM | Structure | LCMS $t_R$ (min) | M + H | Method | 1H NMR |
|---|---|---|---|---|---|---|
| 104 | 0.82 | 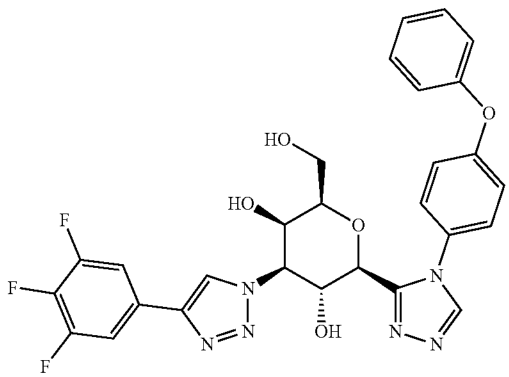 [SMILES: OC[C@H]1O[C@@H](c2nncn2-c2ccc(Oc3ccccc3)cc2)[C@H](O)[C@@H](n2cc(-c3cc(F)c(F)c(F)c3)nn2)[C@H]1O] | 1.544 | 581.2 | A | 1H NMR (400 MHz, METHANOL-d4) δ 8.68 (br. s., 1H), 8.47 (s, 1H), 7.59-7.49 (m, 4H), 7.37-7.30 (m, 2H), 7.14-7.05 (m, 3H), 7.04-6.99 (m, 2H), 4.95-4.88 (m, 1H), 4.84-4.79 (m, 1H), 4.41 (d, J = 9.3 Hz, 1H), 4.03 (dd, J = 2.9, 0.7 Hz, 1H), 3.76-3.64 (m, 2H), 3.62-3.56 (m, 1H) |
| 105 | 0.33 | 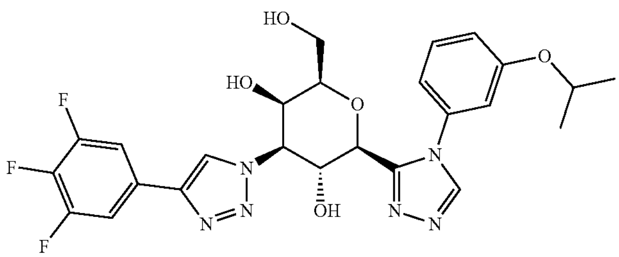 [SMILES: CC(C)Oc1cccc(-n2cnnc2[C@@H]2O[C@H](CO)[C@H](O)[C@H](n3cc(-c4cc(F)c(F)c(F)c4)nn3)[C@H]2O)c1] | 1.508 | 547.2 | A | 1H NMR (400 MHz, METHANOL-d4) δ 8.66 (s, 1H), 8.48 (s, 1H), 7.60-7.52 (m, 2H), 7.43-7.37 (m, 1H), 7.09-7.01 (m, 3H), 4.92 (dd, J = 10.8, 9.3 Hz, 1H), 4.81 (dd, J = 10.8, 2.8 Hz, 1H), 4.62 (dt, J = 12.0, 6.0 Hz, 1H), 4.46-4.41 (m, 1H), 4.04 (d, J = 3.0 Hz, 1H), 3.76-3.65 (m, 2H), 3.64-3.57 (m, 1H), 1.25 (dd, J = 6.0, 1.5 Hz, 6H) |
| 106 | 0.76 | 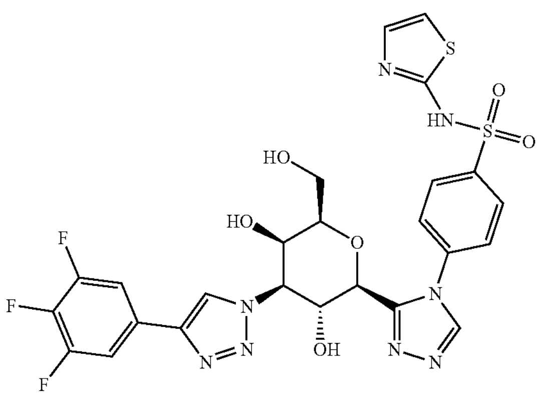 [SMILES: O=S(=O)(Nc1nccs1)c1ccc(-n2cnnc2[C@@H]2O[C@H](CO)[C@H](O)[C@H](n3cc(-c4cc(F)c(F)c(F)c4)nn3)[C@H]2O)cc1] | 1.108 | 651.1 | A | 1H NMR (400 MHz, METHANOL-d4) δ 8.73 (s, 1H), 8.46 (s, 1H), 8.07-8.01 (m, 2H), 7.74-7.68 (m, 2H), 7.61-7.52 (m, 3H), 7.01 (d, J = 4.0 Hz, 1H), 6.63 (d, J = 4.5 Hz, 1H), 4.96-4.88 (m, 1H), 4.81 (dt, J = 13.7, 3.2 Hz, 1H), 4.41 (d, J = 9.0 Hz, 1H), 4.02 (d, J = 2.0 Hz, 1H), 3.75 (dd, J = 7.5, 4.0 Hz, 1H), 3.72-3.64 (m, 1H), 3.64-3.57 (m, 1H) |
| 107 | 0.05 | 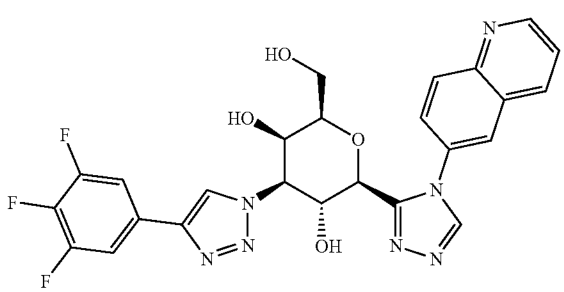 [SMILES: OC[C@H]1O[C@@H](c2nncn2-c2ccc3ncccc3c2)[C@H](O)[C@@H](n2cc(-c3cc(F)c(F)c(F)c3)nn2)[C@H]1O] | 1.177 | 540.2 | A | 1H NMR (400 MHz, METHANOL-d4) δ 8.92 (dd, J = 4.3, 1.8 Hz, 1H), 8.85 (s, 1H), 8.49-8.45 (m, 2H), 8.31 (d, J = 2.5 Hz, 1H), 8.18 (d, J= 9.0 Hz, 1H), 7.93 (dd, J = 8.8, 2.3 Hz, 1H), 7.62-7.52 (m, 3H), 5.02-4.95 (m, 1H), 4.84-4.77 (m, 1H), 4.46 (d, J = 9.5 Hz, 1H), 4.02-4.00 (m, 1H), 3.79-3.71 (m, 2H), 3.66-3.60 (m, 1H) |

-continued

| Ex | hGal3 IC50, uM | Structure | LCMS t_R (min) | M + H | Method | 1H NMR |
|---|---|---|---|---|---|---|
| 108 | 0.37 | 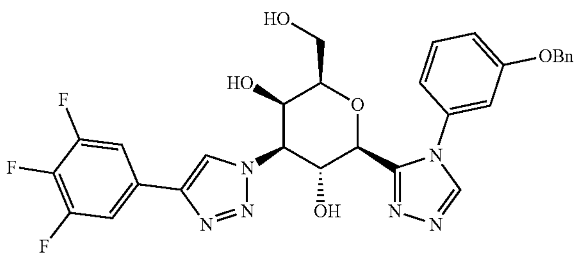 [SMILES: OC[C@H]1O[C@@H](c2nncn2-c2cccc(OCc3ccccc3)c2)[C@H](O)[C@@H](n2cc(-c3cc(F)c(F)c(F)c3)nn2)[C@H]1O] | 1.686 | 595.2 | A | $^1$H NMR (400 MHz, METHANOL-d$_4$) δ 8.66 (s, 1H), 8.47 (s, 1H), 7.56 (dd, J = 8.8, 6.8 Hz, 2H), 7.46-7.35 (m, 3H), 7.32-7.18 (m, 4H), 7.17-7.08 (m, 2H), 5.10 (s, 2H), 4.96-4.89 (m, 1H), 4.85-4.80 (m, 1H), 4.43 (d, J = 9.0 Hz, 1H), 4.03 (d, J = 3.0 Hz, 1H), 3.74-3.57 (m, 3H) |
| 109 | 0.52 | 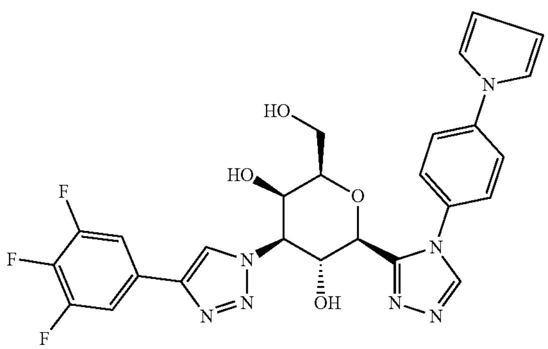 [SMILES: OC[C@H]1O[C@@H](c2nncn2-c2ccc(-n3cccc3)cc2)[C@H](O)[C@@H](n2cc(-c3cc(F)c(F)c(F)c3)nn2)[C@H]1O] | 1.494 | 554.2 | A | $^1$H NMR (400 MHz, METHANOL-d$_4$) δ 8.71 (s, 1H), 8.48 (s, 1H), 7.66-7.60 (m, 4H), 7.56 (dd, J = 9.0, 6.5 Hz, 2H), 7.23-7.19 (m, 2H), 6.28-6.24 (m, 2H), 4.95 (dd, J = 10.8, 9.3 Hz, 1H), 4.85-4.79 (m, 1H), 4.44-4.40 (m, 1H), 4.03 (d, J = 3.0 Hz, 1H), 3.78-3.67 (m, 2H), 3.65-3.58 (m, 1H) |
| 110 | 1.55 | 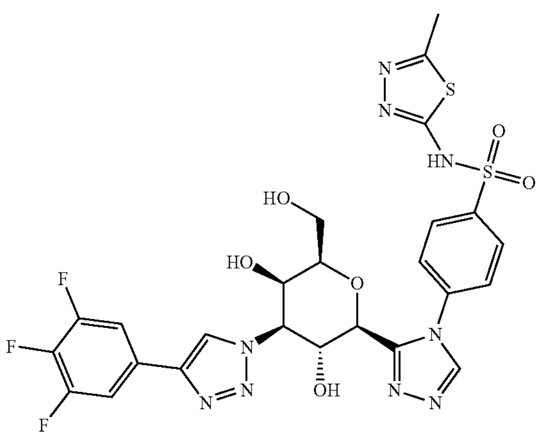 [SMILES: Cc1nnc(NS(=O)(=O)c2ccc(-n3cnnc3[C@@H]3O[C@H](CO)[C@H](O)[C@H](n4cc(-c5cc(F)c(F)c(F)c5)nn4)[C@H]3O)cc2)s1] | 1.033 | 666.1 | A | $^1$H NMR (400 MHz, METHANOL-d$_4$) δ 8.75 (s, 1H), 8.46 (s, 1H), 8.03-7.99 (m, 2H), 7.78-7.73 (m, 2H), 7.56 (dd, J = 9.0, 6.5 Hz, 2H), 4.92-4.90 (m, 1H), 4.84-4.81 (m, 1H), 4.41 (d, J = 9.0 Hz, 1H), 4.02 (d, J = 3.5 Hz, 1H), 3.76-3.75 (m, 1H), 3.67 (d, J = 7.0 Hz, 1H), 3.60 (dd, J = 11.5, 4.5 Hz, 1H), 2.41 (s, 3H) |
| 111 | 0.82 | 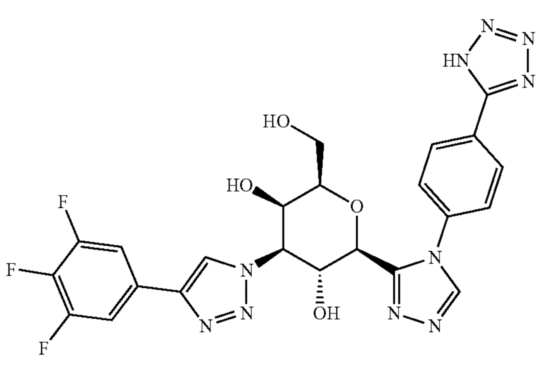 [SMILES: OC[C@H]1O[C@@H](c2nncn2-c2ccc(-c3nnn[nH]3)cc2)[C@H](O)[C@@H](n2cc(-c3cc(F)c(F)c(F)c3)nn2)[C@H]1O] | 0.907 | 557.2 | A | $^1$H NMR (400 MHz, METHANOL-d$_4$) δ 8.78 (s, 1H), 8.47 (s, 1H), 8.22-8.18 (m, 2H), 7.82-7.78 (m, 2H), 7.55 (dd, J = 9.0, 6.5 Hz, 2H), 4.96 (dd, J = 11.0, 9.5 Hz, 1H), 4.84-4.79 (m, 1H), 4.45 (d, J = 9.5 Hz, 1H), 4.03 (d, J = 2.5 Hz, 1H), 3.78-3.67 (m, 2H), 3.63-3.58 (m, 1H) |

-continued

| Ex | hGal3 IC50, uM | Structure | LCMS t_R (min) | M + H | Method | 1H NMR |
|---|---|---|---|---|---|---|
| 112 | 0.64 | 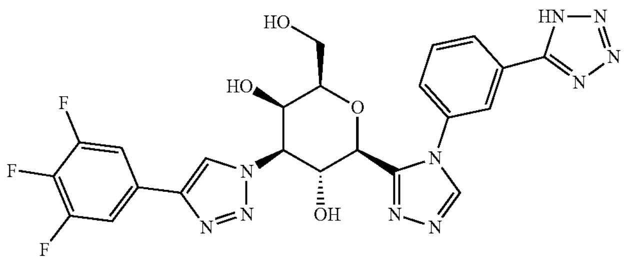 [SMILES: OC[C@H]1O[C@@H](c2nncn2-c2cccc(-c3nnn[nH]3)c2)[C@H](O)[C@@H](n2cc(-c3cc(F)c(F)c(F)c3)nn2)[C@H]1O] | 0.943 | 557.1 | A | $^1$H NMR (400 MHz, METHANOL-d$_4$) δ 8.79 (s, 1H), 8.48 (s, 1H), 8.24-8.19 (m, 2H), 7.84-7.79 (m, 2H), 7.56 (dd, J = 9.0, 6.5 Hz, 2H), 4.97 (dd, J = 11.0, 9.5 Hz, 1H), 4.85-4.80 (m, 1H), 4.46 (d, J = 9.5 Hz, 1H), 4.04 (d, J = 2.5 Hz, 1H), 3.79-3.67 (m, 2H), 3.64-3.59 (m, 1H) |
| 113 | 0.48 | 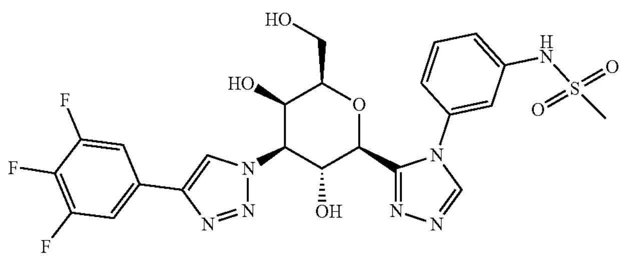 [SMILES: CS(=O)(=O)Nc1cccc(-n2cnnc2[C@@H]2O[C@H](CO)[C@H](O)[C@H](n3cc(-c4cc(F)c(F)c(F)c4)nn3)[C@H]2O)c1] | 1.167 | 582.2 | A | $^1$H NMR (400 MHz, METHANOL-d$_4$) δ 8.71 (s, 1H), 8.49 (s, 1H), 7.56 (dd, J = 8.8, 6.8 Hz, 2H), 7.51-7.44 (m, 2H), 7.38-7.33 (m, 1H), 7.29 (ddd, J = 8.0, 2.0, 1.0 Hz, 1H), 4.91 (dd, J = 10.5, 9.0 Hz, 1H), 4.84-4.79 (m, 1H), 4.49-4.44 (m, 1H), 4.04 (d J = 2.5 Hz, 1H), 3.79-3.75 (m, 1H), 3.70 (dd, J = 11.5, 7.0 Hz, 1H), 3.61 (dd, J = 11.5, 5.0 Hz, 1H), 2.99 (s, 3H) |
| 114 | 0.26 | 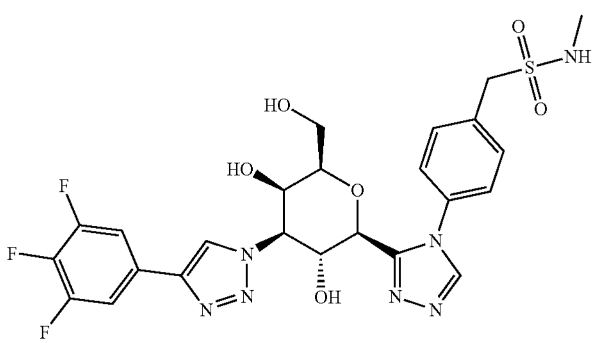 [SMILES: CNS(=O)(=O)Cc1ccc(-n2cnnc2[C@@H]2O[C@H](CO)[C@H](O)[C@H](n3cc(-c4cc(F)c(F)c(F)c4)nn3)[C@H]2O)cc1] | 1.162 | 596.1 | A | $^1$H NMR (400 MHz, METHANOL-d$_4$) δ 8.71 (s, 1H), 8.42 (s, 1H), 7.59 (s, 4H), 7.58-7.54 (m, 2H), 4.84-4.77 (m, 2H), 4.45 (d, J = 9.0 Hz, 1H), 4.37 (s, 2H), 4.02 (d, J = 2.5 Hz, 1H), 3.76-3.67 (m, 2H), 3.64-3.58 (m, 1H), 2.66 (s, 3H) |
| 115 | 11.11 | 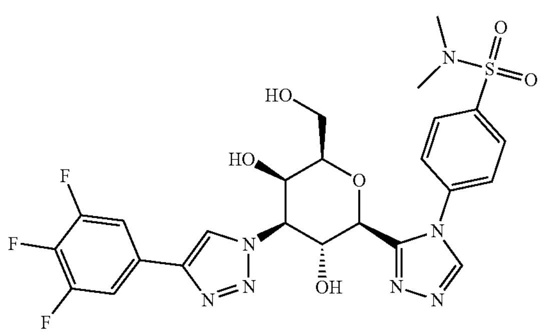 [SMILES: CN(C)S(=O)(=O)c1ccc(-n2cnnc2[C@@H]2O[C@H](CO)[C@H](O)[C@H](n3cc(-c4cc(F)c(F)c(F)c4)nn3)[C@H]2O)cc1] | 1.391 | 596.2 | A | $^1$H NMR (400 MHz, METHANOL-d$_4$) δ 8.50 (s, 1H), 8.23 (s, 1H), 7.42-7.37 (m, 2H), 7.28 (d, J = 9.0 Hz, 2H), 6.74 (d, J = 9.0 Hz, 2H), 5.62 (t, J = 9.8 Hz, 1H), 5.29 (dd, J = 10.5, 3.0 Hz, 1H), 4.89 (d, J = 9.5 Hz, 1H), 4.20 (d, J = 2.5 Hz, 1H), 4.00-3.95 (m, 1H), 3.78-3.66 (m, 2H), 2.31 (s, 6H) |

-continued

| Ex | hGal3 IC50, uM | Structure | LCMS $t_R$ (min) | M + H | Method | 1H NMR |
|---|---|---|---|---|---|---|
| 116 | 0.67 | 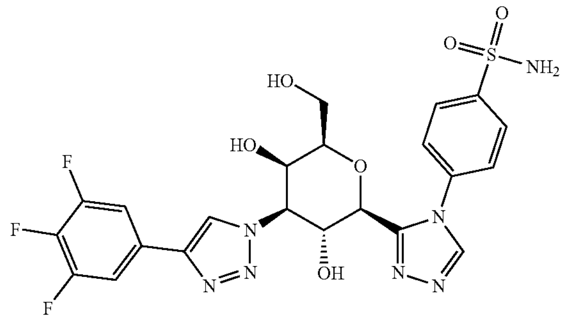 [SMILES: NS(=O)(=O)c1ccc(-n2cnnc2[C@@H]2O[C@H](CO)[C@H](O)[C@H](n3cc(-c4cc(F)c(F)c(F)c4)nn3)[C@H]2O)cc1] | 1.085 | 568.1 | A | ¹H NMR (400 MHz, METHANOL-d₄) δ 8.77 (s, 1H), 8.47 (s, 1H), 8.06-8.03 (m, 2H), 7.79-7.75 (m, 2H), 7.56 (dd, J = 8.8, 6.8 Hz, 2H), 4.98-4.91 (m, 1H), 4.84-4.79 (m, 1H), 4.41 (d, J = 9.0 Hz, 1H), 4.03 (d, J = 3.0 Hz, 1H), 3.78-3.73 (m, 1H), 3.73-3.67 (m, 1H), 3.61 (dd, J = 11.3, 4.3 Hz, 1H) |
| 117 | 1.46 | 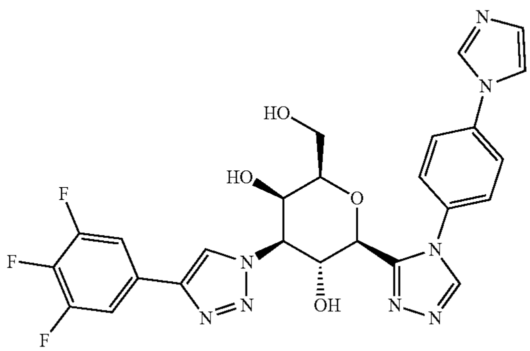 [SMILES: OC[C@H]1O[C@@H](c2nncn2-c2ccc(-n3ccnc3)cc2)[C@H](O)[C@@H](n2cc(-c3cc(F)c(F)c(F)c3)nn2)[C@H]1O] | 1.132 | 555.2 | A | ¹H NMR (400 MHz, METHANOL-d₄) δ 8.74 (s, 1H), 8.49 (s, 1H), 8.19 (s, 1H), 7.79-7.71 (m, 4H), 7.62 (s, 1H), 7.59-7.52 (m, 2H), 7.12 (s, 1H), 4.96 (dd, J = 10.8, 9.3 Hz, 1H), 4.81 (dd, J = 11.0, 3.0 Hz, 1H), 4.43 (d, J = 9.5 Hz, 1H), 4.06-4.02 (m, 1H), 3.77-3.72 (m, 1H), 3.71-3.67 (m, 1H), 3.65-3.58 (m, 1H) |
| 118 | 0.16 | 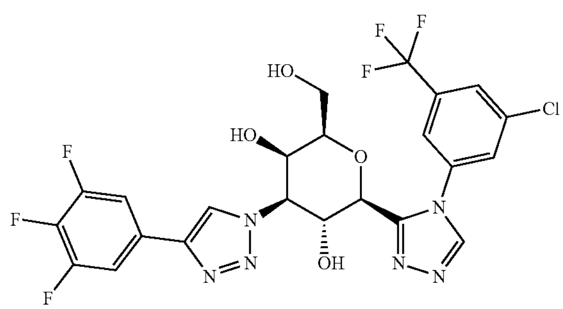 [SMILES: OC[C@H]1O[C@@H](c2nncn2-c2cc(Cl)cc(C(F)(F)F)c2)[C@H](O)[C@@H](n2cc(-c3cc(F)c(F)c(F)c3)nn2)[C@H]1O] | 1.584 | 591.1 | A | ¹H NMR (400 MHz, METHANOL-d₄) δ 8.78 (s, 1H), 8.41 (s, 1H), 8.00 (t, J = 2.0 Hz, 1H), 7.91 (d, J = 5.4 Hz, 2H), 7.55 (dd, J = 9.0, 6.6 Hz, 2H), 5.05-4.98 (m, 1H), 4.84-4.81 (m, 1H), 4.50-4.46 (m, 1H), 4.03 (s, 1H), 3.79-3.74 (m, 1H), 3.68 (dd, J = 11.5, 7.1 Hz, 1H), 3.59 (dd, J = 11.5, 5.1 Hz, 1H) |
| 119 | 2.79 | 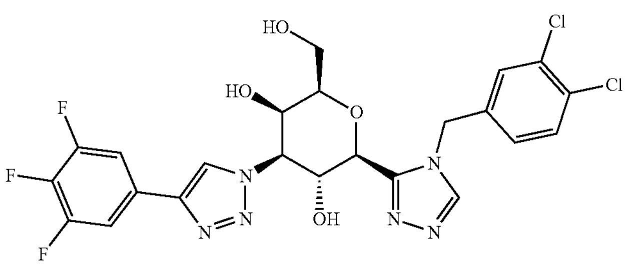 [SMILES: OC[C@H]1O[C@@H](c2nncn2Cc2ccc(Cl)c(Cl)c2)[C@H](O)[C@@H](n2cc(-c3cc(F)c(F)c(F)c3)nn2)[C@H]1O] | 1.553 | 573.1 | A | ¹H NMR (400 MHz, METHANOL-d₄) δ 8.53 (s, 1H), 8.40-8.37 (m, 1H), 7.55 (dd, J = 8.8, 6.6 Hz, 2H), 7.51-7.44 (m, 2H), 7.19 (dd, J = 8.3, 2.2 Hz, 1H), 5.47-5.35 (m, 2H), 4.87 (dd, J = 9.4, 1.8 Hz, 1H), 4.69 (d, J = 9.8 Hz, 1H), 4.49 (s, 1H), 4.09 (d, J = 2.2 Hz, 1H), 3.86-3.81 (m, 1H), 3.63-3.58 (m, 2H) |
| 120 | 0.03 | 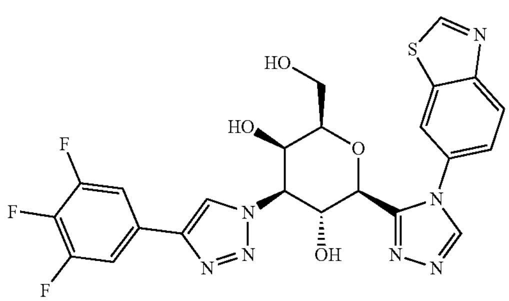 [SMILES: OC[C@H]1O[C@@H](c2nncn2-c2ccc3ncsc3c2)[C@H](O)[C@@H](n2cc(-c3cc(F)c(F)c(F)c3)nn2)[C@H]1O] | 1.174 | 546.1 | A | ¹H NMR (400 MHz, METHANOL-d₄) δ 9.34 (s, 1H), 8.79 (s, 1H), 8.46 (s, 1H), 8.42 (d, J = 2.2 Hz, 1H), 8.19 (d, J = 8.6 Hz, 1H), 7.72 (dd, J = 8.6, 2.2 Hz, 1H), 7.55 (dd, J = 9.0, 6.6 Hz, 2H), 4.95 (dd, J = 10.6, 9.4 Hz, 1H), 4.81 (d, J = 2.9 Hz, 1H), 4.42 (d, J = 9.5 Hz, 1H), 4.00 (d, J = 2.9 Hz, 1H), 3.75-3.67 (m, 2H), 3.64-3.57 (m, 1H) |

| Ex | hGal3 IC50, uM | Structure | LCMS $t_R$ (min) | M + H | Method | 1H NMR |
|---|---|---|---|---|---|---|
| 121 | 0.26 | 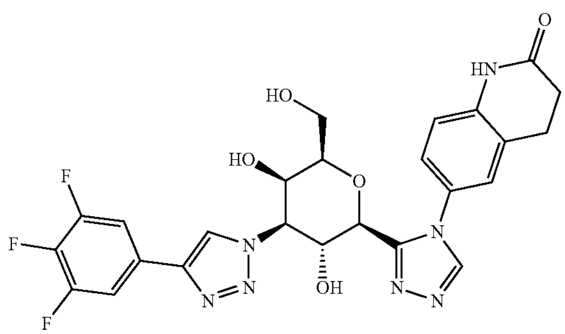 [SMILES: O=C1CCc2cc(-n3cnnc3[C@@H]3O[C@H](CO)[C@H](O)[C@H](n4cc(-c5cc(F)c(F)c(F)c5)nn4)[C@H]3O)ccc2N1] | 1.077 | 558.2 | A | $^1$H NMR (400 MHz, METHANOL-d$_4$) δ 8.65 (s, 1H), 8.48 (s, 1H), 7.56 (dd, J = 8.9, 6.5 Hz, 2H), 7.43 (d, J = 2.2 Hz, 1H), 7.33 (dd, J = 8.6, 2.4 Hz, 1H), 6.97 (d, J = 8.3 Hz, 1H), 4.97-4.88 (m, 1H), 4.85-4.82 (m, 1H), 4.37 (d, J = 9.5 Hz, 1H), 4.02 (d, J = 2.7 Hz, 1H), 3.76-3.71 (m, 1H), 3.70-3.67 (m, 1H), 3.63-3.57 (m, 1H), 2.98 (td, J = 7.7, 4.2 Hz, 2H), 2.57-2.51 (m, 2H) |
| 122 | 3.94 | 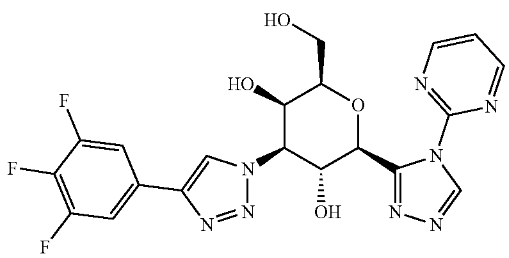 [SMILES: OC[C@H]1O[C@@H](c2nncn2-c2ncccn2)[C@H](O)[C@@H](n2cc(-c3cc(F)c(F)c(F)c3)nn2)[C@H]1O] | 1.388 | 492.1 | A | $^1$H NMR (400 MHz, METHANOL-d$_4$) δ 8.48 (s, 1H), 8.16 (s, 1H), 7.72 (dd, J = 6.8, 2.9 Hz, 2H), 7.56 (dd, J = 8.9, 6.7 Hz, 2H), 7.37-7.32 (m, 1H), 4.83 (dd, J = 10.8, 2.9 Hz, 1H), 4.53 (dd, J = 10.8, 9.3 Hz, 1H), 4.05 (d, J = 2.7 Hz, 1H), 4.00 (d, J = 9.3 Hz, 1H), 3.85-3.81 (m, 1H), 3.79-3.74 (m, 1H), 3.65 (dd, J = 11.2, 4.2 Hz, 1H) |
| 123 | 0.10 | 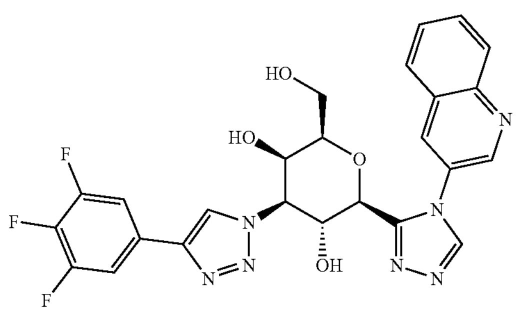 [SMILES: OC[C@H]1O[C@@H](c2nncn2-c2cnc3ccccc3c2)[C@H](O)[C@@H](n2cc(-c3cc(F)c(F)c(F)c3)nn2)[C@H]1O] | 1.271 | 540.1 | A | $^1$H NMR (400 MHz, METHANOL-d$_4$) δ 8.98 (d, J = 2.4 Hz, 1H), 8.89 (s, 1H), 8.72 (d, J = 2.2 Hz, 1H), 8.42 (s, 1H), 8.06 (d, J = 8.6 Hz, 1H), 8.10 (d, J = 8.3 Hz, 1H), 7.85 (ddd, J= 8.5, 7.0, 1.3 Hz, 1H), 7.71-7.65 (m, 1H), 7.54 (dd, J = 9.0, 6.6 Hz, 2H), 4.95-4.88 (m, 1H), 4.81 (d, J = 2.9 Hz, 1H), 4.49 (d, J = 9.5 Hz, 1H), 3.99 (d, J = 2.7 Hz, 1H), 3.78-3.72 (m, 1H), 3.72-3.68 (m, 1H), 3.62-3.57 (m, 1H) |
| 124 | 0.40 | 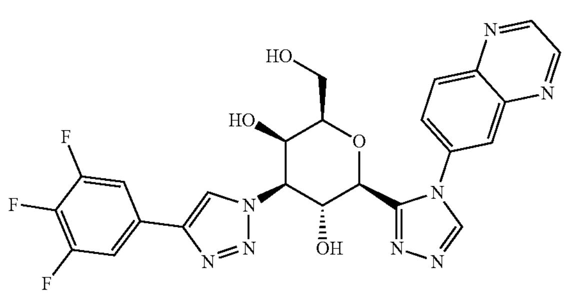 [SMILES: OC[C@H]1O[C@@H](c2nncn2-c2ccc3nccnc3c2)[C@H](O)[C@@H](n2cc(-c3cc(F)c(F)c(F)c3)nn2)[C@H]1O] | 1.122 | 541.1 | A | $^1$H NMR (400 MHz, METHANOL-d$_4$) δ 8.95-8.92 (m, 2H), 8.89 (s, 1H), 8.47 (s, 1H), 8.34 (d, J = 2.0 Hz, 1H), 8.26 (d, J = 8.8 Hz, 1H), 8.05 (dd, J = 9.0, 2.4 Hz, 1H), 7.56 (dd, J = 9.0, 6.6 Hz, 2H), 4.98-4.91 (m, 1H), 4.82 (d, J = 2.9 Hz, 1H), 4.53 (d, J = 9.3 Hz, 1H), 4.01 (d, J = 2.4 Hz, 1H), 3.72 (ddd, J = 18.1, 11.4, 7.0 Hz, 2H), 3.60 (dd, J = 11.2, 4.6 Hz, 1H) |

-continued

| Ex | hGal3 IC50, uM | Structure | LCMS t_R (min) | M + H | Method | 1H NMR |
|---|---|---|---|---|---|---|
| 125 | 10 | 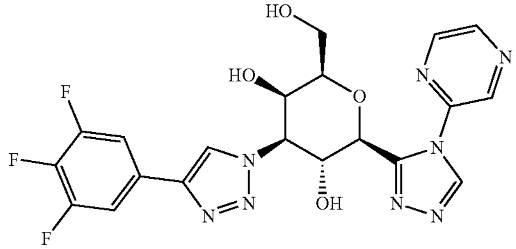 [SMILES: OC[C@H]1O[C@@H](c2nncn2-c2cnccn2)[C@H](O)[C@@H](n2cc(-c3cc(F)c(F)c(F)c3)nn2)[C@H]1O] | 1.388 | 492.1 | A | $^1$H NMR (400 MHz, METHANOL-d$_4$) δ 8.48 (s, 1H), 8.16 (s, 1H), 7.72 (dd, J = 6.7, 2.8 Hz, 2H), 7.56 (dd, J = 9.0, 6.6 Hz, 2H), 7.37-7.31 (m, 1H), 4.83 (dd, J = 10.8, 2.9 Hz, 1H), 4.53 (dd, J = 10.8, 9.5 Hz, 1H), 4.05 (d, J = 2.7 Hz, 1H), 4.00 (d, J = 9.5 Hz, 1H), 3.84-3.71 (m, 2H), 3.68-3.62 (m, 1H) |
| 126 | 0.27 | 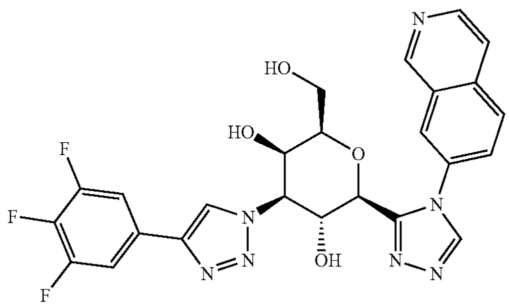 [SMILES: OC[C@H]1O[C@@H](c2nncn2-c2ccc3ccncc3c2)[C@H](O)[C@@H](n2cc(-c3cc(F)c(F)c(F)c3)nn2)[C@H]1O] | 1.178 | 540.2 | A | $^1$H NMR (400 MHz, METHANOL-d$_4$) δ 9.36 (s, 1H), 8.87 (s, 1H), 8.53-8.45 (m, 3H), 8.13 (d, J = 8.6 Hz, 1H), 7.96-7.87 (m, 2H), 7.55 (dd, J = 8.8, 6.6 Hz, 2H), 5.03-4.95 (m, 1H), 4.81 (d, J = 2.9 Hz, 1H), 4.50-4.43 (m, 2H), 4.01 (d, J = 2.9 Hz, 1H), 3.80-3.71 (m, 2H), 3.67-3.59 (m, 1H) |
| 127 | 1.28 | 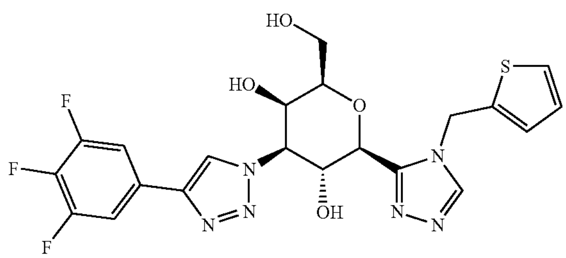 [SMILES: OC[C@H]1O[C@@H](c2nncn2Cc2cccs2)[C@H](O)[C@@H](n2cc(-c3cc(F)c(F)c(F)c3)nn2)[C@H]1O] | 1.252 | 509.1 | A | $^1$H NMR (400 MHz, METHANOL-d$_4$) δ 8.47 (s, 1H), 8.45 (s, 1H), 7.56 (dd, J = 9.2, 6.7 Hz, 2H), 7.38 (dd, J = 5.3, 1.3 Hz, 1H), 7.16 (d, J = 3.4 Hz, 1H), 6.96 (dd, J = 5.1, 3.7 Hz, 1H), 5.61 (d, J = 11.7 Hz, 2H), 4.92-4.87 (m, 2H), 4.73-4.69 (m, 1H), 4.12 (d, J = 2.2 Hz, 1H), 3.89 (t, J = 6.0 Hz, 1H), 3.74-3.62 (m, 2H) |
| 128 | 0.31 | 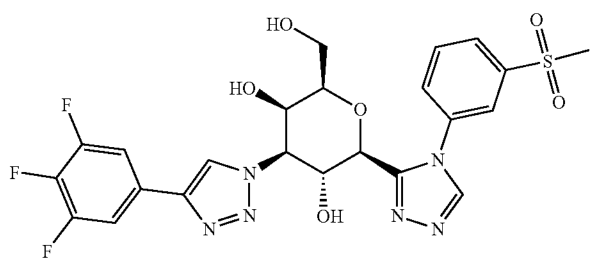 [SMILES: CS(=O)(=O)c1cccc(-n2cnnc2[C@@H]2O[C@H](CO)[C@H](O)[C@H](n3cc(-c4cc(F)c(F)c(F)c4)nn3)[C@H]2O)c1] | 1.262 | 567.2 | A | $^1$H NMR (400 MHz, METHANOL-d$_4$) δ 8.79 (s, 1H), 8.45 (s, 1H), 8.18 (s, 1H), 8.11 (d, J = 7.8 Hz, 1H), 7.95-7.86 (m, 1H), 7.84-7.75 (m, 1H), 7.57 (dd, J = 8.8, 6.6 Hz, 2H), 4.89-4.80 (m, 2H), 4.48 (d, J = 9.0 Hz, 1H), 4.02 (d, J = 2.0 Hz, 1H), 3.80-3.74 (m, 1H), 3.73-3.65 (m, 1H), 3.60 (dd, J = 11.2, 5.1 Hz, 1H), 3.16 (s, 3H) |
| 129 | 0.60 | 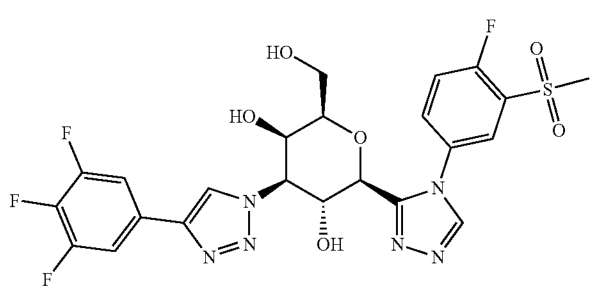 [SMILES: CS(=O)(=O)c1cc(-n2cnnc2[C@@H]2O[C@H](CO)[C@H](O)[C@H](n3cc(-c4cc(F)c(F)c(F)c4)nn3)[C@H]2O)ccc1F] | 1.324 | 585.2 | A | $^1$H NMR (400 MHz, METHANOL-d$_4$) δ 8.74 (s, 1H), 8.41 (s, 1H), 8.15 (dd, J = 5.9, 2.7 Hz, 1H), 7.94 (ddd, J = 8.8, 4.2, 2.7 Hz, 1H), 7.60-7.49 (m, 3H), 4.79 (d, J = 2.7 Hz, 1H), 4.75 (br. s., 1H), 4.54-4.48 (m, 1H), 4.02 (dd, J = 2.7, 0.7 Hz, 1H), 3.78-3.65 (m, 2H), 3.62-3.56 (m, 1H), 3.27 (s, 3H) |

-continued

| Ex | hGal3 IC50, uM | Structure | LCMS t$_R$ (min) | M + H | Method | 1H NMR |
|---|---|---|---|---|---|---|
| 130 | 0.32 | 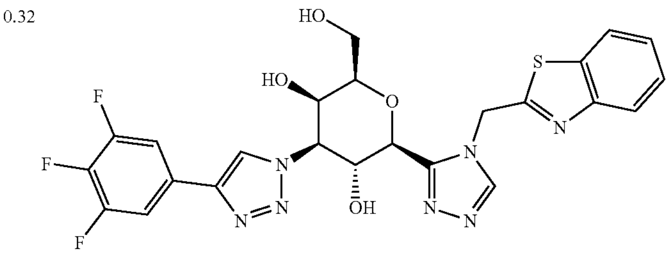 | 1.376 | 560.1 | A | $^1$H NMR (400 MHz, DMS0-d$_6$) δ 8.77 (d, J = 5.9 Hz, 2H), 8.13 (d, J = 7.8 Hz, 1H), 8.02 (d, J = 8.1 Hz, 1H), 7.81 (dd, J = 6.8, 8.8 Hz, 2H), 7.58-7.43 (m, 2H), 5.93 (s, 2H), 5.40 (d, J = 6.1 Hz, 2H), 5.00-4.90 (m, 1H), 4.83-4.74 (m, 2H), 4.63 (t, J = 5.5 Hz, 1H), 4.02 (dd, J = 2.6, 6.2 Hz, 1H), 3.89-3.78 (m, 1H), 3.45-3.37 (m, 1H) |

General Synthetic Scheme-2 for 4-Aryl-1,2,4-triazole Compounds:

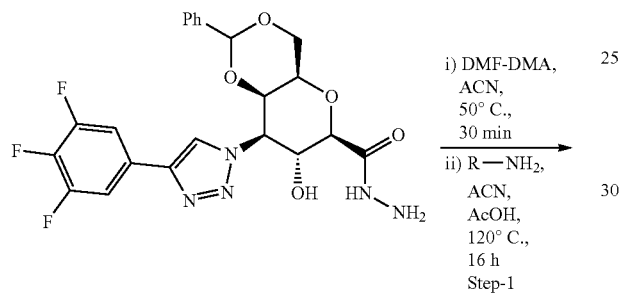

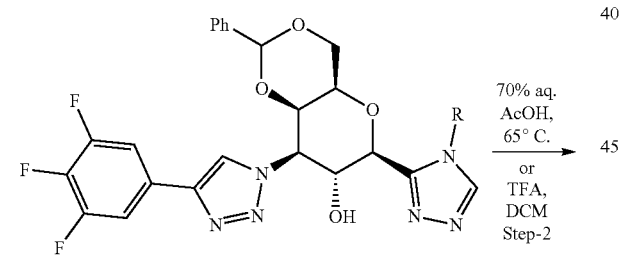

EXAMPLE 131

Preparation of (2S,3R,4R,5R,6R)-2-(4-(3,4-dichlorophenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol

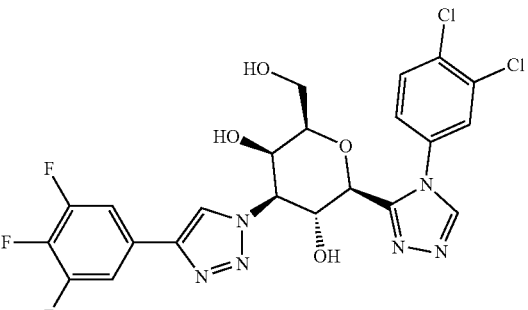

Step 1: Synthesis of (4aR,6S,7R,8R,8aR)-6-(4-(3,4-dichlorophenyl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol: To a stirred solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (100 mg, 0.203 mmol) in acetonitrile (5 mL) was added DMF-DMA (0.027 mL, 0.203 mmol) and the mixture was heated at 50° C. for 30 min. Then 3,4-dichloroaniline (33.0 mg, 0.203 mmol) in acetonitrile (5 mL) followed by acetic acid (1 mL, 17.47 mmol) was added and the mixture was heated at 120° C. for 16 h. The solvent was removed under reduced pressure and the residue was purified by flash chromatography (50-100% of EtOAc in n-hexane) to afford (4aR,6S,7R,8R,8aR)-6-(4-(3,4-dichlorophenyl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (65 mg, 49%) as a yellow solid. LC-MS, [M+H]$^+$=645.1, (Method C: t$_R$=3.25).

Step 2: Synthesis of (2S,3R,4R,5R,6R)-2-(4-(3,4-dichlorophenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol: (4aR,6S,7R,8R,8aR)-6-(4-(3,4-dichlorophenyl)-4H-1,2,4-triazol-3-yl)-2-phenyl-8-(4-(3,4,5-trifluorophenyl)-1H-1,2,3-triazol-1-yl)hexahydropyrano

[3,2-d][1,3]dioxin-7-ol (15 mg, 0.023 mmol) was suspended in 70% aq AcOH (5 mL) and heated at 70° C. for 16 h. The solvent was removed under reduced pressure and purified by HPLC (Method A) to afford (2S,3R,4R,5R,6R)-2-(4-(3,4-dichlorophenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 131) (2.7 mg, 21%). LC-MS, [M+H]$^+$=559.1, (Method C: $t_R$=1.50). 1H NMR (400 MHz, METHANOL-d4): δ 8.83 (s, 1H), 8.57 (s, 1H), 7.96 (d, J=2.4 Hz, 1H), 7.82 (d, J=8.8 Hz, 1H), 7.71-7.60 (m, 3H), 5.04-4.92 (m, 2H), 4.57 (d, J=6.8 Hz, 1H), 4.15 (d, J=2.0 Hz, 1H), 3.90-3.85 (m, 1H), 3.83-3.38 (m, 2H). hGal3 IC$_{50}$=0.10 uM.

The Examples in the table below were prepared in an analogous fashion to Example 131, substituting 3,4-dichloroaniline with the appropriate aryl amine in the synthetic sequence.

| Ex | hGal3 IC50, uM | Structure | LCMS $t_R$ (min) | M + H | Method | 1H NMR |
|---|---|---|---|---|---|---|
| 132 | 0.02 | 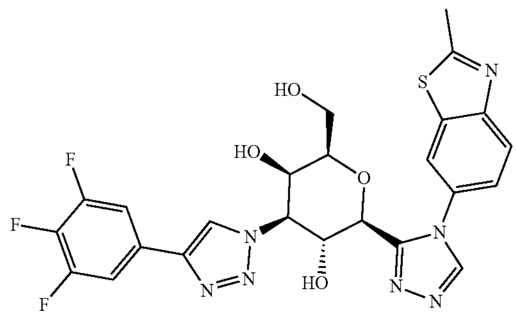 [SMILES: Cc1nc2ccc(-n3cnnc3[C@@H]3O[C@H](CO)[C@H](O)[C@H](n4cc(-c5cc(F)c(F)c(F)c5)nn4)[C@H]3O)cc2s1] | 1.616 | 560.2 | C | $^1$H NMR (400 MHz, METHANOL-d$_4$) δ 8.75 (s, 1H), 8.45 (s, 1H), 8.25 (d, J = 2.5 Hz, 1H), 8.00 (d, J = 8.5 Hz, 1H), 7.67-7.61 (m, 1H), 7.55 (dd, J = 8.8, 6.8 Hz, 2H), 4.98-4.88 (m, 1H), 4.79 (dd, J = 10.5, 3.0 Hz, 1H), 4.41 (d, J = 9.5 Hz, 1H), 4.01 (d, J = 2.5 Hz, 1H), 3.76-3.65 (m, 2H), 3.65-3.55 (m, 1H), 2.80 (s, 3H) |
| 133 | 0.20 | 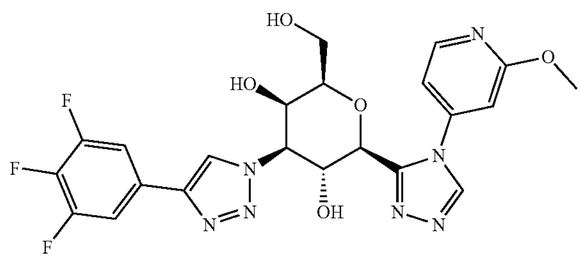 [SMILES: COc1cc(-n2cnnc2[C@@H]2O[C@H](CO)[C@H](O)[C@H](n3cc(-c4cc(F)c(F)c(F)c4)nn3)[C@H]2O)ccn1] | 1.186 | 520.2 | A | $^1$H NMR (400 MHz, METHANOL-d$_4$) δ 8.92 (s, 1H), 8.62 (s, 1H), 8.43-8.37 (m, 1H), 7.72-7.66 (m, 2H), 7.38-7.32 (m, 1H), 7.21-7.16 (m, 1H), 5.10-5.05 (m, 1H), 5.00-4.98 (m, 1H), 4.62-4.60 (m, 1H), 4.19-4.15 (m, 1H), 4.04 (s, 3H), 3.97-3.90 (m, 1H), 3.86-3.70 (m, 2H) |
| 134 | 0.57 | 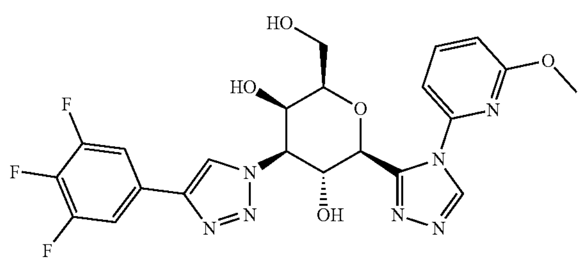 | 1.266 | 520.2 | A | $^1$H NMR (400 MHz, DMSO-d$_6$) δ 9.08 (s, 1H), 8.86 (s, 1H), 8.05-7.94 (m, 1H), 7.92-7.82 (m, 2H), 7.45-7.37 (m, 1H), 7.04-6.97 (m, 1H), 5.42-5.35 (m, 2H), 5.03-4.98 (m, 2H), 4.90-4.84 (m, 1H), 4.78-4.72 (m, 1H), 4.03-4.00 (m, 1H), 3.98 (s, 3H), 3.89-3.84 (m, 1H), 3.51-3.46 (m, 2H) |
| 135 | 0.03 | 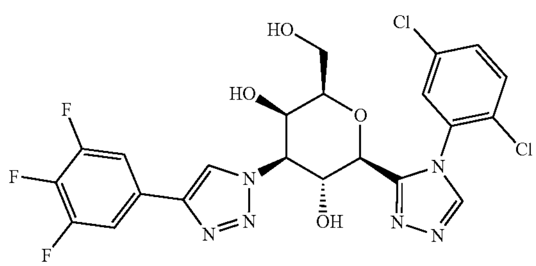 [SMILES: OC[C@H]1O[C@@H](c2nncn2-c2cc(Cl)ccc2Cl)[C@H](O)[C@@H](n2cc(-c3cc(F)c(F)c(F)c3)nn2)[C@H]1O] | 1.786 | 559.1 | A | $^1$H NMR (400 MHz, METHANOL-d$_4$) δ 8.79 (s, 1H), 8.56 (br s, 1H), 7.79-7.60 (m, 4H), 4.94-4.88 (m, 2H), 4.54-4.32 (m, 1H), 4.15-4.10 (m, 1H), 3.79-3.73 (m, 1H), 3.71-3.64 (m, 2H). |

-continued

| Ex | hGal3 IC50, uM | Structure | LCMS t$_R$ (min) | M + H | Method | 1H NMR |
|---|---|---|---|---|---|---|
| 136 | 0.31 | 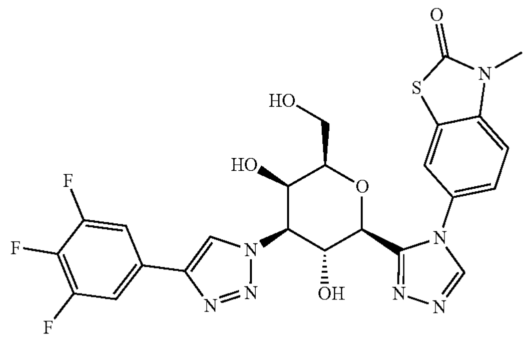 [SMILES: Cn1c(=O)sc2cc(-n3cnnc3[C@@H]3O[C@H](CO)[C@H](O)[C@H](n4cc(-c5cc(F)c(F)c(F)c5)nn4)[C@H]3O)ccc21] | 1.263 | 576.2 | A | ¹H NMR (400 MHz, METHANOL-d₄) δ 8.81 (s, 1H), 8.59 (s, 1H), 7.98 (d, J = 2.0 Hz, 1H), 7.74-7.58 (m, 3H), 7.47 (d, J = 8.8 Hz, 1H), 5.09-5.03 (m, 1H), 4.91 (dd, J = 10.8, 2.9 Hz, 1H), 4.50 (d, J = 9.3 Hz, 1H), 4.13 (d, J = 2.9 Hz, 1H), 3.85-3.78 (m, 2H), 3.75-3.69 (m, 1H), 3.57 (s, 3H). |
| 137 | 0.08 | 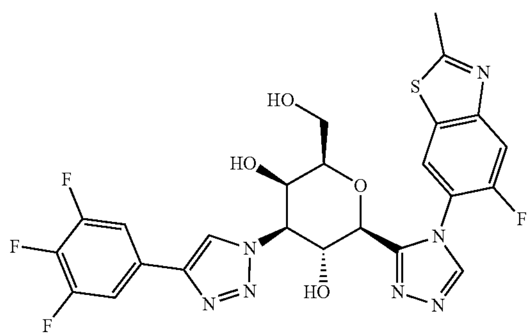 [SMILES: Cc1nc2cc(F)c(-n3cnnc3[C@@H]3O[C@H](CO)[C@H](O)[C@H](n4cc(-c5cc(F)c(F)c(F)c5)nn4)[C@H]3O)cc2s1] | 1.28 | 578.1 | A | ¹H NMR (400 MHz, METHANOL-d₄) δ 8.86 (d, J = 1.5 Hz, 1H), 8.56 (s, 1H), 8.44 (d, J = 7.1 Hz, 1H), 7.95 (d, J = 10.5 Hz, 1H), 7.67 (dd, J = 9.0, 6.6 Hz, 2H), 5.05-4.95 (m, 1H), 4.93-4.88 (m, 1H), 4.51 (d, J = 9.3 Hz, 1H), 4.10 (d, J = 2.4 Hz, 1H), 3.83-3.60 (m, 3H), 2.92 (s, 3H). |
| 138 | 0.04 | 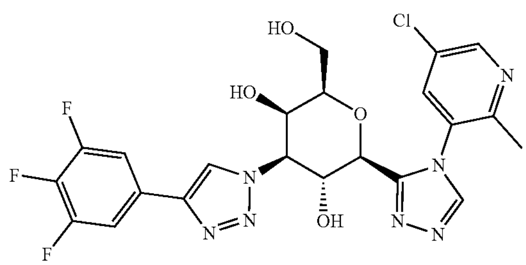 [SMILES: Cc1ncc(Cl)cc1-n1cnnc1[C@@H]1O[C@H](CO)[C@H](O)[C@H](n2cc(-c3cc(F)c(F)c(F)c3)nn2)[C@H]1O] | 1.247 | 538.1 | A | ¹H NMR (400 MHz, METHANOL-d₄) δ 8.78 (s, 1H), 8.72 (d, J = 2.2 Hz, 1H), 8.52 (s, 1H), 8.11 (br. s., 1H), 7.67 (dd, J = 8.8, 6.6 Hz, 2H), 4.46 (br. s., 1H), 4.10 (s, 1H), 3.81-3.71 (m, 1H), 3.71-3.55 (m, 2H), 2.36 (s, 3H). (2 protons buried under solvent) |
| 139 | 0.26 | 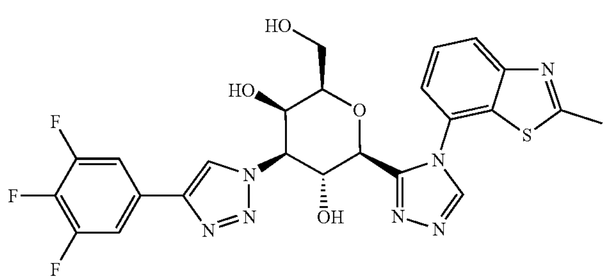 [SMILES: Cc1nc2cccc(-n3cnnc3[C@@H]3O[C@H](CO)[C@H](O)[C@H](n4cc(-c5cc(F)c(F)c(F)c5)nn4)[C@H]3O)c2s1] | 1.243 | 560.2 | A | ¹H NMR (400 MHz, METHANOL-d₄) δ 8.84 (s, 1H), 8.45 (s, 1H), 8.03 (d, J = 8.1 Hz, 1H), 7.69-7.46 (m, 4H), 4.91-4.83 (m, 1H), 4.71 (d, J = 2.9 Hz, 1H), 4.31 (d, J = 9.5 Hz, 1H), 3.97 (d, J = 2.7 Hz, 1H), 3.62-3.46 (m, 3H), 2.76 (s, 3H) |
| 140 | 0.13 | 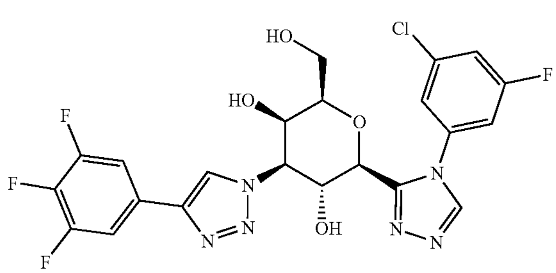 [SMILES: OC[C@H]1O[C@@H](c2nncn2-c2cc(F)cc(Cl)c2)[C@H](O)[C@@H](n2cc(-c3cc(F)c(F)c(F)c3)nn2)[C@H]1O] | 1.51 | 541.2 | B | ¹H NMR (400 MHz, METHANOL-d₄) δ 8.86 (s, 1H), 8.59 (s, 1H), 7.75-7.62 (m, 3H), 7.61-7.50 (m, 2H), 5.01 (d, J = 9.3 Hz, 2H), 4.59 (d, J = 9.0 Hz, 1H), 4.16 (s, 1H), 3.93-3.88 (m, 1H), 3.85-3.79 (m, 1H), 3.76-3.69 (m, 1H). |

General Synthetic Scheme-3 for 4-aryl-1,2,4-triazole Compounds:

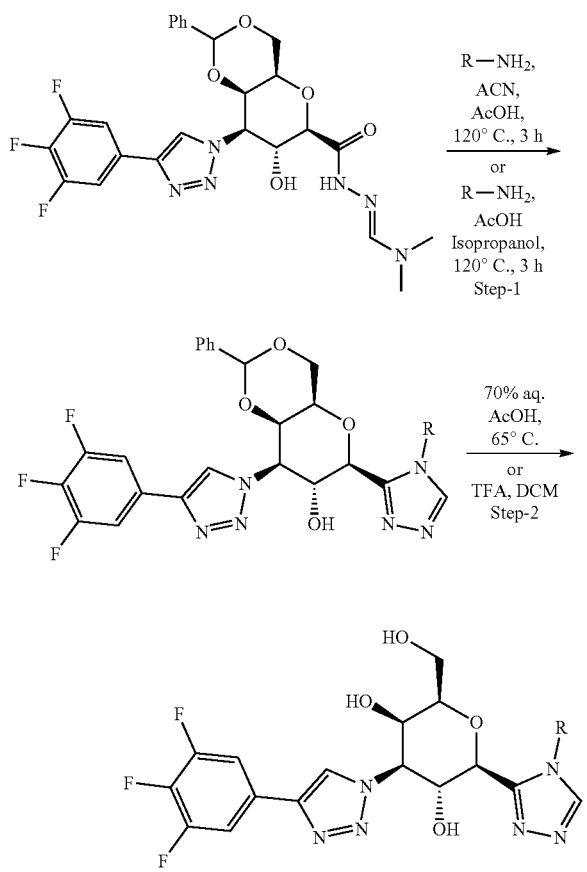

EXAMPLE 141

Preparation of (2S,3R,4R,5R,6R)-2-(4-(3-chloro-4-(piperazin-1-yl)phenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol

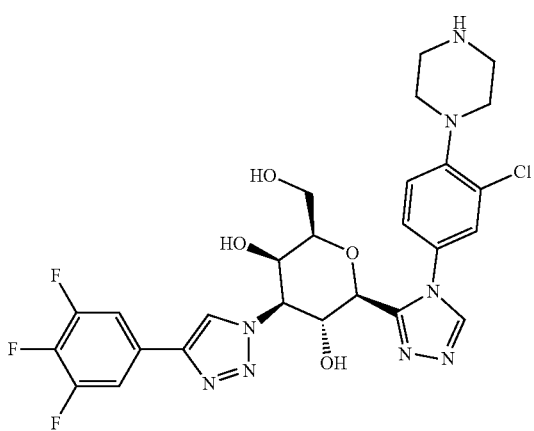 [SMILES: OC[C@H]1O[C@@H](c2nncn2-c2ccc(N3CCNCC3)c(Cl)c2)[C@H](O)[C@@H](n2cc(-c3cc(F)c(F)c(F)c3)nn2)[C@H]1O]

Step 1: Synthesis of (tert-butyl 4-(2-chloro-4-(3-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)phenyl)piperazine-1-carboxylate: To a solution of (E)-N'-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)-N,N-dimethylformohydrazonamide (30 mg, 0.055 mmol) in 2-propanol (3 mL) was added tert-butyl 4-(4-amino-2-chlorophenyl)piperazine-1-carboxylate (17.12 mg, 0.055 mmol) followed by acetic acid (3.14 μL, 0.055 mmol) and the mixture was heated at 120° C. for 3 h. The reaction mixture was cooled to rt and the solvent was removed under reduced pressure to give (tent-butyl 4-(2-chloro-4-(3-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)phenyl)piperazine-1-carboxylate (40 mg, 92%) as an off white solid which was as such taken to the next step without further purification. LC-MS, [M+H]⁺=795.5, (Method E: $t_R$=1.50).

Step 2: Synthesis of ((2S,3R,4R,5R,6R)-2-(4-(3-chloro-4-(piperazin-1-yl)phenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol: tert-butyl 4-(2-chloro-4-(3-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)phenyl)piperazine-1-carboxylate (40 mg, 0.050 mmol) was suspended in 70% aq AcOH (10 mL) and the mixture was heated at 70° C. for 16 h. The solvent was removed under reduced pressure and the residue was purified by HPLC (Method Q) to afford (2S,3R,4R,5R,6R)-2-(4-(3-chloro-4-(piperazin-1-yl)phenyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 141) (2.5 mg, 8%). LC-MS, [M+H]⁺=607.1, (Method A: $t_R$=1.026). 1H NMR (400 MHz, METHANOL-d4): δ 8.77 (s, 1H), 8.58 (s, 1H), 7.80 (d, J=2.4 Hz, 1H), 7.70-7.61 (m, 3H), 7.42 (d, J=8.4 Hz, 1H), 5.07-4.99 (m, 1H), 4.95-4.90 (m, 1H), 4.51 (d, J=9.2 Hz, 1H), 4.15 (d, J=2.8 Hz, 1H), 3.86-3.78 (m, 2H), 3.75-3.69 (m, 1H), 3.38-3.32 (m, 8H). hGal3 IC₅₀=0.13 uM.

The Examples in the table below were prepared in an analogous fashion to Example 141, substituting tent-butyl 4-(4-amino-2-chlorophenyl)piperazine-1-carboxylate with the appropriate aryl amine in the synthetic sequence.

| Ex | hGal3 IC50, uM | Structure | LCMS $t_R$ (min) | M + H | Method | 1H NMR |
|---|---|---|---|---|---|---|
| 142 | 0.13 | 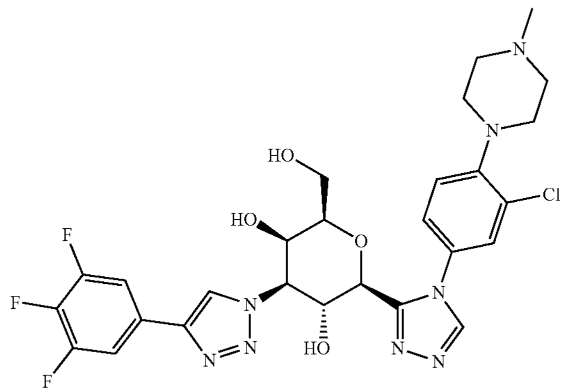 [SMILES: CN1CCN(c2ccc(-n3cnnc3[C@@H]3O[C@H](CO)[C@H](O)[C@H](n4cc(-c5cc(F)c(F)c(F)c5)nn4)[C@H]3O)cc2Cl)CC1] | 1.274 | 622.3 | A | ¹H NMR (400 MHz, METHANOL-d₄) δ 8.73 (s, 1H), 8 54 (s, 1H), 7.74 (d, J = 2.4 Hz, 1H), 7.67-7.61 (m, 2H), 7.58 (dd, J = 8.8, 2.8 Hz, 1H), 7.36 (d, J = 8.8 Hz, 1H), 5.05-4.95 (m, 1H), 4.94-4.87 (m, 1H), 4.48 (d, J = 9.2 Hz, 1H), 4.12 (d, J = 2.8 Hz, 1H), 3.85-3.76 (m, 2H), 3.72-3.65 (m, 1H), 3.24 (br. s., 4H), 2.93 (br. s., 4H), 2.57 (s, 3H) |
| 143 | 0.41 | 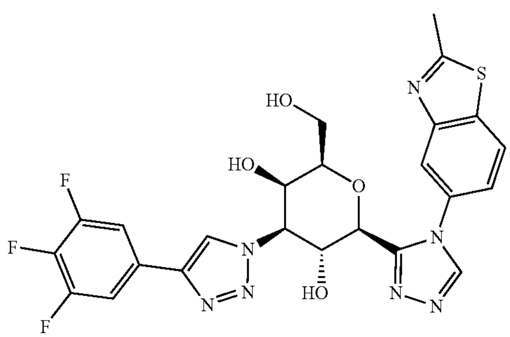 [SMILES: Cc1nc2cc(-n3cnnc3[C@@H]3O[C@H](CO)[C@H](O)[C@H](n4cc(-c5cc(F)c(F)c(F)c5)nn4)[C@H]3O)ccc2s1] | 1.29 | 560.2 | A | ¹H NMR (400 MHz, METHANOL-d₄) δ 8.87 (s, 1H), 8.57 (s, 1H), 8.20-8.16 (m, 2H), 7.70-7.64 (m, 3H), 5.09-5.00 (m, 1H), 4.93-4.88 (m, 1H), 4.57 (d, J = 9.6 Hz, 1H), 4.14 (d, J = 2.8 Hz, 1H), 3.85-3.71 (m, 3H), 2.91 (s, 3H) |
| 144 | 0.30 | 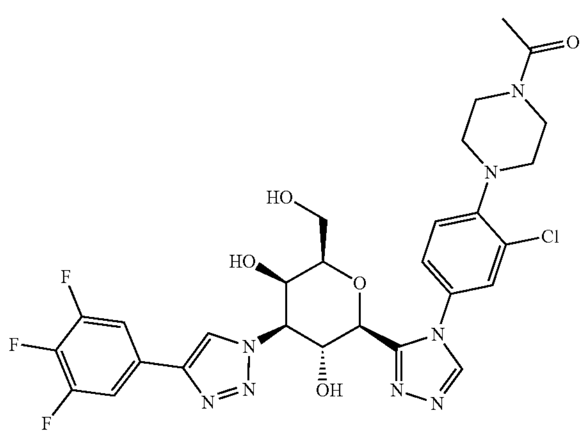 [SMILES: CC(=O)N1CCN(c2ccc(-n3cnnc3[C@@H]3O[C@H](CO)[C@H](O)[C@H](n4cc(-c5cc(F)c(F)c(F)c5)nn4)[C@H]3O)cc2Cl)CC1] | 1.268 | 650.3 | A | ¹H NMR (400 MHz, METHANOL-d₄) δ 8.78 (s, 1H), 8.58 (s, 1H), 7.78 (d, J = 2.4 Hz, 1H), 7.72-7.66 (m, 2H), 7.61 (dd, J = 8.4, 2.4 Hz, 1H), 7.38 (d, J = 8,4 Hz, 1H), 5.03-5.01 (m, 2H), 4.52 (d, J = 9.2 Hz, 1H), 4.14 (d, J 2.0 Hz. 1H), 3.88-3.71 (m, 7H), 3.20-3.12 (m, 4H). 2.19 (s, 3H). |
| 145 | 0.23 | 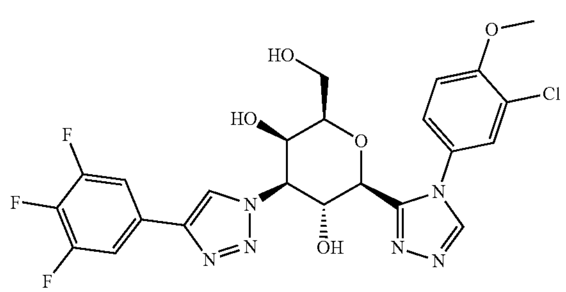 [SMILES: COc1ccc(-n2cnnc2[C@@H]2O[C@H](CO)[C@H](O)[C@H](n3cc(-c4cc(F)c(F)c(F)c4)nn3)[C@H]2O)cc1Cl] | 1.381 | 553.2 | A | ¹H NMR (400 MHz, METHANOL-d₄) δ 8.63 (s, 1H), 8.46 (s, 1H), 7.62 (d, J = 2.4 Hz, 1H), 7.55 (dd, J = 8.7, 6.7 Hz, 2H), 7.47 (dd, J = 8.6, 2.7 Hz, 1H), 7.19 (d, J = 9.0 Hz, 1H), 4.93-4.86 (m, 1H), 4.80 (dd, J = 10.8, 2.9 Hz, 1H), 4.37 (d, J = 9.5 Hz, 1H), 4.03 (d, J = 2.1 Hz, 1H), 3.90 (s, 3H), 3.75-3.66 (m, 2H), 3.63-3.58 (m, 1H) |

-continued

| Ex | hGal3 IC50, uM | Structure | LCMS t_R (min) | M + H | Method | 1H NMR |
|---|---|---|---|---|---|---|
| 146 | 0.05 | 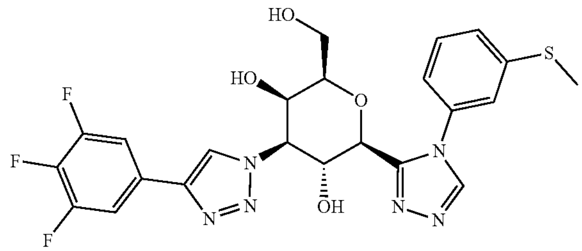 | 1.523 | 535.2 | A | 1H NMR (400 MHz, METHANOL-d$_4$) δ 8.70 (s, 1H), 8.51-8.45 (m, 1H), 7.56 (dd, J = 9.0, 6.6 Hz, 2H), 7.47-7.31 (m, 3H), 7.31-7.26, (m, 1H), 4.97-4.88 (m, 1H), 4.85-4.81 (m, 1H), 4.42 (d, J = 9.5 Hz, 1H), 4.08-3.97 (m, 1H), 3.79-3.65 (m, 2H), 3.64-3.56 (m, 1H), 2.46 (s, 3H) |
| 147 | 0.06 | 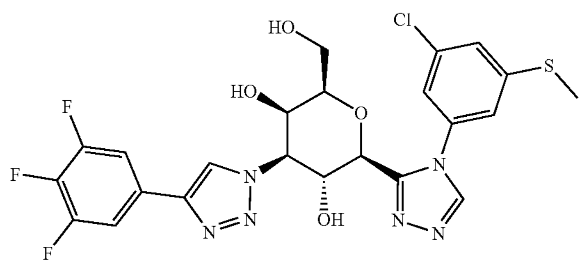 [SMILES: CSc1cc(Cl)cc(-n2cnnc2[C@@H]2O[C@H](CO)[C@H](O)[C@H](n3cc(-c4cc(F)c(F)c(F)c4)nn3)[C@H]2O)c1] | 1.526 | 569.2 | A | 1H NMR (400 MHz, METHANOL-d$_4$) δ 8.84 (s, 1H), 8.57 (s, 1H), 7.76-7.60 (m, 2H), 7.51 (d, J = 1.7 Hz, 2H), 7.47 (t, J = 1.7 Hz, 1H), 5.04-4.94 (m, 2H), 4.57 (d, J= 8.8 Hz, 1H), 4.15 (d, J = 2.0 Hz, 1H), 3.92-3.85 (m, 1H), 3.85-3.76 (m, 1H), 3.76-3.65 (m, 1H), 2.60 (s, 3 H). |
| 148 | 0.08 | 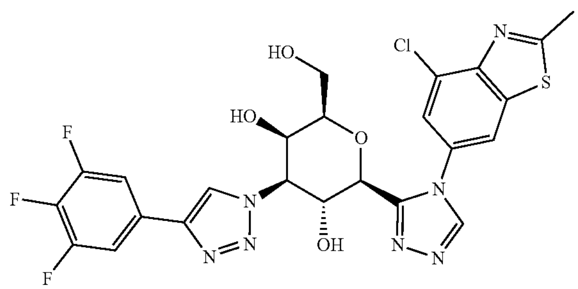 [SMILES: Cc1nc2c(Cl)cc(-n3cnnc3[C@@H]3O[C@H](CO)[C@H](O)[C@H](n4cc(-c5cc(F)c(F)c(F)c5)nn4)[C@H]3O)cc2s1] | 1.337 | 594.2 | A | 1H NMR (400 MHz, METHANOL-d4) δ 8.77 (s, 1H), 8.43 (s, 1H), 8.23 (s, 1H), 7.78 (s, 1H), 7.64-7.43 (m, 2H), 4.93-4.89 (m, 1H), 4.44 (d, J = 9.4 Hz, 1H), 4.01 (br. s., 1H) 3.81-3.64 (m, 3H), 3.60 (d, J = 9.2 Hz, 1H), 2.83 (s, 3H). |
| 149 | 0.03 | 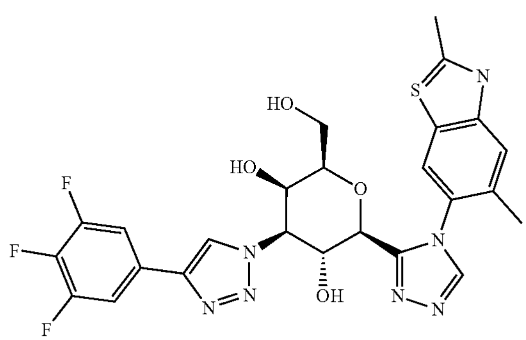 | 1.294 | 574.2 | A | $^1$H NMR (400 MHz, METHANOL-d$_4$) δ 8.80 (br. s., 1H), 8.55 (br. s., 1H), 8.19 (br. s., 1H), 7.99 (s, 1H), 7.67 (dd, J = 8.7, 6.7 Hz, 2H), 5.05 (br. s., 1H), 4.82 (d, J = 2.7 Hz, 1H), 4.41-4.28 (m, 1H), 4.07 (br. s., 1H), 3.73-3.65 (br. s., 3H), 2.90 (s, 3H), 2.27 (br. s., 3H). |
| 150 | 0.16 | 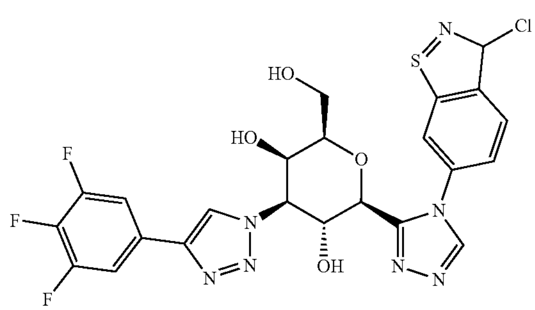 | 1.802 | 580.1 | A | 1H NMR (400 MHz, METHANOL-d$_4$) δ 8.96 (s, 1H). 8.60 (d, J = 1.2 Hz, 1H), 8.58 (s, 1H), 8.31 (d, J = 8.8 Hz, 1H), 7.89 (dd, J = 8.6, 2.0 Hz, 1H), 7.67 (dd, J = 8.9, 6.5 Hz, 2H), 5.11-5.06 (m, 1H), 4.92 (dd, J = 10.8, 2.9 Hz, 1H), 4.56 (d, J = 9.5 Hz, 1H), 4.13 (d, J = 2.7 Hz, 1H). 3.91-3.79 (m, 2H), 3.72 (dd, J = 10.4, 3.1 Hz, 1H). |

-continued

| Ex | hGal3 IC50, uM | Structure | LCMS $t_R$ (min) | M + H | Method | 1H NMR |
|---|---|---|---|---|---|---|
| 151 | 0.11 | 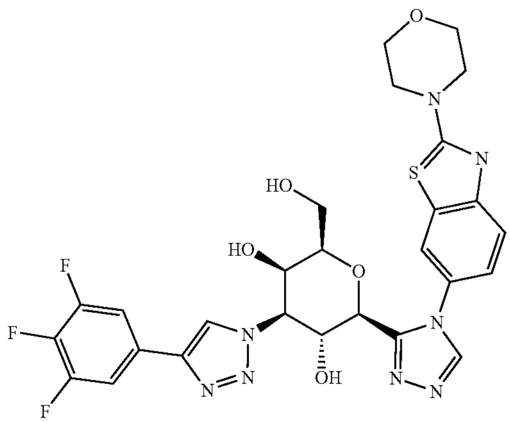 | 1.295 | 631.2 | A | 1H NMR (400 MHz, METHANOL-d$_4$) δ 8.81 (br. s., 1H), 8.56 (s, 1H), 8.08 (d, J = 2.0 Hz, 1H), 7.71-7.60 (m, 3H), 7.55 (d, J = 8.3 Hz, 1H), 5.02 (d, J = 9.8 Hz, 1H), 4.92 (d, J = 2.7 Hz, 1H), 4.52 (d, J = 9.0 Hz, 1H), 4.13 (d, J = 2.7 Hz, 1H), 3.91-3.77 (m, 6H), 3.76-3.62 (m, 5H). |
| 152 | 0.16 | 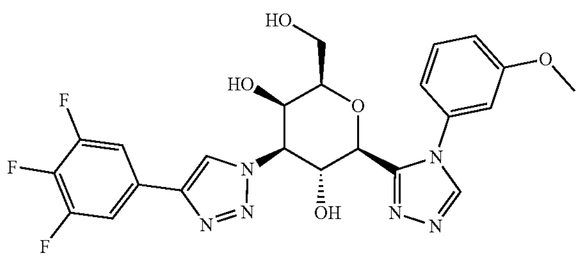 [SMILES: COc1cccc(-n2cnnc2[C@@H]2O[C@H](CO)[C@H](O)[C@H](n3cc(-c4cc(F)c(F)c(F)c4)nn3)[C@H]2O)c1] | 1.293 | 519.2 | A | $^1$H NMR (400 MHz, METHANOL-d$_4$) δ 8.80 (s, 1H), 8.60 (s, 1H), 7.68 (dd, J = 9.0, 6.5 Hz, 2H), 7.54 (t, J = 8.3 Hz, 1H), 7.26-7.15 (m, 3H), 5.06 (dd, J = 10.5, 9.5 Hz, 1H), 4.97-4.89 (m, 1H), 4.55 (d, J = 9.5 Hz, 1H), 4.15 (d, J = 2.5 Hz, 1H), 3.91 (s, 3H), 3.89-3.84 (m, 1H), 3.81 (dd, J = 11.5, 7.0 Hz, 1H), 3.76-3.68 (m, 1H). |
| 153 | 0.14 | 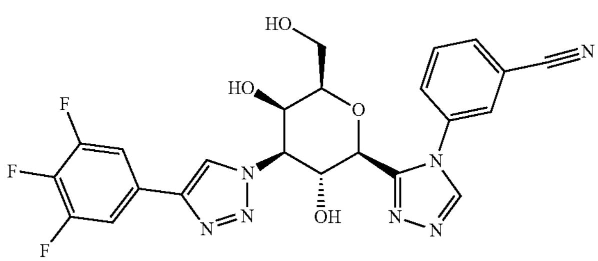 [SMILES: N#Cc1cccc(-n2cnnc2[C@@H]2O[C@H](CO)[C@H](O)[C@H](n3cc(-c4cc(F)c(F)c(F)c4)nn3)[C@H]2O)c1] | 1.215 | 514.2 | A | $^1$H NMR (400 MHz, METHANOL-d$_4$) δ 8.86 (s, 1H), 8.56 (s, 1H), 8.16 (s, 1H), 8.01 (d, J = 8.3 Hz, 2H), 7.86-7.80 (m, 1H), 7.71-7.64 (m, 2H), 5.03-4.92 (m, 2H, obscured with moisture peak), 4.54 (d, J = 8.8 Hz, 1H), 4.14 (s, 1H), 3.90-3.85 (m, 1H), 3.84-3.77 (m, 1H), 3.75-3.69 (m, 1H); |
| 154 | 0.08 | 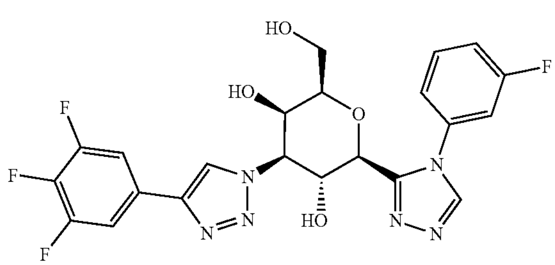 [SMILES: OC[C@H]1O[C@@H](c2nncn2-c2cccc(F)c2)[C@H](O)[C@@H](n2cc(-c3cc(F)c(F)c(F)c3)nn2)[C@H]1O] | 1.267 | 507.2 | A | $^1$H NMR (400 MHz, METHANOL-d$_4$) δ 8.83 (s, 1H), 8.60 (s, 1H), 7.73-7.62 (m, 3H), 7.61-7.50 (m, 2H), 7.41 (t, J = 8.2 Hz, 1H), 5.11-5.01 (m, 1H), 4.94 (dd, J = 10.9, 2.8 Hz, 1H), 4.62-4.50 (m, 1H), 4.16 (d, J = 2.2 Hz, 1H), 3.90-3.85 (m, 1H), 3.81 (dd, J =11.4, 7.2 Hz, 1H), 3.72 (dd, J = 11.7, 4.6 Hz, 1H) |

| Ex | hGal3 IC50, uM | Structure | LCMS $t_R$ (min) | M + H | Method | 1H NMR |
|---|---|---|---|---|---|---|
| 155 | 0.15 | 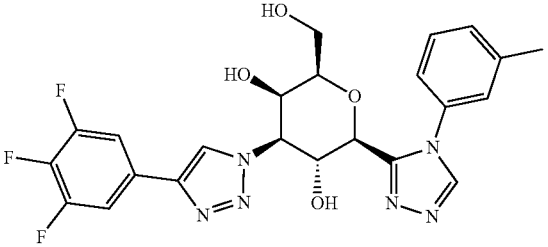 [SMILES: Cc1cccc(-n2cnnc2[C@@H]2O[C@H](CO)[C@H](O)[C@H](n3cc(-c4cc(F)c(F)c(F)c4)nn3)[C@H]2O)c1] | 1.333 | 503.2 | A | $^1$H NMR (400 MHz, METHANOL-d$_4$) δ 8.78 (s, 1H), 8.60 (s, 1H), 7.68 (dd, J = 9.0, 6.5 Hz, 2H), 7.53-7.49 (m, 2H), 7.48-7.42 (m, 2H), 5.10-5.03 (m, 1H), 4.91 (dd, J = 10.8, 2.8 Hz, 1H), 4.49 (d, J = 9.0 Hz, 1H), 4.15 (d, J = 3.0 Hz, 1H), 3.87-3.83 (m, 1H), 3.82-3.78 (m, 1H), 3.75-3.70 (m, 1H), 2.49 (s, 3H) |
| 156 | 0.05 | 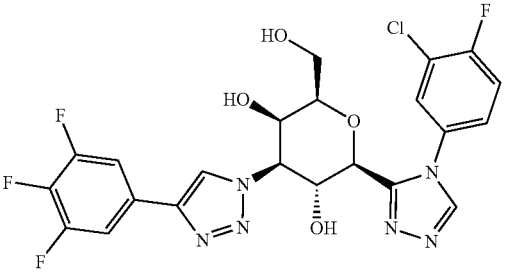 [SMILES: OC[C@H]1O[C@@H](c2nncn2-c2ccc(F)c(Cl)c2)[C@H](O)[C@@H](n2cc(-c3cc(F)c(F)c(F)c3)nn2)[C@H]1O] | 1.445 | 541.1 | A | $^1$H NMR (400 MHz, METHANOL-d$_4$) δ 8.83 (s, 1H), 8.59 (s, 1H), 7.93 (dd, J = 6.4, 2.7 Hz, 1H), 7.68 (dd, J = 8.6, 6.8 Hz, 3H), 7.53 (t, J = 8.8 Hz, 1H), 5.02-4.96 (m, 2H), 4.53 (d, J = 9.0 Hz, 1H), 4.14 (d, J = 2.0 Hz, 1H), 3.90-3.76 (m, 2H), 3.76-3.66 (m, 1H). |
| 157 | 0.03 | 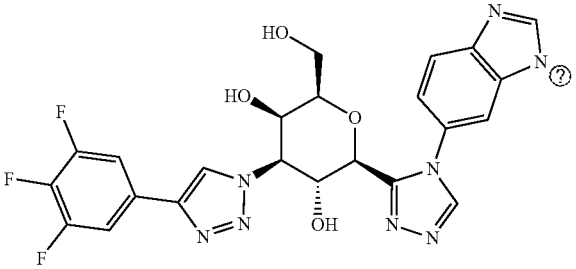 [SMILES: OC[C@H]1O[C@@H](c2nncn2-c2ccc3nc[nH]c3c2)[C@H](O)[C@@H](n2cc(-c3cc(F)c(F)c(F)c3)nn2)[C@H]1O] | 1.214 | 543.2 | A | 1H NMR (400 MHz, METHANOL-d$_4$) δ 8.88 (s, 1H), 8.58 (s, 1H), 8.36 (s, 1H), 7.98 (d, J = 1.5 Hz, 1H), 7.90 (d, J = 8.5 Hz, 1H), 7.68 (dd, J = 9.0, 6.5 Hz, 2H), 7.58-7.49 (m, 1H), 5.07 (dd, J = 10.5, 9.5 Hz, 1H), 4.88 (d, J = 3.0 Hz, 1H), 4.54 (d, J = 9.5 Hz, 1H), 4.12 (d, J = 3.0 Hz, 1H), 4.01 (s, 3H), 3.90-3.81 (m, 2H), 3.76-3.68 (m, 1H) |
| 158 | 2.15 | 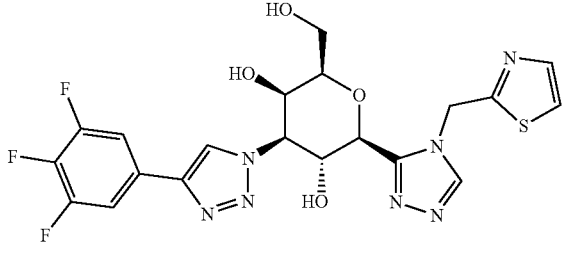 [SMILES: OC[C@H]1O[C@@H](c2nncn2Cc2nccs2)[C@H](O)[C@@H](n2cc(-c3cc(F)c(F)c(F)c3)nn2)[C@H]1O] | 1.141 | 510.2 | A | 1H NMR (400 MHz, DMSO-d$_6$) δ 8.83 (s, 1H), 8.70 (s, 1H), 7.91-7.80 (m, 3H), 7.79 (d, J = 3.2 Hz, 1H), 5.85-5.70 (m, 2H), 5.48-5.36 (m, 2H), 4.95 (dd, J = 10.3, 3.2 Hz, 1H), 4.84-4.73 (m, 2H), 4.71 (t, J = 5.5 Hz, 1H), 4.04 (dd, J = 6.4, 2.7 Hz, 1H), 3.87 (t, J = 6.5 Hz, 1H), 3.48-3.39 (m, 2H). |
| 159 | 0.84 | 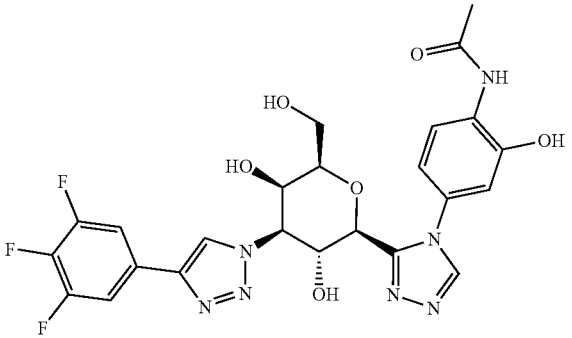 [SMILES: CC(=O)Nc1ccc(-n2cnnc2[C@@H]2O[C@H](CO)[C@H](O)[C@H](n3cc(-c4cc(F)c(F)c(F)c4)nn3)[C@H]2O)cc1O] | 1.093 | 562.2 | A | $^1$H NMR (400 MHz, METHANOL-d$_4$) δ 8.63 (s, 1H), 8.54-8.41 (m, 1H), 7.92 (d, J = 8.3 Hz, 1H), 7.56 (dd, J = 8,8, 6.6 Hz, 2H), 7.05-6.91 (m, 2H), 4.91 (dd, J = 10.8, 9.3 Hz, 1H), 4.85-4.79 (m, 1H), 4.42 (d, J = 9.3 Hz, 1H), 4.03 (d, J = 2.4 Hz, 1H), 3.80-3.48 (m, 3H), 2.12 (s, 2H); |

-continued

| Ex | hGal3 IC50, uM | Structure | LCMS $t_R$ (min) | M + H | Method | 1H NMR |
|---|---|---|---|---|---|---|
| 160 | 0.33 | 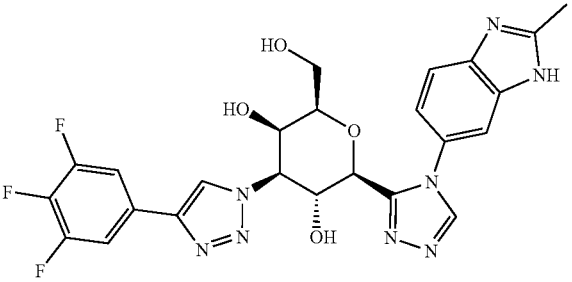 [SMILES: Cc1nc2ccc(-n3cnnc3[C@@H]3O[C@H](CO)[C@H](O)[C@H](n4cc(-c5cc(F)c(F)c(F)c5)nn4)[C@H]3O)cc2[nH]1] | 1.064 | 543.2 | A | 1H NMR (400 MHz, METHANOL-$d_4$) δ 8.70 (s, 1H), 8.47 (s, 1H), 7.67 (d, J = 2.0 Hz, 1H), 7.63-7.43 (m, 3H), 7.38-7.25 (m, 1H), 5.01-4.87 (m, 1H), 4.40 (d, J = 9.3 Hz, 1H), 4.01 (d, J = 2.9 Hz, 1H), 3.76-3.65 (m, 2H), 3.65-3.51 (m, 1H), 2.53 (s, 3H); (one proton obscured with moisture peak) |
| 161 | 0.38 | 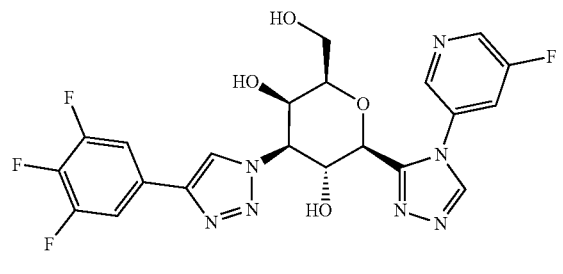 [SMILES: OC[C@H]1O[C@@H](c2nncn2-c2cncc(F)c2)[C@H](O)[C@@H](n2cc(-c3cc(F)c(F)c(F)c3)nn2)[C@H]1O] | 1.099 | 508.2 | A | 1H NMR (400 MHz, METHANOL-$d_4$) δ 8.90 (s, 1H), 8.83-8.70 (m, 2H), 8.61-8.53 (m, 1H), 8.17 (dt, J = 8.7, 2.4 Hz, 1H), 7.68 (dd, J = 8.7, 6.7 Hz, 2H), 5.00-4.93 (m, 2H), 4.66-4.60 (m, 1H), 4.15 (s, 1H), 3.93-3.85 (m, 1H), 3.81-3.74 (m, 1H), 3.74-3.66 (m, 1H). |
| 161 | 0.53 | 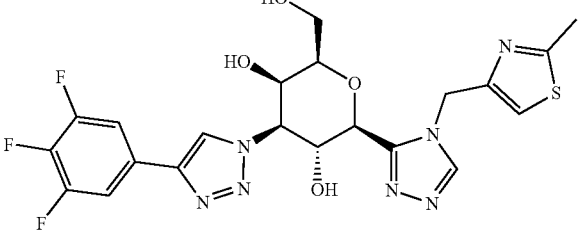 | 1.194 | 524.1 | A | 1H NMR (400 MHz, METHANOL-$d_4$) δ 8.60 (s, 1H), 8.56 (s, 1H), 7.65 (dd, J = 8.8, 6.6 Hz, 2H), 7.52 (s, 1H), 5.60-5.47 (m, 2H), 5.03-4.96 (m, 1H), 4.92 (t, J = 9.8 Hz, 1H), 4.86 (s, 1H), 4.21 (d, J = 2.2 Hz, 1H), 3.98 (t, J = 5.9 Hz, 1H), 3.79 (dd, J = 11.6, 7.0 Hz, 1H), 3.73 (dd, J = 11.4, 5.0 Hz, 1H), 2.70 (s, 3H) |
| 163 | 0.22 | 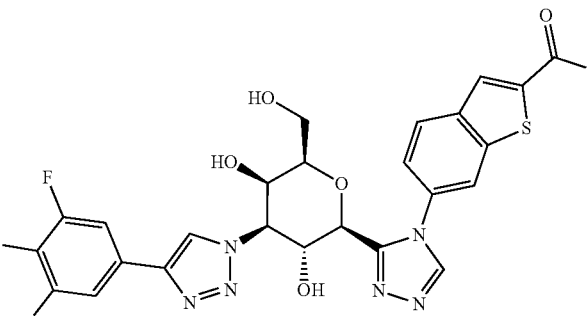 | 1.454 | 603.2 | A | $^1$H NMR (400 MHz, METHANOL-$d_4$) δ 8.90 (s, 1H), 8.57 (s, 1H), 8.42 (s, 1H), 8.26 (s, 1H), 8.21 (d, J = 8.6 Hz, 1H), 7.74-7.59 (m, 3H), 5.11-5.05 (m, 1H), 4.92 (d, J = 2.9 Hz, 1H), 4.54 (d, J = 9.0 Hz, 1H), 4.13 (d, J = 2.9 Hz, 1H), 3.99 (s, 3H), 3.88-3.79 (m, 3H) |
| 164 | 0.63 | 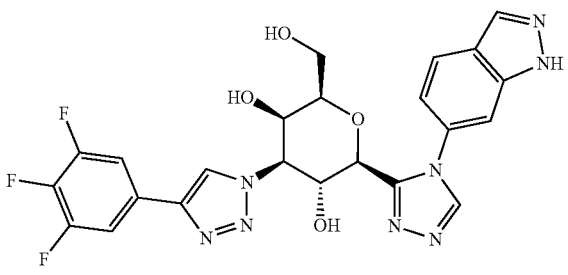 [SMILES: OC[C@H]1O[C@@H](c2nncn2-c2ccc3cn[nH]c3c2)[C@H](O)[C@@H](n2cc(-c3cc(F)c(F)c(F)c3)nn2)[C@H]1O] | 1.13 | 529.2 | A | $^1$H NMR (400 MHz, METHANOL-$d_4$) δ 8.89 (s, 1H), 8.60 (s, 1H), 8.24 (s, 1H), 8.05 (d, J = 8.6Hz, 1H), 7.91 (s, 1H), 7.68 (dd, J = 9.0, 6.6 Hz, 2H), 7.44-7.34 (m, 1H), 5.12-5.04 (m, 1H), 4.93 (br. s., 1H), 4.56 (d, J = 9.5 Hz, 1H), 4.13 (d, J = 2.9 Hz, 1H), 3.91-3.79 (m, 2H), 3.75 (t, J = 7.1 Hz, 1H). |

-continued

| Ex | hGal3 IC50, uM | Structure | LCMS t$_R$ (min) | M + H | Method | 1H NMR |
|---|---|---|---|---|---|---|
| 165 | 0.93 | 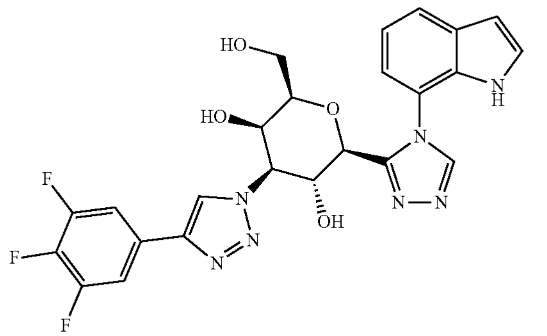 [SMILES: OC[C@H]1O[C@@H](c2nncn2-c2cccc3cc[nH]c23)[C@H](O)[C@@H](n2cc(-c3cc(F)c(F)c(F)c3)nn2)[C@H]1O] | 1.359 | 528.2 | A | 1H NMR (400 MHz, METHANOL-d$_4$) δ 8.84 (s, 1H), 8.58 (s, 1H), 7.87-7.79 (m, 1H), 7.68 (dd, J = 8.9, 6.7Hz, 2H), 7.36 (d, J = 3.2 Hz, 1H), 7.30 (d, J = 7.6 Hz, 1H), 7.23 (t , J = 7.6 Hz, 1H), 6.67 (d, J = 3.2 Hz, 1H), 5.09-5.03 (m, 1H), 4.83 (dd, J = 10.8, 2.9 Hz, 1H), 4.40 (d, J = 9.3 Hz, 1H), 4.08( d, J = 2.9 Hz, 1H), 3.73-3.58 (m, 3H). |
| 166 | 0.15 | 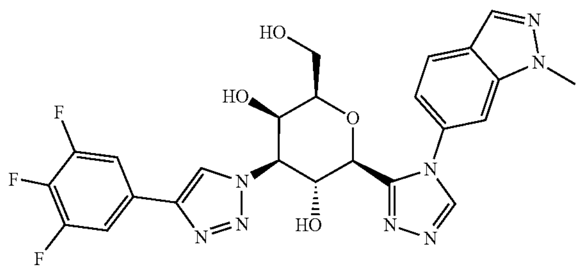 [SMILES: Cn1ncc2ccc(-n3cnnc3[C@@H]3O[C@H](CO)[C@H](O)[C@H](n4cc(-c5cc(F)c(F)c(F)c5)nn4)[C@H]3O)cc21] | 1.22 | 543.2 | A | 1H NMR (400 MHz, METHANOL-d$_4$) δ 8.91 (s, 1H), 8.58 (s, 1H), 8.19 (d, J = 1.0 Hz, 1H), 8.02 (d, J = 8.1 Hz. 1H), 7.98 (s, 1H), 7.67 (dd, J = 8.8, 6.8 Hz, 2H), 7.40 (dd, J = 8.6, 1.7 Hz, 1H), 5.14-5.03 (m, 1H), 4.92 (d, J = 2.7 Hz, 1H), 4.57 (d, J = 9.3 Hz,1H), 4.18 (s, 3H), 4.13 (d, J = 2.4 Hz, 1H), 3.95-3.79 (m. 2H), 3.78-3.67 (m, 1H) |
| 167 | 0.30 | 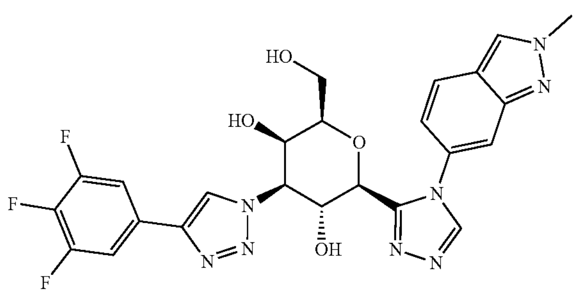 [SMILES: Cn1cc2ccc(-n3cnnc3[C@@H]3O[C@H](CO)[C@H](O)[C@H](n4cc(-c5cc(F)c(F)c(F)c5)nn4)[C@H]3O)cc2n1] | 1.233 | 543.2 | A | 1H NMR (400 MHz, METHANOL-d$_4$) δ 8.88 (s, 1H), 8.61 (s, 1H), 8.42 (s, 1H), 7.97 (d, J = 8.8 Hz, 1H), 7.92 (s, 1H), 7.75-7.58 (m, 2H), 7.31 (dd, J = 8.8, 1.7 Hz, 1H), 5.12-5.00 (m, 1H), 4.92 (br. s., 1H), 4.58 (d, J = 9.5 Hz, 1H), 4.31 (s, 3H), 4.14 (d, J = 2.9 Hz, 1H), 3.87-3.65 (m, 3H) |
| 168 | 0.50 | 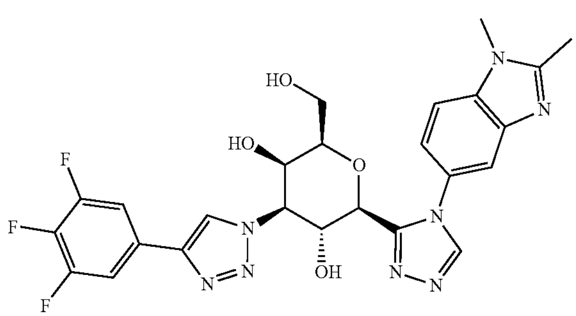 [SMILES: Cc1nc2cc(-n3cnnc3[C@@H]3O[C@H](CO)[C@H](O)[C@H](n4cc(-c5cc(F)c(F)c(F)c5)nn4)[C@H]3O)ccc2n1C] | 1.109 | 557.3 | A | 1H NMR (400 MHz, METHANOL-d$_4$) δ 8.86 (s, 1H), 8.58 (s, 1H), 7.91 (s, 1H), 7.80 (d, J = 8.3 Hz, 1H), 7.68 (dd, J = 8.6, 6.6 Hz, 2H), 7.51 (dd, J = 8.6, 2.0 Hz, 1H). 5.11-5.04 (m, 2H), 4.53 (d, J = 9.5 Hz, 1H), 4.12 (d, J = 2,4 Hz, 1H), 3.91 (s, 3H), 3.89-3.78 (m, 2H), 3.76-3.65 (m, 1H), 2.72 (s, 3H). |

| Ex | hGal3 IC50, uM | Structure | LCMS $t_R$ (min) | M + H | Method | 1H NMR |
|---|---|---|---|---|---|---|
| 169 | 0.28 | 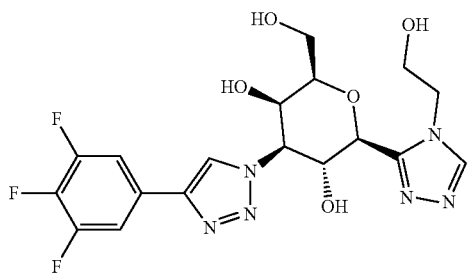 [SMILES: OCCn1cnnc1[C@@H]1O[C@H](CO)[C@H](O)[C@H](n2cc(-c3cc(F)c(F)c(F)c3)nn2)[C@H]1O] | 1.131 | 557.2 | A | 1H NMR (400 MHz, METHANOL-$d_4$) δ 8.84 (s, 1H), 8.60 (s, 1H), 7.87 (s, 1H), 7.76 (d, J = 8.6 Hz, 1H), 7.72-7.61 (m, 2H), 7.58 (d, J = 8.3 Hz, 1H), 5.10-5.01 (m, 1H), 4.86 (d, J = 2.9 Hz, 1H), 4.51 (d, J = 9.3 Hz, 1H), 4.13 (d, J = 2.7 Hz, 1H), 3.93 (s, 3H), 3.84-3.66 (m, 3H), 2.72 (s, 3H) |

General Synthetic Scheme for 4-alkyl-1,2,4-triazole Compounds:

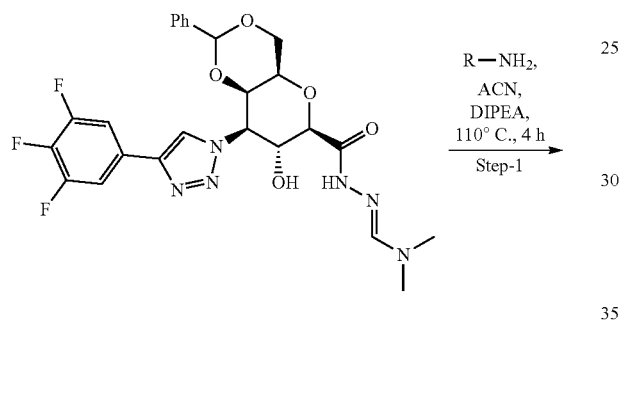

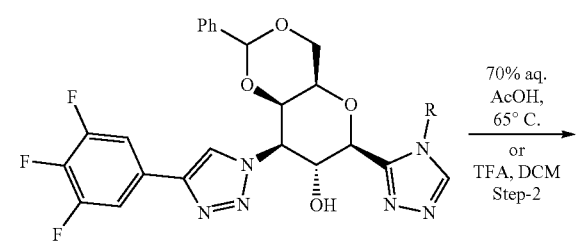

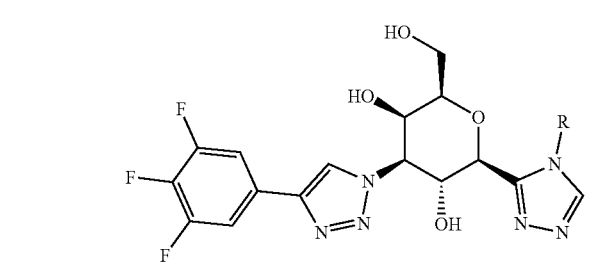

EXAMPLE 170

Preparation of (2S,3R,4R,5R,6R)-2-(4-(2-hydroxyethyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol Step 1: Synthesis of (4aR,6S,7R,8R,8aR)-6-(4-(2-hydroxyethyl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol: To a solution of (E)-N'-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)-N,N-dimethylformohydrazonamide (25 mg, 0.046 mmol) in 2-propanol (2 mL) was added ethanolamine (8.38 mg, 0.137 mmol) and DIPEA (0.040 mL, 0.229 mmol) at rt and reaction mixture was heated at 110° C. for 4 h. The solvent was removed under reduced pressure and the residue was purified by chromatography (0-5% of MeOH in Chloroform) to afford (4aR,6S,7R,8R,8aR)-6-(4-(2-hydroxyethyl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (20 mg, 80%). LC-MS, [M+H]$^+$=545.3, (Method E: $t_R$=1.08). $^1$H NMR (400 MHz, METHANOL-d4) δ=858 (s, 1H), 8.54 (s, 1H), 7.70-7.53 (m, 2H), 7.50-7.42 (m, 2H), 7.42-7.32 (m, 3H), 5.63 (s, 1H), 5.24 (dd, J=3.0, 10.0 Hz, 1H), 5.04-4.93 (m, 2H), 4.65 (d, J=3.0 Hz, 1H), 4.45-4.39 (m, 2H), 4.33-4.19 (m, 2H), 4.09-4.04 (m, 1H), 3.94-3.81 (m, 2H).

Step 2: Synthesis of (2S,3R,4R,5R,6R)-2-(4-(2-hydroxyethyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol: (4aR,6S,7R,8R,8aR)-6-(4-(2-hydroxyethyl)-4H-1,2,4-triazol-3-yl)-2-phenyl-8-(4-(3,4,5- trifluorophenyl)-1H-1,2,3-triazol-1-yl)hexahydropyrano[3,2-d][1,3]dioxin-7-ol (25 mg, 0.046 mmol) was suspended in 70% aq AcOH (3 mL) and the mixture was heated at 70° C. for 16 h. The solvent was removed under reduced pressure and the residue was purified by HPLC (Method A) to afford (2S,3R,4R,5R,6R)-2-(4-(2-hydroxyethyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 170) (2 mg, 10%). LC-MS, [M+H]$^+$=457.2, (Method A: $t_R$=0.94). 1H NMR (400 MHz, METHANOL-d4): δ8.63 (s, 1H), 8.58 (s, 1H), 7.68 (dd, J=9.0, 6.5 Hz, 2H), 5.05-4.97 (m, 1H), 4.93 (t, J=9.8 Hz, 1H), 4.87 (s, 1H), 4.44-4.31 (m, 2H), 4.22 (d, J=2.0 Hz,1H), 4.01 (t,J =6.0 Hz, 1H), 3.92 (t, J=4.8 Hz, 2H), 3.83-3.68 (m, 2H). hGal3 IC50=2 uM.

The Examples in the table below were prepared in an analogous fashion to Example 170, substituting ethanol amine with the appropriate alkyl amine in the synthetic sequence.

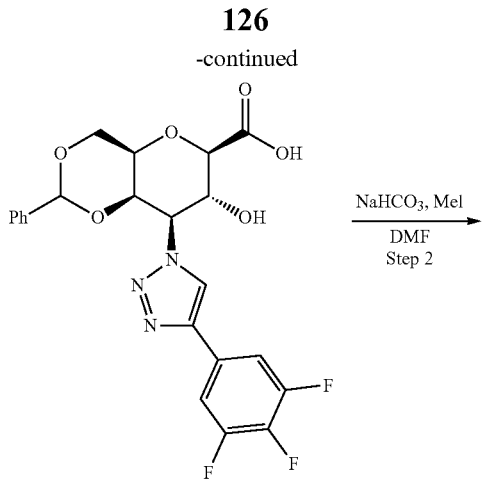

| Ex | hGal3 IC50, uM | Structure | LCMS $t_R$ (min) | M + H | Method | 1H NMR |
|---|---|---|---|---|---|---|
| 171 | 2.02 | 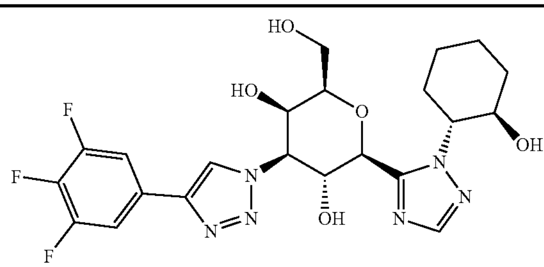 | 1.16 | 511.2 | A | $^1$H NMR (400 MHz, METHANOL-d$_4$) δ 8.77 (s, 1H), 8.57 (s, 1H), 7.71-7.64 (m, 2H), 5.03-5.00 (m, 1H), 4.96-4.92 (m, 1H), 4.63-4.47 (m, 1H), 4.23 (d, J = 2.0 Hz, 1H), 4.01-3.97 (m, 1H), 3.97-3.89 (m, 1H), 3.83-3.73 (m, 3H), 2.23-2.11 (m, 3H), 1.91-1.81 (m, 2H), 1.58-1.48 (m, 3H) |
| 172 | 3.84 | 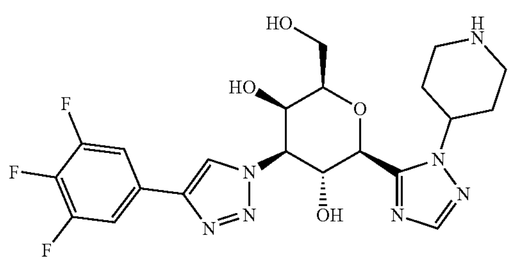 [SMILES: OC[C@H]1O[C@@H](c2ncnn2C2CCNCC2)[C@H](O)[C@@H](n2cc(-c3cc(F)c(F)c(F)c3)nn2)[C@H]1O] | 0.908 | 496.2 | A | $^1$H NMR (400 MHz, METHANOL-d$_4$) δ 8.75 (s, 1H), 8.63 (s, 1H), 7.69 (dd, J = 8.7, 6.7 Hz, 2H), 5.03 (dd, J = 10.0, 2.4 Hz, 1H), 4.82-4.67 (m, 1H), 4.23 (d, J = 2.0 Hz, 1H), 4.08-4.02 (m, 1H), 3.83-3.74 (m, 2H), 3.45-3.36 (m, 2H), 3.08-2.97 (m, 2H), 2.41-2.23 (m, 2H), 2.09-1.98 (m, 2H), 1.41-1.24 (m, 2H). |

General Synthetic Scheme for C2-deoxy-1,2,4-triazole Compounds

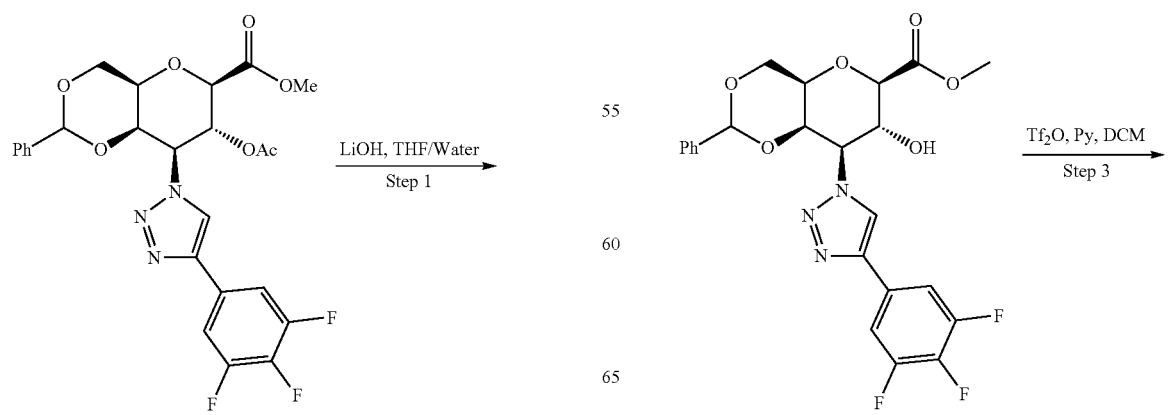

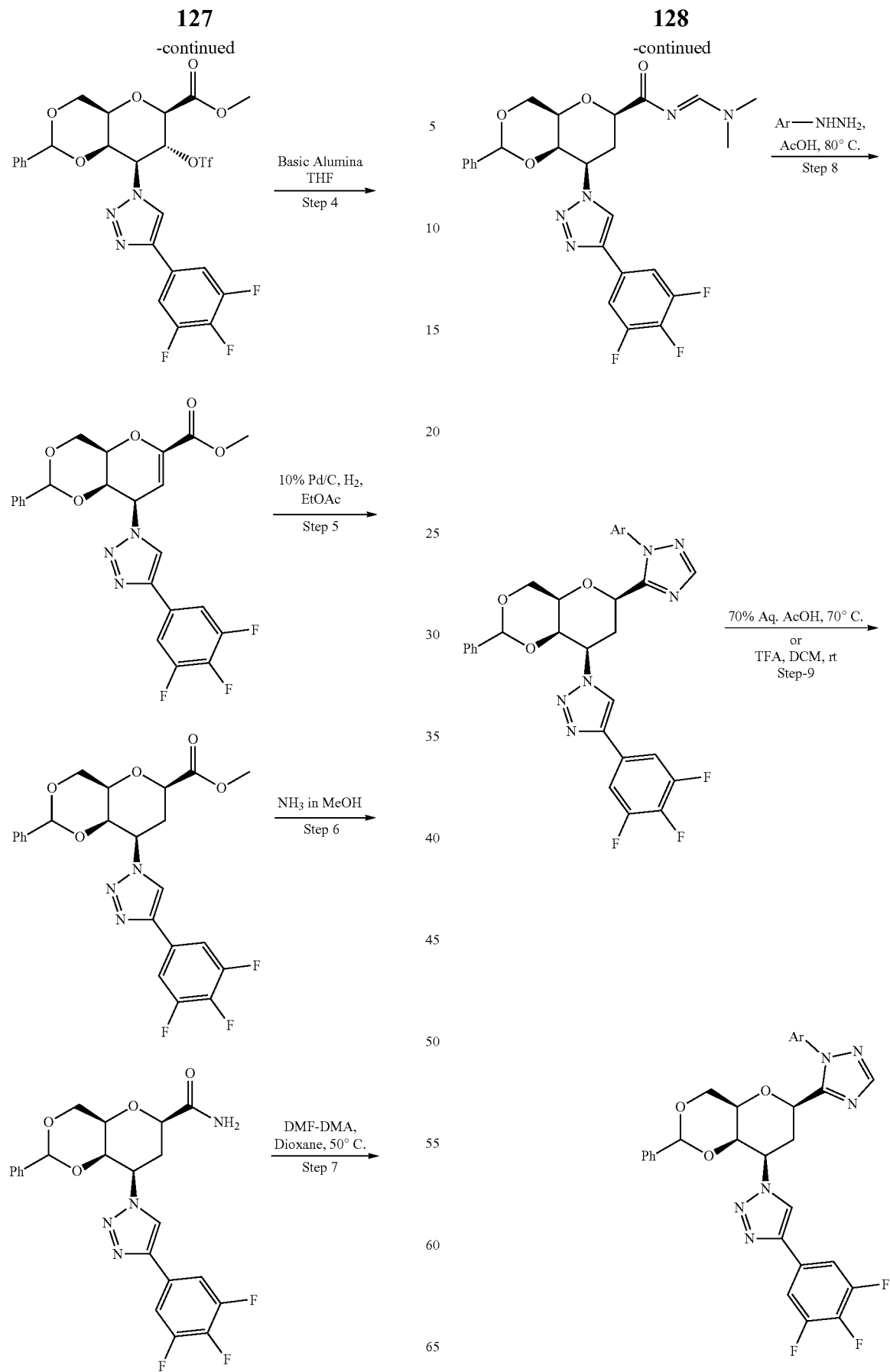

EXAMPLE 173

Preparation of (2R,3R,4R,6R)-6-(1-(3-chlorophenyl)-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol

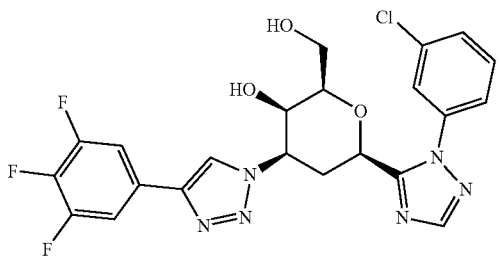 [SMILES: OC[C@H]1O[C@@H](c2ncnn2-c2cccc(Cl)c2)C[C@@H](n2cc(-c3cc(F)c(F)c(F)c3)nn2)[C@H]1O]

Step 1: Synthesis of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid: To a stirred solution of (4aR,6R,7R,8R,8S,8aR)-methyl 7-acetoxy-2-phenyl-8-(4-(3,4,5-trifluorophenyl)-1H-1,2,3-triazol-1-yl)hexahydropyrano[3,2-d][1,3]dioxine-6-carboxylate (6.9 g, 12.93 mmol) in THF (300 mL) and water (100 mL) was added lithium hydroxide (1.549 g, 64.7 mmol) and the mixture was stirred at rt for 4 h. The reaction mixture was concentrated under reduced pressure. The reaction mixture was diluted with water and acidified with 1.5N HCl (pH: 2-3). The solid was filtered, washed with excess water, and dried to afford a solid. The wet solid was dissolved in 10% methanol in DCM (2000 mL) dried over $Na_2SO_4$, filtered, and concentrated to afford (4aR,6R,7R,8R,8aR)-7-hydroxy-2-phenyl-8-(4-(3,4,5-trifluorophenyl)-1H-1,2,3-triazol-lyl)hexahydropyrano[3,2-d][1,3]dioxine-6-carboxylic acid (5.8 g, 94%). LC-MS, [M+H]$^+$=478.0, (Method C: $t_R$=1.84 min). 1H NMR (400 MHz, DMSO-d6) δ 8.87 (s, 1H), 7.98-7.67 (m, 2H), 7.34 (s, 5H), 5.54 (s, 1H), 5.13 (dd, J=3.3, 10.8 Hz, 1H), 4.53-4.40 (m, 2H), 4.18-4.04 (m, 2H), 4.00 (d, J=9.0 Hz, 1H), 3.92 (s, 1H).

Step 2: Synthesis of (4aR,6R,7R,8R,8aR)-methyl 7-hydroxy-2-phenyl-8-(4-(3,4,5-trifluorophenyl)-1H-1,2,3-triazol-1-yl)hexahydropyrano[3,2-d][1,3]dioxine-6-carboxylate: To a stirred solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (5.8 g, 12.15 mmol) in DMF (60 mL) was added sodium bicarbonate (1.531 g, 18.22 mmol) followed by methyl iodide (3.80 mL, 60.7 mmol) and the mixture was stirred at rt for 8 h. The reaction mixture filtered, washed with DMF, (100 mL) and the filtrate was concentrated. The residue was purified via silica gel chromatography (0-10% MeOH in chloroform) to afford (4aR,6R,7R,8R,8aR)-methyl 7-hydroxy-2-phenyl-8-(4-(3,4,5-trifluorophenyl)-1H-1,2,3-triazol-1-yl)hexahydropyrano[3,2-d][1,3]dioxine-6-carboxylate (5.5 g, 92%). LC-MS, [M+H]$^+$=492.0, (Method C: $t_R$=2.7 min). $^1$H NMR (400 MHz, DMSO-$d_6$) δ 8.90 (s, 1H), 7.90-7.71 (m, 2H), 7.34 (s, 5H), 5.82-5.66 (m, 1H), 5.55 (s, 1H), 5.17 (dd, J=3.8, 10.8 Hz, 1H), 4.56-4.44 (m, 2H), 4.15 (d, J=9.0 Hz, 2H), 4.12-4.06 (m, 1H), 3.96 (s, 1H), 3.73 (s, 3H).

Step 3: Synthesis of (4aR,6R,7R,8S,8aR)-methyl 2-phenyl-7-(((trifluoromethyl)sulfonyl)oxy)-8-(4-(3,4,5-trifluorophenyl)-1H-1,2,3-triazol-1-yl)hexahydropyrano[3,2-d][1,3]dioxine-6-carboxylate: To a stirred solution of (4aR,6R,7R,8R,8aR)-methyl 7-hydroxy-2-phenyl-8-(4-(3,4,5-trifluorophenyl)-1H-1,2,3-triazol-1-yl)hexahydropyrano[3,2-d][1,3]dioxine-6-carboxylate (4.5 g, 9.16 mmol) in DCM (100 mL), was added pyridine (11.11 mL, 137 mmol). The reaction mixture cooled to −20° C. Triflic anhydride (2.475 mL, 14.65 mmol) was added and the reaction mixture was allowed to reach rt and was stirred for 14 h. The mixture was concentrated under reduced pressure. Ice cold water was added and the mixture was stirred for 15 min. The solid was filtered, washed with excess water and dried to give (4aR,6R,7R,8S,8aR)-methyl 2-phenyl-7-(((trifluoromethyl)sulfonyl)oxy)-8-(4-(3,4,5-trifluorophenyl)-1H-1,2,3-triazol-1-yl)hexahydropyrano[3,2-d][1,3]dioxine-6-carboxylate (5.0 g, 67%). LC-MS, [M+H]$^+$=624.0, (Method C: $t_R$=3.6 min).

Step 4: Synthesis of (4aR,8R,8aR)-methyl 2-phenyl-8-(4-(3,4,5-trifluorophenyl)-1H-1,2,3-triazol-1-yl)-4,4a,8,8a-tetrahydropyrano[3,2-d][1,3]dioxine-6-carboxylate: To a stirred solution of (4aR,6R,7R,8S,8aR)-methyl 2-phenyl-7-(((trifluoromethyl)sulfonyl)oxy)-8-(4-(3,4,5-trifluorophenyl)-1H-1,2,3-triazol-1-yl)hexahydropyrano[3,2-d][1,3]dioxine-6-carboxylate (5 g, 8.02 mmol) in THF (100 mL) was added aluminium oxide (basic) (40.9 g, 401 mmol) and the mixture was stirred at rt for 36 h. The mixture was concentrated under reduced pressure and the residue was purified via silica gel chromatography (0-10% MeOH in chloroform) to afford (4aR,8R,8aR)-methyl 2-phenyl-8-(4-(3,4,5-trifluorophenyl)-1H-1,2,3-triazol-1-yl)-4,4a,8,8a-tetrahydropyrano[3,2-d][1,3]dioxine-6-carboxylate (3.63 g, 87%) as an off-white solid. LC-MS, [M+H]$^+$=474.0, (Method C: $t_R$=3.09 min). $^1$H NMR (400 MHz, DMSO-$d_6$) δ=8.78 (s, 1H), 7.91-7.77 (m, 2H), 7.33-7.15 (m, 5H), 6.21-6.12 (m, 2H), 5.69 (s, 1H), 4.68-4.65 (m, 1H), 4.52-4.49 (m, 1H), 4.36-4.31 (m, 1H), 4.21 (dd, J=1.0, 12.5 Hz, 1H), 3.79 (s, 3H).

Step 5: Synthesis of methyl (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxylate: To a stirred solution of (4aR,8R,8aR)-methyl 2-phenyl-8-(4-(3,4,5-trifluorophenyl)-1H-1,2,3-triazol-1-yl)-4,4a,8,8a-tetrahydropyrano[3,2-d][1,3]dioxine-6-carboxylate (3.6 g, 7.60 mmol) in ethyl acetate (200 mL) was added palladium on carbon (10% w/w, 50% wet, 0.809 g, 0.760 mmol) and the mixture was stirred at rt under a hydrogen atmosphere for 16 h. The reaction mixture filtered through Celite and was washed with excess methanol. The filtrate was concentrated to afford methyl (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxylate (2 g, 55%). LC-MS, [M+H]$^+$=476.0, (Method C: $t_R$=3.019 min). $^1$H NMR (400 MHz, DMSO-$d_6$) δ=8.88 (s, 1H), 7.84-7.72 (m, 2H), 7.42-7.28 (m, 5H), 5.65 (s, 1H), 5.44-5.23 (m, 1H), 4.56-4.50 (m, 1H), 4.48-4.44 (m, 1H), 4.18-4.12 (m, 2H), 3.85 (s, 1H), 3.73 (s, 3H), 2.47-2.42 (m, 1H), 2.39-2.30 (m, 1H).

Step 6: Synthesis of (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamide: Methyl (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxylate (0.15 g, 0.316 mmol) was suspended in methanolic ammonia (7 nM, 15 mL) at 0° C. and the mixture was allowed to reach rt and was stirred for 12 h. The reaction mixture was concentrated under reduced pressure and the residue was triturated with diethyl ether and filtered. The solid was washed with diethyl ether and dried to afford (4aR,6R,8R,8aR)-2-phenyl-8-(4-(3,4,5-trifluorophenyl)-1H-1,2,3-triazol-1-yl)hexahydropyrano[3,2-d][1,3]dioxine- 6-carboxamide (140 mg, 96%) as a pale brown solid. LC-MS, [M+H]⁺=476.0, (Method C: $t_R$=2.49 min).

Step 7: Synthesis of (4aR,6R,8R,8aR)-N-((E)-(dimethylamino)methylene)-2-phenyl-8-(4-(3,4,5-trifluorophenyl)-1H-1,2,3-triazol-1-yl)hexahydropyrano[3,2-d][1,3]dioxine-6-carboxamide: To a stirred solution of (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamide (0.15 g, 0.326 mmol) in dioxane (5 mL) was added DMF-DMA (0.065 mL, 0.489 mmol) and the mixture was heated at 50° C. for 2 h. The reaction mixture was cooled to rt and concentrated under reduced pressure. The residue was triturated with diethyl ether and filtered. The obtained solid was washed with diethyl ether and dried to afford (4aR,6R,8R,8aR)-N-((E)-(dimethylamino)methylene)-2-phenyl-8-(4-(3,4,5-trifluorophenyl)-1H-1,2,3-triazol-1-yl)hexahydropyrano[3,2-d]dioxine-6-carboxamide (0.15 g, 89%) as a pale brown solid. LC-MS, [M+H]⁺=516.2, (Method C: $t_R$=2.44 min).

Step 8: Synthesis of 1-((4aR,6R,8R,8aR)-6-(1-(3-chlorophenyl)-1H-1,2,4-triazol-5-yl)-2-phenylhexahydropyrano[3,2-d][1,3]dioxin-8-yl)-4-(3,4,5-trifluorophenyl)-1H-1,2,3-triazole: To a stirred solution of (4aR,6R,8R,8aR)-N-((E)-(dimethylamino)methylene)-2-phenyl-8-(4-(3,4,5-trifluorophenyl)-1H-1,2,3-triazol-1-yl)hexahydropyrano[3,2-d][1,3]dioxine-6-carboxamide (0.08 g, 0.155 mmol) in DMF (2 mL) was added (3-chlorophenyl)hydrazine hydrochloride (0.056 g, 0.310 mmol) and acetic acid (0.089 mL, 1.552 mmol). The mixture was heated at 80° C. for 3 h. The reaction mixture was cooled to rt, diluted with water and stirred for 5 min. The solid was filtered, washed with excess water and dried to give a solid which was further purified via silica gel chromatography (0-3% MeOH in chloroform) to afford 1-((4aR,6R,8R,8aR)-6-(1-(3-chlorophenyl)-1H-1,2,4-triazol-5-yl)-2-phenylhexahydropyrano[3,2-d][1,3]dioxin-8-yl)-4-(3,4,5-trifluorophenyl)-1H-1,2,3-triazole (0.04 g, 43%) as a yellow solid. LCMS (ESI) m/e 595.2; LC/MS retention time (Method C); $t_R$=1.52 min.

Step 9: Synthesis of of (2R,3R,4R,6R)-6-(1-(3-chlorophenyl)-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol: To a stirred solution of 1-((4aR,6R,8R,8aR)-6-(1-(3-chlorophenyl)-1H-1,2,4-triazol-5-yl)-2-phenylhexahydropyrano[3,2-d][1,3]dioxin-8-yl)-4-(3,4,5-trifluorophenyl)-1H-1,2,3-triazole (0.04 g, 0.067 mmol) in DCM (1 mL) was added TFA (0.2 mL, 2.60 mmol) at 0° C. The reaction mixture was allowed to reach rt and was stirred for 1 h. The reaction mixture was concentrated under reduced pressure and purified by HPLC (Method D) to afford (2R,3R,4R,6R)-6-(1-(3-chlorophenyl)-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol (Example 173) (8 mg, 23%) as a white solid. LC-MS, [M+H]⁺=507.2, (Method C: $t_R$=2.283). 1H NMR (400 MHz, METHANOL-d4) δ 8.57 (s, 1H), 8.18 (s, 1H), 7.86-7.83 (m, 1H), 7.78-7.74 (m, 1H), 7.68 (dd, J=9.0, 7.0 Hz, 2H), 7.62-7.59 (m, 2H), 5.16-5.09 (m, 1H), 4.92 (dd, J=11.5, 2.5 Hz, 1H), 4.14 (s, 1H), 3.88-3.84 (m, 1H), 3.82-3.71 (m, 2H), 3.28-3.18 (m, 1H), 2.32-2.35 (m, 1H). hGal3 IC₅₀=0.18 uM.

The Examples in the table below were prepared in an analogous fashion to Example 173, substituting (3-chlorophenyl)hydrazine hydrochloride with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 174 | 0.30 | 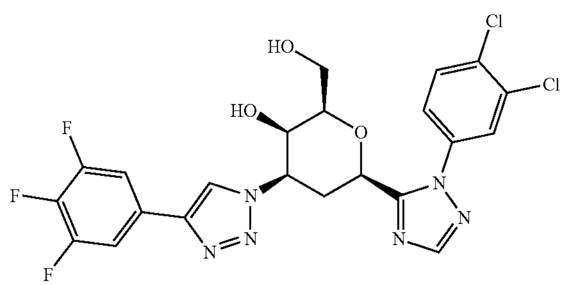 [SMILES: OC[C@H]1O[C@@H](c2ncnn2-c2ccc(Cl)c(Cl)c2)C[C@@H](n2cc(-c3cc(F)c(F)c(F)c3)nn2)[C@H]1O] | 1.735 | 543.1 | A | 1H NMR (400 MHz, METHANOL-d4) δ 8.57 (s, 1H), 8.18 (s, 1H), 8.02 (s, 1H), 7.78 (s, 2H), 7.68 (dd, J = 9.0, 6.5 Hz, 2H), 5.15-5.11 (m, 1H), 4.93 (d, J = 2.0 Hz, 1H), 4.14 (s, 1H), 3.90-3.84 (m, 1H), 3.80 (dd, J = 11.5, 7.0 Hz, 1H), 3.73 (dd, J = 11.5, 5.0 Hz, 1H), 3.24 (br. s., 1H), 2.34 (d, J = 12.0 Hz, 1H). |
| 175 | 0.65 | 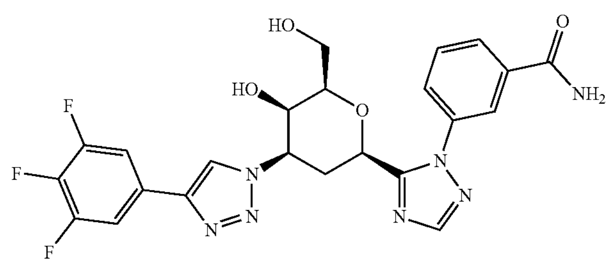 [SMILES: NC(=O)c1cccc(-n2ncnc2[C@H]2C[C@@H](n3cc(-c4cc(F)c(F)c(F)c4)nn3)[C@@H](O)[C@@H](CO)O2)c1] | 1.217 | 516.2 | A | 1H NMR (400 MHz, METHANOL-d4) δ 8.57 (s, 1H), 8.26 (t, J = 2.0 Hz, 1H), 8.20 (s, 1H), 8.13-8.06 (m, 1H), 7.97 (ddd, J = 8.0, 2.0, 1.0 Hz, 1H), 7.78-7.72 (m, 1H), 7.72-7.61 (m, 2H), 5.15-5.09 (m, 1H), 4.94 (dd, J = 11.3, 2.3 Hz, 1H), 4.14 (d, J = 2.5 Hz, 1H), 3.93-3.87 (m, 1H), 3.82 (dd, J = 11.3, 6.8 Hz, 1H), 3.74 (dd, J = 11.0, 5.0 Hz, 1H), 3.24 (d, J = 11.5 Hz, 1H), 2.33 (d, J = 13.1 Hz, 1H). |

-continued

| Ex | hGal3 IC50, uM | Structure | LCMS $t_R$ (min) | M + H | Method | 1H NMR |
|---|---|---|---|---|---|---|
| 176 | 0.04 | 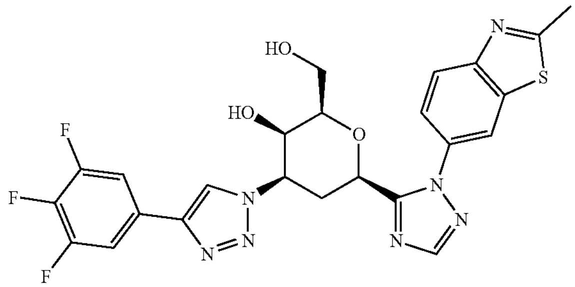 [SMILES: Cc1nc2ccc(-n3ncnc3[C@H]3C[C@@H](n4cc(-c5cc(F)c(F)c(F)c5)nn4)[C@@H](O)[C@@H](CO)O3)cc2s1] | 2.119 | 544.2 | C | 1H NMR (400 MHz, METHANOL-d4) δ 8.50 (s, 1H), 8.45 (d, J = 2.0 Hz, 1H), 8.15 (s, 1H), 8.0 (d, J = 8.6 Hz, 1H), 7.80 (dd, J = 8.7, 2.1 Hz, 1H), 7.70-7.55 (m, 2H), 5.08-5.0 (m, 1H), 4.00 (d, J = 2.4 Hz, 1H), 3.80-3.60 (m, 3H), 3.20 (d, J = 11.5 Hz, 1H), 2.79 (s, 3H), 2.28 (d, J = 13.9 Hz, 1H). Note: 1H buried under solvent moisture peak |
| 177 | 0.13 | 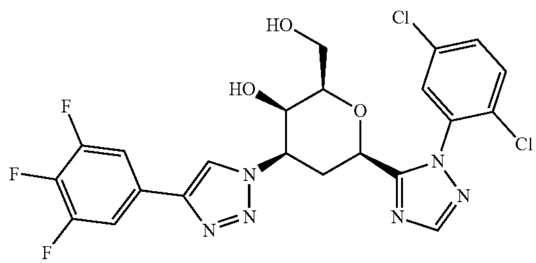 [SMILES: OC[C@H]1O[C@@H](c2ncnn2-c2cc(Cl)ccc2Cl)C[C@@H](n2cc(-c3cc(F)c(F)c(F)c3)nn2)[C@H]1O] | 1.701 | 543.2 | A | 1H NMR (400 MHz, METHANOL-d4) δ 8.54 (s, 1H), 8.21 (s, 1H), 7.78 (d, J = 2.2 Hz, 1H), 7.74-7.57 (m, 4H), 5.19-5.06 (m, 1H), 4.91 (d, J = 9.8 Hz, 1H), 4.11-4.10 (m, 1H), 3.69-3.55 (m, 2H), 3.52-3.46 (m, 1H), 3.01 (q, J = 12.6 Hz, 1H), 2.45 (d, J = 13.2 Hz, 1H). |
| 178 | 0.25 | 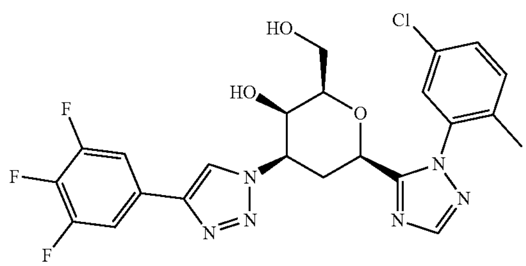 [SMILES: Cc1ccc(Cl)cc1-n1ncnc1[C@H]1C[C@@H](n2cc(-c3cc(F)c(F)c(F)c3)nn2)[C@@H](O)[C@@H](CO)O1] | 1.742 | 521.2 | A | 1H NMR (400 MHz, METHANOL-d4) δ 8.56 (s, 1H), 8.22 (s, 1H), 7.75-7.61 (m, 2H), 7.59 (d, J = 2.2 Hz, 1H), 7.55 (dd, J = 8.1, 2.2 Hz, 1H), 7.46 (d, J = 8.3 Hz, 1H), 5.15-5.04 (m, 1H), 4.80 (dd, J = 11.5, 2.2 Hz, 1H), 4.09 (d, J = 2.2 Hz, 1H), 3.69-3.53 (m, 3H), 3.15-3.03 (m, 1H), 2.37 (d, J = 13.4 Hz, 1H), 2.10 (s, 3H). |
| 179 | 0.25 | 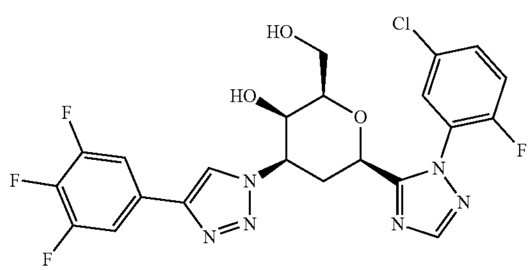 [SMILES: OC[C@H]1O[C@@H](c2ncnn2-c2cc(Cl)ccc2F)C[C@@H](n2cc(-c3cc(F)c(F)c(F)c3)nn2)[C@H]1O] | 1.662 | 525.1 | A | 1H NMR (400 MHz, METHANOL-d4) δ 8.56 (s, 1H), 8.22 (s, 1H), 7.79 (dd, J = 6.4, 2.7 Hz, 1H), 7.74-7.57 (m, 3H), 7.45 (t, J = 9.3 Hz, 1H), 5.19-5.09 (m, 1H), 4.98 (dd, J = 11.2, 2.2 Hz, 1H ), 4.11 (s, 1H), 3.75-3.68 (m, 1H), 3.61 (dd, J = 11.2, 5.9 Hz, 1H), 3.51 (dd, J = 11.1, 6.5 Hz, 1H), 3.09-2.93 (m, 1H), 3.48-2.45 (m, 1H). |
| 180 | 0.21 | 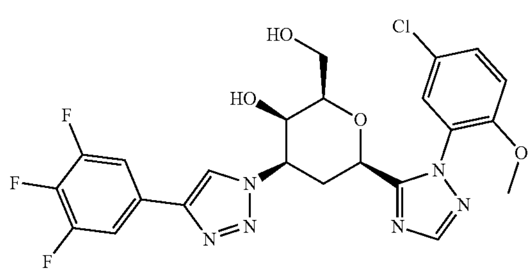 [SMILES: COc1ccc(Cl)cc1-n1ncnc1[C@H]1C[C@@H](n2cc(-c3cc(F)c(F)c(F)c3)nn2)[C@@H](O)[C@@H](CO)O1] | 1.681 | 537.2 | A | 1H NMR (400 MHz, METHANOL-d4) δ 8.56 (s, 1H), 8.18 (s, 1H), 7.75-7.62 (m, 2H), 7.59 (dd, J = 8.8, 2.7 Hz, 1H), 7.55 (d, J = 2.4 Hz, 1H), 7.27 (d, J = 9.0 Hz, 1H), 5.19-5.07 (m, 1H), 4.86 (dd, J = 11.5, 2.2 Hz, 1H), 4.09 (d, J = 2.4 Hz, 1H), 3.88 (s, 3H), 3.72-3.58 (m, 2H), 3.58-3.50 (m, 1H), 3.04-2.89 (m, 1H) 2.37 (d, J = 13.2 Hz, 1H). |

| Ex | hGal3 IC50, uM | Structure | LCMS $t_R$ (min) | M + H | Method | 1H NMR |
|---|---|---|---|---|---|---|
| 181 | 0.04 | 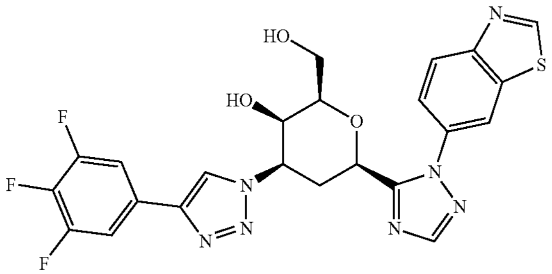 [SMILES: OC[C@H]1O[C@@H](c2ncnn2-c2ccc3ncsc3c2)C[C@@H](n2cc(-c3cc(F)c(F)c(F)c3)nn2)[C@H]1O] | 2.029 | 530.2 | C | 1H NMR (400 MHz, METHANOL-d4) δ 9.41 (s, 1H), 8.67 (d, J = 2.0 Hz, 1H), 8.55 (s, 1H), 8.31-8.15 (m, 2H), 7.92 (dd, J = 8.8, 2.3 Hz, 1H), 7.66 (dd, J = 8.8, 6.8 Hz, 2H), 5.15-5.04 (m, 1H), 4.91 (dd, J = 2.0, 11.0 Hz, 1H), 4.11 (d, J = 2.0 Hz, 1H), 3.87-3.67 (m, 2H), 3.58-3.52 (m, 1H), 2.34 (d, J = 12.5 Hz, 1H). (1H buried with solvent peak) |
| 182 | 0.12 | 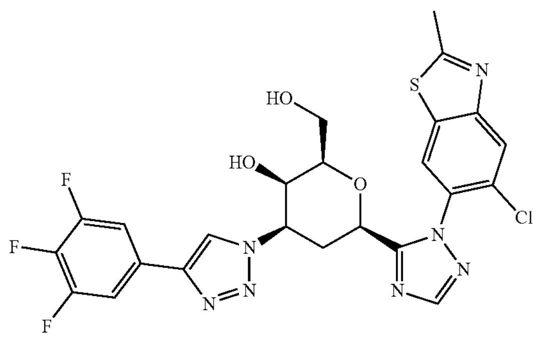 [SMILES: Cc1nc2cc(Cl)c(-n3ncnc3[C@H]3C[C@@H](n4cc(-c5cc(F)c(F)c(F)c5)nn4)[C@@H](O)[C@@H](CO)O3)cc2s1] | 2.288 | 578.2 | C | 1H NMR (400 MHz, METHANOL-d4) δ 8.52 (s, 1H), 8.33 (s, 1H), 8.26-8.13 (m, 2H), 7.65 (dd, J = 8.8, 6.8 Hz, 2H), 5.12-5.02 (m, 1H), 4.08-3.99 (m, 1H), 3.64-3.46 (m, 3H), 3.20-3.10 (m, 1H), 2.92 (s, 3H), 2.49-2.36 (m, 1H) (1H buried with solvent peak) |

General Scheme for the Preparation of C-2 deoxy, 4-methyl, 1,2,4-triazole Compounds:

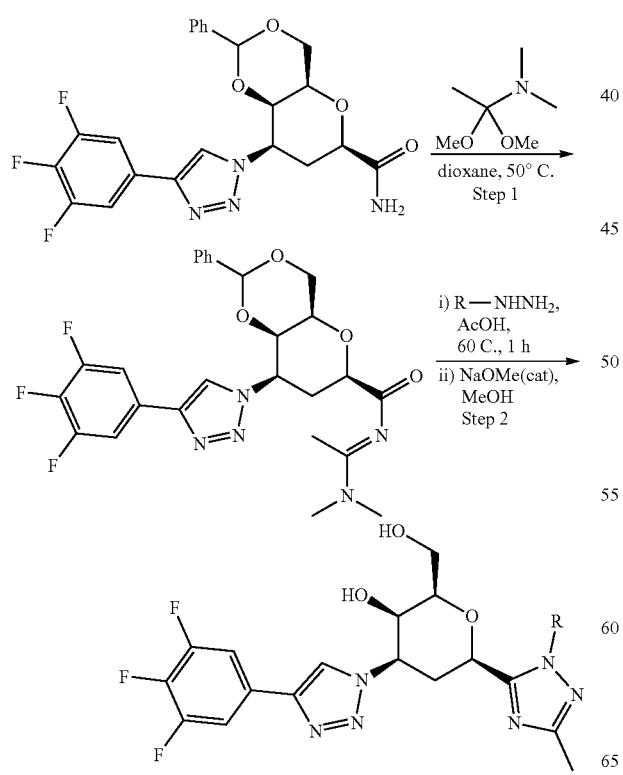

EXAMPLE 183

Preparation of (2R,3R,4R,6R)-6-(1-(5-chloro-2-methoxyphenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol

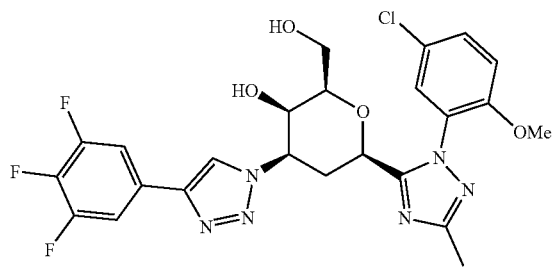 [SMILES: COc1ccc(Cl)cc1-n1nc(C)nc1[C@H]1C[C@@H](n2cc(-c3cc(F)c(F)c(F)c3)nn2)[C@@H](O)[C@@H](CO)O1]

Step 1: Synthesis of (4aR,6R,8R,8aR)-N-((Z)-1-(dimethylamino)ethylidene)-2-phenyl-8-(4-(3,4,5-trifluorophenyl)-1H-1,2,3-triazol-1-yl)hexahydropyrano[3,2-d][1,3]dioxine-6-carboxamide: To a solution of (4aR,6R,8R,8aR)-2-phenyl-8-(4-(3,4,5-trifluorophenyl)-1H-1,2,3-triazol-1-yl) hexahydropyrano[3,2-d][1,3]dioxine-6-carboxamide (0.4 g, 0.869 mmol) in dioxane (5 mL) was added N,N-dimethylacetamide dimethyl acetal (0.129 mL, 0.869 mmol) at rt and the mixture was heated to 60° C. for 3 h. The solvent was removed under reduced pressure to get the crude material. Then reaction mixture was cooled to rt and concentrated under reduced pressure. The residue was triturated with diethyl ether and filtered. The obtained solid was washed with diethyl ether and dried to afford (4aR,6R,8R,8aR)-N-

((Z)-1-(dimethylamino)ethylidene)-2-phenyl-8-(4-(3,4,5-trifluorophenyl)-1H-1,2,3-triazol-1-yl)hexahydropyrano[3,2-d][1,3]dioxine-6-carboxamide (300 mg, 65%). LC-MS, [M+H]$^+$=530.3, (Method E: $t_R$=1.58 min).

Step 2: Synthesis of (4aR,6R,8R,8aR)-N-((Z)-1-(dimethylamino)ethylidene)-2-phenyl-8-(4-(3,4,5-trifluorophenyl)-1H-1,2,3-triazol-1-yl)hexahydropyrano[3,2-d][1,3]dioxine-6-carboxamide: (4aR,6R,8R,8aR)-N-((Z)-1-(Dimethylamino)ethylidene)-2-phenyl-8-(4-(3,4,5-trifluorophenyl)-1H-1,2,3-triazol-1-yOhexahydropyrano[3,2-d][1,3]dioxine-6-carboxamide (50 mg, 0.094 mmol) and (5-chloro-2-methoxyphenyl)hydrazine (16.30 mg, 0.094 mmol) were taken in AcOH (1 mL) and heated to 60° C. for 2 h. Then reaction mixture was concentrated and the residue was dried. The crude residue was dissolved in MeOH (1 mL) and 25% sodium methoxide in MeOH (1.276 mg, 5.90 μmol) was added and the mixture was stirred at rt for 1 h.

The solvent was removed under reduced pressure and the residue was purified by prep HPLC (Method A) to afford ((2R,3R,4R,6R)-6-(1-(5-chloro-2-methoxyphenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol (Example 183) (10.5 mg, 32%). LC-MS, [M+H]$^+$=551.2, (Method A: $t_R$=1.718). 1H NMR (400 MHz, METHANOL-d4): d 8.54 (s, 1H), 7.74-7.61 (m, 2H), 7.58 (dd, J=8.8, 2.7 Hz, 1H), 7.53 (d, J=2.4 Hz, 1H), 7.26 (d, J=9.0 Hz, 1H), 5.13-5.05 (m, 1H), 4.79 (dd, J=11.5, 2.4 Hz, 1H), 4.09 (d, J=2.2 Hz, 1H), 3.88 (s, 3H), 3.80 (s, 1H), 3.70-3.59 (m, 2H), 3.59-3.53 (m, 1H), 3.03-2.88 (m, 1H), 2.44 (s, 3H). hGal3 IC$_{50}$=0.16 uM.

The examples in the table below were prepared in an analogous fashion to Example 183, substituting (5-chloro-2-methoxyphenyl)hydrazine with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 184 | 0.09 | 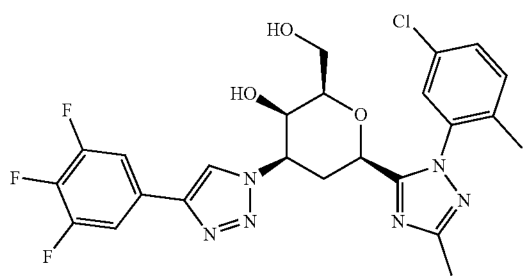 [SMILES: Cc1nc([C@H]2C[C@@H](n3cc(-c4cc(F)c(F)c(F)c4)nn3)[C@@H](O)[C@@H](CO)O2)n(-c2cc(Cl)ccc2C)n1] | 1.777 | 535.2 | A | 1H NMR (400 MHz, METHANOL-d4) δ 8.54 (s, 1H), 7.73-7.60 (m, 2H), 7.59-7.48 (m, 2H), 7.47-7.39 (m, 1H), 5.11-5.02 (m, 1H), 4.74 (dd, J = 11.5, 2.4 Hz, 1H), 4.09 (d, J = 2.4 Hz, 1H), 3.69-3.51 (m, 3H), 3.10-2.97 (m, 1H), 2.46 (s, 3H), 2.35-2.32 (m, 1H), 2.11 (s, 3H). |
| 185 | 0.17 | 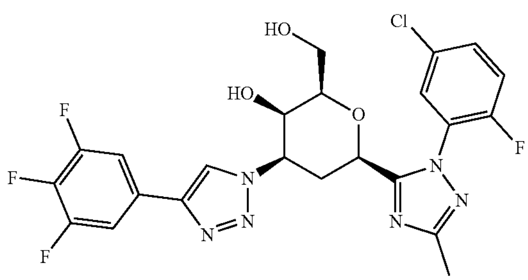 [SMILES: Cc1nc([C@H]2C[C@@H](n3cc(-c4cc(F)c(F)c(F)c4)nn3)[C@@H](O)[C@@H](CO)O2)n(-c2cc(Cl)ccc2F)n1] | 1.726 | 539.1 | A | 1H NMR (400 MHz, METHANOL-d4) δ 8.54 8.54 (s, 1H), 7.76 (dd, J = 6.4, 2.7 Hz, 1H), 7.72-7.56 (m, 3H), 7.43 (t, J = 9.3 Hz, 1H), 5.16-5.07 (m, 1H), 4.92 (dd, J = 11.6, 2.3 Hz, 1H), 4.11 (d, J = 2.2 Hz, 1H), 3.73-3.65 (m, 1H), 3.64-3.56 (m, 1H), 3.56-3.47 (m, 1H), 3.04-2.91 (m, 1H), 2.55-2.32 (m, 4H). |
| 186 | 0.05 | 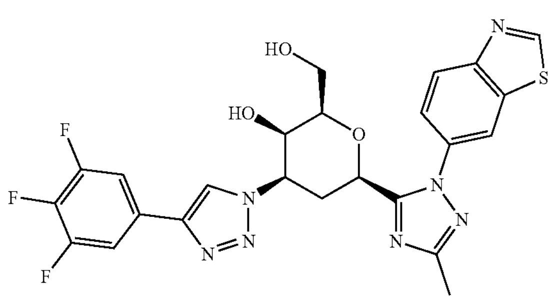 [SMILES: Cc1nc([C@H]2C[C@@H](n3cc(-c4cc(F)c(F)c(F)c4)nn3)[C@@H](O)[C@@H](CO)O2)n(-c2ccc3ncsc3c2)n1] | 2.118 | 544.3 | C | 1H NMR (400 MHz, METHANOL-d4) δ 9.41 (s, 1H), 8.64 (d, J = 2.0 Hz, 1H), 8.56 (s, 1H), 8.27 (d, J = 8.5 Hz, 1H), 7.94-7.87 (m, 1H), 7.67 (dd, J = 6.5, 9.0 Hz, 2H), 5.12-5.05 (m, 1H), 4.95-4.90 (m, 1H), 4.10 (d, J = 2.5 Hz, 1H), 3.87-3.67 (m, 3H), 3.26-3.14 (m, 1H), 2.49 (s, 3H), 2.36-2.29 (m, 1H) |

| Ex | hGal3 IC50, uM | Structure | LCMS $t_R$ (min) | M + H | Method | 1H NMR |
|---|---|---|---|---|---|---|
| 187 | 0.11 | 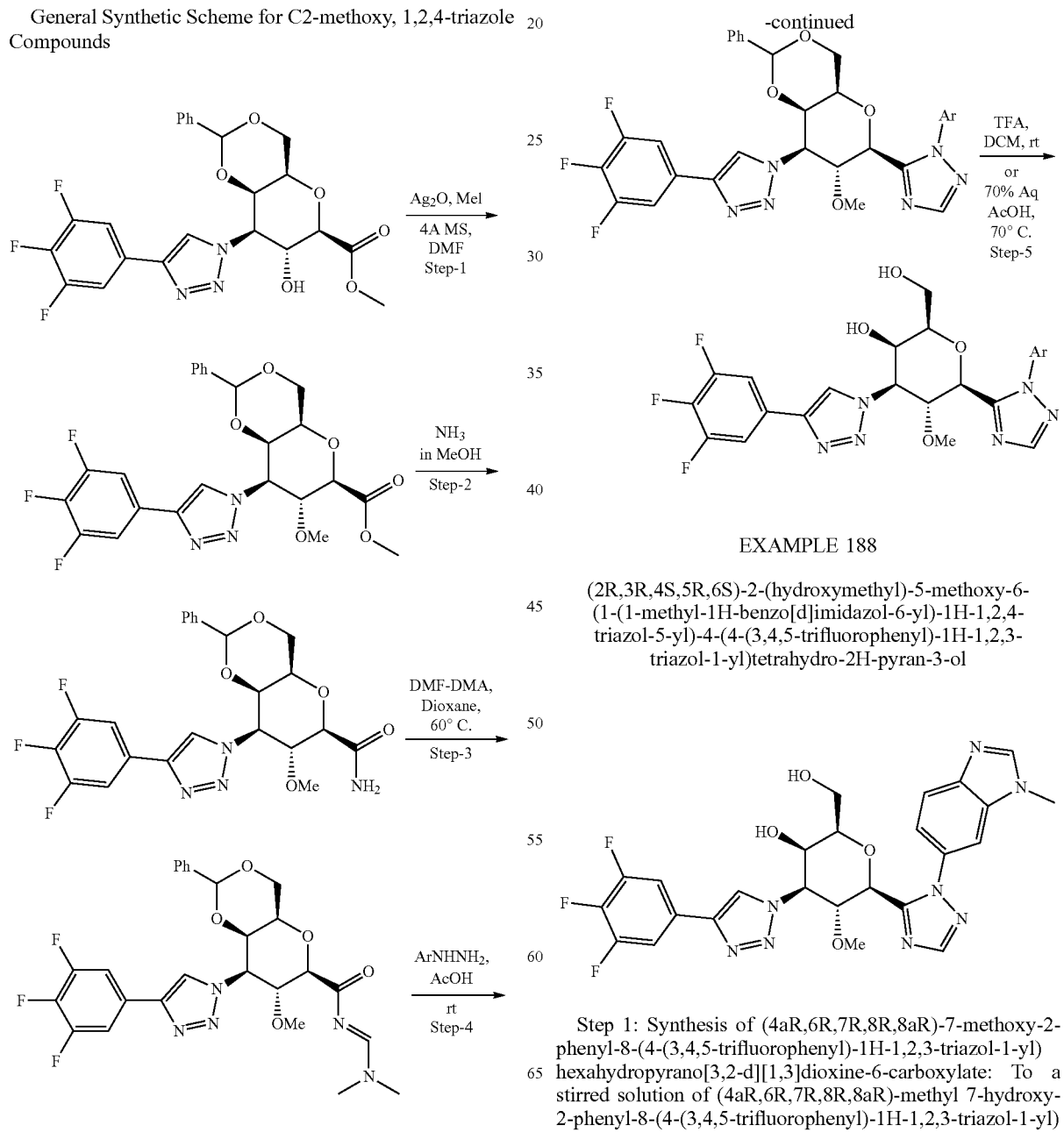 | 2.21 | 558.2 | C | 1H NMR (400 MHz, METHANOL-d4) δ 8.55 (s, 1H), 8.46 (d, J = 2.5 Hz, 1H), 8.11-8.05 (m, 1H), 7.82 (dd, J = 2.3, 8.8 Hz, 1H), 7.67 (dd, J = 7.0, 9.0 Hz, 2H), 5.11-5.06 (m, 1H), 4.91-4.88 (m, 1H), 4.10 (d, J = 2.5 Hz, 1H), 3.85-3.68 (m, 3H), 3.24-3.16 (m, 1H), 2.96 (s, 3H), 2.48 (s, 3H), 2.35-2.28 (m, 1H). |

General Synthetic Scheme for C2-methoxy, 1,2,4-triazole Compounds

EXAMPLE 188

(2R,3R,4S,5R,6S)-2-(hydroxymethyl)-5-methoxy-6-(1-(1-methyl-1H-benzo[d]imidazol-6-yl)-1H-1,2,4-triazol-5-yl)-4-(4-(3,4,5-trifluorophenyl)-1H-1,2,3-triazol-1-yl)tetrahydro-2H-pyran-3-ol Step 1: Synthesis of (4aR,6R,7R,8R,8aR)-7-methoxy-2-phenyl-8-(4-(3,4,5-trifluorophenyl)-1H-1,2,3-triazol-1-yl) hexahydropyrano[3,2-d][1,3]dioxine-6-carboxylate: To a stirred solution of (4aR,6R,7R,8R,8aR)-methyl 7-hydroxy-2-phenyl-8-(4-(3,4,5-trifluorophenyl)-1H-1,2,3-triazol-1-yl)

hexahydropyrano[3,2-d][1,3]dioxine-6-carboxylate (1.6 g, 3.26 mmol) in DMF (20 mL) was added molecular sieves and the mixture was stirred at rt for 10 min. Silver oxide (3.77 g, 16.28 mmol) and methyl iodide (1.018 mL, 16.28 mmol) were added and the mixture was stirred at rt 16 h. The reaction mixture filtered, washed with DMF (100 mL) and the filtrate was concentrated. The crude residue was purified by silica gel chromatography (4-6% MeOH in chloroform) to afford (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate (1.1 g, 60%) LC-MS, [M+H]$^+$=506.0, (Method E: $t_R$=3.72 min). $^1$H NMR (400 MHz, DMSO-d$_6$) δ 9.09 (s, 1H), 7.85-7.76 (m, 2H), 7.41-7.32 (m, 5H), 5.57 (s, 1H), 5.36 (dd, J=3.5, 10.5 Hz, 1H), 4.46 (d, J=3.0 Hz, 1H), 4.42-4.32 (m, 1H), 4.28-4.22 (m, 1H), 4.18-4.06 (m, 2H), 3.96 (s, 1H), 3.78 (s, 3H), 3.08 (s, 3H).

Step 2: Synthesis of (4aR,6R,7R,8R,8aR)-7-methoxy-2-phenyl-8-(4-(3,4,5-trifluorophenyl)-1H-1,2,3-triazol-1-yl) hexahydropyrano[3,2-d][1,3]dioxine-6-carboxamide: Methyl (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate (500 mg, 0.989 mmol) was suspended in methanolic ammonia (7N, 20 mL) at 0° C. The reaction mixture was then allowed to warm to rt and was stirred for 48 h. The reaction mixture was concentrated under reduced pressure and purified via silica gel chromatography (5% MeOH in chloroform) to give (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxamide (400 mg, 82%). LC-MS, [M+H]$^+$=491.0, (Method E: $t_R$=1.18 min).

Step 3: Synthesis of (4aR,6R,7R,8R,8aR)-N-((E)-(dimethylamino)methylene)-7-methoxy-2-phenyl-8-(4-(3,4,5-trifluorophenyl)-1H-1,2,3-triazol-1-yl)hexahydropyrano[3,2-d][1,3]dioxine-6-carboxamide: To a stirred solution of (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxamide (100 mg, 0.204 mmol) in 1,4-dioxane (10 mL) was added DMF-DMA (0.027 mL, 0.204 mmol) and the mixture was stirred at 55° C. for 1 h. The reaction mixture was concentrated under reduced pressure. The residue was triturated with diethyl ether and filtered. The solid was washed with excess diethyl ether and dried to afford (4aR,6R,7R,8R,8aR)-N-((E)-(dimethylamino)methylene)-7-methoxy-2-phenyl-8-(4-(3,4,5-trifluorophenyl)-1H-1,2,3-triazol-1-yl)hexahydropyrano[3,2-d][1,3]dioxine-6-carboxamide (100 mg, 90%). LC-MS, [M+H]$^+$=546.4, (Method E: $t_R$=1.65 min).

Step 4: Synthesis of 6-(5-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-1H-1,2,4-triazol-1-yl)-1-methyl-1H-benzo[d]imidazole: A solution of (4aR,6R,7R,8R,8aR)-N-((E)-(dimethylamino)methylene)-7-methoxy-2-phenyl-8-(4-(3,4,5-trifluorophenyl)-1H-1,2,3-triazol-1-yl)hexahydropyrano[3,2-d][1,3]dioxine-6-carboxamide (50 mg, 0.092 mmol) and 6-hydrazinyl-1-methyl-1H-benzo[d]imidazole (37.2 mg, 0.229 mmol) in acetic acid (2 mL) was stirred at rt for 4 h. The reaction mixture was concentrated under reduced pressure to give 6-(5-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-1H-1,2,4-triazol-1-yl)-1-methyl-1H-benzo[d]imidazole (40 mg, 68%), which was taken directly to the next step without further purification. LC-MS, [M+H]$^+$=645.04, (Method E: $t_R$=1.84 min).

Step 5: Synthesis of (2R,3R,4S,5R,6S)-2-(hydroxymethyl)-5-methoxy-6-(1-(1-methyl-1H-benzo[d]imidazol-6-yl)-1H-1,2,4-triazol-5-yl)-4-(4-(3,4,5-trifluorophenyl)-1H-1,2,3-triazol-1-yl)tetrahydro-2H-pyran-3-ol: To a stirred solution of 6-(5-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-1H-1,2,4-triazol-1-yl)-1-methyl-1H benzo[d]imidazole (40 mg, 0.062 mmol) in DCM (1 mL) was added TFA (0.048 mL, 0.621 mmol). The mixture was stirred at rt for 2 h. The reaction mixture was concentrated and purified by HPLC (Method O) to give (2R,3R,4S,5R,6S)-2-(hydroxymethyl)-5-methoxy-6-(1-(1-methyl-1H-benzo[d]imidazol-6-yl)-1H-1,2,4-triazol-5-yl)-4-(4-(3,4,5-trifluorophenyl)-1H-1,2,3-triazol-1-yl)tetrahydro-2H-pyran-3-ol (Example 188) (9.9 mg, 29%). LC-MS, [M+H]$^+$=557.2, (Method A: $t_R$=1.42 min and Method B: $t_R$=1.26 min). 1H NMR (400 MHz, METHANOL-d4) d 8.77 (s, 1H), 8.35 (s, 1H), 8.27 (s, 1H), 7.99 (d, J=1.7 Hz, 1H), 7.90 (d, J=8.6 Hz, 1H), 7.70 (dd, J=8.7, 6.7 Hz, 2H), 7.61 (dd, J=8.6, 2.0 Hz, 1H), 4.99(dd, J=10.5, 2.8 Hz, 1H), 4.78 (d, J=10.5 Hz, 1H), 4.64 (d, J=9.4 Hz, 1H), 4.11 (d, J=2.7 Hz,1H), 4.02 (s, 3H), 3.95-3.81 (m, 2H), 3.74 (dd, J=10.6, 2.9 Hz, 1H), 2.96 (s, 3H).

The Examples in the table below were prepared in an analogous fashion to Example 188, substituting 6-hydrazinyl-1-methyl-1H-benzo[d]imidazole with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 189 | 0.09 | 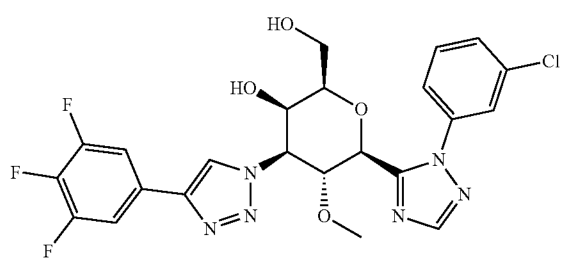 [SMILES: CO[C@@H]1[C@@H](n2cc(-c3cc(F)c(F)c(F)c3)nn2)[C@@H](O)[C@@H](CO)O[C@H]1c1ncnn1-c1cccc(Cl)c1] | 2.338 | 537.2 | C | 1H NMR (400 MHz, METHANOL-d4) δ 8.76 (s, 1H), 8.23 (s, 1H), 7.80-7.77 (m, 1H), 7.73-7.66 (m, 3H), 7.63-7.59 (m, 2H), 5.02 (dd, J = 10.5, 3.0 Hz, 1H), 4.79-4.71 (m, 1H), 4.63-4.58 (m, 1H), 4.12 (d, J = 3.0 Hz, 1H), 3.93-3.88 (m, 1H), 3.86-3.79 (m, 1H), 3.76-3.69 (m, 1H), 2.92 (s, 3H). |

| Ex | hGal3 IC50, uM | Structure | LCMS $t_R$ (min) | M + H | Method | 1H NMR |
|---|---|---|---|---|---|---|
| 190 | 0.18 | 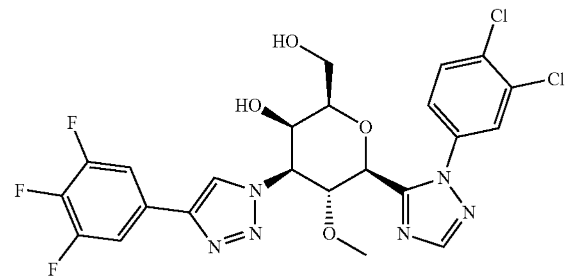 [SMILES: CO[C@@H]1[C@@H](n2cc(-c3cc(F)c(F)c(F)c3)nn2)[C@@H](O)[C@@H](CO)O[C@H]1c1ncnn1-c1ccc(Cl)c(Cl)c1] | 2.583 | 573 | C | 1H NMR (400 MHz, METHANOL-d4) δ 8.78 (s, 1H), 8.25 (s, 1H), 7.98 (d, J = 2.5 Hz, 1H), 7.82-7.79 (m, 1H), 7.74-7.68 (m, 3H), 5.05 (dd, J = 10.0, 2.8 Hz, 1H), 4.79-4.73 (m, 1H), 4.63 (d, J = 9.0 Hz, 1H), 4.14 (d, J = 2.0 Hz, 1H), 3.96-3.90 (m, 1H), 3.88-3.81 (m, 1H), 3.77-3.71 (m, 1H), 2.94 (s, 3H). |
| 191 | 0.06 | 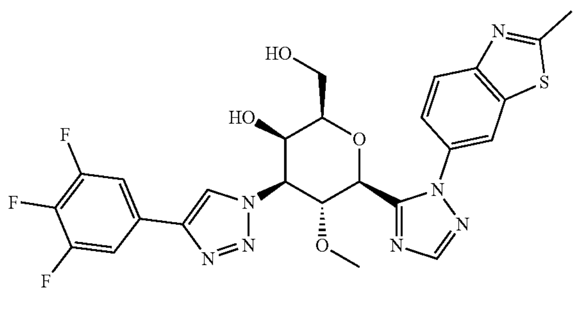 [SMILES: CO[C@@H]1[C@@H](n2cc(-c3cc(F)c(F)c(F)c3)nn2)[C@@H](O)[C@@H](CO)O[C@H]1c1ncnn1-c1ccc2nc(C)sc2c1] | 1.63 | 574.1 | A | 1H NMR (400 MHz, METHANOL-d4) δ 8.78 (s, 1H), 8.41 (d, J = 2.0 Hz, 1H), 8.27 (s, 1H), 8.11 (d, J = 8.8 Hz, 1H), 7.82 (dd, J = 8.7, 2.1 Hz, 1H), 7.71 (dd, J = 8.7, 6.7 Hz, 2H), 5.02 (dd, J = 10.4, 2.8 Hz, 1H), 4.78 (t, J = 9.9 Hz, 1H), 4.63 (d, J = 9.3 Hz, 1H), 4.11 (d, J = 2.9 Hz, 1H), 3.94-3.81 (m, 2H), 3.78-3.69 (m, 1H), 2.96 (s, 3H), 2.92 (s, 3H) |
| 192 | 0.04 | 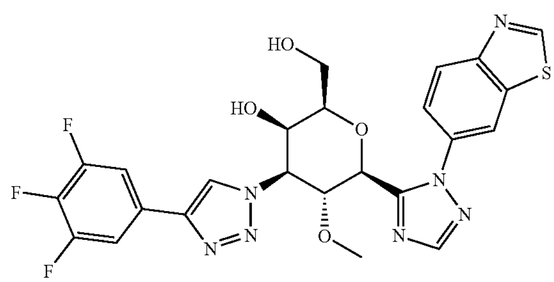 [SMILES: CO[C@@H]1[C@@H](n2cc(-c3cc(F)c(F)c(F)c3)nn2)[C@@H](O)[C@@H](CO)O[C@H]1c1ncnn1-c1ccc2ncsc2c1] | 1.55 | 560.2 | B | 1H NMR (400 MHz, METHANOL-d4) δ 9.45 (s, 1H), 8.78 (s, 1H), 8.59 (d, J = 1.7 Hz, 1H), 8.37-8.19 (m, 2H), 7.91 (dd, J = 8.4, 2.1 Hz, 1H), 7.78-7.58 (m, 2H), 5.06-5.01 (m, 1H), 4.79 (s, 1H), 4.66 (s, 1H), 4.11 (d, J = 2.4 Hz, 1H), 3.95-3.78 (m, 2H), 3.78-3.67 (m, 1H), 2.97 (s, 3H). |
General Synthetic Scheme for C3-amide, 1,2,3-triazole on 1,2,4-triazole Series:
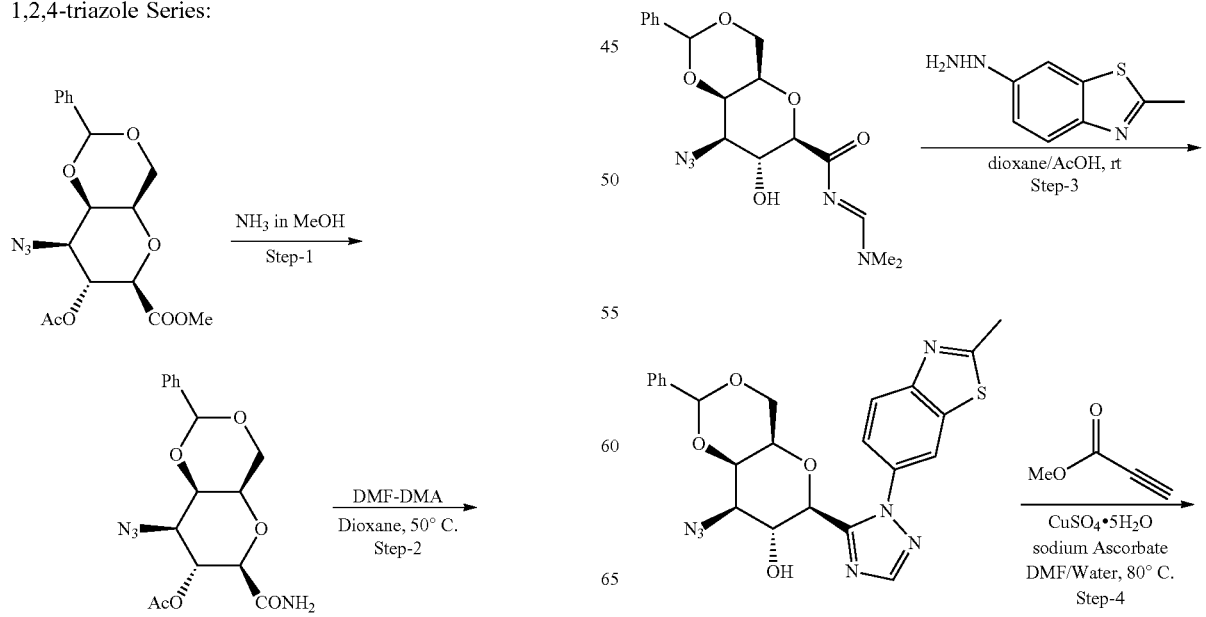

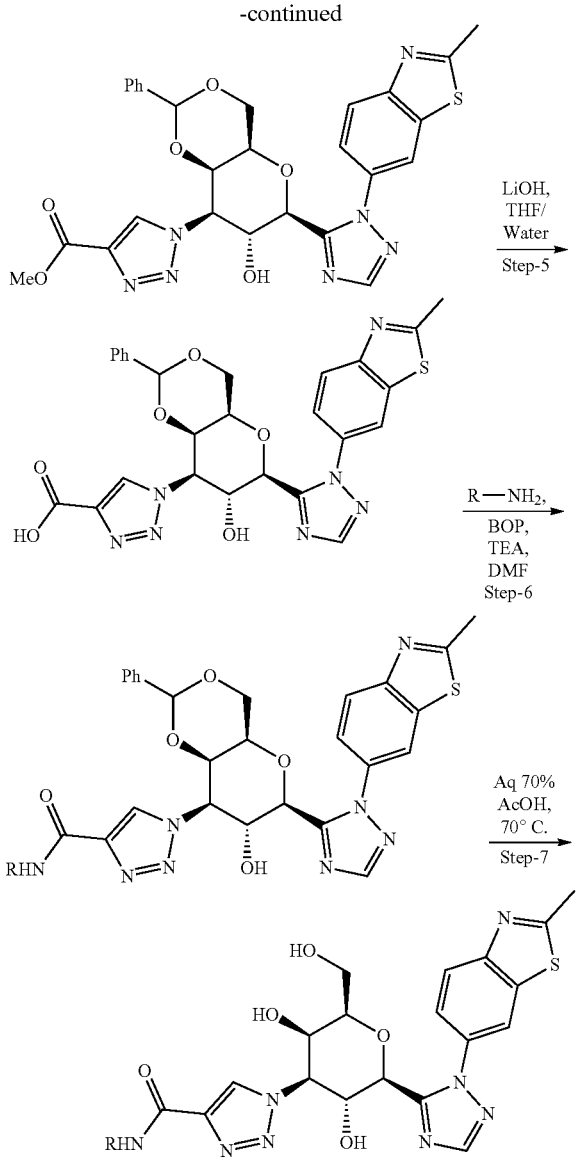

EXAMPLE 193

Preparation of N-(1-((2R,3R,4R,5R,6S)-3,5-dihydroxy-2-(hydroxymethyl)-6-(1-(2-methylbenzo[d]thiazol-6-yl)-1H-1,2,4-triazol-5-yl)tetrahydro-2H-pyran-4-yl)-1H-1,2,3-triazol-4-yl)cyclopropanecarboxamide

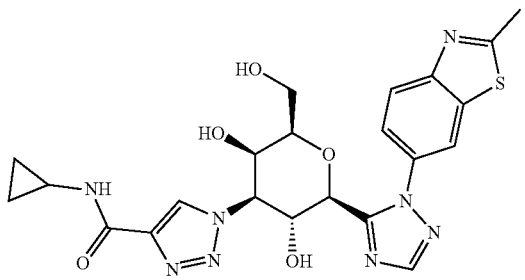 [SMILES: Cc1nc2ccc(-n3ncnc3[C@@H]3O[C@H](CO)[C@H](O)[C@H](n4cc(C(=O)NC5CC5)nn4)[C@H]3O)cc2s1]

Step 1: Synthesis of ((4aR,6R,7R,8R,8aR)-8-azido-7-hydroxy-2-phenylhexahydropyrano[3,2-d][1,3]dioxine-6-carboxamide: Methyl (4aR,6R,7R,8S,8aR)-7-acetoxy-8-azido-2-phenylhexahydropyrano[3,2-d][1,3]dioxine-6-carboxylate (5 g, 13.25 mmol) and methanolic ammonia (7 M, 200 mL) were combined at 0° C. The mixture was allowed to warm to rt and was stirred for 18 h. The reaction mixture was concentrated under reduced pressure, co-distilled with acetonitrile (2×50 mL) and dried to afford (4aR,6R,7R,8R,8aR)-8-azido-7-hydroxy-2-phenylhexahydropyrano[3,2-d][1,3]dioxine-6-carboxamide (4.0 g, 94%) as a white solid. LC-MS, [M+H]$^+$=321.2, (Method C: $t_R$=1.48 min). 1H NMR (400 MHz, DMSO-$d_6$) δ 7.49-7.33 (m, 5H), 7.25 (br s, 1H), 6.66 (br s, 1H), 5.65 (s, 1H), 5.63 (d, J=5.0 Hz, 1H), 4.33 (d, J=3.5 Hz, 1H), 4.14-4.03 (m, 2H), 4.00-3.90 (m, 1H), 3.68 (d, J=9.0 Hz, 1H), 3.59 (s, 1H), 3.52 (dd, J=3.5, 10.0 Hz, 1H).

Step 2: Synthesis of 4aR,6R,7R,8R,8aR)-8-azido-N-((E)-(dimethylamino)methylene)-7-hydroxy-2-phenylhexahydropyrano[3,2-d][1,3]dioxine-6-carboxamide: To a solution of ((4aR,6R,7R,8R,8aR)-8-azido-7-hydroxy-2-phenylhexahydropyrano[3,2-d][1,3]dioxine-6-carboxamide (2.0 g, 6.24 mmol) in dioxane (15 mL) was added DMF-DMA (4.18 mL, 31.2 mmol) and the mixture was heated at 50° C. for 4 h. The solvent was removed under reduced pressure. The residue was triturated with diethyl ether and filtered. The solid obtained was washed with excess diethyl ether and dried to afford (4aR,6R,7R,8R,8aR)-8-azido-N-((E)-(dimethylamino)methylene)-7-hydroxy-2-phenylhexahydropyrano[3,2-d][1,3]dioxine-6-carboxamide (1.77 g, 60%) as an off white solid. LC-MS, [M+H]$^+$=376.2, (Method E: $t_R$=1.05).

Step 3: Synthesis of (4aR,6S,7R,8R,8aR)-8-azido-6-(1-(2-methylbenzo[d]thiazol-5-yl)-1H-1,2,4-triazol-5-yl)-2-phenylhexahydropyrano[3,2-d][1,3]dioxin-7-ol: To a stirred suspension of (4aR,6R,7R,8R,8aR)-8-azido-N-((E)-(dimethylamino)methylene)-7-hydroxy-2-phenylhexahydropyrano[3,2-d][1,3]dioxine-6-carboxamide (1.1 g, 2.93 mmol) and 6-hydrazinyl-2-methylbenzo[d]thiazole (0.630 g, 3.52 mmol) in 1,4-dioxane (7 mL) at 0° C. was added AcOH (5 mL, 87 mmol). The reaction mixture was slowly warmed to rt and was stirred for 4 h. The reaction mixture was quenched with aq. 10% NaHCO$_3$ solution and extracted with DCM (3×100 mL). The combined organic extracts were washed with water, brine, and dried over Na$_2$SO$_4$. The solvent was removed under reduced pressure and the product was purified via silica gel chromatography (0-3% MeOH in CHCl$_3$) to furnish (4aR,6S,7R,8R,8aR)-8-azido-6-(1-(2-methylbenzo[d]thiazol-5-yl)-1H-1,2,4-triazol-5-yl)-2-phenylhexahydropyrano[3,2-d][1,3]dioxin-7-ol (1.0 g, 69%) as brown solid. LC-MS, [M+H]$^+$=492.2, (Method E: $t_R$=1.36). $^1$H NMR (400 MHz, METHANOL-$d_4$) δ 8.24-8.22 (m, 1H), 8.18 (s, 1H), 7.97 (s, 1H), 7.74 (d, J=8.5 Hz, 1H), 7.48-7.43 (m, 2H), 7.43-7.31 (m, 3H), 5.64 (s, 1H), 4.62-4.57 (m, 1H), 4.49 (d, J=10.0 Hz, 1H), 4.39 (dd, J=1.0, 3.5 Hz, 1H), 4.28-4.20 (m, 2H), 4.18-4.12 (m, 1H), 3.68-3.66 (m, 1H), 3.49-3.43 (m, 1H), 2.86 (s, 3H).

Step 4: Synthesis of methyl 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylate: To a stirred solution of (4aR,6S,7R,8R,8aR)-8-azido-6-(1-(2-methylbenzo[d]thiazol-6-yl)-1H-1,2,4-triazol-5-yl)-2-phenylhexahydropyrano[3,2-d][1,3]dioxin-7-ol (400 mg, 0.814 mmol) in DMF (8 mL) was added water (2 mL), methyl propiolate (82 mg, 0.977 mmol), copper(II) sulfate pentahydrate (183 mg, 0.732 mmol) and sodium ascorbate (177 mg, 0.895 mmol) and the mixture was stirred at 80° C. for 1 h. The reaction mixture was diluted with DCM (20 mL), stirred for 30 min and filtered through a pad of Celite. The filtrate was concentrated under reduced pressure and diluted with 20 mL of water resulting in the formation of a solid, which was filtered and dried to afford methyl 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylate (250 mg, 45%) as a brown solid. LC-MS, [M+H]$^+$=576.2, (Method E: $t_R$=1.26 min). $^1$H NMR (400 MHz, METHANOL-d$_4$) δ 8.54 (s, 1H), 8.30-8.21 (m, 2H), 8.06 (d, J=8.5 Hz, 1H), 7.85-7.71 (m, 1H), 7.44-7.33 (m, 5H), 5.56 (s, 1H), 5.24 (d, J=8.0 Hz, 1H), 5.02-4.91 (m, 1H, obscured with moisture peak), 4.61-4.51 (m, 1H), 4.36-4.12 (m, 2H), 393-3.92 (m, 1H), 3.92 (s, 3H), 3.01 (s, 3H). [NMR contains a DMF solvent peak].

Step 5: Synthesis of 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylic acid: To a stirred solution of methyl 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylate (250 mg, 0.434 mmol) in THF (5 mL) was added LiOH (52.0 mg, 2.172 mmol) in water (1.5 mL) and the mixture was stirred at rt for 2 h. The reaction mixture was concentrated under reduced pressure, diluted with water and acidified with 1.5N HCl (pH 4-5). The resultant solid was filtered and dried to give 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylic acid (200 mg, 72%) as white solid. LC-MS, [M+H]$^+$=562.2, (Method C: $t_R$=1.26 min).

Step 6: Synthesis of N-cyclopropyl-1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxamide: To a stirred solution of 1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxylic acid (30 mg, 0.053 mmol) in DMF (2 mL) was added triethylamine (0.015 ml, 0.107 mmol), BOP (35.4 mg, 0.080 mmol) and cyclopropanamine (0.040 ml, 0.080 mmol) and the mixture was stirred at rt for 3 h. The reaction mixture was diluted with water and was stirred for 5 min. The resultant solid was filtered, washed with excess water and dried to give N-cyclopropyl-1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxamide (35 mg, 49%). LC-MS, [M+H]$^+$=601.4, (Method E: $t_R$=1.25 min).

Step 7: Synthesis of N-cyclopropyl-1-((2R,3R,4R,5R,6S)-3,5-dihydroxy-2-(hydroxymethyl)-6-(1-(2-methylbenzo[d]thiazol-6-yl)-1H-1,2,4-triazol-5-yl)tetrahydro-2H-pyran-4-yl)-1H-1,2,3-triazole-4-carboxamide: N-Cyclopropyl-1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazole-4-carboxamide (25 mg, 0.042 mmol) was suspended in AcOH (70% in water) (0.5 mL, 8.73 mmol). The mixture was heated at 70° C. for 16 h. The reaction mixture was concentrated and purified by HPLC (Method A) to afford N-cyclopropyl-1-((2R,3R,4R,5R,6S)-3,5-dihydroxy-2-(hydroxymethyl)-6-(1-(2-methylbenzo[d]thiazol-6-yl)-1H-1,2,4-triazol-5-yl)tetrahydro-2H-pyran-4-yl)-1H-1,2,3-triazole-4-carboxamide (Example 193) (1.3 mg). LC-MS, [M+H]$^+$= 513.2, (Method A: $t_R$=0.85 min) and LC-MS, [M+H]$^+$= 513.2, (Method B: $t_R$=0.84 min). 1H NMR (400 MHz, METHANOL-d$_4$) δ 8.53 (s, 1H), 8.41 (d, J=2.0 Hz, 1H), 8.23 (s, 1H), 8.09 (d, J=8.6 Hz, 1H), 7.83 (dd, J=2.1, 8.7 Hz, 1H), 4.95 (s, 2H), 4.65-4.56 (m, 1H), 4.11 (s, 1H), 3.92-3.78 (m, 2H), 3.76-3.69 (m, 1H), 2.91 (s, 3H), 2.89-2.87 (m, 1H), 2.90-2.84 (m, 1H), 0.86-0.81 (m, 2H), 0.74-0.61 (m, 2H). hGal3 IC$_{50}$: 0.18 uM.

The Examples in the table below were prepared in an analogous fashion to Example 193, substituting cyclopropyl amine with the appropriate amines in the synthetic sequence.

| Ex | hGal3 IC50, uM | Structure | LCMS $t_R$ (min) | M + H | Method | 1H NMR |
|---|---|---|---|---|---|---|
| 194 | 4.09 | 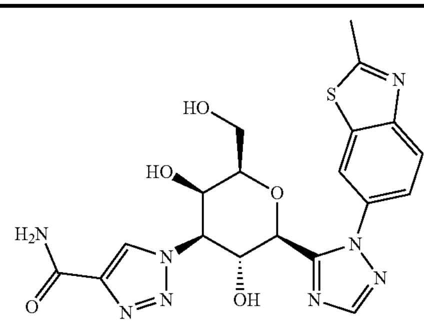 | 0.703 | 473.1 | A | 1H NMR (400 MHz, METHANOL-d4) δ 8.55 (s, 1H), 8.41 (d, J = 1.7 Hz, 1H), 8.23 (s, 1H), 8.10 (d, J = 8.6 Hz, 1H), 7.83 (dd, J = 8.7, 2.1 Hz, 1H), 5.01-4.92 (m, 2H), 4.65-4.58 (m, 1H), 4.12 (s, 1H), 3.93-3.77 (m, 2H), 3.76-3.69 (m, 1H), 2.92 (s, 3H). |
| 195 | 1.16 | 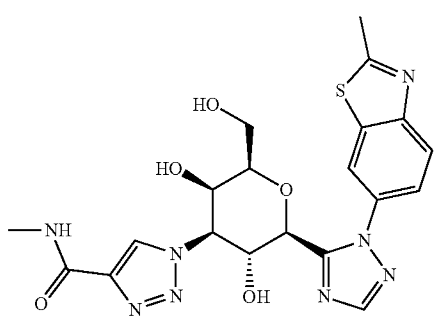 [SMILES: CNC(=O)c1cn([C@H]2[C@@H](O)[C@@H](CO)O[C@@H](c3ncnn3-c3ccc4nc(C)sc4c3)[C@@H]2O)nn1] | 0.753 | 487.1 | A | 1H NMR (400 MHz, METHANOL-d4) δ 8.51 (s, 1H), 8.41 (d, J = 2.2 Hz, 1H), 8.23 (s, 1H), 8.10 (d, J = 8.6 Hz, 1H), 7.83 (dd, J = 8.6, 2.2 Hz, 1H), 4.96 (d, J = 5.9 Hz, 2H), 4.66-4.59 (m, 1H), 4.11 (s, 1H), 3.94-3.77 (m, 2H), 3.76-3.66 (m, 1H), 2.91 (s, 3H), 2.95 (s, 3H). |

-continued

| Ex | hGal3 IC50, uM | Structure | LCMS $t_R$ (min) | M + H | Method | 1H NMR |
|---|---|---|---|---|---|---|
| 196 | 5.65 | 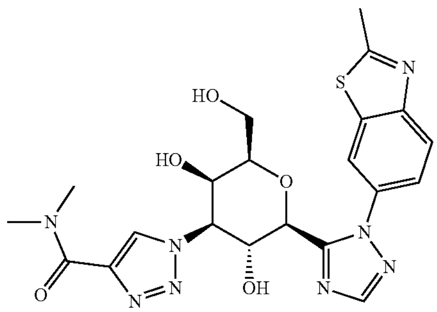 [SMILES: Cc1nc2ccc(-n3ncnc3[C@@H]3O[C@H](CO)[C@H](O)[C@H](n4cc(C(=O)N(C)C)nn4)[C@H]3O)cc2s1] | 0.793 | 501.2 | A | 1H NMR (400 MHz, METHANOL-d4) δ 8.47 (s, 1H), 8.42 (d, J = 2.0 Hz, 1H), 8.23 (s, 1H), 8.10 (d, J = 8.8 Hz, 1H), 7.83 (dd, J = 8.6, 2.2 Hz, 1H), 5.01-4.92 (m, 2H), 4.62 (d, J = 8.8 Hz, 1H), 4.13 (d, J = 1.2 Hz, 1H), 3.93-3.78 (m, 2H), 3.76-3.69 (m, 1H), 3.45 (s, 3H), 3.14 (s, 3H), 2.96 (s, 3H). |
| 197 | 1.32 | 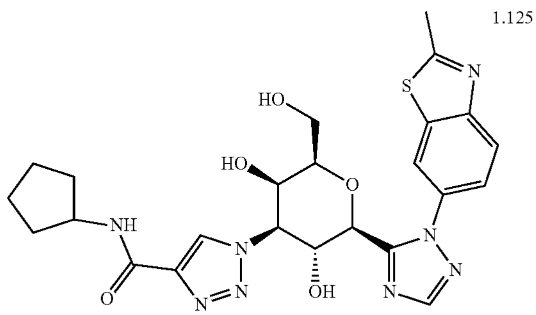 | 1.125 | 541.2 | B | 1H NMR (400 MHz, METHANOL-d4) δ 8.52 (s, 1H), 8.41 (d, J = 2.0 Hz, 1H), 8.23 (s, 1H), 8.10 (d, J = 8.6 Hz, 1H), 7.83 (dd, J = 8.7, 2.1 Hz, 1H), 5.02-4.89 (m, 2H), 4.66-4.59 (m, 1H), 4.11 (s, 1H), 3.96-3.77 (m, 3H), 3.76-3.68 (m, 1H), 2.91 (s, 3H), 1.97 (d, J = 8.8 Hz, 2H), 1.81 (br. s., 2H), 1.70 (d, J = 12.5 Hz, 1H), 1.51-1.22 (m, 4H). |
| 198 | 1.02 | 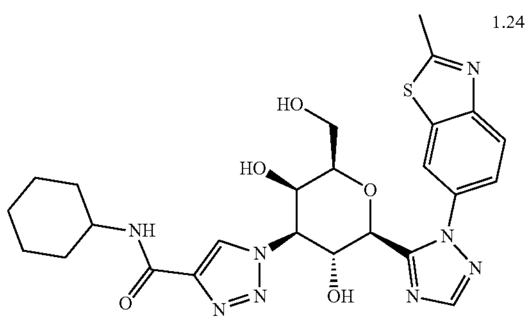 | 1.24 | 555.2 | B | 1H NMR (400 MHz, METHANOL-d4) δ 8.52 (s, 1H), 8.41 (d, J = 1.7 Hz, 1H), 8.23 (s, 1H), 8.10 (d, J = 8.6 Hz, 1H), 7.83 (dd, J = 8.8, 2.2 Hz, 1H), 4.96 (d, J = 6.1 Hz, 2H), 4.66-4.59 (m, 1H), 4.40-4.31 (m, 1H), 4.12 (s, 1H), 3.94-3.86 (m, 1H), 3.86-3.76 (m, 2H), 3.75-3.69 (m, 1H), 2.92 (s, 3H), 2.11-1.98 (m, 2H), 1.89-1.75 (m, 2H), 1.73-1.54 (m, 4H). |
| 199 | 0.36 | 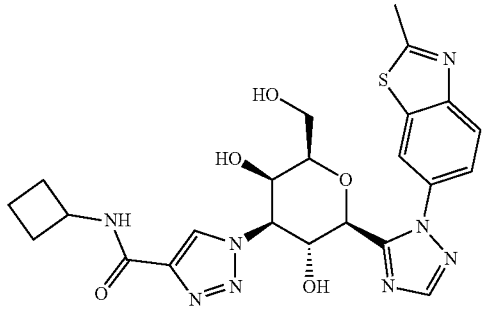 [SMILES: Cc1nc2ccc(-n3ncnc3[C@@H]3O[C@H](CO)[C@H](O)[C@H](n4cc(C(=O)NC5CCC5)nn4)[C@H]3O)cc2s1] | 1.042 | 527.2 | A | 1H NMR (400 MHz, METHANOL-d4) δ 8.52 (s, 1H), 8.41 (d, J = 2.0 Hz, 1H), 8.23 (s, 1H), 8.10 (d, J = 8.8 Hz, 1H), 7.83 (dd, J = 8.8, 2.2 Hz, 1H), 4.96 (d, J = 5.6 Hz, 2H), 4.65-4.51 (m, 2H), 4.11 (s, 1H), 3.92-3.77 (m, 2H), 3.72 (dd, J = 11.4, 4.0 Hz, 1H), 2.92 (s, 3H), 2.36 (d, J = 3.7 Hz, 2H), 2.23-2.08 (m, 2H), 1.89-1.70 (m, 2H). |

| Ex | hGal3 IC50, uM | Structure | LCMS $t_R$ (min) | M + H | Method | 1H NMR |
|---|---|---|---|---|---|---|
| 200 | 0.86 | 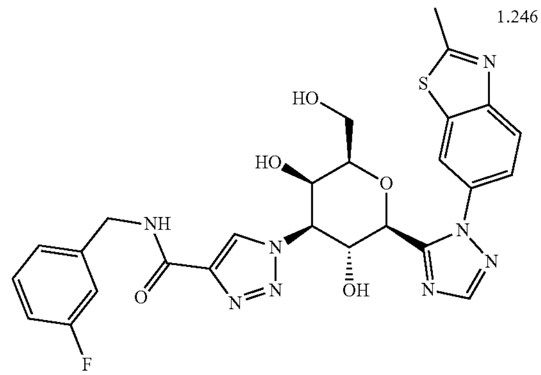 | 1.246 | 581.2 | A | 1H NMR (400 MHz, METHANOL-d4) δ 8.56 (s, 1H), 8.41 (d, J = 2.0 Hz, 1H), 8.23 (s, 1H), 8.10 (d, J = 8.8 Hz, 1H), 7.83 (dd, J = 8.6, 2.2 Hz, 1H), 7.35 (td, J = 7.9, 5.9 Hz, 1H), 7.19 (d, J = 8.3 Hz, 1H), 7.11 (d, J = 10.5 Hz, 1H), 6.99 (td, J = 8.9, 2.6 Hz, 1H), 4.97 (d, J = 5.6 Hz, 2H), 4.65-4.56 (m, 3H), 4.12 (s, 1H), 3.94-3.78 (m, 2H), 3.76- 3.69(m, 1H), 2.98 (s, 3H). |

General Synthetic Scheme 1 for C3-aryl, 1,2,3-triazole, in 1,2,4-triazole Series:

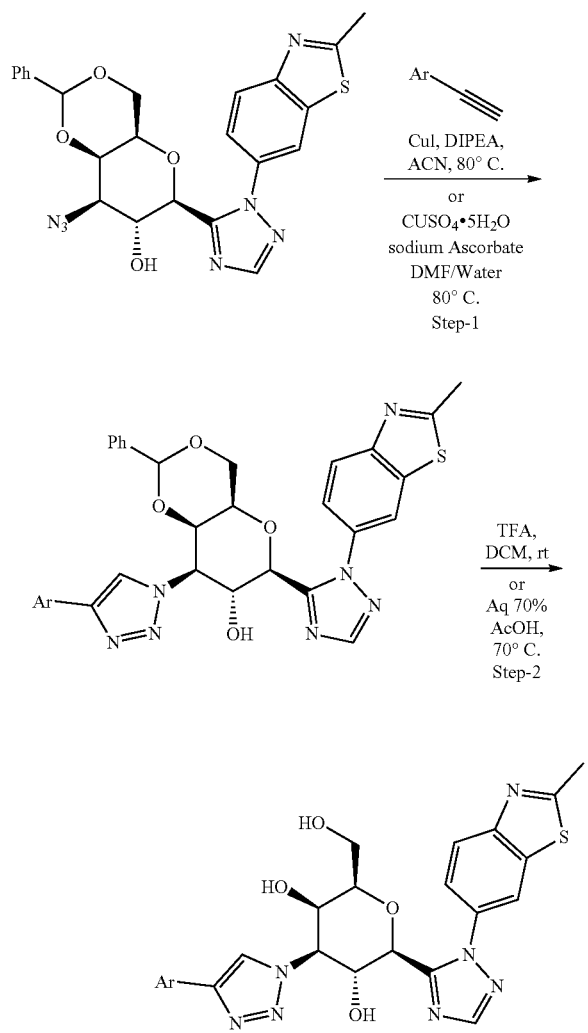

EXAMPLE 201

Preparation of (2R,3R,4R,5R,6S)-4-(4-(4-cyclopropyl-3-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol

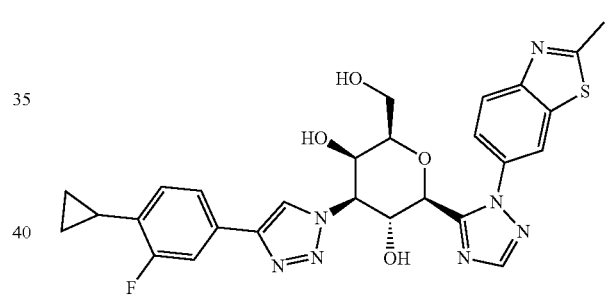

Step 1: Synthesis of (4aR,6S,7R,8R,8aR)-8-(4-(4-cyclopropyl-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol: To a stirred solution of (4aR,6S,7R,8R,8aR)-8-azido-6-(1-(2-methylbenzo[d]thiazol-6-yl)-1H-1,2,4-triazol-5-yl)-2-phenylhexahydropyrano[3,2-d][1,3]dioxin-7-ol (30 mg, 0.061 mmol) in acetonitrile (1 mL) was added copper(I) iodide (2.325 mg, 0.012 mmol), ((4-cyclopropyl-3-fluorophenyl)ethynyl) trimethylsilane (28.4 mg, 0.122 mmol) and DIPEA (0.032 mL, 0.183 mmol) and the mixture was heated at 80° C. for 1 h. The reaction mixture was cooled to rt and was extracted with 10% MeOH in DCM (2×10 mL). The combined organic layers were washed with water, brine solution, dried over sodium sulfate and concentrated. The crude residue was purified via silica gel chromatography (5-10% MeOH in chloroform) to give (4aR,6S,7R,8R,8aR)-8-(4-(4-cyclopropyl-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol (20 mg, 50%). LC-MS, [M+1]$^+$=652.5, (Method E: $t_R$=1.82 min).

Step 2: Synthesis of (2R,3R,4R,5R,6S)-4-(4-(4-cyclopropyl-3-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol: To a stirred solution of (4aR,6S,7R,8R,8aR)-8-(4-(4-cyclopropyl-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol (20 mg, 0.031 mmol) in DCM (1 mL), was added TFA (0.012 mL, 0.153 mmol) at 0° C. Then the reaction mixture was allowed to reach rt and was stirred for 1 h. The reaction mixture concentrated and purified by prep HPLC (Method A) to give (2R,3R,4R,5R,6S)-4-(4-(4-cyclopropyl-3-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol (Example 201) (1.4 mg, 8%). LC-MS, [M+1]$^+$=564.2, (Method A & Method B: $t_R$=1.69 min). 1H NMR (400 MHz, METHANOL-d4) δ 8.47 (s, 1H), 8.42 (d, J=2.0 Hz, 1H), 8.25 (s, 1H), 8.11(d, J=8.8 Hz, 1H), 7.84 (dd, J=8.7, 2.1 Hz, 1H), 7.61-7.48 (m, 2H), 7.05 (t, J=8.1 Hz, 1H), 5.06-5.00 (m, 1H), 4.92 (dd, J=10.9, 2.8 Hz, 1H), 4.62 (d, J=9.0 Hz, 1H), 4.15 (d, J=2.4 Hz, 1H), 3.94-3.80 (m, 2H), 3.77-3.70 (m, 1H), 2.92 (s, 3H), 2.16-2.09 (m, 1H), 1.36-1.28 (m,1H), 1.08-0.99 (m, 2H), 0.91 (d, J=9.8 Hz, 1H), 0.83-0.73 (m, 2H). hGal3 IC50: 0.35 uM The Examples in the table below were prepared in an analogous fashion to Example 201, substituting ((4-cyclopropyl-3-fluorophenyl)ethynyl) trimethylsilane with the appropriate aryl acetylene or aryl TMS-acetylene in the synthetic sequence.

| Ex | hGal3 IC50, uM | Structure | LCMS $t_R$ (min) | M + H | Method | 1H NMR |
|---|---|---|---|---|---|---|
| 202 | 0.44 | 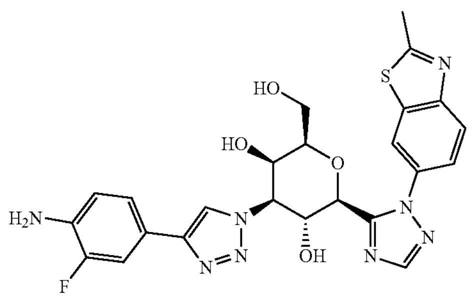 [SMILES: Cc1nc2ccc(-n3ncnc3[C@@H]3O[C@H](CO)[C@H](O)[C@H](n4cc(-c5ccc(N)c(F)c5)nn4)[C@H]3O)cc2s1] | 0.943 | 539.2 | A | 1H NMR (400 MHz, METHANOL-d4) δ 8.42 (d, J = 2.0 Hz, 1H), 8.32 (s, 1H), 8.24 (s, 1H), 8.11 (d, J = 8.6 Hz, 1H), 7.84 (dd, J = 8.7, 2.1 Hz, 1H), 7.47 (dd, J = 12.2, 2.0 Hz, 1H), 7.41 (dd, J = 8.6, 1.7 Hz, 1H), 6.91 (dd, J = 9.0, 8.3 Hz, 1H), 5.05-4.99 (m, 1H), 4.91-4.88 (m, 1H), 4.62 (d, J = 9.3 Hz, 1H), 4.14 (d, J = 2.4 Hz, 1H), 3.94-3.78 (m, 3H), 2.92 (s, 3H). |
| 203 | 2.12 | 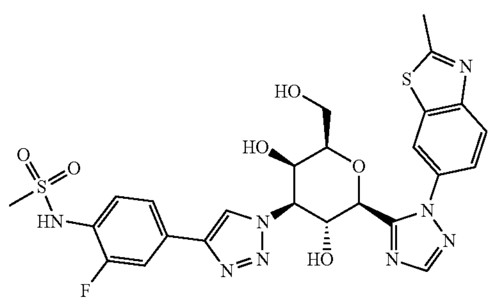 [SMILES: Cc1nc2ccc(-n3ncnc3[C@@H]3O[C@H](CO)[C@H](O)[C@H](n4cc(-c5ccc(NS(C)(=O)=O)c(F)c5)nn4)[C@H]3O)cc2s1] | 0.962 | 617.1 | A | 1H NMR (400 MHz, METHANOL-d4) δ 8.54 (s, 1H), 8.43 (d, J = 1.7 Hz, 1H), 8.25 (s, 1H), 8.11 (d, J = 8.8 Hz, 1H), 7.84 (dd, J = 8.8, 2.2 Hz, 1H), 7.77-7.65 (m, 2H),7.63-7.55 (m, 1H), 5.08-5.02 (m, 1H), 4.95 (br. s., 1H), 4.57 (s, 1H), 4.16 (d, J = 2.4 Hz, 1H), 3.95-3.78 (m, 2H), 3.74 (dd, J = 11.4, 3.8 Hz, 1H), 3.06 (s, 3H), 2.92 (s, 3H). |
| 204 | 5 | 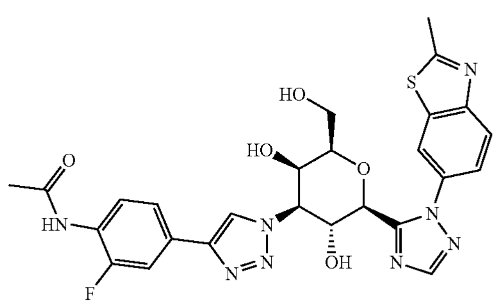 [SMILES: CC(=O)Nc1ccc(-c2cn([C@H]3[C@@H](O)[C@@H](CO)O[C@@H](c4ncnn4-c4ccc5nc(C)sc5c4)[C@@H]3O)nn2)cc1F] | 0.943 | 581.2 | A | 1H NMR (400 MHz, METHANOL-d4) δ 8.51 (s, 1H) 8.37-8.46 (m, 1H) 8.22-8.31 (m, 1H) 7.96-8.16 (m, 2H) 7.85 (d, J = 2.20 Hz, 1H) 7.54-7.76 (m, 2H) 5.00-5.12 (m, 1H) 4.93 (d, J = 7.83 Hz, 1H) 4.58-4.67 (m, 1H) 4.16 (dd, J = 2.81, 2.08 Hz, 1H) 3.80-3.97 (m, 2H) 3.65-3.80 (m, 1H) 2.92 (s, 3 H) 2.21 (s, 3 H) |

-continued

| Ex | hGal3 IC50, uM | Structure | LCMS $t_R$ (min) | M + H | Method | 1H NMR |
|---|---|---|---|---|---|---|
| 205 | 1.11 | 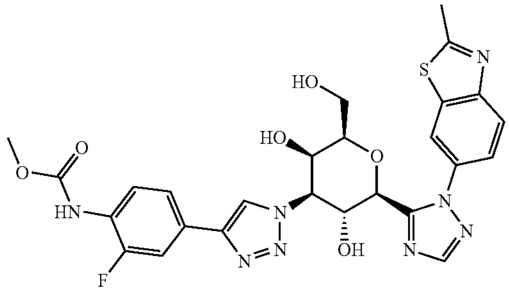 [SMILES: COC(=O)Nc1ccc(-c2cn([C@H]3[C@@H](O)[C@@H](CO)O[C@@H](c4ncnn4-c4ccc5nc(C)sc5c4)[C@@H]3O)nn2)cc1F] | 1.076 | 597.2 | A | 1H NMR (400 MHz, METHANOL-d4) δ 8.49 (s, 1H), 8.42 (d, J = 1.7 Hz, 1H), 8.25 (s, 1H), 8.11 (d, J = 8.8 Hz, 1H), 7.98 (br. s., 1H), 7.84 (dd, J = 8.6, 2.2 Hz, 1H), 7.71-7.57 (m, 2H), 5.09-4.98 (m, 1H), 4.92 (dd, J = 10.8, 2.9 Hz, 1H), 4.63 (d, J = 9.3 Hz, 1H), 4.16 (d, J = 2.7 Hz, 1H), 3.95-3.77 (m, 5H), 3.77-3.68 (m, 1H), 2.92 (s, 3H). |
| 206 | 1.54 | 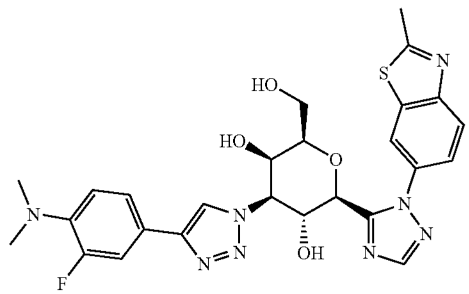 [SMILES: Cc1nc2ccc(-n3ncnc3[C@@H]3O[C@H](CO)[C@H](O)[C@H](n4cc(-c5ccc(N(C)C)c(F)c5)nn4)[C@H]3O)cc2s1] | 1.237 | 567.2 | A | 1H NMR (400 MHz, METHANOL-d4) δ 8.47-8.36 (m, 2H), 8.25 (s, 1H), 8.11 (d, J = 8.8 Hz, 1H), 7.84 (dd, J = 8.6, 2.2 Hz, 1H), 7.62-7.44 (m, 2H), 7.07 (t, J = 8.8 Hz, 1H), 5.08-4.97 (m, 1H), 4.92-4.89 (m, 1H), 4.62 (d, J = 9.3 Hz, 1H), 4.15 (d, J = 2.9 Hz, 1H), 3.96-3.78 (m, 2H), 3.78-3.65 (m, 1H), 2.99-2.78 (m, 9H). |
| 207 | 0.74 | 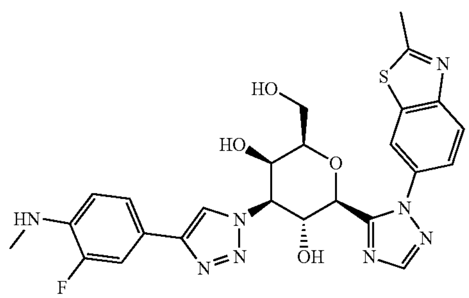 [SMILES: CNc1ccc(-c2cn([C@H]3[C@@H](O)[C@@H](CO)O[C@@H](c4ncnn4-c4ccc5nc(C)sc5c4)[C@@H]3O)nn2)cc1F] | 1.124 | 553.2 | A | 1H NMR (400 MHz, METHANOL-d4) δ 8.42 (d, J = 2.0 Hz, 1H), 8.31 (s, 1H), 8.24 (s, 1H), 8.11 (d, J = 8.6 Hz, 1H), 7.84 (dd, J = 8.6, 2.2 Hz, 1H), 7.50 (dd, J = 7.8, 1.7 Hz, 1H), 7.46 (dd, J = 12.8, 1.8 Hz, 1H), 6.78 (t, J = 8.7 Hz, 1H), 5.06-4.98 (m, 1H), 4.90 (d, J = 2.9 Hz, 1H), 4.62 (d, J = 9.3 Hz, 1H), 4.15 (d, J = 2.7 Hz, 1H), 3.95-3.79 (m, 2H), 3.78-3.67 (m, 1H), 2.89 (s, 3H), 2.92 (s, 3H). |
| 208 | 3.82 | 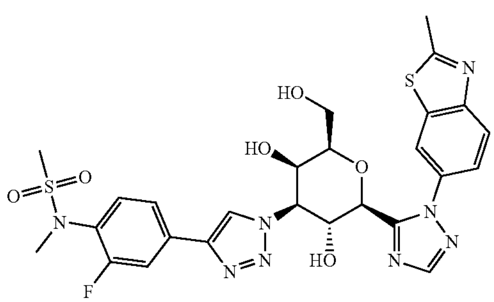 [SMILES: Cc1nc2ccc(-n3ncnc3[C@@H]3O[C@H](CO)[C@H](O)[C@H](n4cc(-c5ccc(N(C)S(C)(=O)=O)c(F)c5)nn4)[C@H]3O)cc2s1] | 1.111 | 631.2 | A | 1H NMR (400 MHz, METHANOL-d4) δ 8.64-8.54 (m, 1H), 8.42 (d, J = 2.2 Hz, 1H), 8.25 (s, 1H), 8.11 (d, J = 8.6 Hz, 1H), 7.84 (dd, J = 8.6, 2.2 Hz, 1H), 7.81-7.69 (m, 2H), 7.60-7.51 (m, 1H), 5.16-5.00 (m, 1H), 4.95 (dd, J = 10.6, 3.1 Hz, 1H), 4.63 (d, J = 9.3 Hz, 1H), 4.16 (d, J = 2.4 Hz, |

-continued

| Ex | hGal3 IC50, uM | Structure | LCMS $t_R$ (min) | M + H | Method | 1H NMR |
|---|---|---|---|---|---|---|
| | | | | | | 1H), 3.96-3.79 (m, 3H), 3.07 (s, 3H), 2.92 (s, 3H) (3 Protons burried under solvent). |
| 209 | 0.08 | 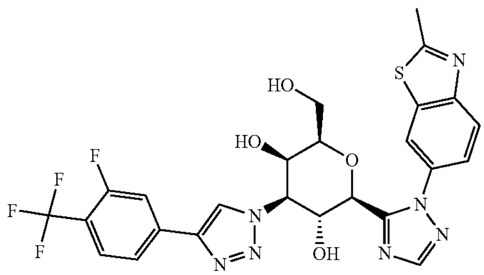 [SMILES: Cc1nc2ccc(-n3ncnc3[C@@H]3O[C@H](CO)[C@H](O)[C@H](n4cc(-c5ccc(C(F)(F)F)c(F)c5)nn4)[C@H]3O)cc2s1] | 1.901 | 592.2 | A | 1H NMR (400 MHz, DMSO-d6) δ 7.89 (s, 1H), 7.6 (d, J = 2.0 Hz, 1H), 7.44 (s, 1H), 7.30 (d, J = 8.8 Hz, 1H), 7.14-7.00 (m, 3H), 7.00-6.94 (m, 1H), 4.27-4.22 (m, 1H), 4.17 (d, J = 2.9 Hz, 1H), 3.82 (d, J = 8.8 Hz, 1H), 3.35 (d, J = 2.4 Hz, 1H),3.13-2.99 (m, 2H), 2.96-2.90 (m, 1H), 2.11 |
| 210 | 0.04 | 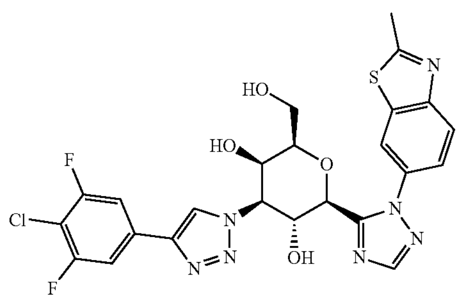 [SMILES: Cc1nc2ccc(-n3ncnc3[C@@H]3O[C@H](CO)[C@H](O)[C@H](n4cc(-c5cc(F)c(Cl)c(F)c5)nn4)[C@H]3O)cc2s1] | 1.467 | 576.1 | A | 1H NMR (400 MHz, METHANOL-d4) δ 8.64 (s, 1H), 8.42 (d, J = 2.0 Hz, 1H), 8.25 (s, 1H), 8.11 (d, J = 8.6 Hz, 1H), 7.84 (dd, J = 8.6, 2.2 Hz,1H), 7.74-7.58 (m, 2H), 5.09-4.99 (m, 1H), 4.98-4.92 (m, 1H), 4.63 (d, J = 9.0 Hz, 1H), 4.15 (d, J = 2.2 Hz, 1H), 3.96-3.79 (m, 2H), 3.77-3.69 (m, 1H), 2.99 (s, 3H). |
| 211 | 0.06 | 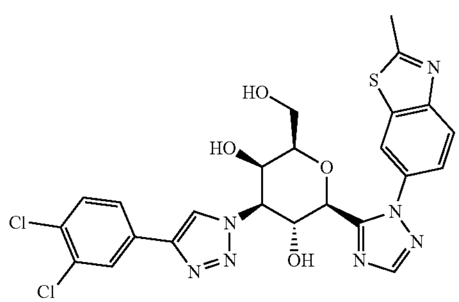 [SMILES: Cc1nc2ccc(-n3ncnc3[C@@H]3O[C@H](CO)[C@H](O)[C@H](n4cc(-c5ccc(Cl)c(Cl)c5)nn4)[C@H]3O)cc2s1] | 1.485 | 576 | A | 1H NMR (400 MHz, METHANOL-d4) δ 8.59 (s, 1H), 8.42 (d, J = 2.0 Hz, 1H), 8.25 (s, 1H), 8.11 (d, J = 8.8 Hz, 1H), 8.07 (d, J = 2.0 Hz, 1H), 7.81 (dd, J = 8.4, 2.1 Hz, 1H), 7.84 (dd, J = 8.8, 2.2 Hz, 1H), 7.62 (d, J = 8.3 Hz, 1H), 5.04 (dd, J = 10.6, 9.2 Hz, 1H), 4.94 (dd, J = 10.8, 2.9 Hz, 1H), 4.63 (d, J = 9.0 Hz, 1H), 4.16 (d, J = 2.4 Hz, 1H), 3.95-3.89 (m, 1H), 3.88-3.81 (m, 1H), 3.74 (dd, J = 11.4, 4.0 Hz, 1H), 2.92 (s, 3H). |

-continued

| Ex | hGal3 IC50, uM | Structure | LCMS t<sub>R</sub> (min) | M + H | Method | 1H NMR |
|---|---|---|---|---|---|---|
| 212 | 0.06 | 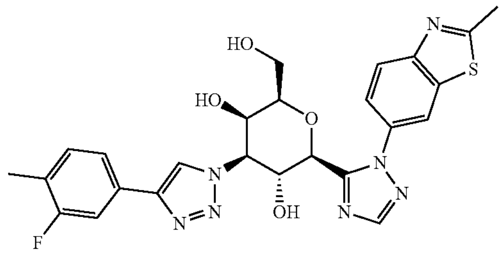 | 1.373 | 538.2 | A | 1H NMR (400 MHz, METHANOL-d4) δ 8.48 (s, 1H), 8.43 (d, J = 2.0 Hz, 1H), 8.25 (s, 1H), 8.11 (d, J = 8.8 Hz, 1H), 7.84 (dd, J = 8.7, 2.1 Hz, 1H), 7.61-7.48 (m, 2H), 7.33 (t, J = 7.8 Hz, 1H), 5.07-4.99 (m, 1H), 4.92 (dd, J = 10.8, 2.9 Hz, 1H), 4.62 (d, J = 9.3 Hz, 1H), 4.15 (d, J = 2.4 Hz, 1H), 3.95-3.80 (m, 2H), 3.77-3.70 (m, 1H), 2.92 (s, 3H), 2.31 (s, 3H). |
| 213 | 0.12 | 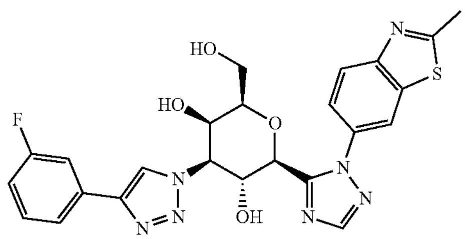 [SMILES: Cc1nc2ccc(-n3ncnc3[C@@H]3O[C@H](CO)[C@H](O)[C@H](n4cc(-c5cccc(F)c5)nn4)[C@H]3O)cc2s1] | 1.182 | 524.2 | A | 1H NMR (400 MHz, METHANOL-d4) δ 8.42 (s, 1H), 8.30 (d, J = 2.2 Hz, 1H), 8.14 (s, 1H), 7.99 (d, J = 8.8 Hz, 1H), 7.72 (dd, J = 8.6, 2.2 Hz, 1H), 7.57 (d, J = 7.8 Hz, 1H), 7.54-7.48 (m, 1H), 7.36 (td, J = 8.1, 5.9 Hz, 1H), 6.98 (td, J = 8.7, 2.7 Hz, 1H), 4.97-4.89 (m, 1H), 4.82 (dd, J = 10.4, 2.8 Hz, 1H), 4.51 (d, J = 9.0 Hz, 1H), 4.04 (d, J = 2.9 Hz, 1H), (m, 3.83-3.78 (m, 1H), 3.77-3.70 1H), 3.62-3.63 (m, 1H), 2.80 (s, 3H). |
| 214 | 0.60 | 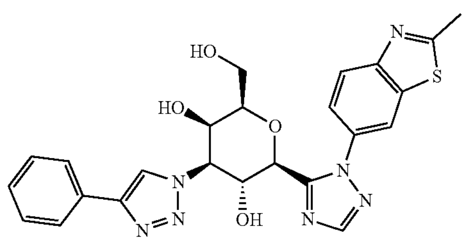 [SMILES: Cc1nc2ccc(-n3ncnc3[C@@H]3O[C@H](CO)[C@H](O)[C@H](n4cc(-c5ccccc5)nn4)[C@H]3O)cc2s1] | 1.11 | 506.2 | A | 1H NMR (400 MHz, METHANOL-d4) δ 8.36 (br. s., 1H), 8.29 (s, 1H), 8.15 (br. s., 1H), 7.99 (d, J = 8.6 Hz, 1H), 7.78-7.69 (m, 3H), 7.34 (t, J = 7.5 Hz, 2H), 7.28-7.22 (m, 1H), 4.94 (br. s., 1H), 4.79 (br. s., 1H), 4.06 (br. s., 1H), 3.79 (br. s., 1H), 3.73 (br. s., 1H), 3.65 (br. s., 1H), 2.80 (s, 3H) |
| 215 | 0.14 | 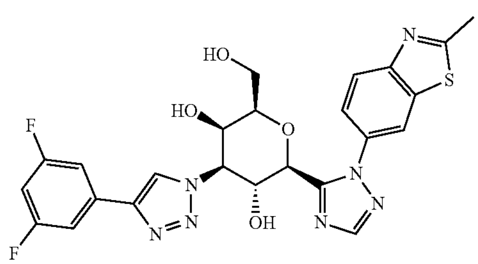 [SMILES: Cc1nc2ccc(-n3ncnc3[C@@H]3O[C@H](CO)[C@H](O)[C@H](n4cc(-c5cc(F)cc(F)c5)nn4)[C@H]3O)cc2s1] | 1.269 | 542.1 | A | 1H NMR (400 MHz, METHANOL-d4) δ 8.50 (s, 1H), 8.31 (d, J = 1.7 Hz, 1H), 8.15 (br. s., 1H), 8.00 (d, J = 8.6 Hz, 1H), 7.72-7.75 (m, 1H), 7.40 (d, J = 6.4 Hz, 2H), 6.84 (t, J =8.9 Hz, 1H), 4.97-4.88 (m, 1H), 4.87-4.79 (m, 1H), 4.05 (br. s., 1H), 3.79-3.80 (m, 1H), 3.78-3.68 (m, 1H), 3.67-3.61 (m, 1H), 2.81 (s, 3H) |

-continued

| Ex | hGal3 IC50, uM | Structure | LCMS $t_R$ (min) | M + H | Method | 1H NMR |
|---|---|---|---|---|---|---|
| 216 | 0.05 | 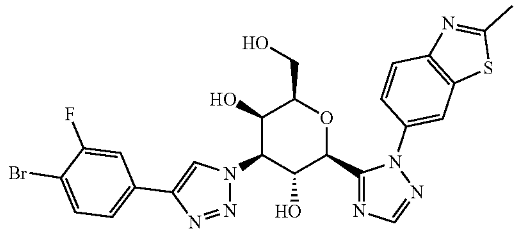 [SMILES: Cc1nc2ccc(-n3ncnc3[C@@H]3O[C@H](CO)[C@H](O)[C@H](n4cc(-c5ccc(Br)c(F)c5)nn4)[C@H]3O)cc2s1] | 1.402 | 602.1 | A | 1H NMR (400 MHz, METHANOL-d4) δ 8.59 (s, 1H), 8.42 (d, J = 2.0 Hz, 1H), 8.25 (s, 1H), 8.10 (d, J = 8.8 Hz, 1H), 7.84 (dd, J = 8.7, 2.1 Hz, 1H), 7.77-7.69 (m, 2H), 7.65-7.61 (m, 1H), 5.08-5.01 (m, 1H), 4.95 (dd, J = 10.6, 2.6 Hz, 1H), 4.63 (d, J = 9.0 Hz, 1H), 4.57 (s, 1H), 4.16 (br. s., 1H), 3.94-3.89 (m, 1H), 3.88-3.82 (m, 1H), 3.77-3.71 (m, 1H), 2.92 (s, 3H). |
| 217 | 0.07 | 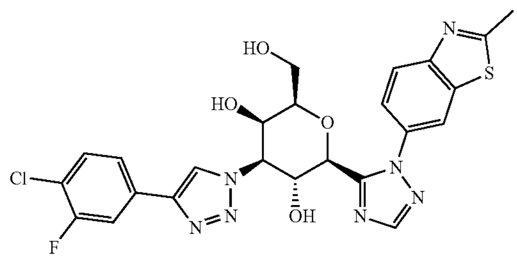 [SMILES: Cc1nc2ccc(-n3ncnc3[C@@H]3O[C@H](CO)[C@H](O)[C@H](n4cc(-c5ccc(Cl)c(F)c5)nn4)[C@H]3O)cc2s1] | 1.365 | 558.1 | A | 1H NMR (400 MHz, METHANOL-d4) δ 8.58 (s, 1H), 8.42 (d, J = 2.0 Hz, 1H), 8.25 (s, 1H), 8.11 (d, J = 8.8 Hz, 1H), 7.84 (dd, J = 8.6, 2.2 Hz, 1H), 7.78 (dd, J = 10.4, 1.8 Hz, 1H), 7.70 (dd, J = 8.6, 1.7 Hz, 1H), 7.57 (t, J = 7.9 Hz, 1H), 5.04 (dd, J = 10.8, 9.3 Hz, 1H), 4.94 (dd, J = 10.8, 2.9 Hz, 1H), 4.63 (d, J = 9.0 Hz, 1H), 4.16 (d, J = 2.2 Hz, 1H), 3.97-3.78 (m, 2H), 3.78-3.69 (m, 1H), 2.92 (s, 3H). |
| 218 | 0.02 | 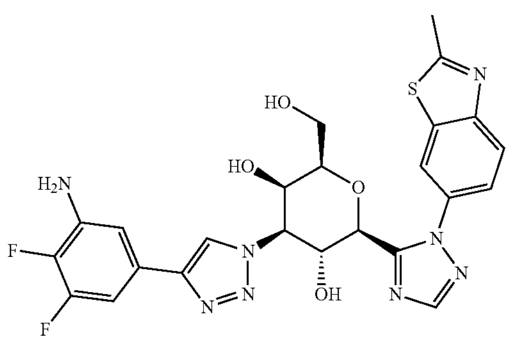 [SMILES: Cc1nc2ccc(-n3ncnc3[C@@H]3O[C@H](CO)[C@H](O)[C@H](n4cc(-c5cc(N)c(F)c(F)c5)nn4)[C@H]3O)cc2s1] | 1.139 | 557.1 | A | 1H NMR (400 MHz, METHANOL-d4) δ 8.42 (d, J = 2.0 Hz, 1H), 8.39 (s, 1H), 8.24 (s, 1H), 8.11 (d, J = 8.6 Hz, 1H), 7.84 (dd, J = 8.7, 2.1 Hz, 1H), 7.16-7.06 (m, 1H), 6.97 (ddd, J = 11.2, 6.7, 2.0 Hz, 1H), 5.07-4.96 (m, 1H), 4.95-4.88 (m, 1H), 4.62 (d, J = 9.3 Hz, 1H), 4.14 (d, J = 2.4 Hz, 1H), 3.96-3.78 (m, 3H), 2.92 (s, 3H). |
| 219 | 0.07 | 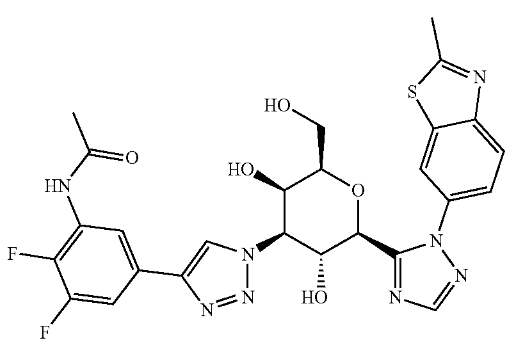 [SMILES: CC(=O)Nc1cc(-c2cn([C@H]3[C@@H](O)[C@@H](CO)O[C@@H](c4ncnn4-c4ccc5nc(C)sc5c4)[C@@H]3O)nn2)cc(F)c1F] | 1.097 | 599.2 | A | 1H NMR (400 MHz, METHANOL-d4) δ 8.50 (s, 1H), 8.42 (d, J = 2.0 Hz, 1H), 8.25 (s, 1H), 8.20 (d, J = 5.9 Hz, 1H), 8.11 (d, J = 8.8 Hz, 1H), 7.84 (dd, J = 8.8, 2.2 Hz 1H), 7.66-7.55 (m, 1H), 5.10- 4.98 (m, 1H), 4.93 (dd, J = 10.8, 2.9 Hz, 1H), 4.62 (d, J = 9.3 Hz, 1H), 4.15 (d, J = 2.9 Hz, 1H), 3.97-3.77 (m, |

| Ex | hGal3 IC50, uM | Structure | LCMS $t_R$ (min) | M + H | Method | 1H NMR |
|---|---|---|---|---|---|---|
| | | | | | | 2H), 3.77-3.65 (m, 1H), 2.92 (s, 3H), 2.23 (s, 3H). |
| 220 | 0.07 | 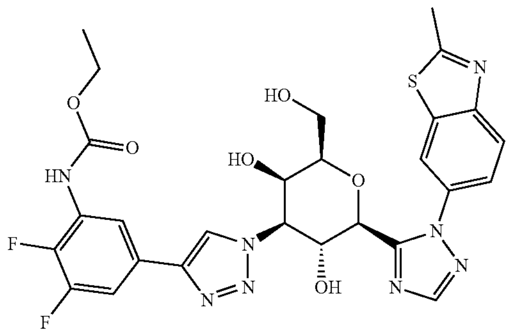 [SMILES: CCOC(=O)Nc1cc(-c2cn([C@H]3[C@@H](O)[C@@H](CO)O[C@@H](c4ncnn4-c4ccc5nc(C)sc5c4)[C@@H]3O)nn2)cc(F)c1F] | 1.35 | 629.2 | A | 1H NMR (400 MHz, METHANOL-d4) δ 8.49 (s, 1H), 8.42 (d, J = 2.0 Hz, 1H), 8.24 (s, 1H), 8.19 (d, J = 5.9 Hz, 1H), 8.11 (d, J = 8.8 Hz, 1H), 7.84 (dd, J = 8.6, 2.2 Hz, 1H), 7.51 (ddd, J = 10.9, 6.9, 2.0 Hz, 1H), 5.04 (dd, J = 10.6, 9.2 Hz, 1H), 4.93 (dd, J = 10.9, 2.8 Hz, 1H), 4.63 (d, J = 9.3 Hz, 1H), 4.27 (q, J = 7.3 Hz, 2H), 4.16 (d, J = 2.7 Hz, 1H), 3.95-3.88(m, 1H), 3.88-3.79 (m, 1H), 3.78 3.69 (m, 1H), 2.92 (s, 3H), 1.36 (t, J = 7.2 Hz, 3H). |
General Synthetic Scheme 2 for C3-aryl 1,2,3-Triazole:
(click followed by Suzuki coupling with Aryl bromides)
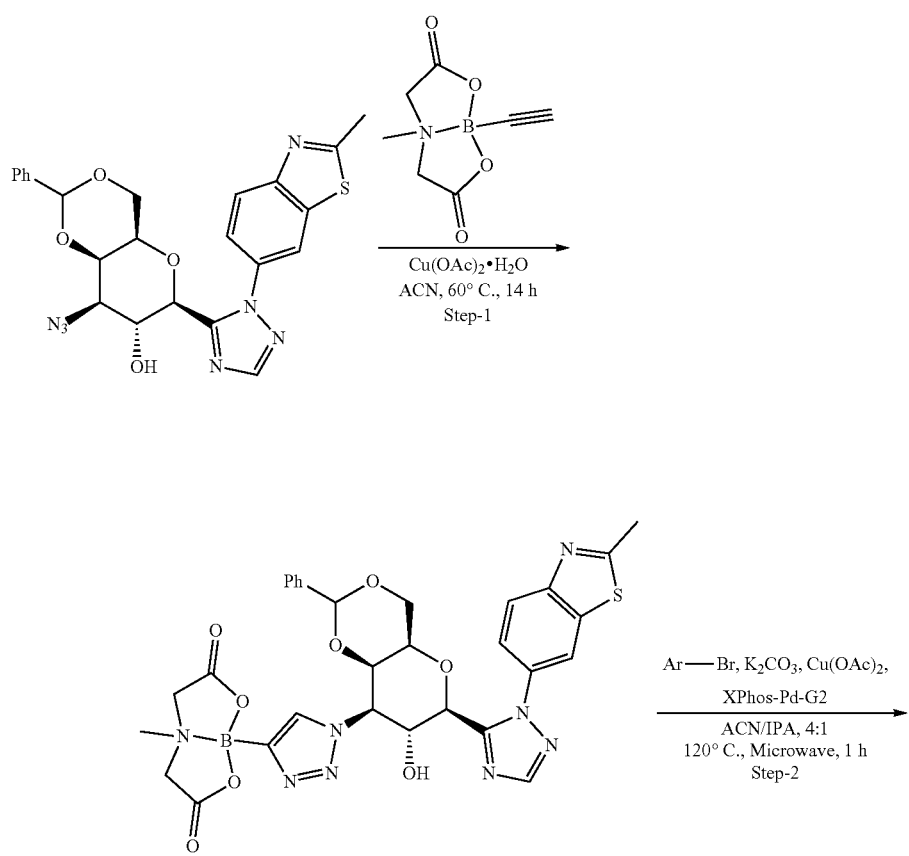

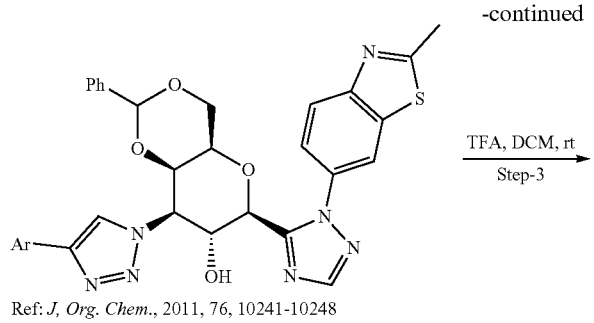 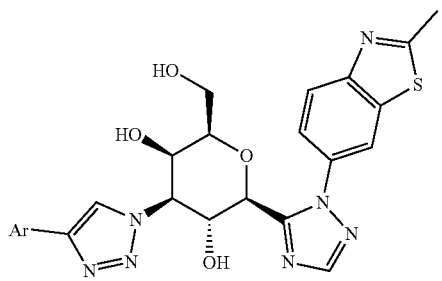

Ref: *J. Org. Chem.*, 2011, 76, 10241-10248

EXAMPLE 221

Preparation of (2R,3R,4R,5R,6S)-4-(4-(3,4-di-chloro-5-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol

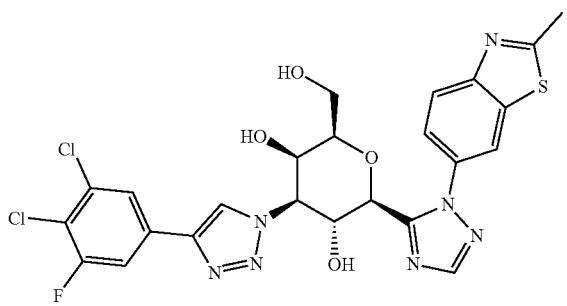 [SMILES: Cc1nc2ccc(-n3ncnc3[C@@H]3O[C@H](CO)[C@H](O)[C@H](n4cc(-c5cc(F)c(Cl)c(Cl)c5)nn4)[C@H]3O)cc2s1]

Step 1: Synthesis of 2-(1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)-6-methyl-1,3,6,2-dioxazaborocane-4,8-dione: To a stirred solution of (4aR,6S,7R,8R,8aR)-8-azido-6-(1-(2-methylbenzo[d]thiazol-6-yl)-1H-1,2,4-triazol-5-yl)-2 phenyl hexahydropyrano[3,2-d][1,3]dioxin-7-ol (400 mg, 0.814 mmol) in acetonitrile (10 mL) was added copper(II) acetate monohydrate (16.25 mg, 0.081 mmol) and acetyleneboronic acid mida ester (147 mg, 0.814 mmol) at rt. The reaction mixture was heated at 60° C. for 14 h. The reaction mixture was cooled to rt and was concentrated under reduced pressure to afford 2-(1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)-6-methyl-1,3,6,2-dioxazaborocane-4,8-dione (300 mg, 55%) which was taken to the next step without further purification. LC-MS, [M+1]$^+$= 672.2, (Method E: $t_R$=1.08 min).

Step 2: Synthesis of (4aR,6S,7R,8R,8aR)-8-(4-(3,4-dichloro-5-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol: To a stirred solution of 2-(1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)-6-methyl-1,3,6,2-dioxazaborocane-4,8-dione (50 mg, 0.074 mmol) in 2-propanol (2 mL) and acetonitrile (1 mL) was added 5-bromo-1,2-dichloro-3-fluorobenzene (21.76 mg, 0.089 mmol), copper(II) acetate monohydrate (14.84 mg, 0.074 mmol), K$_2$CO$_3$ (30.8 mg, 0.223 mmol) and Xphos-Pd-G2 (5.85 mg, 7.44 µmol). The reaction mixture degassed with nitrogen for 10 min and was irradiated in the microwave at 100° C. for 1 h. The reaction mixture was concentrated and the residue was taken up in 10% MeOH in DCM (2×10 mL) and was washed with aq. NaHCO$_3$, water, brine solution, dried over sodium sulfate and concentrated. The residue was purified via silica gel chromatography (5-15% MeOH in chloroform) to give (4aR,6S,7R,8R,8aR)-8-(4-(3,4-dichloro-5-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol (30 mg, 59%). LC-MS, [M+1]$^+$=680.3, (Method E: $t_R$=1.91 min).

Step 3: Synthesis of (2R,3R,4R,5R,6S)-4-(4-(3,4-dichloro-5-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol: To a stirred solution of (4aR,6S,7R,8R,8aR)-8-(4-(3,4-dichloro-5-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol (25 mg, 0.037 mmol) in DCM (1 mL) was added TFA (0.014 mL, 0.184 mmol) and the reaction mixture was stirred at rt for 1 h. The reaction mixture concentrated and purified by HPLC (Method A) to give (2R,3R,4R,5R,6S)-4-(4-(3,4-dichloro-5-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol (Example 221) (3.4 mg, 16%). LC-MS, [M+1]$^+$=594.1, (Method A and Method B: $t_R$=1.56 min). 1H NMR (400 MHz, METHANOL-d4): δ 8.63 (s, 1H), 8.40 (s, 1H), 8.23 (s, 1H), 8.09 (d, J=8.8 Hz, 1H), 7.93 (s, 1H), 7.82 (d, J=8.8 Hz, 1H), 7.76 (d, J=9.5 Hz, 1H), 5.05-4.98 (m, 1H), 4.95 (d, J=2.4 Hz, 1H), 4.61 (d, J=9.3 Hz, 1H), 4.13 (br. s., 1H), 3.94-3.77 (m, 2H), 3.76-3.68 (m, 1H), 2.90 (s, 3H). hGal3 IC$_{50}$=0.05 uM.

The Examples in the table below were prepared in an analogous fashion to Example 221, substituting 5-bromo-1,2-dichloro-3-fluorobenzene with the appropriate aryl bromides in the synthetic sequence.

| Ex | hGal3 IC50, uM | Structure | LCMS $t_R$ (min) | M + H | Method | 1H NMR |
|---|---|---|---|---|---|---|
| 222 | 0.24 | 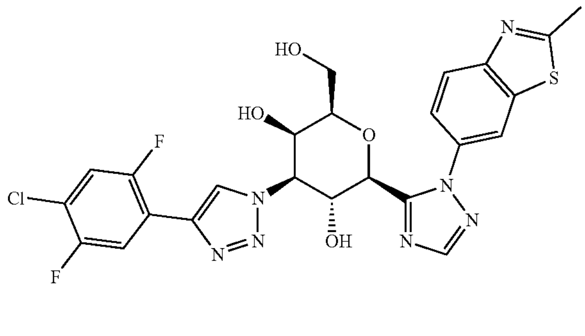 [SMILES: Cc1nc2ccc(-n3ncnc3[C@@H]3O[C@H](CO)[C@H](O)[C@H](n4cc(-c5cc(F)c(Cl)cc5F)nn4)[C@H]3O)cc2s1] | 1.427 | 576.2 | A | 1H NMR (400 MHz, METHANOL-d4) δ 8.48 (d, J = 4.0 Hz, 1H), 8.43 (d, J = 2.0 Hz, 1H), 8.24 (s, 1H), 8.10 (d, J = 8.5 Hz, 1H), 8.02 (dd, J = 9.8, 6.3 Hz, 1H), 7.84 (dd, J = 8.8, 2.3 Hz, 1H), 7.52 (dd, J = 10.0, 6.0 Hz, 1H), 5.09-4.94 (m, 2H), 4.63 (d, J = 9.0 Hz, 1H), 4.16 (d, J = 2.5 Hz, 1H), 3.96-3.88 (m, 1H), 3.88-3.82 (m, 1H), 3.78-3.70 (m, 1H), 2.92 (s, 3H). |
| 223 | 0.20 | 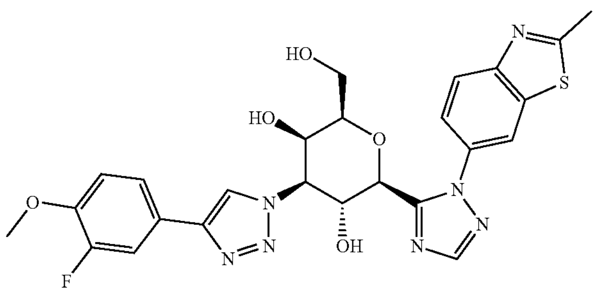 | 1.177 | 554.2 | A | 1H NMR (400 MHz, METHANOL-d4) δ 8.49-8.36 (m, 2H), 8.25 (s, 1H), 8.11 (d, J = 8.5 Hz, 1H), 7.84 (dd, J = 8.5, 2.0 Hz, 1H), 7.68-7.55 (m, 2H), 7.19 (t, J = 8.8 Hz, 1H), 5.09-4.99 (m, 1H), 4.91 (dd, J = 10.5, 3.0 Hz, 1H), 4.62 (d, J = 9.5 Hz, 1H), 4.15 (d, J = 3.0 Hz, 1H), 4.00-3.79 (m, 5H), 3.78-3.70 (m, 1H), 2.92 (s, 3H). |

General Synthetic Scheme 1 for C3-aryl 1,2,3-triazole in benzothiathole 1,2,4-triazole Series:

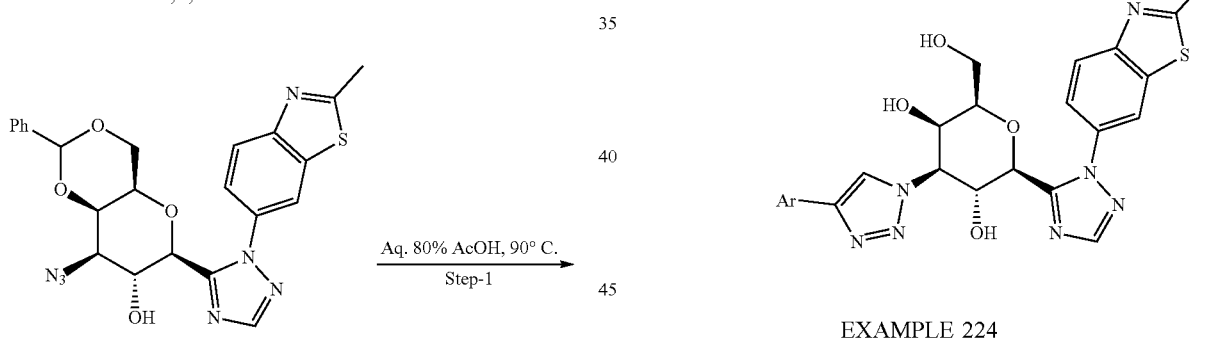

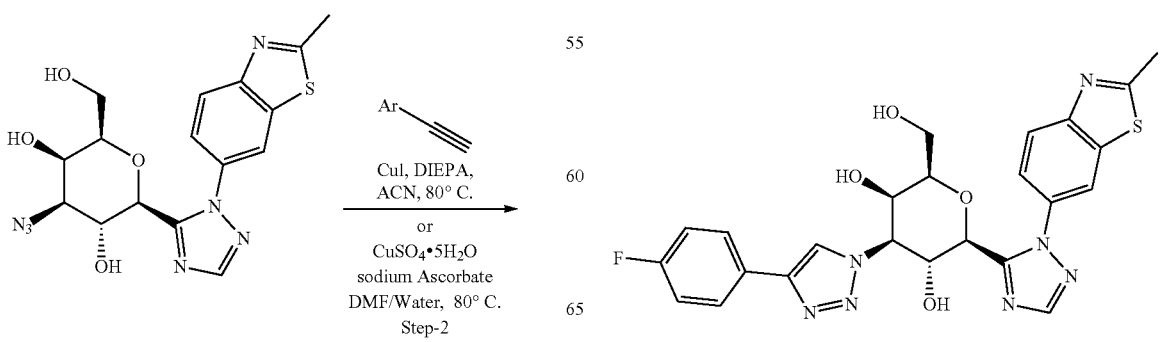

EXAMPLE 224

Preparation of (2R,3R,4R,5R,6S)-4-(4-(4-fluorophenyl)-1H-1,2,3-triazol-1-yl)-2-(hydroxymethyl)-6-(4-(2-methylbenzo[d]thiazol-6-yl)-4H-1,2,4-triazol-3-yl)tetrahydro-2H-pyran-3,5-diol Step 1: Synthesis of (2R,3R,4R,5R,6S)-4-azido-2-(hydroxymethyl)-6-(1-(2-methylbenzo[d]thiazol-6-yl)-1H-1,2,4-triazol-5-yl)tetrahydro-2H-pyran-3,5-diol: A mixture of (4aR,6S,7R,8R,8aR)-8-azido-6-(1-(2-methylbenzo[d]thiazol-6-yl)-1H-1,2,4-triazol-5-yl)-2-phenylhexahydropyrano[3,2-d][1,3]dioxin-7-ol (900 mg, 1.831 mmol) in aq. AcOH (80%, 100 mL) was heated at 90° C. for 2.5 h. The reaction mixture was concentrated, co-distilled with toluene (3×20 mL) and dried to afford (2R,3R,4R,5R,6S)-4-azido-2-(hydroxymethyl)-6-(1-(2-methylbenzo[d]thiazol-6-yl)-1H-1,2,4-triazol-5-yl)tetrahydro-2H-pyran-3,5-diol (700 mg, 95%) LC-MS, [M+H]$^+$=404.0, (Method E: $t_R$=0.59).

Step 2: Synthesis of ((2R,3R,4R,5R,6S)-4-(4-(4-fluorophenyl)-1H-1,2,3-triazol-1-yl)-2-(hydroxymethyl)-6-(4-(2-methylbenzo[d]thiazol-6-yl)-4H-1,2,4-triazol-3-yl)tetrahydro-2H-pyran-3,5-diol: To a stirred solution of (2R,3R,4R,5R,6S)-4-azido-2-(hydroxymethyl)-6-(1-(2-methylbenzo[d]thiazol-6-yl)-1H-1,2,4-triazol-5-yl)tetrahydro-2H-pyran-3,5-diol (30 mg, 0.074 mmol) and 1-ethynyl-4-fluorobenzene (8.93 mg, 0.074 mmol) in acetonitrile (5 mL) was added DIPEA (0.065 ml, 0.372 mmol) followed by copper(I) iodide (2.83 mg, 0.015 mmol). The mixture was heated at 80° C. for 1.5 h. The reaction mixture was cooled to rt, diluted with DCM and stirred for 15 min. The reaction mixture was then filtered through a pad of Celite, washed with excess DCM and concentrated. The crude residue was purified by HPLC (Method A) to afford (2R,3R,4R,5R,6S)-4-(4-(4-fluorophenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol (Example 224) (30.3 mg, 78%). LC-MS, [M+H]$^+$=524.2, (Method A: $t_R$=1.171). 1H NMR (400 MHz, METHANOL-d4) δ 8.46 (s, 1H), 8.43 (d, J=2.2 Hz, 1H), 8.25 (s, 1H), 8.11 (d, J=8.8 Hz, 1H), 7.93-7.75 (m, 3H), 7.28-7.11 (m, 2H), 5.08-5.00 (m, 1H), 4.93 (dd, J=10.8, 2.9 Hz, 1H), 4.63 (d, J=9.3 Hz, 1H), 4.16 (d, J=2.9 Hz, 1H), 3.96-3.78 (m, 2H), 3.78-3.68 (m, 1H), 2.92 (s, 3H). hGal3 IC$_{50}$=0.33 uM.

The Examples in the table below were prepared in an analogous fashion to Example 201, substituting 1-ethynyl-4-fluorobenzene with the appropriate aryl acetylene in the synthetic sequence.

| Ex | hGal3 IC50, uM | Structure | LCMS $t_R$ (min) | M + H | Method | 1H NMR |
|---|---|---|---|---|---|---|
| 225 | 0.21 | 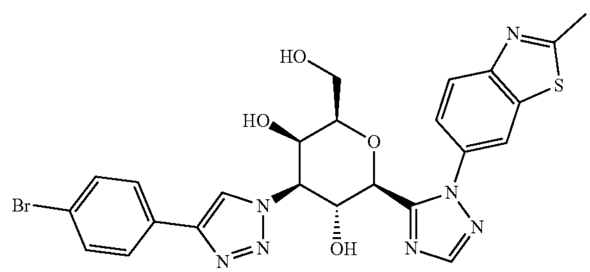 [SMILES: Cc1nc2ccc(-n3ncnc3[C@@H]3O[C@H](CO)[C@H](O)[C@H](n4cc(-c5ccc(Br)cc5)nn4)[C@H]3O)cc2s1] | 1.347 | 586.1 | A | 1H NMR (400 MHz, METHANOL-d4) δ 8.50 (s, 1H), 8.40 (d, J = 2.2 Hz, 1H), 8.23 (s, 1H), 8.09 (d, J = 8.6 Hz, 1H), 7.82 (dd, J = 8.8, 2.0 Hz, 1H), 7.80-7.70 (m, J = 8.3 Hz, 2H), 7.67-7.47 (m, J = 8.6 Hz, 2H), 5.08-4.98 (m, 1H), 4.96-4.90 (m, 1H), 4.61 (d, J = 9.3 Hz, 1H), 4.14 (d, J = 2.7 Hz, 1H), 3.93-3.77 (m, 2H), 3.76-3.67 (m, 1H), 2.90 (s, 3H). |
| 226 | 0.07 | 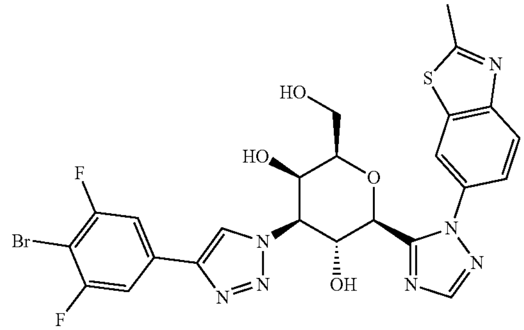 [SMILES: Cc1nc2ccc(-n3ncnc3[C@@H]3O[C@H](CO)[C@H](O)[C@H](n4cc(-c5cc(F)c(Br)c(F)c5)nn4)[C@H]3O)cc2s1] | 1.48 | 622.2 | B | 1H NMR (400 MHz, METHANOL-d4) δ 8.65 (s, 1H), 8.42 (s, 1H), 8.26 (s, 1H), 8.11 (d, J = 8.6 Hz, 1H), 7.84 (d, J = 8.6 Hz, 1H), 7.64 (d, J = 7.6 Hz, 2H), 5.03 (d, J = 9.3 Hz, 1H), 4.95 (d, J = 10.8 Hz, 1H), 4.62 (d, J = 8.8 Hz, 1H), 4.15 (br. s., 1H), 3.98-3.78 (m, 2H), 3.75 (d, J = 12.0 Hz, 1H), 3.90 (s, 3H). |

-continued

| Ex | hGal3 IC50, uM | Structure | LCMS t<sub>R</sub> (min) | M + H | Method | 1H NMR |
|---|---|---|---|---|---|---|
| 227 | 0.25 | 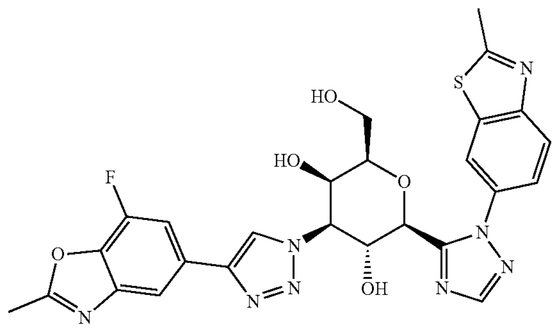 [SMILES: Cc1nc2cc(-c3cn([C@H]4[C@@H](O)[C@@H](CO)O[C@@H](c5ncnn5-c5ccc6nc(C)sc6c5)[C@@H]4O)nn3)cc(F)c2o1] | 1.199 | 579.2 | A | 1H NMR (400 MHz, METHANOL-d4) δ 8.58 (s, 1H), 8.43 (d, J = 2.0 Hz, 1H), 8.25 (s, 1H), 8.11 (d, J = 8.6 Hz, 1H), 7.95 (d, J = 1.2 Hz, 1H), 7.85 (dd, J = 8.8, 2.2 Hz, 1H), 7.73 (dd, J = 11.1, 1.3 Hz, 1H), 5.10-5.03 (m, 1H), 4.94 (dd, J = 10.8, 2.9 Hz, 1H), 4.63 (d, J = 9.3 Hz, 1H), 4.17 (d, J = 2.4 Hz, 1H), 3.96-3.89 (m, 1H), 3.89-3.82 (m, 1H), 3.75 (dd, J = 11.5, 3.9 Hz, 1H), 2.92 (s, 3H), 2.71 (s, 3H). |
| 228 | 0.42 | 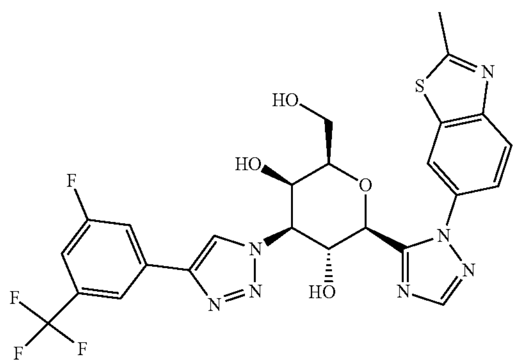 [SMILES: Cc1nc2ccc(-n3ncnc3[C@@H]3O[C@H](CO)[C@H](O)[C@H](n4cc(-c5cc(F)cc(C(F)(F)F)c5)nn4)[C@H]3O)cc2s1] | 1.508 | 592.2 | A | 1H NMR (400 MHz, METHANOL-d4) δ 8.70 (s, 1H), 8.40 (d, J = 1.7 Hz, 1H), 8.24 (s, 1H), 8.09 (d, J = 8.6 Hz, 1H), 8.04 (s, 1H), 7.91 (d, J = 9.8 Hz, 1H), 7.83 (dd, J = 8.7, 1.8 Hz, 1H), 7.43 (d, J = 8.8 Hz, 1H), 5.11-5.00 (m, 1H), 4.99-4.91 (m, 1H), 4.62 (d, J = 9.0 Hz, 1H), 4.15 (br. s., 1H), 3.95-3.77 (m, 2H), 3.73 (dd, J = 11.2, 3.9 Hz, 1H), 2.92 (s, 3H). |
| 229 | 0.98 | 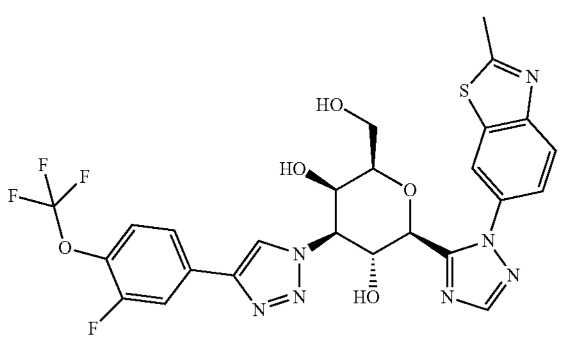 [SMILES: Cc1nc2ccc(-n3ncnc3[C@@H]3O[C@H](CO)[C@H](O)[C@H](n4cc(-c5ccc(OC(F)(F)F)c(F)c5)nn4)[C@H]3O)cc2s1] | 1.551 | 608.2 | A | 1H NMR (400 MHz, METHANOL-d4) δ 8.60 (s, 1H), 8.40 (d, J = 2.0 Hz, 1H), 8.24 (s, 1H), 8.09 (d, J = 8.8 Hz, 1H), 7.92-7.79 (m, 2H), 7.77 (d, J = 8.6 Hz, 1H), 7.50 (t, J = 8.1 Hz, 1H), 5.08-4.98 (m, 1H), 4.97-4.92 (m, 1H), 4.61 (d, J = 9.0 Hz, 1H), 4.15 (br. s., 1H), 3.95-3.87 (m, 1H), 3.87-3.78 (m, 1H), 3.77-3.69 (m, 1H), 2.90 (s, 3H). |
| 230 | 0.45 | 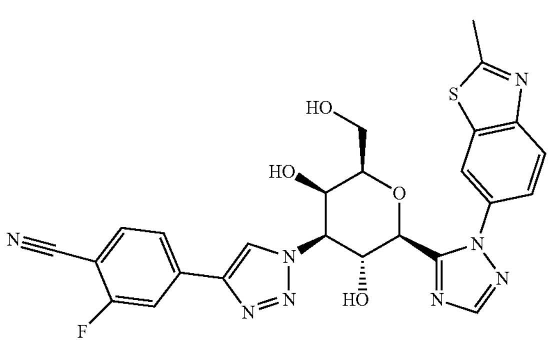 [SMILES: Cc1nc2ccc(-n3ncnc3[C@@H]3O[C@H](CO)[C@H](O)[C@H](n4cc(-c5ccc(C#N)c(F)c5)nn4)[C@H]3O)cc2s1] | 1.207 | 549.2 | A | 1H NMR (400 MHz, METHANOL-d4) δ 8.71 (s, 1H), 8.42 (d, J = 2.0 Hz, 1H), 8.25 (s, 1H), 8.11 (d, J = 8.8 Hz, 1H), 7.96-7.87 (m, 2H), 7.87-7.78 (m, 2H), 5.10-5.01 (m, 1H), 5.00-4.94 (m, 1H), 4.63 (d, J = 8.8 Hz, 1H), 4.16 (br. s., 1H), 3.96-3.89 (m, 1H), 3.89-3.82 (m, 1H), 3.77-3.69 (m, 1H), 2.92 (s, 3H). |

-continued

| Ex | hGal3 IC50, uM | Structure | LCMS t_R (min) | M + H | Method | 1H NMR |
|---|---|---|---|---|---|---|
| 231 | 0.39 | 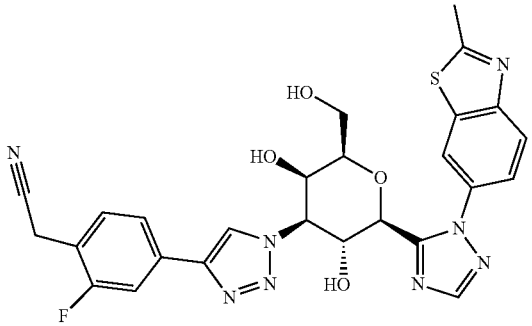 [SMILES: Cc1nc2ccc(-n3ncnc3[C@@H]3O[C@H](CO)[C@H](O)[C@H](n4cc(-c5ccc(CC#N)c(F)c5)nn4)[C@H]3O)cc2s1] | 1.14 | 563.2 | A | 1H NMR (400 MHz, DMSO-d6) δ 8.56 (s, 1H), 8.40 (d, J = 2.0 Hz, 1H), 8.24 (s, 1H), 8.09 (d, J = 8.5 Hz, 1H), 7.82 (dd, J = 8.8, 2.3 Hz, 1H), 7.78-7.62 (m, 2H), 7.57-7.49 (m, 1H), 5.03 (t, J = 9.5 Hz, 1H), 4.92 (d, J = 10.0 Hz, 1H), 4.61 (d, J = 9.0 Hz, 1H), 4.14 (br. s., 1H), 3.97-3.92 (m, 1H), 3.93-3.79 (m, 1H), 3.76-3.68 (m, 1H), 2.90 (s, 3H). |
| 232 | 0.04 | 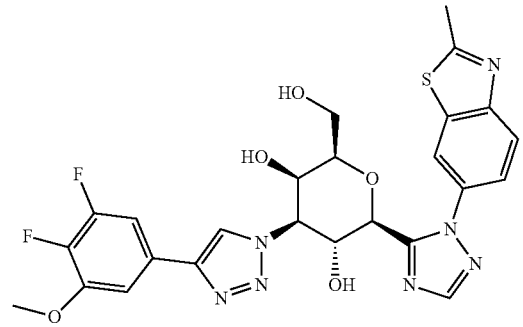 [SMILES: COc1cc(-c2cn([C@H]3[C@@H](O)[C@@H](CO)O[C@@H](c4ncnn4-c4ccc5nc(C)sc5c4)[C@@H]3O)nn2)cc(F)c1F] | 1.329 | 572.2 | A | 1H NMR (400 MHz, METHANOL-d4) δ 8.56 (s, 1H), 8.42 (d, J = 2.0 Hz, 1H), 8.25 (s, 1H), 8.11 (d, J = 8.6 Hz, 1H), 7.84 (dd, J = 8.6, 2.2 Hz, 1H), 7.46 (d, J = 6.8 Hz, 1H), 7.36 (ddd, J = 10.8, 6.5, 1.8 Hz, 1H), 5.11-4.99 (m, 1H), 4.93 (dd, J = 10.6, 2.8 Hz, 1H), 4.63 (d, J = 9.3 Hz, 1H), 4.16 (d, J = 2.7 Hz, 1H), 4.01 (s, 3H), 3.95-3.78 (m, 2H), 3.77-3.69 (m, 1H), 2.92 (s, 3H). |
| 233 | 0.24 | 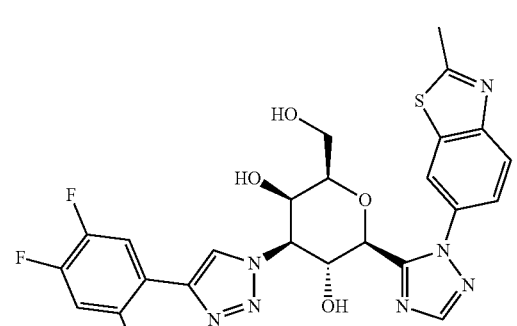 | 1.324 | 572.2 | A | 1H NMR (400 MHz, METHANOL-d4) δ 8.50 (s, 1H), 8.44 (d, J = 2.0 Hz, 1H), 8.24 (s, 1H), 8.11 (d, J = 8.6 Hz, 1H), 8.01 (dd, J = 11.7, 9.0 Hz, 1H), 7.85 (dd, J = 8.7, 2.1 Hz, 1H), 7.12 (dd, J = 12.5, 6.6 Hz, 1H), 5.08-4.98 (m, 1H), 4.96-4.91 (m, 1H), 4.63 (d, J = 9.3 Hz, 1H), 4.15 (d, J = 2.4 Hz, 1H), 3.99 (s, 3H), 3.94-3.82 (m, 2H), 3.78-3.68 (m, 1H), 2.79 (s, 3H). |
| 234 | | 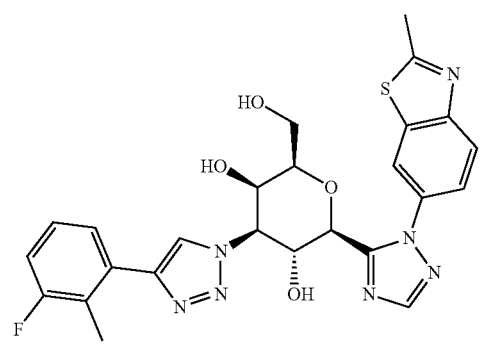 [SMILES: Cc1nc2ccc(-n3ncnc3[C@@H]3O[C@H](CO)[C@H](O)[C@H](n4cc(-c5cccc(F)c5C)nn4)[C@H]3O)cc2s1] | 1.271 | 538.2 | A | 1H NMR (400 MHz, METHANOL-d4) δ 8.44 (d, J = 2.0 Hz, 1H), 8.30 (s, 1H), 8.24 (s, 1H), 8.11 (d, J = 8.6 Hz, 1H), 7.85 (dd, J = 8.7, 2.2 Hz, 1H), 7.48 (d, J = 7.8 Hz, 1H), 7.35-7.22 (m, 1H), 7.12 (t, J = 8.8 Hz, 1H), 5.09-5.00 (m, 1H), 5.00-4.94 (m, 1H), 4.64 (d, J = 9.0 Hz, 1H), 4.18 (d, J = 2.4 Hz, 1H), 3.97- |

| Ex | hGal3 IC50, uM | Structure | LCMS t$_R$ (min) | M + H | Method | 1H NMR |
|---|---|---|---|---|---|---|
| | | | | | | 3.82 (m, 2H), 3.78-3.69 (m, 1H), 2.92 (s, 3H), 2.38 (d, J = 2.1 Hz, 3H). |
| 235 | 0.39 | 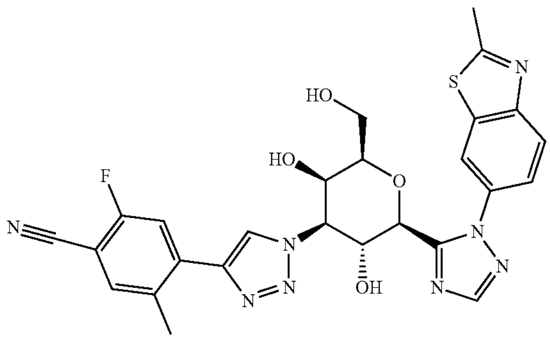 [SMILES: Cc1nc2ccc(-n3ncnc3[C@@H]3O[C@H](CO)[C@H](O)[C@H](n4cc(-c5cc(F)c(C#N)cc5C)nn4)[C@H]3O)cc2s1] | 1.287 | 563.2 | A | 1H NMR (400 MHz, METHANOL-d4) δ 8.37 (s, 1H), 8.32 (d, J = 1.8 Hz, 1H), 8.13 (s, 1H), 7.99 (d, J = 8.7 Hz, 1H), 7.81-7.67 (m, 2H), 7.61 (d, J = 6.5 Hz, 1H), 4.98-4.86 (m, 2H), 4.52 (d, J = 8.9 Hz, 1H), 4.05 (d, J = 2.3 Hz, 1H), 3.87-3.78 (m, 1H), 3.78-3.70 (m, 1H), 3.66-3.57 (m, 1H), 2.80 (s, 3H), 2.43 (s, 3H). |
| 236 | 0.24 | 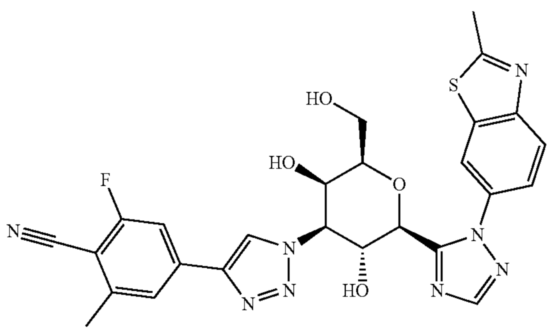 [SMILES: Cc1nc2ccc(-n3ncnc3[C@@H]3O[C@H](CO)[C@H](O)[C@H](n4cc(-c5cc(C)c(C#N)c(F)c5)nn4)[C@H]3O)cc2s1] | 1.316 | 563.2 | A | 1H NMR (400 MHz, METHANOL-d4) δ 8.60 (s, 1H), 8.30 (d, J = 2.1 Hz, 1H), 8.14 (s, 1H), 7.99 (d, J = 8.7 Hz, 1H), 7.72 (dd, J = 8.7, 2.1 Hz, 1H), 7.69 (s, 1H), 7.59 (d, J = 10.1 Hz, 1H), 4.98-4.88 (m, 1H), 4.88-4.83 (m, 1H), 4.51 (d, J = 9.0 Hz, 1H), 4.03 (d, J = 2.2 Hz, 1H), 3.86-3.77 (m, 1H), 3.76-3.69 (m, 1H), 3.62 (dd, J = 11.4, 3.9 Hz, 1H), 2.80 (s, 3H), 2.51 (s, 3H). |
| 237 | 0.21 | 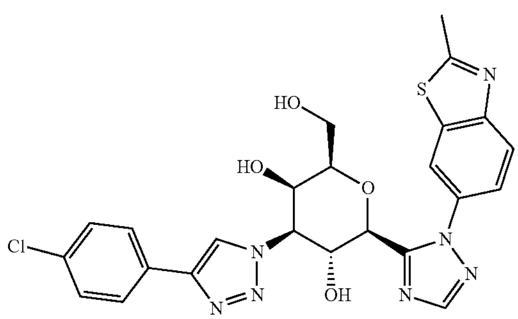 [SMILES: Cc1nc2ccc(-n3ncnc3[C@@H]3O[C@H](CO)[C@H](O)[C@H](n4cc(-c5ccc(Cl)cc5)nn4)[C@H]3O)cc2s1] | 1.312 | 540.2 | A | 1H NMR (400 MHz, METHANOL-d4) δ 8.49 (s, 1H), 8.40 (s, 1H), 8.23 (s, 1H), 8.09 (d, J = 8.8 Hz, 1H), 7.92-7.71 (m, 3H), 7.46 (d, J = 8.6 Hz, 2H), 5.01 (d, J = 9.5 Hz, 1H), 4.93 (br. s., 1H), 4.61 (d, J = 9.5 Hz, 1H), 4.14 (br. s., 1H), 3.93-3.77 (m, 2H), 3.73 (dd, J = 10.9, 3.3 Hz, 1H), 2.90 (s, 3H). |
| 238 | | 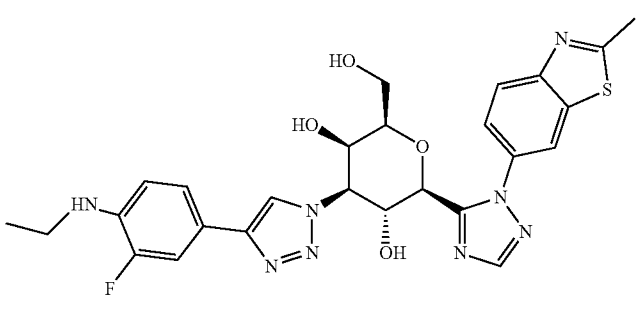 [SMILES: CCNc1ccc(-c2cn([C@H]3[C@@H](O)[C@@H](CO)O[C@@H](c4ncnn4-c4ccc5nc(C)sc5c4)[C@@H]3O)nn2)cc1F] | 1.276 | 567.3 | A | 1H NMR (400 MHz, METHANOL-d4) δ 8.31 (d, J = 2.0 Hz, 1H), 8.20 (s, 1H), 8.13 (s, 1H), 7.99 (d, J = 8.8 Hz, 1H), 7.72 (dd, J = 8.6, 2.2 Hz, 1H), 7.44-7.24 (m, 2H), 6.70 (t, J = 8.8 Hz, 1H), 4.95-4.86 (m, 1H), 4.78 (d, J = 2.9 Hz, 1H), 4.54-4.47 (m, 1H), 4.03 (d, J = 2.7 Hz, 1H), 3.85-3.66 (m, 3H), 3.13 (q, J = |

-continued
| Ex | hGal3 IC50, uM | Structure | LCMS $t_R$ (min) | M + H | Method | 1H NMR |
|---|---|---|---|---|---|---|
| | | | | | | 7.1 Hz, 2H), 2.80 (s, 3H), 1.17 (t, J = 7.1 Hz, 3H). |
| 239 | | 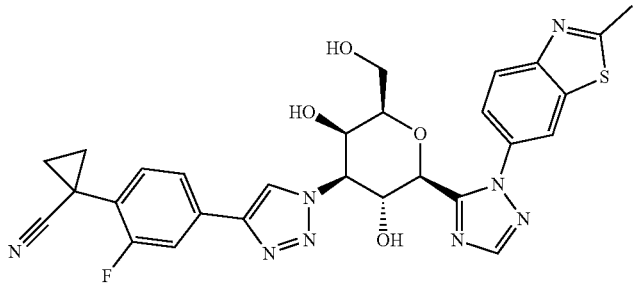 [SMILES: Cc1nc2ccc(-n3ncnc3[C@@H]3O[C@H](CO)[C@H](O)[C@H](n4cc(-c5ccc(C6(C#N)CC6)c(F)c5)nn4)[C@H]3O)cc2s1] | 1.267 | 589.2 | A | 1H NMR (400 MHz, METHANOL-d4) δ 8.47 (s, 1H), 8.31 (d, J = 2.0 Hz, 1H), 8.13 (s, 1H), 7.99 (d, J = 8.7 Hz, 1H), 7.72 (dd, J = 8.7, 2.1 Hz, 1H), 7.66-7.52 (m, 2H), 7.40 (t, J = 7.9 Hz, 1H), 4.99-4.88 (m, 1H), 4.83 (dd, J = 10.8, 2.9 Hz, 1H), 4.51 (d, J = 9.2 Hz, 1H), 4.04 (d, J = 2.4 Hz, 1H), 3.85-3.76 (m, 1H), 3.76-3.70 (m, 1H), 3.66-3.55 (m, 1H), 2.80 (s, 3H), 1.66-1.56 (m, 2H), 1.42-1.33 (m, 2H) |
| 240 | 0.16 | 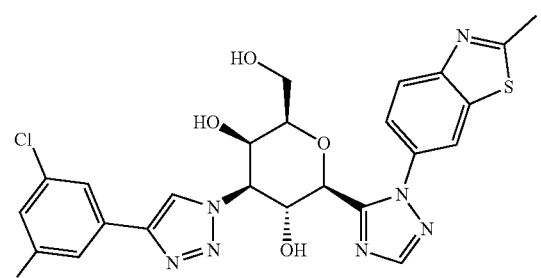 | 1.395 | 558.2 | A | 1H NMR (400 MHz, METHANOL-d4) δ 8.62 (s, 1H), 8.42 (d, J = 2.0 Hz, 1H), 8.25 (s, 1H), 8.11 (d, J = 8.5 Hz, 1H), 7.84 (dd, J = 8.5, 2.0 Hz, 1H), 7.77 (s, 1H), 7.61 (dq, J = 9.6,1.3 Hz, 1H), 7.20 (dt, J = 8.7, 2.2 Hz, 1H), 5.10-4.99 (m, 1H), 4.98-4.92 (m, 1H), 4.63 (d, J = 9.0 Hz, 1H), 4.15 (d, J = 2.5 Hz, 1H), 3.95-3.88 (m, 1H), 3.88-3.81 (m, 1H), 3.74 (dd, J = 11.5, 4.0 Hz, 1H), 2.92 (s, 3H). |
General Synthetic Scheme 2 for C3-aryl 1,2,3-triazole in benzothiazole 1,2,4-triazole Series:
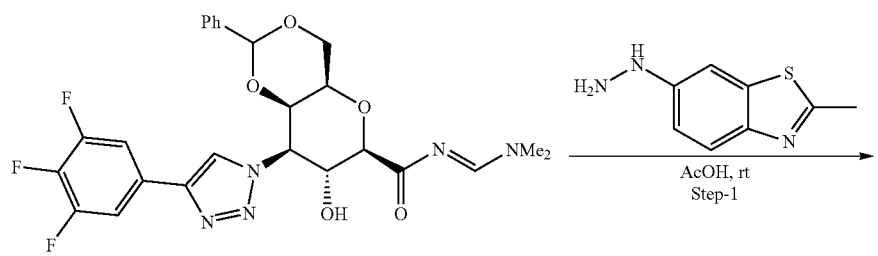

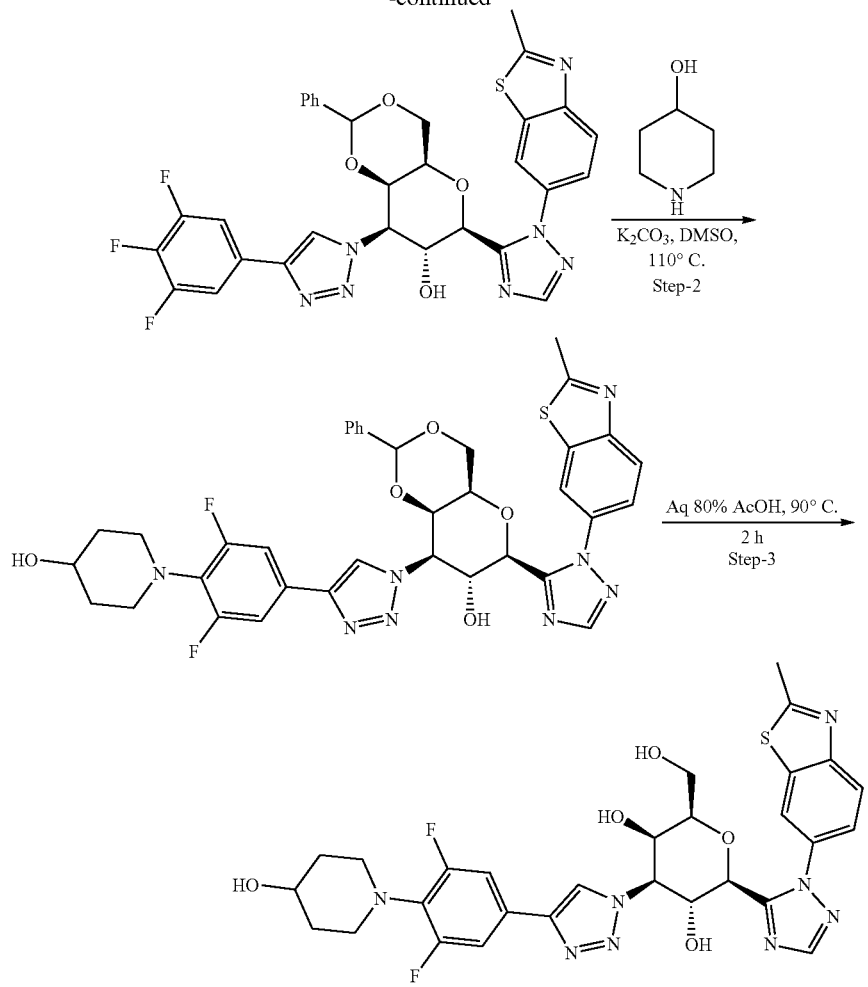

EXAMPLE 241

(2R,3R,4R,5R,6S)-4-(4-(3,5-difluoro-4-(4-hydroxypiperidin-1-yl)phenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol

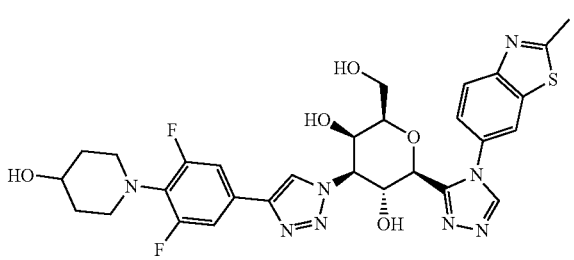 [SMILES: Cc1nc2ccc(-n3cnnc3[C@@H]3O[C@H](CO)[C@H](O)[C@H](n4cc(-c5cc(F)c(N6CCC(O)CC6)c(F)c5)nn4)[C@H]3O)cc2s1]

Step 1: Synthesis of (4aR,6S,7R,8R,8aR)-6-(1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To a stirred solution of (4aR,6R,7R,8R,8aR)-N-((E)-(dimethylamino)methylene)-7-hydroxy-2-phenyl-8-(4-(3,4,5-trifluorophenyl)-1H-1,2,3-triazol-1-yl)hexahydropyrano[3,2-d][1,3]dioxine-6-carboxamide (850 mg, 1.599 mmol) in acetic acid (20 mL) was added 6-hydrazinyl-2-methylbenzo[d]thiazole.HCl (1371 mg, 5.44 mmol) and the mixture was stirred at rt for 2 h. The resultant solid was filtered, washed with excess water and dried to afford (4aR,6S,7R,8R,8aR)-6-(1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (600 mg, 58%) as a white solid. LC-MS, [M+H]$^+$=648.2, (Method E: $t_R$=1.32).

Step 2: Synthesis of (2,6-difluoro-4-(1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)phenyl)piperidin-4-ol: A sealed tube was charged with (4aR,6S,7R,8R,8aR)-6-(1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (20 mg, 0.031 mmol), piperidin-4-ol (15.62 mg, 0.154 mmol), K$_2$CO$_3$ (21.34 mg, 0.154 mmol) and DMSO (0.5 mL). The vial was sealed and heated at 110° C. for 14 h. The reaction mixture was cooled to rt and was extracted with EtOAc (3×20 mL). The combined organic layers were washed with water and brine and were concentrated. The crude residue was purified via silica gel chromatography (4-6% MeOH in chloroform) to afford 1-(2,6-difluoro-4-(1-((4aR,6S,7R,8R,8aR)-7-hydroxy-6-(1-

(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)phenyl)piperidin-4-ol (15 mg, 67%) as brown solid. LC-MS, [M+H]⁺=729.5, (Method E: $t_R$=1.50).

The Examples in the table below were prepared in an analogous fashion to Example 241, substituting 4-hydroxy pipridine with the appropriate amine in the synthetic sequence.

| Ex | hGal3 IC50, uM | Structure | LCMS $t_R$ (min) | M + H | Method | 1H NMR |
|---|---|---|---|---|---|---|
| 242 | 0.06 | 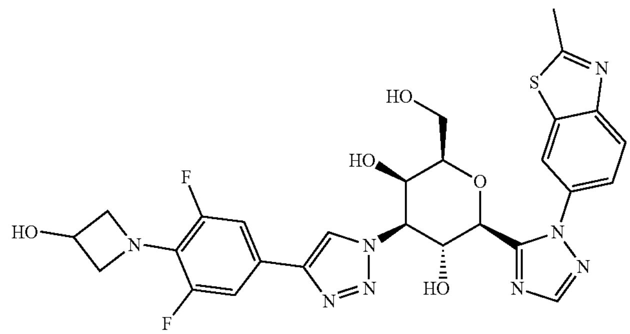 [SMILES: Cc1nc2ccc(-n3ncnc3[C@@H]3O[C@H](CO)[C@H](O)[C@H](n4cc(-c5cc(F)c(N6CC(O)C6)c(F)c5)nn4)[C@H]3O)cc2s1] | 1.334 | 613.3 | A | 1H NMR (400 MHz, METHANOL-d4) δ 8.47 (s, 1H), 8.42 (d, J = 2.2 Hz, 1H), 8.25 (s, 1H), 8.11(d, J = 8.8 Hz, 1H), 7.84 (dd, J = 8.7, 2.1 Hz, 1H), 7.09 (ddd, J = 11.1, 6.5, 2.0 Hz, 1H), 6.85 (d, J = 7.6 Hz, 1H), 5.08-4.98 (m, 1H), 4.91 (dd, J = 10.8, 2.7 Hz, 1H), 4.71 (dt, J = 11.4, 5.8 Hz, 1H), 4.62 (d, J = 9.0 Hz, 1H), 4.34 (t, J = 6.5 Hz, 2H), 4.15 (d, J = 2.4 Hz, 1H), 3.97-3.79 (m, 4H), 3.77-3.69 (m, 1H), 2.92 (s, 3H). |
| 243 | 0.08 | 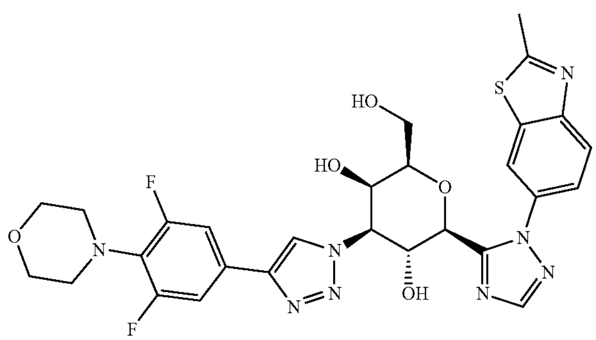 [SMILES: Cc1nc2ccc(-n3ncnc3[C@@H]3O[C@H](CO)[C@H](O)[C@H](n4cc(-c5cc(F)c(N6CCOCC6)c(F)c5)nn4)[C@H]3O)cc2s1] | 1.328 | 627.2 | A | 1H NMR (400MHz, MeOH-d4) δ 8.52 (s, 1H), 8.42 (d, J = 2.2 Hz, 1H), 8.25 (s, 1H), 8.11 (d, J = 8.8 Hz, 1H), 7.83 (dd, J = 8.7, 2.3 Hz, 1H), 7.40-7.30 (m, 2H), 5.07-5.02 (m, 1H), 4.92 (dd, J = 10.8, 2.7 Hz, 1H), 4.62 (d, J = 9.0 Hz, 1H), 4.15 (d, J = 2.7 Hz, 1H), 3.93-3.81 (m, 7H), 3.76-3.71 (m, 1H), 3.24-3.14 (m, 3H), 2.90 (s, 3H). |

Step 3: Synthesis of (2R,3R,4R,5R,6S)-4-(4-(3,5-difluoro-4-(4-hydroxypiperidin-1-yl)phenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol:

1-(2,6-Difluoro-4-(1-((4aR,6S,7R,8R,8aR)-7-hydroxy-6-(1-(2-methylbenzo[d]thiazol-6-yl)-1H-1,2,4-triazol-5-yl)-2-phenylhexahydropyrano[3,2-d][1,3]dioxin-8-yl)-1H-1,2,3-triazol-4-yl)phenyl)piperidin-4-ol (15 mg, 0.021 mmol) was suspended in aq. 80% AcOH (5 mL) and the mixture was heated at 90° C. for 2 h. The solvent was removed under reduced pressure, and the crude residue was purified by HPLC (Method A) to afford (2R,3R,4R,5R,6S)-4-(4-(3,5-difluoro-4-(4-hydroxypiperidin-1-yl)phenyl)-1H-1,2,3-triazol-1-yl)-2-(hydroxymethyl)-6-(1-(2-methylbenzo[d]thiazol-6-yl)-1H-1,2,4-triazol-5-yl)tetrahydro-2H-pyran-3,5-diol (Example 241) (3.8 mg, 28%). LC-MS, [M+H]⁺=641.2, (Method A: $t_R$=1.541). 1H NMR (400 MHz, METHANOL-d4) δ 8.51 (s, 1H), 8.42 (d, J=2.0 Hz, 1H), 8.25 (s, 1H), 8.15-8.07 (m, 1H), 7.84 (dd, J=8.6, 2.2 Hz, 1H), 7.40-7.27 (m, 2H), 5.04 (dd, J=10.8, 9.3 Hz, 1H), 4.92 (dd, J=10.8, 2.9 Hz, 1H), 4.62 (d, J=9.3 Hz, 1H), 4.15 (d, J=2.9 Hz, 1H), 3.95-3.77 (m, 3H), 3.74 (dd, J=11.4, 4.0 Hz, 1H), 3.52-3.44 (m, 2H), 3.01-2.88 (m, 5H), 2.04-2.01 (m, 2H), 1.80-1.69 (m, 2H). hGal3 IC₅₀=0.13 uM.

General Synthetic Scheme for 1,2,4-triazole Compounds:

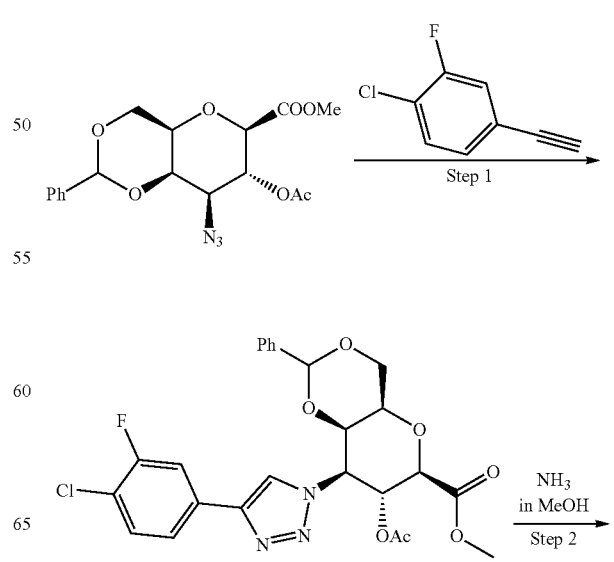

EXAMPLE 244

(2S,3R,4R,5R,6R)-4-(4-(4-chloro-3-fluorophenyl)-1H-1,2,3-triazol-1-yl)-2-(1-(3-chlorophenyl)-3-methyl-1H-1,2,4-triazol-5-yl)-6-(hydroxymethyl)tetrahydro-2H-pyran-3,5-diol

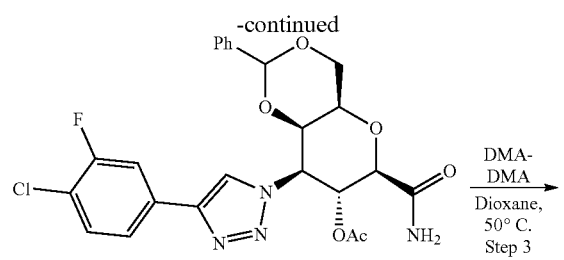

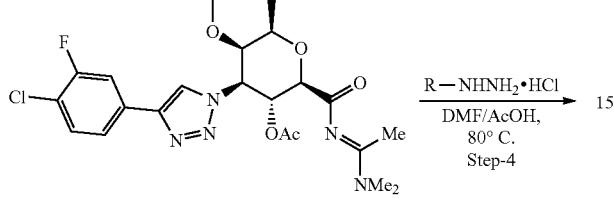

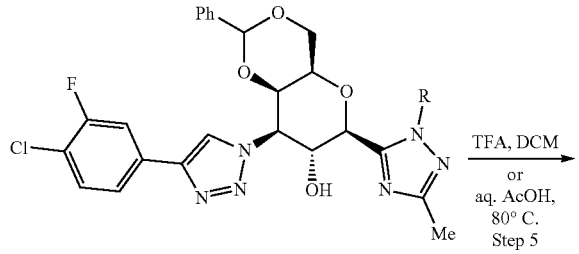

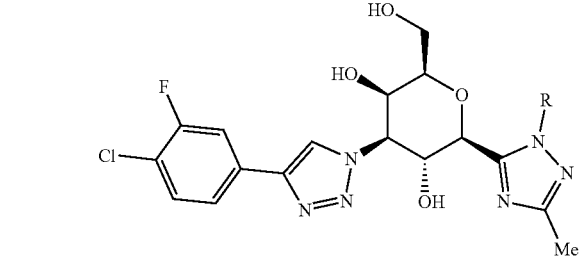

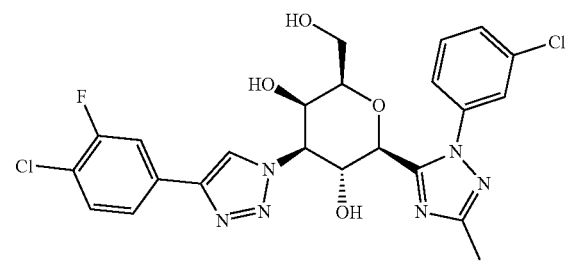 [SMILES: Cc1nc([C@@H]2O[C@H](CO)[C@H](O)[C@H](n3cc(-c4ccc(Cl)c(F)c4)nn3)[C@H]2O)n(-c2cccc(Cl)c2)n1]

Prepared in similar fashion as similar to Example 57. LC-MS, [M+H]⁺=537.1, (Method A: t$_R$=1.542). 1H NMR (400 MHz, METHANOL-d4) d 8.58 (s, 1H), 7.85-7.74 (m, 2H), 7.74-7.65 (m, 2H), 7.65-7.50 (m, 3H), 5.03-4.92 (m, 2H), 4.61-4.55 (m, 1H), 4.17 (d, J=1.7 Hz, 1H), 3.92 (dd, J=6.8, 4.4 Hz, 1H), 3.87-3.79 (m, 1H), 3.78-3.68 (m, 1H), 2.47 (s, 3H). hGal3 IC50: 0.080 uM;

The Examples in the table below were prepared in an analogous fashion to Example 244, to substituting (3-chlorophenyl)hydrazine hydrochloride with the appropriate aryl hydrazines in the synthetic sequence.

| Ex | hGal3 IC50, uM | Structure | LCMS t$_R$ (min) | M + H | Method | 1H NMR |
|---|---|---|---|---|---|---|
| 245 | 0.04 | 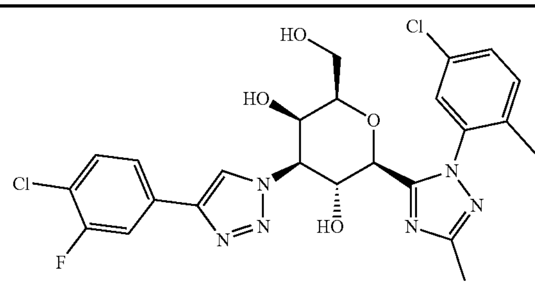 | 2.301 | 550.2 | C | 1H NMR (400 MHz, METHANOL-d4) δ 8.55 (s, 1H), 7.76-7.79 (m, 1H), 7.69 (dd, J = 8.3, 1.3 Hz, 1H), 7.60-7.50 (m, 3H), 7.49-7.43 (m, 1H), 4.91-4.87 (m, 2H), 4.34-4.29 (m, 1H), 4.12 (s, 1H), 3.80-3.67 (m, 3H), 2.48 (s, 3H), 2.13 (s, 3H). |
| 246 | 0.03 | 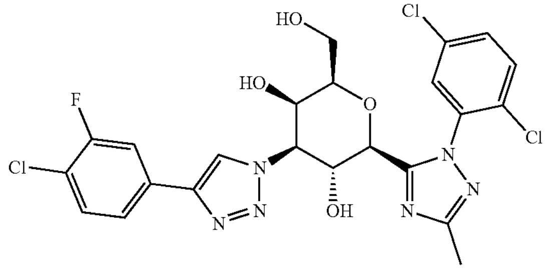 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2Cl)n1] | 1.584 | 571 | A | 1H NMR (400 MHz, METHANOL-d4) δ 8.54 (s, 1H), 7.77 (dd, J = 10.4, 1.8 Hz, 1H), 7.74-7.62 (m, 4H), 7.61-7.52 (m, 1H), 4.91-4.87 (m, 2H), 4.40 (d, J = 8.8 Hz, 1H), 4.13 (d, J = 1.7 Hz, 1H), 3.85-3.75 (m, 1H), 3.75-3.62 (m, 2H), 2.48 (s, 3H). |

-continued

| Ex | hGal3 IC50, uM | Structure | LCMS $t_R$ (min) | M + H | Method | 1H NMR |
|---|---|---|---|---|---|---|
| 247 | 0.45 | 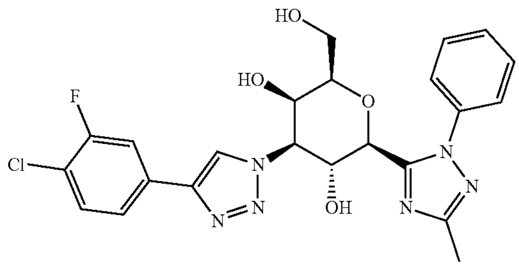 [SMILES: Cc1nc([C@@H]2O[C@H](CO)[C@H](O)[C@H](n3cc(-c4ccc(Cl)c(F)c4)nn3)[C@H]2O)n(-c2ccccc2)n1] | 1.377 | 501.1 | A | 1H NMR (400 MHz, METHANOL-d4) δ 8.58 (s, 1H), 7.78 (dd, J = 10.5, 2.0 Hz, 1H), 7.75-7.65 (m, 3H), 7.65-7.51 (m, 4H), 5.04-4.90 (m, 2H), 4.56 (d, J = 8.8 Hz, 1H), 4.16 (d, J = 2.0 Hz, 1H), 3.92-3.85 (m, 1H), 3.85-3.78 (m, 1H), 3.78-3.68 (m, 1H), 2.48 (s, 3H). |
| 248 | 0.03 | 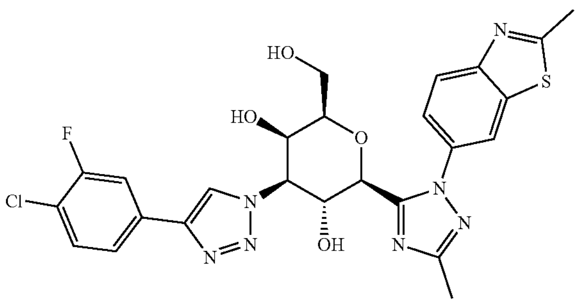 [SMILES: Cc1nc([C@@H]2O[C@H](CO)[C@H](O)[C@H](n3cc(-c4ccc(Cl)c(F)c4)nn3)[C@H]2O)n(-c2ccc3nc(C)sc3c2)n1] | 1.427 | 573.1 | A | 1H NMR (400 MHz, METHANOL-d4) δ 8.56 (s, 1H), 8.38 (d, J = 2.0 Hz, 1H), 8.09 (d, J = 8.8 Hz, 1H), 7.79 (dd, J = 4.0, 2.1 Hz, 1H), 7.86-7.73 (m, 1H), 7.69 (dd, J = 8.3, 1.2 Hz, 1H), 7.59-7.57 (m,, 1H), 5.03-4.90 (m, 2H), 4.58 (d, J = 8.8 Hz, 1H), 4.15 (d, J = 2.4 Hz, 1H), 3.94-3.78 (m, 2H), 3.78-3.69 (m, 1H), 2.91 (s,3H), 2.49 (s, 3H). |
| 249 | 0.09 | 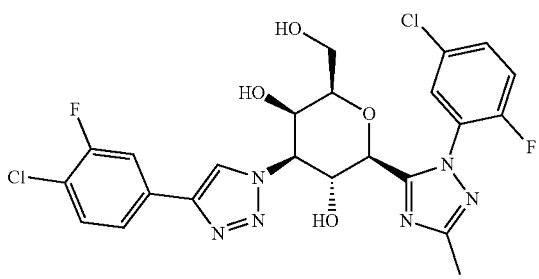 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2F)n1] | 1.583 | 555.1 | A | 1H NMR (400 MHz, METHANOL-d4) δ 8.54 (s, 1H), 7.82-7.72 (m, 2H), 7.71-7.62 (m, 2H), 7.60-7.53 (m, 1H), 7.45 (t, J = 9.2 Hz, 1H), 4.95-4.88 (m, 1H), 4.83 (br. s., 1H), 4.49 (d, J = 9.3 Hz, 1H), 4.15 (d, J = 2.4 Hz, 1H), 3.87-3.81 (m, 1H), 3.76-3.64 (m, 2H), 2.47 (s, 3H). |
| 250 | 0.01 | 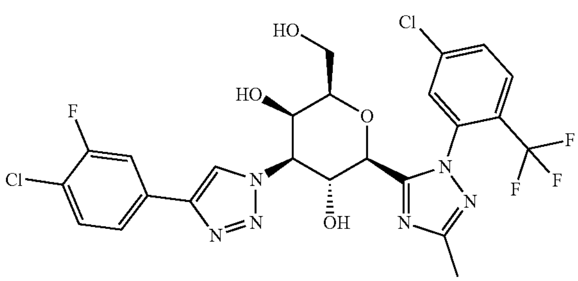 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2C(F)(F)F)n1] | 1.683 | 605.1 | A | 1H NMR (400 MHz, METHANOL-d4) δ 8.55 (s, 1H), 7.98 (d, J = 8.6 Hz, 1H), 7.92 -7.85 (m, 1H), 7.76 (d, J = 2.0 Hz, 1H), 7.79 (d, J = 1.7 Hz, 1H), 7.69 (dt, J = 8.3, 1.0 Hz, 1H), 7.62-7.53 (m, 1H), 4.93-4.86 (m, 2H), 4.37 (d, J = 8.8 Hz, 1H), 4.17-4.09 (m, 1H), 3.77-3.71 (m, 1H), 3.71-3.61 (m, 2H), 2.47 (s, 3H). |
| 251 | 0.08 | 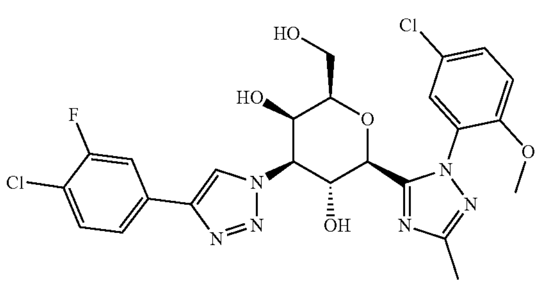 [SMILES: COc1ccc(Cl)cc1-n1nc(C)nc1[C@@H]1O[C@H](CO)[C@H](O)[C@H](n2cc(-c3ccc(Cl)c(F)c3)nn2)[C@H]1O] | 1.555 | 567.1 | A | 1H NMR (400 MHz, METHANOL-d4) δ 8.59-8.50 (m, 1H), 7.77 (dd, J = 10.3, 1.8 Hz, 1H), 7.69 (dd, J = 8.3, 1.3 Hz, 1H), 7.62-7.53 (m, 2H), 7.50 (d, J = 2.5 Hz, 1H), 7.27 (d, J = 9.0 Hz, 1H), 4.89 (d, J = 3.0 Hz, 1H), 4.81-4.74 (m, 1H), 4.37 (d, J = 9.5 Hz, 1H), 4.13 (d, J = 2.5 Hz, 1H), 3.88 (s, 3H), 3.83-3.76 (m, 2H), 3.76-3.66 (m,2H), 2.46 (s, 3H). |

-continued

| Ex | hGal3 IC50, uM | Structure | LCMS $t_R$ (min) | M + H | Method | 1H NMR |
|---|---|---|---|---|---|---|
| 252 | 0.11 | 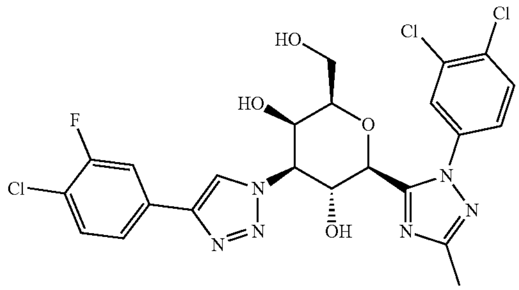 [SMILES: Cc1nc([C@@H]2O[C@H](CO)[C@H](O)[C@H](n3cc(-c4ccc(Cl)c(F)c4)nn3)[C@H]2O)n(-c2ccc(Cl)c(Cl)c2)n1] | 1.705 | 571.1 | A | 1H NMR (400 MHz, METHANOL-d4) δ 8.55 (s, 1H), 7.94 (d, J = 2.2 Hz, 1H), 7.76 (d, J = 8.6 Hz, 2H), 7.73-7.62 (m, 2H), 7.60-7.47 (m, 1H), 5.00-4.90 (m, 2H), 4.57 (br. s., 1H), 4.15 (s, 1H), 3.92 (dd, J = 7.3, 4.9 Hz, 1H), 3.86-3.75 (m, 1H), 3.75-3.65 (m, 1H), 2.45 (s, 3H). |
| 253 | 0.08 | 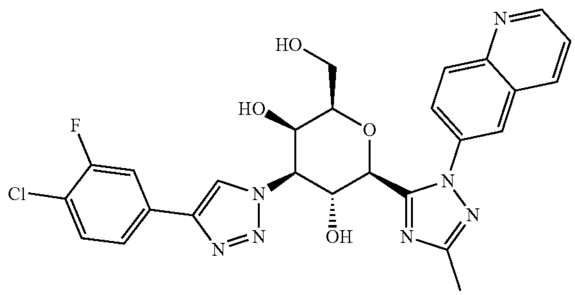 [SMILES: Cc1nc([C@@H]2O[C@H](CO)[C@H](O)[C@H](n3cc(-c4ccc(Cl)c(F)c4)nn3)[C@H]2O)n(-c2ccc3ncccc3c2)n1] | 1.345 | 552.2 | A | 1H NMR (400 MHz, METHANOL-d4) δ 8.89 (dd, J = 4.3, 1.6 Hz, 1H), 8.56-8.39 (m, 2H), 8.36 (d, J = 2.2 Hz, 1H), 8.15 (d, J = 9.0 Hz, 1H), 7.98 (dd, J = 9.0, 2.4 Hz, 1H), 7.66 (dd, J = 10.4, 1.8 Hz, 1H), 7.62-7.51 (m, 2H), 7.50-7.40 (m, 1H), 5.01-4.88 (m, 1H), 4.83 (dd, J = 10.8, 2.9 Hz, 1H), 4.51 (d, J = 9.3 Hz, 1H), 4.04 (d, J = 2.7 Hz, 1H), 3.90-3.71 (m, 2H), 3.70-3.55 (m, 1H), 2.40 (s, 3H). |
| 254 | 0.11 | 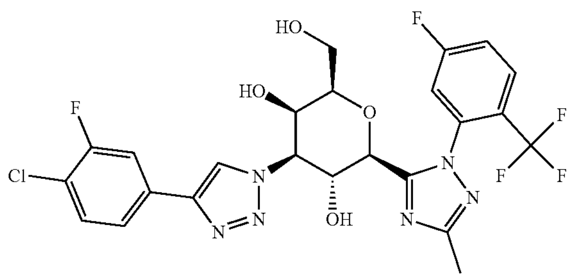 [SMILES: Cc1nc([C@@H]2O[C@H](CO)[C@H](O)[C@H](n3cc(-c4ccc(Cl)c(F)c4)nn3)[C@H]2O)n(-c2cc(F)ccc2C(F)(F)F)n1] | 1.598 | 587.2 | A | 1H NMR (400 MHz, METHANOL-d4) δ 8.56 (s, 1H), 8.04 (dd, J = 8.9, 5.5 Hz, 1H), 7.78 (dd, J = 10.4, 1.8 Hz, 1H), 7.70 (dt, J = 8.3, 1.0 Hz, 1H), 7.66-7.47 (m, 3H), 4.38 (d, J = 9.0 Hz, 1H), 4.13 (s, 1H), 3.78-3.71 (m, 1H), 3.71-3.60 (m, 2H), 2.47 (s, 3H)(2 Protons burried under solvent). |
| 255 | 0.07 | 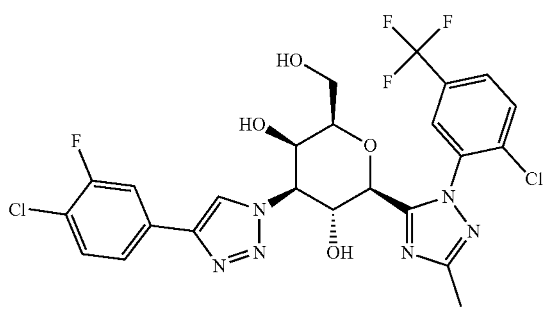 [SMILES: Cc1nc([C@@H]2O[C@H](CO)[C@H](O)[C@H](n3cc(-c4ccc(Cl)c(F)c4)nn3)[C@H]2O)n(-c2cc(C(F)(F)F)ccc2Cl)n1] | 1.706 | 605.2 | A | 1H NMR (400 MHz, METHANOL-d4) δ 8.51 (s, 1H), 8.08-7.86 (m, 3H), 7.76 (dd, J = 10.4, 1.8 Hz, 1H), 7.68 (dd, J = 8.3, 1.5 Hz, 1H), 7.57 (t, J = 7.9 Hz, 1H), 4.89 (d, J = 2.9 Hz, 1H), 4.80 (br. s., 1H), 4.42 (d, J = 9.0 Hz, 1H), 4.12 (d, J= 2.0 Hz, 1H), 3.77 (t, J = 6.1 Hz, 1H), 3.66 (d, J = 5.4 Hz, 2H), 2.49 (s, 3H). |
| 256 | 0.08 | 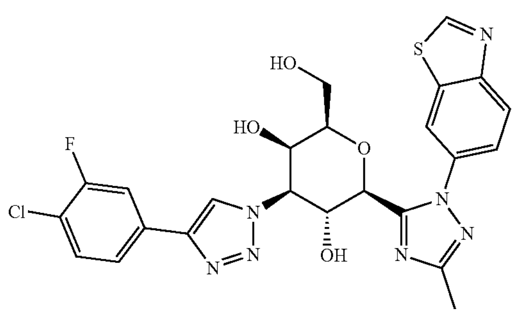 [SMILES: Cc1nc([C@@H]2O[C@H](CO)[C@H](O)[C@H](n3cc(-c4ccc(Cl)c(F)c4)nn3)[C@H]2O)n(-c2ccc3ncsc3c2)n1] | 1.348 | 558.1 | A | 1H NMR (400 MHz, METHANOL-d4) δ 9.43 (s, 1H), 8.57 (s, 1H), 8.55 (d, J = 1.7 Hz, 1H), 8.29 (d, J = 8.6 Hz, 1H), 7.89 (dd, J = 8.7, 2.1 Hz, 1H), 7.78 (dd, J = 10.3, 2.0 Hz, 1H), 7.73-7.67 (m, 1H), 7.61-7.53 (m, 1H), 5.03-4.94 (m,2H), 4.58-4.55 (m, 1H), 4.15 (d, J = 2.9 Hz, 1H), 3.94-3.71 (m, 3H), 2.50 (s, 3H). |

189

General Scheme for the Preparation of 1,2,4-triazole Compounds

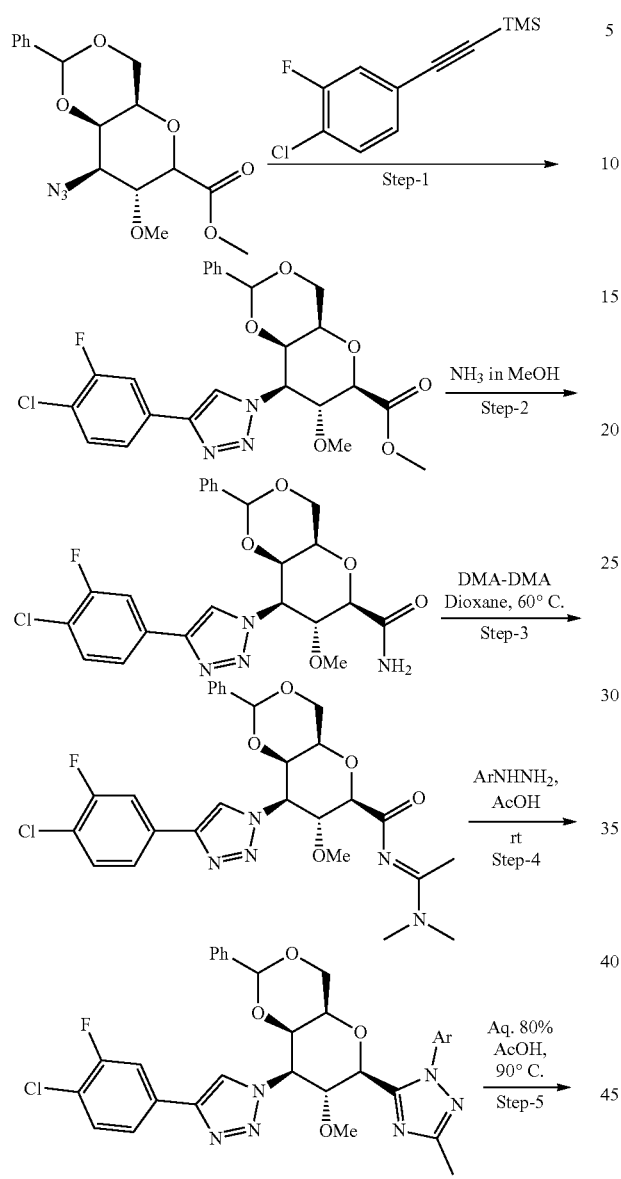

190

-continued

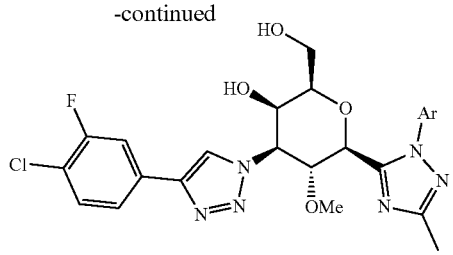

EXAMPLE 257

(2R,3R,4S,5R,6S)-4-(4-(4-chloro-3-fluorophenyl)-1H-1,2,3-triazol-1-yl)-6-(1-(2,5-dichlorophenyl)-3-methyl-1H-1,2,4-triazol-5-yl)-2-(hydroxymethyl)-5-methoxytetrahydro-2H-pyran-3-ol

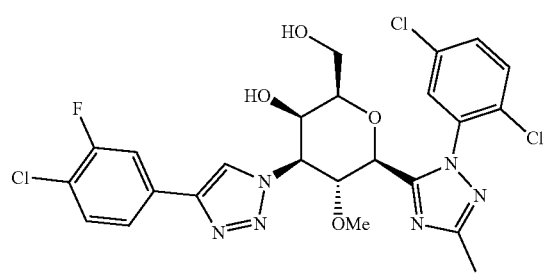 [SMILES: CO[C@@H]1[C@@H](n2cc(-c3ccc(Cl)c(F)c3)nn2)[C@@H](O)[C@@H](CO)O[C@H]1c1nc(C)nn1-c1cc(Cl)ccc1Cl]

Prepared in similar fashion as similar to Example 244. LC-MS, [M+H]$^+$=585.2, (Method A: $t_R$=1.873). 1H NMR (400 MHz, METHANOL-d4) d 8.71 (s, 1H), 7.80 (dd, J=10.4, 1.8 Hz, 1H), 7.76-7.63 (m, 4H), 7.57 (t, J=7.9 Hz, 1H), 4.96 (dd, J=10.4, 2.8 Hz, 1H), 4.57 (s, 1H), 4.40 (br. s., 1H), 4.10 (d, J=2.7 Hz, 1H), 3.79-3.64 (m, 3H), 2.96 (s, 3H), 2.49 (s, 3H). hGal3 IC$_{50}$: 0.05 uM.

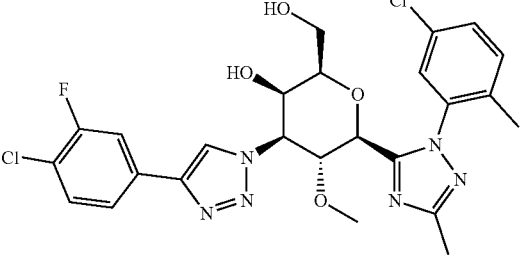

| Ex | hGal3 IC50, uM | Structure | LCMS $t_R$ (min) | M + H | Method | 1H NMR |
|---|---|---|---|---|---|---|
| 258 | 0.06 | 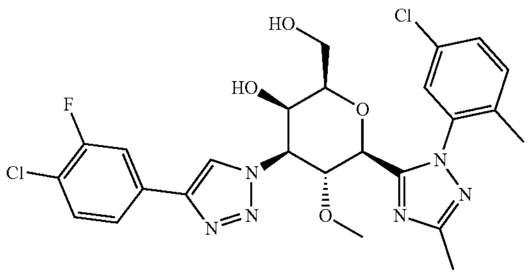 [SMILES: CO[C@@H]1[C@@H](n2cc(-c3ccc(Cl)c(F)c3)nn2)[C@@H](O)[C@@H](CO)O[C@H]1c1nc(C)nn1-c1cc(Cl)ccc1C] | 1.888 | 565.2 | A | 1H NMR: 1H NMR (400 MHz, METHANOL-d4) δ 8.79-8.70 (m, 1H), 7.80 (dd, J = 10.4, 1.8 Hz, 1H), 7.72 (dt, J = 8.4, 0.9 Hz, 1H), 7.62-7.52 (m, 2H), 7.52-7.41 (m, 2H), 4.95 (dd, J = 10.6, 2.8 Hz, 1H), 4.66 (t, J = 9.8 Hz, 1H), 4.30 (d, J = 9.3 Hz, 1H), 4.09 (d, J = 2.9 Hz, 1H), 3.78-3.63 (m, 3H), 2.96 (s, 3H), 2.49 (s, 3H), 2.12 (s, 3H). |

-continued

| Ex | hGal3 IC50, uM | Structure | LCMS $t_R$ (min) | M + H | Method | 1H NMR |
|---|---|---|---|---|---|---|
| 259 | | (structure shown) | 1.618 | 574.1 | A | 1H NMR (400 MHz, METHANOL-d4) δ 9.48-9.40 (m, 1H), 8.73 (s, 1H), 8.53 (d, J = 2.0 Hz, 1H), 8.29 (d, J = 8.6 Hz, 1H), 7.87 (dd, J = 8.7, 2.1 Hz, 1H), 7.80 (dd, J = 10.3, 2.0 Hz, 1H), 7.75-7.67 (m, 1H), 7.62-7.51 (m, 1H), 5.00 (dd, J = 10.5, 2.9 Hz, 1H), 4.79-4.69 (m, 1H), 4.60 (d, J = 9.3 Hz, 1H), 4.12 (d, J = 2.7 Hz, 1H), 3.93-3.82 (m, 2H), 3.78-3.67 (m, 1H), 2.97 (s, 3H), 2.51 (s, 3H). |

General Synthetic Scheme for 1,2,4-triazole Compounds:

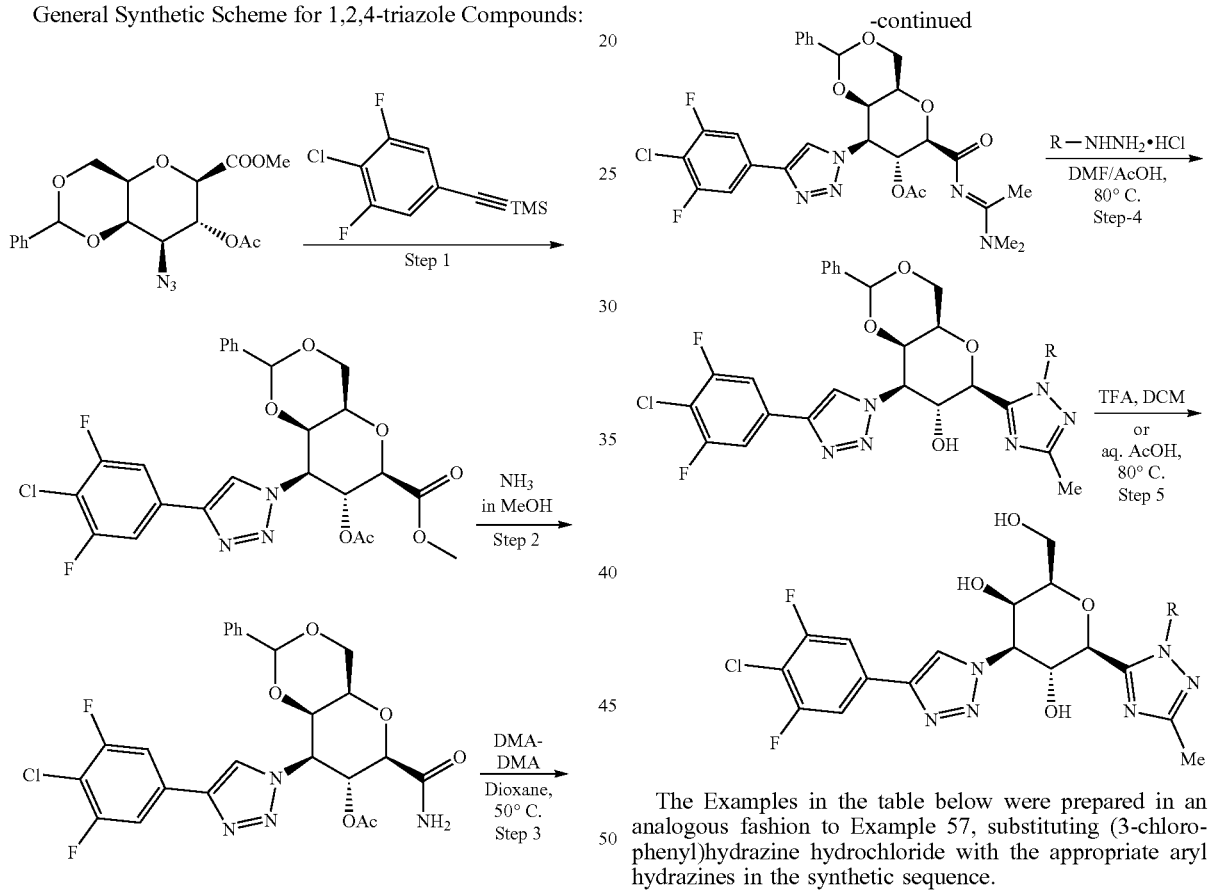

The Examples in the table below were prepared in an analogous fashion to Example 57, substituting (3-chlorophenyl)hydrazine hydrochloride with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 260 | 0.05 | (structure shown) | 1.855 | 589.1 | A | 1H NMR (400 MHz, METHANOL-d4) δ 8.60 (s, 1H), 7.79-7.59 (m, 5H), 4.92-4.88 (m, 2H), 4.39 (d, J = 8.8 Hz, 1H), 4.13 (d, J = 2.0 Hz, 1H), 3.79 (t, J = 6.2 Hz, 1H), 3.75-3.63 (m, 2H), 2.48 (s, 3H). |

-continued
| Ex | hGal3 IC50, uM | Structure | LCMS $t_R$ (min) | M + H | Method | 1H NMR |
|---|---|---|---|---|---|---|
| 261 | 0.02 | 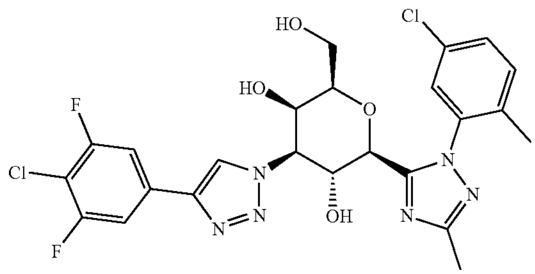 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2C)n1] | 1.856 | 569.2 | A | 1H NMR (400 MHz, METHANOL-d4) δ 8.62 (s, 1H), 7.77-7.62 (m, 2H), 7.59-7.49 (m, 2H), 7.49-7.41 (m, 1H), 4.88 (m, 2H), 4.36-4.26 (m, 1H), 4.12 (s, 1H), 3.83-3.63 (m, 3H), 2.48 (s, 3H), 2.13 (s, 3H). |
General Synthetic Scheme 2 for 1,2,4-triazole Compounds:
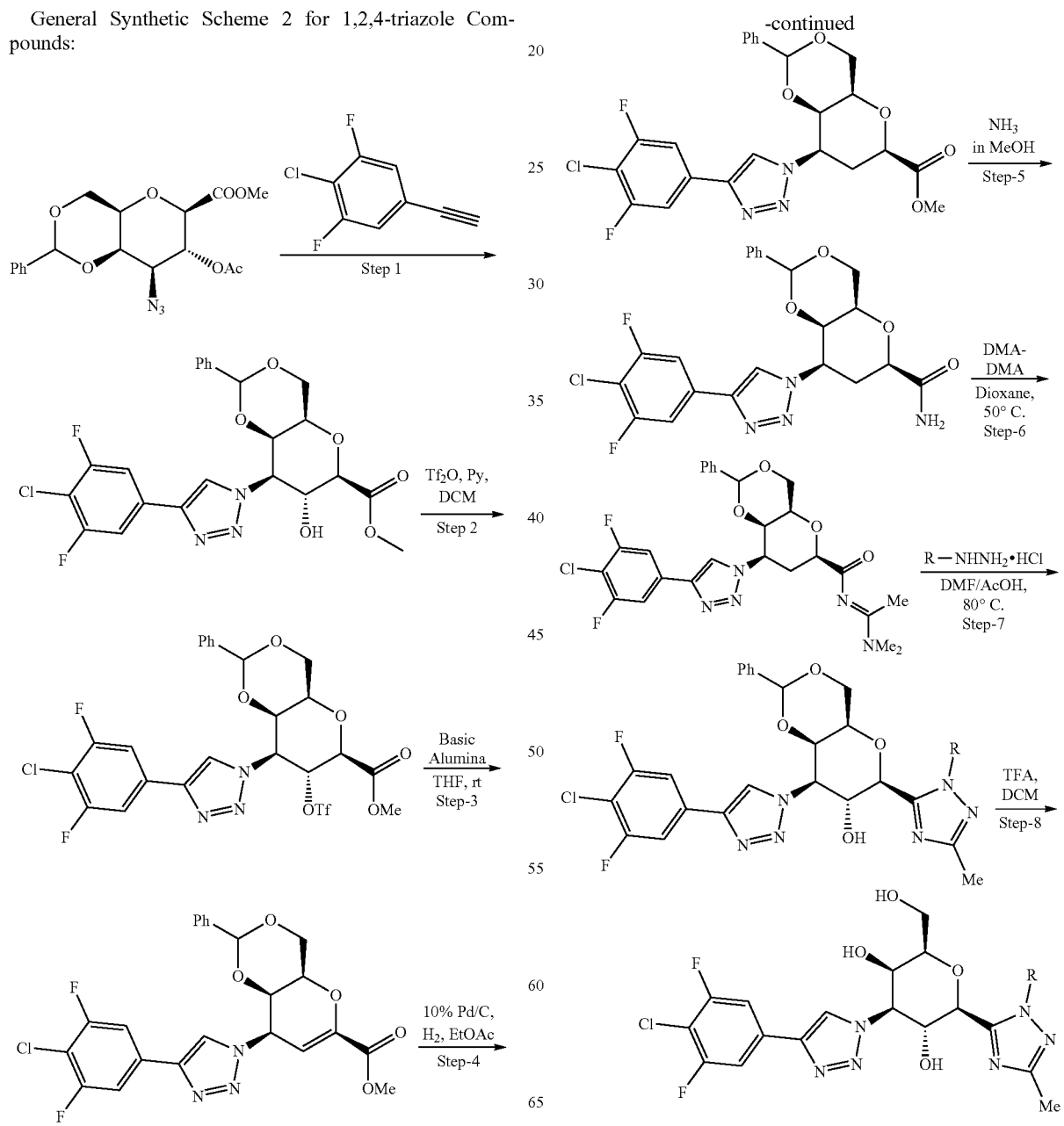

The Examples in the table below were prepared in an analogous similar fashion to Example 173 and Example 183, substituting (3-chlorophenyl)hydrazine hydrochloride with the appropriate aryl hydrazines in the synthetic sequence.

| Ex | hGal3 IC50, uM | Structure | LCMS $t_R$ (min) | M + H | Method | 1H NMR |
|---|---|---|---|---|---|---|
| 262 | 0.10 | 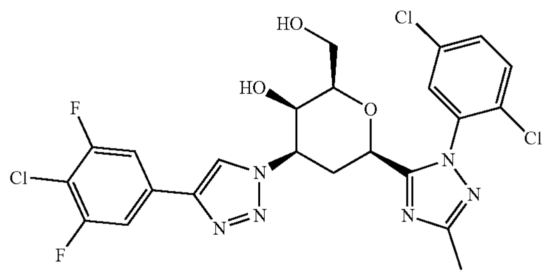 [SMILES: Cc1nc([C@H]2C[C@@H](n3cc(-c4cc(F)c(Cl)c(F)c4)nn3)[C@@H](O)[C@@H](CO)O2)n(-c2cc(Cl)ccc2Cl)n1] | 2.033 | 573.1 | A | 1H NMR (400 MHz, METHANOL-d4) δ 8.56 (s, 1H), 7.74 (s, 1H), 7.71-7.51 (m, 4H), 5.09 (d, J = 13.0 Hz, 1H), 4.07 (s, 1H), 3.67-3.53 (m, 2H), 3.52-3.45 (m, 2H), 3.01-2.88 (m, 1H), 2.45 (s, 1H), 2.45-2.30 (m, 3H). |
| 263 | 0.12 | 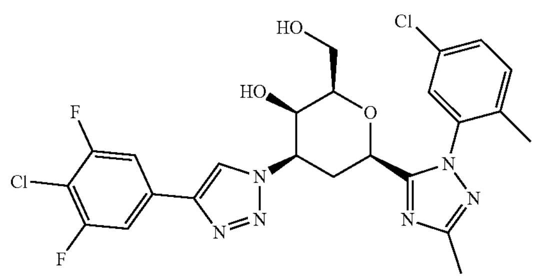 [SMILES: Cc1nc([C@H]2C[C@@H](n3cc(-c4cc(F)c(Cl)c(F)c4)nn3)[C@@H](O)[C@@H](CO)O2)n(-c2cc(Cl)ccc2C)n1] | 1.879 | 553.2 | A | 1H NMR (400 MHz, METHANOL-d4) δ 8.57 (s, 1H), 7.72-7.59 (m, 2H), 7.57-7.46 (m, 2H) 7.46-7.39 (m, 1H), 5.06 (dt, J = 12.7, 3.5 Hz, 1H), 4.72 (dd, J = 11.5, 2.0 Hz, 1H), 4.08 (s, 1H), 3.79 (s, 1H), 3.68-3.52 (m, 2H), 3.03 (q, J = 12.6 Hz, 1H), 2.44 (s, 3H), 2.32 (d, J = 13.7 Hz, 1H), 2.09 (s, 3H). |
| 264 | 0.08 | 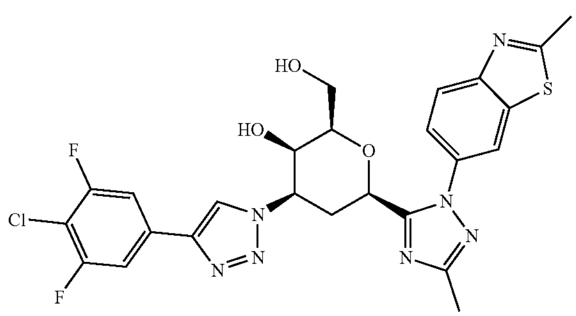 [SMILES: Cc1nc([C@H]2C[C@@H](n3cc(-c4cc(F)c(Cl)c(F)c4)nn3)[C@@H](O)[C@@H](CO)O2)n(-c2ccc3nc(C)sc3c2)n1] | 1.692 | 575.2 | B | 1H NMR (400 MHz, METHANOL-d4) δ 8.61-8.54 (m, 1H), 8.44 (s, 1H), 8.08-8.00 (m, 1H), 7.81 (d, J = 9.3 Hz, 1H), 7.66 (d, J = 8.6 Hz, 2H), 5.08 (d, J = 13.2 Hz, 1H), 4.09 (br. s., 1H), 3.87-3.75 (m, 2H), 3.74-3.67 (m, 1H), 3.35 (s, 1H), 3.24-3.15 (m, 1H), 2.94-2.83 (m, 3H), 2.46 (s, 3H), 2.30 (d, J = 9.3 Hz, 1H). |
| 265 | 0.03 | 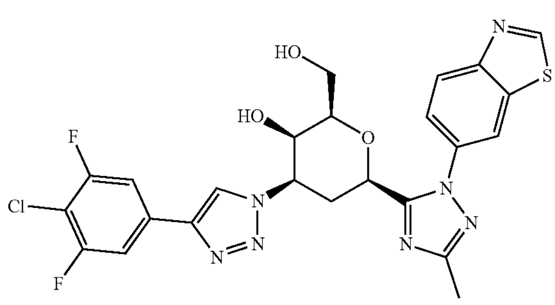 [SMILES: Cc1nc([C@H]2C[C@@H](n3cc(-c4cc(F)c(Cl)c(F)c4)nn3)[C@@H](O)[C@@H](CO)O2)n(-c2ccc3ncsc3c2)n1] | 1.782 | 560.2 | A | 1H NMR (400 MHz, METHANOL-d4) δ 9.43-9.36 (m, 1H), 8.66-8.54 (m, 2H), 8.25 (d, J = 8.6 Hz, 1H) 7.93-7.86 (m, 1H), 7.66 (d, J = 13.0 Hz, 1H), 4.09 (s, 1H), 3.88-3.76 (m, 2H), 3.71 (d, J = 6.8 Hz, 1H), 3.27-3.15 (m, 2H), 2.47 (s, 3H), 2.31 (d, J = 13.2 Hz, H). |

General Synthetic Scheme C3-substitution on 1-Aryl-1,2,4-Triazole

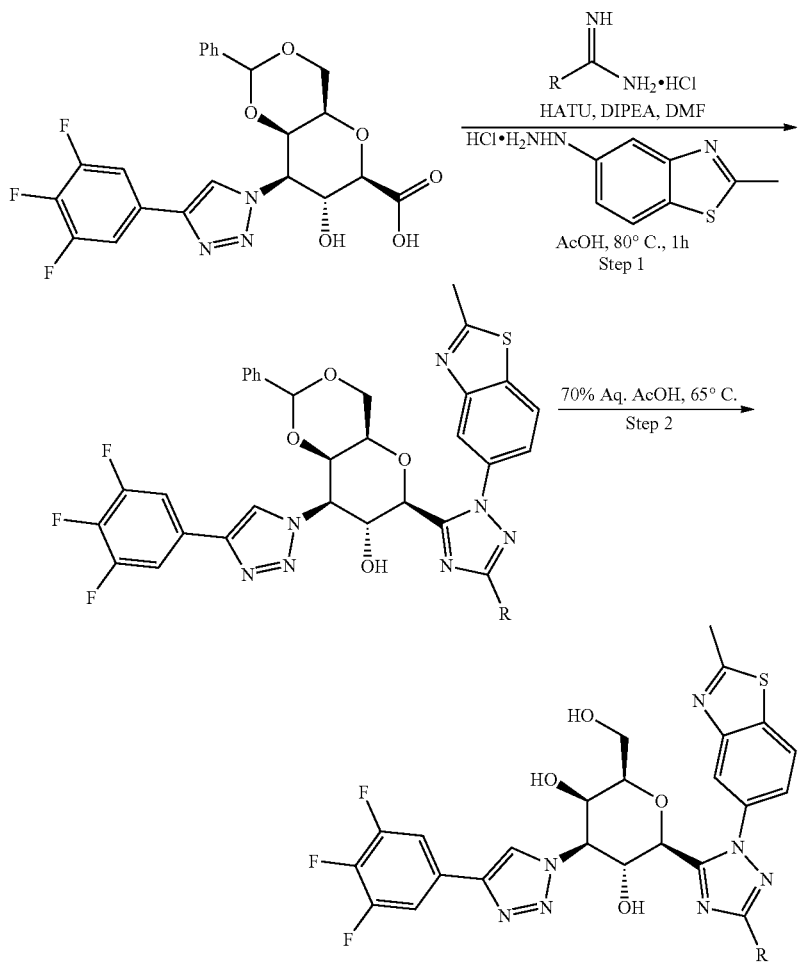

EXAMPLE 266

(2S,3R,4R,5R,6R)-2-(3-cyclopropyl-1-(2-methylbenzo[d]thiazol-6-yl)-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol

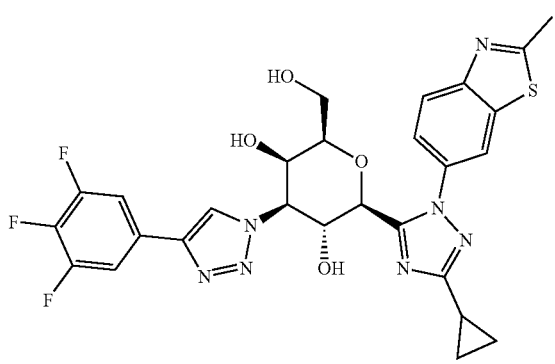 [SMILES: Cc1nc2ccc(-n3nc(C4CC4)nc3[C@@H]3O[C@H](CO)[C@H](O)[C@H](n4cc(-c5cc(F)c(F)c(F)c5)nn4)[C@H]3O)cc2s1]

Step 1: Synthesis of (4aR,6S,7R,8R,8aR)-6-(3-cyclopropyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: To an ice cooled stirred solution of (4aR,6R,7R,8R,8aR)-7-hydroxy-2-phenyl-8-(4-(3,4,5-trifluorophenyl)-1H-1,2,3-triazol-1-yl) hexahydropyrano[3,2-d][1,3]dioxine-6-carboxylic acid (0.18 g, 0.377 mmol) in DMF (1.5 mL), DIPEA (0.263 mL, 1.508 mmol) was added sequentially cyclopropanecarboximidamide hydrochloride (0.068 g, 0.566 mmol) and HATU (0.158 g, 0.415 mmol). The reaction mixture was allowed to reach rt and was stirred for 2 h. Acetic acid (1.5 mL, 26.2 mmol) and 6-hydrazinyl-2-methylbenzo[d]thiazole hydrochloride (0.089 g, 0.415 mmol) were then added and the mixture was heated at 80° C. for 1 h. The reaction mixture was cooled to rt, concentrated under reduced pressure and purified via silica gel chromatography (0-10% MeOH in chloroform) to give (4aR,6S,7R,8R,8aR)-6-(3-cyclopropyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl) hexahydropyrano[3,2-d][1,3]dioxin-7-ol (0.12 g, 40%) as a yellow solid. LC-MS, [M+1]$^+$=688.5, (Method E: $t_R$=1.91 min). 1H NMR (400 MHz, DMSO-d6) δ 8.96 (s, 1H), 8.30 (d, J=2.0 Hz, 1H), 8.09 (d, J=8.5 Hz, 1H), 7.92-7.82 (m, 2H), 7.69 (br d, J=9.0 Hz, 1H), 7.37-7.33 (s, 5H), 5.58 (s, 2H), 5.31-5.17 (m, 1H), 4.96-4.84 (m, 1H), 4.72-4.61 (m, 1H), 4.52-4.40 (m, 1H), 4.29-4.08 (m, 2H), 4.05-3.94 (m, 1H), 2.14-2.01 (m, 1H), 1.33-1.18 (m, 2H), 1.03-0.89 (m, 2H).

Step 2: Synthesis of (2S,3R,4R,5R,6R)-2-(3-cyclopropyl-1-(2-methylbenzo[d]thiazol-6-yl)-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol: (4aR,6S,7R,8R,8aR)-6-(3-Cyclopropyl-1-(2-methylbenzo[d]thiazol-6-yl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.05 g, 0.073 mmol) was suspended in 70% aq. AcOH (10 mL) and the mixture was heated at 65° C. for 14 h. The reaction mixture was concentrated under reduced pressure and was purified by prep HPLC (Method P) to afford (2S,3R,4R,5R,6R)-2-(3-cyclopropyl-1-(2-methylbenzo[d]thiazol-6-yl)-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol (Example 264) (26.7 mg, 61%) as a white solid. LC-MS, [M+H]$^+$=600.2, (Method A & Method B: $t_R$=1.58 min). 1H NMR (400 MHz, METHANOL-d4) δ 8.58 (s, 1H), 8.35 (d, J=2.0 Hz, 1H), 8.08 (d, J=8.8 Hz, 1H), 7.80 (dd, J=8.7, 2.1 Hz, 1H), 7.67 (dd, J=8.8, 6.6 Hz, 2H), 4.99-4.91 (m, 2H), 4.56 (d, J=8.8 Hz, 1H), 4.13 (d, J=2.0 Hz, 1H), 3.92-3.78 (m, 2H), 3.77-3.68 (m, 1H), 2.98-2.86 (m, 3H), 2.22-2.10 (m, 1H), 1.31 (s, 1H), 1.17-0.97 (m, 4H).

The Examples in the table below were prepared in an analogous fashion to Example 266, substituting cyclopropanecarboximidamide.HCl with the appropriate alkylcarboximidamide.HCl in the synthetic sequence.

EXAMPLE 269

Preparation of 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-1-(2-methylbenzo[d]thiazol-6-yl)-1H-1,2,4-triazole-3-carboxylic acid

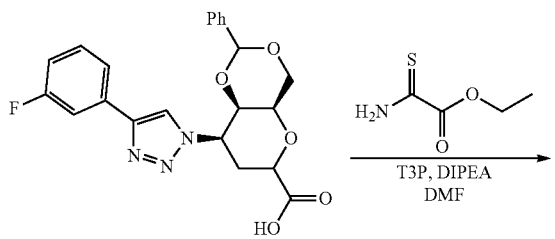

| Ex | hGal3 IC50, uM | Structure | LCMS $t_R$ (min) | M + H | Method | 1H NMR |
|---|---|---|---|---|---|---|
| 267 | 0.06 | 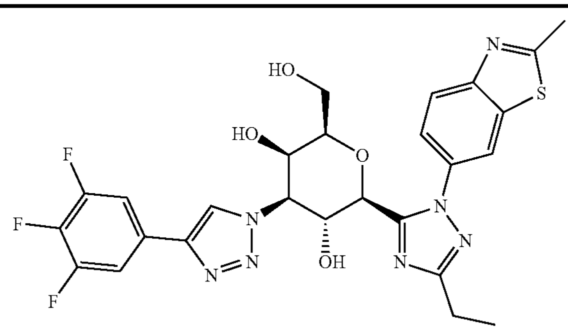 | 1.535 | 588.2 | A | 1H NMR (400 MHz, METHANOL-d4) δ 8.58 (s, 1H), 8.37 (d, J = 2.0 Hz, 1H), 8.09 (d, J = 8.6 Hz, 1H), 7.81 (dd, J = 8.6, 2.2 Hz, 1H), 7.67 (dd, J = 9.0, 6.6 Hz, 2H), 5.02-4.92 (m, 2H), 4.59 (d, J = 8.8 Hz, 1H), 4.14 (d, J = 2.2 Hz, 1H), 3.93-3.79 (m, 2H), 3.78-3.69 (m, 1H), 2.91 (s, 3H), 2.87 (q, J = 7.7 Hz, 2H), 1.29 (t, J = 7.6 Hz, 3H). |
| 268 | 0.12 | 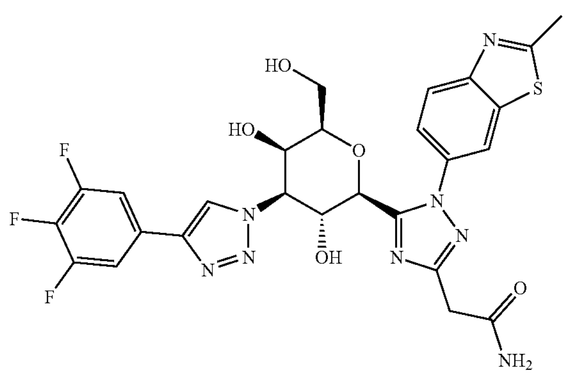 [SMILES: Cc1nc2ccc(-n3nc(CC(N)=O)nc3[C@@H]3O[C@H](CO)[C@H](O)[C@H](n4cc(-c5cc(F)c(F)c(F)c5)nn4)[C@H]3O)cc2s1] | 1.247 | 617.2 | A | 1H NMR (400 MHz, DMSO-d6) δ 8.89 (s, 1H), 8.48 (d, J = 2.0 Hz, 1H), 8.09 (d, J = 8.8 Hz, 1H), 7.89 (dd, J = 9.2, 6.7 Hz, 2H), 7.78 (dd, J = 8.6, 2.2 Hz, 1H), 7.53 (br. s., 1H), 7.10 (br. s., 1H), 5.40 (d, J = 6.1 Hz, 1H), 5.35 (d, J = 6.4 Hz, 1H), 5.00 (t, J = 5.9 Hz, 1H), 4.98-4.81 (m, 2H), 4.49 (d, J = 8.6 Hz, 1H), 3.96 (d, J = 4.2 Hz, 1H), 3.86 (dd, J = 7.8, 3.9 Hz, 1H), 3.71-3.56 (m, 3H), 3.54-3.46 (m, 1H), 2.87 (s, 3H). |

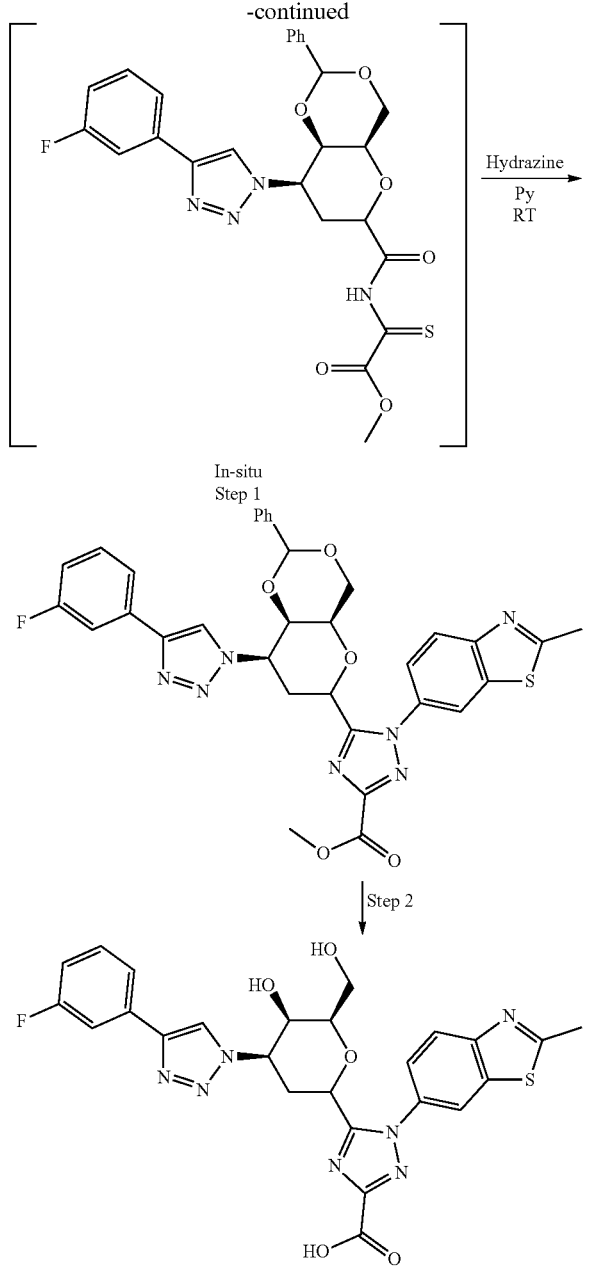

Step 1: Synthesis of ethyl 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylate: To a stirred solution of (4aR,6R,8R,8aR)-8-(4-(3-fluorophenyl)-1H-1,2,3-triazol-1-yl)-2-phenylhexahydropyrano[3,2-d][1,3]dioxine-6-carboxylic acid (0.05 g, 0.118 mmol) in DMF (1.5 mL) at 0° C. was added sequentially ethyl 2-amino-2-thioxoacetate (0.023 g, 0.176 mmol), 1-propanephosphonic anhydride (50% ethyl acetate) (0.212 mL, 0.353 mmol) and DIPEA (0.103 mL, 0.588 mmol) and the mixture was stirred at rt for 14 h. The reaction mixture was quenched with water. The solid was collected by filtration and was dried for 30 min. The obtained solid was suspended in pyridine (2 mL, 24.73 mmol) and 6-hydrazinyl-2-methylbenzo[d]thiazole.HCl (0.038 g, 0.176 mmol) was added and the mixture was stirred at rt for 14 h. The reaction mixture was diluted with EtOAc (2×30 mL), washed with water, brine solution, dried over sodium sulfate and concentrated. The residue was purified via silica gel chromatography (1-3% MeOH in chloroform) to give ethyl 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylate (0.01 g, 13%) as a solid. LC-MS, [M+1]+=668.5, (Method E: $t_R$=1.85 min).

Step 2: Synthesis of 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-1-(2-methylbenzo[d]thiazol-6-yl)-1H-1,2,4-triazole-3-carboxylic acid: ethyl 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylate (0.01 g, 0.015 mmol) was suspended in HCl (3 mL) and water (7 mL) and the mixture was heated at 60° C. for 14 h. The reaction mixture was concentrated and purified by HPLC (Method A) to give 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-1-(2-methylbenzo[d]thiazol-6-yl)-1H-1,2,4-acid (Example 269) (3 mg, 36%). LC-MS, [M+H]+=552.2, (Method A: $t_R$=0.87 min). 1H NMR (400 MHz, METHANOL-d4) 8.56 (s, 2H), 8.10 (d, J=8.8 Hz, 1H), 7.91 (dd, J=8.7, 1.8 Hz, 1H), 7.69 (d, J=7.8 Hz, 1H), 7.63 (d, J=9.5 Hz, 1H), 7.48 (td, J=8.0, 6.0 Hz, 1H), 7.12-7.07 (m, 1H), 5.11 (d, J=12.2 Hz, 1H), 4.91 (d, J=10.3 Hz, 2H), 4.12 (d=2.4 Hz, 1H), 3.90-3.77 (m, 2H), 3.75-3.64 (m, 1H), 3.34-3.36 (m, 1H), 2.91 (s, 3H), 2.38 (d, J=10.3 Hz, 1H). hGal3 IC50: 0.33 uM

EXAMPLE 270

Preparation of (2R,3R,4R,6R)-2-(hydroxymethyl)-6-(3-(2-hydroxypropan-2-yl)-1-(2-methylbenzo[d]thiazol-6-yl)-1H-1,2,4-triazol-5-yl)-4-(4-(3,4,5-trifluorophenyl)-1H-1,2,3-triazol-1-yl)tetrahydro-2H-pyran-3-ol

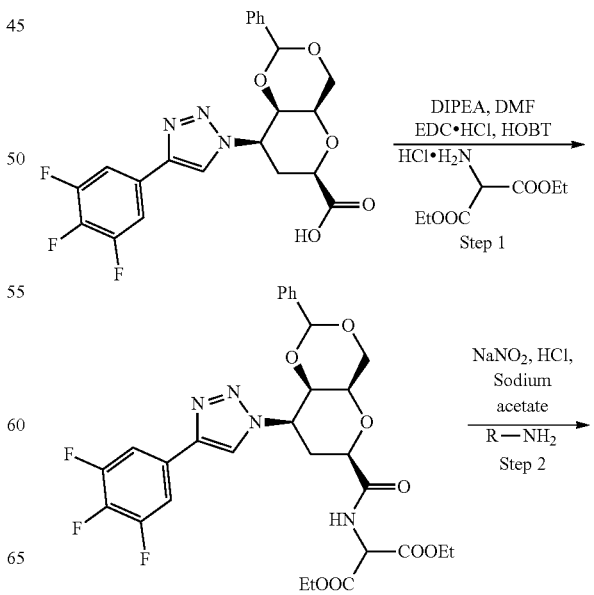

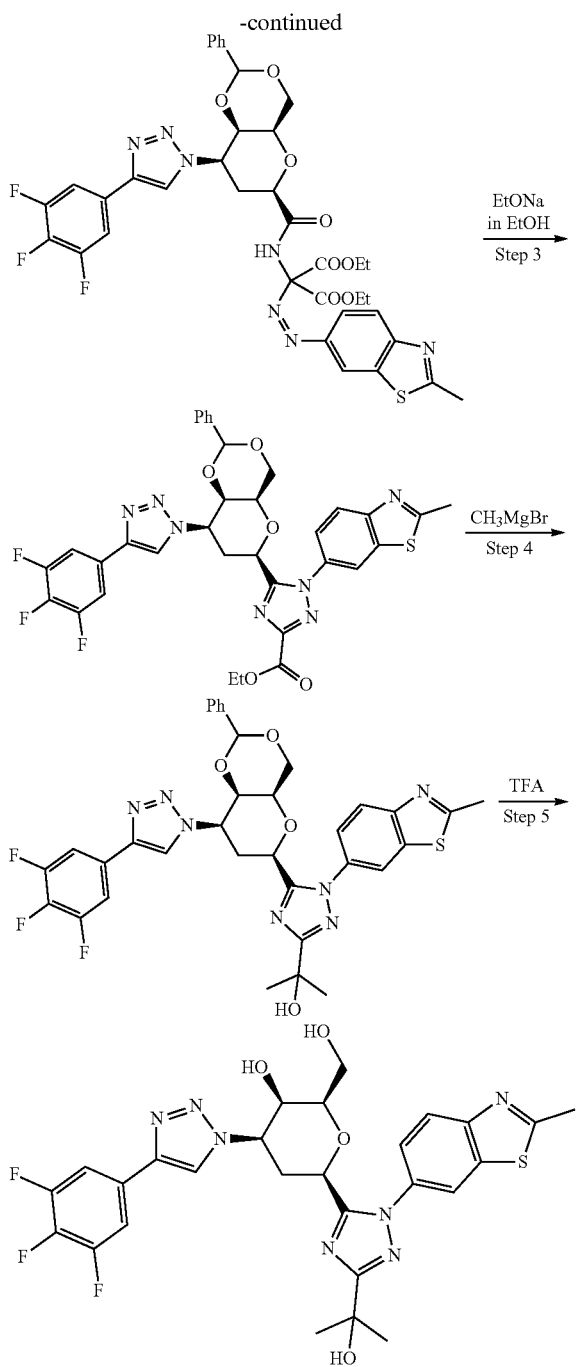

Step 1: Synthesis of diethyl 2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate: To a stirred solution of (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxylic acid (0.3 g, 0.650 mmol) in DMF (10 mL) was added 3-(((ethylimino)methylene)amino)-N,N-dimethylpropan-1-amine hydrochloride (0.150 g, 0.780 mmol), HOBt (0.119 g, 0.780 mmol), DIPEA (0.341 mL, 1.951 mmol), 2-aminomalonate.HCl (0.151 g, 0.715 mmol) and the mixture was stirred at rt for 14 h. The reaction mixture was quenched with ice cold water and stirred for 10 min. The solid obtained was filtered, dried and further purified via silica gel chromatography (1-10% MeOH in chloroform) to give diethyl 2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate (0.3 g, 75%) as a white solid. LC-MS, [M+1]$^+$=619.2, (Method C: $t_R$=3.33 min).

Step 2: Synthesis of diethyl 2-((E)-(2-methylbenzo[d]thiazol-6-yl)diazenyl)-2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate: To a stirred solution of 2-methylbenzo[d]thiazol-6-amine (0.033 g, 0.201 mmol) in acetic acid (0.2 mL) at 0° C. was added hydrochloric acid (37%, 0.06 mL) and a solution of sodium nitrite (0.015 g, 0.221 mmol) in H$_2$O (0.1 mL). The reaction mixture was allowed to stir for 30 min at 0° C. and the diazonium solution was slowly added to a precooled stirring solution of diethyl 2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate (0.099 g, 0.161 mmol), sodium acetate (0.049 g, 0.603 mmol) in ethanol (2 mL). Then the reaction mixture was allowed to reach rt and stirred at rt for 2 h. The formed precipitate was collected by filtration, washed with (EtOH/H$_2$O) 1/1 (v/v) and dried under vaccum to give diethyl 2-((E)-(2-methylbenzo[d]thiazol-6-yl)diazenyl)-2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate (0.09 g, 43%) as a brown solid, as such taken for next step without further purification. LC-MS, [M+1]$^+$=794.2, (Method E: $t_R$=2.08 min).

Step 3: Synthesis of ethyl 1-(2-methylbenzo[d]thiazol-6-yl)-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-1H-1,2,4-triazole-3-carboxylate: To a stirred solution of diethyl 2-((E)-(2-methylbenzo[d]thiazol-6-yl)diazenyl)-2-((4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxamido)malonate (0.08 g, 0.101 mmol) in ethanol (3 mL) was added sodium ethoxide in EtOH (21%) (0.01 mL, 0.027 mmol) in ethanol (1 mL) and the mixture was stirred at rt for 1 h. The reaction mixture was cooled to 0° C., acidified with amberlite IR 120(H$^+$ resin), filtered and filtrate was concentrated under reduced pressure to give pale pink solid. The residue was purified via chromatography on silica gel (0-10% MeOH in chloroform) to give ethyl 1-(2-methylbenzo[d]thiazol-6-yl)-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-1H-1,2,4-triazole-3-carboxylate (70 mg, 82%) as a brown solid. LC-MS, [M+1]$^+$=704.3, (Method E: $t_R$=2.0 min).

Step 4: Synthesis of 2-(1-(2-methylbenzo[d]thiazol-6-yl)-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-1H-1,2,4-triazol-3-yl)propan-2-ol: To a stirred solution of ethyl 1-(2-methylbenzo[d]thiazol-6-yl)-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-1H-1,2,4-triazole-3-carboxylate (0.05 g, 0.071 mmol) in THF (2 mL) at −78° C. was added methylmagnesium bromide (2M in THF, 0.178 mL, 0.355 mmol) and the mixture was stirred for 1 h. The reaction mixture was cooled to 0° C. and was quenched with ammonium chloride solution. The aqueous layer was extracted with ethyl acetate (2×15 mL). The combined organicl layers were washed with water, brine solution, dried over sodium sulfate and concentrated. The residue was purified purified via in silica gel chromatography (0-5% MeOH in chloroform) to give 2-(1-(2-methylbenzo[d]thiazol-6-yl)-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-1H-1,2,4-triazol-3-yl) propan-2-ol (15 mg, 0.022 mmol) as a solid. LC-MS, [M+1]$^+$=690.4, (Method E: $t_R$=1.82 min). 1H NMR (400 MHz, DMSO-d6) δ 8.80 (s, 1H), 7.91 (dd, J=2.0, 10.5 Hz, 1H), 7.77 (dd, J=2.0, 8.5 Hz, 1H), 7.72-7.62 (m, 1H), 7.38-7.31 (m, 6H), 5.57-5.53 (m, 2H), 5.11 (dd, J=3.5, 10.5 Hz, 1H), 4.56-4.41 (m, 1H), 4.44-4.37 (m, 1H), 4.20-4.04 (m, 3H), 4.04-3.95 (m, 1H), 3.86 (s, 1H), 3.10 (s, 3H), 3.06 (s, 3H), 2.24 (s, 3H).

Step 5: Synthesis of (2R,3R,4R,6R)-2-(hydroxymethyl)-6-(3-(2-hydroxypropan-2-yl)-1-(2-methylbenzo[d]thiazol-6-yl)-1H-1,2,4-triazol-5-yl)-4-(4-(3,4,5-trifluorophenyl)-1H-1,2,3-triazol-1-yl)tetrahydro-2H-pyran-3-ol: To a stirred solution of 2-(1-(2-methylbenzo[d]thiazol-6-yl)-5-((4aR, 6R,8R,8aR)-2-phenyl-8-(4-(3,4,5-trifluorophenyl)-1H-1,2, 3-triazol-1-yl)hexahydropyrano[3,2-d][1,3]dioxin-6-yl)-1H-1,2,4-triazol-3-yl)propan-2-ol (0.015 g, 0.022 mmol) in DCM (1.5 mL) and MeOH (0.1 mL) at 0° C. was added TFA (0.3 mL, 3.89 mmol) and the mixture was stirred at rt for 3 h. The reaction mixture was concentrated under reduced pressure and the residue was purified by HPLC (Method A) to give (2R,3R,4R,6R)-2-(hydroxymethyl)-6-(3-(2-hydroxypropan-2-yl)-1-(2-methylbenzo[d]thiazol-6-yl)-1H-1, 2,4-triazol-5-yl)-4-(4-(3,4,5-trifluorophenyl)-1H-1,2,3-triazol-1-yl)tetrahydro-2H-pyran-3-ol (Example 270) (1.4 mg, 11%) as a solid. LC-MS, [M+1]$^+$=602.3, (Method A & Method B: $t_R$=1.72 min). $^1$H NMR (400 MHz, METHANOL-d4) δ 8.58 (s, 1H), 8.47 (d, J=2.0 Hz, 1H), 8.08 (d, J=8.6 Hz,1H), 7.85 (dd, J=8.8, 2.2 Hz, 1H), 7.66-7.61 (m, 2H), 5.12-5.06 (m, 1H), 4.88 (d, J=2.2 Hz, 1H), 4.11 (d, J=2.4 Hz, 1H), 3.90-3.77 (m, 2H), 3.77-3.69 (m, 1H), 3.28 (d, J=11.7 Hz, 1H), 2.96-2.83 (m, 3H), 2.34 (d, J=13.0 Hz, 1H), 1.79-1.59 (m, 6H). hGal3 IC50: 0.17 uM

EXAMPLE 271

Preapation of 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-N-methyl-1-(2-methylbenzo[d]thiazol-6-yl)-1H-1,2,4-triazole-3-carboxamide

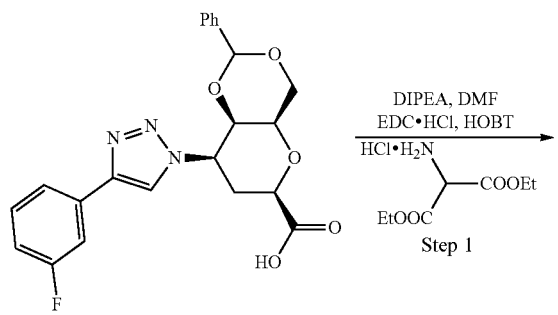

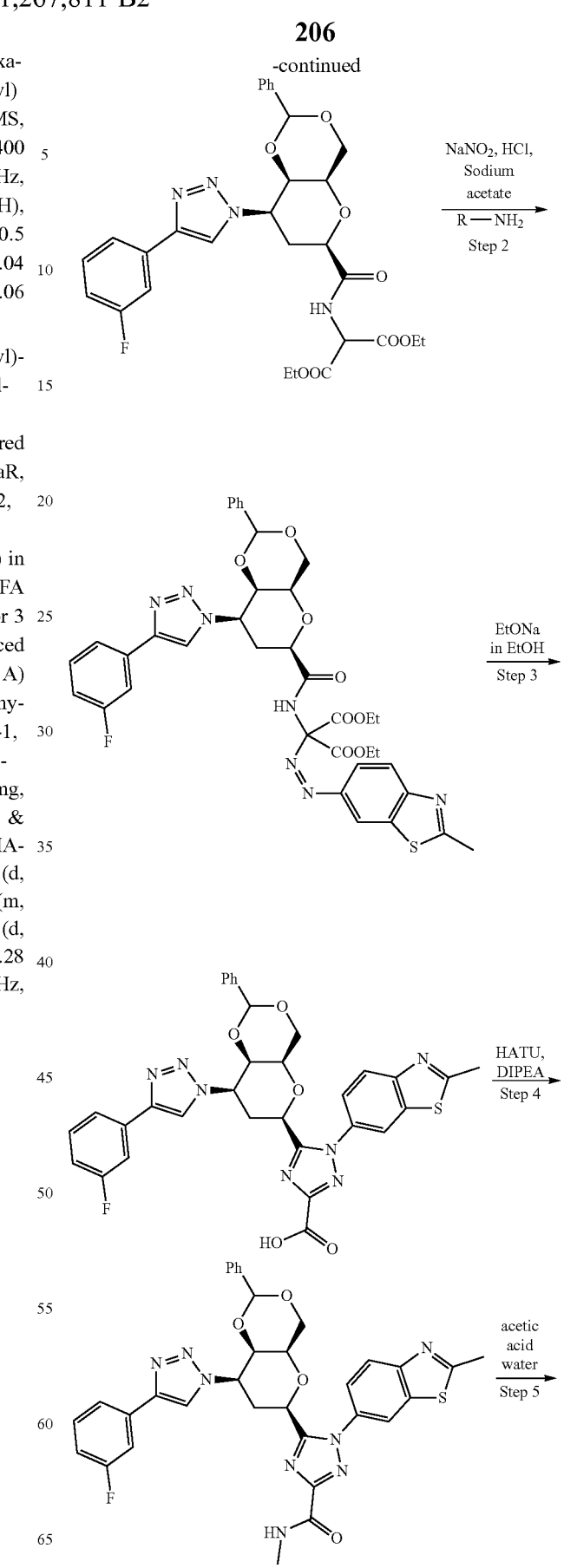

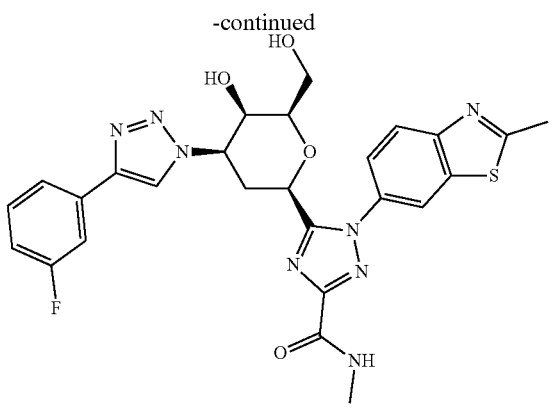

Step 1: Synthesis of diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)malonate: To a stirred solution of (4aR,6R,8R,8aR)-8-(4-(3-fluorophenyl)-1H-1,2,3-triazol-1-yl)-2-phenylhexahydropyrano[3,2-d][1,3]dioxine-6-carboxylic acid (0.05 g, 0.118 mmol) in DMF (1.5 mL) was added 3-(((ethylimino)methylene)amino)-N,N-dimethylpropan-1-amine hydrochloride (0.027 g, 0.141 mmol), HOBt (0.022 g, 0.141 mmol), DIPEA (0.062 mL, 0.353 mmol) and diethyl 2-aminomalonate.HCl (0.027 g, 0.129 mmol) and the mixture was stirred at rt for 14 h. The reaction mixture was quenched with ice-cold water, stirred for 10 min, solid was filtered through buchner funnel and dried under vacuum for 15 min to give diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)malonate (0.05 g, 45%) as a solid. LC-MS, [M+H]$^+$=583.1, (Method A: $t_R$=1.76 min).

Step 2: Synthesis of diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)-2-((2-methylbenzo[d]thiazol-6-yl)diazenyl)malonate: Prepared in a similar fashion as described in (Example 268, step 2), using diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)malonate (0.043 g, 0.073 mmol) as the starting material to afford to give diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)-2-((2-methylbenzo[d]thiazol-6-yl)diazenyl)malonate (44 mg, 48%) as a brown solid, as such taken to the next step without further purification. LC-MS, [M+1]$^+$=758.1, (Method E: $t_R$=1.94 min).

Step 3: synthesis of 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylic acid: To a stirred solution of diethyl 2-((4aR,6R,8R,8aR)-8-(4-(3-fluorophenyl)-1H-1,2,3-triazol-1-yl)-2-phenylhexahydropyrano[3,2-d][1,3]dioxine-6-carboxamido)-2-((2-methylbenzo[d]thiazol-6-yl)diazenyl)malonate (0.044 g, 0.058 mmol) in ethanol (1.5 mL) was added sodium ethoxide in EtOH (21%, 10.94 µl, 0.029 mmol) and the mixture was stirred for 1 h. The reaction mass cooled to 0° C., acidified with amberlite IR 120 (H+resin) and filtered. The filtrate was concentrated under reduced pressure to give 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylic acid (0.02 g, 0.031 mmol) which was taken as such to next step without further purification. LC-MS, [M+1]$^+$=640.2, (Method E: $t_R$=1.12 min).

Step 4: Synthesis of 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-N-methyl-1-(2-methylbenzo[d]thiazol-6-yl)-1H-1,2,4-triazole-3-carboxamide: To a stirred solution of methylamine hydrochloride (0.013 g, 0.188 mmol) in DMF (1 mL) at 0° C., DIPEA (0.033 mL, 0.188 mmol) was added 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-1-(2-methylbenzo[d]thiazol-6-yl)-1H-1,2,4-triazole-3-carboxylic acid (0.02 g, 0.031 mmol) and HATU (0.018 g, 0.047 mmol) and the mixture was stirred at rt for 2 h. The reaction mixture was transferred to a separatory funnel containing aq. NaHCO$_3$. The aqueous layer was extracted with EtOAc (2×30 mL). The combined organic layers were washed with water, brine solution, dried over sodium sulfate and concentrated. The residue was purified via chromatography on silica gel (0-2% MeOH in chloroform) to give 5-((4aR,6R,8R,8aR)-8-(4-(3-fluorophenyl)-1H-1,2,3-triazol-1-yl)-2-phenylhexahydropyrano[3,2-d][1,3]dioxin-6-yl)-N-methyl-1-(2-methylbenzo[d]thiazol-6-yl)-1H-1,2,4-triazole-3-carboxamide (10 mg, 49%) as a yellow solid. LC-MS, [M+1]$^+$=653.3, (Method E: $t_R$=1.59 min).

Step 5: Synthesis of 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-N-methyl-1-(2-methylbenzo[d]thiazol-6-yl)-1H-1,2,4-triazole-3-carboxamide: 5-((4aR,6R,8R,8aR)-8-(4-(3-Fluorophenyl)-1H-1,2,3-triazol-1-yl)-2-phenylhexahydropyrano[3,2-d][1,3]dioxin-6-yl)-N-methyl-1-(2-methylbenzo[d]thiazol-6-yl)-1H-1,2,4-triazole-3-carboxamide (0.01 g, 0.015 mmol) was suspended in acetic acid (7 mL) and water (3 mL) and heated at 65° C. for 14 h. The reaction mixture was concentrated and purified by HPLC (Method A) to give 5-((2R,4R,5R,6R)-4-(4-(3-fluorophenyl)-1H-1,2,3-triazol-1-yl)-5-hydroxy-6-(hydroxymethyl)tetrahydro-2H-pyran-2-yl)-N-methyl-1-(2-methylbenzo[d]thiazol-6-yl)-1H-1,2,4-triazole-3-carboxamide (Example 271) (2 mg, 23%). LC-MS, [M+1]$^+$=565.2, (Method A & Method B: $t_R$=1.27 min). $^1$H NMR (400 MHz, METHANOL-d4) δ 8.58 (d, J=2.0 Hz, 1H), 8.53 (s, 1H), 8.10 (d, J=8.8 Hz, 1H), 7.92 (dd, J=8.8, 2.2 Hz, 1H), 7.69 (d, J=7.8 Hz, 1H), 7.66-7.60 (m, 1H), 7.48 (td, J=8.0, 6.0 Hz, 1H), 7.14-7.05 (m, 1H), 5.14-5.08 (m, 1H), 4.92 (d, J=2.2 Hz, 1H), 4.14 (d, J=2.7 Hz, 1H), 3.90-3.78 (m, 2H), 3.78-3.69 (m, 1H), 3.37-3.33(m, 1H), 3.00 (s, 3H), 2.92 (s, 3H), 2.40 (d, J=10.3 Hz, 1H). hGal3 IC50: 0.39 uM Synthetic Scheme for C3-substituted-4-aryl 1,2,4-triazole Compounds:

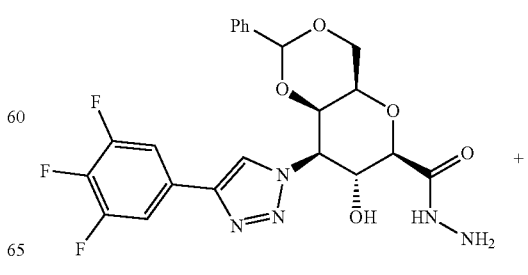

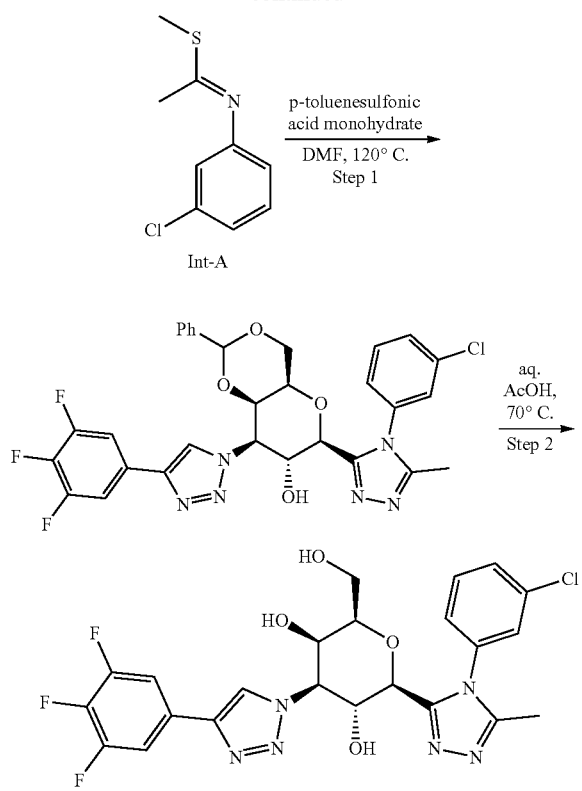

EXAMPLE 272

Preparation of (2S,3R,4R,5R,6R)-2-(4-(3-chlorophenyl)-5-methyl-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol Synthesis of Int-A:

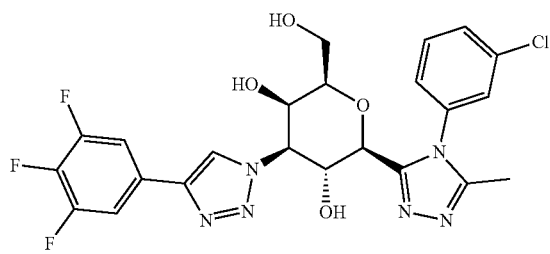 [SMILES: Cc1nnc([C@@H]2O[C@H](CO)[C@H](O)[C@H](n3cc(-c4cc(F)c(F)c(F)c4)nn3)[C@H]2O)n1-c1cccc(Cl)c1]

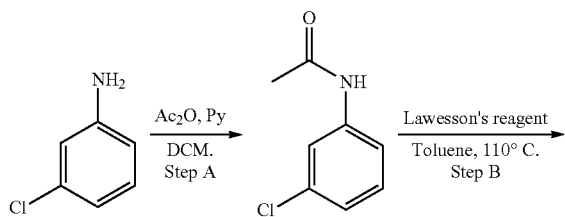

Step A: Synthesis of N-(3-chlorophenyl)acetamide: To a solution of 3-chloroaniline (1 g, 7.84 mmol) in dichloromethane (10 mL) at 0° C. was added pyridine (0.951 mL, 11.76 mmol) and acetic anhydride (0.888 mL, 9.41 mmol) and the mixture was stirred for 4 h. The reaction mixture was diluted with DCM (50 mL), washed with 1.5N HCl solution, brine solution (50 mL), dried over $Na_2SO_4$, and concentrated to give N-(3-chlorophenyl)acetamide (900 mg, 67%) as a brown solid. LC-MS, $[M+H]^+$=168.0, (Method E: $t_R$=0.94). 1H NMR (400 MHz, CHLOROFORM-d) δ 7.62 (s, 2H), 7.34 (d, J=8.0 Hz, 1H), 7.22 (t, J=8.0 Hz, 1H), 7.07 (d, J=7.5 Hz, 1H), 2.17 (s, 3H).

Step B: Synthesis of N-(3-chlorophenyl)ethanethioamide: To a solution of N-(3-chlorophenyl)acetamide (500 mg, 2.95 mmol) in toluene (10 mL) was added Lawesson's reagent (596 mg, 1.474 mmol) was the mixture was heated at 110° C. for 2 h. The reaction mixture was diluted with EtOAc (50 mL), washed with 10% $NaHCO_3$ solution, brine solution (50 mL), dried over $Na_2SO_4$, and concentrated. The residue was purified via silica gel chromatography (0-20% EtOAc in hexanes) to give N-(3-chlorophenyl)ethanethioamide (500 mg, 71%) as a brown liquid. LC-MS, $[M+H]^+$=186.1, (Method E: $t_R$=1.13).

Step C: Synthesis of methyl (E)-N-(3-chlorophenyl)ethanimidothioate: To a solution of N-(3-chlorophenyl)ethanethioamide (0.4 g, 2.154 mmol) in acetonitrile (10 mL) was added $K_2CO_3$ (0.298 g, 2.154 mmol) and methyl iodide (0.202 mL, 3.23 mmol) and the mixture was stirred for 2 h. The reaction mixture was concentrated and the residue was dissolved in EtOAc (50 mL) and was washed with water (50 mL), dried over $Na_2SO_4$, and concentrated. The crude residue was purified via silica gel chromatography (0-25% EtOAc in hexanes) to give methyl (E)-N-(3-chlorophenyl) ethanimidothioate (0.4 g, 93%) as a brown liquid. LC-MS, $[M+H]^+$=200.2, (Method C: $t_R$=2.893). 1H NMR (400 MHz, CHLOROFORM-d) δ 7.22 (t, J=8.0 Hz, 1H), 7.03 (d, J=8.0 Hz, 1H), 6.75 (t, J=1.8 Hz, 1H), 6.62 (d, J=7.5 Hz, 1H), 2.40 (s, 3H), 2.01 (s, 3H).

Step 1: Synthesis of (4aR,6S,7R,8R,8aR)-6-(4-(3-chlorophenyl)-5-methyl-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol: To a solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (50 mg, 0.102 mmol) in N,N-dimethylformamide (3 mL) was added methyl (E)-N-(3-chlorophenyl) ethanimidothioate (20.32 mg, 0.102 mmol) and p-toluenesulfonic acid monohydrate (1.935 mg, 10.17 μmol) and the mixture was heated at 120° C. for 1 h. The reaction mixture was concentrated and was purified via silica gel chromatography (70-100% EtOAc in hexanes) to give (4aR,6S,7R,8R,8aR)-6-(4-(3-chlorophenyl)-5-methyl-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (30 mg, 45%) as an off-white solid. LC-MS,

[M+H]$^+$=625.0, (Method C: $t_R$=3.209). 1H NMR (400 MHz, METHANOL-d4) δ 8.43 (s, 1H), 7.72-7.46 (m, 6H), 7.39 (br s, 5H), 5.59-5.48 (m, 1H), 5.19-5.07 (m, 1H), 5.04-4.94 (m, 1H), 4.58-4.44 (m, 2H), 4.31-4.04 (m, 2H), 3.86-3.72 (m, 1H), 2.35 (s, 3H).

Step 2: A solution of (4aR,6S,7R,8R,8aR)-6-(4-(3-chlorophenyl)-5-methyl-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (30 mg, 0.048 mmol) in 70% as acetic acid (10 mL) was heated at 70° C. for 16 h. The solvent was removed and purified by HPLC (Method A) to afford (2S,3R,4R,5R,6R)-2-(4-(3-chlorophenyl)-5-methyl-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 272) (11.1 mg, 43%). LC-MS, [M+H]$^+$=537.2, (Method A: $t_R$=1.389 and Method B: $t_R$=1.37). 1H NMR (400 MHz, METHANOL-$d_4$) δ 8.55 (s, 1H), 7.76-7.59 (m, 5H), 7.56-7.45 (m, 1H),4.99-4.88 (m, 2H), 4.34 (d, J=9.2 Hz, 1H), 4.11 (d, J=2.4 Hz, 1H), 3.80-3.63 (m, 3H), 2.36 (s,3H). hGal3 IC$_{50}$=0.07 uM.

Synthetic Scheme for C3-substituted-4-aryl 1,2,4-triazole Compounds:

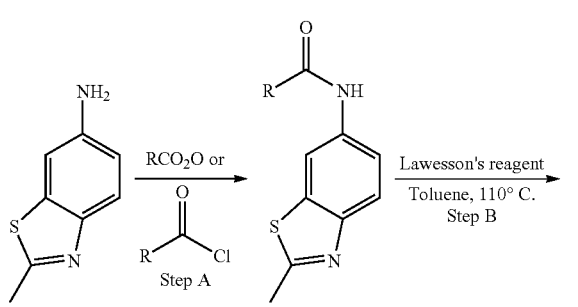

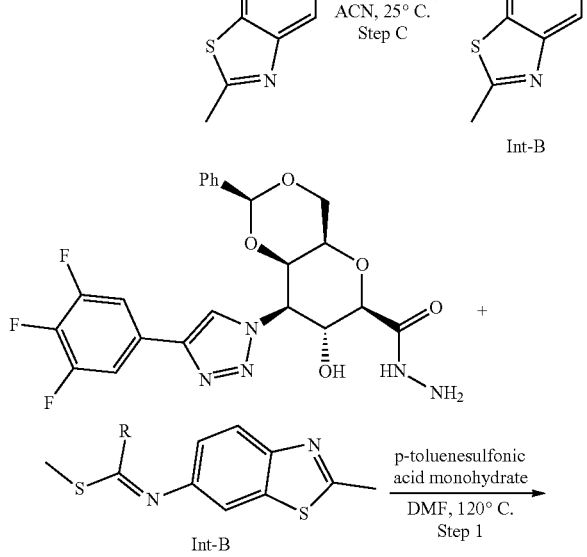

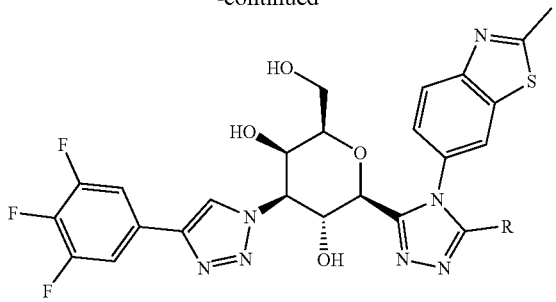

EXAMPLE 273

Preparation of (2R,3R,4R,5R,6S)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol

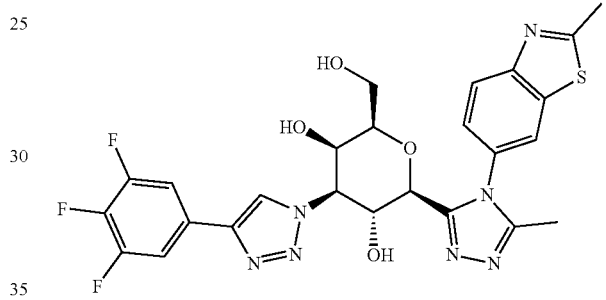

Synthesis of Int-B: Prepared in similar fashion to Int-A by substituting 3-chloroaniline with 2-methylbenzo[d]thiazol-6-amine and using appropriate alkyl anhydrides or alkyl acid chlorides Step 1: Synthesis of (2R,3R,4R,5R,6S)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol: To a solution of ((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (50 mg, 0.102 mmol) in N,N-dimethylformamide (3 mL) was added methyl (E)-N-(2-methylbenzo[d]thiazol-6-yl)ethanimidothioate (24.05 mg, 0.102 mmol) and p-toluenesulfonic acid monohydrate (1.935 mg, 10.17 μmol) and the mixture was heated at 120° C. for 1 h. The reaction mixture was concentrated to give crude compound which was purified HPLC (Method A) to give (2R,3R,4R,5R,6S)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol (Example 271) (13.3 mg, 23%) as an off white solid. LC-MS, [M+H]$^+$=574.2, (Method A: $t_R$=1.283 and Method B: $t_R$=1.252). 1H NMR (400 MHz, METHANOL-d4) d 8.50 (s, 1H), 8.20 (br. s., 1H), 8.11 (d, J=8.8 Hz, 1H),7.65-7.58 (m, 3H), 4.95-4.80 (m, 1H), 4.79 (d, J=2.8 Hz, 2H), 4.30 (d, J=9.3 Hz, 1H), 4.03(d,J=2.8 Hz, 1H), 3.67-3.59 (m, 1H), 3.59-3.46 (m, 2H), 2.89 (s, 3H), 2.35 (s, 3H). hGal3 IC50=0.04 uM.

The Examples in the table below were prepared in an analogous fashion to Example 273, substituting methyl (E)-N-(2-methylbenzo[d]thiazol-6-yl)ethanimidothioate with the appropriate imidothioates in the synthetic sequence.

| Ex | hGal3 IC50, uM | Structure | LCMS $t_R$ (min) | M + H | Method | 1H NMR |
|---|---|---|---|---|---|---|
| 274 | 0.05 | 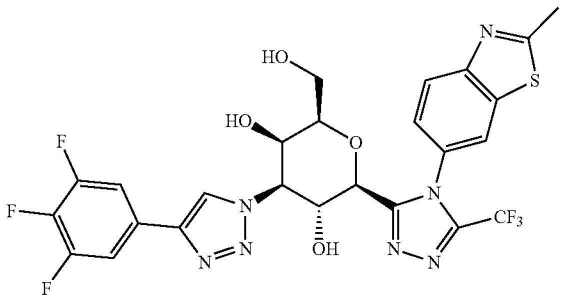 [SMILES: Cc1nc2ccc(-n3c([C@@H]4O[C@H](CO)[C@H](O)[C@H](n5cc(-c6cc(F)c(F)c(F)c6)nn5)[C@H]4O)nnc3C(F)(F)F)cc2s1] | 2.134 | 628.2 | C | 1H NMR (400 MHz, METHANOL-d4) δ 8.65-8.47 (m, 1H), 8.41-8.07 (m, 2H), 7.78-7.55 (m, 3H), 5.21-4.93 (m, 1H), 4.42-4.26 (m, 1H), 4.06 (d, J = 2.5 Hz, 1H), 3.84-3.54 (m, 3H), 2.94 (s, 3H), (one proton obscured with moisture peak). |
| 275 | 0.06 | 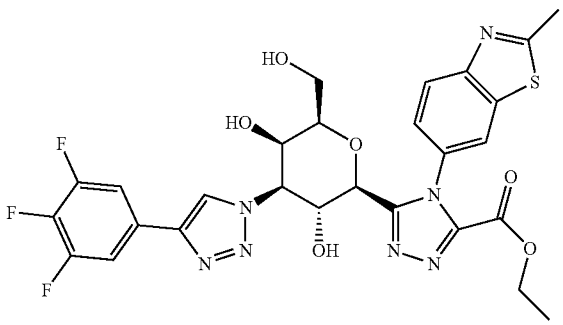 [SMILES: CCOC(=O)c1nnc([C@@H]2O[C@H](CO)[C@H](O)[C@H](n3cc(-c4cc(F)c(F)c(F)c4)nn3)[C@H]2O)n1-c1ccc2nc(C)sc2c1] | 1.430 | 632.2 | A | 1H NMR (400 MHz, METHANOL-d4) δ 8.57 (s, 1H), 8.37-8.16 (m, 1H), 8.15-8.06 (m, 1H), 7.74-7.55 (m, 3H), 5.18-5.00 (m, 1H), 4.37-4.23 (m, 3H), 4.07 (d, J = 2.4 Hz, 1H), 3.92-3.70 (m, 1H), 3.69-3.61 (m, 2H), 2.93 (s, 3H), 1.18 (t, J = 7.2 Hz, 3H), (one proton obscured with moisture peak) |

EXAMPLE 276

Preparation of (2R,3R,4R,5R,6S)-2-(hydroxymethyl)-6-(5-(2-hydroxypropan-2-yl)-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol

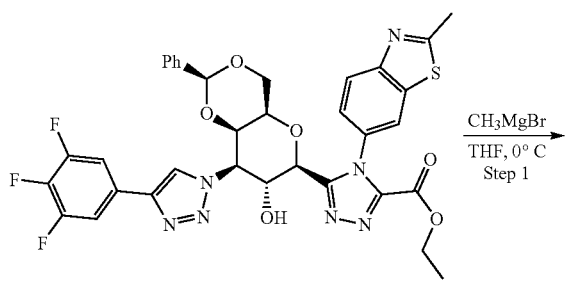

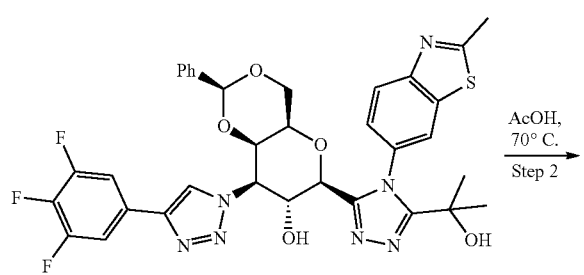

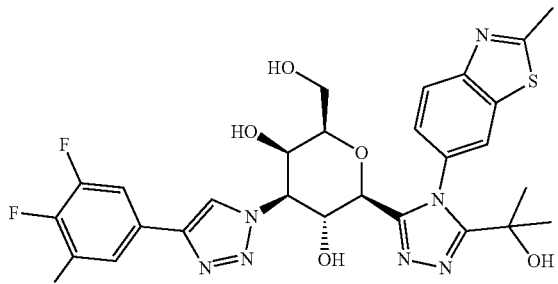

Step 1: Synthesis of (4aR,6S,7R,8R,8aR)-6-(5-(2-hydroxypropan-2-yl)-4-(2-methylbenzo[d]thiazol-6-yl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol:
To a solution of ethyl 5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4-(2-methylbenzo[d]thiazol-6-yl)-4H-1,2,4-triazole-3-carboxylate (40 mg, 0.056 mmol) in tetrahydrofuran (5 mL) was added methyl magnesium bromide (0.093 mL, 0.278 mmol) at 0° C. and the mixture was stirred for 1 h. The reaction mixture was quenched with sat NH$_4$Cl solution (10 mL), extracted with EtOAc (3×30 mL), dried over Na$_2$SO$_4$, and concentrated to give (4aR,6S,7R,8R,8aR)-6-(5-(2-hydroxypropan-2-yl)-4-(2-methylbenzo[d]thiazol-6-yl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (50 mg, 64%) as brown liquid which was as such taken to the next step without further purification. LC-MS, [M+H]$^+$=706.4, (Method E: $t_R$=1.24).

Step 2: Synthesis of (2R,3R,4R,5R,6S)-2-(hydroxymethyl)-6-(5-(2-hydroxypropan-2-yl)-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol: A solution of (4aR,6S,7R,8R,8aR)-6-(5-(2-hydroxypropan-2-yl)-4-(2-methylbenzo[d]thiazol-6-yl)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (50 mg, 0.071 mmol) in 70% aq AcOH (10 mL) was heated at 70° C. for 16 h. The reaction mixture was concentrated and purified HPLC (Method A) afford (2R,3R,4R,5R,6S)-2-(hydroxymethyl)-6-(5-(2-hydroxypropan-2-yl)-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3,5-diol (Example 276) (8.1 mg, 19%). LC-MS, [M+H]⁺=618.2, (Method A: $t_R$=1.258 and Method B: $t_R$=1.241). 1H NMR (400 MHz, METHANOL-d4) δ 8.58-8.52 (m, 1H), 8.29-8.00 (m, 2H), 7.74-7.58 (m, 3H), 5.10-4.97 (m, 1H), 4.82-4.74 (m, 1H), 4.62 (s, 1H), 4.18-4.08 (m, 1H), 4.07-4.01 (m, 1H), 3.75-3.45 (m, 2H), 2.92 (s, 3H), 1.62 (s, 3H), 1.54 (d, J=2.7 Hz, 3H). hGal3 IC$_{50}$=0.05 uM.

EXAMPLE 277

Preparation of 5-((2S,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)-4-(2-methylbenzo[d]thiazol-6-yl)-4H-1,2,4-triazole-3-carboxamide

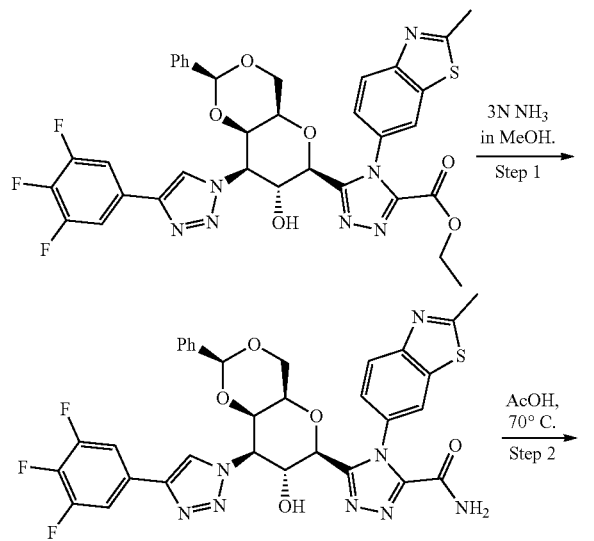

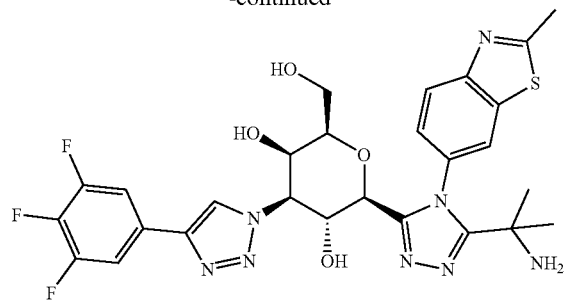

Step 1: Synthesis of 5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4-(2-methylbenzo[d]thiazol-6-yl)-4H-1,2,4-triazole-3-carboxamide: A solution of ethyl 5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4-(2-methylbenzo[d]thiazol-6-yl)-4H-1,2,4-triazole-3-carboxylate (30 mg, 0.042 mmol) in 3 N methanolic ammonia (5 mL) was stirred at rt for 16 h. The reaction mixture was concentrated to give 5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4-(2-methylbenzo[d]thiazol-6-yl)-4H-1,2,4-triazole-3-carboxamide (30 mg, 59%) as brown liquid. LC-MS, [M+H]⁺=691.2, (Method E: $t_R$=1.63).

Step 2: Synthesis of 5-((2S,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)-4-(2-methylbenzo[d]thiazol-6-yl)-4H-1,2,4-triazole-3-carboxamide: A solution of 5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-4-(2-methylbenzo[d]thiazol-6-yl)-4H-1,2,4-triazole-3-carboxamide (30 mg, 0.043 mmol) in 70% aq AcOH (5 mL) was heated at 70° C. for 16 h. The reaction mixture was concentrated and purified by HPLC (Method A) to afford 5-((2S,3R,4R,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)-4-(2-methylbenzo[d]thiazol-6-yl)-4H-1,2,4-triazole-3-carboxamide (Example 277) (3.2 mg, 12%). LC-MS, [M+H]⁺=603.2, (Method A: $t_R$=1.209). 1H NMR (400 MHz, METHANOL-d4) δ 8.54 (s, 1H), 8.17 (br s, 1H), 8.05 (d, J=8.8 Hz, 1H), 7.72-7.56 (m, 3H), 5.08-4.98 (m, 1H), 4.82 (d, J=2.9 Hz, 1H), 4.30 (d, J=9.3 Hz, 1H), 4.07 (d, J=2.7 Hz, 1H), 3.78-3.63 (m, 3H), 2.91 (s, 3H). hGal3 IC$_{50}$=0.04 uM.

EXAMPLE 278

Preparation of (2S,3R,4R,5R,6R)-2-(4-(3,4-dichlorophenyl)-5-(methylthio)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol

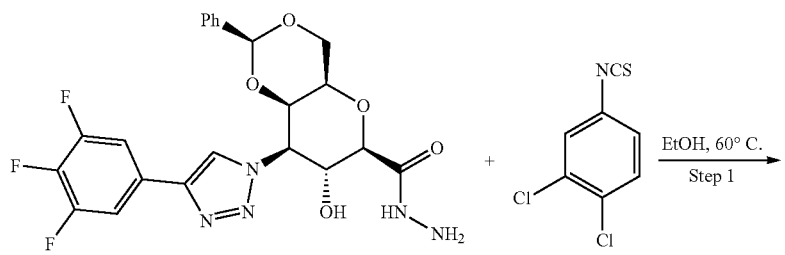

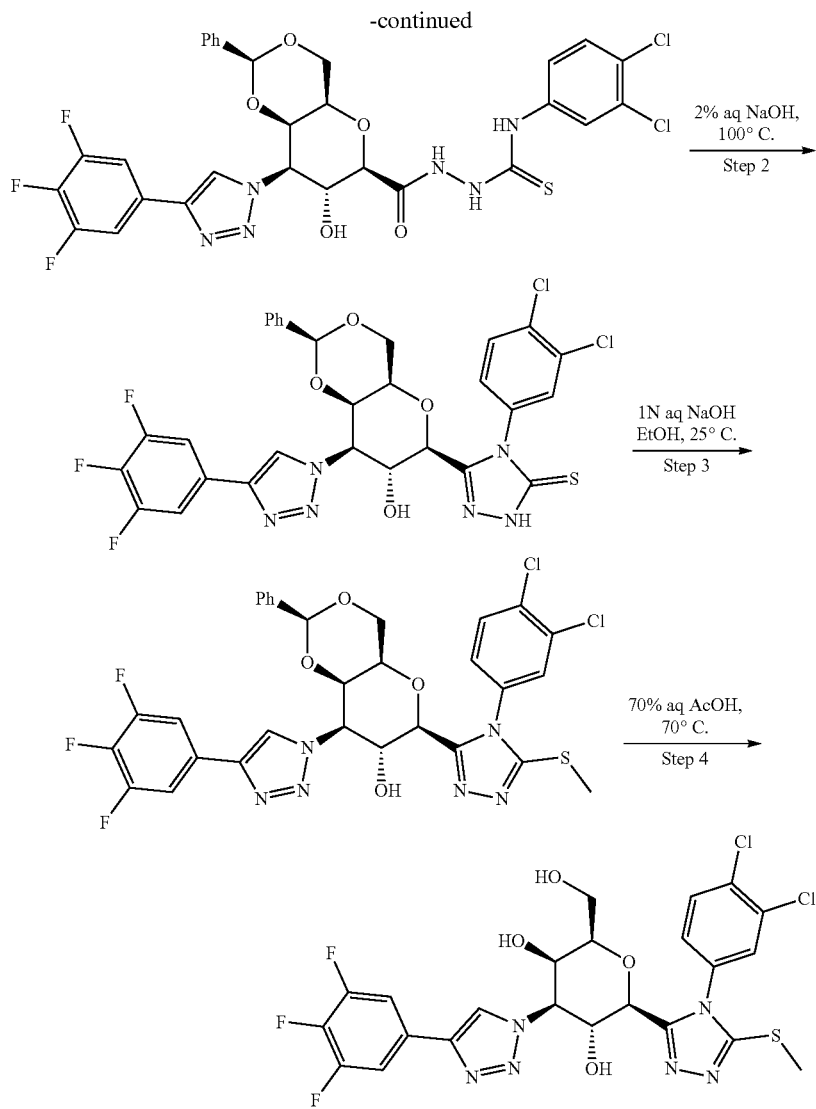

Step 1: Synthesis of N-(3,4-dichlorophenyl)-2-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)hydrazine-1-carbothioamide: To a solution of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide (100 mg, 0.203 mmol) in ethanol (10 mL), was added 1,2-dichloro-4-isothiocyanatobenzene (41.5 mg, 0.203 mmol) and the mixture was heated at 60° C. for 1 h. The reaction mixture was concentrated to give crude compound which was triturated with diethyl ether and dried to give N-(3,4-dichlorophenyl)-2-((4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)hydrazine-1-carbothioamide (60 mg, 42%) as a brown solid. LC-MS, [M+H]⁺=697.0, (Method C: $t_R$=3.038).

Step 2: Synthesis of 4-(3,4-dichlorophenyl)-5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-2,4-dihydro-3H-1,2,4-triazole-3-thione: A solution of N-(3,4-dichlorophenyl)-2-((4aR,6R,7R,8R, 8aR)-7-hydroxy-2-phenyl-8-(4-(3,4,5-trifluorophenyl)-1H-1,2,3-triazol-1-yl)hexahydropyrano[3,2-d][1,3]dioxine-6-carbonyl)hydrazine-1-carbothioamide (80 mg, 0.115 mmol) in 2% aqueous NaOH (10 mL) was heated at 100° C. for 3 h. The reaction mixture was acidified with 6 N HCl and the solid was filtered and dried to give 4-(3,4-dichlorophenyl)-5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-2,4-dihydro-3H-1,2,4-triazole-3-thione (90 mg, 70%) as a brown solid. LC-MS, [M+H]⁺=679.0, (Method C: $t_R$=3.227).

Step 3: Synthesis of (4aR,6S,7R,8R,8aR)-6-(4-(3,4-dichlorophenyl)-5-(methylthio)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol: To a solution of 4-(3,4-dichlorophenyl)-5-((4aR,6S,7R,8R,8aR)-7-hydroxy-2-phenyl-8-(4-(3,4,5-trifluorophenyl)-1H-1,2,3-triazol-1-yl)hexahydropyrano[3,2-d][1,3]dioxin-6-yl)-2,4-dihydro-3H-1,2,4-triazole-3-thione (90 mg, 0.133 mmol) in 1 M aqueous NaOH (10 mL) was added iodomethane (0.042 mL, 0.664 mmol) in EtOH (1 mL) at rt and the mixture was stirred for 16 h. The reaction mixture was filtered and dried to give (4aR,6S,7R,8R,8aR)-6-(4-(3,4-dichlorophenyl)-5-(methylthio)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (60 mg, 65%) as a brown solid. LC-MS, [M+H]⁺= 692.0, (Method C: $t_R$=3.406).

Step 4: Synthesis of (2S,3R,4R,5R,6R)-2-(4-(3,4-dichlorophenyl)-5-(methylthio)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol: A solution of (4aR,6S,7R,8R,8aR)-6-(4-(3,4-dichlorophenyl)-5-(methylthio)-4H-1,2,4-triazol-3-yl)-2-phenyl-8-(4-(3,4,5-trifluorophenyl)-1H-1,2,3-triazol-1-yl)hexahydropyrano[3,2-d][1,3]dioxin-7-ol (60 mg, 0.087 mmol) in 70% aq AcOH (5 mL) was heated at 70° C. for 16 h. The reaction mixture was concentrated under reduced pressure and the residue was purified by HPLC (Method A) to afford (2S,3R,4R,5R,6R)-2-(4-(3,4-dichlorophenyl)-5-(methylthio)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 278) (11.0 mg, 21%). LC-MS, [M+H]⁺=605.1, (Method A: $t_R$=1.668 and Method B: $t_R$=1.658). 1H NMR (400 MHz, METHANOL-d₄) δ 8.52 (s, 1H), 7.86-7.79 (m, 2H), 7.76-7.60 (m, 2H), 7.54 (dd, J=8.4, 2.3 Hz, 1H), 4.93-4.88 (m, 2H), 4.40 (d, J=9.2 Hz, 1H), 4.10 (s, 1H), 3.80-3.63 (m, 3H), 2.70 (s, 3H). hGal3 IC₅₀=0.12 uM.

EXAMPLE 279

Preparation of (2S,3R,4R,5R,6R)-2-(4-(3,4-dichlorophenyl)-5-(methylsulfonyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol

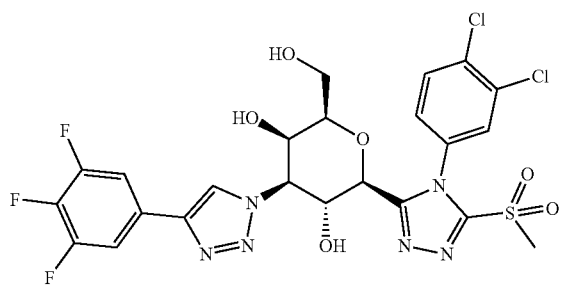 [SMILES: CS(=O)(=O)c1nnc([C@@H]2O[C@H](CO)[C@H](O)[C@H](n3cc(-c4cc(F)c(F)c(F)c4)nn3)[C@H]2O)n1-c1ccc(Cl)c(Cl)c1]

To a solution of (2S,3R,4R,5R,6R)-2-(4-(3,4-dichlorophenyl)-5-(methylthio)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (30 mg, 0.050 mmol) in dichloromethane (5 mL), was added m-CPBA (7.15 mg, 0.025 mmol) at 5° C. and the mixture was stirred for 1 h. The reaction mixture was concentrated and the residue was purified by HPLC (Method A) to afford (2S,3R,4R,5R,6R)-2-(4-(3,4-dichlorophenyl)-5-(methylsulfonyl)-4H-1,2,4-triazol-3-yl)-6-(hydroxymethyl)-4-(4-(3,4,5-trifluorophenyl)-1H-1,2,3-triazol-1-yl)tetrahydro-2H-pyran-3,5-diol (Example 279) (8.8 mg, 28%). LC-MS, [M+H]⁺=637.1, (Method A: $t_R$=1.60 and Method B: $t_R$=1.61). 1H NMR (400 MHz, METHANOL-d4) δ 8.55 (s, 1H), 7.91 (br s, 1H), 7.80 (d, J=8.6 Hz, 1H), 7.71-7.58 (m, 3H), 5.16-4.95 (m, 1H), 4.94-4.88 (m, 1H), 4.41 (d, J=9.3 Hz, 1H), 4.11 (d, J=2.7 Hz, 1H), 3.81-3.64 (m, 3H), 3.49 (s, 3H). hGal3 IC₅₀=0.07 uM.

EXAMPLE 280

Preparation of (2R,3R,4R,6R)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol Step 1: Synthesis of (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carbohydrazide: To a solution of methyl (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carboxylate (200 mg, 0.421 mmol) in EtOH (10 mL) was added hydrazine hydrate (1 mL, 0.421 mmol) and the mixture was heated at 85° C. for 16 h. The reaction mixture was concentrated and the crude product was purified by washing with diethyl ether to give (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carbohydrazide (180 mg, 74%) as off white solid. LC-MS, [M+H]⁺=476.2, (Method C: $t_R$=2.297).

Step 2: Synthesis of 2-methyl-6-(3-methyl-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)benzo[d]thiazole: To a solution of (4aR,6R,8R,8aR)-2-phenyl-8-(4-(3,4,5-trifluorophenyl)-1H-1,2,3-triazol-1-yl)hexahydropyrano[3,2-d][1,3]dioxine-6- carbohydrazide (50 mg, 0.105 mmol) in acetonitrile (10 mL) was added N,N-dimethylacetamide dimethyl acetal (14.01 mg, 0.105 mmol) and the mixture was heated at 50° C. for 30 min. 2-Methylbenzo[d]thiazol-6-amine (17.27 mg, 0.105 mmol) in acetonitrile (10.00 mL) was then added at 50° C. followed by acetic acid (1 mL, 17.47 mmol) and the reaction mixture was slowly warmed to 120° C. and stirred for 16 h. The reaction mixture was concentrated and the residue was purified via silica gel chromatography (0-4% MeOH in DCM) to give 2-methyl-6-(3-methyl-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)benzo[d]thiazole (50 mg, 74%) as an off-white solid. LC-MS, [M+H]$^+$=646.2, (Method C: $t_R$=2.99).

Step 3: Synthesis of (2R,3R,4R,6R)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol: A solution of 2-methyl-6-(3-methyl-5-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)benzo[d]thiazole (50 mg, 0.077 mmol) in 70% aq AcOH (5 mL) was heated at 70° C. for 16 h. The reaction mixture was concentrated under reduced pressure and the residue was purified by HPLC (Method A) to afford (2R,3R,4R,6R)-2-(hydroxymethyl)-6-(5-methyl-4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol (Example 280) (11.8 mg, 26%). LC-MS, [M+H]$^+$=558.2, (Method A: $t_R$=1.40 and Method B: $t_R$=1.35). 1H NMR (400 MHz, METHANOL-$d_4$) δ 8.54 (s, 1H), 8.27 (br s, 1H), 8.12 (d, J=8.6 Hz, 1H), 7.67 (dd, J=6.8, 8.8 Hz, 3H), 5.07-4.98 (m, 1H), 4.74-4.63 (m, 1H), 4.03 (s, 1H), 3.61 (d, J=5.9 Hz, 2H), 3.57-3.48 (m, 1H), 3.22-3.11 (m, 1H), 2.93 (s, 3H), 2.42 (s, 3H), 2.41-2.35 (m, 1H). hGal3 IC$_{50}$=0.07 uM.

EXAMPLE 281

Preparation of (2R,3R,4R,6R)-2-(hydroxymethyl)-6-(4-(2-methylbenzo[d]thiazol-6-yl)-5-(trifluoromethyl)-4H-1,2,4-triazol-3-yl)-4-(4-(3,4,5-trifluorophenyl)-1H-1,2,3-triazol-1-yl)tetrahydro-2H-pyran-3-ol

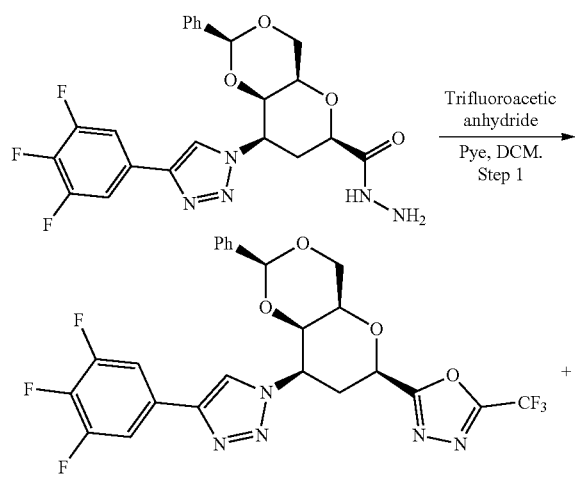

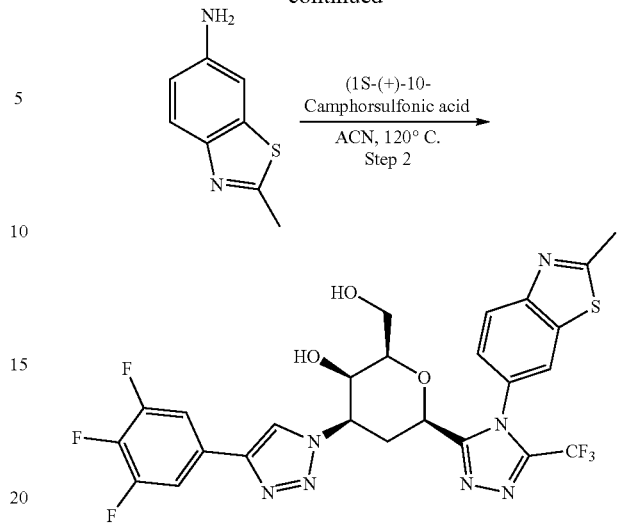

Step 1: Synthesis of 2-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-5-(trifluoromethyl)-1,3,4-oxadiazole: To a solution of (4aR,6R,8R,8aR)-2-phenyl-8-(4-(3,4,5-trifluorophenyl)-1H-1,2,3-triazol-1-yl)hexahydropyrano[3,2-d][1,3]dioxine-6-carbohydrazide (50 mg, 0.105 mmol) in dichloromethane (5 mL) was added pyridine (0.017 mL, 0.210 mmol) and trifluoroacetic anhydride (0.030 mL, 0.210 mmol) at 0° C. and the mixture was stirred for 16 h at rt. The reaction mixture was diluted with DCM (20 mL) and was washed with water (30 mL), 1.5N HCl (30 mL), 10% NaHCO$_3$ solution (30 mL), and brine solution (50 mL), dried over Na$_2$SO$_4$, and concentrated to give 2-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-5-(trifluoromethyl)-1,3,4-oxadiazole (50 mg, 86%) as an off white solid. LC-MS, [M+H]$^+$=554.4, (Method E: $t_R$=2.01).

Step 2: Synthesis of (2R,3R,4R,6R)-2-(hydroxymethyl)-6-(4-(2-methylbenzo[d]thiazol-6-yl)-5-(trifluoromethyl)-4H-1,2,4-triazol-3-yl)-4-(4-(3,4,5-trifluorophenyl)-1H-1,2,3-triazol-1-yl)tetrahydro-2H-pyran-3-ol: To a solution of 2-((4aR,6R,8R,8aR)-2-phenyl-8-(4-(3,4,5-trifluorophenyl)-1H-1,2,3-triazol-1-yl)hexahydropyrano[3,2-d][1,3]dioxin-6-yl)-5-(trifluoromethyl)-1,3,4-oxadiazole (50 mg, 0.090 mmol) in acetonitrile (3 mL) was added 2-methylbenzo[d]thiazol-6-amine (37.1 mg, 0.226 mmol) and (1S)-(+)-10-camphorsulfonic acid (2.099 mg, 9.03 µmol) and the reaction mixture was heated at 120° C. for 16 h. The reaction mixture was concentrated and the residue was purified by HPLC (Method D) afford (2R,3R,4R,6R)-2-(hydroxymethyl)-6-(4-(2-methylbenzo[d]thiazol-6-yl)-5-(trifluoromethyl)-4H-1,2,4-triazol-3-yl)-4-(4-(3,4,5-trifluorophenyl)-1H-1,2,3-triazol-1-yl)tetrahydro-2H-pyran-3-ol (Example 281) (22.7 mg, 41%). LC-MS, [M+H]$^+$=612.2, (Method A: $t_R$=1.625 and Method B: $t_R$=1.525). 1H NMR (400 MHz, METHANOL-$d_4$) δ 8.56 (s, 1H), 8.37 (br s, 1H), 8.11 (d, J=8.6 Hz, 1H), 7.78-7.62 (m, 3H), 5.10-4.95 (m, 1H), 4.79-4.62 (m, 1H), 4.02 (br s, 1H), 3.63-3.42 (m, 3H), 3.28-3.16 (m, 1H), 2.93 (s, 3H), 2.50-2.40 (m, 1H). hGal3 IC$_{50}$=0.08 uM.

EXAMPLE 282

Preparation of (2R,3R,4S,5R,6S)-2-(hydroxymethyl)-5-methoxy-6-(4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol

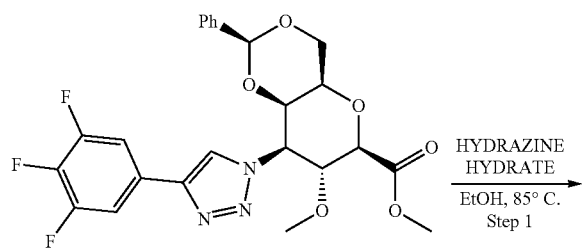

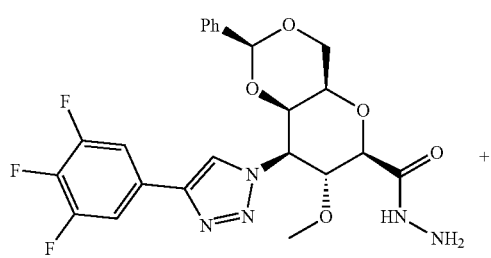

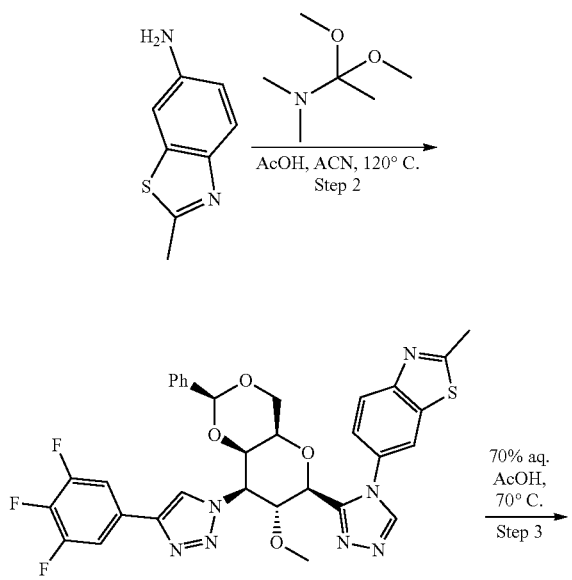

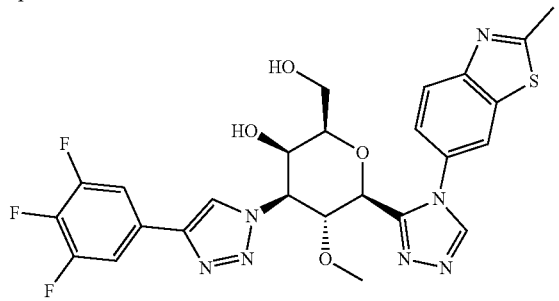

Step 1: Synthesis of (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carbohydrazide: To a solution of methyl (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carboxylate (600 mg, 1.187 mmol) in ethanol (30 mL) was added hydrazine hydrate (0.578 mL, 11.87 mmol) and the reaction mixture was heated at 85° C. for 16 h. The reaction mixture was concentrated and the residue was triturated with diethyl ether to give (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carbohydrazide (400 mg, 56%) as off white solid. LC-MS, $[M+H]^+$=506.3, (Method C: $t_R$=2.45). 1H NMR (400 MHz, DMSO-d6) δ 9.61 (br s, 1H), 9.10 (s, 1H), 7.83 (dd, J=6.5, 9.0 Hz, 2H), 7.41-7.33 (m, 5H), 6.55 (br s, 2H), 5.55 (s, 1H), 5.26 (dd, J=3.5, 10.5 Hz, 1H), 4.48-4.38 (m, 3H), 4.17-4.04 (m, 2H), 3.90-3.77 (m, 2H), 3.08 (s, 3H);

Step 2: Synthesis of 6-(3-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)-2-methylbenzo[d]thiazole: To a solution of (4aR,6R,7R,8R,8aR)-7-methoxy-2-phenyl-8-(4-(3,4,5-trifluorophenyl)-1H-1,2,3-triazol-1-yl)hexahydropyrano[3,2-d][1,3]dioxine-6-carbohydrazide (50 mg, 0.099 mmol) in acetonitrile (10 mL), was added DMF-DMA (0.013 mL, 0.099 mmol) and the reaction mixture was heated at 50° C. for 30 min. 2-Methylbenzo[d]thiazol-6-amine (16.25 mg, 0.099 mmol) in acetonitrile (10.00 mL) was then added followed by acetic acid (1 mL, 17.47 mmol) and the reaction mixture was heated to 120° C. for 16 h. The reaction mixture was concentrated and the residue was purified by washing with diethyl ether to give 6-(3-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)-2-methylbenzo[d]thiazole (50 mg, 76%) as an off-white solid. LC-MS, $[M+H]^+$=662.2, (Method C: $t_R$=2.45).

Step 3: Synthesis of (2R,3R,4S,5R,6S)-2-(hydroxymethyl)-5-methoxy-6-(4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol: A solution of 6-(3-((4aR,6S,7R,8R,8aR)-7-methoxy-2-phenyl-8-(4-(3,4,5-trifluorophenyl)-1H-1,2,3-triazol-1-yl)hexahydropyrano[3,2-d][1,3]dioxin-6-yl)-4H-1,2,4-triazol-4-yl)-2-methylbenzo[d]thiazole (50 mg, 0.076 mmol) in 70% aq AcOH (10 mL) was heated at 70° C. for 16 h. The reaction mixture was concentrated under reduced pressure and the residue was purified by HPLC (Method P) to afford (2R,3R,4S,5R,6S)-2-(hydroxymethyl)-5-methoxy-6-(4-(2-methylbenzo[d]thiazol-6-yl)-4H-1,2,4-triazol-3-yl)-4-(4-(3,4,5-trifluorophenyl)-1H-1,2,3-triazol-1-yl)tetrahydro-2H-pyran-3-ol (Example 282) (8.6 mg, 19%). LC-MS, $[M+H]^+$=574.2, (Method C: $t_R$=1.889). 1H NMR (400 MHz, METHANOL-d4) δ 8.89 (s, 1H), 8.76 (s, 1H), 8.38 (d, J=2.0 Hz, 1H), 8.12 (d, J=8.5 Hz, 1H), 7.77-7.67 (m, 3H), 4.98 (dd, J=3.0, 10.5 Hz, 1H), 4.79 (d, J=9.0 Hz, 1H), 4.52 (d, J=9.5 Hz, 1H), 4.09 (d, J=3.0 Hz, 1H), 3.87-3.78 (m, 2H), 3.74-3.69 (m, 1H), 3.01 (s, 3H), 2.92 (s, 3H); hGal3 $IC_{50}$=0.03 uM.

The Examples in the table below were prepared in an analogous fashion to Example 282, substituting methylbenzo[d]thiazol-6-amine with 3,4-dichloroaniline in the synthetic sequence.

| Ex | hGal3 IC50, uM | Structure | LCMS $t_R$ (min) | M + H | Method | 1H NMR |
|---|---|---|---|---|---|---|
| 283 | 0.08 | 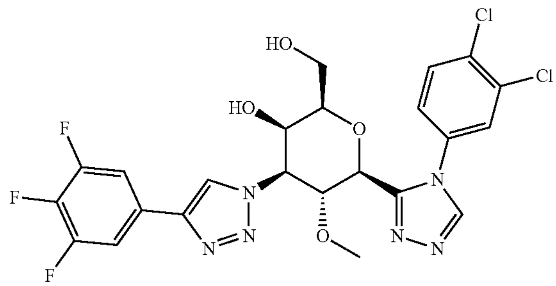 [SMILES: CO[C@@H]1[C@@H](n2cc(-c3cc(F)c(F)c(F)c3)nn2)[C@@H](O)[C@@H](CO)O[C@H]1c1nncn1-c1ccc(Cl)c(Cl)c1] | 1.694 | 571.1 | A | 1H NMR (400 MHz, METHANOL-$d_4$) δ 8.85 (s, 1H), 8.77 (s, 1H), 7.97 (d, J = 2.4 Hz, 1H), 7.84-7.80 (m, 1H), 7.75-7.63 (m, 3H), 5.03 (dd, J = 10.4, 2.8 Hz, 1H), 4.86-4.74 (m, 1H), 4.56-4.53 (m, 1H), 4.11 (d, J = 2.8 Hz, 1H), 3.87-3.71 (m, 3H), 2.99 (s, 3H). |
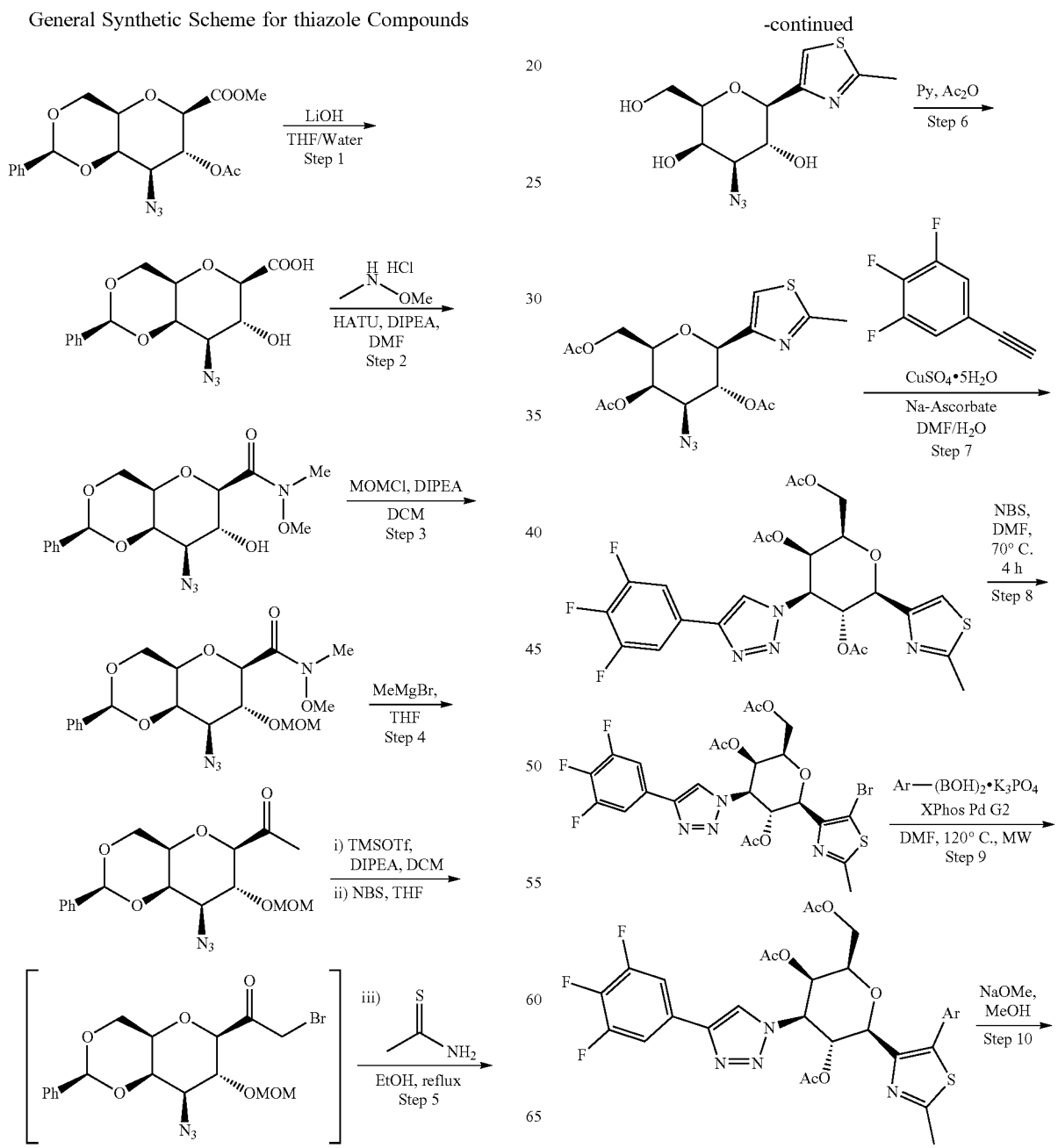
General Synthetic Scheme for thiazole Compounds -continued

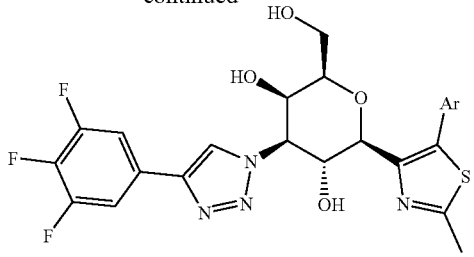

EXAMPLE 284

Preparation of (2S,3R,4R,5R,6R)-2-(5-(3-chlorophenyl)-2-methylthiazol-4-yl)-6-(hydroxymethyl)-4-(4-(3,4,5-trifluorophenyl)-1H-1,2,3-triazol-1-yl)tetrahydro-2H-pyran-3,5-diol

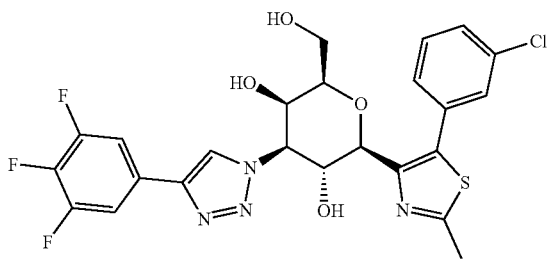 [SMILES: Cc1nc([C@@H]2O[C@H](CO)[C@H](O)[C@H](n3cc(-c4cc(F)c(F)c(F)c4)nn3)[C@H]2O)c(-c2cccc(Cl)c2)s1]

Step 1: Synthesis of (2S,4aR,6R,7R,8R,8aR)-8-azido-7-hydroxy-2-phenylhexahydropyrano[3,2-d][1,3]dioxine-6-carboxylic acid: Prepared in similar fashion as described in Example G1, step 1 using methyl (2S,4aR,6R,7R,8S,8aR)-7-acetoxy-8-azido-2-phenylhexahydropyrano[3,2-d][1,3]dioxine-6-carboxylate (4 g, 10.63 mmol) as the starting material to afford (2S,4aR,6R,7R,8R,8aR)-8-azido-7-hydroxy-2-phenylhexahydropyrano[3,2-d][1,3]dioxine-6-carboxylic acid (3.2 g, 9.96 mmol, 93%) as an off-white solid. LC-MS, [M+18]+=339.0 {Method C: $t_R$=0.80 min, ELSD detector}. 1H NMR (400 MHz, DMSO-d6): δ 7.46-7.33 (m, 5H), 5.65 (s, 1H), 4.34 (d, J=3.2 Hz, 1H), 4.09-4.02 (m, 2H), 3.95 (dd, J=10.0, 9.6 Hz, 1H), 3.75 (d, J=9.6 Hz, 1H), 3.62 (s, 1H), 3.51 (dd, J=10.0, 3.2 Hz, 1H).

Step 2: Synthesis of (2S,4aR,6R,7R,8R,8aR)-8-azido-7-hydroxy-N-methoxy-N-methyl-2-phenylhexahydropyrano[3,2-d][1,3]dioxine-6-carboxamide: To a stirred solution of (2S,4aR,6R,7R,8R,8aR)-8-azido-7-hydroxy-2-phenylhexahydropyrano[3,2-d][1,3]dioxine-6-carboxylic acid (2.01 g, 6.26 mmol) in DMF (30 mL), N,O-dimethylhydroxylamine hydrochloride (0.73 g, 7.51 mmol), DIPEA (3.28 mL, 18.77 mmol) and HATU (3.57 g, 9.38 mmol) were added sequentially at rt and the mixture was stirred for 1 h. The reeaction mixture was diluted with EtOAc (2×100 mL), washed with water, brine solution, dried over sodium sulphate and concentrated to give a crude residue which was purified via chromatography in silica gel (0-100% EtOAc in n-hexane) to yield (2S,4aR,6R,7R,8R,8aR)-8-azido-7-hydroxy-N-methoxy-N-methyl-2-phenylhexahydropyrano[3,2-d][1,3]dioxine-6-carboxamide (1.85 g, 5.06 mmol, 81%) as an off-white solid. LC-MS, [M+18]+=382.2 {Method C: tR=1.57 min, ELSD detector}. 1H NMR (400 MHz, CHLOROFORM-d): δ 7.48-7.54 (m, 2H), 7.31-7.40 (m, 3H), 5.59 (s, 1H), 4.55-4.65 (m, 1H), 4.25-4.32 (m, 2H), 4.17 (d, J=9.0 Hz, 1H), 4.09 (dd, J=12.5, 1.8 Hz, 1H), 3.79 (s, 3H), 3.56 (br. s., 1H), 3.45 (dd, J=10.5, 3.5 Hz, 1H), 3.23 (s, 3H), 3.05 (d, J=2.0 Hz, 1H).

Step 3: Synthesis of (2S,4aR,6R,7R,8R,8aR)-8-azido-N-methoxy-7-(methoxymethoxy)-N-methyl-2-phenylhexahydropyrano[3,2-d][1,3]dioxine-6-carboxamide: To a stirred solution of (2S,4aR,6R,7R,8R,8aR)-8-azido-7-hydroxy-N-methoxy-N-methyl-2-phenylhexahydropyrano[3,2-d][1,3]dioxine-6-carboxamide (3 g, 8.23 mmol) in DCM (50 mL), DIPEA (14.38 mL, 82 mmol), MOM-Cl (3.13 mL, 41.2 mmol) and DMAP (0.101 g, 0.823 mmol) were added sequentially at −10° C. The reaction mixture was allowed to warm to rt and stirred for 36 h. Then it was diluted with DCM (2×1000 mL), washed with 10% aq NaHCO₃ solution, water, brine, dried over sodium sulphate and concentrated. The crude residue was purified by flash chromatography (0-80% EtOAc in n-hexane) to yield (2S,4aR,6R,7R,8R,8aR)-8-azido-N-methoxy-7-(methoxymethoxy)-N-methyl-2-phenylhexahydropyrano[3,2-d][1,3]dioxine-6-carboxamide (2.93 g, 7.17 mmol, 87%) as a pale yellow solid. LC-MS, [M+18]+=426.2 {Method C: tR=2.105 min}. 1H NMR (400 MHz, CHLOROFORM-d): δ 7.55-7.53 (m, 2H), 7.30-7.41 (m, 3H), 5.60 (s, 1H), 4.81 (d, J=6.0 Hz, 1H), 4.72 (d, J=6.5 Hz, 1H), 4.56 (t, J=9.8 Hz, 1H), 4.35 (d, J=3.0 Hz, 1H), 4.30 (dd, J=12.5, 1.5 Hz, 1H), 4.26 (d, J=9.5 Hz, 1H), 4.06 (dd, J=12.5, 1.5 Hz, 1H), 3.75 (s, 3H), 3.50 (s, 1H), 3.42 (s, 3H), 3.31 (dd, J=10.0, 3.0 Hz, 1H), 3.23 (s, 3H).

Step 4: Synthesis of 1-((2S,4aR,6R,7R,8R,8aR)-8-azido-7-(methoxymethoxy)-2-phenylhexahydropyrano[3,2-d][1,3]dioxin-6-yl)ethan-1-one: To a stirred solution of (2S,4aR,6R,7R,8R,8aR)-8-azido-N-methoxy-7-(methoxymethoxy)-N-methyl-2-phenylhexahydropyrano[3,2-d][1,3]dioxine-6-carboxamide (2.7 g, 6.61 mmol) in THF (30 mL), at 0° C., MeMgBr (in diethylether, 4.41 mL, 13.22 mmol) was added drop wise under argon and the mixture was stirred for 30 min at same temperature. The reaction was quenched with sat NH₄Cl and extracted with EtOAc (3×100 mL). The combined organic extract was washed with water, brine, dried over sodium sulphate and concentrated. The residue was purified chromatography (30-40% EtOAc in n-hexane) to yield 1-((2S,4aR,6R,7R,8R,8aR)-8-azido-7-(methoxymethoxy)-2-phenylhexahydropyrano[3,2-d][1,3]dioxin-6-yl)ethan-1-one (1.8 g, 4.95 mmol, 75%) as an off-white solid. LC-MS, [M+18]+=381.0 {Method C: tR=2.42 min}. 1H NMR (400 MHz, CHLOROFORM-d): δ 7.58-7.46 (m, 2H), 7.46-7.30 (m, 3H), 5.60 (s, 1H), 4.78 (d, J=7.0 Hz, 1H), 4.64 (d, J=7.0 Hz, 1H), 4.34 (dt, J=3.4, 1.6 Hz, 1H), 4.30 (d, J=1.5 Hz, 1H), 4.15 (t, J=9.8 Hz, 1H), 4.07 (dd, J=12.5, 1.8 Hz, 1H), 3.74 (d, J=9.5 Hz, 1H), 3.48 (d, J=1.3 Hz, 1H), 3.39 (dd, J=9.9, 3.4 Hz, 1H), 3.35 (s, 3H), 2.35 (s, 3H).

Step 5: Synthesis of (2R,3R,4R,5R,6S)-4-azido-2-(hydroxymethyl)-6-(2-methylthiazol-4-yl)tetrahydro-2H-pyran-3,5-diol: To a stirred solution of 1-((2S,4aR,6R,7R,8R,8aR)-8-azido-7-(methoxymethoxy)-2-phenylhexahydropyrano[3,2-d][1,3]dioxin-6-yl)ethan-1-one (0.75 g, 2.064 mmol) in DCM (10 mL), DIPEA (1.442 mL, 8.26 mmol) and trimethylsilyl trifluoromethanesulfonate (0.746 mL, 4.13 mmol) were added sequentially at 0° C. under argon. The reaction mixture was allowed to warm to rt. After 3 h, another equivalent of trimethylsilyl trifluoromethanesulfonate (0.746 mL, 4.13 mmol) was added at 0° C. After 3 h at rt, the reaction mixture was quenched with aq 10% NaHCO₃ and extracted with DCM (3×50 mL). The combined organic extract was washed with water, brine, dried over sodium sulphate and concentrated. The crude enolate thus obtained was dissolved in THF (15 mL), cooled to 0° C. and NBS (0.735 g, 4.13 mmol) in THF (5 mL) was added and stirred at 0° C. for 30 min. The mixture was diluted with EtOAc (3×50 mL), washed with aq. sodium thiosulphate, water, brine, dried over sodium sulphate concentrated to give the crude acetyl bromide.

To a stirred solution of above acetyl bromide (0.8 g, 1.809 mmol) in EtOH (15 mL), thioacetamide (0.204 g, 2.71 mmol) was added and an the mixture was heated at 80° C. for 12 h. The solvent was removed under reduced pressure to get (2R,3R,4R,5R,6S)-4-azido-2-(hydroxymethyl)-6-(2-methylthiazol-4-yl)tetrahydro-2H-pyran-3,5-diol (0.4 g, 1.39 mmol, 50%, purity: 66%) as a gummy liquid which was used as such in the next step. LC-MS, [M+H]+=287.0, $\{t_R=1.52\ min,\ Method\ E,\ ELSD\}$.

Step 6: Synthesis of (2R,3R,4R,5R,6S)-2-(acetoxymethyl)-4-azido-6-(2-methylthiazol-4-yl)tetrahydro-2H-pyran-3,5-diyl diacetate: To a stirred solution of (2R,3R,4R,5R,6S)-4-azido-2-(hydroxymethyl)-6-(2-methylthiazol-4-yl)tetrahydro-2H-pyran-3,5-diol (0.4 g, 1.397 mmol) in pyridine (5 mL), $Ac_2O$ (3.95 mL, 41.9 mmol) was added and the mixture was stirred at rt for 12 h. The solution was concentrated to dryness and the residue was purified by flash chromatography (40-70% EtOAc in n-hexane) to yield (2R,3R,4R,5R,6S)-2-(acetoxymethyl)-4-azido-6-(2-methylthiazol-4-yl)tetrahydro-2H-pyran-3,5-diyl diacetate (150 mg, 0.364 mmol, 26%) as a gummy liquid. LC-MS, [M+H]+=413.2, $\{t_R=1.05,\ Method\ E\}$.

Step 7: Synthesis of (2R,3R,4R,5R,6S)-2-(acetoxymethyl)-6-(2-methylthiazol-4-yl)-4-(4-(3,4,5-trifluorophenyl)-1H-1,2,3-triazol-1-yOtetrahydro-2H-pyran-3,5-diyl diacetate: Prepared in a similar fashion as described in Example 1, Step 3 using (2R,3R,4R,5R,6S)-2-(acetoxymethyl)-4-azido-6-(2-methylthiazol-4-yl)tetrahydro-2H-pyran-3,5-diyl diacetate (0.15 g, 0.364 mmol) and 5-ethynyl-1,2,3-trifluorobenzene to afford (2R,3R,4R,5R,6S)-2-(acetoxymethyl)-6-(2-methylthiazol-4-yl)-4-(4-(3,4,5-trifluorophenyl)-1H-1,2,3-triazol-1-yl)tetrahydro-2H-pyran-3,5-diyl diacetate (0.15 g, 0.26 mmol, 75%) as an off-white solid. LC-MS, [M+H]+=569.5, $\{t_R=1.23,\ Method\ E\}$.

Step 8: Synthesis of (2R,3R,4R,5R,6S)-2-(acetoxymethyl)-6-(5-bromo-2-methylthiazol-4-yl)-4-(4-(3,4,5-trifluorophenyl)-1H-1,2,3-triazol-1-yl)tetrahydro-2H-pyran-3,5-diyl diacetate: To a stirred solution of (2R,3R,4R,5R,6S)-2-(acetoxymethyl)-6-(2-methylthiazol-4-yl)-4-(4-(3,4,5-trifluorophenyl)-1H-1,2,3-triazol-1-yl)tetrahydro-2H-pyran-3,5-diyl diacetate (0.1 g, 0.176 mmol) in DMF (3 mL), NBS (0.038 g, 0.211 mmol) was added and the mixture was heated at 70° C. for 4 h. The reaction mixture was diluted with EtOAc (3×50 mL), washed with water, brine, dried over sodium sulphate and concentrated. The residue was purified by flash chromatography (40-70% EtOAc in n-hexane) to yield (2R,3R,4R,5R,6S)-2-(acetoxymethyl)-6-(5-bromo-2-methylthiazol-4-yl)-4-(4-(3,4,5-trifluorophenyl)-1H-1,2,3-triazol-1-yl)tetrahydro-2H-pyran-3,5-diyl diacetate (0.1 g, 0.154 mmol, 88%) as an off-white solid. LC-MS, [M+2]+=649.1, $\{t_R=1.35\ min,\ Method\ D\}$ Step 9: A microwave vial was charged with (2R,3R,4R,5R,6S)-2-(acetoxymethyl)-6-(5-bromo-2-methylthiazol-4-yl)-4-(4-(3,4,5-trifluorophenyl)-1H-1,2,3-triazol-1-yl)tetrahydro-2H-pyran-3,5-diyl diacetate (0.065 g, 0.100 mmol), (3-chlorophenyl)boronic acid (0.031 g, 0.201 mmol), potassium phosphate tribasic (0.064 g, 0.301 mmol), DMF (3 mL), water (1 mL) and the mixture was degassed with argon for 5 min. Then XPhos Pd G2 (7.90 mg, 10.04 μmol) was added under argon, the vial was sealed and heated at 120° C. under microwave for 1 h. The mixture was cooled to rt and diluted with EtOAc (3×20 mL), washed with water, brine, dried over sodium sulphate and concentrated.

Step 10: The crude residue from above was dissolved in MeOH (3 mL)/DCM (1 mL), sodium methoxide (25 μL, 0.118 mmol) was added drop wise and the mixture was stirred at rt for 1 h. Then, the solvent was removed under reduced pressure and purified by prep-HPLC Method D to afford Example 284 (2S,3R,4R,5R,6R)-2-(5-(3-chlorophenyl)-2-methylthiazol-4-yl)-6-(hydroxymethyl)-4-(4-(3,4,5-trifluorophenyl)-1H-1,2,3-triazol-1-yl)tetrahydro-2H-pyran-3,5-diol (4 mg, 0.007 mmol, 6%) as off-white solid. LC-MS, [M+H]+=553, {Method C: $t_R$=2.41 min}. 1H NMR (400 MHz, METHANOL-d4): δ 8.56 (s, 1H), 7.75-7.32 (m, 6H), 4.94-4.87 (m, 2H), 4.50-4.46 (m, 1H), 4.13 (s, 1H), 3.89-3.85 (m, 1H), 3.82-3.69 (m, 2H), 2.77 (s, 3H). hGal-3 $IC_{50}$=2.4 uM.

General Synthetic Scheme for Pyrazole Compounds

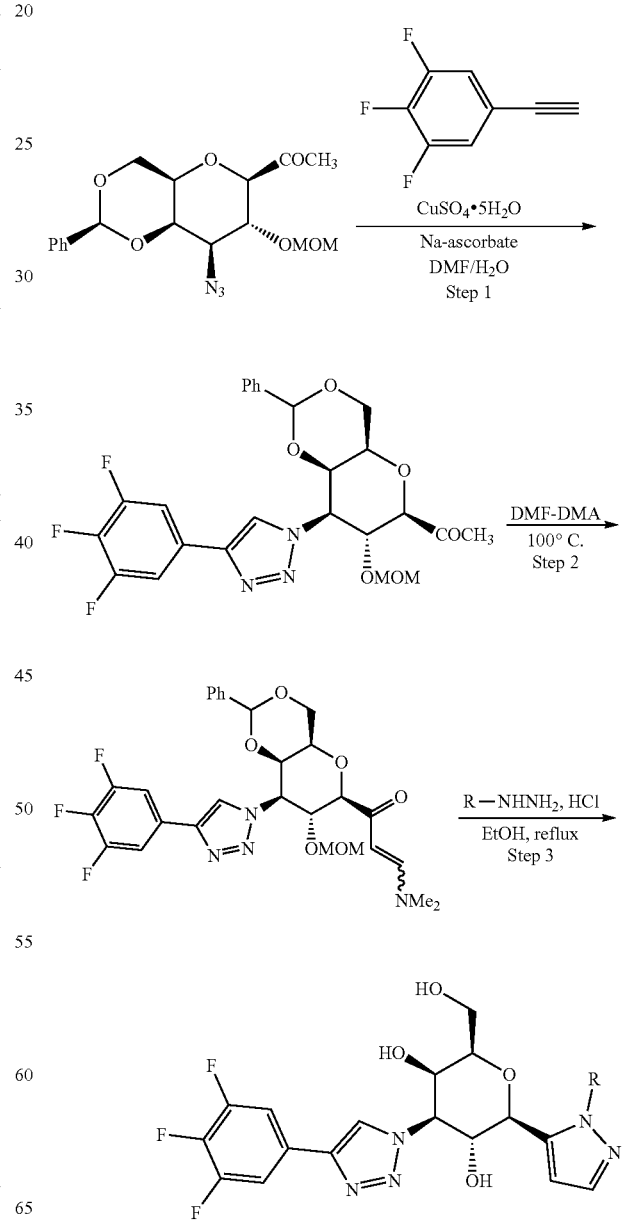

EXAMPLE 285

Preparation of (2S,3R,4R,5R,6R)-2-(1-(3,4-dichlorophenyl)-1H-pyrazol-5-yl)-6-(hydroxymethyl)-4-(4-(3,4,5-trifluorophenyl)-1H-1,2,3-triazol-1-yl)tetrahydro-2H-pyran-3,5-diol

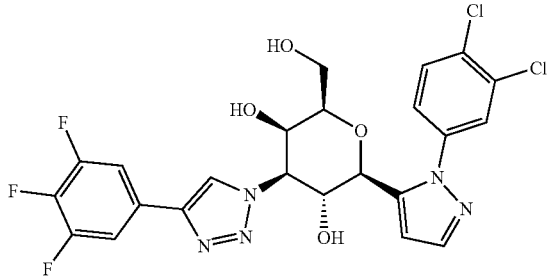 [SMILES: OC[C@H]1O[C@@H](c2ccnn2-c2ccc(Cl)c(Cl)c2)[C@H](O)[C@@H](n2cc(-c3cc(F)c(F)c(F)c3)nn2)[C@H]1O]

Step 1: Synthesis of 1-((2S,4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-yl)ethan-1-one: Prepared in a similar fashion as described in Example 1, Step 3 using of 1-((2S 4aR,6R,7R,8R,8aR)-8-azido-7-(methoxymethoxy)-2-phenylhexahydropyrano[3,2-d][1,3]dioxin-6-yl)ethan-1-one (0.7 g, 1.926 mmol) and 5-ethynyl-1,2,3-trifluorobenzene to afford 1-((4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-yl)ethan-1-one (1 g, 1.92 mmol, 100%). LC-MS, [M+H]+=520.0 {$t_R$=3.17, Method C}. 1H NMR (400 MHz, CHLOROFORM-d): δ 8.08-7.98 (m, 1H), 7.50-7.34 (m, 7H), 5.51 (s, 1H), 5.12 (dd, J=3.5, 10.5 Hz, 1H), 4.55-4.34 (m, 4H), 4.21-4.06 (m, 2H), 3.99 (d, J=9.5 Hz, 1H), 3.85-3.67 (m, 1H), 2.71 (s, 3H), 2.41 (s, 3H).

Step 2: Synthesis of (E)-3-(dimethylamino)-1-((2S,4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-yl)prop-2-en-1-one: A mixture of 1-((2S,4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-yl)ethan-1-one (0.3 g, 0.578 mmol) and DMF-DMA (0.773 ml, 5.78 mmol) was heated at 100° C. for 3 h. The mixture was concentrated to dryness and the residue was taken as such for next step without further purification. LC-MS, [M+H]+=520.0 {$t_R$=3.17, Method C}.

Step 3: To a solution of (E)-3-(dimethylamino)-1-((2S,4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-yl)prop-2-en-1-one (40 mg, 0.070 mmol) in EtOH (2 mL), (3,4-dichlorophenyl)hydrazine (30.8 mg, 0.174 mmol) was added at rt and the reaction mixture was refluxed at 85° C. for 14 h. The mixture was concentrated to dryness and the residue was purified by prep-HPLC Method A to afford Example 285 (2S,3R,4R,5R,6R)-2-(1-(3,4-dichlorophenyl)-1H-pyrazol-5-yl)-6-(hydroxymethyl)-4-(4-(3,4,5-trifluorophenyl)-1H-1,2,3-triazol-1-yl)tetrahydro-2H-pyran-3,5-diol (12.7 mg, 0.023 mmol, 32%) as off-white solid. 1H NMR (400 MHz, METHANOL-d4): δ 8.59 (s, 1H), 7.92 (s, 1H), 7.77 (s, 1H), 7.74-7.58 (m,4H), 6.81 (d, J=1.0 Hz, 1H), 4.94-4.89 (m, 1H), 4.79 (d, J=9.5 Hz, 1H), 4.44 (d, J=9.5 Hz, 1H),4.17 (s, 1H), 3.92-3.77 (m, 2H), 3.76-3.65 (m, 1H). LC-MS, [M]+= 556.2, {Method C: $t_R$=1.57 and Method D: $t_R$=1.57}. hGal-3 $IC_{50}$=0.445 uM.

The Examples in the table below were prepared in an analogous fashion to Example 285, substituting (3,4-dichlorophenyl)hydrazine with the appropriate hydrazine in the synthetic sequence.

| Ex | hGal3 IC50, uM | Structure | LCMS $t_R$ (min) | M + H | Method | 1H NMR |
|---|---|---|---|---|---|---|
| 286 | 10 | (structure shown) | 1.03<br>1.03 | 4.26<br>4.26 | C<br>D | ¹H NMR (400 MHz, METHANOL-d₄) δ 8.58 (s, 1H), 7.65 (dd, J = 8.7, 6.7 Hz, 2 H), 7.44 (d, J = 2.0 Hz, 1H), 6.48 (d, J = 2.0 Hz, 1H), 4.97 (dd, J = 10.3, 2.8 Hz, 1 H), 4.69-4.64 (m, 2 H), 4.20 (d, J = 2.8 Hz, 1 H), 4.01-3.92 (m, 4 H), 3.82-3.67 (m, 2 H). |

Some pyrazole analogs can be further derivatized as follows:

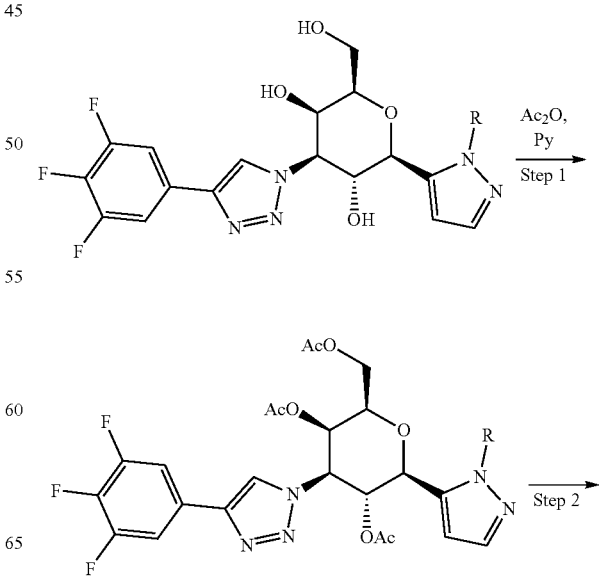

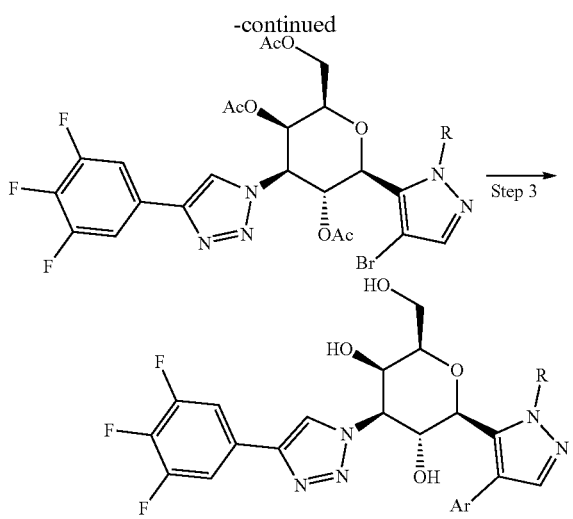

EXAMPLE 287

Preparation of (2S,3R,4R,5R,6R)-2-(4-(3-chlorophenyl)-1-methyl-1H-pyrazol-5-yl)-6-(hydroxymethyl)-4-(4-(3,4,5-trifluorophenyl)-1H-1,2,3-triazol-1-yl)tetrahydro-2H-pyran-3,5-diol

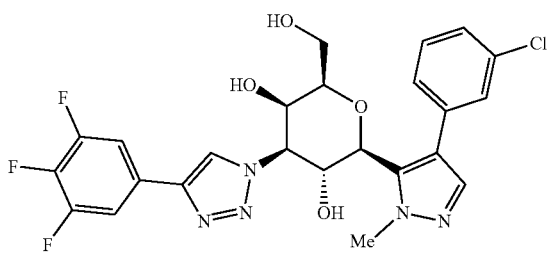 [SMILES: Cn1ncc(-c2cccc(Cl)c2)c1[C@@H]1O[C@H](CO)[C@H](O)[C@H](n2cc(-c3cc(F)c(F)c(F)c3)nn2)[C@H]1O]

Step 1: Synthesis of (2R,3R,4R,5R,6S)-2-(acetoxymethyl)-6-(1-methyl-1H-pyrazol-5-yl)-4-(4-(3,4,5-trifluorophenyl)-1H-1,2,3-triazol-1-yl)tetrahydro-2H-pyran-3,5-diyl diacetate: Prepared in similar fashion as described in Example 27, step 6, from (2R,3R,4R,5R,6S)-2-(hydroxymethyl)-6-(1-methyl-1H-pyrazol-5-yl)-4-(4-(3,4,5-trifluorophenyl)-1H-1,2,3-triazol-1-yl)tetrahydro-2H-pyran-3,5-diol (120 mg, 0.282 mmol) to afford (2R,3R,4R,5R,6S)-2-(acetoxymethyl)-6-(1-methyl-1H-pyrazol-5-yl)-4-(4-(3,4,5-trifluorophenyl)-1H-1,2,3-triazol-1-yl)tetrahydro-2H-pyran-3,5-diyl diacetate (0.11 g, 0.2 mmol, 71%). LC-MS, [M+H]+= 552.0, {Method C: $t_R$=2.60}.

Step 2: Synthesis of (2R,3R,4R,5R,6S)-2-(acetoxymethyl)-6-(4-bromo-1-methyl-1H-pyrazol-5-yl)-4-(4-(3,4,5-trifluorophenyl)-1H-1,2,3-triazol-1-yl)tetrahydro-2H-pyran-3,5-diyl diacetate: To a solution of (2R,3R,4R,5R,6S)-2-(acetoxymethyl)-6-(1-methyl-1H-pyrazol-5-yl)-4-(4-(3,4,5-trifluorophenyl)-1H-1,2,3-triazol-1-yl)tetrahydro-2H-pyran-3,5-diyl diacetate (30 mg, 0.054 mmol) in THF (2 mL), NBS (9.68 mg, 0.054 mmol) was added at 0° C. Then, the reaction mixture was allowed to reach rt and stirred for 1 h. The reaction mixture was diluted with EtOAc (2×50 mL), washed with water, brine solution, dried over sodium sulphate and concentrated. The residue was purified by flash chromatography (25-40% EtOAc in n-hexane) to yield 2R,3R,4R,5R,6S)-2-(acetoxymethyl)-6-(4-bromo-1-methyl-1H-pyrazol-5-yl)-4-(4-(3,4,5-trifluorophenyl)-1H-1,2,3-triazol-1-yOtetrahydro-2H-pyran-3,5-diyl diacetate (15 mg, 0.023 mmol, 44%). LC-MS, [M+2]+=632, {Method C: tR=2.96}

Step 3: Prepared in a similar fashion as described in Example 27, step 9 using (2R,3R,4R,5R,6S)-2-(acetoxymethyl)-6-(4-bromo-1-methyl-1H-pyrazol-5-yl)-4-(4-(3,4,5-trifluorophenyl)-1H-1,2,3-triazol-1-yl) tetrahydro-2H-pyran-3,5-diyl diacetate (30 mg, 0.048 mmol) and 3-chlorophenyl)boronic acid as the reactants. The resulting crude was purified by prep-HPLC Method A to afford Example 287 (2S,3R,4R,5R,6R)-2-(4-(3-chlorophenyl)-1-methyl-1H-pyrazol-5-yl)-6-(hydroxymethyl)-4-(4-(3,4,5-trifluorophenyl)-1H-1,2,3-triazol-1-yl)tetrahydro-2H-pyran-3,5-diol (3.1 mg, 5.78 μmol, 12%). LC-MS, [M+H]+= 563.2, {Method A: $t_R$=1.63 and Method B: $t_R$=1.63}. 1H NMR (400 MHz, METHANOL-d4): δ 8.55 (br. s 1H), 7.69 (d, J=7.1 Hz, 1H),7.68 (d, J=6.1 Hz, 2H), 7.60 (s, 1H), 7.57 (d, J=7.8 Hz, 1H), 7.42-7.36 (m, 1H), 7.36-7.30 (m,1H), 4.95 (d, J=8.6 Hz, 1H), 4.81 (s, 1H), 4.23 (s, 2H), 4.20 (s, 3H), 3.89-3.80 (m, 2H), 3.75 (d, J=7.6 Hz, 1H). hGal-3 $IC_{50}$=10 uM.

General Synthetic Scheme for Isoxazole Compounds

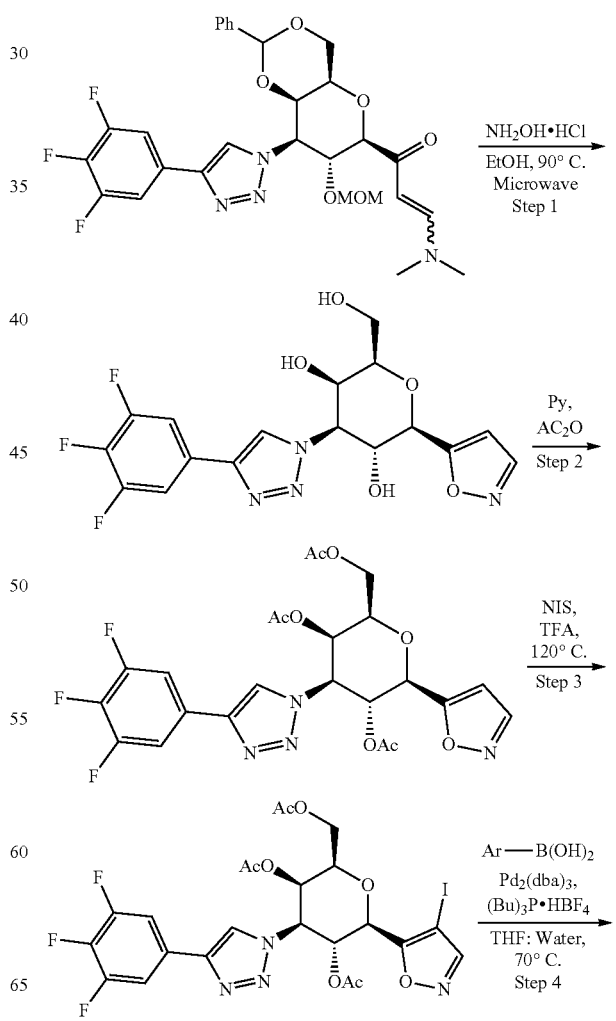

-continued

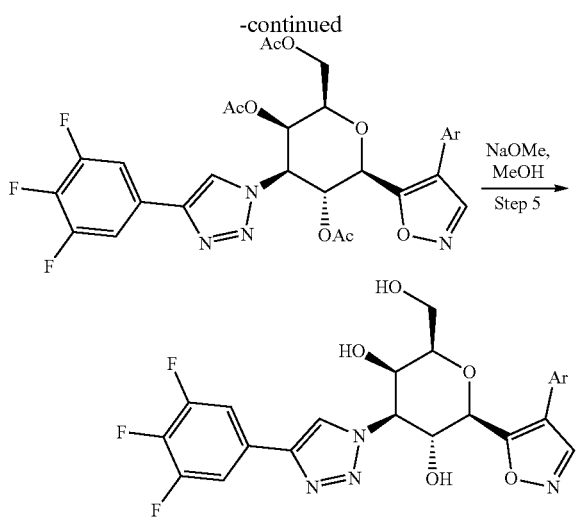

EXAMPLE 288

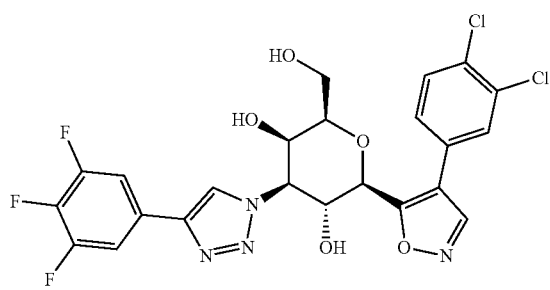 [SMILES: OC[C@H]1O[C@@H](c2oncc2-c2ccc(Cl)c(Cl)c2)[C@H](O)[C@@H](n2cc(-c3cc(F)c(F)c(F)c3)nn2)[C@H]1O]

Step 1: Synthesis of (2R,3R,4S,5R,6R)-2-(hydroxymethyl)-6-(isoxazol-5-yl)-4-(4-(3,4,5-trifluorophenyl)-1H-1,2,3-triazol-1-yl)tetrahydro-2H-pyran-3,5-diol: A microwave vial was charged with (E)-3-(dimethylamino)-1-((4aR,6R,7R,8R,8aR)-7-(methoxymethoxy)-2-phenyl-8-(4-(3,4,5-trifluorophenyl)-1H-1,2,3-triazol-1-yl)hexahydropyrano[3,2-d][1,3]dioxin-6-y0prop-2-en-1-one (400 mg, 0.696 mmol), EtOH (15 mL), hydroxylamine hydrochloride (242 mg, 3.48 mmol) and heated at 90° C. for 40 min under microwave. The reaction mixture was concentrated to and purified via chromatography in silica gel (0-10% MeOH in CHCl$_3$) to yield (2R,3R,4S,5R,6R)-2-(hydroxymethyl)-6-(isoxazol-5-yl)-4-(4-(3,4,5-trifluorophenyl)-1H-1,2,3-triazol-1-yl)tetrahydro-2H-pyran-3,5-diol (500 mg, 1.213 mmol, 87%) as off white solid. LC-MS, [M+H]+=413.2, {tR=0.88, Method E}

Step 2: Synthesis of (2R,3R,4S,5R,6R)-2-(acetoxymethyl)-6-(isoxazol-5-yl)-4-(4-(3,4,5-trifluorophenyl)-1H-1,2,3-triazol-1-yl)tetrahydro-2H-pyran-3,5-diyl diacetate: Prepared in a similar fashion as described in Example 282, step 6 using (2R,3R,4S,5R,6R)-2-(hydroxymethyl)-6-(isoxazol-5-yl)-4-(4-(3,4,5-trifluorophenyl)-1H-1,2,3-triazol-1-yl)tetrahydro-2H-pyran-3,5-diol (500 mg, 1.213 mmol) as starting material to afford (2R,3R,4S,5R,6R)-2-(acetoxymethyl)-6-(isoxazol-5-yl)-4-(4-(3,4,5-trifluorophenyl)-1H-1,2,3-triazol-1-yl)tetrahydro-2H-pyran-3,5-diyl diacetate (450 mg, 0.836 mmol, 69%). LC-MS, [M+H]+=539.3, {t$_R$=1.25, Method D}. 1H NMR (400 MHz, CHLOROFORM-d): δ 8.28 (d, J=2.0 Hz, 1H), 7.81 (s, 1H), 7.42-7.39 (m, 2H), 6.45 (d, J=2.0 Hz, 1H), 5.96 (dd, J=11.2, 9.6 Hz, 1H), 5.67 (d, J=3.2 Hz, 1H), 5.28 (dd, J=11.2, 3.2 Hz, 1H), 4.88 (d, J=9.6 Hz, 1H), 4.29-4.26 (m, 1H), 4.22-4.15 (m, 2H), 2.09 (s, 3H), 2.08 (s, 3H), 2.06 (s, 3H).

Step 3: Synthesis of (2R,3R,4S,5R,6R)-2-(acetoxymethyl)-6-(4-iodoisoxazol-5-yl)-4-(4-(3,4,5-trifluorophenyl)-1H-1,2,3-triazol-1-yl)tetrahydro-2H-pyran-3,5-diyl diacetate: To a solution of (2R,3R,4S,5R,6R)-2-(acetoxymethyl)-6-(isoxazol-5-yl)-4-(4-(3,4,5-trifluorophenyl)-1H-1,2,3-triazol-1-yl)tetrahydro-2H-pyran-3,5-diyl diacetate (300 mg, 0.557 mmol) in TFA (2 mL), was added NIS (201 mg, 0.891 mmol) and heated at 120° C. for 20 min under microwave. The mixture was concentrated to dryness, diluted with EtOAc (2×50 mL), and washed with sat. sodium thiosulphate solution, water, brine solution, dried over sodium sulphate and concentrated. The residue was purified by flash chromatography (0-40% EtOAc in n-hexane) to yield (2R,3R,4S,5R,6R)-2-(acetoxymethyl)-6-(4-iodoisoxazol-5-yl)-4-(4-(3,4,5-trifluorophenyl)-1H-1,2,3-triazol-1-yl)tetrahydro-2H-pyran-3,5-diyl diacetate (100 mg, 0.151 mmol, 27%) as off white solid. LC-MS, [M+H]+=605.0, {Method C: t$_R$=2.96}

Step 4: Synthesis of ((2R,3R,4S,5R,6R)-2-(acetoxymethyl)-6-(4-(3,4-dichlorophenyl)isoxazol-5-yl)-4-(4-(3,4,5-trifluorophenyl)-1H-1,2,3-triazol-1-yl)tetrahydro-2H-pyran-3,5-diyl diacetate: To a solution of (2R,3R,4S,5R,6R)-2-(acetoxymethyl)-6-(4-iodoisoxazol-5-yl)-4-(4-(3,4,5-trifluorophenyl)-1H-1,2,3-triazol-1-yl)tetrahydro-2H-pyran-3,5-diyl diacetate (40 mg, 0.060 mmol) in THF (0.5 mL), (3,4-dichlorophenyl)boronic acid (25.3 mg, 0.132 mmol) was added followed by sodium bicarbonate (35.4 mg, 0.421 mmol) in water (0.5 mL) and the mixture was degassed with argon for 10 min. Then Pd$_2$(dba)$_3$ (11.03 mg, 0.012 mmol) and tri-tert-butylphosphonium tetrafluoroborate (8.73 mg, 0.030 mmol) were added sequentially and teh mixture was heated at 75° C. for 1 h under microwave. The reaction mixture was diluted with EtOAc (2×20 mL), washed with water, brine solution, dried over sodium sulphate and concentrated. The residue was purified by flash chromatography (0-40% EtOAc in n-hexane) to yield (2R,3R,4S,5R,6R)-2-(acetoxymethyl)-6-(4-(3,4-dichlorophenyl)isoxazol-5-yl)-4-(4-(3,4,5-trifluorophenyl)-1H-1,2,3-triazol-1-yl)tetrahydro-2H-pyran-3,5-diyl diacetate (25 mg, 0.037 mmol, 61%) as off white solid. LC-MS, [M+H]+=684.5, {Method C: tR=3.56}.

Step 5: Prepared in a similar fashion as described in Example 15, step 4 using (2R,3R,4S,5R,6R)-2-(acetoxymethyl)-6-(4-(3,4-dichlorophenyl)isoxazol-5-yl)-4-(4-(3,4,5-trifluorophenyl)-1H-1,2,3-triazol-1-yl)tetrahydro-2H-pyran-3,5-diyl diacetate (25 mg, 0.037 mmol) as starting material. The resulting crude was purified by prep-HPLC Method A to afford Example 288 (2R,3R,4S,5R,6R)-2-(4-(3,4-dichlorophenyl)isoxazol-5-yl)-6-(hydroxymethyl)-4-(4-(3,4,5-trifluorophenyl)-1H-1,2,3-triazol-1-yl)tetrahydro-2H-pyran-3,5-diol (5.9 mg, 10.37 μmol, 28%). LC-MS, [M+2]+=559.1, {Method A: t$_R$=1.50 and Method B: t$_R$=1.85}. 1H NMR (400 MHz, METHANOL-d4): δ 8.54 (s, 1H), 8.10 (d, J=2.0 Hz, 1H), 7.76-7.61 (m, 4H), 7.48 (d, J=9.0 Hz, 1H), 4.99 (dd, J=10.8, 2.8 Hz, 1H), 4.74 (d, J=9.6 Hz, 1H), 4.59 (dd, J=10.8, 9.6 Hz, 1H), 4.24 (d, J=2.8 Hz, 1H), 4.01-3.94 (m, 1H), 3.87-3.80 (m, 1H), 3.79-3.72 (m, 1H). hGal-3 IC$_{50}$=4.0 uM.

The Examples in the table below were prepared in an analogous fashion to Example 288, substituting (3,4-dichlorophenyl)boronic acid with the appropriate arylboronic acid in the synthetic sequence.

| Ex | hGal3 IC50, uM | Structure | LCMS $t_R$ (min) | M + H | Method |
|---|---|---|---|---|---|
| 289 | 8.1 | 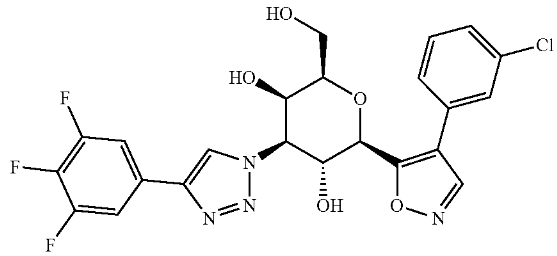 [SMILES: OC[C@H]1O[C@@H](c2oncc2-c2cccc(Cl)c2)[C@H](O)[C@@H](n2cc(-c3cc(F)c(F)c(F)c3)nn2)[C@H]1O] | 1.36 | 523.2 | A |
EXAMPLE 290
Preparation of (2S,3R,4R,5R,6R)-2-(5-(3-chlorophenyl)-1H-1,2,3-triazol-4-yl)-6-(hydroxymethyl)-4-(4-(3,4,5-trifluorophenyl)-1H-1,2,3-triazol-1-yl)tetrahydro-2H-pyran-3,5-diol
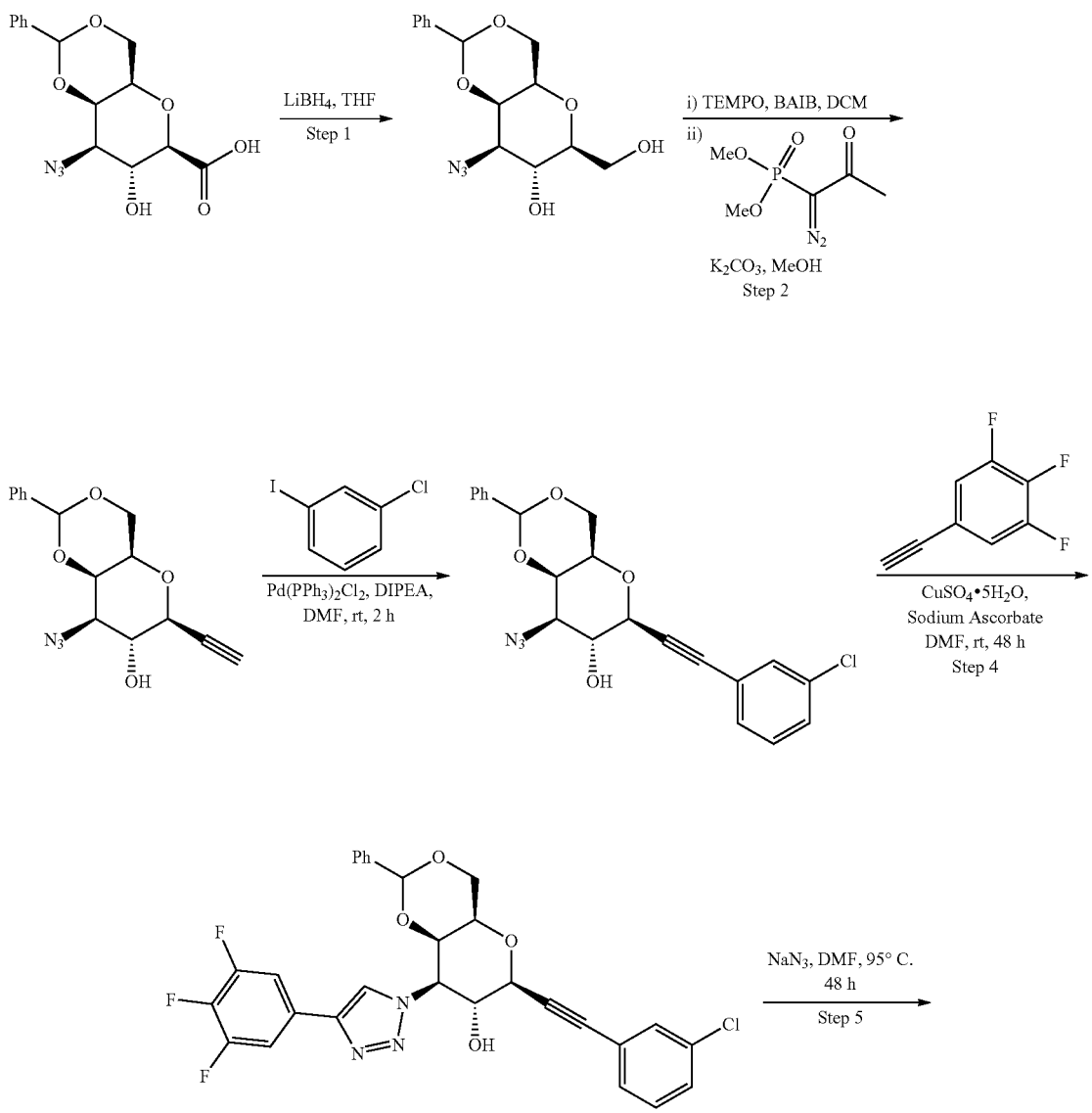

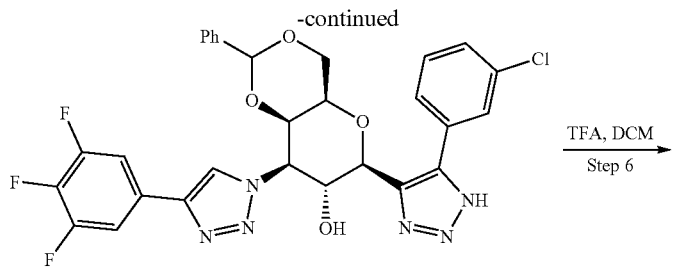

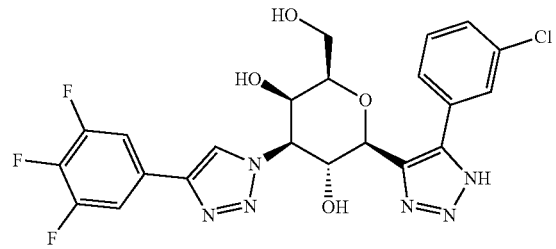

Step 1: Synthesis of (2S,4aR,6S,7R,8R,8aR)-8-azido-6-(hydroxymethyl)-2-phenylhexahydropyrano[3,2-d][1,3]dioxin-7-ol: To a solution of (2S,4aR,6R,7R,8S,8aR)-methyl 7-acetoxy-8-azido-2-phenylhexahydropyrano[3,2-d][1,3]dioxine-6-carboxylate (2 g, 5.30 mmol) in THF (50 mL), LiBH$_4$ (5.30 mL, 10.60 mmol) was added at 0° C. The reaction mixture was allowed to warm to rt and stirred for 12 h. The reaction mixture was cooled to 0° C., quenched with sat.NH$_4$Cl solution drop wise and stirred for 15 min. The solution was diluted with EtOAc (2×100 mL), washed with water, brine solution, dried over sodium sulphate and concentrated. The residue was purified by flash chromatography (0-10% MeOH in CHCl$_3$) to yield (2S,4aR,6S,7R,8R,8aR)-8-azido-6-(hydroxymethyl)-2-phenylhexahydropyrano[3,2-d][1,3]dioxin-7-ol (1.2 g, 3.90 mmol, 73%) as an off-white solid. LC-MS, [M+18]$^+$=325.1, {Method C: t$_R$=1.26}. 1H NMR (400 MHz, DMSO-d6): δ 7.48-7.27 (m, 5H), 5.64 (s, 1H), 5.49 (d, J=6.6 Hz, 1H, —OH), 4.64 (t, J=5.9 Hz, 1H, —OH), 4.30 (dd, J=3.4, 0.7 Hz, 1H), 4.11-4.00 (m, J=11.2 Hz, 2H), 3.79-3.72 (m, 1H), 3.70-3.61 (m, 1H), 3.55-3.43 (m, 3H), 3.28-3.21 (m, 1H).

Step 2: Synthesis of (2S,4aR,6S,7R,8R,8aR)-8-azido-6-ethynyl-2-phenylhexahydropyrano[3,2-d][1,3]dioxin-7-ol: To a stirred solution of (2S,4aR,6S,7R,8R,8aR)-8-azido-6-(hydroxymethyl)-2-phenylhexahydropyrano[3,2-d][1,3]dioxin-7-ol (0.75 g, 2.441 mmol) in DCM (15 mL) at 0° C., iodobenzene diacetate (1.179 g, 3.66 mmol) and TEMPO (0.076 g, 0.488 mmol) were added sequentially. Then, the reaction mixture was allowed to warm to rt and stirred for 6 h. The reaction mixture was diluted with DCM (100 mL), washed with sodium thiosulphate solution, NaHCO$_3$ solution, water, brine and dried over sodium sulphate. The solvent was removed under reduced pressure to get the corresponding crude aldehyde which was taken as such for next step without further purification. The crude aldehyde was dissolved in methanol (15 mL) and K$_2$CO$_3$ (1.012 g, 7.32 mmol) was added and the mixture was cooled to 0° C. Dimethyl (1-diazo-2-oxopropyl)phosphonate (0.938 g, 4.88 mmol) in MeOH (3 mL) was added drop wise and the mixture was allowed to warm to rt and stirred for 12 h. The solvent was removed under reduced pressure to give crude residue which was diluted with DCM (2×100 mL), washed with water, brine solution, dried over sodium sulphate and concentrated. The residue was purified by flash chromatography (30-80% EtOAc in n-hexane) to yield (2S,4aR,6S,7R,8R,8aR)-8-azido-6-ethynyl-2-phenylhexahydropyrano[3,2-d][1,3]dioxin-7-ol (0.15 g, 0.498 mmol, 20%) as an off-white solid. 1H NMR (400 MHz, CHLOROFORM-d): δ 7.54-7.50 (m, 2H), 7.40-7.33 (m, 3H), 5.59 (s, 1H), 4.36 (dd, J=12.6, 1.6 Hz, 1H), 4.29 (d, J=3.4 Hz, 1H), 4.22-4.15 (m, J=3.4 Hz, 1H), 4.08-4.01 (m, 2H), 3.49-3.46 (m, 1H), 3.35 (dd, J=10.0, 3.4 Hz, 1H), 2.61 (d, J=2.2 Hz, 1H), 2.47 (d, J=3.2 Hz, 1H, —OH).

Step 3: Synthesis of (2S,4aR,6S,7R,8R,8aR)-8-azido-6-((3-chlorophenyl)ethynyl)-2-phenylhexahydropyrano[3,2-d][1,3]dioxin-7-ol: To a stirred solution of (2S,4aR,6S,7R,8R,8aR)-8-azido-6-ethynyl-2-phenylhexahydropyrano[3,2-d][1,3]dioxin-7-ol (0.025 g, 0.083 mmol) in DMF (1 mL), 1-chloro-3-iodobenzene (0.024 g, 0.100 mmol), triethylamine (0.035 mL, 0.249 mmol), were added sequentially and reaction mixture was degassed with argon for 5 min. Then, bis(triphenylphosphine)palladium(II) chloride (2.91 mg, 4.15 μmol) and copper(I) iodide (0.790 mg, 4.15 μmol) were added sequentially under argon and the mixture was stirred at rt for 4 h. The solvent was evaporated and the residue was purified by flash chromatography (40-60% EtOAc in n-hexane) to give (4aR,6S,7R,8R,8aR)-8-azido-6-((3-chlorophenyl)ethynyl)-2-phenylhexahydropyrano[3,2-d][1,3]dioxin-7-ol (20 mg, 0.049 mmol, 59%) as a pale yellow solid. LC-MS, [M+18]$^+$=429.3, {Method D: t$_R$=1.37}. $^1$H NMR (400 MHz, CHLOROFORM-d): δ 7.62-7.48 (m, 3H), 7.42-7.30 (m, 6H), 5.62 (s, 1H), 4.43-4.35 (m, 1H), 4.33 (d, J=3.7 Hz, 1H), 4.29-4.23 (m, 2H), 4.09 (dd, J=12.7, 1.7 Hz, 1H), 3.54 (d, J=1.2 Hz, 1H), 3.46-3.33 (m, 1H), 2.50 (d, J=2.2 Hz, 1H).

Step 4: Synthesis of (2S,4aR,6S,7R,8R,8aR)-6-((3-chlorophenyl)ethynyl)-2-phenyl-8-(4-(3,4,5-trifluorophenyl)-1H-1,2,3-triazol-1-yl)hexahydropyrano[3,2-d][1,3]dioxin-7-ol: To a stirred solution of (2S,4aR,6S,7R,8R,8aR)-8-azido-6-((3-chlorophenyl)ethynyl)-2-phenylhexahydropyrano[3,2-d][1,3]dioxin-7-ol (0.02 g, 0.049 mmol) in DMF (1 mL) & water (0.3 mL), 5-ethynyl-1,2,3-trifluorobenzene (9.86 mg, 0.063 mmol), sodium ascorbate (10.58 mg, 0.053 mmol) and copper (II) sulfate pentahydrate (10.91 mg, 0.044 mmol) were added sequentially and the mixture was stirred for 24 h at rt. The reaction mixture was diluted with DCM/water (1:1, 20 mL) and stirred for 30 min. Then filtered through celite pad, washed with excess DCM and the aqueous layer was separated and extracted with DCM (2×20 mL). The combined organic extract was washed with brine, dried over sodium sulphate and concentrated. The residue was purified by flash chromatography (70-90% EtOAc in n-hexane) to yield (2S,4aR,6S,7R,8R,8aR)-6-((3-chlorophenyl)ethynyl)-2-phenyl-8-(4-(3,4,5-trifluorophenyl)-1H-1,2,3-triazol-1-yl) hexahydropyrano[3,2-d][1,3]dioxin-7-ol (0.025 g, 0.044 mmol, 91%) as off-white solid. LC-MS, [M+1]$^+$=568.3, {Method D: $t_R$=1.52}

Step 5: Synthesis of (2S,4aR,6S,7R,8R,8aR)-6-(5-(3-chlorophenyl)-1H-1,2,3-triazol-4-yl)-2-phenyl-8-(4-(3,4,5-trifluorophenyl)-1H-1,2,3-triazol-1-yl)hexahydropyrano[3,2-d][1,3]dioxin-7-ol: To a stirred solution of (2S,4aR,6S,7R,8R,8aR)-6-((3-chlorophenyl)ethynyl)-2-phenyl-8-(4-(3,4,5-trifluorophenyl)-1H-1,2,3-triazol-1-yl)hexahydropyrano[3,2-d][1,3]dioxin-7-ol (0.02 g, 0.035 mmol) in DMF (2 mL), sodium azide (3.43 mg, 0.053 mmol) was added and the mixture was heated at 80° C. for 30 h. The reaction mixture was diluted with EtOAc (3×30 mL), washed with water, brine and dried over sodium sulphate. The solvent was removed under reduced pressure and the residue was taken as such for next step without further purification. LC-MS, [M+1]$^+$=611.4, {Method D: $t_R$=1.43}.

Step 6: To a stirred solution of (2S,4aR,6S,7R,8R,8aR)-6-(4-(3-chlorophenyl)-1H-1,2,3-triazol-5-yl)-2-phenyl-8-(4-(3,4,5-trifluorophenyl)-1H-1,2,3-triazol-1-yl)hexahydropyrano[3,2-d][1,3]dioxin-7-ol (0.02 g, 0.033 mmol) in DCM (2 mL), trifluoroacetic acid (0.126 mL, 1.637 mmol) was added at rt and stirred for 1 h. The mixture was concentrated to dryness and purified by Prep-HPLC Method-A to afford Example 290 (2S,3R,4R,5R,6R)-2-(4-(3-chlorophenyl)-1H-1,2,3-triazol-5-yl)-6-(hydroxymethyl)-4-(4-(3,4,5-trifluorophenyl)-1H-1,2,3-triazol-1-yl)tetrahydro-2H-pyran-3,5-diol (3 mg, 0.006 mmol, 17%). LC-MS, [M+H]$^+$=523.2, {Method A: $t_R$=1.41 and Method B: $t_R$=1.44}. 1H NMR (400 MHz, METHANOL-d4): δ 8.55 (s, 1H), 7.94-7.91 (m, 1H), 7.89-7.79 (m, 1H), 7.72-7.58 (m, 2H), 7.55-7.39 (m, 2H), 5.05-4.91 (m, 2H), 4.75 (d, J=9.0 Hz, 1H), 4.26 (d, J=2.0 Hz, 1H), 4.05-3.96 (m, 1H), 3.88-3.81 (m, 1H), 3.81-3.77 (m, 1H). hGal-3 IC$_{50}$=3.0 uM.

EXAMPLE 291

Preparation of (2R,3R,4S,5R,6R)-2-(5-chloro-1H-indol-1-yl)-6-(hydroxymethyl)-4-(4-(3,4,5-trifluorophenyl)-1H-1,2,3-triazol-1-yl)tetrahydro-2H-pyran-3,5-diol

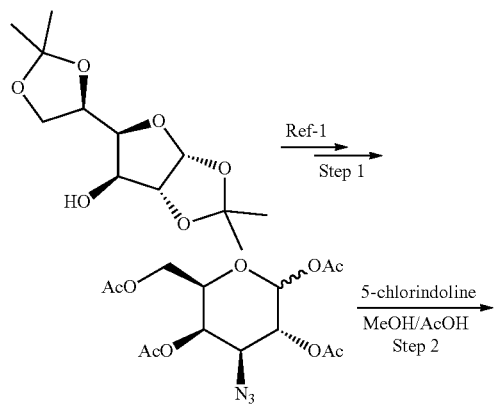

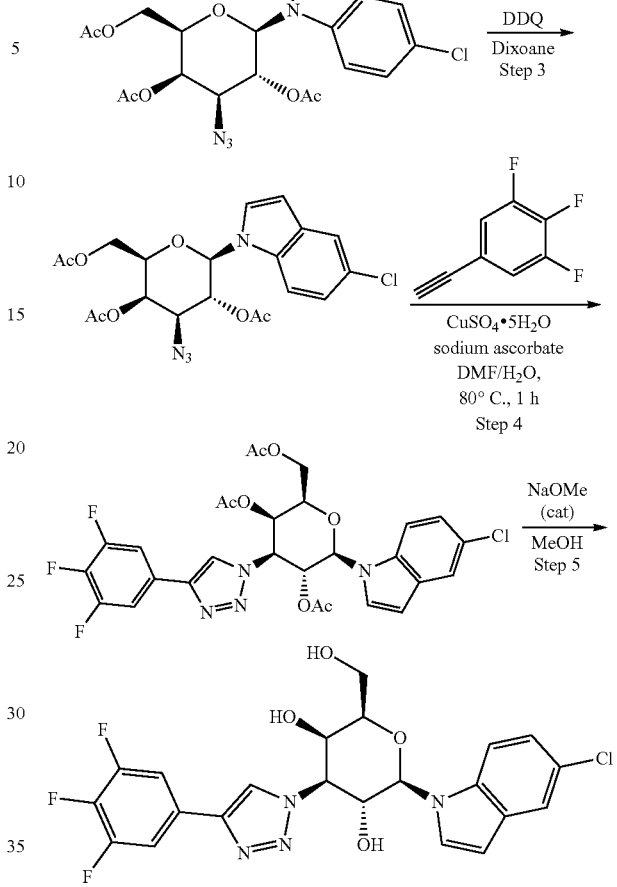

Step 1: Synthesis of (3R,4S,5R,6R)-6-(acetoxymethyl)-4-azidotetrahydro-2H-pyran-2,3,5-triyltriacetate: Synthesized from (3aR,5S,6S,6aR)-5-((R)-2,2-dimethyl-1,3-dioxolan-4-yl)-2,2-dimethyltetrahydrofuro[2,3-d][1,3]dioxol-6-ol by following the literature procedure {Ref: Carbohydr. Res. 251 (1994) 33-67}.

Step 2: Synthesis of (2R,3R,4S,5R,6R)-2-(acetoxymethyl)-4-azido-6-(5-chloroindolin-1-yl)tetrahydro-2H-pyran-3,5-diyl diacetate: To a mixture of (3R,4S,5R,6R)-6-(acetoxymethyl)-4-azidotetrahydro-2H-pyran-2,3,5-triyltriacetate (0.2 g, 0.536 mmol) and 5-chloroindoline (0.082 g, 0.536 mmol) in MeOH (2 mL), acetic acid (0.215 mL, 3.75 mmol) was added and the mixture was stirred at rt for 16 h. The solvent was removed under reduced pressure and the residue was purified by flash chromatography (0-100% EtOAc in n-hexane) to yield (2R,3R,4S,5R)-2-(acetoxymethyl)-4-azido-6-(5-chloroindolin-1-yl)tetrahydro-2H-pyran-3,5-diyldiacetate (0.16 g, 0.343 mmol, 64%) as off white solid. LC-MS, [M+H]+=467.3, {Method D: $t_R$=1.46 min}.

Step 3: Synthesis of (2R,3R,4S,5R,6R)-2-(acetoxymethyl)-4-azido-6-(5-chloro-1H-indol-1-yl)tetrahydro-2H-pyran-3,5-diyl diacetate: To a stirred solution of (2R,3R,4S,5R)-2-(acetoxymethyl)-4-azido-6-(5-chloroindolin-1-yl)tetrahydro-2H-pyran-3,5-diyl diacetate (50 mg, 0.107 mmol) in dioxane (2 mL), DDQ (48.6 mg, 0.214 mmol) was added and the mixture was stirred at rt for 16 h. The solvent was removed under reduced pressure to get the crude residue which was purified by flash chromatography (30-50%

EtOAc in n-hexane) to yield (2R,3R,4S,5R,6R)-2-(acetoxymethyl)-4-azido-6-(5-chloro-1H-indol-1-yl)tetrahydro-2H-pyran-3,5-diyl diacetate (40 mg, 0.086 mmol, 80%). LC-MS, [M+H]+=465.5, {Method E: $t_R$=1.37 min}.

Step 4: Synthesis of (2R,3R,4S,5R,6R)-2-(acetoxymethyl)-6-(5-chloro-1H-indol-1-yl)-4-(4-(3,4,5-trifluorophenyl)-1H-1,2,3-triazol-1-yl)tetrahydro-2H-pyran-3,5-diyl diacetate: Prepared in a similar fashion as described in Example 1, step 3 using (2R,3R,4S,5R,6R)-2-(acetoxymethyl)-4-azido-6-(5-chloro-1H-indol-1-yl)tetrahydro-2H-pyran-3,5-diyl diacetate (35 mg, 0.075 mmol) and 5-ethynyl-1,2,3-trifluorobenzene to afford (2R,3R,4S,5R,6R)-2-(acetoxymethyl)-6-(5-chloro-1H-indol-1-yl)-4-(4-(3,4,5-trifluorophenyl)-1H-1,2,3-triazol-1-yl)tetrahydro-2H-pyran-3,5-diyl diacetate (25 mg, 0.040 mmol, 53%). LC-MS, [M+H]+=621.2, {Method E: $t_R$=1.52 min}.

Step 5: Prepared in a similar fashion as described in Example 15, step 4 using (2R,3R,4S,5R,6R)-2-(acetoxymethyl)-6-(5-chloro-1H-indol-1-yl)-4-(4-(3,4,5-trifluorophenyl)-1H-1,2,3-triazol-1-yl)tetrahydro-2H-pyran-3,5-diyl diacetate (25 mg, 0.040 mmol) as the starting material to afford (2R,3R,4S,5R,6R)-2-(5-chloro-1H-indol-1-yl)-6-(hydroxymethyl)-4-(4-(3,4,5-trifluorophenyl)-1H-1,2,3-triazol-1-yl)tetrahydro-2H-pyran-3,5-diol (10 mg, 0.020 mmol, 50%). LC-MS, [M+H]+=495.2, {Method A: $t_R$=1.68 and Method B: $t_R$=1.67}. 1H NMR (400 MHz, METHANOL-d4): δ 8.61 (s, 1H), 7.73 (d, J=8.5 Hz, 1H), 7.66 (dd, J=9.0, 6.5 Hz, 2H), 7.57 (dd, J=8.8, 2.8 Hz, 2H), 7.17 (dd, J=9.0, 2.0 Hz, 1H), 6.53 (d, J=3.5 Hz, 1H), 5.66 (d, J=8.5 Hz, 1H), 5.10 (dd, J=11.0, 3.0 Hz, 1H), 4.92 (dd, J=11.0, 8.5 Hz, 1H), 4.28 (d, J=3.0 Hz, 1H), 4.12 (t, J=6.0 Hz, 1H), 3.87-3.73 (m, 2H). hGal-3 $IC_{50}$=10 uM.

EXAMPLE 292

Preparation of 2R,3R,4R,5R,6S)-2-(hydroxymethyl)-6-(4-methoxyphenyl)-4-(4-(3,4,5-trifluorophenyl)-1H-1,2,3-triazol-1-yl)tetrahydro-2H-pyran-3,5-diol

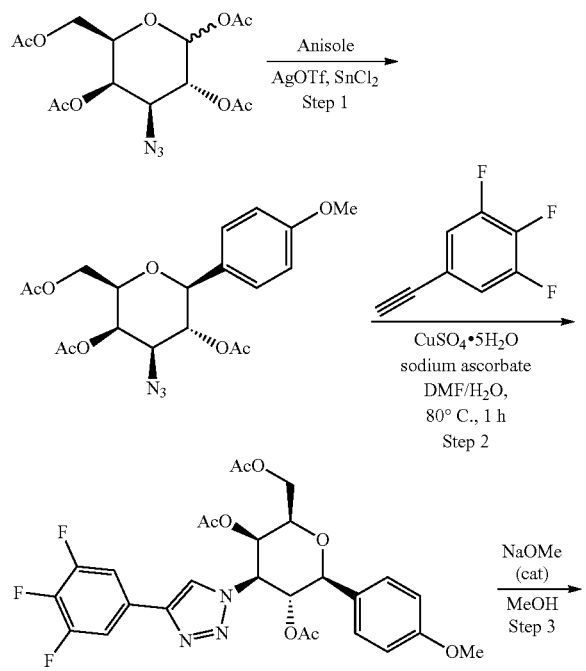

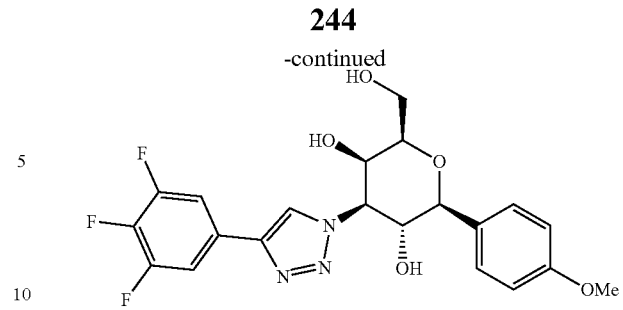

Step 1: Synthesis of (2R,3R,4R,5R,6S)-2-(acetoxymethyl)-4-azido-6-(4-methoxyphenyl)tetrahydro-2H-pyran-3,5-diyl diacetate: To a solution of (3R,4S,5R,6R)-6-(acetoxymethyl)-4-azidotetrahydro-2H-pyran-2,3,5-triyltriacetate (0.2 g, 0.536 mmol) and anisole (0.116 g, 1.071 mmol) in DCM (2 mL), silver trifluoromethanesulfonate (0.183 g, 0.713 mmol) and tin(IV) chloride (1.875 mL, 1.875 mmol) were added at 0° C. and reaction mixture was stirred at 0° C. for 2 h. The reaction mixture was quenched with sat NaHCO3 and filtered. The filtrate was extracted with EtOAc (2×50 mL), washed with water, brine solution, dried over sodium sulphate and concentrated. The residue was purified by flash chromatography (25-40% EtOAc in n-hexane) to yield (2R,3R,4R,5R,6S)-2-(acetoxymethyl)-4-azido-6-(4-methoxyphenyl)tetrahydro-2H-pyran-3,5-diyl diacetate (90 mg, 0.213 mmol, 40%) as a gummy solid. LC-MS, [M+18]+= 439.2 {Method C: $t_R$=2.55}.

Step 2: Synthesis of (2R,3R,4R,5R,6S)-2-(acetoxymethyl)-6-(4-methoxyphenyl)-4-(4-(3,4,5-trifluorophenyl)-1H-1,2,3-triazol-1-yl)tetrahydro-2H-pyran-3,5-diyl diacetate: Prepared in a similar fashion as described in Example 1, step 3 using (2R,3R,4R,5R,6S)-2-(acetoxymethyl)-4-azido-6-(4-methoxyphenyl)tetrahydro-2H-pyran-3,5-diyl diacetate (90 mg, 0.214 mmol) and 5-ethynyl-1,2,3-trifluorobenzene to afford ((2R,3R,4R,5R,6S)-2-(acetoxymethyl)-6-(4-methoxyphenyl)-4-(4-(3,4,5-trifluorophenyl)-1H-1,2,3-triazol-1-yl)tetrahydro-2H-pyran-3,5-diyldiacetate (50 mg, 0.087 mmol, 40%). LC-MS, [M+H]+=578.1, {Method C: $t_R$=3.14 min}.

Step 3: Prepared in a similar fashion as described in Example 15, step 4 using (2R,3R,4R,5R,6S)-2-(acetoxymethyl)-6-(4-methoxyphenyl)-4-(4-(3,4,5-trifluorophenyl)-1H-1,2,3-triazol-1-yl)tetrahydro-2H-pyran-3,5-diyl diacetate (40 mg, 0.069 mmol) as the starting material to afford Example 292 (2R,3R,4R,5R,6S)-2-(hydroxymethyl)-6-(4-methoxyphenyl)-4-(4-(3,4,5-trifluorophenyl)-1H-1,2,3-triazol-1-yl)tetrahydro-2H-pyran-3,5-diol (6 mg, 0.013 mmol, 19%) as off-white solid. LC-MS, [M+H]+=452.1, {Method C: $t_R$=1.98}. 1H NMR (400 MHz, METHANOL-d4): δ 8.52 (s, 1H), 7.64 (dd, J=6.6, 8.9 Hz, 2H), 7.49-7.45 (m, 2H), 6.97-6.91 (m, 2H), 4.73-4.71 (m, 1H), 4.61 (d, J=1.6 Hz, 1H), 4.41-4.29 (m, 2H), 4.05-4.04 (m, 2H), 3.93-3.88 (m, 1H), 3.49 (s, 3H). hGal-3 $IC_{50}$=10 uM General Synthetic Scheme for alpha-1,2,3-triazole:

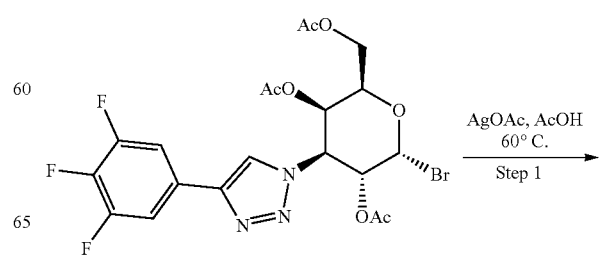

-continued

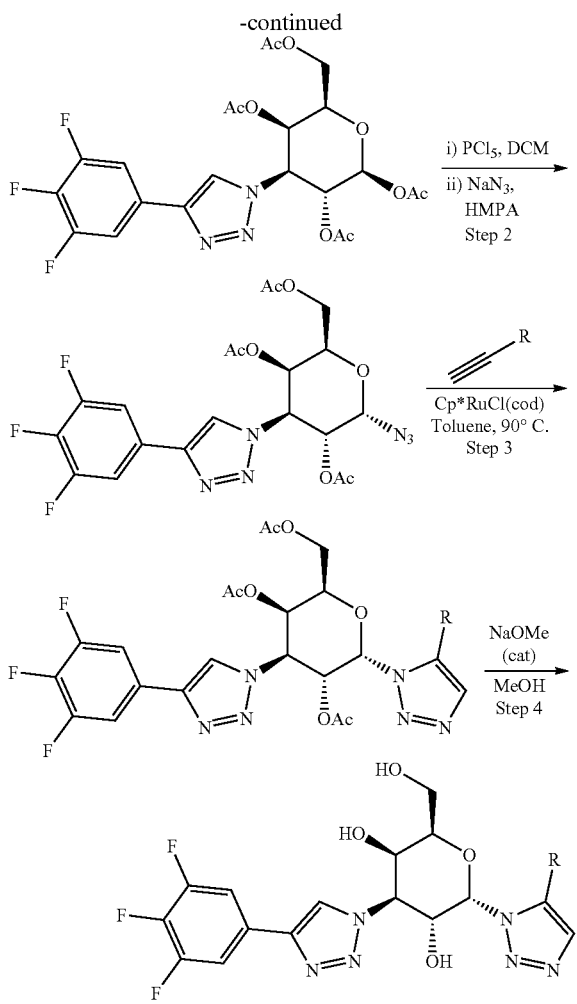

EXAMPLE 293

Preparation of (2S,3R,4S,5R,6R)-2-(5-(3-chlorophenyl)-1H-1,2,3-triazol-1-yl)-6-(hydroxymethyl)-4-(4-(3,4,5-trifluorophenyl)-1H-1,2,3-triazol-1-yl)tetrahydro-2H-pyran-3,5-diol

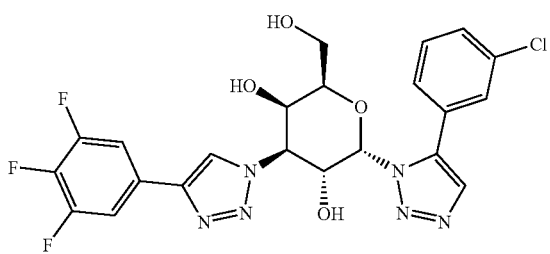 [SMILES: OC[C@H]1O[C@H](n2nncc2-c2cccc(Cl)c2)[C@H](O)[C@@H](n2cc(-c3cc(F)c(F)c(F)c3)nn2)[C@H]1O]

Step 1: Synthesis of (2S,3R,4S,5R,6R)-6-(acetoxymethyl)-4-(4-(3,4,5-trifluorophenyl)-1H-1,2,3-triazol-1-yl) tetrahydro-2H-pyran-2,3,5-triyltriacetate: To a stirred solution of (2R,3R,4S,5R,6R)-2-(acetoxymethyl)-6-bromo-4-(4-(3,4,5-trifluorophenyl)-1H-1,2,3-triazol-1-yl)tetrahydro-2H-pyran-3,5-diyl diacetate (0.2 g, 0.363 mmol) in acetic acid (2.5 mL), silver acetate (0.079 g, 0.472 mmol) was added and the suspension was stirred at 60° C. for 6 h under nitrogen. The reaction mixture was diluted with DCM, filtered through celite pad and washed with excess DCM. The filtrate was washed with water, aq NaHCO$_3$, water, brine, dried over sodium sulphate and concentrated. The residue was purified via chromatography in silicagel (30-60% EtOAc in n-hexane) to yield (2S,3R,4S,5R,6R)-6-(acetoxymethyl)-4-(4-(3,4,5-trifluorophenyl)-1H-1,2,3-triazol-1-yl)tetrahydro-2H-pyran-2,3,5-triyltriacetate (0.15 g, 0.283 mmol, 78%) as an off-white solid. LC-MS, [M+1]$^+$= 530.2, {Method D: t$_R$=1.21}. 1H NMR (400 MHz, CHLOROFORM-d): δ 7.79 (s, 1H), 7.48-7.36 (m, 2H), 5.92-5.79 (m, 2H), 5.58 (d, J=3.0 Hz, 1H), 5.23-5.13 (m, 1H), 4.28-4.08 (m, 3H), 2.17 (s, 3H), 2.07 (s, 3H), 2.05 (s, 3H).

Step 2: Synthesis of (2R,3R,4S,5R,6S)-2-(acetoxymethyl)-6-azido-4-(4-(3,4,5-trifluorophenyl)-1H-1,2,3-triazol-1-yl)tetrahydro-2H-pyran-3,5-diyl diacetate: To a stirred solution of (2S,3R,4S,5R,6R)-6-(acetoxymethyl)-4-(4-(3,4,5-trifluorophenyl)-1H-1,2,3-triazol-1-yl)tetrahydro-2H-pyran-2,3,5-triyltriacetate (0.2 g, 0.378 mmol) in DCM (5 mL), PCl$_5$ (0.094 g, 0.453 mmol) was added followed by BF$_3$-OEt$_2$ (9.57 µl, 0.076 mmol) and the mixture was stirred at rt for 2 h under nitrogen. The reaction mixture was diluted with DCM (50 mL), washed with water, aq. NaHCO$_3$, water, brine and dried over sodium sulphate. The solvent was removed under reduced pressure and the crude residue containing the corresponding choro derivative was taken as such for next step without further purification.

The above crude chloro derivative (0.15 g, 0.297 mmol) was dissolved in HMPA (5 mL) and sodium azide (0.096 g, 1.483 mmol) was added at rt under nitrogen and stirred for 12 h. The reaction mixture was diluted with ice-cold water and stirred for 20 min. The solid was filtered, dried and purified via chromatography in silicagel (30-70% EtOAc in n-hexane) to yield (2R,3R,4S,5R,6S)-2-(acetoxymethyl)-6-azido-4-(4-(3,4,5-trifluorophenyl)-1H-1,2,3-triazol-1-yl)tetrahydro-2H-pyran-3,5-diyl diacetate (0.075 g, 0.146 mmol, 49%) as an off-white solid. LC-MS, [M+1]$^+$=513.2, {Method D: t$_R$=1.27}. 1H NMR (400 MHz, CHLOROFORM-d): δ 7.73 (s, 1H), 7.46-7.38 (m, 2H), 5.91 (dd, J=11.4, 4.1 Hz, 1H), 5.82 (d, J=4.0 Hz, 1H), 5.56 (d, J=2.8 Hz, 1H), 5.18 (dd, J=11.4, 2.8 Hz, 1H), 4.56-4.48 (m, 1H), 4.23-4.09 (m, 2H), 2.07 (s, 3H), 2.06 (s, 3H), 1.95 (s, 3H).

Step 3: Synthesis of ((2R,3R,4S,5R,6S)-2-(acetoxymethyl)-6-(5-(3-chlorophenyl)-1H-1,2,3-triazol-1-yl)-4-(4-(3,4,5-trifluorophenyl)-1H-1,2,3-triazol-1-yl)tetrahydro-2H-pyran-3,5-diyl diacetate: A microwave vial was charged with (2R,3R,4S,5R,6S)-2-(acetoxymethyl)-6-azido-4-(4-(3,4,5-trifluorophenyl)-1H-1,2,3-triazol-1-yl)tetrahydro-2H-pyran-3,5-diyl diacetate (0.025 g, 0.049 mmol), 1-chloro-3-ethynylbenzene (0.017 g, 0.122 mmol), chloro(1,5-cyclooctadiene)(pentamethylcyclopentadienyl)ruthenium (1.854 mg, 4.88 µmol) and 1,4-dioxane (3 mL). The vial was sealed and heated at 80° C. under microwave for 1 h. The solvent was removed under reduced pressure to get crude product which was purified via chromatography in silica gel (30-60% EtOAc in n-hexane) to yield (2R,3R,4S,5R,6S)-2-(acetoxymethyl)-6-(5-(3-chlorophenyl)-1H-1,2,3-triazol-1-yl)-4-(4-(3,4,5-trifluorophenyl)-1H-1,2,3-triazol-1-yl)tetrahydro-2H-pyran-3,5-diyl diacetate (0.02 g, 0.031 mmol, 63%) as a brown solid. LC-MS, [M+1]$^+$=649.3, {Method D: t$_R$=1.45}.

Step 4: To a stirred solution of (2R,3R,4S,5R,6S)-2-(acetoxymethyl)-6-(5-(3-chlorophenyl)-1H-1,2,3-triazol-1-yl)-4-(4-(3,4,5-trifluorophenyl)-1H-1,2,3-triazol-1-yl)tetrahydro-2H-pyran-3,5-diyl diacetate (0.020 g, 0.031 mmol) in MeOH (3 mL), sodium methoxide (15 µL, 0.031 mmol) was added at rt and teh mixture was stirred for 1 h. The solvent was removed under reduced pressure and purified by prep- HPLC Method-A to afford Example 293 (2S,3R,4S,5R,6R)-2-(5-(3-chlorophenyl)-1H-1,2,3-triazol-1-yl)-6-(hydroxymethyl)-4-(4-(3,4,5-trifluorophenyl)-1H-1,2,3-triazol-1-yl)tetrahydro-2H-pyran-3,5-diol (5 mg, 0.01 mmol, 30%) as off-white solid. LC-MS, [M+H]$^+$=523.2, {Method A: $t_R$=1.41 and Method B: $t_R$=1.44}. 1H NMR (400 MHz, METHANOL-d4): δ 8.62 (s, 1H), 7.97 (s, 1H), 7.75-7.64 (m, 3H), 7.62-7.48 (m, 3H), 6.30-6.06 (m, 2H), 5.14 (dd, J=11.5, 6.0 Hz, 1H), 4.48 (dd, J=6.5, 6.0 Hz, 1H), 4.40 (d, J=3.0 Hz, 1H), 3.78 (d, J=6.0 Hz, 2H). hGal-3 IC$_{50}$=5.0 uM.

EXAMPLE 294

The Title Compound was Prepared Following the Procedure Described for Example 290, Using 1-chloro-3-ethynylbenzene as the Reagent

| Ex | hGal3 IC50, uM | Structure | LCMS $t_R$ (min) | M + H | Method |
|---|---|---|---|---|---|
| 291 | 10 | 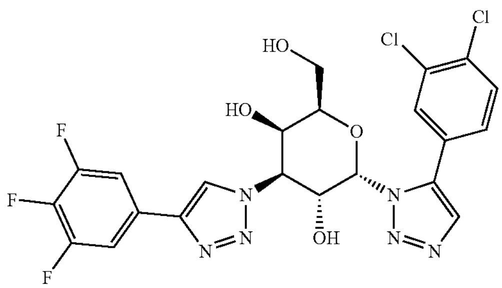 [SMILES: OC[C@H]1O[C@H](n2nncc2-c2ccc(Cl)c(Cl)c2)[C@H](O)[C@@H](n2cc(-c3cc(F)c(F)c(F)c3)nn2)[C@H]1O] | 1.62 | 557.2 | A |

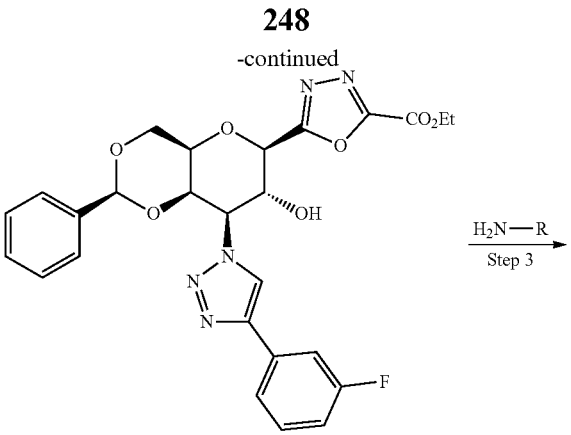

General Synthetic Scheme for 1,3,4-oxadiazole:

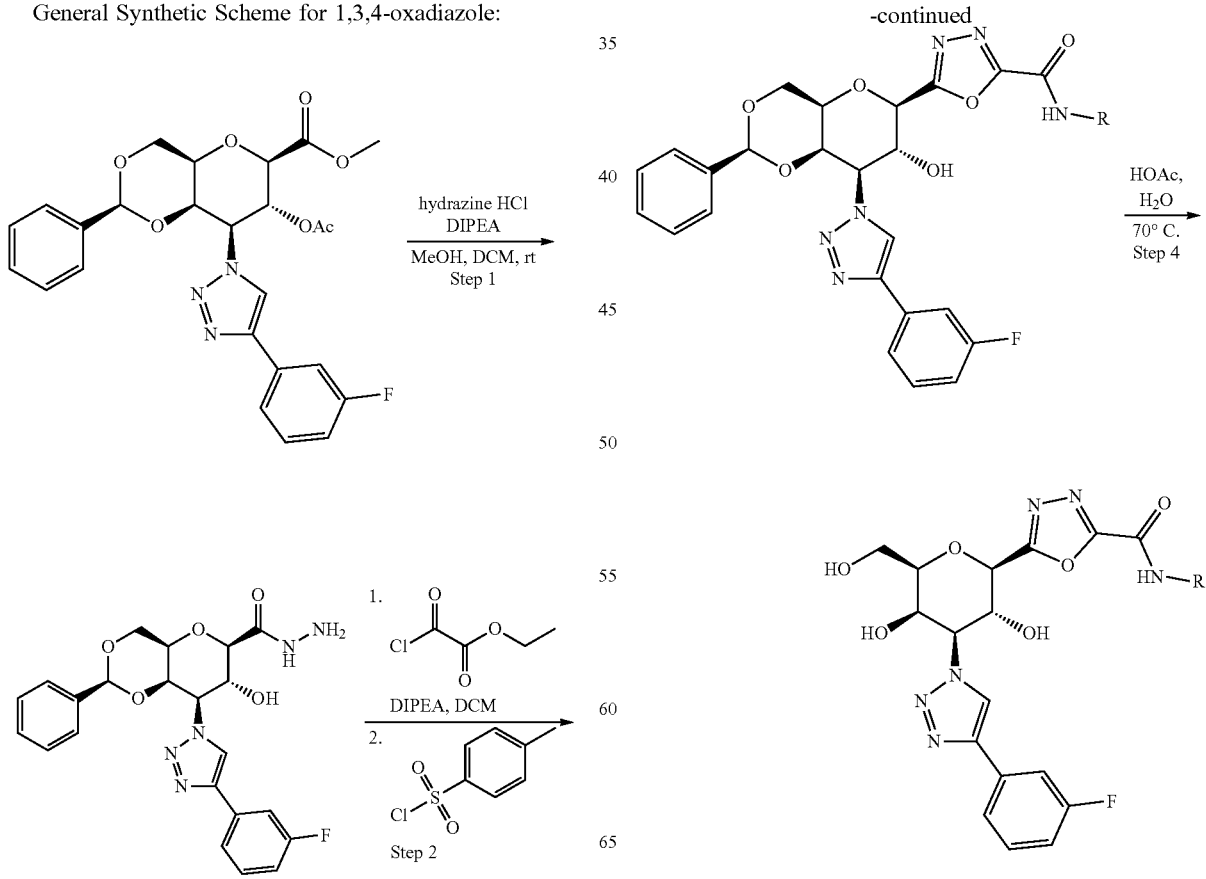

EXAMPLE 295

Preparation of 5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-methyl-1,3,4-oxadiazole-2-carboxamide

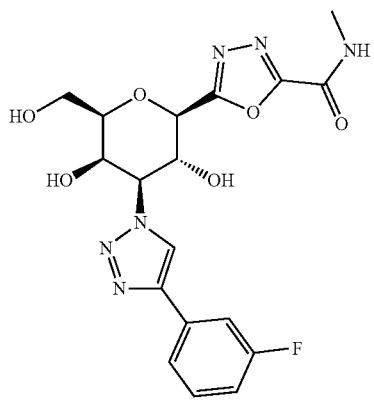 [SMILES: CNC(=O)c1nnc([C@@H]2O[C@H](CO)[C@H](O)[C@H](n3cc(-c4cccc(F)c4)nn3)[C@H]2O)o1]

Step 1: Preparation of (2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carbohydrazide: To a suspension of (2S,4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate (0.230 g, 0.462 mmol) in methanol (7 mL) and dichloromethane (7 mL) was added DIPEA (0.807 mL, 4.62 mmol) followed by hydrazine monohydrochloride (0.253 g, 3.70 mmol). The mixture was stirred at rt for 69 h then was concentrated under reduced pressure. The residue was diluted with water (40 mL) and extracted with dichloromethane (3×50 mL). The organic layers were dried over sodium sulfate, filtered and concentrated under reduced pressure to give the title product as an off-white solid (0.102 g, 0.224 mmol, 48% yield). LC-MS, [M+H]$^+$=456.1, {Method F: $t_R$=0.95 min}. $^1$H NMR (500 MHz, METHANOL-d$_4$) δ=8.49 (s, 1H), 7.63 (td, J=1.1, 7.7 Hz, 1H), 7.59-7.55 (m, 1H), 7.50-7.42 (m, 3H), 7.38-7.34 (m, 3H), 7.13-7.06 (m, 1H), 5.59 (s, 1H), 5.15 (dd, J=3.4, 10.6 Hz, 1H), 4.63 (dd, J=9.5, 10.5 Hz, 1H), 4.59-4.54 (m, 1H), 4.34 (dd, J=1.4, 12.6 Hz, 1H), 4.22 (dd, J=1.7, 12.6 Hz, 1H), 4.07 (d, J=9.5 Hz, 1H), 3.92 (d, J=0.8 Hz, 1H).

Step 2: Preparation of ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate: To a solution of (2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carbohydrazide (0.10 g, 0.220 mmol) in dichloromethane (3 mL) and DIPEA (0.192 mL, 1.098 mmol) was added ethyl oxalyl chloride (0.031 mL, 0.274 mmol). After 3h of stirring tosyl-Cl (0.054 g, 0.285 mmol) was added and the mixture was stirred at rt for an additional 18 h. The mixture was diluted with water (15 mL) and extracted with dichloromethane (3×15 mL). The organic layers were dried over sodium sulfate, filtered and concentrated under reduced pressure. The residue was purified by flash chromatography using a 40-80% ethyl acetate in hexanes gradient and a 12 g silica gel column. The fractions containing the product were combined and concentrated under reduced pressure to give the title product as a white solid (0.083 g, 0.154 mmol, 70% yield). LC-MS, [M+H]$^+$=538.0, {Method F: $t_R$=1.18 min}. $^1$H NMR (500 MHz, CHLOROFORM-d) δ=8.13 (s, 1H), 7.61-7.34 (m, 8H), 7.05 (dt, J=2.5, 8.4 Hz, 1H), 5.56 (s, 1H), 5.27-5.21 (m, 1H), 5.14-5.05 (m, 1H), 4.90 (d, J=9.3 Hz, 1H), 4.62 (d, J=3.0 Hz, 1H), 4.59-4.53 (m, 2H), 4.52-4.44 (m, 1H), 4.25-4.14 (m, 1H), 3.98 (s, 1H), 3.50 (d, J=4.3 Hz, 1H), 1.49 (t, J=7.2 Hz, 3H).

Step 3: Preparation of 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-methyl-1,3,4-oxadiazole-2-carboxamide: To a flask containing ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate (0.033 g, 0.061 mmol) was added a solution of methylamine (1M in THF) (3 ml, 3.00 mmol). The mixture was stirred at rt for 19.5 h then was concentrated under reduced pressure to give the title product which was used directly in the next step with no purification. LC-MS, [M+H]$^+$=523.1, {Method F: $t_R$=1.06 min}. $^1$H NMR (500 MHz, CHLOROFORM-d) δ=8.17 (s, 1H), 7.61-7.52 (m, 2H), 7.46-7.35 (m, 7H), 7.18 (br d, J=4.6 Hz, 1H), 7.05 (dt, J=2.2, 8.4 Hz, 1H), 5.54 (s, 1H), 5.24 (dd, J=3.2, 10.7 Hz, 1H), 5.08 (t, J=10.0 Hz, 1H), 4.91 (d, J=9.3 Hz, 1H), 4.59 (d, J=3.2 Hz, 1H), 4.45 (br d, J=12.5 Hz, 1H), 4.19-4.11 (m, 1H), 3.95 (s, 1H), 3.06 (d, J=5.0 Hz, 3H).

Step 4: To a flask containing 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-methyl-1,3,4-oxadiazole-2-carboxamide (0.032 g, 0.061 mmol) was added acetic acid (1.4 mL) and Water (0.6 mL). The mixture was heated to 70° C. for 22 h, then was cooled to rt, diluted with methanol and was purified by prep HPLC (acetonitrile/water/TFA gradient). The fractions containing the product were combined and concentrated under reduced pressure to give Example 295 (TFA salt form) as a white solid (7.5 mg, 0.014 mmol, 23% yield). LC-MS, [M+H]$^+$=435.2, {Method F: $t_R$=1.21 min}. $^1$H NMR (500 MHz, METHANOL-d$_4$) δ 9.19 (d, J=4.6 Hz, 1H), 8.57 (s, 1H), 7.72-7.68 (m, 1H), 7.66-7.61 (m, 1H), 7.48 (td, J=8.0, 6.0 Hz, 1H), 7.10 (td, J=8.5, 1.7 Hz, 1H), 5.05 (dd, J=10.4, 3.0 Hz, 1H), 4.94-4.89 (m, 2H), 4.25 (d, J=2.2 Hz, 1H), 4.04 (t, J=6.0 Hz, 1H), 3.85-3.80 (m, 1H), 3.78-3.72 (m, 1H), 3.00-2.97 (m, 3H). hGal-3 IC$_{50}$=14.4 µM.

EXAMPLE 296

Preparation of 5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(pyridin-4-ylmethyl)-1,3,4-oxadiazole-2-carboxamide

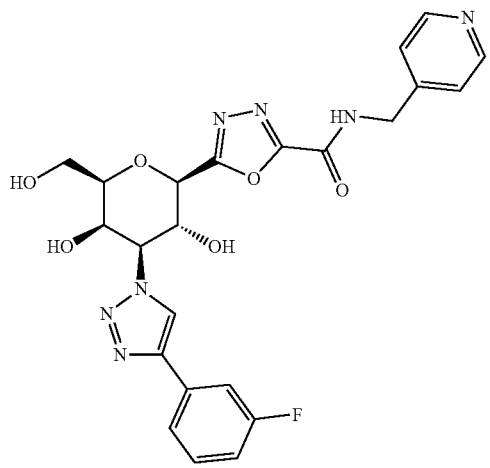 [SMILES: O=C(NCc1ccncc1)c1nnc([C@@H]2O[C@H](CO)[C@H](O)[C@H](n3cc(-c4cccc(F)c4)nn3)[C@H]2O)o1]

Step 3: Preparation of 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(pyridin-4-ylmethyl)-1,3,4-oxadiazole-2-carboxamide: To a solution of ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate (0.024 g, 0.045 mmol) in THF (0.5 mL) was added 4-(aminomethyl)pyridine (0.023 mL, 0.223 mmol). The mixture was stirred at rt for 16.5 h, then was diluted with water (3 mL) and extracted with dichloromethane (3×3 mL). The organic layers were dried over sodium sulfate, filtered and concentrated under reduced pressure. The drying agent that was filtered was diluted with DCM and a small amount of methanol and was filtered again because of the poor solubility of the compound. The filtrate (combined with the first filtrate) was concentrated under reduced pressure to give the title compound as a white film (0.027 g, 0.045 mmol, 100%). LC-MS, [M+H]$^+$=600.3, {Method F: $t_R$=1.20 min}.

Step 4: To a flask containing 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(pyridin-4-ylmethyl)-1,3,4-oxadiazole-2-carboxamide (27.0 mg, 0.045 mmol) was added acetic acid (1.4 mL) and water (0.6 mL). The mixture was heated to 70° C. for 19 h, then was cooled to rt, diluted with methanol and purified by prep HPLC (method E). The fractions containing the product were concentrated under reduced pressure to give Example 296 (12.1 mg, 0.023 mmol, 51% yield). LC-MS, [M+H]$^+$=512.0, {Method F: $t_R$=0.81 min}. $^1$H NMR (500 MHz, DMSO-d6) δ=8.72 (s, 1H), 8.53 (br d, J=4.4 Hz, 2H), 7.76 (d, J=8.1 Hz, 1H), 7.70 (br d, J=10.3 Hz, 1H), 7.53-7.46 (m, 1H), 7.35 (d, J=5.1 Hz, 2H), 7.17-7.10 (m, 1H), 5.04 (dd, J=2.9, 10.6 Hz, 1H), 4.94 (d, J=9.5 Hz, 1H), 4.75-4.68 (m, 1H), 4.54 (br s, 2H), 4.09 (br d, J=1.8 Hz, 1H), 4.00 (t, J=6.1 Hz, 1H), 3.58 (br s, 2H). hGal-3 IC$_{50}$=1.49 µM.

EXAMPLE 297

Preparation of N-(2-(diethylamino)ethyl)-5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-1,3,4-oxadiazole-2-carboxamide

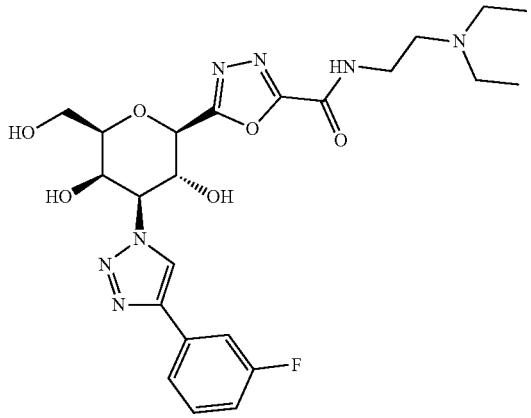 [SMILES: CCN(CC)CCNC(=O)c1nnc([C@@H]2O[C@H](CO)[C@H](O)[C@H](n3cc(-c4cccc(F)c4)nn3)[C@H]2O)o1]

Step 3: Preparation of N-(2-(diethylamino)ethyl)-5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxamide: To a solution of ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate (0.024 g, 0.045 mmol) in THF (0.5 mL) was added N,N-diethylethylenediamine (0.032 mL, 0.223 mmol). The mixture was stirred at rt for 16.5 h, then was diluted with water (3 mL) and extracted with dichloromethane (3×3 mL). The organic layers were dried over sodium sulfate, filtered and concentrated under reduced pressure to give the title product as a tan film. The crude product was used in the next step with no additional purification. LC-MS, [M+H]$^+$=608.3, {Method F: $t_R$=1.22 min}.

Step 4: To a flask containing N-(2-(diethylamino)ethyl)-5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxamide (0.029 g, 0.048 mmol) was added acetic acid (1.4 mL) and water (0.6 mL). The mixture was heated to 70° C. overnight. After heating the mixture for 33 h, it was cooled to rt, diluted with methanol and purified by prep HPLC (method F then method G). The fractions containing the product were concentrated under reduced pressure to give Example 297 (20.4 mg, 0.039 mmol, 82% yield). LC-MS, [M+H]$^+$=520.4, {Method F: $t_R$=0.10 min}. $^1$H NMR (500 MHz, DMSO-d$_6$) δ=8.72 (s, 1H), 7.76 (d, J=7.7 Hz, 1H), 7.72-7.67 (m, 1H), 7.53-7.45 (m, 1H), 7.18-7.12 (m, 1H), 5.03 (dd, J=2.8, 10.8 Hz, 1H), 4.92 (d, J=9.5 Hz, 1H), 4.71 (t, J=10.1 Hz, 1H), 4.09 (br d, J=1.5 Hz, 1H), 4.01-3.97 (m, 1H), 3.58 (d, J=5.9 Hz, 2H), 3.41-3.31 (m, 2H), 2.61 (t, J=6.8 Hz, 2H), 2.55 (m, 6H), 0.99 (t, J=7.0 Hz, 6H). hGal-3 IC$_{50}$=9.77 µM.

EXAMPLE 298

Preparation of 5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(pyridin-3-ylmethyl)-1,3,4-oxadiazole-2-carboxamide

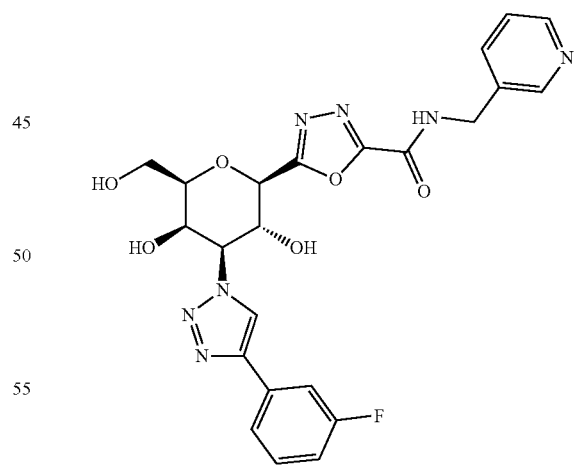

Step 3: Preparation of 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(pyridin-3-ylmethyl)-1,3,4-oxadiazole-2-carboxamide: To a solution of ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate (0.024 g, 0.045 mmol) in THF (0.5 mL) was added 3-(aminomethyl)pyridine (0.023 mL, 0.223 mmol). The mixture was stirred at rt for 16.5 h, then was diluted with water (3 mL). Dichloromethane was added and solids that formed between the layers were collected by filtration and were washed with DCM to give the title compound as a white solid. LC-MS, [M+H]$^+$=600.3, {Method F: $t_R$=1.20 min}.

Step 4: To a flask containing 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(pyridin-3-ylmethyl)-1,3,4-oxadiazole-2-carboxamide (9.2 mg, 0.015 mmol) was added acetic acid (1.4 mL) and water (0.6 mL). The mixture was heated to 70° C. for 33 h, then was cooled to rt, diluted with methanol and purified by prep HPLC (method G then method F). The fractions containing the product were concentrated under reduced pressure to give Example 298 (3.9 mg, 7.6 μmol, 51% yield). LC-MS, [M+H]$^+$=512.3, {Method F: $t_R$=0.97 min}. $^1$H NMR (500 MHz, DMSO-d$_6$) δ=9.89 (br t, J=5.9 Hz, 1H), 8.71 (s, 1H), 7.84 (br d, J=7.3 Hz, 1H), 7.75 (d, J=7.7 Hz, 1H), 7.69 (br d, J=11.0 Hz, 1H), 7.53-7.43 (m, 2H), 7.23-6.96 (m, 2H), 5.03 (dd, J=2.9, 10.6 Hz, 1H), 4.92 (d, J=9.2 Hz, 1H), 4.71 (t, J=9.9 Hz, 1H), 4.61-4.52 (m, 2H), 4.09 (d, J=2.2 Hz, 1H), 3.99 (t, J=6.2 Hz, 1H), 3.58 (d, J=5.9 Hz, 2H). hGal-3 IC$_{50}$=43.6 μM.

EXAMPLE 299

Preparation of 5-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-N-(2-morpholinoethyl)-1,3,4-oxadiazole-2-carboxamide

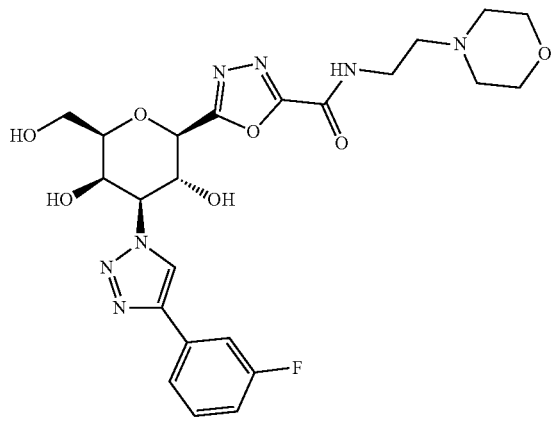 [SMILES: O=C(NCCN1CCOCC1)c1nnc([C@@H]2O[C@H](CO)[C@H](O)[C@H](n3cc(-c4cccc(F)c4)nn3)[C@H]2O)o1]

Step 3: Preparation of 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(2-morpholinoethyl)-1,3,4-oxadiazole-2-carboxamide: To a solution of ethyl 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-1,3,4-oxadiazole-2-carboxylate (0.024 g, 0.045 mmol) in THF (0.5 mL) was added 4-(2-aminoethyl)morpholine (0.029 mL, 0.223 mmol). The mixture was stirred at rt for 16.5 h, then was diluted with water (3 mL) and extracted with dichloromethane (3×3 mL). The organic layers were dried over sodium sulfate, filtered and concentrated under reduced pressure to give the title compound as a tan solid (0.028 g, 0.045 mmol, 100% yield). LC-MS, [M+H]$^+$=622.4, {Method F: $t_R$=1.20 min}.

Step 4: To a flask containing 5-((2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxin-6-yl)-N-(2-morpholinoethyl)-1,3,4-oxadiazole-2-carboxamide (0.028 g, 0.045 mmol) was added acetic acid (1.4 mL) and water (0.6 mL). The mixture was heated to 70° C. for 33 h, then was cooled to rt, diluted with methanol and purified by prep HPLC (Method E then I). The fractions containing the product were concentrated under reduced pressure to give Example 299 (8.1 mg, 0.015 mmol, 34% yield). LC-MS, [M+H]$^+$=534.3, {Method F: $t_R$=0.98 min}. $^1$H NMR (500 MHz, DMSO-d$_6$) δ=9.42 (br d, J=4.0 Hz, 1H), 8.73 (s, 1H), 7.76 (d, J=7.7 Hz, 1H), 7.70 (br d, J=9.5 Hz, 1H), 7.54-7.47 (m, 1H), 7.18-7.11 (m, 1H), 5.05 (dd, J=2.8, 10.8 Hz, 1H), 4.94 (d, J=9.5 Hz, 1H), 4.73 (br t, J=10.1 Hz, 1H), 4.10 (br s, 1H), 4.00 (t, J=6.1 Hz, 1H), 3.92-3.61 (m, 3H), 3.58 (dd, J=3.1, 5.7 Hz, 2H), 2.51 (br s, 9H) (several of the morpholine peaks have broadened into the baseline and are not shown in the integrations). hGal-3 IC$_{50}$=10.6 μM.

EXAMPLE 300

Preparation of (2R,3R,4S,5R,6R)-4-(4-(3-fluorophenyl)-1H-1,2,3-triazol-1-yl)-2-(hydroxymethyl)-6-(5-(hydroxymethyl)-4-methyloxazol-2-yl)tetrahydro-2H-pyran-3,5-diol

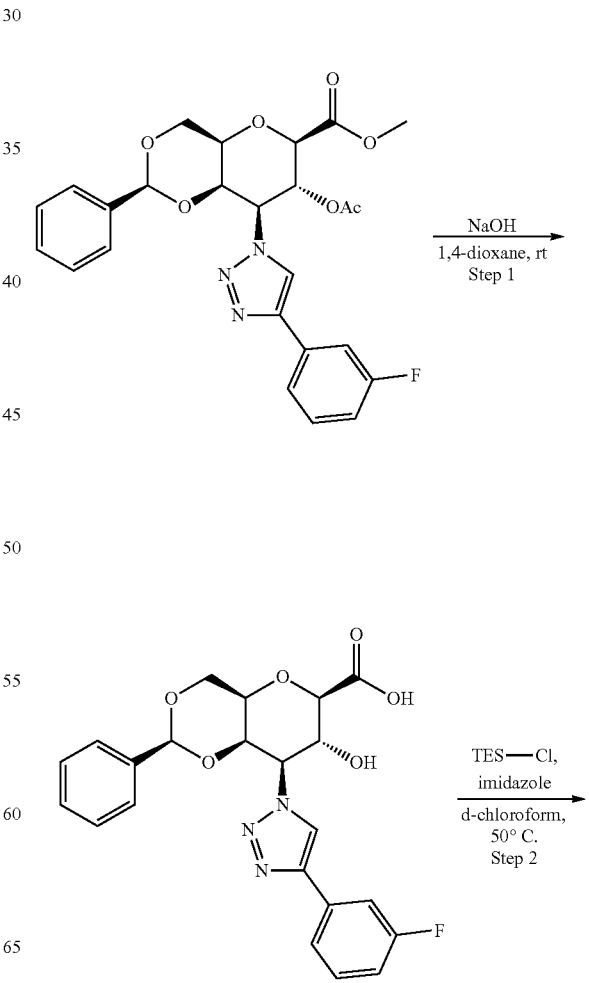

-continued

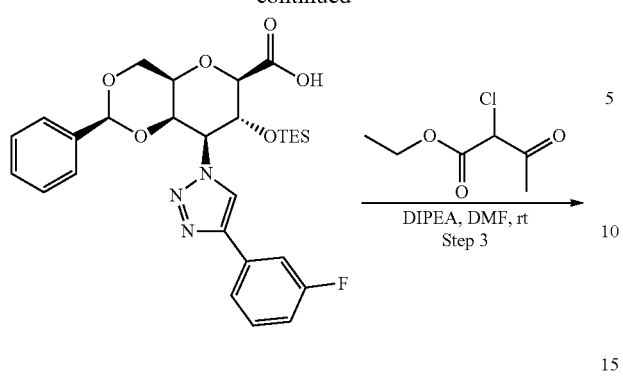

DIPEA, DMF, rt
Step 3

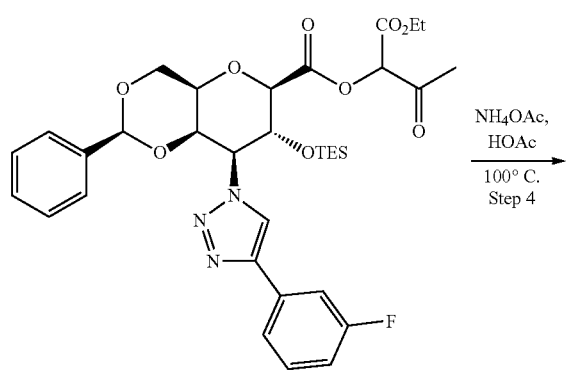

NH₄OAc,
HOAc
―――――→
100° C.
Step 4

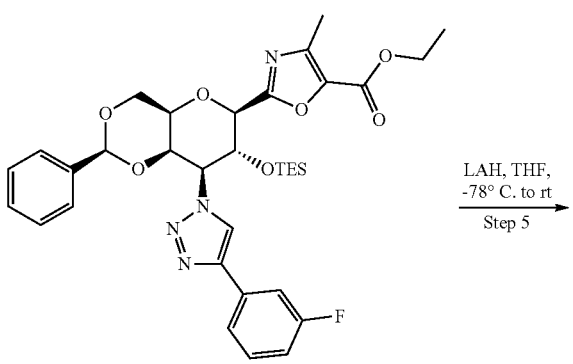

LAH, THF,
-78° C. to rt
―――――→
Step 5

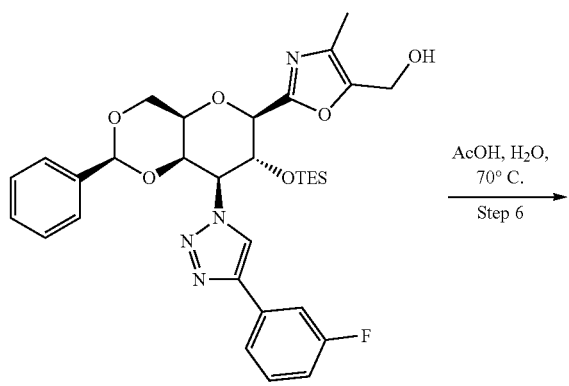

AcOH, H₂O,
70° C.
―――――→
Step 6

-continued

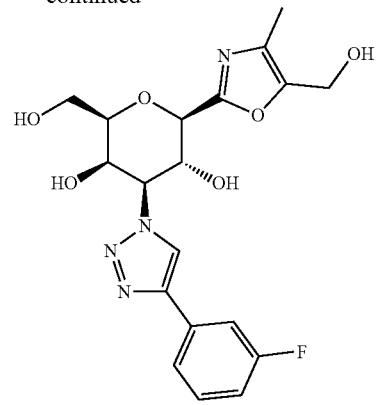

Step 1: Preparation of (2S,4aR,6R,7R,8R,8aR)-8-(4-(3-fluorophenyl)-1H-1,2,3-triazol-1-yl)-7-hydroxy-2-phenyl-hexahydropyrano[3,2-d][1,3]dioxine-6-carboxylic acid: To suspension of (2S,4aR,6R,7R,8S,8aR)-methyl 7-acetoxy-8-(4-(3-fluorophenyl)-1H-1,2,3-triazol-1-yl)-2-phenylhexahydropyrano[3,2-d][1,3]dioxine-6-carboxylate (1.0 g, 2.010 mmol) in 1,4-dioxane (20 mL) was added 1N NaOH (10.05 mL, 10.05 mmol). The mixture was stirred at rt for 18.5 h then was partially concentrated under reduced pressure and was poured into cold 1N HCl and extracted with ethyl acetate (100 mL then 2×50 mL). The combined organic layers were dried over magnesium sulfate, filtered and concentrated under reduced pressure to give the title product as a white solid (0.89 g, 2.01 mmol, 100% yield). LC-MS, [M+H]⁺=442.1, {Method F: $t_R$=1.03 min}.

Step 2: Preparation of (2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxine-6-carboxylic acid: To a solution of (2S,4aR,6R,7R,8R,8aR)-8-(4-(3-fluorophenyl)-1H-1,2,3-triazol-1-yl)-7-hydroxy-2-phenylhexahydropyrano[3,2-d][1,3]dioxine-6-carboxylic acid (0.05 g, 0.113 mmol) in d-chloroform (2 mL) was added imidazole (0.023 g, 0.340 mmol) followed by chlorotriethylsilane (0.095 mL, 0.566 mmol). The mixture was heated to 50° C. for 5 h then was cooled to rt and stirred 3 days. The mixture was diluted with water (30 mL) and extracted with dichloromethane (3×20 mL). The organic layers were dried over sodium sulfate, filtered and concentrated under reduced pressure. The crude, white solid was used in the next step with no additional purification. LC-MS, [M+H]⁺=556.1, {Method F: $t_R$=1.36 min}.

Step 3: Preparation of (2S,4aR,6R,7R,8S,8aR)-1-ethoxy-1,3-dioxobutan-2-yl 8-(4-(3-fluorophenyl)-1H-1,2,3-triazol-1-yl)-2-phenyl-7-((triethylsilyl)oxy)hexahydropyrano[3,2-d][1,3]dioxine-6-carboxylate: To a solution of (2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxine-6-carboxylic acid (0.063 g, 0.113 mmol) in DMF (2 mL) was added DIPEA (0.099 mL, 0.565 mmol) followed by ethyl 2-chloroacetoacetate (0.019 mL, 0.136 mmol). The mixture was stirred at rt for 3 days then was diluted with water (15 mL) and extracted with ethyl acetate (2×20 mL). The organic layers were washed with water 3×, then with brine, dried over magnesium sulfate, filtered and concentrated under reduced pressure. The residue was purified by flash chromatography using a 20-60% EtOAc in hexanes gradient and a 12 g silica gel column. The fractions containing the major peak were combined and concentrated under reduced pressure to give the title product as a clear film (0.056 g, 0.082 mmol, 72.5% yield over two steps). LC-MS, [M+H]⁺=684.2, {Method F: $t_R$=1.55 min}. ¹H NMR (500 MHz, CHLOROFORM-d) δ=8.02 (d, J=0.8 Hz, 1H), 7.58-7.50 (m, 2H), 7.47-7.39 (m, 6H), 7.10-7.03 (m, 1H), 5.60 (d, J=12.5 Hz, 1H), 5.49 (s, 1H), 5.13-5.02 (m, 1H), 4.73 (ddd, J=7.5, 8.9, 10.2 Hz, 1H), 4.46 (dd, J=1.3, 12.7 Hz, 1H), 4.40-4.37 (m, 1H), 4.38-4.29 (m, 2H), 4.26 (dd, J=6.9, 9.0 Hz, 1H), 4.10 (ddd, J=1.8, 3.5, 12.8 Hz, 1H), 3.84-3.79 (m, 1H), 2.40 (s, 3H), 1.38-1.33 (m, 3H), 0.77-0.71 (m, 9H), 0.35-0.24 (m, 3H), 0.23-0.13 (m, 3H).

Step 4: Preparation of ethyl 2-((2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxin-6-yl)-4-methyloxazole-5-carboxylate: To a mixture of (2S,4aR,6R,7R,8S,8aR)-1-ethoxy-1,3-dioxobutan-2-yl 8-(4-(3-fluorophenyl)-1H-1,2,3-triazol-1-yl)-2-phenyl-7-((triethylsilyl)oxy)hexahydropyrano[3,2-d][1,3]dioxine-6-carboxylate (0.053 g, 0.078 mmol) in acetic acid (2 mL) was added ammonium acetate (0.030 g, 0.388 mmol) and the mixture was heated to 100° C. After 1 h of heating, the mixture was cooled to rt and was stirred overnight. The mixture was concentrated under reduced pressure, diluted with ethyl acetate and poured into sat. aq. NaHCO₃ (20 mL). The organic layer was collected and the aqueous layer was extracted with ethyl acetate two additional times. The combined organic layers were washed with brine, dried over magesium sulfate, filtered and concentrated under reduced pressure to give a mixture of the expected product and the des-silyl product which was carried to the next step with no additional purification. LC-MS, [M+H]⁺=551.1 (Pk A, minor peak) and 665.2 (pk B, major peak), {Method F: Pk A $t_R$=1.23 min, Pk B=1.60 min}.

Step 5: Preparation of (2-((2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxin-6-yl)-4-methyloxazol-5-yl)methanol: A solution of ethyl 2-((2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxin-6-yl)-4-methyloxazole-5-carboxylate (0.028 g, 0.042 mmol) in THF (2 mL) was cooled to −78° C. and lithium aluminum hydride (1M in THF) (0.063 mL, 0.063 mmol) was added. The mixture was removed from the ice bath and warmed to rt. After 1 h of stirring at rt, the mixture was carefully quenched with sat. aq. NH₄Cl and was extracted with ethyl acetate (3×20 mL). The organic layers were washed with brine, dried over magnesium sulfate, filtered and concentrated under reduced pressure. The off-white residue was used in the next step with no additional purification. LC-MS, [M+H]⁺=509.05 (Pk A, minor peak) and 623.15 (pk B, major peak), {Method F: Pk A $t_R$=1.04 min, Pk B=1.39 min}.

Step 6: A solution of (2-((2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxin-6-yl)-4-methyloxazol-5-yl)methanol (0.026 g, 0.042 mmol) in acetic acid (2 mL) and Water (1 mL) was heated to 70° C. for 21 h, then was diluted with DMF, filtered through a plug of glass wool and was purified by prep HPLC (method H). Fractions containing the product were combined and concentrated under reduced pressure to give Example 300 (6.8 mg, 0.016 mmol, 21% yield over three steps). LC-MS, [M+H]⁺= 421.00, {Method F: $t_R$=0.76 min}. ¹H NMR (500 MHz, DMSO-d₆) δ=8.65 (s, 1H), 7.73 (d, J=7.7 Hz, 1H), 7.68 (br d, J=10.3 Hz, 1H), 7.52-7.44 (m, 1H), 7.15 (dt, J=1.8, 8.4 Hz, 1H), 5.61 (d, J=7.7 Hz, 1H), 5.52 (t, J=5.7 Hz, 1H), 5.48 (d, J=6.2 Hz, 1H), 5.00 (br t, J=5.5 Hz, 1H), 4.92 (dd, J=2.8, 10.8 Hz, 1H), 4.68-4.60 (m, 1H), 4.47 (d, J=9.9 Hz, 1H), 4.44 (br d, J=4.4 Hz, 2H), 3.99 (dd, J=2.6, 6.2 Hz, 1H), 3.50 (t, J=5.9 Hz, 2H), 2.08 (s, 3H). hGal-3 IC₅₀=9.43 μM.

EXAMPLE 301

Preparation of 2-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-4-methyloxazole-5-carboxylic acid

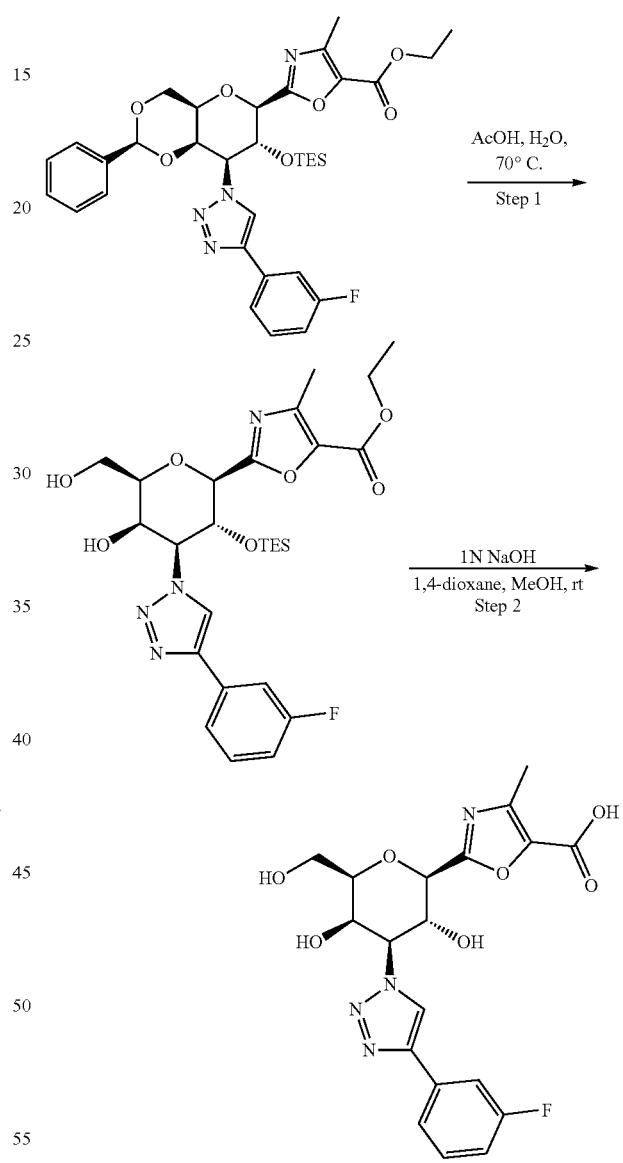

Step 1: Preparation of ethyl 2-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-4-methyloxazole-5-carboxylate: A solution of ethyl 2-((2S,4aR,6R,7R,8S,8aR)-8-(4-(3-fluorophenyl)-1H-1,2,3-triazol-1-yl)-2-phenyl-7-((triethylsilyl)oxy)hexahydropyrano[3,2-d][1,3]dioxin-6-yl)-4-methyloxazole-5-carboxylate (0.022 g, 0.033 mmol) in acetic acid (2 mL) and water (1 mL) was heated to 70° C. for 16.5 h, then was cooled to rt and concentrated under reduced pressure. The crude product was used in the next step with no additional purification. LC-MS, [M+H]⁺= 463.00, {Method F: $t_R$=0.92 min}.

Step 2: To a solution of ethyl 2-((2R,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)-4-methyloxazole-5-carboxylate (15 mg, 0.033 mmol) in 1,4-dioxane (1 mL) and methanol (0.5 mL) was added 1M NaOH (0.165 mL, 0.165 mmol) and the mixture was stirred at rt. After stirring the mixture at rt for 17.5 h it was filtered through a filter tip and was purified by prep HPLC. The fractions containing the product were combined and concentrated under reduced pressure to give example 299 (5.5 mg, 0.013 mmol, 39% yield over two steps). LC-MS, [M+H]⁺=435.0, {Method F: $t_R$=0.78 min}. ¹H NMR (500 MHz, DMSO-$d_6$) δ=8.68 (s, 1H), 7.74 (d, J=7.7 Hz, 1H), 7.72-7.66 (m, 1H), 7.53-7.46 (m, 1H), 7.15 (dt, J=2.4, 8.5 Hz, 1H), 4.93 (dd, J=2.8, 10.8 Hz, 1H), 4.66 (t, J=10.1 Hz, 1H), 4.50 (d, J=9.5 Hz, 1H), 3.99 (br s, 1H), 3.90-3.84 (m, 1H), 3.78-3.68 (m, 1H), 3.57-3.45 (m, 2H), 2.32 (s, 3H). hGal-3 IC₅₀=6.35

The Examples in the table below were prepared in an analogous fashion to Example 73, substituting methyl (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate with the appropriate methylcarboxylate. Aniline was replaced with the appropriate arylamine, and DMF-DMA was replaced with 1,1-dimethoxy-N,N-dimethylethan-1-amine, where appropriate.

| Ex | hGal3 IC₅₀ (µM) | Structure | LCMS $t_R$ (min) | M + H | Method | ¹H NMR |
|---|---|---|---|---|---|---|
| 302 | 0.028 | 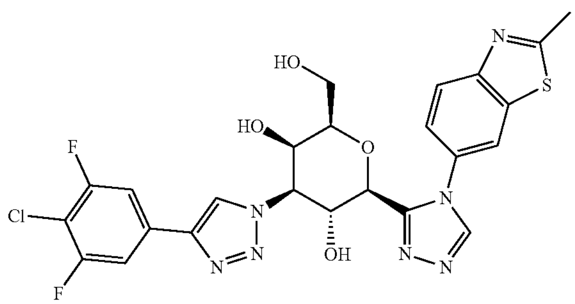 [SMILES: Cc1nc2ccc(-n3cnnc3[C@@H]3O[C@H](CO)[C@H](O)[C@H](n4cc(-c5cc(F)c(Cl)c(F)c5)nn4)[C@H]3O)cc2s1] | 1.33 | 576.2 | A | ¹H NMR (500 MHz, DMSO-$d_6$) δ 8.97-8.91 (m, 1H), 8.89-8.83 (m, 1H), 8.44-8.40 (m, 1H), 8.11-8.05 (m, 1H), 7.88-7.81 (m, 1H), 7.75-7.67 (m, 2H), 7.75-7.67 (m, 1H), 5.50-5.42 (m, 1H), 5.42-5.35 (m, 1H), 5.04-4.94 (m, 1H), 4.94-4.88 (m, 2H), 4.43-4.33 (m, 1H), 4.00-3.90 (m, 1H), 3.80-3.72 (m, 1H), 3.63-3.54 (m, 1H), 3.54-3.45 (m, 1H), 2.86 (s, 3H) |
| 303 | 0.023 | 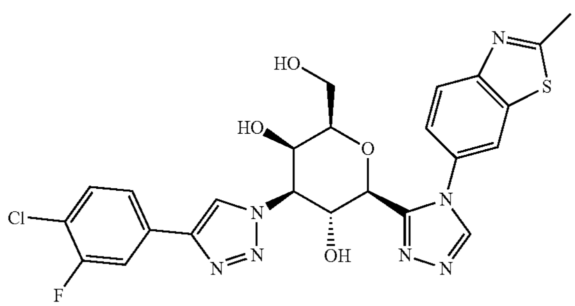 [SMILES: Cc1nc2ccc(-n3cnnc3[C@@H]3O[C@H](CO)[C@H](O)[C@H](n4cc(-c5ccc(Cl)c(F)c5)nn4)[C@H]3O)cc2s1] | 1.32 | 558.0 | A | ¹H NMR (500 MHz, DMSO-$d_6$) δ 8.96-8.91 (m, 1H), 8.75-8.70 (m, 1H), 8.44-8.39 (m, 1H), 8.12-8.06 (m, 1H), 7.93-7.88 (m, 1H), 7.81-7.76 (m, 1H), 7.75-7.70 (m, 1H), 7.70-7.63 (m, 1H), 5.55-5.46 (m, 1H), 5.43-5.37 (m, 1H), 5.05-4.96 (m, 1H), 4.93-4.85 (m, 1H), 4.42-4.33 (m, 1H), 3.98-3.93 (m, 1H), 3.80-3.74 (m, 1H), 3.61-3.54 (m, 1H), 3.21-3.14 (m, 1H), 2.86 (s, 3H) |
| 304 | 0.067 | 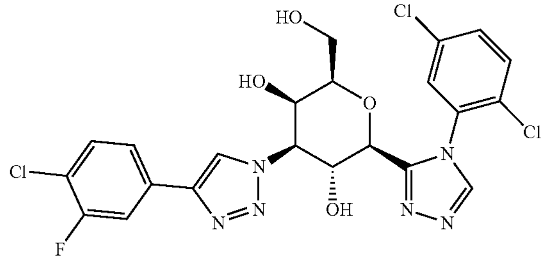 [SMILES: OC[C@H]1O[C@@H](c2nncn2-c2cc(Cl)ccc2Cl)[C@H](O)[C@@H](n2cc(-c3ccc(Cl)c(F)c3)nn2)[C@H]1O] | 1.41 | 555.0 | A | ¹H NMR (500 MHz, DMSO-$d_6$) δ 8.91-8.81 (m, 1H), 8.77-8.69 (m, 1H), 7.96-7.90 (m, 1H), 7.85-7.77 (m, 1H), 7.76-7.72 (m, 1H), 7.71-7.65 (m, 1H), 4.96-4.88 (m, 1H), 4.86-4.61 (m, 1H), 4.40-4.25 (m, 1H), 3.97-3.92 (m, 1H), 3.92-3.88 (m, 1H), 3.69-3.60 (m, 1H), 3.56-3.34 (m, 1H), (three protons obscured) |

| Ex | hGal3 IC$_{50}$ (μM) | Structure | LCMS t$_R$ (min) | M + H | Method | $^1$H NMR |
|---|---|---|---|---|---|---|
| 305 | 0.031 | 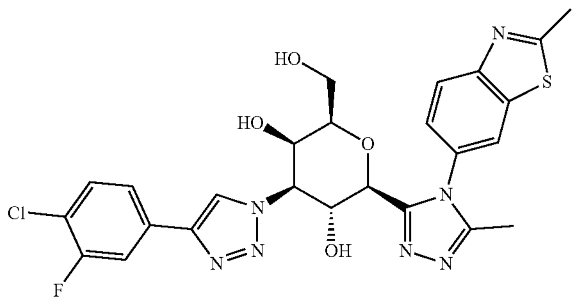 [SMILES: Cc1nc2ccc(-n3c(C)nnc3[C@@H]3O[C@H](CO)[C@H](O)[C@H](n4cc(-c5ccc(Cl)c(F)c5)nn4)[C@H]3O)cc2s1] | 1.35 | 572.2 | A | $^1$H NMR (500 MHz, DMSO-d$_6$) δ 8.75-8.70 (m, 1H), 8.34-8.26 (m, 1H), 8.12-8.05 (m, 1H), 7.95-7.89 (m, 1H), 7.83-7.75 (m, 1H), 7.71-7.65 (m, 1H), 7.65-7.60 (m, 1H), 5.50-5.38 (m, 1H), 5.37-5.29 (m, 1H), 4.96-4.90 (m, 1H), 4.88-4.81 (m, 1H), 4.16 (d, J = 9.3 Hz, 1H), 3.94-3.86 (m, 1H), 3.63-3.56 (m, 1H), 3.55-3.50 (m, 1H), 3.46 (br, d, J = 3.1 Hz, 1H), 3.00 (s, 1H), 2.90-2.83 (m, 3H), 2.30 (s, 3H) |
| 306 | 0.035 | 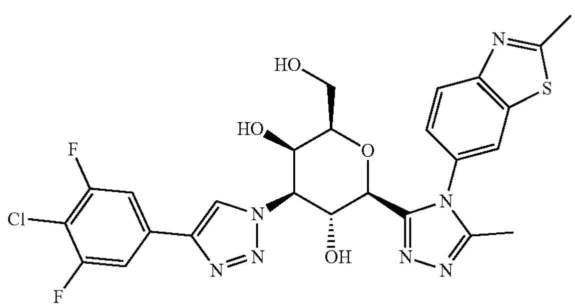 [SMILES: Cc1nc2ccc(-n3c(C)nnc3[C@@H]3O[C@H](CO)[C@H](O)[C@H](n4cc(-c5cc(F)c(Cl)c(F)c5)nn4)[C@H]3O)cc2s1] | 1.35 | 590.1 | A | $^1$H NMR (500 MHz, DMSO-d$_6$) δ 8.90-8.81 (m, 1H), 8.35-8.28 (m, 1H), 8.12-8.02 (m, 1H), 7.91-7.83 (m, 1H), 7.67-7.59 (m, 1H), 5.43-5.38 (m, 1H), 5.36-5.30 (m, 1H), 4.97-4.89 (m, 1H), 4.88-4.81 (m, 1H), 4.18-4.12 (m, 1H), 3.93-3.86 (m, 1H), 3.62-3.56 (m, 1H), 3.55-3.48 (m, 1H), 3.47-3.43 (m, 2H), 2.87 (s, 3H), 2.30 (s, 3H) |
| 307 | 0.46 | 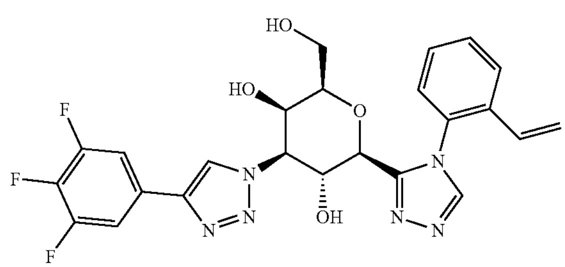 [SMILES: C=Cc1ccccc1-n1cnnc1[C@@H]1O[C@H](CO)[C@H](O)[C@H](n2cc(-c3cc(F)c(F)c(F)c3)nn2)[C@H]1O] | 1.47 | 514.2 | A | $^1$H NMR (500 MHz, DMSO-d$_6$) δ 8.80-8.75 (m, 1H), 8.72-8.68 (m, 1H), 7.89-7.81 (m, 1H), 7.64-7.58 (m, 1H), 7.54-7.47 (m, 1H), 7.46-7.30 (m, 1H), 6.27-6.13 (m, 1H), 5.88-5.77 (m, 1H), 5.48-5.34 (m, 1H), 5.33-5.29 (m, 1H), 4.96-4.79 (m, 2H), 4.22-4.06 (m, 1H), 3.98-3.83 (m, 1H), 3.47-3.27 (m, 2H) |

The Examples in the table below were prepared in an analogous fashion to Example 272, substituting (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carbohydrazide with the appropriate carbohydrazide and substituting methyl (E)-N-(3-chlorophenyl)ethanimidothioate with the appropriate imidothioate.

| Ex | hGal3 IC$_{50}$ (μM) | Structure | LCMS t$_R$ (min) | M + H | Method | $^1$H NMR |
|---|---|---|---|---|---|---|
| 308 | 0.022 | 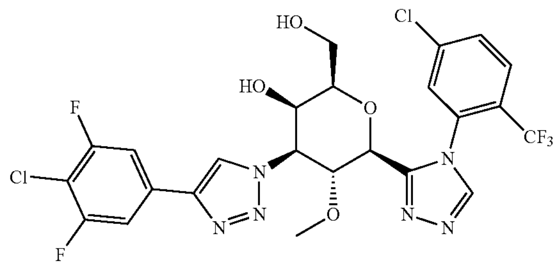 [SMILES: CO[C@@H]1[C@@H](n2cc(-c3cc(F)c(Cl)c(F)c3)nn2)[C@@H](O)[C@@H](CO)O[C@H]1c1nncn1-c1cc(Cl)ccc1C(F)(F)F] | 1.77 | 621.2 | A | $^1$H NMR (500 MHz, DMSO-d$_6$) δ 9.16 (s, 1H), 8.88 (s, 1H), 8.06 (d, J = 8.5 Hz, 1H), 8.01-7.95 (m, 1H), 7.94-7.85 (m, 3H), 5.48-5.40 (m, 1H), 5.10-5.00 (m, 1H), 4.84-4.76 (m, 1H), 4.74-4.66 (m, 1H), 4.59-4.39 (m, 1H), 4.29-4.19 (m, 1H), 3.92-3.81 (m, 1H), 3.64-3.54 (m, 1H), 3.49-3.39 (m, 1H), 3.34-3.28 (m, 1H), 3.03 (s, 3H) |
| 309 | 0.020 | 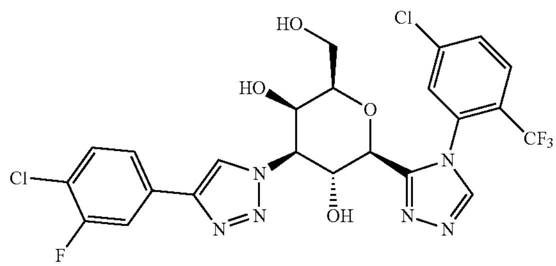 [SMILES: OC[C@H]1O[C@@H](c2nncn2-c2cc(Cl)ccc2C(F)(F)F)[C@H](O)[C@@H](n2cc(-c3ccc(Cl)c(F)c3)nn2)[C@H]1O] | 1.47 | 589.2 | A | $^1$H NMR (500 MHz, DMSO-d$_6$) δ 8.85-8.78 (m, 1H), 8.77-8.71 (m, 1H), 8.07-802 (m, 1H), 7.97-7.88 (m, 3H), 7.81-7.76 (m, 1H), 7.71-7.65 (m, 1H), 5.46-5.39 (m, 1H), 5.33-5.25 (m, 1H), 4.99-4.85 (m, 2H), 4.74-4.62 (m, 1H), 4.60-4.52 (m, 1H), 4.35-4.19 (m, 1H), 3.96-3.88 (m, 1H), 3.62-3.53 (m, 1H), 3.38-3.29 (m, 1H) |
| 310 | 0.022 | 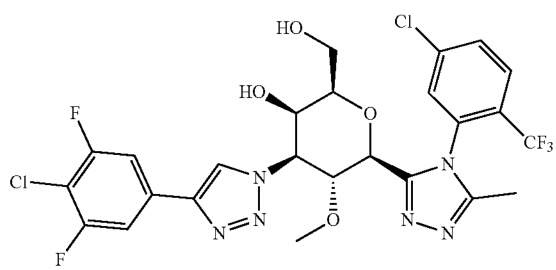 [SMILES: CO[C@@H]1[C@@H](n2cc(-c3cc(F)c(Cl)c(F)c3)nn2)[C@@H](O)[C@@H](CO)O[C@H]1c1nnc(C)n1-c1cc(Cl)ccc1C(F)(F)F] | 1.78 | 635.0 | A | $^1$H NMR (500 MHz, DMSO-d$_6$) δ 9.08 (s, 1H), 8.07 (br d, J = 7.9 Hz, 1H), 7.98 (br s, 1H), 7.92-7.83 (m, 3H), 5.52-5.41 (m, 1H), 5.05-4.93 (m, 1H), 4.81-4.68 (m, 2H), 4.20-4.07 (m, 1H), 3.40-3.33 (m, 1H), 3.10 (s, 3H), 2.15 (s, 3H) (three protons obscured) |
| 311 | 0.012 | 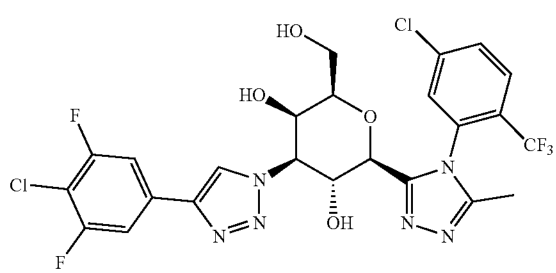 [SMILES: Cc1nnc([C@@H]2O[C@H](CO)[C@H](O)[C@H](n3cc(-c4cc(F)c(Cl)c(F)c4)nn3)[C@H]2O)n1-c1cc(Cl)ccc1C(F)(F)F] | 1.58 | 621.2 | A | $^1$H NMR (500 MHz, DMSO-d$_6$) δ 8.79-8.74 (m, 1H), 8.10-8.00 (m, 1H), 7.99-7.89 (m, 1H), 7.85-7.77 (m, 3H), 5.52-5.42 (m, 1H), 5.33-5.22 (m, 1H), 4.86 (br d, J = 2.4 Hz, 2H), 4.11 (d, J = 8.9 Hz, 1H), 3.93-3.81 (m, 1H), 3.74-3.60 (m, 1H), 3.49-3.31 (m, 1H), 3.39-3.28 (m, 2H), 2.16 (s, 3H) |

-continued

| Ex | hGal3 IC$_{50}$ (μM) | Structure | LCMS t$_R$ (min) | M + H | Method | $^1$H NMR |
|---|---|---|---|---|---|---|
| 312 | 1.60 | 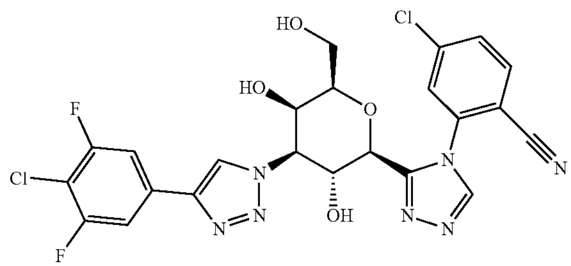 [SMILES: N#Cc1ccc(Cl)cc1-n1cnnc1[C@@H]1O[C@H](CO)[C@H](O)[C@H](n2cc(-c3cc(F)c(Cl)c(F)c3)nn2)[C@H]1O] | 1.62 | 564.1 | A | $^1$H NMR (500 MHz, DMSO-d$_6$) δ 8.50 (d, J = 8.5 Hz, 1H), 8.24-8.17 (m, 1H), 7.87 (s, 3H), 5.49-5.43 (m, 1H), 5.35-5.26 (m, 1H), 5.11-5.00 (m, 1H), 4.88-4.75 (m, 2H), 4.71-4.63 (m, 1H), 4.11-4.03 (m, 1H), 3.99-3.91 (m, 1H), 3.59-3.52 (m, 1H), 3.45-3.40 (m, 1H) |
| 313 | 0.0087 | 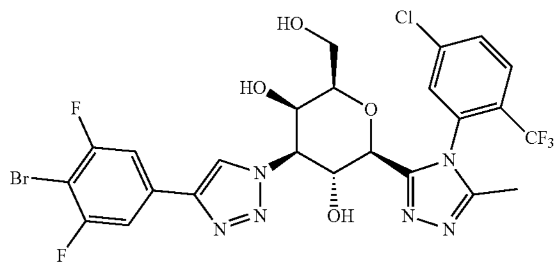 | 1.58 | 665.2 | A | $^1$H NMR (500 MHz, DMSO-d$_6$) δ 8.86-8.80 (m, 1H), 8.09-8.04 (m, 1H), 8.00-7.92 (m, 1H), 7.86 (br s, 1H), 7.80 (br dd, J = 7.6, 3.3 Hz, 2H), 5.51-5.40 (m, 1H), 5.34-5.25 (m, 1H), 4.96-4.83 (m, 1H), 4.74-4.56 (m, 1H), 4.16-4.09 (m, 1H), 3.92-3.83 (m, 1H), 3.71-3.56 (m, 1H), 3.42-3.25 (m, 1H), 2.17 (s, 3H) |
| 314 | 0.057 | 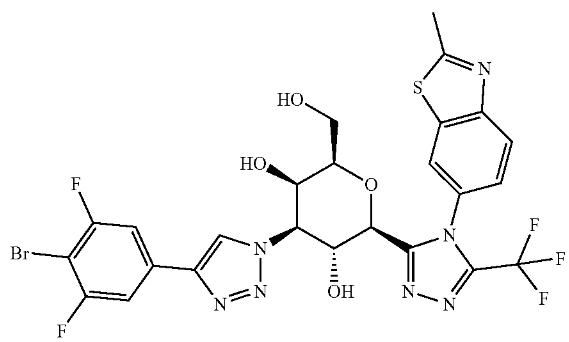 [SMILES: Cc1nc2ccc(-n3c([C@@H]4O[C@H](CO)[C@H](O)[C@H](n5cc(-c6cc(F)c(Br)c(F)c6)nn5)[C@H]4O)nnc3C(F)(F)F)cc2s1] | 1.77 | 688.2 | A | $^1$H NMR (500 MHz, DMSO-d$_6$) δ 8.90-8.77 (m, 1H), 8.48-8.26 (m, 1H), 8.16-8.07 (m, 1H), 7.83-7.76 (m, 2H), 7.74-7.58 (m, 1H), 5.72-5.56 (m, 1H), 5.44-5.27 (m, 1H), 4.88 (br s, 3H), 4.33-4.16 (m, 1H), 3.93-3.81 (m, 1H), 3.54 (br d, J = 5.2 Hz, 3H), 2.87 (s, 3H) |
| 315 | 0.98 | 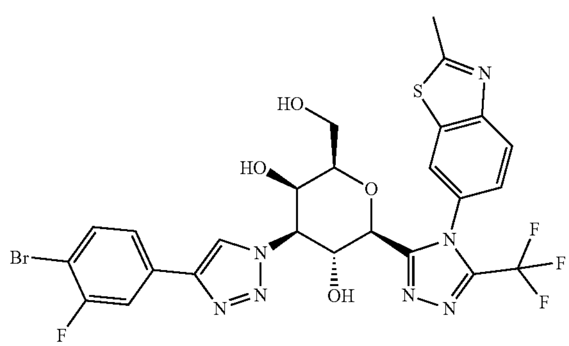 [SMILES: Cc1nc2ccc(-n3c([C@@H]4O[C@H](CO)[C@H](O)[C@H](n5cc(-c6ccc(Br)c(F)c6)nn5)[C@H]4O)nnc3C(F)(F)F)cc2s1] | 1.6 | 670.1 | A | $^1$H NMR (500 MHz, DMSO-d$_6$) δ 8.79-8.72 (m, 1H), 8.48-8.42 (m, 1H), 8.33-8.28 (m, 1H), 8.16-8.10 (m, 1H), 7.91-7.87 (m, 1H), 7.82-7.77 (m, 1H), 7.75-7.71 (m, 1H), 4.97-4.91 (m, 1H), 4.90-4.85 (m, 1H), 4.31-4.26 (m, 1H), 4.24-4.19 (m, 1H), 3.90-3.86 (m, 1H), 3.64-3.60 (m, 2H), 2.96-2.91 (m, 1H), 2.88 (s, 3H) (two protons obscured) |

-continued
| Ex | hGal3 IC$_{50}$ (μM) | Structure | LCMS t$_R$ (min) | M + H | Method | $^1$H NMR |
|---|---|---|---|---|---|---|
| 316 | n.d. | 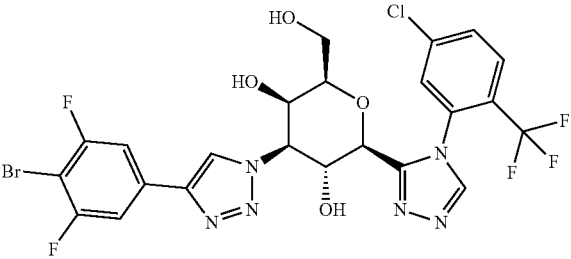 [SMILES: OC[C@H]1O[C@@H](c2nncn2-c2cc(Cl)ccc2C(F)(F)F)[C@H](O)[C@@H](n2cc(-c3cc(F)c(Br)c(F)c3)nn2)[C@H]1O] | 0.86 | 653.3 | F | $^1$H NMR (500 MHz, ACETONITRILE-d$_3$) δ 8.58 (br s, 1H), 8.00-7.93 (m, 1H), 7.87-7.76 (m, 2H), 7.70-7.60 (m, 2H), 5.21-5.08 (m, 1H), 5.08-4.97 (m, 1H), 4.91-4.80 (m, 1H), 4.59-4.49 (m, 1H), 4.42-4.31 (m, 1H), 4.21-4.13 (m, 1H), 3.60 (br s, 2H), 3.49-3.39 (m, 1H) (one proton obscured) |
| 317 | n.d. | 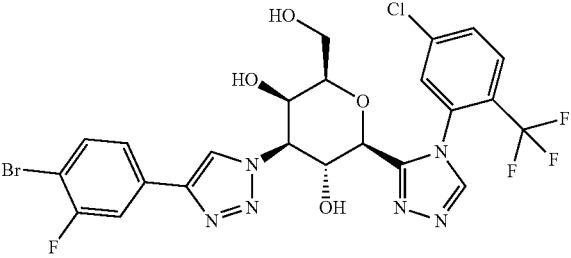 [SMILES: OC[C@H]1O[C@@H](c2nncn2-c2cc(Cl)ccc2C(F)(F)F)[C@H](O)[C@@H](n2cc(-c3ccc(Br)c(F)c3)nn2)[C@H]1O] | 0.83 | 635.2 | F | $^1$H NMR (500 MHz, ACETONITRILE-d$_3$) δ 8.58-8.46 (m, 2H), 7.99-7.92 (m, 1H), 7.89-7.83 (m, 1H), 7.82-7.77 (m, 2H), 7.75-7.70 (m, 1H), 7.69-7.63 (m, 1H), 5.17-5.08 (m, 1H), 5.03-4.96 (m, 1H), 4.88-4.78 (m, 2H), 4.56-4.48 (m, 1H), 4.40-4.32 (m, 1H), 4.19-4.14 (m, 1H), 3.66-3.57 (m, 2H), 356 (s, 1H) |
| 318 | 0.011 | 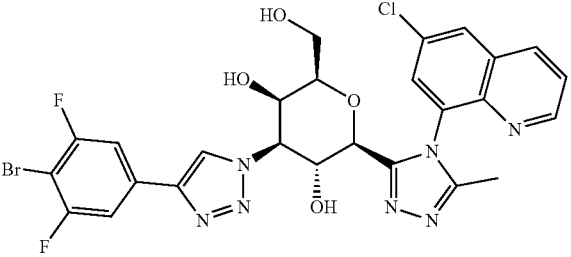 [SMILES: Cc1nnc([C@@H]2O[C@H](CO)[C@H](O)[C@H](n3cc(-c4cc(F)c(Br)c(F)c4)nn3)[C@H]2O)n1-c1cc(Cl)cc2cccnc12] | 0.83 | 650.2 | F | $^1$H NMR (500 MHz, METHANOL-d$_4$) δ 8.91-8.88 (m, 1H), 8.64-8.62 (m, 1H), 8.50-8.45 (m, 1H), 8.34-8.32 (m, 1H), 8.20-8.16 (m, 1H), 7.70-7.66 (m, 1H), 7.64-7.59 (m, 2H), 5.10-5.02 (m, 1H), 4.79-4.74 (m, 1H), 4.63-4.57 (m, 1H), 4.22-4.15 (m, 1H), 4.13-4.03 (m, 1H), 3.66-3.55 (m, 1H), 3.37-3.29 (m, 1H), 2.24 (s, 3H) |
| 319 | 0.014 | 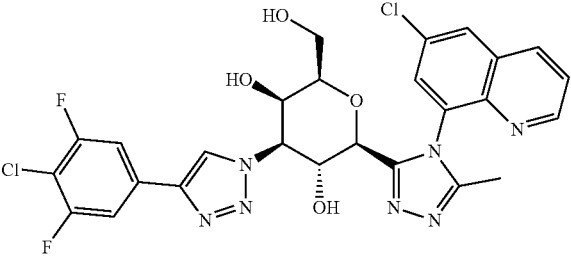 [SMILES: Cc1nnc([C@@H]2O[C@H](CO)[C@H](O)[C@H](n3cc(-c4cc(F)c(Cl)c(F)c4)nn3)[C@H]2O)n1-c1cc(Cl)cc2cccnc12] | 0.82 | 604.2 | F | $^1$H NMR (500 MHz, METHANOL-d$_4$) δ 8.91-8.87 (m, 1H), 8.64-8.60 (m, 1H), 8.50-8.47 (m, 1H), 8.35-8.31 (m, 1H), 8.20-8.17 (m, 1H), 7.71-7.64 (m, 1H), 5.10-5.02 (m, 1H), 4.79-4.73 (m, 1H), 4.21-4.15 (m, 1H), 4.09-4.04 (m, 1H), 3.63-3.60 (m, 1H), 3.35-3.32 (m, 1H), 2.24 (s, 3H) |

| Ex | hGal3 IC$_{50}$ (μM) | Structure | LCMS t$_R$ (min) | M + H | Method | $^1$H NMR |
|---|---|---|---|---|---|---|
| 320 | n.d. | 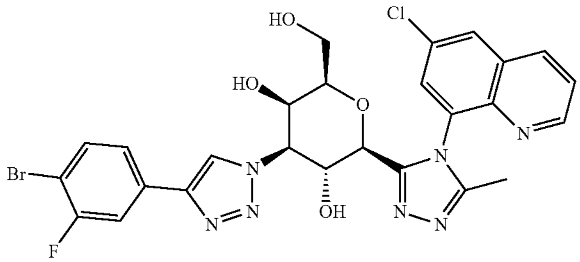 [SMILES: Cc1nnc([C@@H]2O[C@H](CO)[C@H](O)[C@H](n3cc(-c4ccc(Br)c(F)c4)nn3)[C@H]2O)n1-c1cc(Cl)cc2cccnc12] | 1.4 | 630.2 | A | $^1$H NMR (500 MHz, DMSO-d$_6$) δ 8.94 (br d, J = 4.0 Hz, 1H), 8.59-8.54 (m, 1H), 8.45 (dd, J = 5.5, 2.1 Hz, 1H), 8.13 (d, J = 1.8 Hz, 1H), 7.99 (d, J = 2.1 Hz, 1H), 7.88 (br d, J = 10.7 Hz, 1H), 7.83-7.77 (m, 1H), 7.77-7.66 (m, 2H), 5.02-4.93 (m, 1H), 4.84-4.74 (m, 1H), 4.66-4.56 (m, 1H), 4.31-4.24 (m, 1H), 4.08-4.00 (m, 1H), 3.92-3.86 (m, 1H), 3.84-3.77 (m, 1H), 3.53-3.47 (m, 1H), 3.24-3.14 (m, 1H), 2.88-2.82 (m, 1H), 2.12 (s, 3H) |
General Synthetic Scheme-1 for [C2: 2,2-difluoroethoxy] 4-aryl-1,2,4-triazole Compounds:
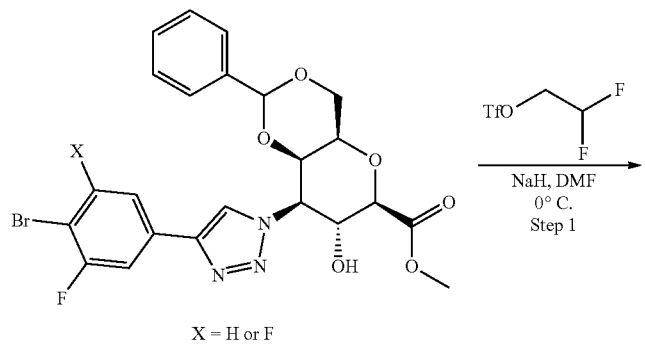
X = H or F
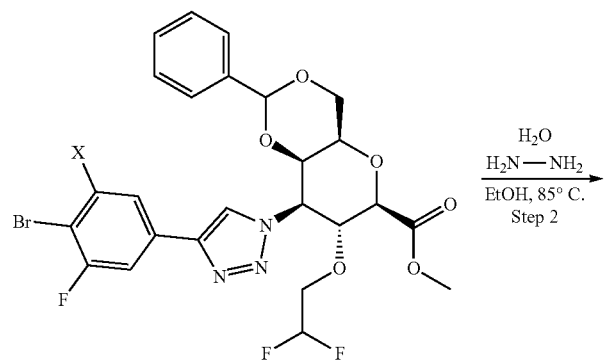

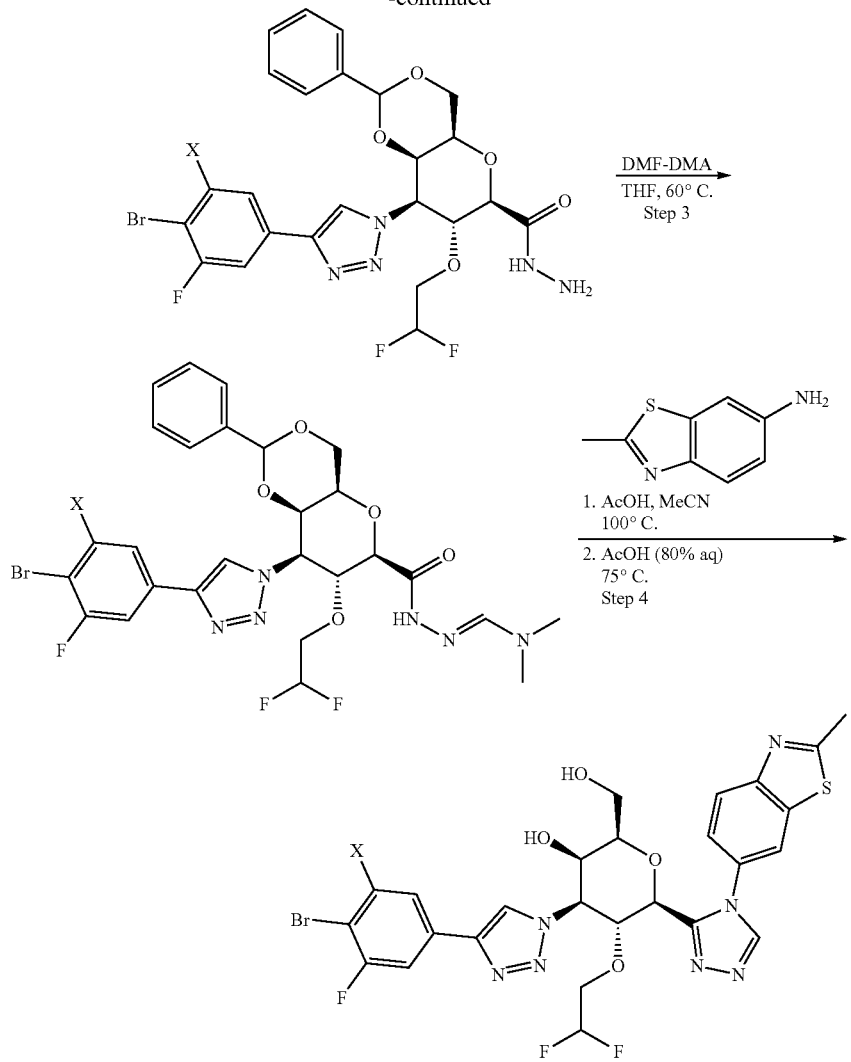

EXAMPLE 321

Preparation of (2R,3R,4S,5R,6S)-4-(4-(4-bromo-3,5-difluorophenyl)-1H-1,2,3-triazol-1-yl)-5-(2,2-difluoroethoxy)-2-(hydroxymethyl)-6-(4-(2-methylbenzo[d]thiazol-6-yl)-4H-1,2,4-triazol-3-yl)tetrahydro-2H-pyran-3-ol

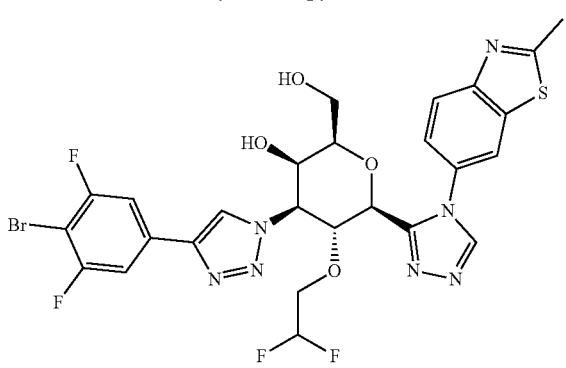

Step 1: Synthesis of methyl (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carboxylate: To a 25 mL round bottomed flask were added methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6-carboxylate (0.40 g, 0.72 mmol) and DMF (15 mL). The reaction was cooled to 0° C., then NaH (60% dispersion in mineral oil) (0.087 g, 2.2 mmol) was added. After stirring at this temperature for 45 min, 2,2-difluoroethyl trifluoromethanesulfonate (0.29 ml, 2.2 mmol) was added and the reaction was continued at 0° C. After stirring at this temperature for 1 h, the reaction was quenched with sat. $NH_4Cl$ (100 mL) and extracted with EtOAc (2×50 mL). The organic phase was combined, washed with brine, dried over $Na_2SO_4$, filtered and concentrated. The solid was triturated with ether, the product was collected by vacuum filtration, and dried in vacuo to provide the title compound (0.43 g, 0.70 mmol, 96% yield) as an off white solid. LC-MS, $[M+1]^+$=618.0, (Method F: $t_R$=1.07 min). $^1$H NMR (500 MHz, DMSO-$d_6$) δ 9.19-9.12 (m, 1H), 7.75-7.70 (m, 2H), 7.39-7.36 (m, 5H), 5.74-5.69 (m, 1H), 5.62-5.58 (m, 1H), 5.53-5.46 (m, 1H), 4.66-4.58 (m, 1H), 4.56-4.47 (m, 2H), 4.38-4.33 (m, 1H), 4.20-4.10 (m, 2H), 4.02-3.97 (m, 1H), 3.79 (s, 3H), 3.69-3.59 (m, 1H).

Step 2: Synthesis of (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbohydrazide: To a 100 mL pear shaped flask were added methyl (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carboxylate (0.43 g, 0.70 mmol) and EtOH (30 mL). To this mixture was added hydrazine hydrate (0.34 mL, 7.0 mmol) and the reaction was stirred at 85° C. for 30 h. The solvent was concentrated and the resultant semisolid was precipitated with ether, sonicated, and the solid product was collected by vacuum filtration. The filter cake was washed with ether, and the product was dried in vacuo to provide the title compound (0.36 g, 0.58 mmol, 84% yield) as a tan solid. LC-MS, [M+1]$^+$=618.1, (Method F: $t_R$=0.95 min). $^1$H NMR (500 MHz, DMSO-$d_6$) δ 9.74-9.67 (m, 1H), 9.19-9.16 (m, 1H), 7.77-7.72 (m, 2H), 7.38-7.35 (m, 5H), 5.77-5.75 (m, 2H), 5.71-5.63 (m, 1H), 5.59-5.57 (m, 1H), 5.44-5.38 (m, 1H), 4.69-4.64 (m, 1H), 4.49-4.44 (m, 3H), 4.18-4.07 (m, 2H), 3.97-3.92 (m, 1H), 3.89-3.86 (m, 1H).

Step 3: Synthesis of (E)-N'-((4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbonyl)-N,N-dimethylformohydrazonamide: To a 20 mL pear shaped flask were added (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbohydrazide (0.075 g, 0.12 mmol), THF (5 mL), and DMF-DMA (0.065 mL, 0.49 mmol). The reaction was heated to 60° C. for 2 h. The solvent was concentrated, the residue was suspended in ether, the ether was decanted from the solid (3×), and the solid was dried in vacuo to provide the title compound (0.081 g, 0.12 mmol, 99% yield) as a tan solid. LC-MS, [M+1]$^+$=673.2, (Method F: $t_R$=0.89 min).

Step 4: To a 10 mL pear shaped flask were added (E)-N'-((4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbonyl)-N,N-dimethylformohydrazonamide (81 mg, 0.12 mmol), 2-methylbenzo[d]thiazol-6-amine (28 mg, 0.17 mmol), MeCN (1 mL), and AcOH (1 mL). The reaction was stirred at 100° C. under $N_2$. After 1.5 h, the solvent was concentrated and the residue was dissolved in toluene and concentrated again. The residue was purified by flash column chromatography (24 g silica gel cartridge; A=Hex, B=EtOAc; 15 min grad.; 0% B to 10% B; flow rate=24 mL/min, product comes off at 100% B). The pure fractions were combined, concentrated and dried in vacuo. The resultant intermediate was dissolved in AcOH (80% aq) (3 mL) and stirred at 75° C. After 18 h, the solvent was concentrated, then co-evaporated with toluene (2×). The crude residue was purified by preparative HPLC (Method L) to afford the title compound (14 mg, 0.020, 17% yield). LC-MS, [M+1]$^+$=684.0, (Method A: $t_R$=1.64 min). $^1$H NMR (500 MHz, DMSO-$d_6$) δ 9.12-9.08 (m, 1H), 8.99 (s, 1H), 8.44-8.36 (m, 1H), 8.13-8.06 (m, 1H), 7.83-7.76 (m, 2H), 7.73-7.67 (m, 1H), 5.61-5.33 (m, 2H), 5.22-5.13 (m, 1H), 5.09-5.00 (m, 2H), 4.58-4.50 (m, 1H), 3.97-3.91 (m, 1H), 3.85-3.78 (m, 1H), 3.64-3.54 (m, 2H), 3.53-3.47 (m, 1H), 3.46-3.35 (m, 1H), 2.86 (s, 3H). hGal-3 IC$_{50}$=0.053 μM

EXAMPLE 322

Preparation of (2R,3R,4S,5R,6S)-4-(4-(4-bromo-3-fluorophenyl)-1H-1,2,3-triazol-1-yl)-5-(2,2-difluoroethoxy)-6-(hydroxymethyl)-6-(4-(2-methylbenzo[d]thiazol-6-yl)-4H-1,2,4-triazol-3-yl)tetrahydro-2H-pyran-3-ol

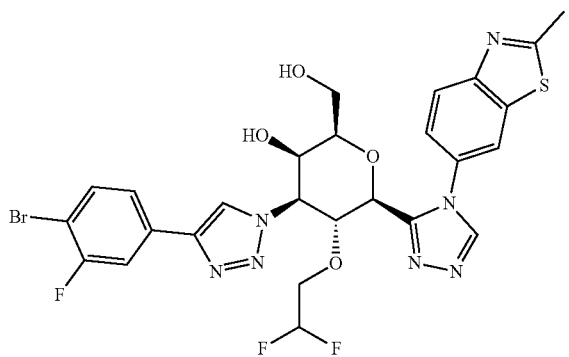 [SMILES: Cc1nc2ccc(-n3cnnc3[C@@H]3O[C@H](CO)[C@H](O)[C@H](n4cc(-c5ccc(Br)c(F)c5)nn4)[C@H]3OCC(F)F)cc2s1]

Example 320 was prepared in an analogous fashion to Example 321, substituting methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6-carboxylate with methyl (4aR,6R,7R,8R,8aR)-8-(4-(4-bromo-3-fluorophenyl)-1H-1,2,3-triazol-1-yl)-7-(2,2-difluoroethoxy)-2-phenylhexahydropyrano[3,2-d][1,3]dioxine-6-carboxylate. LC-MS, [M+1]$^+$=666.2, (Method A: $t_R$=1.60 min). $^1$H NMR (500 MHz, DMSO-$d_6$) δ 9.00 (d, J=18.6 Hz, 2H), 8.40 (s, 1H), 8.12-8.06 (m, 1H), 7.91-7.85 (m, 1H), 7.83-7.76 (m, 1H), 7.75-7.66 (m, 2H), 5.60-5.31 (m, 2H), 5.19-5.10 (m, 1H), 5.09-5.01 (m, 1H), 4.58-4.49 (m, 1H), 3.98-3.92 (m, 1H), 3.85-3.77 (m, 1H), 3.67-3.54 (m, 3H), 3.53-3.47 (m, 1H), 3.46-3.34 (m, 1H), 2.86 (s, 3H). hGal-3 IC$_{50}$=0.072 μM

EXAMPLE 323

Preparation of (2R,3R,4S,5R,6S)-4-(4-(4-bromo-3-fluorophenyl)-1H-1,2,3-triazol-1-yl)-6-(4-(6-chloroquinolin-8-yl)-4H-1,2,4-triazol-3-yl)-5-(2,2-difluoroethoxy)-2-(hydroxymethyl)tetrahydro-2H-pyran-3-ol

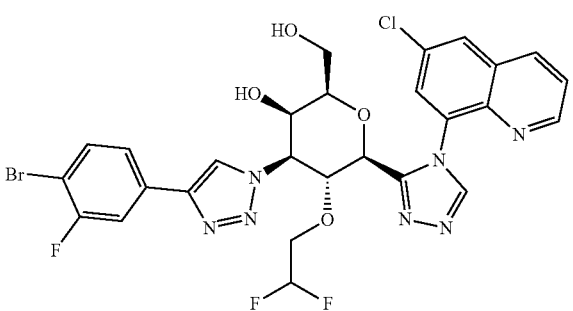 [SMILES: OC[C@H]1O[C@@H](c2nncn2-c2cc(Cl)cc3cccnc23)[C@H](OCC(F)F)[C@@H](n2cc(-c3ccc(Br)c(F)c3)nn2)[C@H]1O]

Example 323 was prepared in an analogous fashion to Example 321, substituting methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6- carboxylate with methyl (4aR,6R,7R,8R,8aR)-8-(4-(4-bromo-3-fluorophenyl)-1H-1,2,3-triazol-1-yl)-7-(2,2-difluoroethoxy)-2-phenylhexahydropyrano[3,2-d][1,3]dioxine-6-carboxylate and substituting 2-methylbenzo[d]thiazol-6-amine with 6-chloroquinolin-8-amine where appropriate. LC-MS, [M+1]+=680.0, (Method A: $t_R$=1.77 min). $^1$H NMR (500 MHz, DMSO-$d_6$) δ 9.02-8.99 (m, 1H), 8.96-8.94 (m, 1H), 8.93 (s, 1H), 8.59-8.54 (m, 1H), 8.46-8.42 (m, 1H), 8.13-8.08 (m, 1H), 7.91-7.86 (m, 1H), 7.84-7.78 (m, 1H), 7.78-7.70 (m, 3H), 5.58-5.28 (m, 1H), 5.13-5.04 (m, 1H), 4.98-4.90 (m, 1H), 4.54-4.46 (m, 1H), 3.94-3.86 (m, 1H), 3.78-3.67 (m, 1H), 3.64-3.53 (m, 1H) (three protons obscured). hGal-3 $IC_{50}$=0.13 μM.

General Synthetic Scheme-2 for [C2: 2,2-difluoroethoxy] 4-aryl-1,2,4-triazole Compounds:

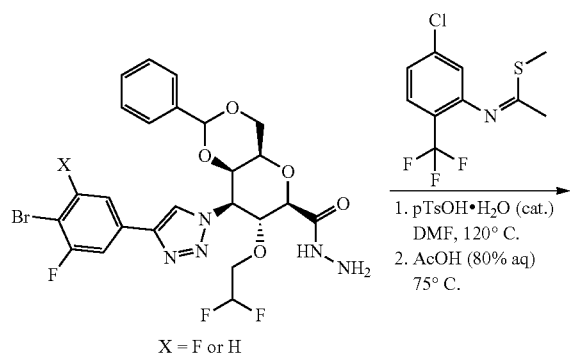

EXAMPLE 324

Preparation of (2R,3R,4S,5R,6S)-4-(4-(4-bromo-3,5-difluorophenyl)-1H-1,2,3-triazol-1-yl)-6-(4-(5-chloro-2-(trifluoromethyl)phenyl)-5-methyl-4H-1,2,4-triazol-3-yl)-5-(2,2-difluoroethoxy)-2-(hydroxymethyl)tetrahydro-2H-pyran-3-ol

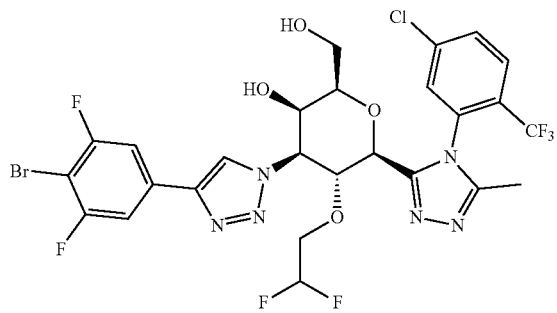 [SMILES: Cc1nnc([C@@H]2O[C@H](CO)[C@H](O)[C@H](n3cc(-c4cc(F)c(Br)c(F)c4)nn3)[C@H]2OCC(F)F)n1-c1cc(Cl)ccc1C(F)(F)F]

To a 40 mL vial equipped with a pressure release cap were added (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbohydrazide (80 mg, 0.13 mmol), methyl (Z)-N-(5-chloro-2-(trifluoromethyl)phenyl)ethanimidothioate (40.0 mg, 0.150 mmol), TsOH (2.5 mg, 0.013 mmol), and DMF (5 mL). The vessel was flushed with $N_2$, capped and stirred at 120° C. The residue was purified by preparative HPLC (2×2 mL injection; Method: Grad. Solv. System: From 20% A: 80% B to 0% A: 100% B; (A=10% MeCN/90% $H_2O$+0.1% TFA); (B=90% MeCN/10% $H_2O$+0.1% TFA); Detection at 220 nm; 10 min grad; Phenomenex AXIA 5u C18, 30×100 mm). The respective pure fractions were combined and concentrated. The resultant residue was dried in vacuo. The intermediate thus obtained was dissolved in AcOH (2 mL) (80% aq) and stirred at 75° C. After 18 h, the solvent was concentrated and the residue was purified by preparative HPLC (2 mL injection; Method: Grad. Solv. System: From 80% A: 20% B to 0% A: 100% B; (A=10% MeCN/90% $H_2O$+0.1% TFA); (B=90% MeCN/10% $H_2O$+0.1% TFA); Detection at 220 nm; 10 min grad; Phenomenex AXIA 5u C18, 30×100 mm). The pure fractions were combined and concentrated. The resultant residue was dried in vacuo to afford the title compound (1.5 mg, 2.0 μmol, 2% yield) as a white solid. LC-MS, [M+1]+=731.2, (Method F: $t_R$=0.99 min). $^1$H NMR (500 MHz, METHANOL-$d_4$) δ 8.84-8.80 (m, 1H), 8.08-8.03 (m, 1H), 7.97-7.92 (m, 1H), 7.91-7.88 (m, 1H), 7.69-7.65 (m, 2H), 5.49-5.22 (m, 1H), 5.14-5.06 (m, 1H), 5.04-4.97 (m, 1H), 4.35-4.26 (m, 1H), 4.12-4.04 (m, 1H), 3.94-3.81 (m, 1H), 3.68-3.55 (m, 3H), 3.46-3.37 (m, 1H), 2.37-2.28 (m, 3H).

EXAMPLE 325

Preparation of (2R,3R,4S,5R,6S)-4-(4-(4-bromo-3-fluorophenyl)-1H-1,2,3-triazol-1-yl)-6-(4-(5-chloro-2-(trifluoromethyl)phenyl)-5-methyl-4H-1,2,4-triazol-3-yl)-5-(2,2-difluoroethoxy)-2-(hydroxymethyl)tetrahydro-2H-pyran-3-ol

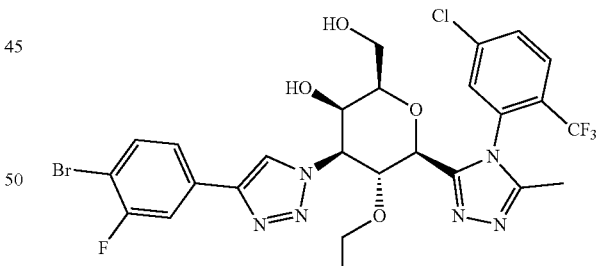

Example 323 was prepared in an analogous fashion to Example 324 substituting methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6-carboxylate with methyl (4aR,6R,7R,8R,8aR)-8-(4-(4-bromo-3-fluorophenyl)-1H-1,2,3-triazol-1-yl)-7-(2,2-difluoroethoxy)-2-phenylhexahydropyrano[3,2-d][1,3]dioxine-6-carboxylate. LC-MS, [M+1]+=713.2, (Method F: $t_R$=0.96 min). $^1$H NMR (500 MHz, METHANOL-$d_4$) δ 8.79-8.74 (m, 1H), 8.08-8.02 (m, 1H), 7.97-7.92 (m, 1H), 7.91-7.87 (m, 1H), 7.80-7.76 (m, 1H), 7.75-7.70 (m, 1H), 7.68-7.64 (m, 1H), 5.50-5.22 (m, 1H), 5.16-5.06 (m, 1H), 5.04-4.95 (m, 1H), 4.35-4.22 (m, 1H), 4.14-4.01 (m, 1H), 3.96-3.78 (m, 1H), 3.72-3.54 (m, 3H), 3.46-3.36 (m, 1H), 2.31 (s, 3H). hGal-3 IC$_{50}$=0.020 μM.

EXAMPLE 326

Preparation of (2S,3R,4R,5R,6R)-4-(4-(4-chloro-3,5-difluorophenyl)-1H-1,2,3-triazol-1-yl)-2-(4-(2,5-dichlorophenyl)-4H-1,2,4-triazol-3-yl)-6-(hydroxymethyl)tetrahydro-2H-pyran-3,5-diol

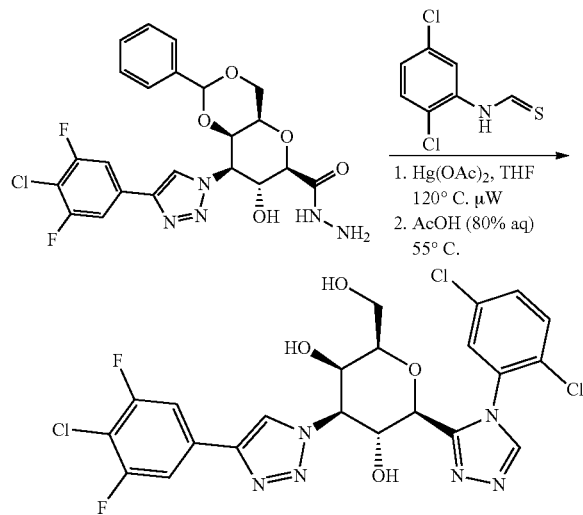

To a 5 mL microwave vial were added (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carbohydrazide (70 mg, 0.14 mmol), N-(2,5-dichlorophenyl)methanethioamide (34 mg, 0.17 mmol), mercury(II) acetate (53 mg, 0.17 mmol), and THF (5 mL). The vial was capped and irradiated by microwave at 120° C. for 1 h. The dark gray precipitate was filtered, the filtrate concentrated and the residue was purified by flash column chromatography (24 g silica gel cartridge; A=DCM, B=MeOH; 15 min grad.; 0% B to 10% B; flow rate=24 mL/min). The pure fractions were combined, concentrated and dried in vacuo. The intermediate thus obtained was dissolved in AcOH (80% solution aq.) (2 mL) and stirred at 55° C. After 18 h, the solvent was concentrated and the residue was suspended in toluene and concentrated (2×). The resultant crude product was purified by preparative HPLC (Method L) to afford the title compound (5 mg, 0.0087 mmol, 6% yield). LC-MS, [M+1]$^+$=573.2, (Method A: t$_R$=1.51 min). $^1$H NMR (500 MHz, DMSO-d$_6$) δ 8.90-8.81 (m, 2H), 7.90-7.84 (m, 2H), 7.81 (s, 1H), 7.77-7.72 (m, 2H), 5.50-5.43 (m, 1H), 5.40-5.27 (m, 1H), 5.01-4.85 (m, 1H), 4.76-4.58 (m, 1H), 4.41-4.22 (m, 1H), 3.97-3.89 (m, 1H), 3.71-3.59 (m, 1H) (three protons obscured). hGal-3 IC$_{50}$=0.044 μM.

EXAMPLE 327

Preparation of (2R,3R,4S,5R,6S)-4-(4-(4-chloro-3,5-difluorophenyl)-1H-1,2,3-triazol-1-yl)-6-(4-(2,5-dichlorophenyl)-4H-1,2,4-triazol-3-yl)-2-(hydroxymethyl)-5-methoxytetrahydro-2H-pyran-3-ol

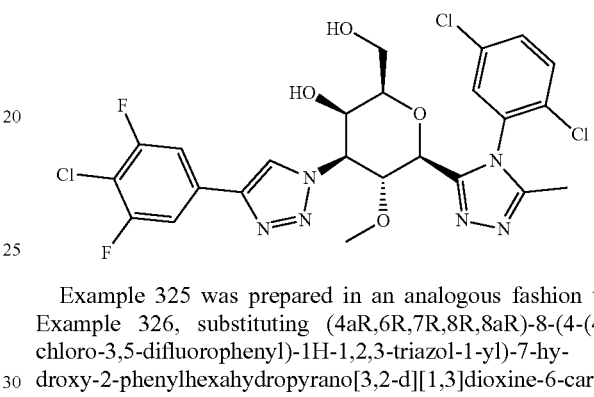

Example 325 was prepared in an analogous fashion to Example 326, substituting (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carbohydrazide with (4aR,6R,7R,8R,8aR)-8-(4-(4-chloro-3,5-difluorophenyl)-1H-1,2,3-triazol-1-yl)-7-methoxy-2-phenylhexahydropyrano[3,2-d][1,3]dioxine-6-carbohydrazide. LC-MS, [M+1]$^+$=587.0, (Method A: t$_R$=1.73 min). $^1$H NMR (500 MHz, DMSO-d$_6$) δ 9.18-9.07 (m, 1H), 8.93-8.87 (m, 1H), 7.90 (d, J=8.5 Hz, 2H), 7.86-7.80 (m, 2H), 7.78-7.73 (m, 1H), 5.10 (dd, J=10.6, 2.4 Hz, 1H), 3.92 (br s, 1H), 3.91 (s, 3H), 3.67-3.60 (m, 1H), 3.45-3.35 (m, 1H), 3.03-2.94 (m, 2H), 2.90-2.78 (m, 1H) (three protons obscured). hGal-3 IC$_{50}$=0.040 μM.

EXAMPLE 328

Preparation of (2R,3R,4S,5R,6S)-2-(hydroxymethyl)-5-(non-8-en-1-yloxy)-4-(4-(3,4,5-trifluorophenyl)-1H-1,2,3-triazol-1-yl)-6-(4-(2-vinylphenyl)-4H-1,2,4-triazol-3-yl)tetrahydro-2H-pyran-3-ol

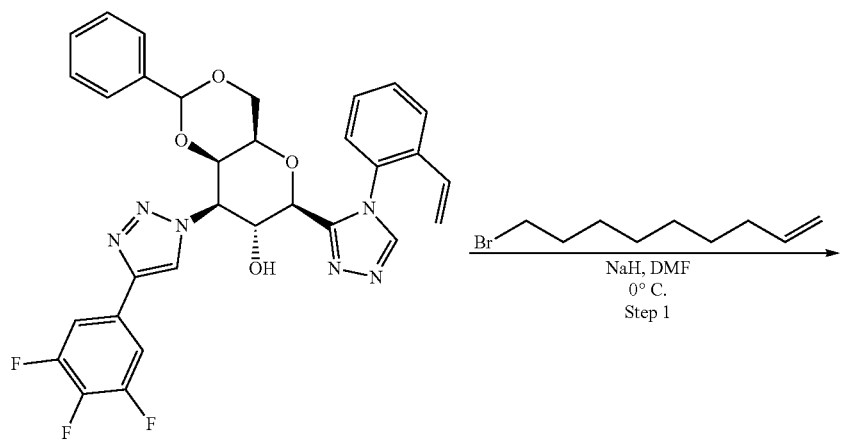

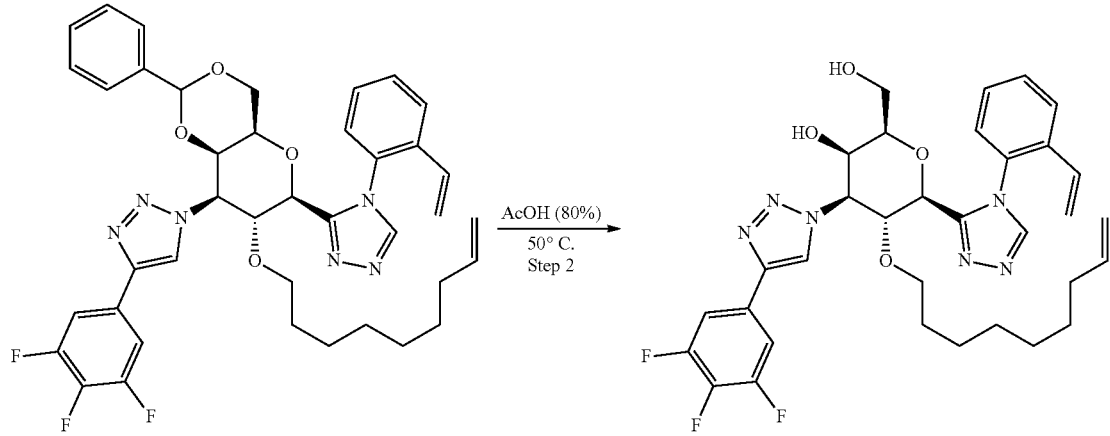

Step 1: Synthesis of 1-((4aR,6S,7R,8R,8aR)-7-(non-8-en-1-yloxy)-2-phenyl-6-(4-(2-vinylphenyl)-4H-1,2,4-triazol-3-yl)hexahydropyrano[3,2-d][1,3]dioxin-8-yl)-4-(3,4,5-trifluorophenyl)-1H-1,2,3-triazole: To a 100 mL pear shaped flask were added (4aR,6S,7R,8R,8aR)-2-phenyl-8-(4-(3,4,5-trifluorophenyl)-1H-1,2,3-triazol-1-yl)-6-(4-(2-vinylphenyl)-4H-1,2,4-triazol-3-yl)hexahydropyrano[3,2-d][1,3]dioxin-7-ol (0.16 g, 0.27 mmol) and DMF (10 mL). The reaction was cooled to 0° C., then NaH (60% dispersion in mineral oil) (0.032 g, 0.80 mmol) was added and the reaction was stirred at rt for 1 h. The mixture was cooled to 0° C., then 9-bromonon-1-ene (0.163 g, 0.797 mmol) was added and the reaction was stirred at rt. After 18 h, the reaction was quenched with ice water (100 mL) and extracted with EtOAc (2×50 mL). The organic phase was combined, washed with brine, dried over $Na_2SO_4$, filtered and concentrated. The residue was purified by flash column chromatography (40 g silica gel cartridge; A=Hex, B=EtOAc; 15 min grad.; 0% B to 100% B; flow rate=40 mL/min). The pure fractions were combined, concentrated and dried in vacuo to afford the title compound (72 mg, 0.099 mmol, 37% yield) as a white solid. LC-MS, $[M+1]^+$=727.3, (Method F: $t_R$=1.18 min). $^1$H NMR (500 MHz, METHANOL-$d_4$) δ 8.72 (s, 1H), 8.66 (s, 1H), 7.94-7.85 (m, 1H), 7.63 (s, 3H), 7.49 (br s, 4H), 7.42-7.38 (m, 3H), 6.48-6.18 (m, 1H), 5.99-5.81 (m, 1H), 5.77-5.68 (m, 1H), 5.56 (s, 1H), 5.46-5.31 (m, 1H), 5.22-5.16 (m, 1H), 4.95-4.92 (m, 1H), 4.92-4.89 (m, 1H), 4.88-4.87 (m, 1H), 4.52-4.43 (m, 2H), 4.24-4.14 (m, 1H), 4.14-4.06 (m, 1H), 3.73-3.63 (m, 1H), 3.01-2.94 (m, 1H), 1.95-1.87 (m, 2H), 1.23-1.15 (m, 2H), 1.12-1.03 (m, 4H), 1.01-0.92 (m, 3H), 0.90-0.79 (m, 2H).

Step 2: To a 20 mL scintillation vial equipped with a pressure release cap were added 1-((4aR,6S,7R,8R,8aR)-7-(non-8-en-1-yloxy)-2-phenyl-6-(4-(2-vinylphenyl)-4H-1,2,4-triazol-3-yl)hexahydropyrano[3,2-d][1,3]dioxin-8-yl)-4-(3,4,5-trifluorophenyl)-1H-1,2,3-triazole (14 mg, 0.019 mmol), and AcOH (80%) (770 μL). The vial was capped and the mixture was stirred at 50° C. After 2 d, the solvent was concentrated and the residue was purified by preparative HPLC (Column: XBridge C18, 200 mm×19 mm, 5-μm). particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 44% B, 44-84% B over 20 minutes, then a 4-minute hold at 100% B; Flow Rate: 20 mL/min) to afford the title compound (6.4 mg, 0.010 mmol, 51% yield). LC-MS, $[M+1]^+$=639.2, (Method A: $t_R$=2.40 min). $^1$H NMR (500 MHz, DMSO-$d_6$) δ 9.04 (br s, 1H), 8.76 (s, 1H), 7.94-7.85 (m, 3H), 7.63 (br t, J=7.9 Hz, 1H), 7.52 (br t, J=7.3 Hz, 2H), 6.29-6.02 (m, 1H), 5.92-5.79 (m, 1H), 5.74-5.60 (m, 1H), 5.49-5.41 (m, 1H), 5.39-5.22 (m, 1H), 5.05-4.98 (m, 1H), 4.94-4.85 (m, 2H), 4.85-4.54 (m, 2H), 4.23-4.10 (m, 1H), 3.94-3.82 (m, 1H), 3.65-3.51 (m, 1H), 3.41-3.29 (m, 1H), 2.97-2.88 (m, 1H), 1.87-1.73 (m, 2H), 1.14-1.01 (m, 2H), 0.99-0.88 (m, 4H), 0.88-0.79 (m, 2H), 0.76-0.61 (m, 2H) (two protons obscured). hGal-3 $IC_{50}$=5.6 μM.

EXAMPLE 327

Preparation of ethyl 2-(((2S,3R,4S,5R,6R)-4-(4-(4-chloro-3-fluorophenyl)-1H-1,2,3-triazol-1-yl)-5-hydroxy-6-(hydroxymethyl)-2-(1-(2-methylbenzo[d]thiazol-6-yl)-1H-1,2,4-triazol-5-yl)tetrahydro-2H-pyran-3-yl)oxy)acetate

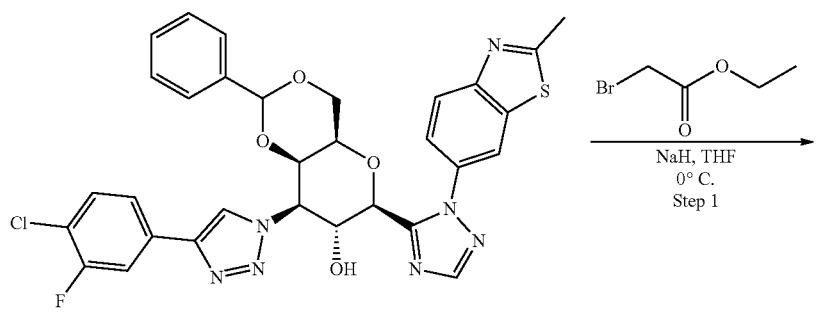

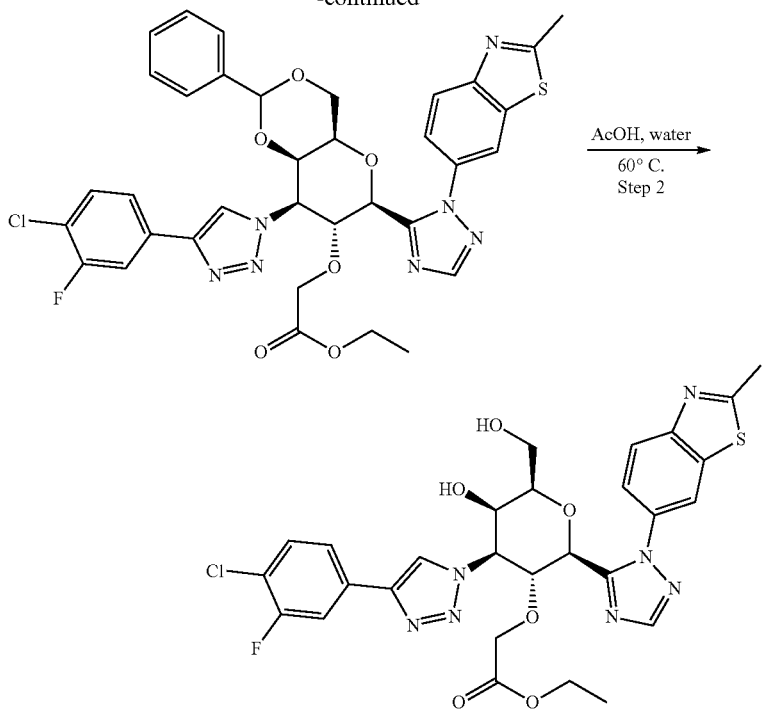

Step 1: Synthesis of ethyl 2-(((4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-yl)oxy)acetate: To a 200 mL pear shaped flask were added (4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-ol (0.56 g, 0.87 mmol) and THF (40 mL). A suspension formed. To homogenize this mixture, DMF (10 mL) was added, and the solution was cooled to 0° C. To this mixture was added NaH (60% dispersion in mineral oil) (0.17 g, 4.3 mmol). After stirring at this temperature for 15 min, ethyl 2-bromoacetate (0.19 mL, 1.7 mmol) was added and the reaction was allowed to slowly reach rt over a period of 3 h. The mixture was quenched with sat. NH$_4$Cl, further diluted with water (200 mL) and extracted with EtOAc (2×100 mL). The organic phase was combined, washed with brine, dried over Na$_2$SO$_4$, filtered and concentrated. The residue was purified by flash column chromatography (80 g silica gel cartridge; A=Hex, B=EtOAc; 20 min grad.; 0% B to 100% B; flow rate=60 mL/min; product elutes at 100% B). The pure fractions were combined, concentrated and dried in vacuo to afford the title compound (0.56 g, 0.77 mmol, 88% yield) as a white solid. LC-MS, [M+1]$^+$=732.3, (Method F: t$_R$=1.10 min). $^1$H NMR (500 MHz, DMSO-d$_6$) δ 9.20-9.18 (m, 1H), 8.36-8.33 (m, 1H), 8.31-8.29 (m, 1H), 8.19-8.15 (m, 1H), 7.91-7.87 (m, 1H), 7.80-7.76 (m, 1H), 7.76-7.69 (m, 2H), 7.42-7.35 (m, 5H), 5.61-5.54 (m, 2H), 5.16-5.08 (m, 1H), 4.99-4.93 (m, 1H), 4.53-4.47 (m, 1H), 4.26-4.22 (m, 1H), 4.20-4.15 (m, 1H), 4.15-4.10 (m, 1H), 4.05-4.02 (m, 1H), 3.88-3.84 (m, 1H), 3.83-3.75 (m, 2H), 2.90 (s, 3H), 0.99 (s, 3H).

Step 2: To a 40 mL vial equipped with a pressure release cap were added ethyl 2-(((4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-yl)oxy)acetate (20 mg, 0.027 mmol) and AcOH (80% aq.) (5 mL). The vial was capped and heated at 60° C. After 2 d, the solvent was concentrated, the residue was co-evaporated with toluene (2×) and the residue was purified by preparative HPLC (Method L) to afford the title compound (11 mg, 0.017 mmol, 64% yield). LC-MS, [M+1]$^+$=644.3, (Method A: t$_R$=1.72 min). $^1$H NMR (500 MHz, DMSO-d$_6$) δ 9.05 (s, 1H), 8.52-8.45 (m, 1H), 8.27 (s, 1H), 8.14-8.08 (m, 1H), 7.96-7.90 (m, 1H), 7.83-7.76 (m, 2H), 7.72-7.66 (m, 1H), 5.54-5.46 (m, 1H), 5.26-5.17 (m, 1H), 5.08-4.98 (m, 1H), 4.74-4.64 (m, 1H), 4.23-4.14 (m, 1H), 4.00-3.96 (m, 1H), 3.95-3.90 (m, 1H), 3.88-3.82 (m, 1H), 3.81-3.71 (m, 2H), 3.64-3.57 (m, 1H), 3.47-3.41 (m, 1H), 2.91-2.83 (m, 3H), 1.08-0.92 (m, 3H) (one proton obscured). hGal-3 IC$_{50}$=0.07 μM.

EXAMPLE 328

Preparation of 2-(((2S,3R,4S,5R,6R)-4-(4-(4-chloro-3-fluorophenyl)-1H-1,2,3-triazol-1-yl)-5-hydroxy-6-(hydroxymethyl)-2-(1-(2-methylbenzo[d]thiazol-6-yl)-1H-1,2,4-triazol-5-yl)tetrahydro-2H-pyran-3-yl)oxy)acetic acid

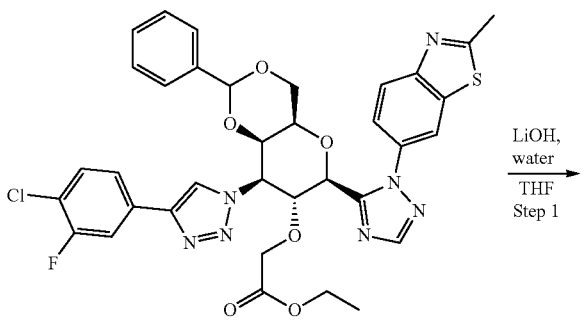

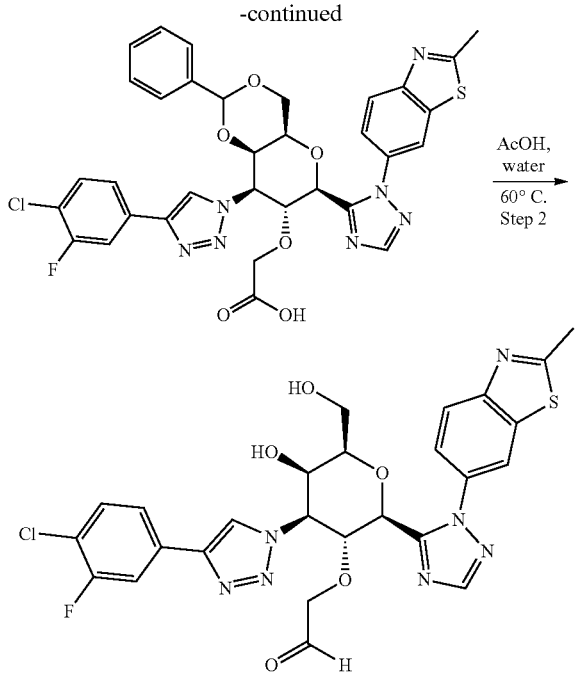

Step 1: Synthesis of 2-(((4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-yl)oxy)acetic acid: To a 200 mL pear shaped flask were added ethyl 2-(((4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-yl)oxy)acetate (0.54 g, 0.74 mmol), and THF (25 mL). To this mixture was added LiOH (0.071 g, 3.0 mmol) dissolved in water (5 mL). The reaction was stirred. After 3 h, the reaction was diluted with 1 N HCl (100 mL) and extracted with EtOAc (2×50 mL). The organic phase was combined, washed with brine, dried over $Na_2SO_4$, filtered and concentrated. The product was dried in vacuo to provide the title compound (0.52 g, 0.74 mmol, 100% yield) as a white solid. LC-MS, $[M+1]^+$=704.3, (Method F: $t_R$=1.00 min). $^1$H NMR (500 MHz, DMSO-$d_6$) δ 9.22-9.16 (m, 1H), 8.39-8.34 (m, 1H), 8.31-8.26 (m, 1H), 8.17-8.11 (m, 1H), 7.93-7.87 (m, 1H), 7.80-7.76 (m, 1H), 7.76-7.73 (m, 1H), 7.73-7.68 (m, 1H), 7.41-7.36 (m, 5H), 5.61-5.56 (m, 1H), 5.54-5.46 (m, 1H), 5.13-5.04 (m, 1H), 4.96-4.88 (m, 1H), 4.53-4.46 (m, 1H), 4.26-4.19 (m, 1H), 4.15-4.10 (m, 1H), 3.74-3.64 (m, 1H), 2.89 (s, 3H) (two protons obscured).

Step 2: To a vial equipped with a pressure release cap were added 2-(((4aR,6S,7R,8R,8aR)-8-(4-(4-chloro-3-fluorophenyl)-1H-1,2,3-triazol-1-yl)-6-(1-(2-methylbenzo[d]thiazol-6-yl)-1H-1,2,4-triazol-5-yl)-2-phenylhexahydropyrano[3,2-d][1,3]dioxin-7-yl)oxy)acetic acid (20 mg, 0.028 mmol) and AcOH (80% aq.) (5 mL). The vial was capped and stirred at 60° C. After 2 d, the solvent was concentrated, the residue was co-evaporated with toluene (2×) and the residue was purified by preparative HPLC (Method L) to provide the title compound (9.9 mg, 0.016 mmol, 55% yield). LC-MS, $[M+1]^+$=616.3, (Method A: $t_R$=1.06 min). $^1$H NMR (500 MHz, DMSO-$d_6$) δ 9.09-9.05 (m, 1H), 8.50-8.46 (m, 1H), 8.27 (s, 1H), 8.13-8.09 (m, 1H), 7.97-7.93 (m, 1H), 7.84-7.77 (m, 2H), 7.72-7.64 (m, 1H), 5.51-5.46 (m, 1H), 5.22-5.17 (m, 1H), 5.04-4.99 (m, 1H), 4.70-4.65 (m, 1H), 4.11-4.05 (m, 1H), 4.00-3.95 (m, 1H), 3.94-3.90 (m, 1H), 3.75-3.67 (m, 1H), 3.65-3.57 (m, 1H), 3.55-3.48 (m, 1H), 2.88 (s, 3H) (one proton obscured). hGal-3 $IC_{50}$=0.03 μM.

EXAMPLE 329 AND EXAMPLE 330

Preparation of (2R,3R,4S,5R,6S)-5-(((E)-3-bromoallyl)oxy)-6-(1-(2,5-dichlorophenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol and (2R,3R,4S,5R,6S)-5-(((Z)-3-bromoallyl)oxy)-6-(1-(2,5-dichlorophenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol

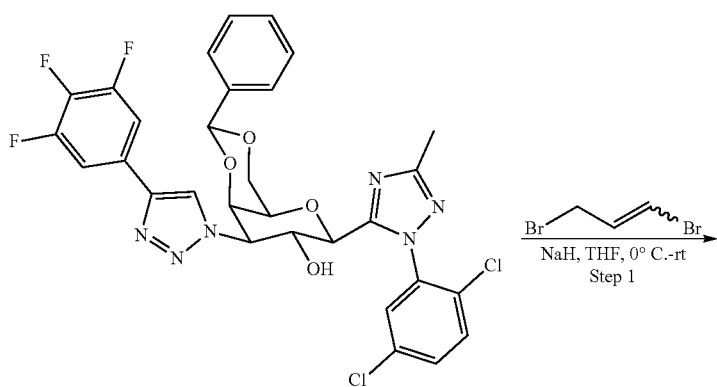

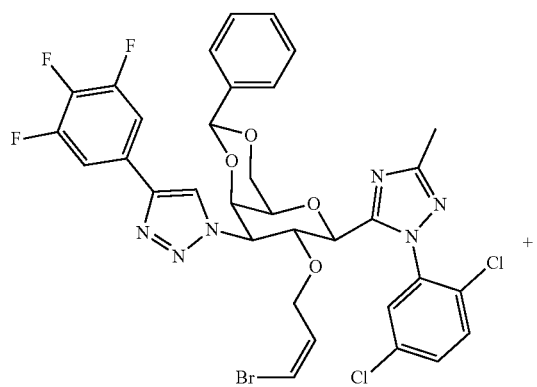

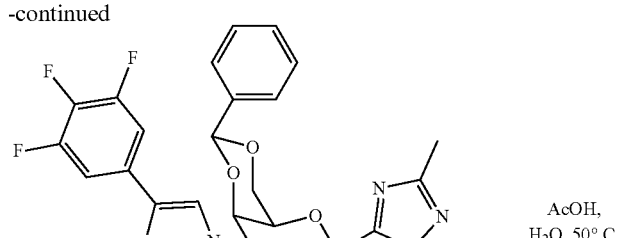

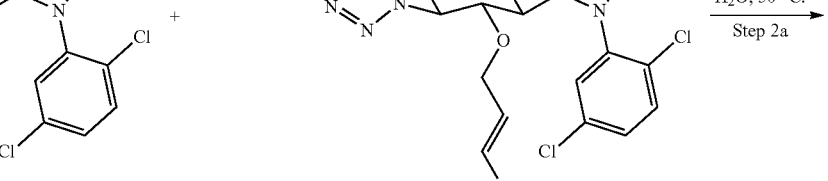

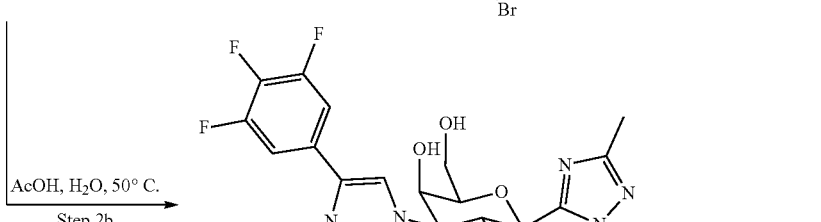

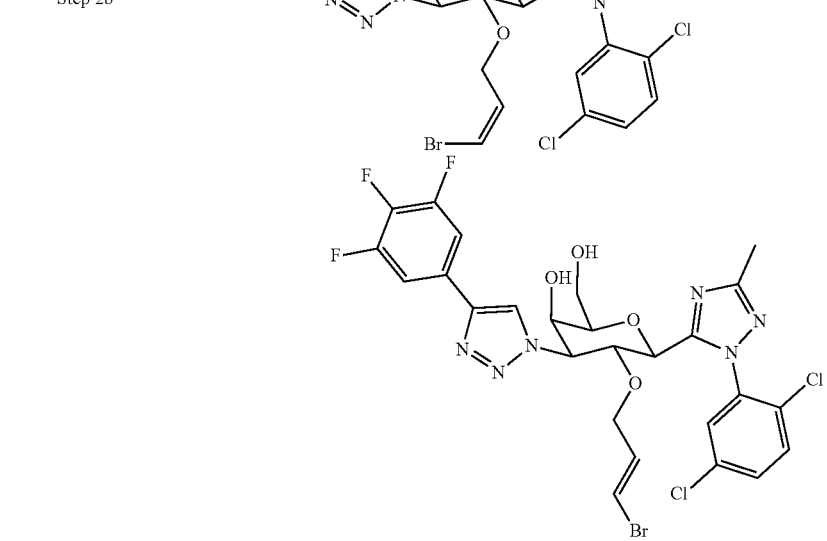

Step 1. Preparation of 1-((2S,4aR,6S,7R,8R,8aR)-7-(((E)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole and 1-((2S,4aR,6S,7R,8R,8aR)-7-(((Z)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole. A solution of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (34 mg, 0.052 mmol) in THF (2 mL) was cooled to 0° C. and to the solution was added sodium hydride (60% in mineral oil) (10.31 mg, 0.258 mmol). The mixture was stirred for 15 minutes and 1,3-dibromo-1-propene (0.015 mL, 0.155 mmol) was added. The mixture was removed from the ice bath and was stirred at rt for 17 h. The mixture was diluted with 10 mL of water and was extracted with ethyl acetate (2×10 mL). The organic layers were washed with brine, dried over magnesium sulfate, filtered and concentrated under reduced pressure. The residue was purified by flash chromatography using a 10-50% EtOAc in hexanes gradient and a 12 g silica gel column. The fractions containing the major isolates were combined and concentrated under reduced pressure to give each of the title products as an off-white film.

1-((2S,4aR,6S,7R,8R,8aR)-7-(((E)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole: LCMS: m/e 778.9 (MH$^+$), 1.13 min (method G). $^1$H NMR (500 MHz, CDCl$_3$) δ 8.10 (s, 1H), 7.55-7.39 (m, 10H), 6.00 (d, J=13.8 Hz, 1H), 5.63-5.56 (m, 1H), 5.52 (s, 1H), 5.04 (dd, J=10.5, 3.3 Hz, 1H), 4.68 (br s, 1H), 4.41 (d, J=3.0 Hz, 1H), 4.38-4.30 (m, 2H), 4.06 (dd, J=12.7, 1.1 Hz, 1H), 3.72 (br d, J=3.9 Hz, 1H), 3.62 (s, 1H), 3.40 (br s, 1H), 2.49 (s, 3H).

1-((2S,4aR,6S,7R,8R,8aR)-7-(((Z)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole: LCMS: m/e 778.9

(MH+), 1.13 min (method G). ¹H NMR (500 MHz, CDCl₃) δ 8.14 (s, 1H), 7.57-7.34 (m, 10H), 5.99 (br d, J=6.9 Hz, 1H), 5.69-5.62 (m, 1H), 5.53-5.47 (m, 1H), 5.09-5.01 (m, 1H), 4.71 (br s, 1H), 4.44-4.30 (m, 3H), 4.09-3.53 (m, 4H), 2.50 (s, 3H).

Step 2a. Preparation of (2R,3R,4S,5R,6S)-5-(((E)-3-bromoallyl)oxy)-6-(1-(2,5-dichlorophenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol (Example 329): To a solution of 1-((2S,4aR,6S,7R,8R,8aR)-7-(((E)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole (12 mg, 0.015 mmol) in acetic acid (1 mL) was added water (0.4 mL) and the mixture was heated to 50° C. After 40 h of heating, the mixture was cooled to rt and was concentrated under a stream of nitrogen. The residue was dissolved in DMF and methanol and was purified by preparative HPLC (Method R) to give the title product as a white film. LCMS: m/e 688.9, 690.9 (MH+), 0.99 min (method G). ¹H NMR (400 MHz, CDCl₃) δ 8.28 (br s, 1H), 7.64-7.40 (m, 5H), 6.04 (d, J=13.6 Hz, 1H), 5.55 (dt, J=13.5, 6.6 Hz, 1H), 4.81-3.16 (m, 11H), 2.54 (s, 3H).

Step 2b. Preparation of (2R,3R,4S,5R,6S)-5-(((Z)-3-bromoallyl)oxy)-6-(1-(2,5-dichlorophenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol (Example 330): To a solution of 1-((2S,4aR,6S,7R,8R,8aR)-7-(((Z)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole (11 mg, 0.014 mmol) in acetic acid (1 mL) was added water (0.4 mL) and the mixture was heated to 50° C. After 40 h of heating, the mixture was cooled to rt. And was concentrated under a stream of nitrogen. The residue was dissolved in DMF purified by prep HPLC (method R). LCMS: m/e 689.0, 690.9 (MH+), 0.97 min (method G). ¹H NMR (400 MHz, CDCl₃) δ 8.33 (br d, J=1.1 Hz, 1H), 7.61-7.42 (m, 5H), 6.09 (br d, J=6.4 Hz, 1H), 5.64-5.54 (m, 1H), 4.86-3.32 (m, 11H), 2.56 (br s, 3H).

EXAMPLE 331

Preparation of (2R,3R,4S,5R,6S)-5-(allyloxy)-6-(1-(2,5-dichlorophenyl)-3-methyl-1H-1,2,4-triazol-5-yl)-2-(hydroxymethyl)-4-(4-(3,4,5-trifluorophenyl)-1H-1,2,3-triazol-1-yl)tetrahydro-2H-pyran-3-ol

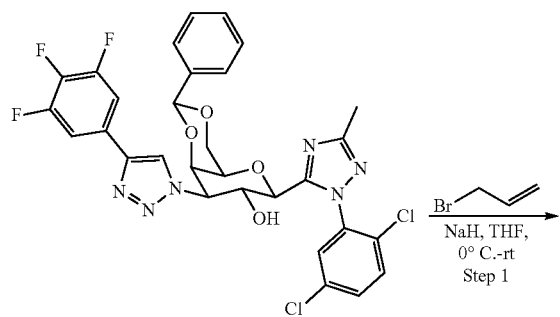

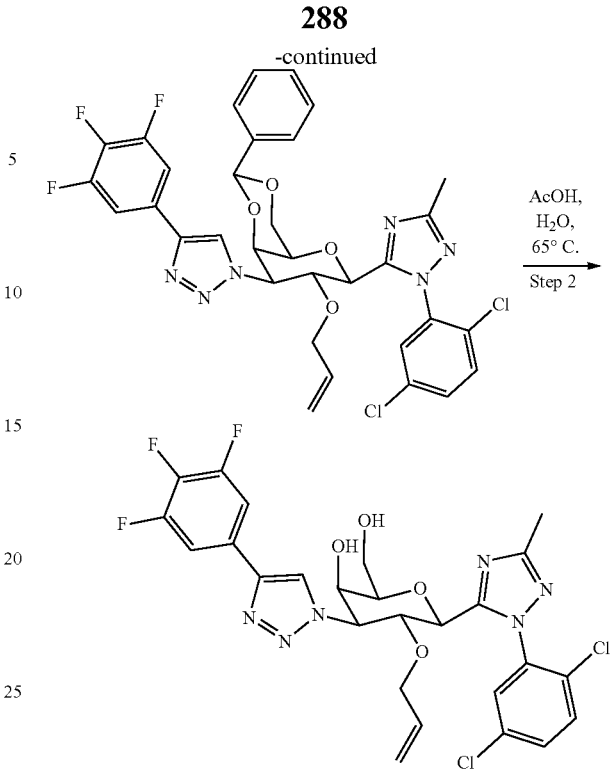

Step 1. Preparation of 1-((2S,4aR,6S,7R,8R,8aR)-7-(allyloxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole: A solution of (2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (0.197 g, 0.299 mmol) in THF (5 mL) was cooled to 0° C. and sodium hydride (60% in mineral oil, 0.08 g, 2.00 mmol) was added. The mixture was stirred for 15 minutes, then allyl bromide (0.078 mL, 0.896 mmol) was added. The mixture was warmed to rt as the ice bath melted and was stirred overnight at rt. After stirring the mixture for 17 h, it was carefully diluted with water (15 mL) and was extracted with ethyl acetate (2×15 mL). The organic layers were washed with brine, dried over magnesium sulfate, filtered and concentrated under reduced pressure. The residue was purified by flash chromatography using a 0-50% EtOAc in hexanes gradient and a 24 g silica gel column. The fractions containing the major peak were combined and concentrated under reduced pressure to give the expected product as a white solid. LCMS: m/e 699.1 (MH+), 1.11 min (method G). ¹H NMR (400 MHz, CDCl₃) δ 8.09 (s, 1H), 7.55-7.37 (m, 10H), 5.51 (s, 1H), 5.32-5.18 (m, 1H), 5.05 (dd, J=10.5, 3.4 Hz, 1H), 4.92-4.80 (m, 2H), 4.66 (br s, 1H), 4.44-4.30 (m, 3H), 4.06 (dd, J=12.8, 1.8 Hz, 1H), 3.81-3.61 (m, 2H), 3.39 (br d, J=6.2 Hz, 1H), 2.49 (s, 3H).

Step 2. A solution of 1-((2S,4aR,6S,7R,8R,8aR)-7-(allyloxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole (0.01 g, 0.014 mmol) in acetic acid (2 mL) and water (0.6 mL) was heated to 65° C. After 8 of heating, the mixture was cooled to rt and was stirred for 2 days. The mixture was concentrated under reduced pressure, diluted with DMF, filtered through a plug of glass wool and was purified by preparative HPLC (method S) to give the title product (5.8 mg, 0.0095 mmol, 68% yield). LCMS: m/e 611.3 (MH+), 2.03 min (method H). ¹H NMR (500 MHz, DMSO-d₆ with water suppression) δ 9.02 (s, 1H), 7.95-7.58 (m, 5H), 5.47 (br d, J=5.5 Hz, 1H), 5.26 (ddt, J=16.6, 10.9, 5.2 Hz, 1H), 5.12 (br d, J=10.4 Hz, 1H), 4.84-4.63 (m, 3H), 4.83-4.40 (m, 1H), 4.37 (br d, J=8.9 Hz, 1H), 3.90 (br s, 1H), 3.72 (br t, J=6.0 Hz, 1H), 3.62-2.84 (m, 2H), 2.38 (s, 3H).

EXAMPLE 332

Preparation of ((E)-3-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)prop-1-en-1-yl)diphenylphosphine oxide

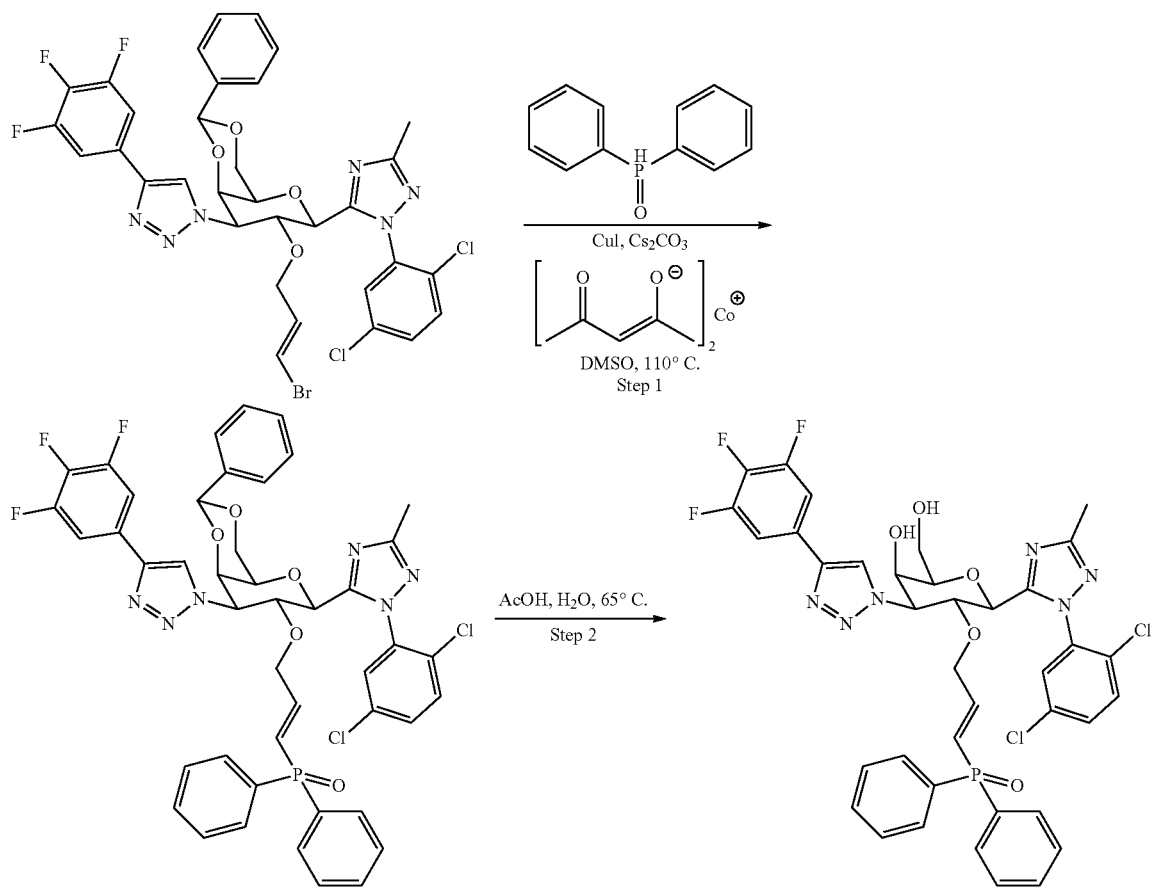

Chemistry Reference: *New J. Chem.* 2016, 40, 9556-9564.

Step 1. Preparation of ((E)-3-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)prop-1-en-1-yl)diphenylphosphine oxide: To a flask containing 1-((2S,4aR,6S,7R,8R,8aR)-7-(((E)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole (0.026 g, 0.033 mmol) was added diphenylphosphine oxide (10.13 mg, 0.050 mmol), cesium carbonate (0.022 g, 0.067 mmol), cobalt (II) acetylacetonate (5 mg, 0.019 mmol) and copper (I) iodide (5 mg, 0.026 mmol) followed by DMSO (2 mL). The mixture was flushed with nitrogen then heated to 110° C. for 16 h. The mixture was cooled to rt, diluted with water (10 mL) and extracted with ethyl acetate (2×10 mL). The organic layers were washed with water (3×10 mL), then with brine and were dried over magnesium sulfate. The drying agent was removed by filtration and the filtrate was concentrated under reduced pressure. The residue was purified by prep HPLC (method V). The fraction containing the product were concentrated under reduced pressure to give the product as an off-white film (0.01 g, 0.011 mmol, 33% yield). LCMS: m/e 899.6 (MH+), 1.07 min (method G).

Step 2. To a vial containing ((E)-3-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy) prop-1-en-1-yl)diphenylphosphine oxide (0.01 g, 0.011 mmol) was added acetic acid (1 mL) and water (0.2 mL). The mixture was heated to 65° C. overnight for 25 h, then was cooled rt, concentrated under a stream of nitrogen, dissolved in DMF, filtered through a plug of glass wool and was purified by preparative HPLC (method W) to give the title product (3.2 mg, 0.0039 mmol, 35% yield). LCMS: m/e 811.08 (MH+), 1.85 min (method H). ¹H NMR (500 MHz, DMSO-d₆ with water suppression) δ 8.98 (s, 1H), 7.97-7.69 (m, 5H), 7.60-7.26 (m, 10H), 6.16 (br s, 1H), 5.50 (br d, J=5.8 Hz, 1H), 5.31 (br d, J=10.7 Hz, 1H), 5.13 (br t, J=9.8 Hz, 1H), 4.57 (br d, J=8.9 Hz, 1H), 4.06-3.86 (m, 2H), 3.74 (br t, J=6.0 Hz, 1H), 3.54-3.32 (m, 3H), 2.35 (s, 3H).

EXAMPLE 333

Preparation of ((E)-3-(((2S,3R,4S,5R,6R)-2-(1-(2,5-dichlorophenyl)-3-methyl-1H-1,2,4-triazol-5-yl)-5-hydroxy-6-(hydroxymethyl)-4-(4-(3,4,5-trifluorophenyl)-1H-1,2,3-triazol-1-yl)tetrahydro-2H-pyran-3-yl)oxy)prop-1-en-1-yl)diethylphosphine oxide

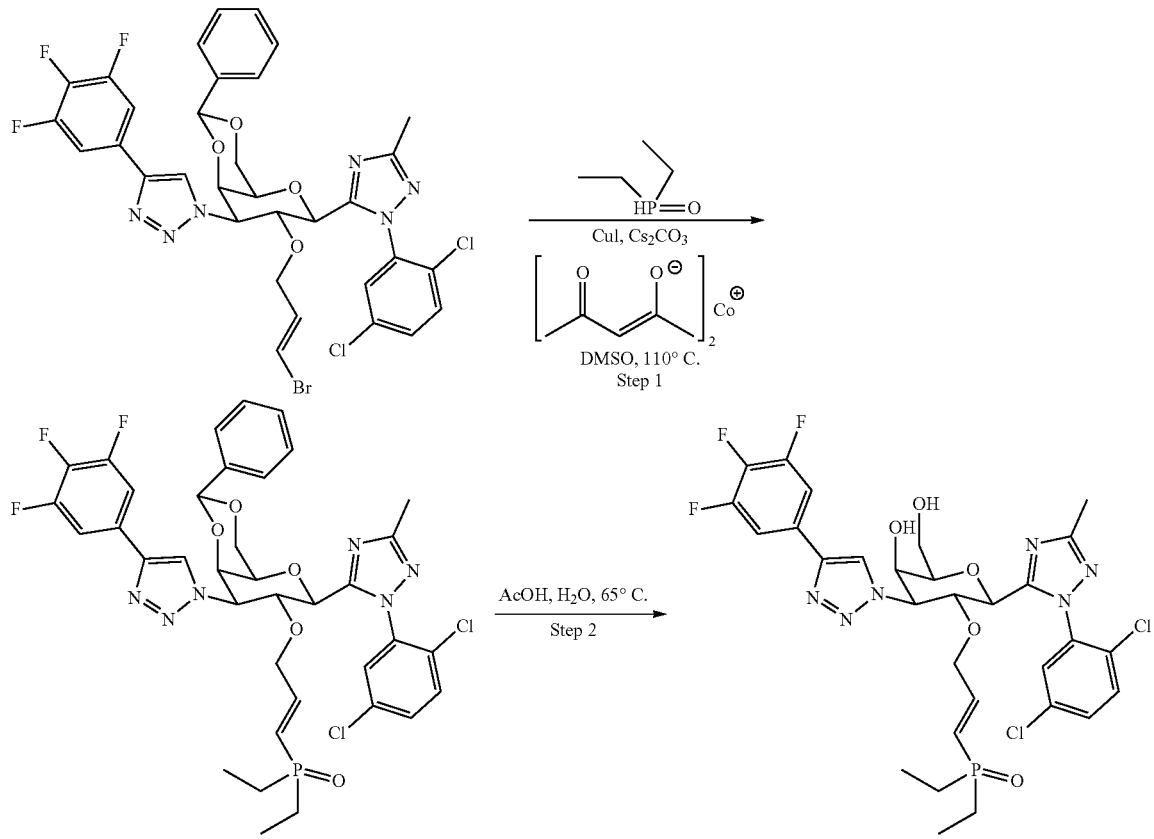

Chemistry Reference: *New J. Chem.* 2016, 40, 9556-9564.

Step 1. Preparation of ((E)-3-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)prop-1-en-1-yl)diethylphosphine oxide: To a flask containing 1-((2S,4aR,6S,7R,8R,8aR)-7-(((E)-3-bromoallyl)oxy)-6-(1-(2,5-dichlorophenyl)-3-methyl-1H-1,2,4-triazol-5-yl)-2-phenylhexahydropyrano[3,2-d][1,3]dioxin-8-yl)-4-(3,4,5-trifluorophenyl)-1H-1,2,3-triazole (0.027 g, 0.035 mmol) was added diethylphosphine oxide (10 mg, 0.094 mmol), cesium carbonate (40 mg, 0.123 mmol), cobalt(II) acetylacetonate (3 mg, 0.012 mmol) and copper(I) iodide (3 mg, 0.016 mmol) followed by DMSO (1 mL). The mixture was flushed with nitrogen then heated to 110° C. for 16 h. The mixture was cooled to rt and was stirred at rt for 2 days, then was diluted with water (10 mL) and extracted with ethyl acetate (2×10 mL). The organic layers were washed with water (3×10 mL), then with brine and were dried over magnesium sulfate. The drying agent was removed by filtration and the filtrate was concentrated under reduced pressure. The residue was purified by preparative HPLC (method T). The fractions containing the major peak were concentrated under reduced pressure to give the product as an off-white film (7.0 mg, 0.009 mmol, 26% yield). LCMS: m/e 803.5 (MH$^+$), 0.99 min (method G).

Step 2. A solution of ((E)-3-(((2S,4aR,6S,7R,8R,8aR)-6-(1-(2,5-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl)oxy)prop-1-en-1-yl)diethylphosphine oxide (0.007 g, 8.71 μmol) in acetic acid (1 mL) and water (0.2 mL) was heated to 65° C. for 15.5 h. The mixture was cooled to rt, concentrated under a stream of nitrogen, dissolved in DMF, filtered through a plug of glass wool and was purified by preparative HPLC (method U) to give the title product (2.9 mg, 0.004 mmol, 46% yield). LCMS: m/e 715.06 (MH$^+$), 1.54 min (method H). $^1$H NMR (500 MHz, DMSO-d6 with water suppression) δ 9.02 (br d, J=15.3 Hz, 1H), 8.00-7.49 (m, 5H), 6.24-3.25 (m, 11H), 2.37 (br d, J=3.4 Hz, 3H), 1.60-1.02 (m, 4H), 0.89-0.61 (m, 6H).

Section 2

LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile:water with 0.1% TFA; Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in experimental procedures.

Preparation of Hydrazine Intermediates Preparation of (5-Chloro-2-(trifluoromethyl)phenyl)hydrazine hydrochloride

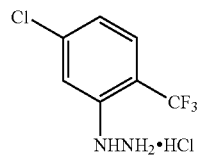

To a solution of 5-chloro-2-(trifluoromethyl)aniline (0.587 g, 3.0 mmol) in acetic acid (1.5 mL, 26.2 mmol) at rt was added concentrated hydrochloric acid (3.0 mL, 99 mmol) in one portion. To the resulting mixture at −10 to −5° C. was added a solution of sodium nitrite (0.248 g, 3.60 mmol) in water (0.9 mL) over 10 min. The mixture was stirred at −10 to 0° C. for 45 min before a solution of tin(II) chloride dihydrate (1.489 g, 6.60 mmol) in concentrated hydrochloric acid (3.0 mL, 99 mmol), pre-cooled at 0° C., over 10 min. The mixture was stirred at −10 to 0° C. for 1 h and then at 0 to 5° C. for 1 h. The precipitating product, (5-chloro-2-(trifluoromethyl)phenyl)hydrazine, HCl (0.49 g, 1.983 mmol, 66.1% yield), was collected as a pale solid by suction filtration and dried at 50° C. under vacuum. MS (ESI) m/z: 211.08 [M+H]$^+$; $^1$H NMR (500 MHz, METHANOL-$d_4$) δ 7.69 (d, J=8.3 Hz, 1H), 7.28-7.19 (m, 2H).

Preparation of (5-Chloro-2-(trifluoromethyl)phenyl)hydrazine

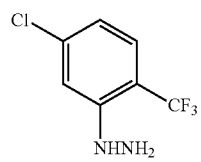 [SMILES: NNc1cc(Cl)ccc1C(F)(F)F]

To a solution of 5-chloro-2-(trifluoromethyl)aniline (6.0 g, 30.7 mmol) in acetic acid (16.1 mL, 281 mmol) at rt was added concentrated hydrochloric acid (32 mL, 1053 mmol). To the resulting suspension at 0° C. was added a solution of sodium nitrite (2.54 g, 36.8 mmol) in water (9.2 mL) over 10 min. The mixture was stirred at rt for 4 h before a solution of tin(II) chloride dihydrate (15.23 g, 67.5 mmol) in concentrated hydrochloric acid (32 mL, 1053 mmol) was added over 10 min. The mixture was stirred at rt for 1.5 h. The precipitating solid was collected by suction filtration, then dissolved in water (100 mL), basified with 6N NaOH solution to pH 9, and extracted with EtOAc (4×50 mL). The combined extract was dried over MgSO$_4$ and concentrated to a crude solid. The crude was purified with a silica gel flash column, eluting with 0-5% MeOH in DCM to afford (5-chloro-2-(trifluoromethyl)phenyl)hydrazine (5.35 g, 25.4 mmol, 83% yield) as an off-white solid. MS (ESI) m/z: 210.9/212.9 (M+H)$^+$; $^1$H NMR (400 MHz, METHANOL-$d_4$) δ 7.36-7.44 (m, 2H), 6.79 (br d, J=7.92 Hz, 1H).

Preparation of 5-Chloro-3-hydrazineyl-2-(trifluoromethyl)pyridine hydrochloride

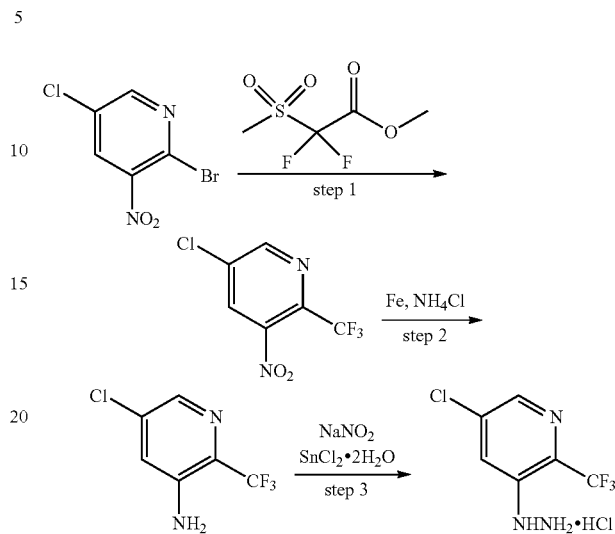

Step 1. Preparation of 5-Chloro-3-nitro-2-(trifluoromethyl)pyridine: A mixture of 2-bromo-5-chloro-3-nitropyridine (1.00 g, 4.21 mmol), methyl 2,2-difluoro-2-(fluorosulfonyl)acetate (0.971 g, 5.05 mmol), and copper(I) iodide (0.963 g, 5.05 mmol) in DMF (10 mL) was heated at 85° C. for 16 h. Upon cooling to rt, the mixture was diluted with ethyl acetate (20 mL) and filtered through Celite. The filtrate was concentrated under vacuum to almost dryness. The residue was diluted with ethyl acetate (180 mL), washed with water (3×40 mL) and brine (30 mL), and dried over anhydrous MgSO$_4$. The desired product, 5-chloro-3-nitro-2-(trifluoromethyl)pyridine (0.578 g, 2.55 mmol, 60.6% yield), was isolated as a light yellow oil by flash chromatography (80 g silica gel, solid loading, 5-20% ethyl acetate/hexane). $^1$H NMR (500 MHz, CHLOROFORM-d) δ 8.89 (d, J=2.2 Hz, 1H), 8.25 (d, J=1.7 Hz, 1H).

Step 2. Preparation of 5-Chloro-2-(trifluoromethyl)pyridin-3-amine: A mixture of 5-chloro-3-nitro-2-(trifluoromethyl)pyridine (0.578 g, 2.55 mmol), ammonium chloride (0.682 g, 12.76 mmol), and iron mesh (0.570 g, 10.21 mmol) in ethanol (15 mL) and water (1.5 mL) was heated at 80° C. for 15 h. Upon cooling to rt, the mixture was diluted with THF (15 mL) and filtered through Celite. The filtrate was concentrated under vacuum to dryness. To the residue was added water (15 mL) and saturated NaHCO$_3$ solution (3 mL). The mixture was extracted with dichloromethane (4×40 mL). The combined extract was dried over anhydrous Na$_2$SO$_4$ and concentrated under vacuum. The residue was subjected to flash chromatography (40 g silica gel, solid loading, 10-20% ethyl acetate/hexane) to provide 5-chloro-2-(trifluoromethyl)pyridin-3-amine (0.371 g, 1.887 mmol, 74.0% yield) as a white solid. MS (ESI) m/z: 196.9 [M+H]$^+$.

Step 3. Preparation of 5-Chloro-3-hydrazineyl-2-(trifluoromethyl)pyridine hydrochloride: To a solution of 5-chloro-2-(trifluoromethyl)pyridin-3-amine (0.300 g, 1.526 mmol) in acetic acid (0.8 mL, 13.97 mmol) at rt was added concentrated hydrochloric acid (1.6 mL, 52.7 mmol). To the resulting mixture at −5 to 0° C. was added a solution of sodium nitrite (0.126 g, 1.832 mmol) in water (0.5 mL) over 5 min. The mixture was stirred at −5 to 5° C. for 45 min before a solution of tin(II) chloride dihydrate (0.758 g, 3.36 mmol) in concentrated hydrochloric acid (1.6 mL, 52.7 mmol), pre-cooled at 0° C., over 10 min. The mixture was stirred at −5 to 5° C. for 2 h. To the mixture was added methanol (5 mL), and the insoluble inorganic salt was removed by suction filtration. The filtrate was concentrated under vacuum to a volume of approximately 12 mL. The residue was subjected to prep. HPLC (Column: Sunfire C18 OBD 5u 30×100 mm; Solvent A: 90% H$_2$O-10% methanol-0.1% TFA, Solvent B: 10% methanol-90% H$_2$O 0.1% TFA; Gradient: 0-100% B over 10 min; Flow rate: 40 ml/min) with multiple injections. The correct fractions were combined and concentrated under vacuum to a volume of approximately 20 mL. To the residue was added concentrated hydrochloric acid (5 mL). The mixture was cooled to −78° C. and lyophilized to provide 5-chloro-3-hydrazineyl-2-(trifluoromethyl)pyridine, HCl (50 mg, 0.202 mmol, 13.2% yield) as a beige solid.

Preparation of 6-Hydrazineyl-2-(trifluoromethyl)benzo[d]thiazole hydrochloride

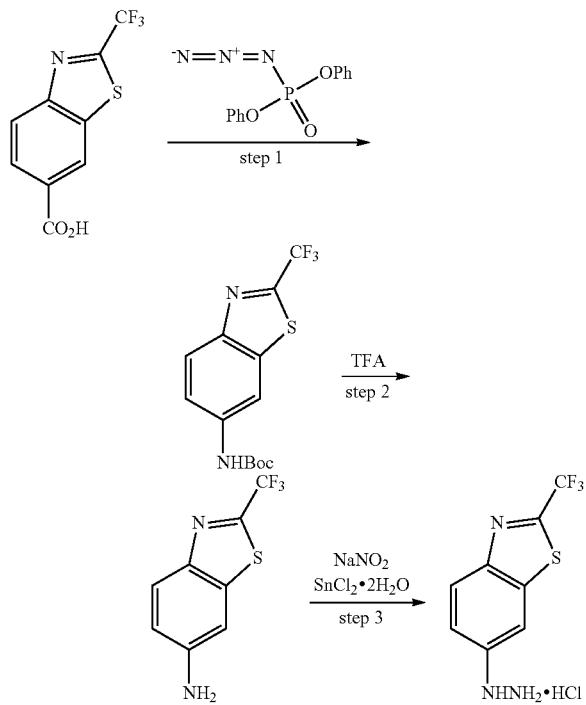

Step 1. Preparation of tert-Butyl (2-(trifluoromethyl)benzo[d]thiazol-6-yl)carbamate: To a solution of 2-(trifluoromethyl)benzo[d]thiazole-6-carboxylic acid (0.48 g, 1.942 mmol) and triethylamine (0.261 ml, 1.873 mmol) in anhydrous t-BuOH (10 mL) at rt was added diphenyl phosphorazidate (0.502 ml, 2.330 mmol) over 3 min. The mixture was heated at reflux for 4 h. The volatiles were removed under vacuum. The residue was submitted to flash chromatography (80 g silica gel, solid loading, 5-20% ethyl acetate/hexane) to provide tert-butyl (2-(trifluoromethyl)benzo[d]thiazol-6-yl)carbamate (0.772 g) as a beige solid. The product was used in the next step without further purification. MS (ESI) m/z: 319.0 [M+H]⁺.

Step 2. Preparation of 2-(Trifluoromethyl)benzo[d]thiazol-6-amine: To a solution of tert-butyl (2-(trifluoromethyl)benzo[d]thiazol-6-yl)carbamate (0.772 g, <2.425 mmol) in dichloromethane (15 mL) at 0° C. was trifluoroacetic acid (15 mL, 195 mmol) over 1 min. The mixture was stirred at rt for 30 min and then concentrated under vacuum to dryness. The residue was dissolved in water (10 mL), basified with 1 N NaOH solution, and extracted with dichloromethane (3×25 mL). The combined extract was dried over anhydrous Na$_2$SO$_4$. The desired product, 2-(trifluoromethyl)benzo[d]thiazol-6-amine (0.282 g, 1.292 mmol, 66% over two steps), was isolated as a beige solid by flash chromatography (40 g silica gel, solid loading, 20-50% ethyl acetate/hexane).

Step 3. Preparation of 6-Hydrazineyl-2-(trifluoromethyl)benzo[d]thiazole hydrochloride: To a solution of 2-(trifluoromethyl)benzo[d]thiazol-6-amine (0.282 g, 1.292 mmol) in acetic acid (0.8 mL, 13.97 mmol) at rt was added concentrated hydrochloric acid (1.8 mL, 59.2 mmol) in one portion. To the resulting mixture at −10 to −5° C. was added a solution of sodium nitrite (0.107 g, 1.551 mmol) in water (0.5 mL) over 10 min. The mixture was stirred at −5 to 0° C. for 45 min before a solution of tin(II) chloride dihydrate (0.642 g, 2.84 mmol) in conc. hydrochloric acid (1.8 mL, 59.2 mmol), precooled at 0° C., over 10 min. The mixture was stirred at −10 to 5° C. for 2 h. The precipitating product, 6-hydrazineyl-2-(trifluoromethyl)benzo[d]thiazole, HCl (271 mg, 1.005 mmol, 78% yield), was collected as a pale solid by suction filtration and dried at 50° C. under vacuum. $^1$H NMR (500 MHz, METHANOL-d$_4$) δ 8.15 (d, J=9.1 Hz, 1H), 7.66 (d, J=2.2 Hz, 1H), 7.32 (dd, J=8.9, 2.3 Hz, 1H).

Preparation of 6-Chloro-8-hydrazineylquinoline hydrochloride

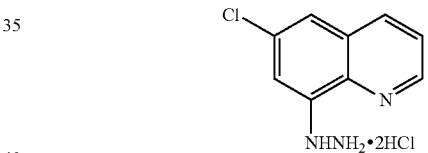

To a solution of 6-chloroquinolin-8-amine (0.350 g, 1.959 mmol) in acetic acid (1.2 mL, 20.96 mmol) at rt was added concentrated hydrochloric acid (2.4 mL, 79 mmol). To the resulting mixture at −10 to −5° C. was added a solution of sodium nitrite (0.169 g, 2.449 mmol) in water (0.7 mL) over 5 min. The mixture was stirred at −10 to −5° C. for 60 min before a solution of tin(II) chloride dihydrate (0.973 g, 4.31 mmol) in concentrated hydrochloric acid (2.4 mL, 79 mmol), pre-cooled at 0° C., over 5 min. The mixture was stirred at −5 to 5° C. for 2 h. The insoluble material was collected as a pale solid by suction filtration. The filter cake was dissolved in methanol (15 mL) and injected to prep. HPLC (Column: Sunfire C18 OBD 5u 30×100 mm; Solvent A: 90% H$_2$O-10% methanol-0.1% TFA, Solvent B: 10% methanol-90% H$_2$O 0.1% TFA; Gradient: 0-100% B over 10 min; Flow rate: 40 ml/min). The filtrate was also subjected to prep. HPLC. The correct fractions were combined, concentrated under vacuum to a volume of approximately 200 mL. To the residue was added concentrated hydrochloric acid (15 mL). The mixture was frozen at −78° C. and then lyophilized to provided 6-chloro-8-hydrazineylquinoline, 2 HCl (0.360 g, 1.351 mmol, 68.9% yield) as a beige solid. MS (ESI) m/z: 193.9 [M+H]⁺; $^1$H NMR (500 MHz, METHANOL-d$_4$) δ 8.93 (dd, J=4.4, 1.7 Hz, 1H), 8.42 (dd, J=8.4, 1.5 Hz, 1H), 7.74-7.68 (m, 2H), 7.33 (d, J=2.2 Hz, 1H).

Preparation of 7-Chloro-5-hydrazineylquinoline hydrochloride

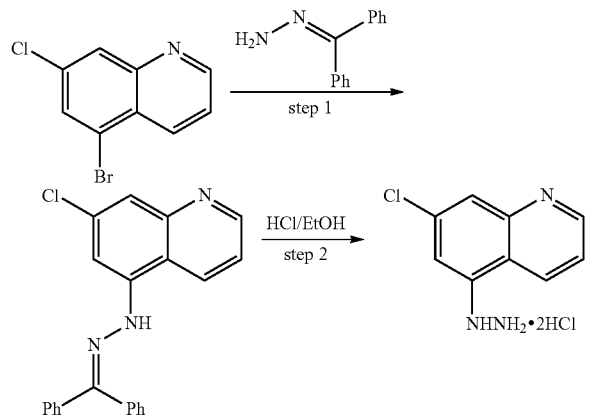

Step 1. Preparation of 7-Chloro-5-(2-(diphenylmethylene)hydrazineyl)quinoline: To a degassed mixture of 5-bromo-7-chloroquinoline (240 mg, 0.990 mmol), (diphenylmethylene)hydrazine (214 mg, 1.089 mmol), palladium(II) acetate (6.67 mg, 0.030 mmol), xantphos (17.18 mg, 0.030 mmol) in toluene (2.5 mL) at rt was added sodium tert-butoxide (143 mg, 1.485 mmol) in one portion. The mixture was heated at 110° C. under microwave conditions for 1 h. Upon cooling, the mixture was diluted with ethyl acetate (120 mL), washed with water (2×30 mL) and brine (30 mL), and dried over anhydrous $MgSO_4$. The desired product, 7-chloro-5-(2-(diphenylmethylene)hydrazineyl)quinoline (211 mg, 0.590 mmol, 59.6% yield), was isolated as a yellow solid by flash chromatography (40 g silica gel, solid loading, 20-55% ethyl acetate/hexane). MS (ESI) m/z: 358.1 $[M+H]^+$.

Step 2. Preparation of 7-Chloro-5-hydrazineylquinoline hydrochloride: To 7-chloro-5-(2-(diphenylmethylene)hydrazineyl)quinoline (200 mg, 0.559 mmol) in ethanol (2 mL) at rt was added concentrated hydrochloric acid (20 mL, 658 mmol) in one portion. The mixture was stirred at rt for 3.5 h and then concentrated under vacuum to a volume of approximately 15 mL. The residue was extracted with dichloromethane (2×20 mL). The aqueous solution was diluted with water (15 mL), cooled to −78° C. and lyophilized to 7-chloro-5-hydrazineylquinoline, 2 HCl (149 mg, 0.559 mmol, 100% yield). MS (ESI) m/z: 194.0 $[M+H]^+$; $^1H$ NMR (400 MHz, METHANOL-$d_4$) δ 9.18-9.08 (m, 2H), 7.97 (dd, J=8.7, 5.4 Hz, 1H), 7.75 (dd, J=1.5, 0.9 Hz, 1H), 7.21 (d, J=1.8 Hz, 1H).

Preparation of (5-Chloro-2-(trifluoromethoxy)phenyl)hydrazine hydrochloride

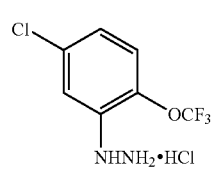

To a solution of 5-chloro-2-(trifluoromethoxy)aniline (1.269 g, 6.0 mmol) in acetic acid (3.0 mL, 52.4 mmol) at rt was added concentrated hydrochloric acid (6.0 mL, 197 mmol) in one portion. To the resulting mixture at −10 to −5° C. was added a solution of sodium nitrite (0.497 g, 7.20 mmol) in water (1.8 mL) over 10 min. The mixture was stirred at −5 to 0° C. for 45 min before a solution of tin(II) chloride dihydrate (2.98 g, 13.20 mmol) in concentrated hydrochloric acid (6.0 mL, 197 mmol), pre-cooled at 0° C., was added over 10 min. The mixture was stirred at −10 to 0° C. for 2 h. The precipitating product, (5-chloro-2-(trifluoromethoxy)phenyl)hydrazine, HCl (2 g, 6.0 mmol, 100% yield), was collected as a pale solid by suction filtration and dried at 50° C. under vacuum. MS (ESI) m/z: 226.9 $[M+H]^+$; $^1H$ NMR (400 MHz, Methanol-$d_4$) δ 7.36 (dq, J=8.8, 1.7 Hz, 1H), 7.19-7.16 (m, 1H), 7.13 (dd, J=8.7, 2.4 Hz, 1H).

Preparation of 6-Hydrazineylbenzo[d]thiazole dihydrochloride

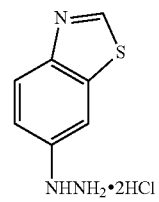

To a solution of benzo[d]thiazol-6-amine (0.901 g, 6.0 mmol) in acetic acid (3.0 mL, 52.4 mmol) at rt was added concentrated hydrochloric acid (6.0 mL, 197 mmol) in one portion. To the resulting mixture at −10 to −5° C. was added a solution of sodium nitrite (0.497 g, 7.20 mmol) in water (1.8 mL) over 10 min. The mixture was stirred at −5 to 0° C. for 45 min before a solution of tin(II) chloride dihydrate (2.98 g, 13.20 mmol) in concentrated hydrochloric acid (6.0 mL, 197 mmol), pre-cooled at 0° C., was added over 10 min. The mixture was stirred at −10 to 0° C. for 2 h. The precipitating product, 6-hydrazineylbenzo[d]thiazole, 2 HCl (1.68 g, 6.0 mmol, 100% yield, 85% pure), was collected as a pale solid by suction filtration and dried under vacuum. MS (ESI) m/z: 165.9 $[M+H]^+$; $^1H$ NMR (400 MHz, Methanol-$d_4$) δ 9.19 (s, 1H), 8.04 (d, J=8.8 Hz, 1H), 7.65 (d, J=2.3 Hz, 1H), 7.25 (dd, J=8.9, 2.4 Hz, 1H).

Preparation of 6-Hydrazineyl-2-methyl-5-(trifluoromethyl)benzo[d]thiazole TFA

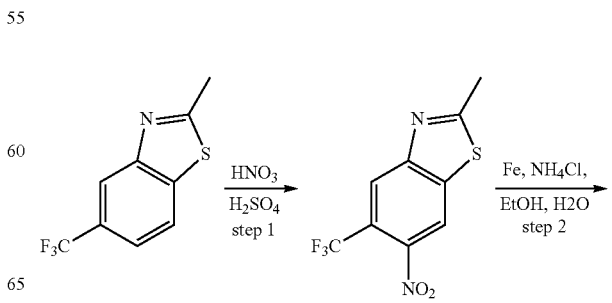

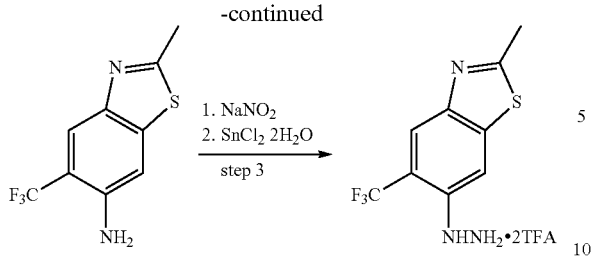

Step 1. Preparation of 2-Methyl-6-nitro-5-(trifluoromethyl)benzo[d]thiazole: To a solution of 2-methyl-5-(trifluoromethyl)benzo[d]thiazole (0.83 g, 3.82 mmol) in concentrated sulfuric acid (2 mL, 37.5 mmol) at rt was added concentrated nitric acid (3 mL, 66.2 mmol) dropwise. The reaction was then allowed to stir at rt for 4 h then heated at 80° C. for 1.5 h. The reaction mixture was poured into ice water (5 mL), extracted with EtOAc (2×25 mL). The organic layer was separated and washed with water, saturated NaHCO$_3$ solution, and brine. The organic phase was dried over MgSO$_4$, filtered, and concentrated to give a crude product, which was subjected to flash chromatography (40 g silica gel, 0-20% ethyl acetate/hexane) to afford 2-methyl-6-nitro-5-(trifluoromethyl)benzo[d]thiazole (625 mg, 2.384 mmol, 62.4% yield) as a white solid. MS (ESI) m/z: 262.8 [M+H]$^+$; $^1$H NMR (400 MHz, Chloroform-d) δ 8.46 (d, J=2.1 Hz, 1H), 8.36 (d, J=3.4 Hz, 1H), 2.95 (d, J=1.1 Hz, 3H).

Step 2. Preparation of 5-Chloro-2-(trifluoromethyl)pyridin-3-amine: A mixture of 2-methyl-6-nitro-5-(trifluoromethyl)benzo[d]thiazole (0.605 g, 2.307 mmol), ammonium chloride (0.617 g, 11.54 mmol) and iron mesh (0.515 g, 9.23 mmol) in ethanol (10.5 mL) and water (1.05 mL) was heated at 80° C. for 4 h. Upon cooling to rt, volatile solvent of the reaction mixture was removed under vacuum. The residue was diluted with CH$_2$Cl$_2$ (20 mL) and water (10 mL), and filtered through Celite. The organic layer of the filtrate was separated and concentrated under vacuum to dryness. The residue was subjected to flash chromatography (80 g silica gel, 0-45% ethyl acetate/hexane) to afford 2-methyl-5-(trifluoromethyl)-benzo[d]thiazol-6-amine (466 mg, 2.007 mmol, 87% yield) as a white solid. MS (ESI) m/z: 232.9 [M+H]$^+$; $^1$H NMR (400 MHz, Chloroform-d) δ 8.01 (s, 1H), 7.13 (s, 1H), 4.37-4.05 (bs, 2H), 2.76 (s, 3H).

Step 3. Preparation of 6-Hydrazineyl-2-methyl-5-(trifluoromethyl)benzo[d]thiazole TFA: To a solution of 2-methyl-5-(trifluoromethyl)benzo[d]thiazol-6-amine (0.466 g, 2.007 mmol) in acetic acid (1.0 mL, 17.5 mmol) at rt was added concentrated hydrochloric acid (2.0 mL, 65.8 mmol) in one portion. To the resulting mixture at −10 to −5° C. was added a solution of sodium nitrite (0.166 g, 2.41 mmol) in water (0.6 mL) over 10 min. The mixture was stirred at −5 to 0° C. for 45 min before a solution of tin(II) chloride dihydrate (0.996 g, 4.41 mmol) in concentrated hydrochloric acid (2.0 mL, 65.8 mmol), pre-cooled at 0° C., was added over 10 min. The mixture was stirred at −10 to 0° C. for 2 h. The reaction mixture was subjected to filtration. The pH of filtrate was basified with aqueous saturated NaHCO$_3$ solution. The resulting mixture was extracted with CHCl$_3$ (3×70 mL). The combined organic layer was dried over MgSO$_4$ and concentrated to give a crude product as yellow foam. The crude product was purified by preparative HPLC (Column: Sunfire C18 OBD, 30×100 mm, 5-μm particles; Mobile Phase A: 5:95 acetonitrile:water with 0.1% TFA; Mobile Phase B: 95:5 acetonitrile:water with 0.1% TFA; Gradient: 5-100% B over 10 minutes, then a 5-minute hold at 100% B; Flow: 40 mL/min) to afford 6-hydrazineyl-2-methyl-5-(trifluoromethyl)benzo[d]thiazole TFA (108 mg, 15% yield) as beige solid: MS (ESI) m/z: 247.9 [M+H]$^+$; $^1$H NMR (400 MHz, Chloroform-d) δ 8.08 (s, 1H), 7.76 (s, 1H), 2.83 (s, 3H).

Preparation of
5-Chloro-2-cyclopropylphenyl)hydrazine
hydrochloride

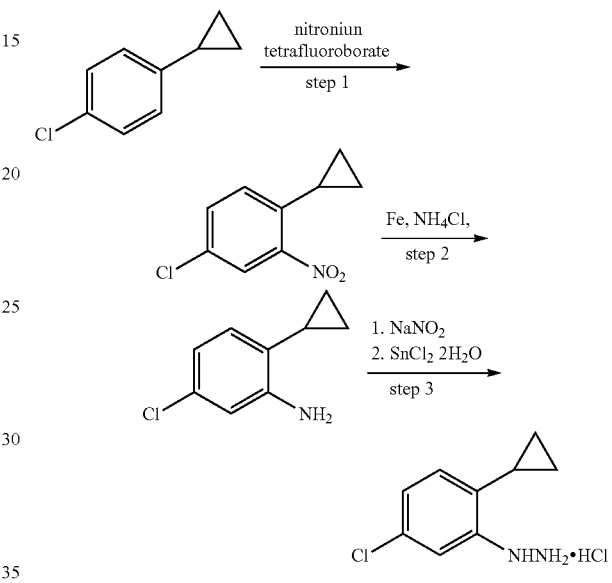

Step 1. Preparation of 4-Chloro-1-cyclopropyl-2-nitrobenzene: To a solution of 1-chloro-4-cyclopropylbenzene (1.0 g, 6.55 mmol) at 0° C. was added nitronium tetrafluoroborate (14.41 mL, 7.21 mmol, 0.5 M solution in sulfolane). The reaction mixture was stirred at rt for 0.5 h. Aqueous saturated NaHCO$_3$ solution (40 mL) and water (20 mL) were added. The resulting mixture was extracted with EtOAc (2×125 mL). The combined organic layers were dried over MgSO$_4$, filtered and concentrated to give a crude product, which was subjected to flash chromatography (80 g silica gel, 0-20% ethyl acetate/hexane) to afford 4-chloro-1-cyclopropyl-2-nitrobenzene (350 mg, 1.771 mmol, 27.0% yield) as yellow oil. $^1$H NMR (400 MHz, Chloroform-d) δ 7.84 (d, J=2.2 Hz, 1H), 7.47 (dd, J=8.4, 2.2 Hz, 1H), 7.13 (d, J=8.3 Hz, 1H), 2.37 (tt, J=8.6, 5.4 Hz, 1H), 1.15-1.05 (m, 2H), 0.77-0.65 (m, 2H).

Step 2. Preparation of 5-Chloro-2-cyclopropylaniline: A mixture of 4-chloro-1-cyclopropyl-2-nitrobenzene (0.33 g, 1.670 mmol), ammonium chloride (0.447 g, 8.35 mmol) and iron mesh (0.373 g, 6.68 mmol) in ethanol (7.6 mL) and water (0.76 mL) was heated at 80° C. for 5 h. Additional iron mesh (200 mg), water (0.1 mL) and ammonium chloride (300 mg) were added. The reaction mixture was heated at 80° C. for another 5 h. Upon cooling to rt, the solvent was removed under vacuum. The residue was diluted with CH$_2$Cl$_2$ (20 mL), water (10 mL) and filtered through Celite. The organic layer of the filtrate was separated and concentrated under vacuum to dryness. The residue was subjected to flash chromatography (24 g silica gel, 0-35% ethyl acetate/hexane) to afford 5-chloro-2-cyclopropylaniline (280 mg, 99% yield) as a white solid. MS (ESI) m/z: 168.0

[M+H]+; 1H NMR (500 MHz, Chloroform-d) δ 6.96 (dt, J=7.4, 1.1 Hz, 1H), 6.69-6.60 (m, 2H), 1.60-1.68 (m, 1H), 0.97-0.88 (m, 2H), 0.63-0.44 (m, 2H).

Step 3. Preparation of 5-Chloro-2-cyclopropylphenyl)hydrazine hydrochloride: To a solution of 5-chloro-2-cyclopropylaniline (0.312 g, 1.861 mmol) in acetic acid (0.94 mL, 16.4 mmol) at rt was added concentrated hydrochloric acid (1.8 mL, 59.2 mmol) in one portion. To the resulting mixture at −10 to −5° C. was added a solution of sodium nitrite (0.154 g, 2.23 mmol) in water (0.55 mL) over 10 min. The mixture was stirred at −5 to 0° C. for 45 min before a solution of tin(II) chloride dihydrate (0.776 g, 4.09 mmol) in concentrated hydrochloric acid (1.8 mL, 59.2 mmol), pre-cooled at 0° C., was added over 10 min. The mixture was stirred at −10 to 5° C. for 2 h. The precipitating product, 5-chloro-2-cyclopropylphenyl)hydrazine, HCl (465 mg, 114% yield), was collected as a pale solid by suction filtration and dried under vacuum. MS (ESI) m/z: 183.2 [M+H]+.

Preparation of 6-Chloro-8-hydrazineylisoquinoline dihydrochloride

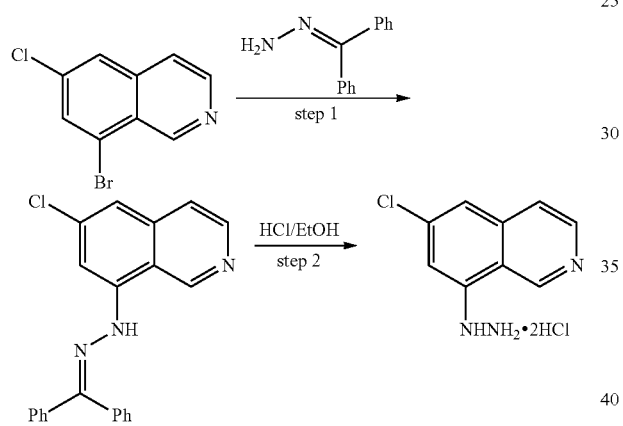

Step 1. Preparation of 6-Chloro-8-(2-(diphenylmethylene)hydrazineyl)isoquinoline: To a degassed mixture of -bromo-6-chloroisoquinoline (200 mg, 0.825 mmol), (diphenylmethylene)hydrazine (178 mg, 0.907 mmol), palladium (II) acetate (5.55 mg, 0.025 mmol), xantphos (14.32 mg, 0.025 mmol) in toluene (2.0 mL) at rt was added sodium tert-butoxide (119 mg, 1.24 mmol) in one portion. The mixture was heated at 110° C. under microwave conditions for 1 h. Upon cooling, the mixture was diluted with ethyl acetate (50 mL), washed with water (2×10 mL) and brine (10 mL), dried over anhydrous MgSO4. The desired product, 6-chloro-8-(2-(diphenylmethylene)hydrazineyl)isoquinoline, was isolated as a dark purple solid (255 mg, 69% yield) by flash chromatography (40 g silica gel, solid loading, 0-60% ethyl acetate/hexane). MS (ESI) m/z: 358.1 [M+H]+; 1H NMR (400 MHz, Chloroform-d) δ 8.73 (d, J=0.9 Hz, 1H), 8.42-8.48 (m, 2H), 7.78 (d, J=1.9 Hz, 1H), 7.74-7.59 (m, 5H), 7.53-7.35 (m, 6H), 7.27 (d, J=2.1 Hz, 1H).

Step 2. Preparation of 6-Chloro-8-hydrazineylisoquinoline dihydrochloride: To 6-chloro-8-(2-(diphenylmethylene)hydrazineyl)quinoline (255 mg, 0.713 mmol) in ethanol (1 mL) at rt was added concentrated hydrochloric acid (10 mL, 658 mmol) in one portion. The mixture was stirred at rt for 18 h. The volatiles were removed under vacuum. The residue was extracted with dichloromethane (2×10 mL). The aqueous layer was concentrated to give a crude product as a purple solid. The crude product was diluted with CH2Cl2 (3 mL) and subjected to filtration. The solid was collected and dried under vacuum to give 6-chloro-8-hydrazineylquinoline, 2 HCl (160 mg, 0.6 mmol, 84% yield). MS (ESI) m/z: 194.0 [M+H]+; 1H NMR (400 MHz, Methanol-d4) δ 9.76 (d, J=1.1 Hz, 1H), 8.61 (d, J=6.6 Hz, 1H), 8.36 (d, J=6.7 Hz, 1H), 7.92 (s, 1H), 7.39 (d, J=1.7 Hz, 1H).

Preparation of (2-Chloro-5-(2,2,2-trifluoroethyl)phenyl)hydrazine hydrochloride

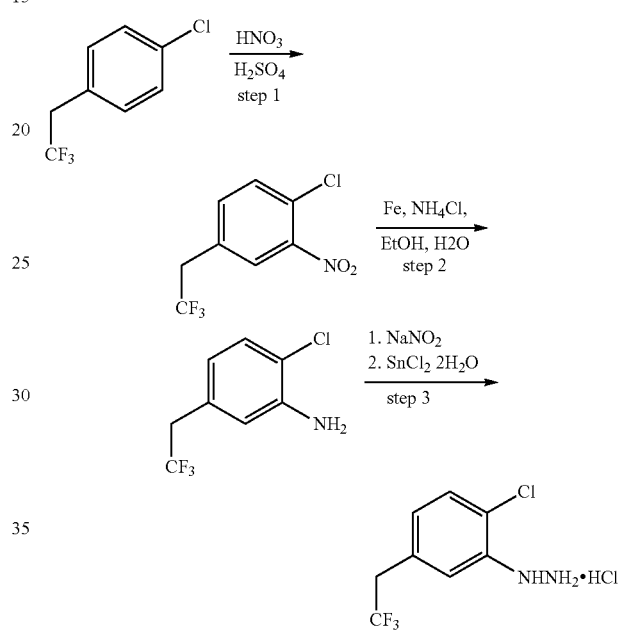

Step 1. Preparation of 1-Chloro-2-nitro-4-(2,2,2-trifluoroethyl)benzene: To a solution of 1-chloro-4-(2,2,2-trifluoroethyl)benzene (1.0 g, 5.14 mmol) in sulfuric acid (2 mL, 5.14 mmol) at rt was added nitric acid (0.7 mL, 15.44 mmol) dropwise. The reaction mixture was stirred at rt for 1.5 h. The reaction mixture was poured into ice water (3 mL), extracted with EtOAc (2×25 mL). The organic layer was separated and washed with water, aqueous saturated NaHCO3 solution, and brine. The organic was dried over MgSO4, filtered and concentrated to give to crude product, which was subjected to flash chromatography (12 g silica gel, 0-20% ethyl acetate/hexane) to afford 1-chloro-2-nitro-4-(2,2,2-trifluoroethyl)benzene (1.1 g, 4.59 mmol, 89% yield) as a white solid. 1H NMR (400 MHz, Chloroform-d) δ 7.86 (d, J=2.0 Hz, 1H), 7.60 (d, J=8.3 Hz, 1H), 7.49 (ddd, J=8.3, 2.1, 0.7 Hz, 1H), 3.47 (q, J=10.3 Hz, 2H).

Step 2. Preparation of 2-Chloro-5-(2,2,2-trifluoroethyl)aniline: A mixture of 1-chloro-2-nitro-4-(2,2,2-trifluoroethyl)benzene (1.1 g, 4.59 mmol), ammonium chloride (1.228 g, 22.96 mmol) and iron mesh (1.026 g, 18.37 mmol) in ethanol (20.9 mL) and water (2.1 mL) was heated at 80° C. for 8 h. Upon cooling to rt, the volatile solvent of the reaction mixture was removed under vacuum. The residue was diluted with CH2Cl2 (20 mL) water (10 mL), and filtered through Celite. The organic layer of the filtrate was separated and concentrated under vacuum to dryness. The residue was subjected to flash chromatography (24 g silica gel, 0-45% ethyl acetate/hexane) to afford of 2-chloro-5-(2,2,2-trifluoroethyl)aniline (490 mg, 2.338 mmol, 50.9% yield) as a white solid. MS (ESI) m/z: 210.0 [M+H]$^+$; $^1$H NMR (400 MHz, Chloroform-d) δ 7.21 (d, J=8.1 Hz, 1H), 6.69 (d, J=2.0 Hz, 1H), 6.61 (dd, J=8.1, 2.0 Hz, 1H), 4.07 (s, 2H), 3.25 (q, J=10.8 Hz, 2H).

Step 3. Preparation of (2-Chloro-5-(2,2,2-trifluoroethyl)phenyl)hydrazine hydrochloride: To a solution of 2-chloro-5-(2,2,2-trifluoroethyl)aniline (0.490 g, 2.338 mmol) in acetic acid (1.2 mL, 20.96 mmol) at rt was added concentrated hydrochloric acid (2.3 mL, 76.0 mmol) in one portion. To the resulting mixture at −10 to −5° C. was added a solution of sodium nitrite (0.194 g, 2.81 mmol) in water (0.7 mL) over 10 min. The mixture was stirred at −5 to 0° C. for 45 min before a solution of tin(II) chloride dihydrate (0.975 g, 5.14 mmol) in concentrated hydrochloric acid (2.3 mL, 76.0 mmol), precooled at 0° C., was added over 10 min. The mixture was stirred at −10 to 0° C. for 1 h. The precipitating product, (2-chloro-5-(2,2,2-trifluoroethyl)phenyl)hydrazine, HCl (800 mg, 131% yield), was collected as a pale solid by suction filtration and dried under vacuum. MS (ESI) m/z: 225.0 [M+H]$^+$; $^1$H NMR (400 MHz, Methanol-d$_4$) δ 7.46 (d, J=8.1 Hz, 1H), 7.08 (dd, J=8.1, 1.9 Hz, 1H), 7.04 (s, 1H), 3.55 (q, J=11.0 Hz, 2H).

Preparation of
(2-(tert-Butyl)-5-chlorophenyl)hydrazine,
trifluoroacetic Acid Salt

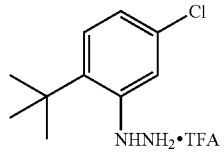

To a solution of 2-(tert-butyl)-5-chloroaniline (0.500 g, 2.72 mmol) in acetic acid (1.5 mL, 26.2 mmol) at rt was added concentrated hydrochloric acid (2.4 mL, 79.0 mmol) in one portion. To the resulting mixture at −10 to −5° C. was added a solution of sodium nitrite (0.225 g, 3.27 mmol) in water (0.7 mL) over 10 min. The mixture was stirred at −5 to 0° C. for 45 min before a solution of tin(II) chloride dihydrate (1.136 g, 5.99 mmol) in concentrated hydrochloric acid (2.4 mL, 79.0 mmol), pre-cooled at 0° C., was added over 10 min. The mixture was stirred at −10 to 0° C. for 1 h. The precipitating product, was collected as a pale solid by suction filtration and dried under vacuum. This product was purified by preparative HPLC (Column: Sunfire C18 OBD, 30×100 mm, 5-μm particles; Mobile Phase A: 5:95 acetonitrile:water with 0.1% TFA; Mobile Phase B: 95:5 acetonitrile:water with 0.1% TFA; Gradient: 10-100% B over 10 minutes, then a 5-minute hold at 100% B; Flow: 40 mL/min) to afford (2-(tert-butyl)-5-chlorophenyl)hydrazine TFA (150 mg, 18% yield) as beige solid: MS (ESI) m/z: 199.2 [M+H]$^+$; $^1$H NMR (400 MHz, Methanol-d$_4$) δ 7.42 (d, J=8.5 Hz, 1H), 7.15 (d, J=2.1 Hz, 1H), 7.12 (dd, J=8.4, 2.2 Hz, 1H), 1.45 (s, 9H).

Preparation of
(2-Chloro-5-(difluoromethyl)phenyl)hydrazine
hydrochloride

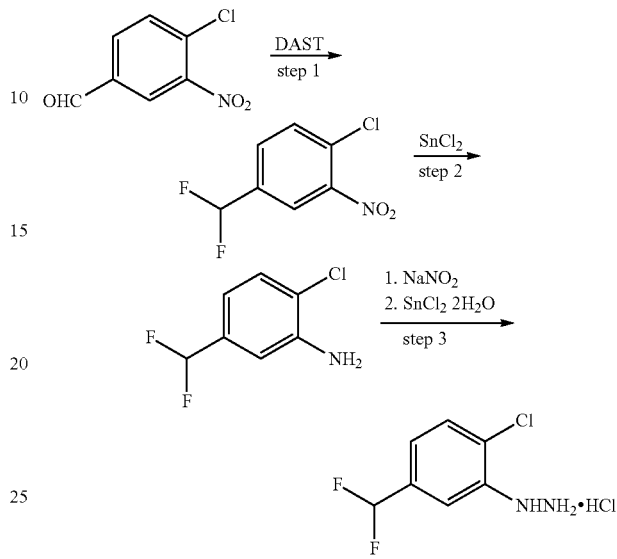

Step 1. Preparation of 1-Chloro-4-(difluoromethyl)-2-nitrobenzene: To a solution of 4-chloro-3-nitrobenzaldehyde (705 mg, 3.80 mmol) in CH$_2$Cl$_2$ (12 mL) at rt was added diethylaminosulfur trifluoride (DAST) (0.653 mL, 4.94 mmol) dropwise over 20 min. The reaction mixture was stirred at rt for 3 h. The reaction mixture was concentrated under vacuum to dryness. The residue was subjected to flash chromatography (40 g silica gel, 0-45% ethyl acetate/hexane) to afford 1-chloro-4-(difluoromethyl)-2-nitrobenzene (0.59 g, 2.84 mmol, 74.8% yield) as an oil: $^1$H NMR (400 MHz, Chloroform-d) δ 8.04 (q, J=1.3 Hz, 1H), 7.68 (d, J=1.3 Hz, 2H), 6.70 (t, J=55.8 Hz, 1H).

Step 2. Preparation of 2-Chloro-5-(difluoromethyl)aniline: To a solution of 1-chloro-4-(difluoromethyl)-2-nitrobenzene (0.49 g, 2.361 mmol) in EtOH (7.93 mL) at 0° C. was added tin(II) chloride dihydrate (2.131 g, 9.44 mmol), followed by concentrated hydrochloric acid (1.59 mL, 37%). The reaction mixture was stirred at rt for 1 h. The volatiles were removed under vacuum. The residue was basified with 5 M aq. NaOH solution at 0° C. The mixture was extracted with EtOAc (2×50 mL). The organic layer was separated and washed with brine, dried over MgSO$_4$, filtered and concentrated to give a crude product. The crude was subjected to flash chromatography (40 g silica gel, 0-10% ethyl acetate/hexane) to afford 2-chloro-5-(difluoromethyl)aniline (239 mg, 1.346 mmol, 57.0% yield) as an oil: MS (ESI) m/z: 178.0 [M+H]$^+$; $^1$H NMR (400 MHz, Chloroform-d) δ 7.36-7.28 (m, 1H), 6.92-6.85 (m, 1H), 6.84-6.76 (m, 1H), 6.52 (t, J=56.5 Hz, 1H), 4.18 (s, 2H).

Step 3. Preparation of (2-Chloro-5-(difluoromethyl)phenyl)hydrazine hydrochloride: To a solution of 2-chloro-5-(difluoromethyl)aniline (0.239 g, 1.346 mmol) in acetic acid (0.72 mL, 12.6 mmol) at rt was added concentrated hydrochloric acid (1.2 mL, 39.5 mmol) in one portion. To the resulting mixture at −10 to −5° C. was added a solution of sodium nitrite (0.111 g, 1.62 mmol) in water (0.4 mL) over 10 min. The mixture was stirred at −5 to 0° C. for 45 min before a solution of tin(II) chloride (0.561 g, 2.96 mmol) in concentrated hydrochloric acid (1.2 mL, 39.5 mmol), pre-cooled at 0° C., was added over 10 min. The mixture was stirred at −10 to 0° C. for 1 h. The precipitating product, (2-Chloro-5-(difluoromethyl)phenyl)hydrazine HCl (345 mg, 112% yield), was collected as a pale solid by suction filtration and dried at under vacuum. MS (ESI) m/z: 193.0 [M+H]+; 1H NMR (400 MHz, Methanol-d4) δ 7.58 (d, J=8.1 Hz, 1H), 7.38-7.15 (m, 2H), 6.83 (t, J=55.9 Hz, 1H).

Preparation of (2,5-Dichloro-4-fluorophenyl)hydrazine hydrochloride

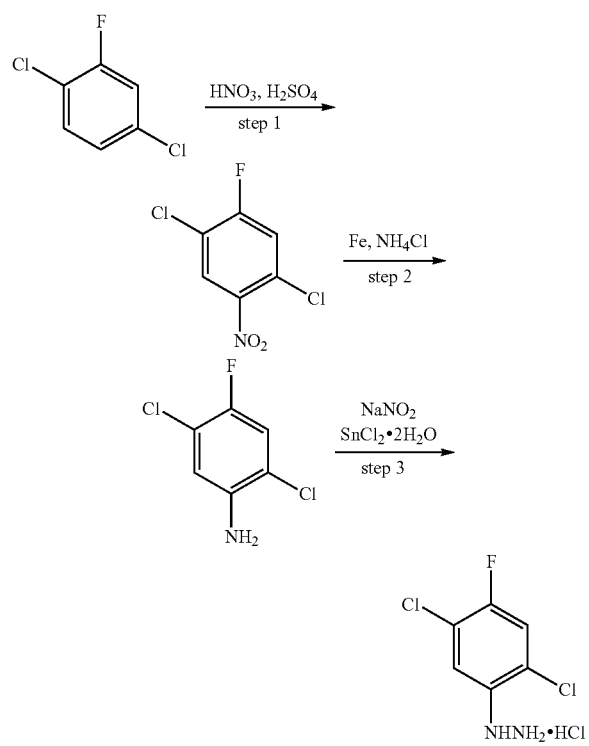

Step 1. Preparation of 1,4-Dichloro-2-fluoro-5-nitrobenzene: To a solution of 1,4-dichloro-2-fluorobenzene (2.227 g, 13.5 mmol) in sulfuric acid (3.59 mL, 67.3 mmol) at 0° C. was added nitric acid (0.612 mL, 13.50 mmol) dropwise over 10 min. The reaction was stirred at rt for 4 h. The mixture was poured into ice water, extracted with EtOAc (150 mL). The extract was washed with water, saturated NaHCO3 solution and brine sequentially, dried over MgSO4, filtered and concentrated under vacuum. The residue was purified with a silica gel flash column, eluting with 0-20% EtOAc in hexane to afford 1,4-dichloro-2-fluoro-5-nitrobenzene (2.79 g, 13.29 mmol, 98% yield) as a tan solid. 1H NMR (CDCl3) d 7.40 (1H, d, J=7.8 Hz), 8.09 (IH, d, J=6.9 Hz).

Step 2. Preparation of 2,5-Dichloro-4-fluoroaniline: A mixture of 1,4-dichloro-2-fluoro-5-nitrobenzene (2.79 g, 13.29 mmol), iron powder (2.97 g, 53.1 mmol) and ammonium chloride (3.55 g, 66.4 mmol) in ethanol (60.4 mL) and water (6.04 mL) was heated at 80° C. overnight. The reaction mixture was concentrated under vacuum to remove the volatiles. The residue was diluted with water (100 mL) and and extracted with DCM (150 mL). The extract was dried over MgSO4, filtered and concentrated under vacuum. The residue was purified with a silica gel flash column, eluting with 0-50% EtOAc in hexane to afford 2,5-dichloro-4-fluoroaniline (2.13 g, 11.83 mmol, 89% yield) as a tan solid. MS (ESI) m/z: 179.9 [M+H]+; 1H NMR (500 MHz, chloroform-d δ 7.12 (d, J=8.25 Hz, 1H), 6.81 (d, J=6.88 Hz, 1H), 3.97 (br s, 2H).

Step 3. Preparation of 2,5-Dichloro-4-fluorophenyl)hydrazine hydrochloride: To a solution of 2,5-dichloro-4-fluoroaniline (2.13 g, 11.83 mmol) in acetic acid (6 mL, 105 mmol) at rt was added conc. hydrochloric acid (12.0 mL, 395 mmol). To the resulting suspension at −10 to −5° C. was added a solution of sodium nitrite (0.980 g, 14.20 mmol) in water (3.5 mL) over 10 min. The mixture was stirred at −10 to −5° C. for 60 min before a solution of tin(II) chloride dihydrate (5.87 g, 26.0 mmol) in conc. hydrochloric acid (12.0 mL, 395 mmol), pre-cooled at 0° C., was added dropwise over 10 min. The mixture was stirred at −10 to −5° C. for 1 h and then at −5 to 0° C. for 1 h. The precipitating product, (2,5-dichloro-4-fluorophenyl)hydrazine, HCl (2.81 g, 11.78 mmol, 100% yield), was collected as a pale solid by suction filtration and dried at 50° C. under vacuum. MS (ESI) m/z: 194.8 [M+H]+; 1H NMR (500 MHz, DMSO-d6) δ 10.24 (br s, 2H), 8.23 (br s, 1H), 7.71 (d, J=8.80 Hz, 1H), 7.38 (d, J=6.88 Hz, 1H).

Preparation of (2,5-Dichloro-3-fluorophenyl)hydrazine

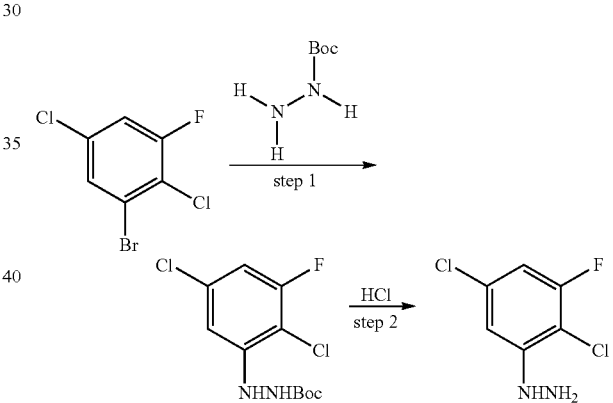

Step 1. tert-Butyl 2-(2,5-dichloro-3-fluorophenyl)hydrazine-1-carboxylate: A mixture of 1-bromo-2,5-dichloro-3-fluorobenzene (0.50 g, 2.050 mmol), tert-butyl hydrazinecarboxylate (0.325 g, 2.460 mmol), palladium(II) acetate (9.21 mg, 0.041 mmol), xantphos (0.024 g, 0.041 mmol) and sodium tert-butoxide (0.296 g, 3.08 mmol) in toluene (4 mL) was degassed and then heated under microwave irridiation at 110° C. for 1 h. The reaction mixture was loaded onto a silica gel flash column via a solid cartridge, eluting with 0-30% EtOAc in hexane to afford tert-butyl 2-(2,5-dichloro-3-fluorophenyl)hydrazine-1-carboxylate (118 mg, 0.400 mmol, 19.50% yield) as a tan solid. MS (ESI) m/z: 238.8 [M−C4H9+H]+; 1H NMR (400 MHz, chloroform-d) δ 6.74-6.78 (m, 1H), 6.70 (dd, J=2.31, 8.47 Hz, 1H), 6.42 (br s, 1H), 6.30 (s, 1H), 1.48 (br s, 9H).

Step 2. Preparation of (2,5-Dichloro-3-fluorophenyl)hydrazine: To a solution of tert-butyl 2-(2,5-dichloro-3-fluorophenyl)hydrazine-1-carboxylate (118 mg, 0.400 mmol) in DCM (1.0 mL) was added HCl (4M in dioxane) (1.000 mL, 4.00 mmol), the mixture was stirred at rt for 1 h and then concentrated under vacuum. The residue was purified with a silica gel flash column, eluting with 0-10% MeOH in DCM to afford (2,5-dichloro-3-fluorophenyl)hydrazine (36 mg, 0.185 mmol, 46.2% yield) as an off-white solid. MS (ESI) m/z: 194.9 [M+H]$^+$; $^1$H NMR (500 MHz, DMSO-d$_6$) δ 9.17-10.47 (m, 2H), 8.51 (br s, 1H), 7.18 (dd, J=1.93, 8.80 Hz, 1H), 7.00-7.06 (m, 1H)

Preparation of
(5-Chloro-2-(difluoromethyl)phenyl)hydrazine

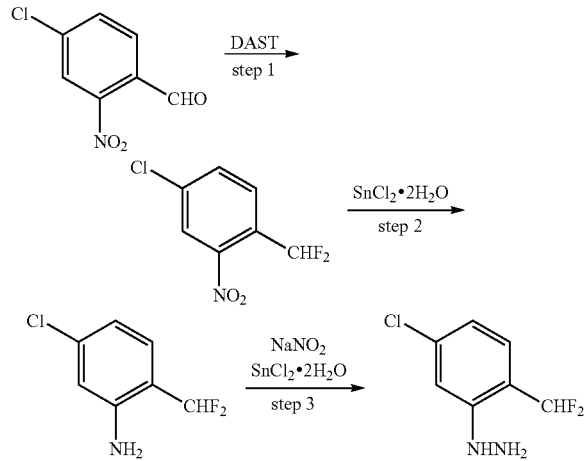

Step 1. Preparation of 4-Chloro-1-(difluoromethyl)-2-nitrobenzene: To a solution of 4-chloro-2-nitrobenzaldehyde (705 mg, 3.80 mmol) in dichloromethane (12 mL) was added diethylaminosulfur trifluoride (DAST) (0.653 mL, 4.94 mmol) dropwise over 20 min. The solution was stirred at rt for 3 h and then concentrated under vacuum. The residue was purified with a silica gel flash column, eluting with 0-20% EtOAc in hexane to afford 4-chloro-1-(difluoromethyl)-2-nitrobenzene (756 mg, 3.64 mmol, 96% yield) as an oil. $^1$H NMR (400 MHz, chloroform-d) δ 8.12-8.16 (m, 1H), 7.82-7.88 (m, 1H), 7.75 (dd, J=1.76, 8.36 Hz, 1H), 7.18-7.50 (m, 1H).

Step 2. Preparation of 5-Chloro-2-(difluoromethyl)aniline: To a solution of 4-chloro-1-(difluoromethyl)-2-nitrobenzene (0.738 g, 3.56 mmol) in ethanol (12 mL) at 0° C. was tin(II) chloride dihydrate (3.21 g, 14.22 mmol), followed by hydrochloric acid, 37% (2.4 mL). The mixture was stirred at rt for 1 h. The solvent was removed under vacuum. To the residue was added ice cold 5M aq NaOH solution, and the mixture was extracted with EtOAc (2×60 mL). The combined extract was washed with water and brine, dried over MgSO$_4$, filtered and concentrated under vacuum. The residue was purified with a silica gel flash column, eluting with 0-10% EtOAc in hexane to afford 5-chloro-2-(difluoromethyl)aniline (260 mg, 1.464 mmol, 41.2% yield) as an oil. MS (ESI) m/z: 177.9 [M+H]$^+$; $^1$H NMR (400 MHz, chloroform-d) δ 7.16 (d, J=8.14 Hz, 1H), 6.73-6.77 (m, 2H), 6.58 (s, 1H), 4.05-4.23 (m, 2H).

Step 3. Preparation of (5-Chloro-2-(difluoromethyl)phenyl)hydrazine: To a mixture of 5-chloro-2-(difluoromethyl) aniline (0.26 g, 1.464 mmol) in acetic acid (0.8 mL, 13.97 mmol) and conc. hydrochloric acid (1.60 mL, 52.7 mmol) at −10 to −5° C. was added a solution of sodium nitrite (0.121 g, 1.757 mmol) in water (0.4 mL) over 10 min. The mixture was stirred at −10 to −5° C. for 60 min before a solution of tin(II) chloride dihydrate (0.727 g, 3.22 mmol) in conc. hydrochloric acid (1.6 mL, 52.7 mmol), pre-cooled at 0° C., was added dropwise over 10 min. The mixture was stirred at −10 to −5° C. for 1 h and then at −5 to 0° C. for 1 h. The reaction mixture was filtered. The filtrate was basified slowly with ice cold 6N NaOH, and then extracted with EtOAc (2×40 mL). The combined extract was dried over MgSO$_4$, filtered and concentrated under vacuum. The residue was purified with a silica gel flash column, eluting with 0-40% EtOAc in hexane to afford (5-chloro-2-(difluoromethyl)phenyl)hydrazine (115 mg, 0.597 mmol, 40.8% yield) as a tan solid. MS (ESI) m/z: 192.9 [M+H]$^+$; $^1$H NMR (400 MHz, chloroform-d) δ 7.29 (d, J=1.54 Hz, 1H), 7.15 (d, J=8.14 Hz, 1H), 6.77 (td, J=0.91, 8.09 Hz, 1H), 6.38-6.70 (m, 1H), 5.90 (br s, 1H), 3.60 (br s, 2H).

Preparation of
(5-Methoxy-2-(trifluoromethyl)phenyl)hydrazine

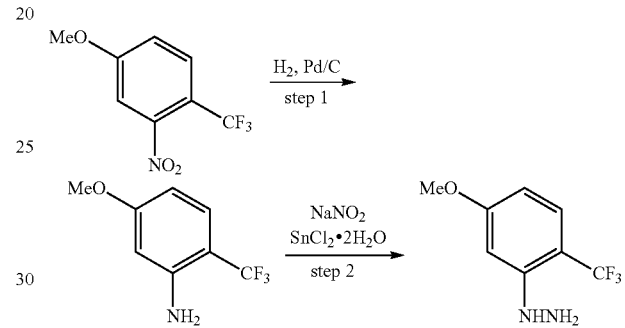

Step 1. Preparation of 5-Methoxy-2-(trifluoromethyl)aniline: A mixture 4-methoxy-2-nitro-1-(trifluoromethyl)benzene (500 mg, 2.261 mmol) and 10% Pd—C (241 mg, 0.226 mmol) in methanol (8 mL) was degassed and then charged with H$_2$, provided with a H$_2$ balloon. The mixture was stirred at rt overnight and then filtered through a pad of Celite. The filtrate was concentrated under vacuum. The residue was purified with a silica gel flash column, eluting with 0-40% EtOAc in hexane to afford 5-methoxy-2-(trifluoromethyl)aniline (236 mg, 1.235 mmol, 54.6% yield) as an oil. MS (ESI) m/z: 192.0 [M+H]$^+$; $^1$H NMR (400 MHz, chloroform-d) δ 7.35 (d, J=8.80 Hz, 1H), 6.28-6.40 (m, 1H), 6.24 (d, J=1.98 Hz, 1H), 4.12 (br s, 2H), 3.79 (s, 3H).

Step 2. Preparation of (5-Methoxy-2-(trifluoromethyl) phenyl)hydrazine: To a mixture of 5-methoxy-2-(trifluoromethyl)aniline (0.236 g, 1.235 mmol) in acetic acid (0.65 mL, 11.35 mmol) and conc. hydrochloric acid (1.3 mL, 42.8 mmol) at 0° C. was added a solution of sodium nitrite (0.102 g, 1.482 mmol) in water (0.4 mL) over 5 min. The mixture was stirred at 0° C. for 1 h before a solution of tin(II) chloride dihydrate (0.613 g, 2.72 mmol) in conc. hydrochloric acid (1.3 mL, 42.8 mmol) was added over 10 min. The mixture was stirred at rt for 1.5 h and then filtered. The filtrate was slowly basified with ice cold 6N NaOH slowly and then extracted with EtOAc (2×40 mL). The combined extract was dried over MgSO$_4$, filtered and concentrated under vacuum. The residue was purified with a silica gel flash column, eluting with 0-40% EtOAc in hexane to afford (5-methoxy-2-(trifluoromethyl)phenyl)hydrazine (171 mg, 0.829 mmol, 67.2% yield) as a tan solid. MS (ESI) m/z: 207.0 [M+H]$^+$; $^1$H NMR (400 MHz, chloroform-d) δ 7.37 (d, J=8.80 Hz, 1H), 6.84 (d, J=2.20 Hz, 1H), 6.33 (dd, J=2.20, 9.02 Hz, 1H), 5.84 (br s, 1H), 3.85 (s, 3H), 3.50 (s, 2H).

Preparation of Final Compounds

EXAMPLE A1

Method A Representative

Preparation of (2S,3R,4R,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-6-(hydroxymethyl)tetrahydro-2H-pyran-3,5-diol 2-chloro-1,3-difluorobenzene (27.3 g, 120 mmol), copper(I) iodide (0.389 g, 2.041 mmol) and bis(triphenylphosphine)palladium(II) chloride (1.432 g, 2.041 mmol) in TEA (120 ml) at rt was added ethynyltrimethylsilane (17.30 ml, 122 mmol) was added over 20 min. A slight exotherm was observed. The mixture was stirred at rt for 8 h, then diluted with hexanes and filtered through Celite. The filtrate was concentrated under vacuum, and the residue was purified with a silica gel flash column, eluting with hexane to afford ((4-chloro-3,5-difluorophenyl)ethynyl)trimethylsilane (29.23 g, 109 mmol, 91% yield) as an oil. $^1$H NMR (500 MHz, CHLOROFORM-d) δ $^1$H NMR (400 MHz, CHLOROFORM-d) δ 7.03-7.10 (m, 2H), 0.22-0.29 (m, 9H).

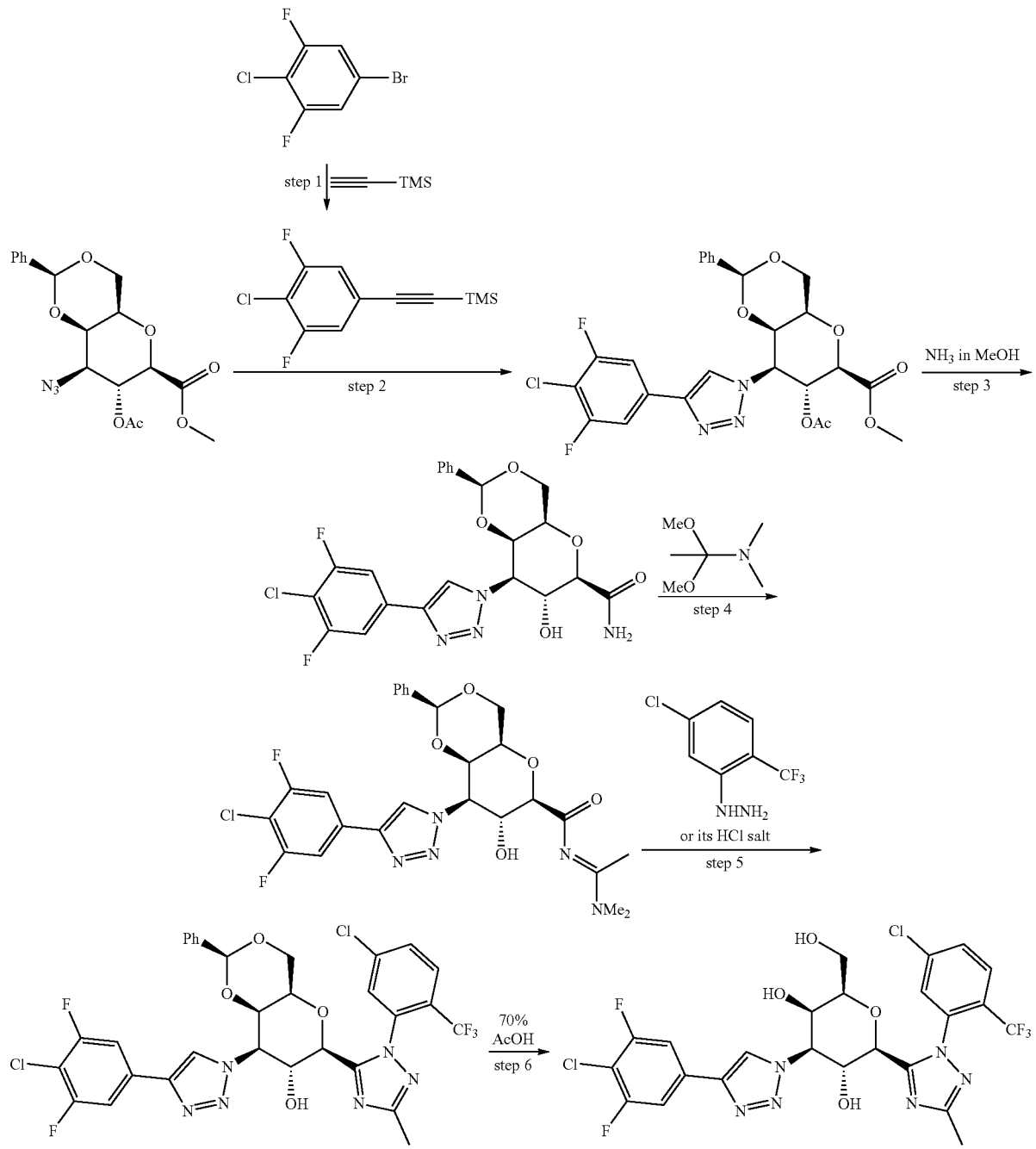

Step 1. Preparation of ((4-Chloro-3,5-difluorophenyl)ethynyl)trimethylsilane: To a degassed mixture of 5-bromo- Step 2. Preparation of Methyl (2S,4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate: To a solution of methyl (4aR,6R,7R,8S,8aR)-7-acetoxy-8-azido-2-phenylhexahydropyrano[3,2-d][1,3]dioxine-6-carboxylate (3.0 g, 7.95 mmol) in DMF (30 mL) and H$_2$O (12 mL) were added (+)-sodium L-ascorbate (1.575 g, 7.95 mmol), copper(II) sulfate pentahydrate (1.786 g, 7.16 mmol) and ((4-chloro-3,5-difluorophenyl)ethynyl)trimethylsilane (3.11 g, 12.72 mmol). The reaction mixture was heated at 85° C. for 1 h. Upon cooling to room temperature, the mixture was mixed with ice cold water (180 mL). The resulting mixture was stirred at rt for 10 min. The brown solid was collected by suction filtration. The solid was diluted with a mixture of CHCl$_3$ (400 mL) and MeOH (60 mL). The resulting mixture was heated to reflux, stirred for 10 min and subjected to filtration when it was hot. The solid residue was washed with mixture of CHCl$_3$ (50 mL) and THF (50 mL). The organic layers were combined and concentrated under vacuum to dryness. The residue was suspended into MeOH (100 mL), stirred at rt for 5 min, and subjected to filtration. The filter cake was collected and dried under vacuum at 50° C. overnight to give methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate 3.87 g, 89% yield). MS (ESI) m/z: 550.0 [M+H]$^+$; $^1$H NMR (400 MHz, Chloroform-d) δ 8.06 (s, 1H), 7.49-7.33 (m, 7H), 5.87 (dd, J=11.0, 9.6 Hz, 1H), 5.51 (s, 1H), 5.19 (dd, J=11.0, 3.3 Hz, 1H), 4.53-4.43 (m, 2H), 4.22 (d, J=9.6 Hz, 1H), 4.11 (dd, J=12.8, 1.8 Hz, 1H), 3.83-3.75 (m, 4H), 3.49 (d, J=4.7 Hz, 1H), 1.87 (s, 3H).

Step 3. Preparation of (4aR,6R,7R,8R,8aR)-8-(4-(4-Chloro-3,5-difluorophenyl)-1H-1,2,3-triazol-1-yl)-7-hydroxy-2-phenylhexahydropyrano[3,2-d][1,3]dioxine-6-carboxamide: Ammonia in methanol (7 N) (700 mL, 4900 mmol), pre-cooled in refrigerator, was added to methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (9.84 g, 17.89 mmol) in one portion. The mixture was stirred at room temperature in a sealed flask for 18 h. The mixture (now clear solution) was concentrated under vacuum to dryness. To the residue was added dichloromethane (30 mL) and the mixture was concentrated under vacuum to give (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (9.28 g, 17.89 mmol, 100% yield, 95% pure) as a white solid: MS (ESI) m/z: 493.0 [M+H]$^+$; $^1$H NMR (400 MHz, Chloroform-d) δ 8.03 (s, 1H), 7.47-7.40 (m, 2H), 7.40-7.31 (m, 5H), 6.88 (s, 1H), 5.66 (s, 1H), 5.49 (s, 1H), 5.04 (dd, J=10.5, 3.3 Hz, 1H), 4.92 (s, 1H), 4.66-4.49 (m, 2H), 4.43 (dd, J=12.8, 1.7 Hz, 1H), 4.15 (dd, J=12.8, 1.7 Hz, 1H), 4.04 (d, J=9.5 Hz, 1H), 3.84 (d, J=1.4 Hz, 1H).

Step 4. Preparation of (4aR,6R,7R,8R,8aR)-8-(4-(4-Chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide: A heterogeneous mixture of (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (3.75 g, 7.30 mmol) and 1,1-dimethoxy-N,N-dimethylethan-1-amine (3.30 g, 22.30 mmol) in 1,4-dioxane (100 mL) was heated at 60° C. for 5 h. The volatiles were removed under vacuum. To the residue was added hexane (100 mL) and diethyl ether (20 mL). The mixture was stirred at rt for 5 min and the insoluble product, (4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (4.34 g, 7.34 mmol, 100% yield, 95% pure), was collected as a beige solid by suction filtration and dried under vacuum overnight. MS (ESI) m/z: 562.1 [M+H]$^+$; $^1$H NMR (400 MHz, Chloroform-d) δ 8.05 (s, 1H), 7.52-7.29 (m, 7H), 6.25 (s, 1H), 5.47 (s, 1H), 5.05 (dd, J=10.5, 3.4 Hz, 1H), 4.57 (dd, J=12.6, 1.5 Hz, 1H), 4.52-4.36 (m, 2H), 4.15-3.89 (m, 2H), 3.76 (d, J=1.5 Hz, 1H), 3.16 (s, 3H), 3.09 (s, 3H), 2.43 (s, 3H).

Step 5. Preparation of (4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol: A mixture of (4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (3.00 g, 5.07 mmol) and (5-chloro-2-(trifluoromethyl)phenyl)hydrazine (1.175 g, 5.58 mmol) in dioxane (24 mL) and acetic Acid (24 mL) was stirred at 80° C. for 60 min. The mixture was concentrated under vacuum to almost dryness. The residue was diluted with ethyl acetate (450 mL), washed with 1M K$_2$HPO$_4$ solution (2×80 mL) and brine (80 mL). The organic layer was dried over anhydrous MgSO$_4$, filtered, and concentrated to give a crude product. This crude product was dissolved in CH$_2$Cl$_2$ (100 mL) and 15 g silica gel was added. The solvent was evaporate to give a solid residue, which was loaded into a solid loading cartridge and purified by ISCO automated chromatography (330 g silica gel, 0-2.5% MeOH/CH$_2$Cl$_2$ in 60 min gradient). The product thus obtain was further recrystallized from hexane and EtOAc to give (4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (1.899 g, 2.68 mmol, 52.8% yield) as a white solid. MS (ESI) m/z: 709.1 [M+H]$^+$; $^1$H NMR (400 MHz, Chloroform-d) δ 8.04 (s, 1H), 7.75 (d, J=8.4 Hz, 1H), 7.69-7.57 (m, 2H), 7.47-7.39 (m, 2H), 7.39-7.28 (m, 5H), 5.38 (s, 1H), 5.07 (dd, J=10.8, 3.3 Hz, 1H), 4.78 (ddd, J=10.9, 9.0, 2.1 Hz, 1H), 4.60 (d, J=2.1 Hz, 1H), 4.55 (d, J=9.0 Hz, 1H), 4.46 (dd, J=3.3, 1.1 Hz, 1H), 3.92 (dd, J=12.8, 1.8 Hz, 1H), 3.76-3.67 (m, 1H), 3.52 (q, J=1.6 Hz, 1H), 2.43 (s, 3H).

Step 6. Preparation of (2S,3R,4R,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-6-(hydroxymethyl)tetrahydro-2H-pyran-3,5-diol: A suspension of (4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (74 mg, 0.104 mmol) in 70% acetic Acid (5 mL) was heated at 70° C. for 8 h. The resulting solution was subjected to prep. HPLC Column: Sunfire C18 OBD 5u 30×100 mm; Solvent A: 90% H$_2$O-10% methanol-0.1% TFA, Solvent B: 10% methanol-90% H$_2$O 0.1% TFA; Gradient: 0-100% B over 15 min; Flow rate: 40 ml/min). The correct fractions were combined, concentrated under vacuum, basified with 1 N K$_2$HPO$_4$ solution to pH 9-10, and extracted with dichloromethane (3×40 mL). The combined extract was dried over anhydrous Na$_2$SO$_4$. Removal of the solvent under vacuum provided (2S,3R,4R,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-6-(hydroxymethyl)tetrahydro-2H-pyran-3,5-diol (40 mg, 0.064 mmol, 61.1% yield) as a white solid. MS (ESI) m/z: 621.0 [M+H]$^+$; $^1$H NMR (600 MHz, CHLOROFORM-d) δ 8.19 (s, 1H), 7.76 (d, J=8.7 Hz, 1H), 7.65 (dd, J=8.5, 1.2 Hz, 1H), 7.52 (s,1H), 7.28 (d, J=7.5 Hz, 2H), 4.92 (br s, 1H), 4.83 (td, J=10.3, 3.3 Hz, 1H), 4.77 (d, J=3.5 Hz, 1H), 4.65 (dd, J=10.6, 2.5 Hz, 1H), 4.51 (br s, 1H), 4.43 (d, J=9.1 Hz, 1H), 3.72-3.66 (m, 1H), 3.65-3.58 (m, 2H), 2.65 (br s, 1H), 2.36 (s, 3H). hGal-3 IC$_{50}$=0.018 µM.

EXAMPLE A2

Method B Representative

Preparation of (2S,3R,4R,5R,6R)-2-(1-(2,3-dichlorophenyl)-3-methyl-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol

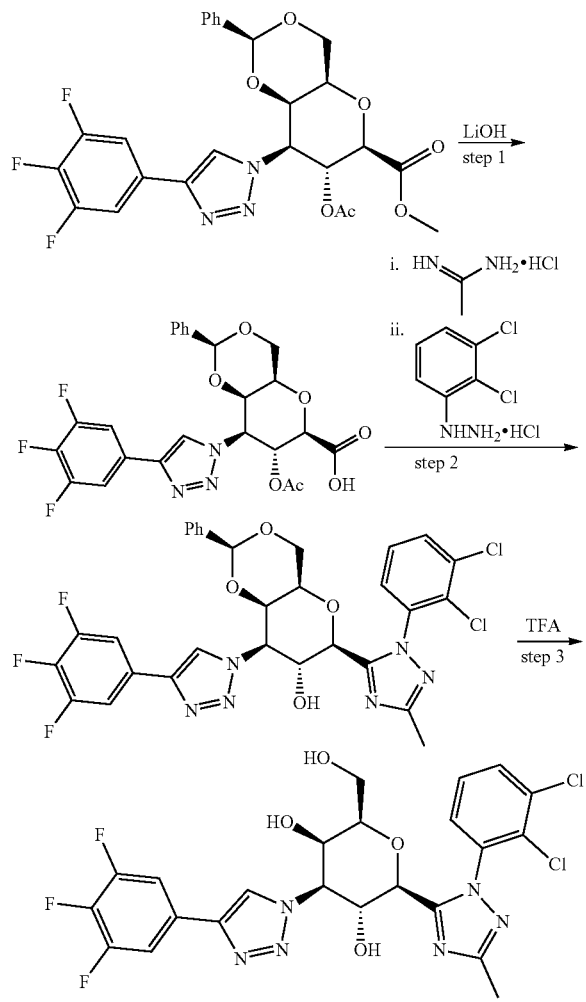

Step 1. Preparation of (2S,4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylic acid: To a solution of methyl (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylate (356 mg, 0.667 mmol) in THF (20 mL) at rt was added a solution of lithium hydroxide (80 mg, 3.34 mmol) in water (4 mL) over 2 min. The mixture was stirred at rt for 2.5 h. The reaction was complete and clean. The reaction mixture was concentrated under vacuum to dryness. To the residue was added water (4 mL) and the resulting mixture was acidified to pH 3-4 with 1 N HCl. The insoluble product, (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (0.320 g, 0.670 mmol, 100% yield), was collected as a beige solid by suction filtration and dried over Drierite under vacuum. MS (ESI) m/z: 478.0 [M+H]$^+$.

Step 2. Preparation of (2S,4aR,6S,7R,8R,8aR)-6-(1-(2,3-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol: A mixture of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (55 mg, 0.115 mmol), acetimidamide hydrochloride, HCl (37.7 mg, 0.288 mmol), HATU (59.1 mg, 0.156 mmol), and N,N-diisopropylethylamine (0.121 mL, 0.691 mmol) in DMF (1 mL) was stirred at rt for 4 h. Then, (2,3-dichlorophenyl)hydrazine, HCl (49.2 mg, 0.230 mmol) was added, followed by acetic acid (0.132 mL, 2.304 mmol). The mixture was heated at 80° C. for 8 h. Upon cooling to rt, the mixture was diluted with ethyl acetate (60 mL), washed with saturated NaHCO$_3$ solution (20 mL), water (2×20 mL), and brine (20 mL). The organic solution was dried over anhydrous MgSO$_4$ and concentrated under vacuum. The residue was subjected to flash chromatography (24 g silica gel, solid loading, 0-5% methanol/dichloromethane) to afford (4aR,6S,7R,8R,8aR)-6-(1-(2,3-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (20 mg, 0.030 mmol, 26.3% yield) as a beige solid. MS (ESI) m/z: 658.9 [M+H]$^+$.

Step 3. Preparation of (2S,3R,4R,5R,6R)-2-(1-(2,3-dichlorophenyl)-3-methyl-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol: To a solution of (4aR,6S,7R,8R,8aR)-6-(1-(2,3-dichlorophenyl)-3-methyl-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-ol (20 mg, 0.030 mmol) in dichloromethane (0.8 mL) at 0° C. was added TFA (0.070 mL, 0.910 mmol). The mixture was stirred at rt for 4.5 h and then concentrated under vacuum to dryness. The residue was dissolved in methanol and injected to prep. HPLC Column: Phenomenex Luna AXIA 5u C18 21.2×100 (10 min): Solvent A: 90% H2O-10% ACN-0.1% TFA, Solvent B: 10% ACN-90% H2O 0.1% TFA; Gradient: 0-100% B over 15 min; Flow rate: 20 ml/min). The correct fraction was concentrated under vacuum, basified with saturated NaHCO$_3$ solution, and extracted with dichloromethane (3×30 mL). The combined extract was dried over anhydrous Na$_2$SO$_4$. Removal of the solvent under vacuum provided the desired product, (2S,3R,4R,5R,6R)-2-(1-(2,3-dichlorophenyl)-3-methyl-1H-1,2,4-triazol-5-yl)-6-(hydroxymethyl)-4-(4-(3,4,5-trifluorophenyl)-1H-1,2,3-triazol-1-yl)tetrahydro-2H-pyran-3,5-diol (3.0 mg, 5.25 µmol, 17.31% yield), as a white solid. MS (ESI) m/z: 571.0 [M+H]$^+$; $^1$H NMR (500 MHz, METHANOL-d$_4$) δ 8.56 (s, 1H), 7.88-7.80 (m, 1H), 7.74-7.59 (m, 3H), 7.58-7.51 (m, 1H), 4.88 (br d, J=2.8 Hz, 2H), 4.42-4.31 (m, 1H), 4.12 (s, 1H), 3.80-3.65 (m, 3H), 2.48 (s, 3H). hGal-3 IC$_{50}$=0.332 µM.

EXAMPLE A3

Method C Representative

Preparation of (2S,3R,4R,5R,6R)-2-(1-(5-Chloro-2-(trifluoromethyl)phenyl)-3-methyl-1H-1,2,4-triazol-5-yl)-4-(4-(3,4-dichlorophenyl)-1H-1,2,3-triazol-1-yl)-6-(hydroxymethyl)tetrahydro-2H-pyran-3,5-diol

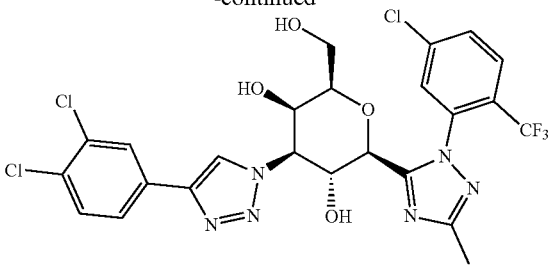

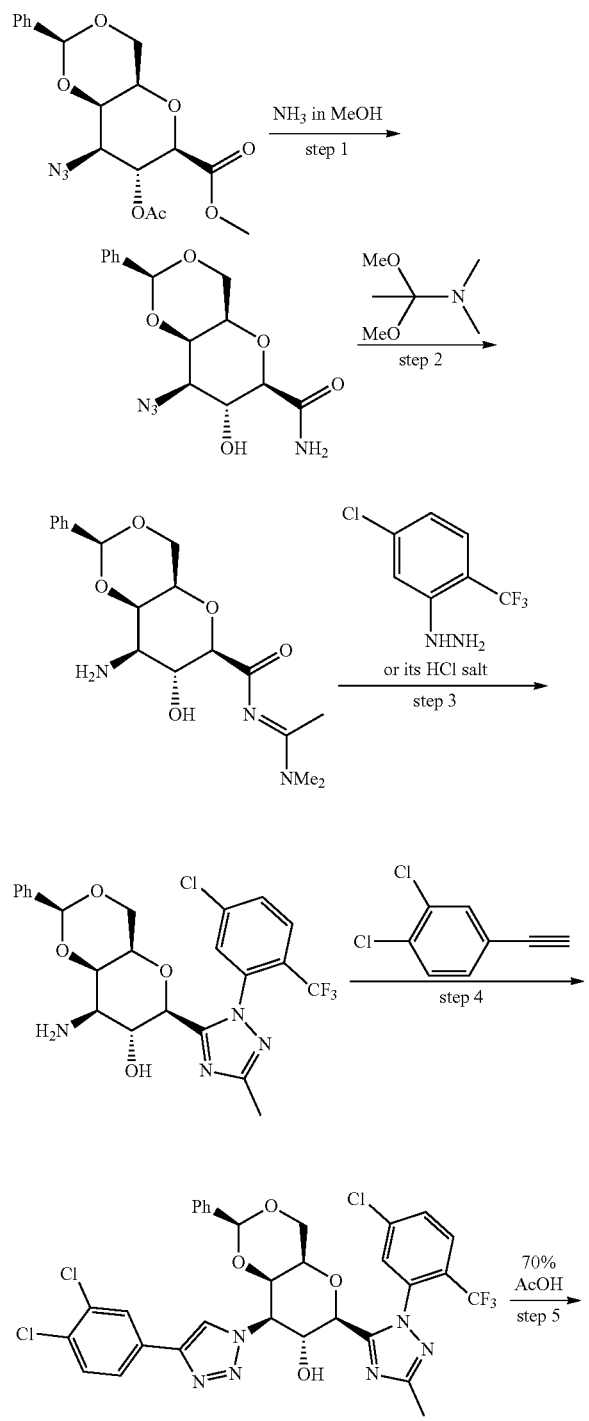

Step 1. Preparation of (4aR,6R,7R,8R,8aR)-8-Azido-7-hydroxy-2-phenylhexahydropyrano[3,2-d][1,3]dioxine-6-carboxamide: A solution of methyl (4aR,6R,7R,8S,8aR)-7-acetoxy-8-azido-2-phenylhexahydropyrano[3,2-d][1,3]dioxine-6-carboxylate (515 mg, 1.365 mmol) in 7M ammonia in MeOH (11.5 ml, 81 mmol) was stirred at rt overnight. The mixture was concentrated under vacuum, and the residue was purified with a silica gel flash column, eluting with 0-10% MeOH in DCM to afford (4aR,6R,7R,8R,8aR)-8-azido-7-hydroxy-2-phenylhexahydropyrano[3,2-d][1,3]dioxine-6-carboxamide (412 mg, 1.286 mmol, 94% yield) as a white solid. MS (ESI) m/z: 321.0 [M+H]$^+$; $^1$H NMR (400 MHz, chloroform-d) δ 7.46-7.54 (m, 2H), 7.34-7.43 (m, 3H), 6.82 (br s, 1H), 5.70-5.83 (m, 1H), 5.60 (s, 1H), 4.74 (s, 1H), 4.34 (dd, J=1.54, 12.54 Hz, 1H), 4.22-4.31 (m, 2H), 4.10 (dd, J=1.76, 12.54 Hz, 1H), 3.82 (d, J=9.68 Hz, 1H), 3.56 (d, J=1.10 Hz, 1H), 3.43 (dd, J=3.30, 9.90 Hz, 1H).

Step 2. Preparation of (4aR,6R,7R,8R,8aR)-8-Azido-N-((E)-1-(dimethylamino)ethylidene)-7-hydroxy-2-phenyl-hexahydropyrano[3,2-d][1,3]dioxine-6-carboxamide: To a solution of (4aR,6R,7R,8R,8aR)-8-azido-7-hydroxy-2-phenylhexahydropyrano[3,2-d][1,3]dioxine-6-carboxamide (285 mg, 0.890 mmol) in DCM (2966 µl) was added 1,1-dimethoxy-N,N-dimethylethan-1-amine (356 mg, 2.67 mmol). The mixture was stirred at 25° C. for 1 h. The reaction was concnetrated in vacuo. The residue was triturated with ether to provide a crude (4aR,6R,7R,8R,8aR)-8-azido-N-((E)-1-(dimethylamino)ethylidene)-7-hydroxy-2-phenylhexahydropyrano[3,2-d][1,3]dioxine-6-carboxamide (365 mg, 0.881 mmol, 99% yield) as tan solid. MS (ESI) m/z: 390.1 [M+H]$^+$.

Step 3. Preparation of (4aR,6S,7R,8R,8aR)-8-Azido-6-(1-(5-chloro-2-fluoromethyl)phenyl)-3-methyl-1H-1,2,4-triazol-5-yl)-2-phenylhexahydropyrano[3,2-d][1,3]dioxin-7-ol: To (4aR,6R,7R,8R,8aR)-8-azido-N-((E)-1-(dimethylamino)ethylidene)-7-hydroxy-2-phenylhexahydropyrano[3,2-d][1,3]dioxine-6-carboxamide (360 mg, 0.869 mmol) in acetic acid (4 mL) and methanol (4 mL) at rt was added (5-chloro-2-(trifluoromethyl)phenyl)hydrazine (183 mg, 0.869 mmol). The resulting mixture was stirred at 25° C. for 4 h and then concentrated under vacuum. The residue was purified with a SiO$_2$ gel flash column, eluting with 0-65% EtOAc in hexane to afford (4aR,6S,7R,8R,8aR)-8-azido-6-(1-(5-chloro-2-(trifluoromethyl)phenyl)-3-methyl-1H-1,2,4-triazol-5-yl)-2-phenylhexahydropyrano[3,2-d][1,3]dioxin-7-ol (191 mg, 0.356 mmol, 40.9% yield) as a tan solid (foam). MS (ESI) m/z: 537.0 [M+H]$^+$;

Step 4. Preparation of (4aR,6S,7R,8R,8aR)-6-(1-(5-Chloro-2-(trifluoromethyl)phenyl)-3-methyl-1H-1,2,4-triazol-5-yl)-8-(4-(3,4-dichlorophenyl)-1H-1,2,3-triazol-1-yl)-2-phenylhexahydropyrano[3,2-d][1,3]dioxin-7-ol: To a solution of (4aR,6S,7R,8R,8aR)-8-azido-6-(1-(5-chloro-2-(trifluoromethyl)phenyl)-3-methyl-1H-1,2,4-triazol-5-yl)-2- phenylhexahydropyrano[3,2-d][1,3]dioxin-7-ol (40 mg, 0.075 mmol) in DMF (621 μl) and water (124 μl) were added (+)-sodium L-ascorbate (14.76 mg, 0.075 mmol), copper(II) sulfate pentahydrate (16.74 mg, 0.067 mmol) and 1,2-dichloro-4-ethynylbenzene (22.93 mg, 0.134 mmol). The reaction mixture was degassed and then heated at 85° C. for 60 min. The reaction mixture was filtered through a pad of Celite. The filtrate was concentrated, and the residue was purified by preparative HPLC (Column: Phenomenex Luna Axia 30×100, 5 μm particles; Mobile Phase A: 10% H$_2$O-90% acetonitrile-0.1% trifluoroacetic acid; Mobile Phase B: 90% H$_2$O-10% acetonitrile-0.1% trifluoroacetic acid; Gradient: 30-80% B over 12 minutes, then 3 minute hold at 100% B; Flow: 40 mL/min). Fractions containing the desired product were combined, concentrated under vacuum, and lyophilized to give (4aR,6S,7R,8R,8aR)-6-(1-(5-chloro-2-(trifluoromethyl)phenyl)-3-methyl-1H-1,2,4-triazol-5-yl)-8-(4-(3,4-dichlorophenyl)-1H-1,2,3-triazol-1-yl)-2-phenylhexahydropyrano[3,2-d][1,3]dioxin-7-ol (11 mg, 0.016 mmol, 20.86% yield) as a white powder. MS (ESI) m/z: 706.9 [M+H]$^+$; $^1$H NMR (500 MHz, CHLOROFORM-d) δ 8.06 (s, 1H), 7.88-7.93 (m, 1H), 7.76 (d, J=8.53 Hz, 1H), 7.59-7.67 (m, 3H), 7.50 (d, J=8.25 Hz, 1H), 7.31-7.41 (m, 5H), 5.40 (s, 1H), 4.82 (br d, J=9.35 Hz, 1H), 4.58 (br d, J=8.80 Hz, 1H), 4.46 (d, J=3.03 Hz, 1H), 3.94 (dd, J=1.38, 12.65 Hz, 1H), 3.76 (br d, J=12.65 Hz, 1H), 3.17 (dd, J=4.68, 7.15 Hz, 3H), 2.45 (s, 3H).

Step 5. Preparation of (2S,3R,4R,5R,6R)-2-(1-(5-Chloro-2-(trifluoromethyl)phenyl)-3-methyl-1H-1,2,4-triazol-5-yl)-4-(4-(3,4-dichlorophenyl)-1H-1,2,3-triazol-1-yl)-6-(hydroxymethyl)tetrahydro-2H-pyran-3,5-diol: A mixture of (4aR,6S,7R,8R,8aR)-6-(1-(5-chloro-2-(trifluoromethyl)phenyl)-3-methyl-1H-1,2,4-triazol-5-yl)-8-(4-(3,4-dichlorophenyl)-1H-1,2,3-triazol-1-yl)-2-phenylhexahydropyrano[3,2-d][1,3]dioxin-7-ol (11 mg, 0.016 mmol) in acetic acid (0.7 mL) and water (0.3 mL) was stirred at 80° C. for 3 h. The reaction was concentrated under vacuum. The residue was purified by preparative HPLC (Column: Phenomenex Luna Axia 30×100, 5 μm particles; Mobile Phase A: 10% H$_2$O-90% acetonitrile-0.1% trifluoroacetic acid; Mobile Phase B: 90% H$_2$O-10% acetonitrile-0.1% trifluoroacetic acid; Gradient: 30-100% B over 12 minutes, then 3 minute hold at 100% B; Flow: 40 mL/min). Fractions containing the desired product were combined, concentrated under vacuum, and liophilized to give (2S,3R,4R,5R,6R)-2-(1-(5-chloro-2-(trifluoromethyl)phenyl)-3-methyl-1H-1,2,4-triazol-5-yl)-4-(4-(3,4-dichlorophenyl)-1H-1,2,3-triazol-1-yl)-6-(hydroxymethyl)tetrahydro-2H-pyran-3,5-diol as a white solid. MS (ESI) m/z: 618.9 [M+H]$^+$; $^1$H NMR (500 MHz, METHANOL-d$_4$) δ 8.55 (s, 1H), 8.05 (d, J=1.93 Hz, 1H), 7.95 (s, 1H), 7.87 (br d, J=1.38 Hz, 1H), 7.79 (dd, J=2.06, 8.39 Hz, 2H), 7.60 (d, J=8.53 Hz, 1H), 4.86 (br s, 2H), 4.35 (br d, J=8.80 Hz, 1H), 4.11 (s, 1H), 3.72 (d, J=6.05 Hz, 1H), 3.65-3.69 (m, 2H), 2.45 (s, 3H). hGal-3 IC$_{50}$=0.033 μM.

EXAMPLE A4

Method D Representative

Preparation of (2R,3R,4R,5R,6S)-2-(Hydroxymethyl)-6-(1-(2-methylbenzo[d]thiazol-6-yl)-3-(trifluoromethyl)-1H-1,2,4-triazol-5-yl)-4-(4-(3,4,5-trifluorophenyl)-1H-1,2,3-triazol-1-yl)tetrahydro-2H-pyran-3,5-diol

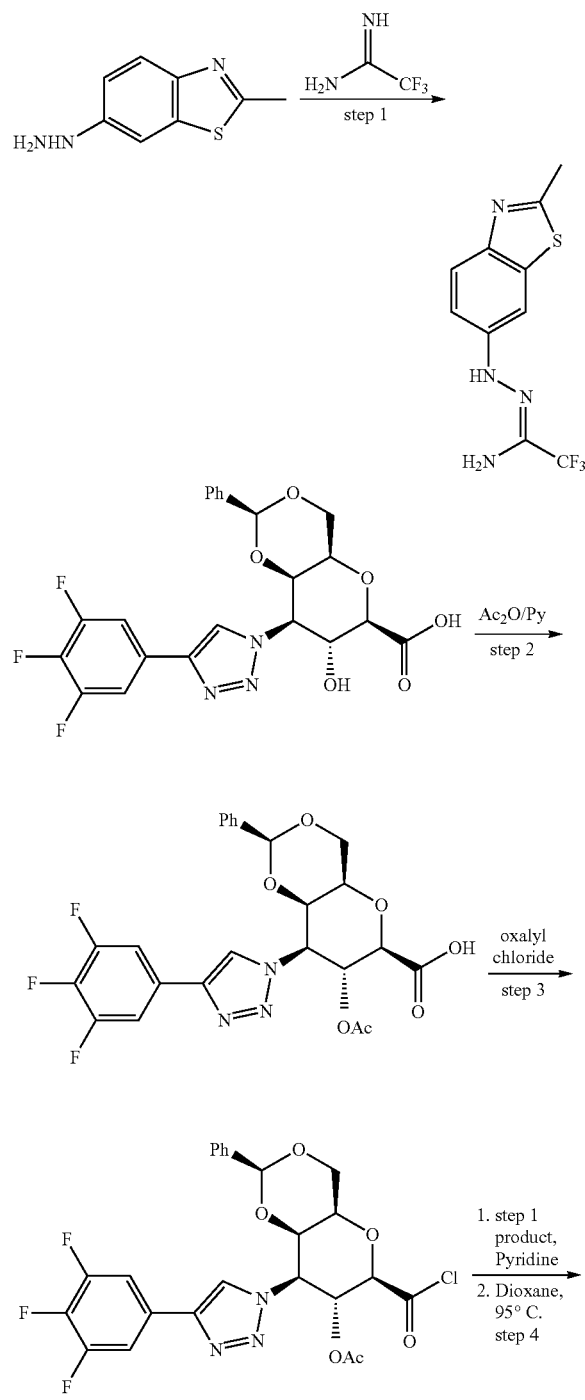

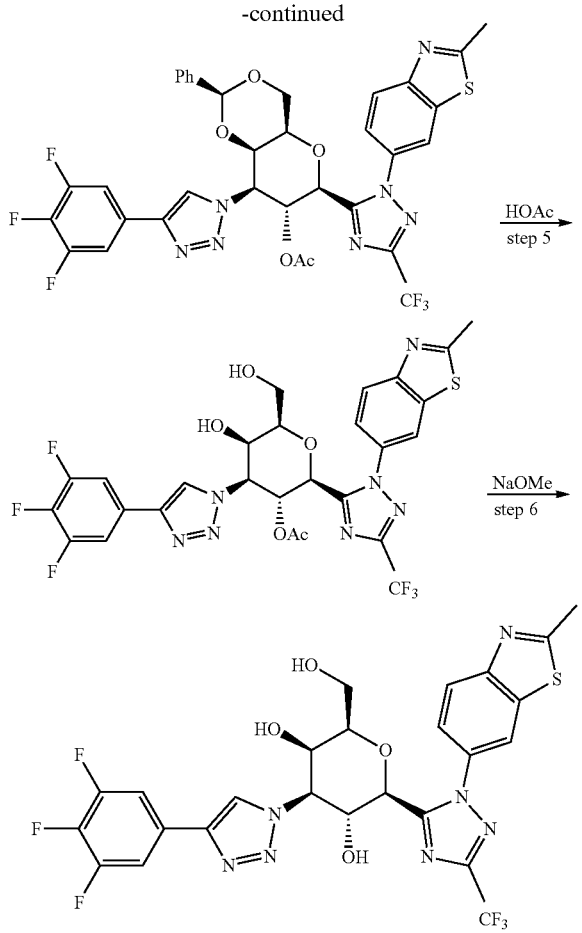

Step 1. Preparation of (Z)-2,2,2-Trifluoro-N'-(2-methylbenzo[d]thiazol-6-yl)acetohydrazonamide: A mixture of 6-hydrazineyl-2-methylbenzo[d]thiazole, 2 HCl (388 mg, 1.539 mmol), 2,2,2-trifluoroacetimidamide (259 mg, 2.308 mmol), and Et₃N (0.388 mL, 2.78 mmol) in THF (6.5 mL) was stirred at rt for 16 h. The solvent was removed under vacuum to give a crude product, which was subjected to flash chromatography (24 g silica gel, 0-55% ethyl acetate/hexane) to afford (Z)-2,2,2-trifluoro-N'-(2-methylbenzo[d]thiazol-6-yl)acetohydrazonamide (38 mg, 0.139 mmol, 24% yield) as light yellow solid. MS (ESI) m/z: 274.9 [M+H]⁺; ¹H NMR (400 MHz, Acetonitrile-d₃) δ 7.75 (d, J=8.8 Hz, 1H), 7.58 (d, J=2.3 Hz, 1H), 7.31 (s, 1H), 7.14 (dd, J=8.8, 2.3 Hz, 1H), 5.18 (s, 2H), 2.74 (s, 3H).

Step 2. Preparation of (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylic acid: To a suspension of (4aR,6R,7R,8R,8aR)-7-hydroxy-2-phenyl-8-(4-(3,4,5-trifluorophenyl)-1H-1,2,3-triazol-1-yl)hexahydropyrano[3,2-d][1,3]dioxine-6-carboxylic acid (Example 2 step 1 product, 20 mg, 0.042 mmol), 2-methylbenzo[d]thiazol-6-amine (20 mg, 0.042 mmol in CH₂Cl₂ (1 mL) was added acetic anhydride (0.1 mL, 0.999 mmol) and pyridine (0.15 mL, 1.86 mmol). The reaction was stirred under argon at rt for 2 h. The solvent was evaporated. The residue was diluted with THF (0.3 mL) and water (0.15 mL) and stirred at rt for 30 min. The mixture was concentrated under vacuum to give a crude product, which was subjected to preparative HPLC (Column: Sunfire C18 OBD, 30×100 mm, 5-μm particles; Mobile Phase A: 5:95 acetonitrile: water with 0.1% TFA; Mobile Phase B: 95:5 acetonitrile: water with 0.1% TFA; Gradient: 35-100% B over 10 minutes, then a 5-minute hold at 100% B; Flow: 40 mL/min) to give (4aR,6R,7R,8S,8aR)-7-acetoxy-2-phenyl-8-(4-(3,4,5-trifluorophenyl)-1H-1,2,3-triazol-1-acid (19 mg, 0.091 mmol, 87% yield) as white solid. MS (ESI) m/z: 520.0 [M+H]⁺.

Step 3. Preparation of (4aR,6R,7R,8S,8aR)-6-(Chlorocarbonyl)-2-phenyl-8-(4-(3,4,5-trifluorophenyl)-1H-1,2,3-triazol-1-yl)hexahydropyrano[3,2-d][1,3]dioxin-7-yl acetate: To a solution of (4aR,6R,7R,8S,8aR)-7-acetoxy-2-phenyl-8-(4-(3,4,5-trifluorophenyl)-1H-1,2,3-triazol-1-yl)hexahydropyrano[3,2-d][1,3]dioxine-6-carboxylic acid (179 mg, 0.345 mmol) in CH₂Cl₂ (12 mL) at 0° C. was added oxalyl chloride (65 μl, 0.742 mmol). A catalytic amount of DMF (3 drops) was added and resulting mixture was stirred at rt for 1 h. The reaction mixture was concentrated to dryness to give (4aR,6R,7R,8S,8aR)-6-(chlorocarbonyl)-2-phenyl-8-(4-(3,4,5-trifluorophenyl)-1H-1,2,3-triazol-1-yl)hexahydropyrano[3,2-d][1,3]dioxin-7-yl acetate as a white solid, which was used for next step immediately.

Step 4. Preparation of (4aR,6S,7R,8S,8aR)-6-(1-(2-Methylbenzo[d]thiazol-6-yl)-3-(trifluoromethyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl acetate: To a mixture of (Z)-2,2,2-trifluoro-N'-(2-methylbenzo[d]thiazol-6-yl)acetohydrazonamide (94 mg, 0.344 mmol) and pyridine (51 μl, 0.632 mmol) in dichloroethane (3 mL) at rt was added a mixture of (4aR,6R,7R,8S,8aR)-6-(chlorocarbonyl)-2-phenyl-8-(4-(3,4,5-trifluorophenyl)-1H-1,2,3-triazol-1-yl)hexahydropyrano[3,2-d][1,3]dioxin-7-yl acetate (185 mg, 0.344 mmol) in dichloroethane (4 mL). The mixture was stirred at rt for 10 min and additional pyridine (51 μl, 0.632 mmol) was added. The reaction mixture was stirred at rt for 1 h. The solvent was evaporated under vacuum. The residue was diluted water (4 mL) and extracted with EtOAc (2×10 mL). The organic layer was separated, washed with aqueous saturated NaHCO₃ solution and brine, dried over MgSO₄, filtered and concentrated to give a product. Dioxane (4 mL) was added to this product and the mixture was heated at 95° C. in a sealed tube for 16 h. The solvent was evaporated under vacuum to give a crude product, which was subjected to flash chromatography (24 g silica gel, 0-100% ethyl acetate/hexane) to afford (4aR,6S,7R,8S,8aR)-6-(1-(2-methylbenzo[d]thiazol-6-yl)-3-(trifluoromethyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl acetate (90 mg, 35% yield) as white solid. MS (ESI) m/z: 758.1 [M+H]⁺; ¹H NMR (400 MHz, Chloroform-d) δ 8.13 (d, J=2.0 Hz, 1H), 8.02 (d, J=8.6 Hz, 1H), 7.97 (s, 1H), 7.72 (dd, J=8.6, 2.2 Hz, 1H), 7.51-7.31 (m, 5H), 7.23-7.14 (m, 2H), 6.06 (dd, J=11.0, 9.7 Hz, 1H), 5.44 (s, 1H), 5.21 (dd, J=10.9, 3.3 Hz, 1H), 4.97 (d, J=9.7 Hz, 1H), 4.45 (dd, J=3.3, 1.1 Hz, 1H), 4.33 (dd, J=12.9, 1.6 Hz, 1H), 4.09 (dd, J=12.8, 1.8 Hz, 1H), 3.79-3.76 (m, 1H), 2.86 (s, 3H), 1.76 (s, 3H).

Step 5. Preparation of (2S,3R,4S,5R,6R)-5-Hydroxy-6-(hydroxymethyl)-2-(1-(2-methylbenzo[d]thiazol-6-yl)-3-(trifluoromethyl)-1H-1,2,4-triazol-5-yl)-4-(4-(3,4,5-trifluorophenyl)-1H-1,2,3-triazol-1-yl)tetrahydro-2H-pyran-3-yl acetate: A mixture of (4aR,6S,7R,8S,8aR)-6-(1-(2-methylbenzo[d]thiazol-6-yl)-3-(trifluoromethyl)-1H-1,2,4-triazol-5-yl)-2-phenyl-8-(4-(3,4,5-trifluorophenyl)-1H-1,2,3-triazol-1-yl)hexahydropyrano[3,2-d][1,3]dioxin-7-yl acetate (42 mg, 0.055 mmol) in acetic acid solution (80% aq., 2.5 mL) was stirred at 70° C. in a sealed vial for 18 h. The reaction mixture was concentrated to dryness to give (2S, 3R,4S,5R,6R)-5-hydroxy-6-(hydroxymethyl)-2-(1-(2-methylbenzo[d]thiazol-6-yl)-3-(trifluoromethyl)-1H-1,2,4-triazol-5-yl)-4-(4-(3,4,5-trifluorophenyl)-1H-1,2,3-triazol-1-yl)tetrahydro-2H-pyran-3-yl acetate (37.1 mg, 100% yield) as foam solid. MS (ESI) m/z: 670.1

Step 6. Preparation of (2R,3R,4R,5R,6S)-2-(Hydroxymethyl)-6-(1-(2-methylbenzo[d]thiazol-6-yl)-1H-tetrazol-5-yl)-4-(4-(3,4,5-trifluorophenyl)-1H-1,2,3-triazol-1-yl)tetrahydro-2H-pyran-3,5-diol: To a mixture of (2S,3R,4S,5R,6R)-5-hydroxy-6-(hydroxymethyl)-2-(1-(2-methylbenzo[d]thiazol-6-yl)-3-(trifluoromethyl)-1H-1,2,4-triazol-5-yl)-4-(4-(3,4,5-trifluorophenyl)-1H-1,2,3-triazol-1-yl)tetrahydro-2H-pyran-3-yl acetate (37 mg, 0.055 mmol) in MeOH (3 mL) was added sodium methoxide solution (40 µL, 0.117 mmol, 25% in MeOH) The mixture was stirred under $N_2$ for 2 h. The solvent was removed under vacuum to give a crude product. The crude product was subjected to preparative HPLC (Column: Sunfire C18 OBD, 30×100 mm, 5-µm particles; Mobile Phase A: 5:95 acetonitrile: water with 0.1% TFA; Mobile Phase B: 95:5 acetonitrile: water with 0.1% TFA; Gradient: 40-100% B over 10 minutes, then a 5-minute hold at 100% B; Flow: 40 mL/min) to give (2R,3R,4R,5R,6S)-2-(hydroxymethyl)-6-(1-(2-methylbenzo[d]thiazol-6-yl)-1H-tetrazol-5-yl)-4-(4-(3,4,5-trifluorophenyl)-1H-1,2,3-triazol-1-yl)tetrahydro-2H-pyran-3,5-diol (16.1 mg, 44.1% yield) as white powder. MS (ESI) m/z: 628.1 [M+H]$^+$; $^1$H NMR (400 MHz, Methanol-$d_4$) δ 8.60 (s, 1H), 8.54-8.40 (m, 1H), 8.13 (d, J=8.7 Hz, 1H), 7.96-7.87 (m, 1H), 7.73-7.54 (m, 2H), 5.09 (dd, J=10.8, 9.3 Hz, 1H), 4.96 (dd, J=10.8, 2.9 Hz, 1H), 4.65 (d, J=9.3 Hz, 1H), 4.15 (dd, J=3.0, 0.9 Hz, 1H), 3.93 (ddd, J=7.5, 3.9, 1.0 Hz, 1H), 3.86 (dd, J=11.5, 7.5 Hz, 1H), 3.74 (dd, J=11.6, 3.9 Hz, 1H), 2.93 (s, 3H). hGal-3 IC$_{50}$=0.058 µM.

EXAMPLE A5

Method E Representative (2R,3R,4S,5R,6S)-6-(1-(Benzo[d]thiazol-6-yl)-3-methyl-1H-1,2,4-triazol-5-yl)-4-(4-(4-chloro-3,5-difluorophenyl)-1H-1,2,3-triazol-1-yl)-2-(hydroxymethyl)-5-methoxytetrahydro-2H-pyran-3-ol

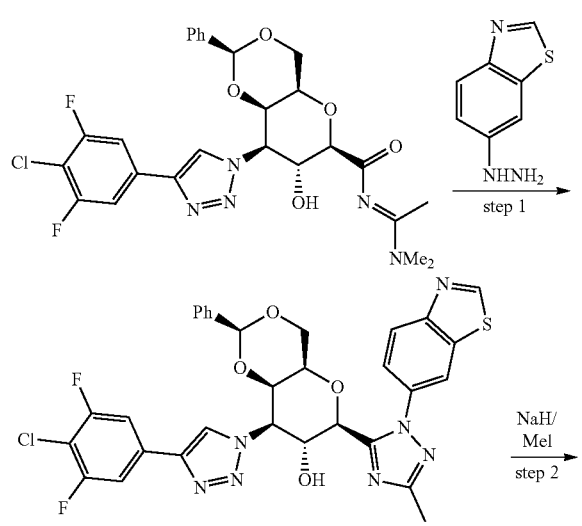

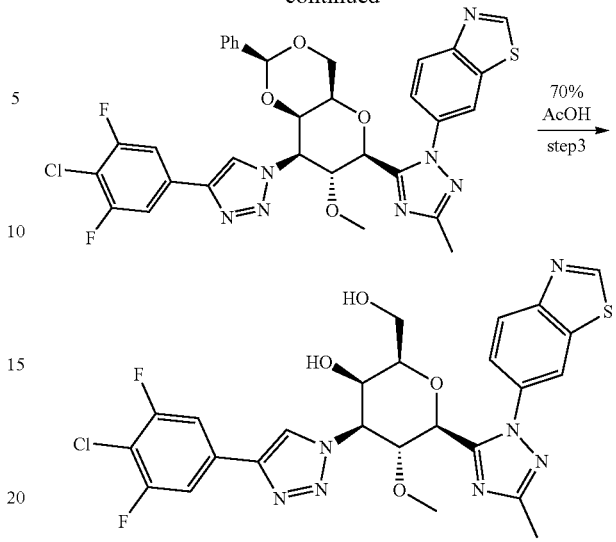

Step 1. (2S,4aR,6S,7R,8R,8aR)-6-(1-(Benzo[d]thiazol-6-yl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol: A mixture of (4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (36 mg, 0.064 mmol) and 6-hydrazineylbenzo[d]thiazole, TFA (25 mg, 0.089 mmol) in dioxane (0.35 mL) and acetic acid (0.35 mL) was stirred at 50° C. for 60 min. The mixture was concentrated under vacuum to almost dryness. The crude product was purified by ISCO automated chromatography (24 g silica gel, 0-2.5% MeOH/CH$_2$Cl$_2$, 25 min gradient time) to give (4aR,6S,7R,8R,8aR)-6-(1-(benzo[d]thiazol-6-yl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (30 mg, 0.045 mmol, 70.5% yield) as a white solid. MS (ESI) m/z: 664.3 [M+H]$^+$; $^1$H NMR (400 MHz, chloroform-d) δ 9.12 (s, 1H), 8.23 (d, J=7.3 Hz, 1H), 8.22 (s, 1H), 8.15 (s, 1H), 7.73 (dd, J=8.6, 2.2 Hz, 1H), 7.49-7.40 (m, 2H), 7.38-7.32 (m, 5H), 5.46 (s, 1H), 5.18-5.05 (m, 2H), 4.71-4.58 (m, 1H), 4.58-4.43 (m, 1H), 4.20-4.11 (m, 1H), 4.04 (dd, J=12.7, 1.8 Hz, 1H), 3.70-3.66 (m, 1H), 2.45 (s, 3H).

Step 2. 6-(5-((2S,4aR,6S,7R,8R,8aR)-8-(4-(4-Chloro-3,5-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole: To a stirred solution of (2S,4aR,6S,7R,8R,8aR)-6-(1-(benzo[d]thiazol-6-yl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (0.030 g, 0.045 mmol) in THF (1.2 mL) at 0° C. was added NaH (60% in mineral oil, 5.42 mg, 0.136 mmol). The mixture was stirred at 0° C. for 5 min. Iodomethane (15 0.226 mmol was added. The resulting mixture was stirred at rt for 2 h then quenched with saturated aq. NH$_4$Cl solution. The solvent was removed under vacuum to give a crude product, which was purified by ISCO automated chromatography (12 g silica gel, 0-100% Hexane/EtOAc, 15 min gradient time) to give 6-(5-((4aR,6S,7R,8R,8aR)-8-(4-(4-chloro-3,5-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole (27 mg, 88% yield) as a white solid. MS (ESI) m/z:

678.3[M+H]⁺; ¹H NMR (400 MHz, Chloroform-d) δ 9.13 (s, 1H), 8.24 (d, J=8.7 Hz, 1H), 8.20 (s, 2H), 7.74 (dd, J=8.6, 2.1 Hz, 1H), 7.60-7.35 (m, 7H), 5.55 (s, 1H), 5.07 (dd, J=10.3, 3.4 Hz, 1H), 4.66 (dd, J=10.3, 9.2 Hz, 1H), 4.57 (d, J=9.3 Hz, 1H), 4.45 (ddd, J=8.2, 4.9, 1.6 Hz, 2H), 4.17-4.06 (m, 1H), 3.72 (q, J=1.3 Hz, 1H), 2.91 (s, 3H), 2.50 (s, 3H).

Step 3. (2R,3R,4S,5R,6S)-6-(1-(Benzo[d]thiazol-6-yl)-3-methyl-1H-1,2,4-triazol-5-yl)-4-(4-(4-chloro-3,5-difluorophenyl)-1H-1,2,3-triazol-1-yl)-2-(hydroxymethyl)-5-methoxytetrahydro-2H-pyran-3-ol: A mixture of 6-(5-((2S,4aR,6S,7R,8R,8aR)-8-(4-(4-chloro-3,5-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole (27 mg, 0.040 mmol) in acetic acid solution (70% aq., 3 mL) was stirred at 70° C. in a sealed vial for 18 h. The reaction mixture was concentrated to dryness to give a crude product, which was subjected to preparative HPLC (Column: Sunfire C18 OBD, 30×100 mm, 5-μm particles; Mobile Phase A: 5:95 acetonitrile:water with 0.1% TFA; Mobile Phase B: 95:5 acetonitrile:water with 0.1% TFA; Gradient: 20-100% B over 10 minutes, then a 5-minute hold at 100% B; Flow: 40 mL/min) to give (2R,3R,4S,5R,6S)-6-(1-(benzo[d]thiazol-6-yl)-3-methyl-1H-1,2,4-triazol-5-yl)-4-(4-(4-chloro-3,5-difluorophenyl)-1H-1,2,3-triazol-1-yl)-2-(hydroxymethyl)-5-methoxytetrahydro-2H-pyran-3-ol (12.2 mg, 50.9% yield as a white solid. MS (ESI) m/z: 590.2 [M+H]⁺; ¹H NMR (400 MHz, Methanol-d₄) δ 9.42 (s, 1H), 8.80 (s, 1H), 8.52 (d, J=2.2 Hz, 1H), 8.28 (d, J=8.7 Hz, 1H), 7.86 (dd, J=8.7, 2.1 Hz, 1H), 7.73-7.63 (m, 2H), 5.01 (dd, J=10.5, 2.9 Hz, 1H), 4.74 (dd, J=10.5, 9.3 Hz, 1H), 4.61 (d, J=9.4 Hz, 1H), 4.12 (d, J=2.9 Hz, 1H), 3.95-3.82 (m, 2H), 3.81-3.71 (m, 1H), 2.97 (s, 3H), 2.51 (s, 3H). hGal-3 IC₅₀=0.02 μM.

The following examples were prepared following synthetic methods A-E described above:

| Ex. # | Structure | Method | LCMS (M + 1)⁺/¹H NMR | hGal IC50 (μM) |
|---|---|---|---|---|
| A6 | 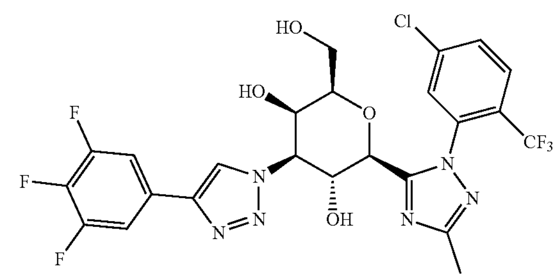 [SMILES: Cc1nc([C@@H]2O[C@H](CO)[C@H](O)[C@H](n3cc(-c4cc(F)c(F)c(F)c4)nn3)[C@H]2O)n(-c2cc(Cl)ccc2C(F)(F)F)n1] | B | MS (ESI) m/z: 605.0; ¹HNMR (500 MHz, methanol-d₄) δ 8.57 (s, 1H), 7.98 (d, J = 8.8 Hz, 1H), 7.88 (dd, J = 8.5, 1.4 Hz, 1H), 7.79 (br s, 1H), 7.72-7.63 (m, 2H), 4.91-4.87 (m, 2H), 4.37 (br d, J = 8.8 Hz, 1H), 4.13 (d J = 1.4 Hz, 1H), 3.78-3.72 (m, 1H), 3.71-3.66 (m, 2H), 2.47 (s, 3H) | 0.022 |
| A7 | 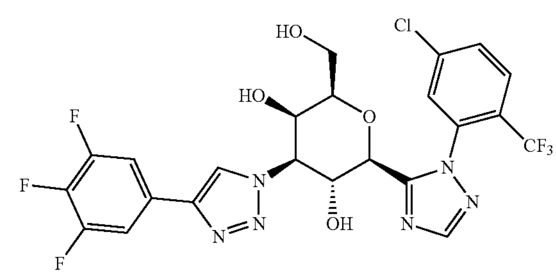 [SMILES: OC[C@H]1O[C@@H](c2ncnn2-c2cc(Cl)ccc2C(F)(F)F)[C@H](O)[C@@H](n2cc(-c3cc(F)c(F)c(F)c3)nn2)[C@H]1O] | A | MS (ESI) m/z: 591.0; ¹H NMR (500 MHz, methanol-d₄) δ 8.58 (s, 1H), 8.25 (s, 1H), 8.00 (d, J = 8.5 Hz, 1H), 7.90 (dd, J =8.5, 1.1 Hz, 1H), 7.82 (br s, 1H), 7.71-7.63 (m, 2H), 4.94-4.88 (m, 2H), 4.48-4.40 (m, 1H), 4.13 (d, J = 0.8 Hz, 1H), 3.79-3.73 (m, 1H), 3.72-3.64 (m, 2H) | 0.027 |
| A8 | 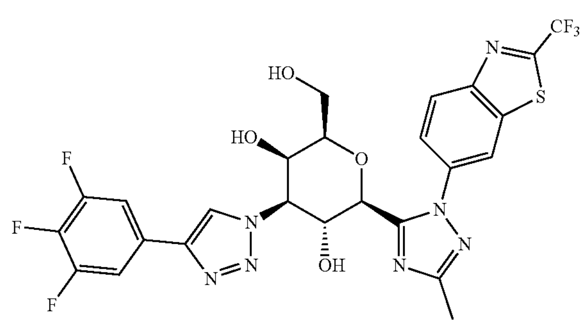 [SMILES: Cc1nc([C@@H]2O[C@H](CO)[C@H](O)[C@H](n3cc(-c4cc(F)c(F)c(F)c4)nn3)[C@H]2O)n(-c2ccc3nc(C(F)(F)F)sc3c2)n1] | B | MS (ESI) m/z: 628.0; ¹H NMR (500 MHz, methanol-d₄) δ 8.72 (d, J = 1.9 Hz, 1H), 8.59 (s, 1H), 8.41 (d, J = 8.8 Hz, 1H), 8.04 (dd, J = 8.8, 2.2 Hz, 1H), 7.68 (dd, J = 8.8, 6.6 Hz, 2H), 5.06-4.99 (m, 1H), 4.97-4.92 (m, 1H), 4.61 (d, J = 9.1 Hz, 1H), 4.15 (d, J = 2.5 Hz, 1H), 3.94 (dd, J = 7.7, 3.9 Hz, 1H), 3.90-3.82 (m, 1H), 3.75 (dd, J = 11.6, 3.9 Hz, 1H), 2.51 (s, 3H) | 0.505 |

-continued

| Ex. # | Structure | Method | LCMS (M + 1)⁺/¹H NMR | hGal IC50 (μM) |
|---|---|---|---|---|
| A9 | 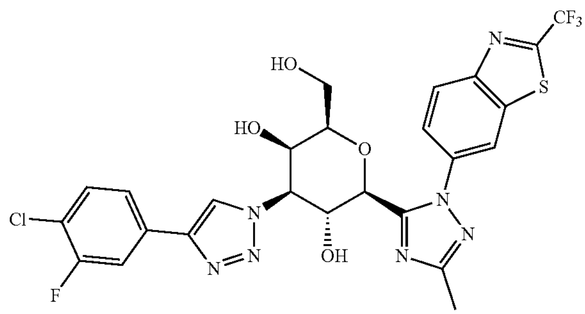 [SMILES: Cc1nc([C@@H]2O[C@H](CO)[C@H](O)[C@H](n3cc(-c4ccc(Cl)c(F)c4)nn3)[C@H]2O)n(-c2ccc3nc(C(F)(F)F)sc3c2)n1] | B | MS (ESI) m/z: 626.0; ¹H NMR (500 MHz, methanol-d$_4$) δ 8.72 (d, J = 1.9 Hz, 1H), 8.58 (s, 1H), 8.41 (d, J = 8.8 Hz, 1H), 8.04 (dd, J = 8.8, 2.2 Hz,1H), 7.78 (dd, J = 10.3,1.8 Hz, 1H), 7.70 (dd, J = 8.3, 1.4 Hz, 1H), 7.57 (t, J = 8.1 Hz, 1H), 5.06-4.99 (m, 1H), 4.98-4.92 (m,1H), 4.61 (d, J = 9.1 Hz,1H), 4.16 (d, J = 2.5 Hz, 1H), 3.94 (dd, J = 7.4, 3.9 Hz, 1H), 3.90-3.83 (m, 1H), 3.76 (dd, J = 11.8, 3.9 Hz, 1H), 2.51 (s, 3H) | 0.837 |
| A10 | 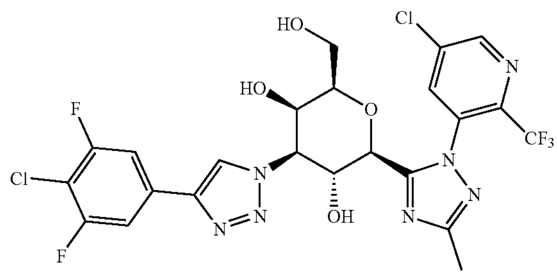 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)cnc2C(F)(F)F)n1] | B | MS (ESI) m/z: 622.0; ¹H NMR (500 MHz, methanol-d$_4$) δ 8.97 (d, J = 1.9 Hz, 1H), 8.61 (s, 1H), 8.34 (s, 1H), 7.70-7.64 (m, 2H), 4.92 -4.88 (m, 1H), 4.84-4.76 (m, 1H), 4.50 (d, J = 9,1 Hz, 1H), 4.12 (d, J = 2.2Hz, 1H), 3.81-3.75 (m, 1H), 3.68-3.60 (m, 2H), 2.47 (s, 3H) | 0.029 |
| A11 | 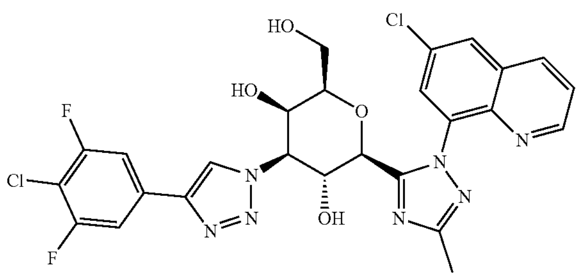 | A | MS (ESI) m/z: 604.0; ¹H NMR (500 MHz, methanol-d$_4$) δ 8.94 (dd, J = 4.1, 1.7 Hz, 1H), 8.56 (s, 1H), 8.49 (dd, J = 8.5, 1.7 Hz, 1H), 8.30 (d, J = 2.5 Hz, 1H), 8.03 (br d, J = 1.1 Hz, 1H), 7.71 (dd, J = 8.4, 4.3 Hz, 1H), 7.68-7.62 (m, 2H), 4.77 (br s, 2H), 4.40 (br d, J = 8.5 Hz, 1H), 4.04 (s, 1H), 3.58 (br s, 3H), 2.53 (s, 3H) | 0.017 |
| A12 | 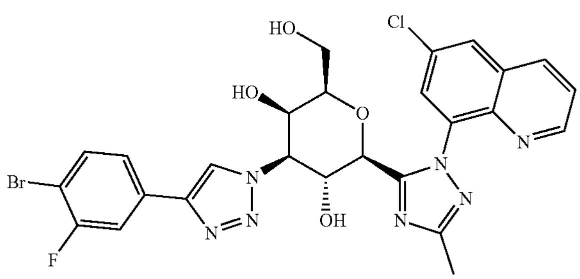 [SMILES: Cc1nc([C@@H]2O[C@H](CO)[C@H](O)[C@H](n3cc(-c4ccc(Br)c(F)c4)nn3)[C@H]2O)n(-c2cc(Cl)cc3cccnc23)n1] | A | MS (ESI) m/z: 630.0; ¹H NMR (500 MHz, methanol-d$_4$) δ 8.94 (dd, J = 4.1, 1.7 Hz, 1H), 8.49 (dd, J = 8.5, 1.7 Hz, 2H), 8.29 (d, J = 2.2 Hz, 1H), 8.03 (br d, J = 1.4 Hz, 1H), 7.75-7.68 (m, 3H), 7.60 (dd, J = 8.3, 1.7 Hz, 1H), 4.76 (br s, 2H), 4.40 (br d, J = 8.5 Hz, 1H), 4.04 (s, 1H), 3.59 (br s, 3H), 2.53 (s, 3H) | 0.046 |
| A13 | 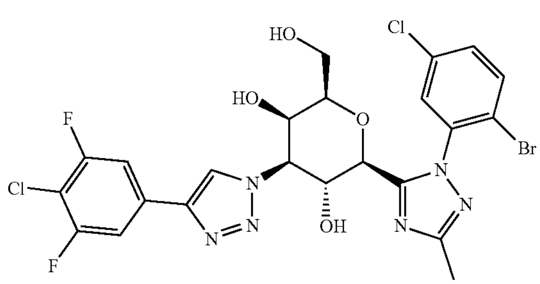 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2Br)n1] | A | MS (ESI) m/z: 631.0; ¹H NMR (500 MHz, methanol-d$_4$) δ 8.61 (s, 1H), 7.86 (d, J = 8.8 Hz, 1H), 7.76-7.63 (m, 3H), 7.59 (dd, J = 8.8, 2.5 Hz, 1H), 4.93-4.87 (m, 2H), 4.38 (br d, J = 8.3 Hz, 1H), 4.13 (d, J = 1.7 Hz, 1H), 3.78 (br d, J = 5.8 Hz, 1H), 3.74-3.66 (m, 2H), 2.48 (s, 3H) | 0.022 |

-continued

| Ex. # | Structure | Method | LCMS (M + 1)+/1H NMR | hGal IC50 (μM) |
|---|---|---|---|---|
| A14 | 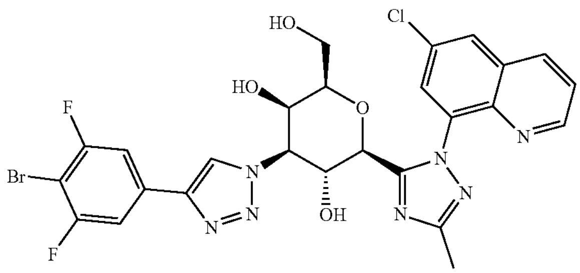 [SMILES: Cc1nc([C@@H]2O[C@H](CO)[C@H](O)[C@H](n3cc(-c4cc(F)c(Br)c(F)c4)nn3)[C@H]2O)n(-c2cc(Cl)cc3cccnc23)n1] | A | MS (ESI) m/z: 648.0; 1H NMR (500 MHz, methanol-d4) δ 8.94 (dd, J = 4.3, 1.5 Hz, 1H), 8.57 (s, 1H), 8.49 (dd, J = 8.5, 1.7 Hz, 1H), 8.30 (d, J = 2.5 Hz, 1H), 8.03 (s, 1H), 7.71 (dd, J = 8.5, 4.1 Hz, 1H), 7.65-7.59 (m, 2H), 4.77 (br s, 2H), 4.40 (br d, J = 8.3 Hz, 1H), 4.04 (s, 1H), 3.59 (br s, 3H), 2.53 (s, 3H) | 0.024 |
| A15 | 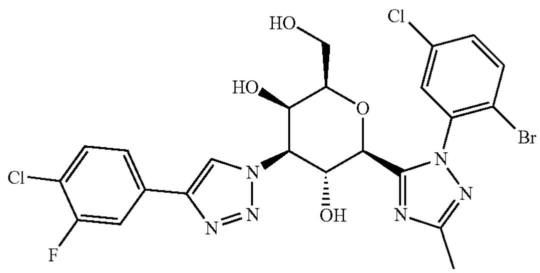 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2Br)n1] | A | MS (ESI) m/z: 613.0; 1H NMR (400 MHz, methanol-d4) δ 8.42 (s, 1H), 7.65 (dd, J = 10.3, 2.0 Hz, 1H), 7.57 (dt, J = 8.4, 1.0 Hz, 2H), 7.49-7.42 (m, 2H), 4.79-4.74 (m, 2H), 4.26 (br d, J = 8.6 Hz, 1H), 4.01 (d, J = 1.3 Hz, 1H), 3.69-3.63 (m, 1H), 3.61-3.53 (m, 2H), 2.36 (s, 3H) | 0.040 |
| A16 | 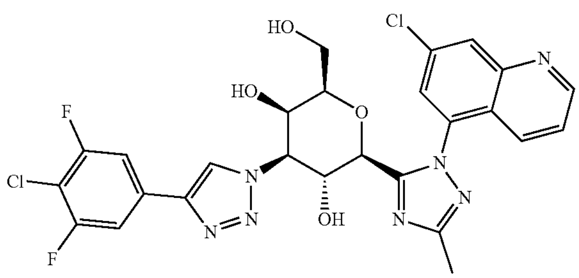 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)cc3ncccc23)n1] | A | MS (ESI) m/z: 604.1; 1H NMR (400 MHz, methanol-d4) δ 9.01 (dd, J = 4.3, 1.7 Hz, 1H), 8.57 (s, 1H), 8.32 (dd, J = 2.0, 0.7 Hz, 1H), 8.03-7.97 (m, 2H), 7.68-7.59 (m, 3H), 4.91-4.79 (m, 2H), 4.41 (d, J = 8.8 Hz, 1H), 4.08 (d, J = 2.2 Hz, 1H), 3.75-3.60 (m, 3H), 2.54 (s, 3H) | 0.051 |
| A17 | 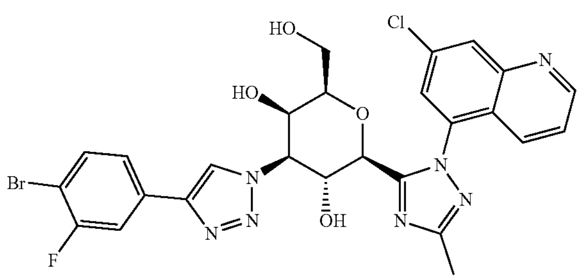 [SMILES: Cc1nc([C@@H]2O[C@H](CO)[C@H](O)[C@H](n3cc(-c4ccc(Br)c(F)c4)nn3)[C@H]2O)n(-c2cc(Cl)cc3ncccc23)n1] | A | MS (ESI) m/z: 630.1; 1H NMR (500 MHz, methanol-d4) δ 9.02 (dd, J = 4.1, 1.7 Hz, 1H), 8.51 (s, 1H), 8.33 (d, J = 1.9 Hz, 1H), 8.03-7.99 (m, 2H), 7.76-7.68 (m, 2H), 7.65-7.59 (m, 2H), 4.89 (br d, J = 5.0 Hz, 1H), 4.84-4.79 (m, 1H), 4.41 (d, J = 9.1 Hz, 1H), 4.08 (d, J = 2.2 Hz, 1H), 3.74-3.60 (m, 3H), 2.55 (s, 3H) | 0.082 |
| A18 | 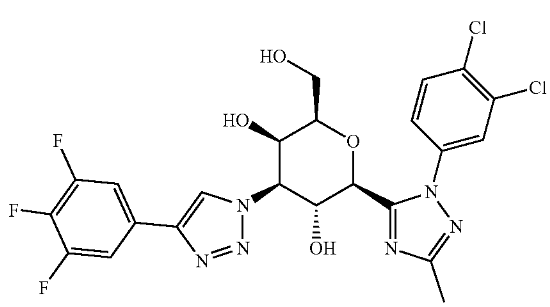 [SMILES: Cc1nc([C@@H]2O[C@H](CO)[C@H](O)[C@H](n3cc(-c4cc(F)c(F)c(F)c4)nn3)[C@H]2O)n(-c2ccc(Cl)c(Cl)c2)n1] | B | MS (ESI) m/z: 571.2; 1H NMR (500 MHz, METHANOL-d4) δ 8.59 (s, 1H), 7.96 (d, J = 2.5 Hz, 1H), 7.81-7.76 (m, 1H), 7.73-7.65 (m, 3H), 4.99-4.95 (m, 2H), 4.61-4.56 (m, 1H), 4.17 (s, 1H), 3.97-3.91 (m, 1H), 3.86-3.80 (m, 1H), 3.78-3.71 (m, 1H), 2.47 (s, 3H) | 0.09 |

-continued

| Ex. # | Structure | Method | LCMS (M + 1)⁺/¹H NMR | hGal IC50 (μM) |
|---|---|---|---|---|
| A19 | 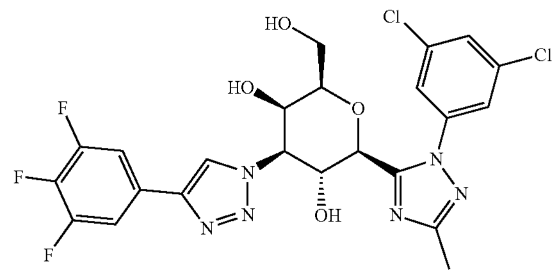 [SMILES: Cc1nc([C@@H]2O[C@H](CO)[C@H](O)[C@H](n3cc(-c4cc(F)c(F)c(F)c4)nn3)[C@H]2O)n(-c2cc(Cl)cc(Cl)c2)n1] | B | MS (ESI) m/z: 571.1; ¹H NMR (500 MHz, METHANOL-d₄) δ 8.59 (s, 1H), 7.79 (d, J = 1.9 Hz, 2H), 7.71-7.64 (m, 3H), 4.99-4.96 (m, 2H), 4.63-4.58 (m, 1H), 4.18 (d, J = 1.1 Hz, 1H), 3.96 (ddd, J = 7.1, 4.7, 0.8 Hz, 1H), 3.87-3.81 (m, 1H), 3.78-3.72 (m, 1H), 2.47 (s, 3H) | 0.068 |
| A20 | 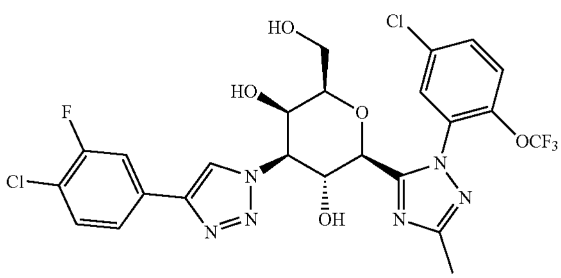 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2OC(F)(F)F)n1] | A | MS (ESI) m/z: 619.0; ¹H NMR (400 MHz, methanol-d₄) δ 8.55 (s, 1H), 7.88-7.73 (m, 3H), 7.69 (ddd, J = 8.4, 1.9, 0.8 Hz, 1H), 7.63 (dq, J = 9.0, 1.5 Hz, 1H), 7.60-7.52 (m, 1H), 4.91 (dd, J = 10.8, 2.8 Hz, 1H), 4.88-4.80 (m, 1H), 4.43 (d, J = 8.9 Hz, 1H), 4.16 (dd, J = 2.6, 1.0 Hz, 1H), 3.81 (ddd, J = 6.6, 5.6, 1.1 Hz, 1H), 3.70 (d, J = 6.0 Hz, 2H), 2.47 (s, 3H). | 0.031 |
| A21 | 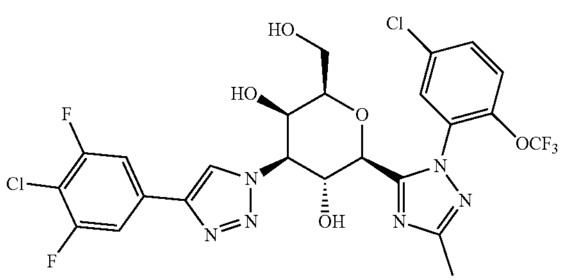 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2OC(F)(F)F)n1] | A | MS (ESI) m/z: 619.0; ¹H NMR (400 MHz, methanol-d₄) δ 8.62 (s, 1H), 7.81 (d, J = 2.6 Hz, 1H), 7.76 (dd, J = 8.9, 2.6 Hz, 1H), 7.73-7.59 (m, 3H), 4.99-4.88 (m, 1H), 4.88-4.79(m, 1H), 4.43 (d, J = 8.9 Hz, 1H), 4.15 (dd, J = 2.8, 1.0 Hz, 1H), 3.81 (ddd, J = 6.8, 5.7, 1.2 Hz, 1H), 3.70 (d, J = 6.1 Hz, 2H), 2.47 (s, 3H). | 0.030 |
| A22 | 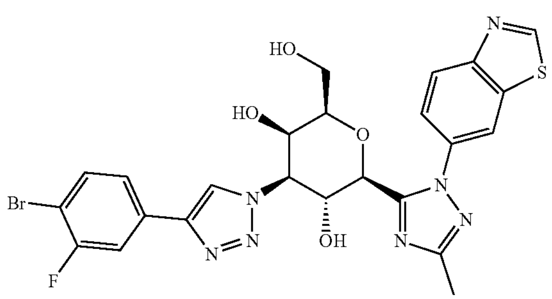 | A | MS (ESI) m/z: 601.9; ¹H NMR (400 MHz, methanol-d₄) δ 8.31 (s, 1H), 8.46 (s, 1H), 8.43 (d, J = 2.1 Hz, 1H), 8.17 (d, J = 8.7 Hz, 1H), 7.77 (dd, J = 8.7, 2.1Hz, 1H), 7.66-7.57 (m, 2H), 7.51 (dd, J = 8.3, 1.9 Hz, 1H), 4.88 (dd, J = 10.8, 9.0 Hz, 1H), 4.81 (dd, J = 10.8, 2.8 Hz, 1H), 4.47 (d, J = 9.0 Hz, 1H), 4.03 (dd, J = 2.8, 0.9 Hz, 1H), 3.82-3.76 (m, 1H), 3.73 (dd, J = 11.3, 7.4 Hz, 1H), 3.62 (dd, J = 11.3, 3.9 Hz, 1H), 2.38 (s, 3H) | 0.022 |
| A23 | 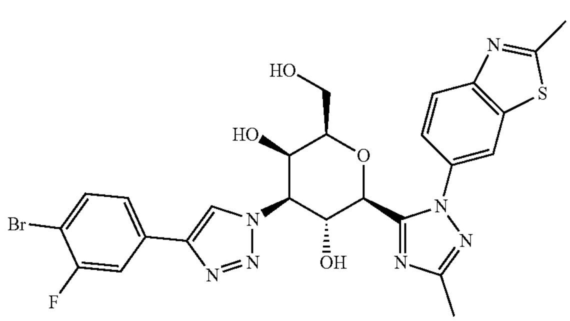 | A | MS (ESI) m/z: 591.8; ¹H NMR (400 MHz, methanol-d₄) δ 8.45 (s, 1H), 8.25 (d, J = 2.1 Hz, 1H), 7.96 (d, J = 8.7 Hz, 1H), 7.68 (dd, J = 8.6, 2.2 Hz, 1H), 7.65-7.55 (m, 2H), 7.51 (dd, J = 8.3, 1.9 Hz, 1H), 4.87 (dd, J = 10.8, 8.9 Hz, 1H), 4.81 (dd, J = 10.8, 2.8 Hz, 1H), 4.46 (d, J = 8.9 Hz, 1H), 4.03 (dd, J = 2.8, 0.9 Hz, 1H), 3.81-3.75 (m, 1H), 3.73 (dd, J = 11.3, 7.3 Hz, 1H), 3.62 (dd, J = 11.3, 3.9 Hz, 1H), 2.79 (s, 3H), 2.37 (s, 3H) | 0.046 |

| Ex. # | Structure | Method | LCMS (M + 1)+/1H NMR | hGal IC50 (μM) |
|---|---|---|---|---|
| A24 | 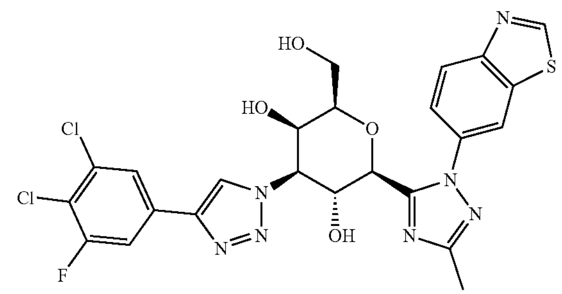 [SMILES: Cc1nc([C@@H]2O[C@H](CO)[C@H](O)[C@H](n3cc(-c4cc(F)c(Cl)c(Cl)c4)nn3)[C@H]2O)n(-c2ccc3ncsc3c2)n1] | A | MS (ESI) m/z: 591.8; 1H NMR (400 MHz, methanol-d4) δ 9.30 (s, 1H), 8.53 (s, 1H), 8.42 (d, J = 2.1 Hz, 1H), 8.16 (d, J = 8.7 Hz, 1H), 7.82 (t, J = 1.7 Hz, 1H), 7.76 (dd, J = 8.7, 2.2 Hz, 1H), 7.65 (dd, J = 9.7, 1.9 Hz, 1H), 4.88 (dd, J = 10.8, 8.8 Hz, 1H), 4.82 (dd, J = 10.7, 2.8 Hz, 1H), 4.47 (d, J = 8.9 Hz, 1H), 4.03 (dd, J = 2.7, 1.0 Hz, 1H), 3.79 (ddd, J = 7.3, 3.9, 1.1 Hz, 1H), 3.73 (dd, J = 11.3, 7.4 Hz, 1H), 3.63 (dd, 11.4, 3.9 Hz, 1H), 2.38 (s, 3H) | 0.034 |
| A25 | 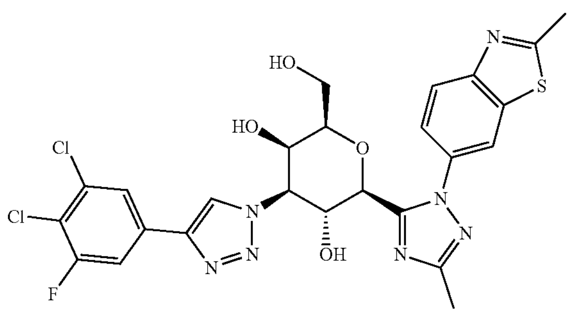 [SMILES: Cc1nc([C@@H]2O[C@H](CO)[C@H](O)[C@H](n3cc(-c4cc(F)c(Cl)c(Cl)c4)nn3)[C@H]2O)n(-c2ccc3nc(C)sc3c2)n1] | A | MS (ESI) m/z: 605.9; 1H NMR (400 MHz, methanol-d4) δ 8.64 (s, 1H), 8.37 (d, J = 2.1 Hz, 1H), 8.09 (d, J = 8.7 Hz, 1H), 7.94 (t, J = 1.7 Hz, 1H), 7.80 (dd, J = 8.6, 2.2 Hz, 1H), 7.77 (dd, J = 9.7, 1.9 Hz, 1H), 4.99 (dd, J = 10.7, 8.6 Hz, 1H), 4.94 (dd, J = 10.7, 2.7 Hz, 1H), 4.58 (d, J = 8.6 Hz, 1H), 4.15 (dd, J = 2.6, 1.1 Hz, 1H), 3.90 (ddd, J = 7.3, 3.9, 1.0 Hz, 1H), 3.84 (dd, J = 11.3, 7.3 Hz, 1H), 3.74 (dd, J = 11.2, 3.9 Hz, 1H), 2.91 (s, 3H), 2.49 (s, 3H) | 0.045 |
| A26 | 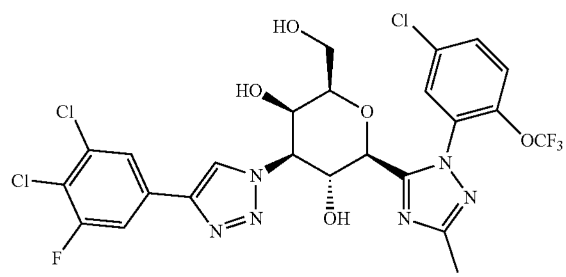 | A | MS (ESI) m/z: 652.8; 1H NMR (400 MHz, methanol-d4) δ 8.51 (s, 1H), 7.82 (t, J = 1.7 Hz, 1H), 7.68 (d, J = 2.6 Hz, 1H), 7.65 (dd, J = 3.7, 2.3 Hz, 1H), 7.63 (t, J = 2.6 Hz, 1H), 7.51 (dq, J = 8.9, 1.5 Hz, 1H), 4.80 (dd, J = 10.8, 2.8 Hz, 1H), 4.67-4.76 (m, 1H), 4.31 (d, J = 9.0 Hz, 1H), 4.04 (dd, J = 2.8, 1.0 Hz, 1H), 3.69 (td, J = 6.1, 1.1 Hz, 1H), 3.58 (d, J = 6.0 Hz, 2H), 2.35 (s, 3H) | 0.036 |
| A27 | 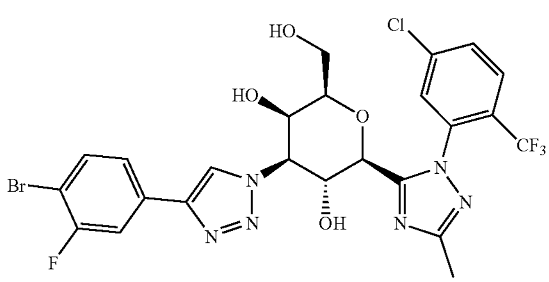 | A | MS (ESI) m/z: 646.9; 1H NMR (400 MHz, methanol-d4) δ 8.56 (s, 1H), 7.98 (d, J = 8.6 Hz, 1H), 7.88 (ddd, J = 8.5, 2.0, 0.9 Hz, 1H), 7.82-7.68 (m, 3H), 7.63 (dd, J = 8.3, 1.9 Hz, 1H), 4.76-4.94 (m, 2H), 4.37 (d, J = 9.1Hz, 1H), 4.13 (q, J = 1.1 Hz, 1H), 3.75-3.72 (m, 1H), 3.71-3.64 (m, 2H), 2.47 (s, 3H) | 0.034 |
| A28 | 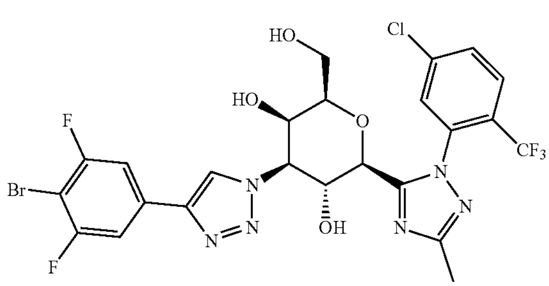 | A | MS (ESI) m/z: 665.0; 1H NMR (400 MHz, methanol-d4) δ 8.63 (s, 1H), 7.98 (d, J = 8.6 Hz, 1H), 7.88 (ddd, J = 8.5, 2.1, 1.0 Hz, 1H), 7.78 (s, 1H), 7.69-7.55 (m, 2H), 4.85 (s, 39H), 4.37 (d, J = 8.7 Hz, 1H), 4.17-4.08 (m, 1H), 3.79-3.71 (m, 1H), 3.71-3.61 (m, 2H), 2.47 (s, 3H) | 0.040 |

| Ex. # | Structure | Method | LCMS (M + 1)+/1H NMR | hGal IC50 (μM) |
|---|---|---|---|---|
| A29 | 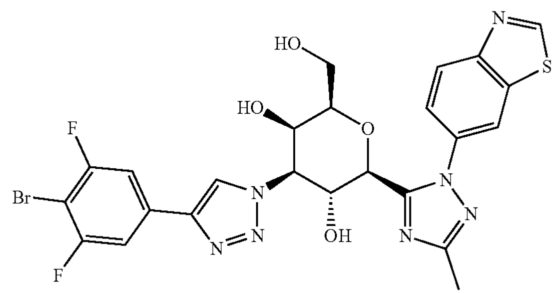 | A | MS (ESI) m/z: 620.1; 1H NMR (400 MHz, methanol-d4) δ 9.30 (s, 1H), 8.53 (s, 1H), 8.42 (d, J = 2.0 Hz, 1H), 8.16 (d, J = 8.7 Hz, 1H), 7.76 (dd, J = 8.8, 2.2 Hz, 1H), 7.57 -7.42 (m, 2H), 4.88 (dd, J = 10.8, 8.9 Hz, 1H), 4.82 (dd, J = 10.7, 2.8 Hz, 1H), 4.47 (d, J = 8.8 Hz, 1H), 4.03 (dd, J = 2.7,1.0 Hz, 1H), 3.79 (ddd, J = 7.3, 3.9, 1.0 Hz, 1H), 3.73 (dd, J = 11.3, 7.4 Hz, 1H), 3.63 (dd, J = 11.3, 3.9 Hz, 1H), 2.38 (s, 3H) | 0.027 |
| A30 | 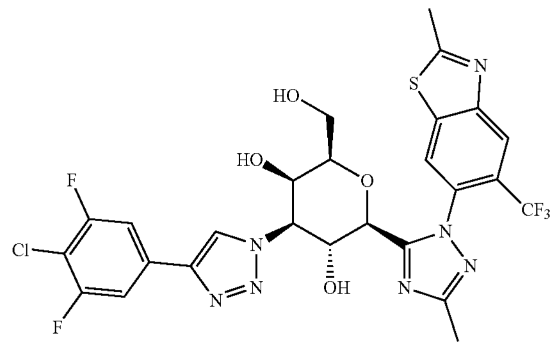 [SMILES: Cc1nc([C@@H]2O[C@H](CO)[C@H](O)[C@H](n3cc(-c4cc(F)c(Cl)c(F)c4)nn3)[C@H]2O)n(-c2cc3sc(C)nc3cc2C(F)(F)F)n1] | A | MS (ESI) m/z: 658.2; 1H NMR (500 MHz, methanol-d4) δ 8.62 (s, 1H), 8.43 (s, 1H), 8.41-8.22 (bs, 1H), 7.76-7.56 (m, 2H), 4.91-4.76 (m, 2H), 4.33 (bs, 1H), 4.08 (s, 1H), 3.80-3.54 (m, 3H), 2.96 (s, 3H), 2.49 (s, 3H) | 0.017 |
| A31 | 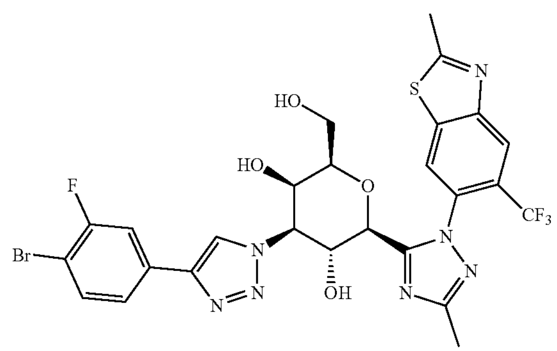 [SMILES: Cc1nc([C@@H]2O[C@H](CO)[C@H](O)[C@H](n3cc(-c4ccc(Br)c(F)c4)nn3)[C@H]2O)n(-c2cc3sc(C)nc3cc2C(F)(F)F)n1] | A | MS (ESI) m/z: 684.0; 1H NMR (400 MHz, methanol-d4) δ 8.45 (s, 1H), 8.31 (s, 1H), 8.20 (s, 1H), 7.65-7.55 (m, 2H), 7.51 (dd, J = 8.3, 1.9 Hz, 1H), 4.91-4.62 (m, 2H), 4.22 (s, 1H), 3.97 (d, J = 2.3 Hz, 1H), 3.57 (d, J = 13.4 Hz, 3H), 2.84 (s, 3H), 2.37 (s, 3H) | 0.022 |
| A32 | 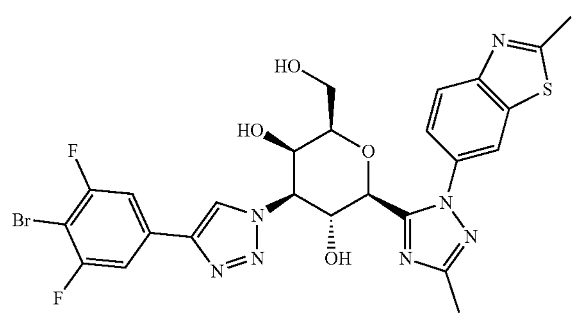 [SMILES: Cc1nc([C@@H]2O[C@H](CO)[C@H](O)[C@H](n3cc(-c4cc(F)c(Br)c(F)c4)nn3)[C@H]2O)n(-c2ccc3nc(C)sc3c2)n1] | A | MS (ESI) m/z: 634.0; 1H NMR (400 MHz, methanol-d4) δ 8.64 (s, 1H), 8.37 (d, J = 2.2 Hz, 1H), 8.08 (d, J = 8.7 Hz,1H), 7.80 (dd, J = 8.7, 2.1 Hz, 1H), 7.70-7.52 (m, 2H), 4.99 (dd, J = 10.8, 8.6 Hz, 1H), 4.94 (dd, J = 10.6, 2.7 Hz, 1H), 4.58 (d, J = 8.6 Hz, 1H), 4.15 (dd, J = 2.7, 0.9 Hz, 1H), 3.90 (ddd, J = 7.4, 4.0, 1.0 Hz, 1H), 3.84 (dd, J = 11.3, 7.3 Hz,1H), 3.74 (dd, J = 11.3, 3.9 Hz, 1H), 2.91 (s, 3H), 2.49 (s, 3H) | 0.041 |

-continued

| Ex. # | Structure | Method | LCMS (M + 1)+/1H NMR | hGal IC50 (μM) |
|---|---|---|---|---|
| A33 | 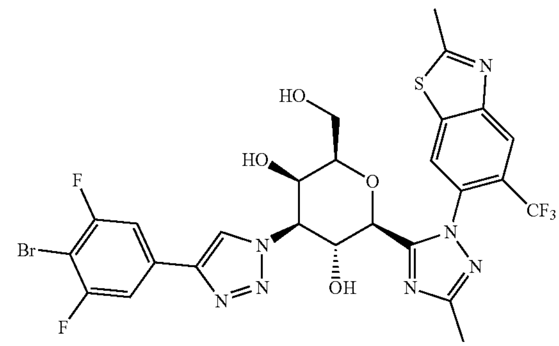 | A | MS (ESI) m/z: 702.1; 1H NMR (400 MHz, methanol-$d_4$) δ 8.51(s, 1H), 8.30 (d, J = 2.2 Hz, 1H), 8.20 (bs, 1H), 7.64 - 7.30 (m, 2H), 4.95-4.56 (m, 2H), 4.22 (bs, 1H), 3.97 (s, 1H), 3.65-3.45 (m, 3H), 2.83 (s, 3H), 2.37 (s, 3H) | 0.103 |
| A34 | 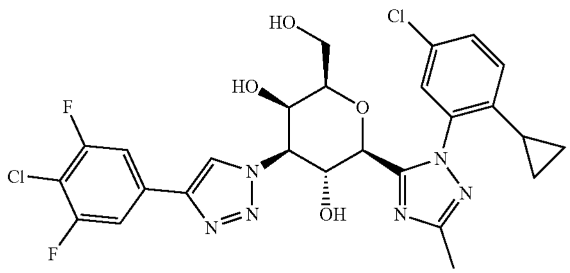 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2C2CC2)n1] | A | MS (ESI) m/z: 593.2; 1H NMR (400 MHz, methanol-$d_4$) δ 8.50 (s, 1H), 7.62-7.50 (m, 2H), 7.41 (dd, J = 8.5, 2.2 Hz, 1H), 7.34 (bs, 1H), 7.03 (d, J = 8.5 Hz, 1H), 4.84-4.63 (m, 2H), 4.24 (d, J = 8.1 Hz, 1H), 4.10-3.93 (m, 1H), 3.70-3.53 (m, 3H), 2.36 (s, 3H), 1.47 (td, J = 8.5, 4.3 Hz, 1H), 0.93-0.45 (m, 4H) | 0.046 |
| A35 | 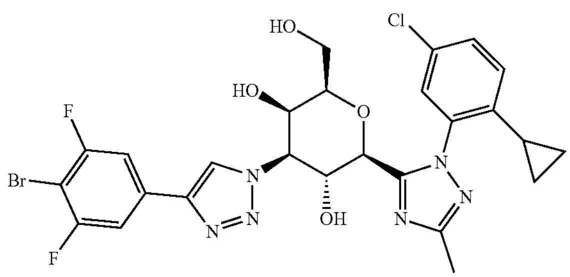 | A | MS (ESI) m/z: 637.1; 1H NMR (400 MHz, methanol-$d_4$) δ 8.63 (s, 1H), 7.68-7.60 (m, 2H), 7.53 (dd, J = 8.5, 2.2 Hz, 1H), 7.46 (bs, 1H), 7.15 (d, J = 8.5 Hz, 1H), 4.93-4.74 (m, 2H), 4.43-4.25 (m, 1H), 4.13 (q, J = 1.0 Hz, 1H), 3.91-3.55 (m, 3H), 2.48 (s, 3H), 1.59 (td, J = 8.5, 4.3 Hz, 1H), 1.12-0.56 (m, 4H). | 0.151 |
| A36 | 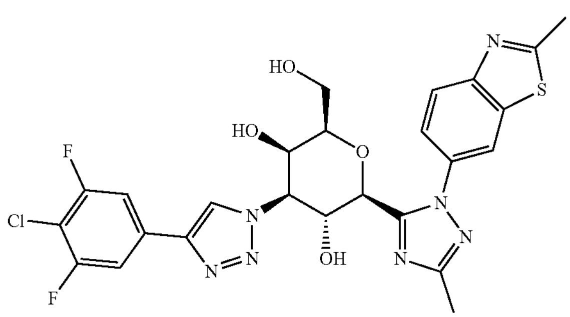 [SMILES: Cc1nc([C@@H]2O[C@H](CO)[C@H](O)[C@H](n3cc(-c4cc(F)c(Cl)c(F)c4)nn3)[C@H]2O)n(-c2ccc3nc(C)sc3c2)n1] | A | MS (ESI) m/z: 590.2; 1H NMR (400 MHz, methanol-$d_4$) δ 8.63 (s, 1H), 8.37 (d, J = 2.0 Hz, 1H), 8.09 (d, J = 8.7 Hz, 1H), 7.80 (dd, 8.7, 2.1 Hz, 1H), 7.73-7.60 (m, 2H), 4.99 (dd, J = 10.8, 8.7 Hz, 1H), 4.94 (dd, J = 10.7, 2.7 Hz, 1H), 4.58 (d, J = 8.6 Hz, 1H), 4.14 (dd, J = 2.7, 1.0 Hz, 1H), 3.90 (ddd, J = 7.4, 3.9, 1.0 Hz, 1H), 3.84 (dd, J = 11.2, 7.3 Hz, 1H), 3.74 (dd, J = 11.2, 3.9 Hz, 1H), 2.91 (s, 3H), 2.49 (s, 3H) | 0.053 |
| A37 | 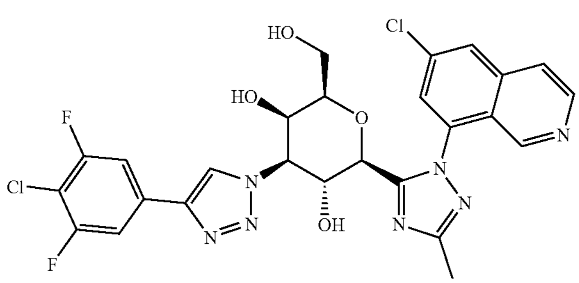 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)cc3ccncc23)n1] | A | MS (ESI) m/z: 604.3; 1H NMR (400 MHz, methanol-$d_4$) δ 8.78 (s, 1H), 8.51 (d, J = 5.9 Hz, 1H), 8.46 (s, 1H), 8.19 (d, J = 2.2 Hz, 1H), 7.92 (d, J = 2.0 Hz, 1H), 7.85 (dd, J = 5.8, 1.0 Hz, 1H), 7.60-7.47 (m, 2H), 4.82-4.66 (m, 2H), 4.36 (d, J = 8.7 Hz, 1H), 3.97 (dd, J = 2.7, 1.0 Hz, 1H), 3.66-3.47 (m, 3H), 2.44 (s, 3H) | 0.051 |

| Ex. # | Structure | Method | LCMS (M + 1)+/1H NMR | hGal IC50 (μM) |
|---|---|---|---|---|
| A38 | 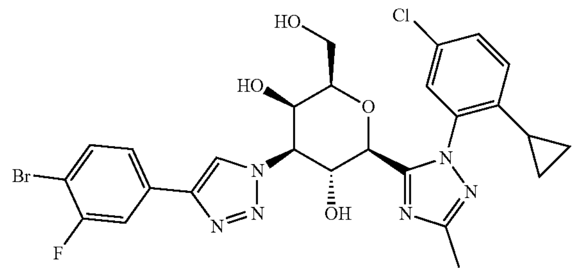 | A | MS (ESI) m/z: 619.2; 1H NMR (400 MHz, methanol-d4) δ 8.44 (s, 1H), 7.67-7.55 (m, 2H), 7.51 (dd, J = 8.3, 1.9 Hz, 1H), 7.41 (dd, J = 8.5, 2.2 Hz, 1H), 7.34 (bs, 1H), 7.03 (d, J = 8.5 Hz, 1H), 4.82-4.61 (m, 2H), 4.25 (d, J = 7.9 Hz, 1H), 4.01 (d, J = 1.6 Hz, 1H), 3.79-3.37 (m, 3H), 2.36 (s, 3H), 1.48 (ddd, J = 13.6, 8.6, 5.2 Hz, 1H), 0.96-0.39 (m, 4H) | 0.072 |
| A39 | 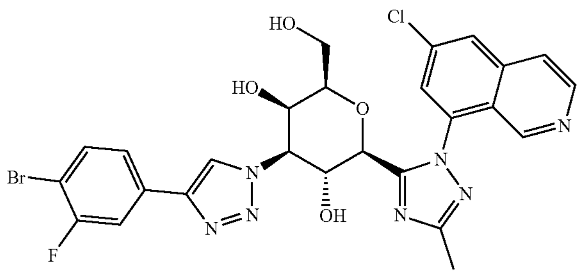 [SMILES: Cc1nc([C@@H]2O[C@H](CO)[C@H](O)[C@H](n3cc(-c4ccc(Br)c(F)c4)nn3)[C@H]2O)n(-c2cc(Cl)cc3ccncc23)n1] | A | MS (ESI) m/z: 630.2; 1H NMR (400 MHz, methanol-d4) δ 8.78 (d, J = 1.0 Hz, 1H), 8.51 (d, J = 5.9 Hz, 1H), 8.39 (s, 1H), 8.26-8.14 (m, 1H), 7.92 (d, J = 1.9 Hz, 1H), 7.85 (dd, J = 5.9, 1.0 Hz, 1H), 7.64-7.56 (m, 2H), 7.49 (dd, J = 8.3, 1.9 Hz, 1H), 4.83-4.64 (m, 2H), 4.36 (d, J = 8.9 Hz, 1H), 3.97 (dd, J = 2.8, 1.0 Hz, 1H), 3.77-3.46 (m, 3H), 2.44 (s, 3H). | 0.161 |
| A40 | 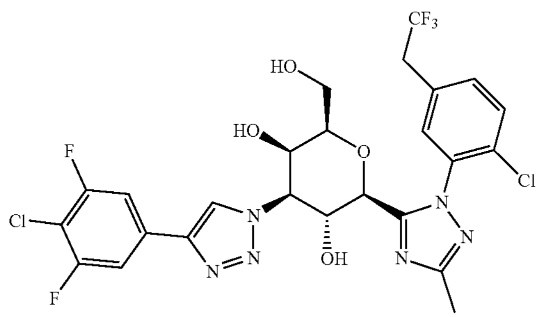 [SMILES: Cc1nc([C@@H]2O[C@H](CO)[C@H](O)[C@H](n3cc(-c4cc(F)c(Cl)c(F)c4)nn3)[C@H]2O)n(-c2cc(CC(F)(F)F)ccc2Cl)n1] | A | MS (ESI) m/z: 635.2; 1H NMR (400 MHz, methanol-d4) δ 8.61 (s, 1H), 7.78-7.52 (m, 5H), 4.93-4.73 (m, 2H), 4.34 (d, J = 6.9 Hz, 1H), 4.12 (d, J = 1.6 Hz, 1H), 3.82-3.57 (m, 5H), 2.48 (s, 3H) | 0.126 |
| A41 | 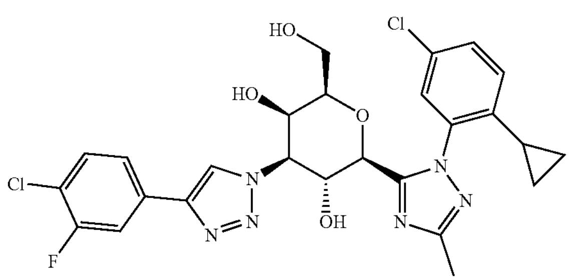 [SMILES: Cc1nc([C@@H]2O[C@H](CO)[C@H](O)[C@H](n3cc(-c4ccc(Cl)c(F)c4)nn3)[C@H]2O)n(-c2cc(Cl)ccc2C2CC2)n1] | A | MS (ESI) m/z: 575.2; 1H NMR (400 MHz, methanol-d4) δ 8.43 (s, 1H), 7.64 (dd, J = 10.4, 1.9 Hz, 1H), 7.56 (ddd, J =8.3, 1.9, 0.8 Hz, 1H), 7.50-7.43 (m, 1H), 7.43-7.36 (m, 1H), 7.37-7.25 (m, 1H), 7.02 (d, J = 8.5 Hz, 1H), 4.91-4.62 (m, 2H), 4.33-4.11 (m, 1H), 4.02 (q, J = 1.0 Hz, 1H), 3.79-3.36 (m, 3H), 2.36 (s, 3H), 1.47 (td, J = 8.5, 4.4 Hz, 1H), 0.96-0.38 (m, 4H). | 0.059 |
| A42 | 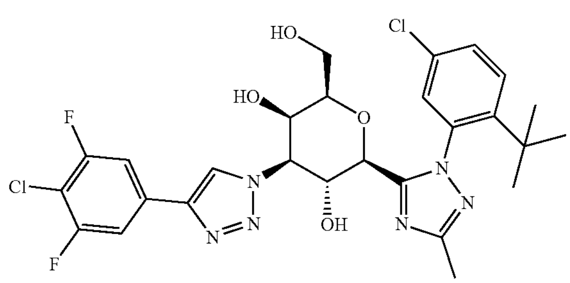 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2C(C)(C)C)n1] | A | MS (ESI) m/z: 609.3; 1H NMR (400 MHz, methanol-d4) δ 8.64 (s, 0.4H), 8.63 (s, 0.6H), 7.78-7.72 (m, 1H), 7.73-7.62 (m, 2H), 7.60-7.54 (m, 1H), 7.41 (d, J = 2.4 Hz, 0.4H), 7.20 (d, J = 2.4 Hz, 0.6H), 5.13-4.74 (m, 2H), 4.35 (d, J = 9.0 Hz, 0.6H) ,4.25 (d, J = 9.3 Hz, 0.4H), 4.13 (t, J = 2.6 Hz, 1H), 3.90-3.57 (m, 3H), 2.48 (s, 1.8H), 2.46 (s, 1.2H), 1.23 (s, 5.4H), 1.21 (s, 3.6H) | 0.011 |

-continued

| Ex. # | Structure | Method | LCMS (M + 1)+/1H NMR | hGal IC50 (μM) |
|---|---|---|---|---|
| A43 | 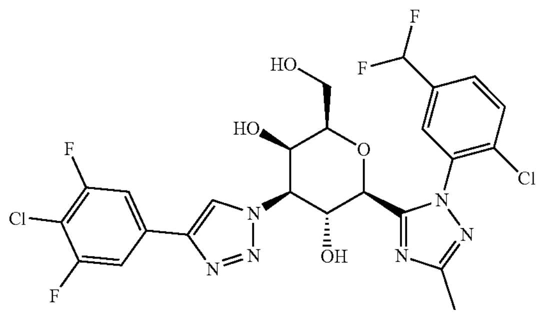 [SMILES: Cc1nc([C@@H]2O[C@H](CO)[C@H](O)[C@H](n3cc(-c4cc(F)c(Cl)c(F)c4)nn3)[C@H]2O)n(-c2cc(C(F)F)ccc2Cl)n1] | A | MS (ESI) m/z: 603.2; 1H NMR (400 MHz, methanol-d4) δ 8.59 (s, 1H), 7.91-7.75 (m, 3H), 7.73-7.60 (m, 2H), 6.91 (t, J = 55.7 Hz, 1H), 4.94-4.74 (m, 2H), 4.38 (d, J = 8.8 Hz, 1H), 4.12 (dd, J = 2.4, 1.1 Hz, 1H), 3.86-3.55 (m, 3H), 2.48 (s, 3H) | 0.05 |
| A44 | 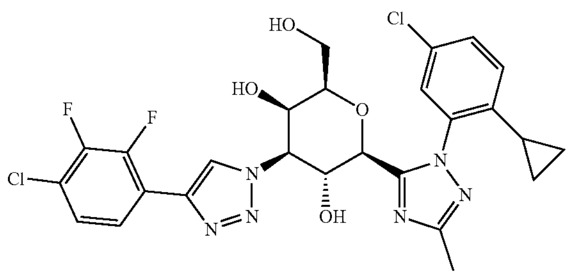 [SMILES: Cc1nc([C@@H]2O[C@H](CO)[C@H](O)[C@H](n3cc(-c4ccc(Cl)c(F)c4F)nn3)[C@H]2O)n(-c2cc(Cl)ccc2C2CC2)n1] | A | MS (ESI) m/z: 593.2; 1H NMR (400 MHz, methanol-d4) δ 8.36 (d, J = 3.3 Hz, 1H), 7.86-7.75 (m, 1H), 7.41 (dd, J = 8.5, 2.2 Hz, 1H), 7.38-7.26 (m, 2H), 7.02 (d, J = 8.6 Hz, 1H), 4.80 (dd, J = 10.6, 2.9 Hz, 1H), 4.77-4.67 m, 1H), 4.26 (d, J = 8.8 Hz, 1H), 4.02 (dd, J = 2.4, 0.9 Hz, 1H), 3.78-3.38 (m, 3H), 2.36 (s, 3H), 1.47 (ddd, J = 13.7, 8.6, 5.2 Hz, 1H), 0.94-0.46 (m, 4H). | 0.14 |
| A45 | 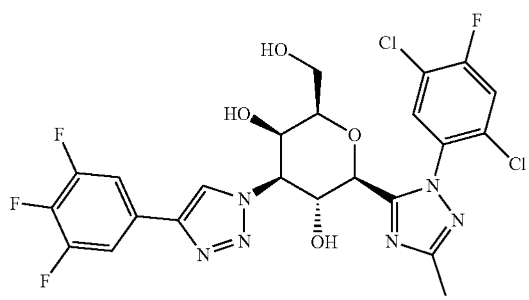 [SMILES: Cc1nc([C@@H]2O[C@H](CO)[C@H](O)[C@H](n3cc(-c4cc(F)c(F)c(F)c4)nn3)[C@H]2O)n(-c2cc(Cl)c(F)cc2Cl)n1] | A | MS (ESI) m/z: 588.9; 1H NMR (500 MHz, chloroform-d) δ 8.17 (s, 1H), 7.61 (br d, J = 6.88 Hz, 1H), 7.36-7.47 (m, 3H), 4.77-4.83 (m, 1H), 4.65 (dd, J = 2.34, 10.59 Hz, 1H), 4.55-4.62 (m, 2H), 4.38 (br s, 1H), 3.70 (br t, J = 4.81 Hz, 3H), 2.41 (s, 3H) | 0.039 |
| A46 | 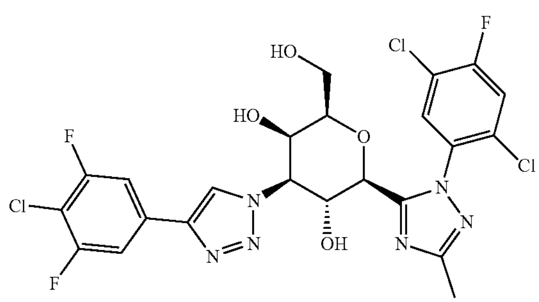 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)c(F)cc2Cl)n1] | A | MS (ESI) m/z: 605.3; 1H NMR (500 MHz, methanol-d4) δ 8.51 (s, 1H), 7.80 (d, J = 7.15 Hz, 1H), 7.66 (d, J = 8.80 Hz, 1H), 7.61 (d, J = 7.98 Hz, 2H), 4.83-4.89 (m, 1H), 4.78 (br s, 1H), 4.40 (d, J = 8.80 Hz. 1H), 4.14 (d, J = 2.48 Hz, 1H), 3.75 (t, J = 5.91 Hz. 1H), 3.63-3.71 (m, 2H), 2.39-2.46 (m, 3H) | 0.033 |
| A47 | 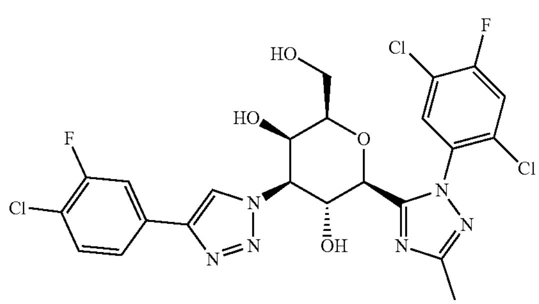 [SMILES: Cc1nc([C@@H]2O[C@H](CO)[C@H](O)[C@H](n3cc(-c4ccc(Cl)c(F)c4)nn3)[C@H]2O)n(-c2cc(Cl)c(F)cc2Cl)n1] | A | MS (ESI) m/z: 587.0; 1H NMR (500 MHz, methanol-d4) δ 8.44 (s, 1H), 7.79 (d, J = 7.15 Hz, 1H), 7.71 (dd, J = 1.79, 10.32 Hz, 1H), 7.62-7.68 (m, 2H), 7.50-7.55 (m, 1H), 4.82-4.87 (m, 1H), 4.79 (br d, J = 9.08 Hz, 1H), 4.40 (d, J = 8.80 Hz, 1H), 4.14 (d, J = 2.48 Hz, 1H), 3.74 (d, J = 5.78 Hz, 1H), 3.64-3.70 (m, 2H), 2.44 (s, 3H) | 0.054 |

-continued

| Ex. # | Structure | Method | LCMS (M + 1)+/1H NMR | hGal IC50 (μM) |
|---|---|---|---|---|
| A48 | 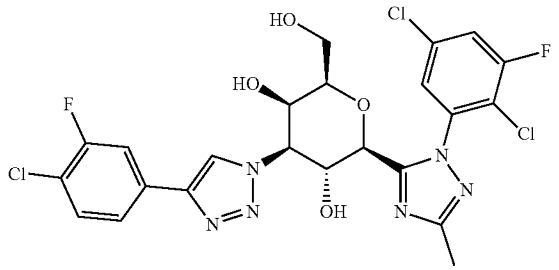 [SMILES: Cc1nc([C@@H]2O[C@H](CO)[C@H](O)[C@H](n3cc(-c4ccc(Cl)c(F)c4)nn3)[C@H]2O)n(-c2cc(Cl)cc(F)c2Cl)n1] | A | MS (ESI) m/z: 586.9; 1H NMR (500 MHz, methanol-d4) δ 8.54 (s, 1H), 7.77 (dd, J = 1.93, 10.45 Hz, 1H), 7.73 (dd, J = 2.48, 8.80 Hz, 1H), 7.69 (dd, J = 1.38, 8.25 Hz, 1H), 7.62 (br s, 1H), 7.55-7.59 (m, 1H), 4.87-4.92 (m, 2H), 4.45 (d, J = 9.08 Hz, 1H), 4.13 (d, J = 2.20 Hz, 1H), 3.77-3.85 (m, 1H), 3.69 (dd, J = 5.91, 8.94 Hz, 2H), 2.48 (s, 3H) | 0.047 |
| A49 | 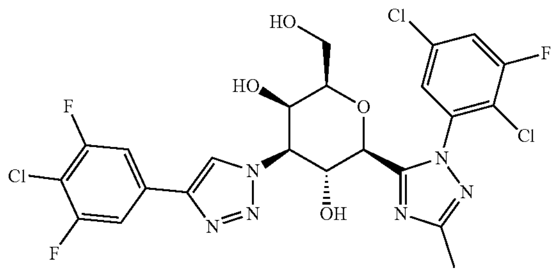 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)cc(F)c2Cl)n1] | A | MS (ESI) m/z: 605.0; 1H NMR (500 MHz, methanol-d4) δ 8.56-8.61 (m, 1H), 7.71 (dd, J = 2.20, 8.80 Hz, 1H), 7.65 (br d, J = 8.25 Hz, 2H), 7.60 (br s, 1H), 4.86-4.91 (m, 2H), 4.43 (br d, J = 9.08 Hz, 1H), 4.11 (br d, J = 1.93 Hz, 1H), 3.74-3.85 (m, 1H), 3.61-3.74 (m, 2H), 2.46 (s, 3H) | 0.046 |
| A50 | 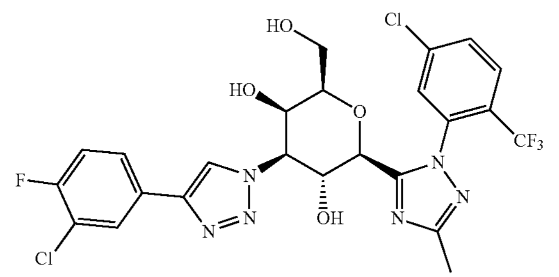 [SMILES: Cc1nc([C@@H]2O[C@H](CO)[C@H](O)[C@H](n3cc(-c4ccc(F)c(Cl)c4)nn3)[C@H]2O)n(-c2cc(Cl)ccc2C(F)(F)F)n1] | C | MS (ESI) m/z: 603.0; 1H NMR (500 MHz, methanol-d4) δ 8.50 (s, 1H), 7.99 (dd, J = 2.06, 7.02 Hz, 1H), 7.94-7.97 (m, 1H), 7.86 (br d, J = 8.53 Hz, 1H), 7.81 (ddd, J = 2.20, 4.61, 8.60 Hz, 1H), 7.77 (br s, 1H), 7.33 (t, J = 8.80 Hz, 1H), 4.85-4.88 (m, 2H), 4.35 (br d, J = 8.53 Hz, 1H), 4.11 (s, 1H), 3.71-3.75 (m, 1H), 3.64-3.69 (m, 2H), 2.45 (s, 3H) | 0.052 |
| A51 | 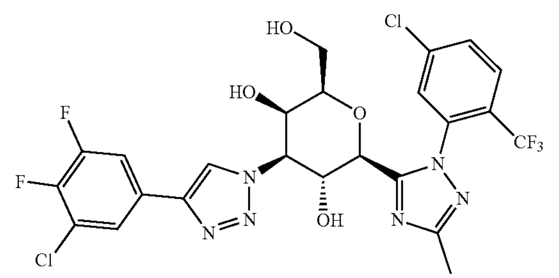 [SMILES: Cc1nc([C@@H]2O[C@H](CO)[C@H](O)[C@H](n3cc(-c4cc(F)c(F)c(Cl)c4)nn3)[C@H]2O)n(-c2cc(Cl)ccc2C(F)(F)F)n1] | C | MS (ESI) m/z: 621.0; 1H NMR (500 MHz, methanol-d4) δ 8.57 (s, 1H), 7.96 (d, J = 8.80 Hz, 1H), 7.85-7.88 (m, 1H), 7.84 (t, J = 1.82, 5.98 Hz, 1H), 7.75-7.80 (m, 2H), 4.86 (br s, 2H), 4.35 (br d, J = 8.80 Hz, 1H), 4.11 (d, J = 1.10 Hz, 1H), 3.73 (s, 1H), 3.62-3.70 (m, 2H), 2.45 (s, 3H) | 0.021 |
| A52 | 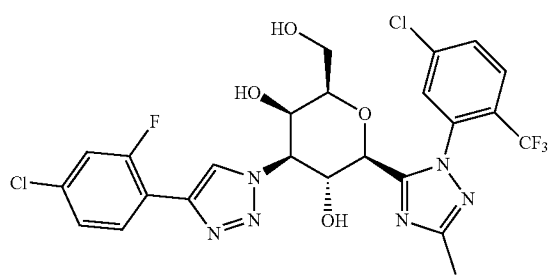 | C | MS (ESI) m/z: 603.0; 1H NMR (500 MHz, methanol-d4) δ 8.41 (d, J = 3.58 Hz, 1H), 8.12 (t, J = 8.12 Hz, 1H), 7.95 (d, J = 8.53 Hz, 1H), 7.85 (dd, J = 1.24, 8.39 Hz, 1H), 7.76 (br s, 1H), 7.30-7.38 (m, 2H), 4.85-4.92 (m, 2H), 4.35 (br d, J = 8.80 Hz, 1H), 4.11 (d, J = 1.65 Hz, 1H), 3.72 (d, J = 6.05 Hz, 1H), 3.61-3.69 (m, 2H), 2.44 (s, 3H) | 0.052 |

| Ex. # | Structure | Method | LCMS (M + 1)+/1H NMR | hGal IC50 (μM) |
|---|---|---|---|---|
| A53 | 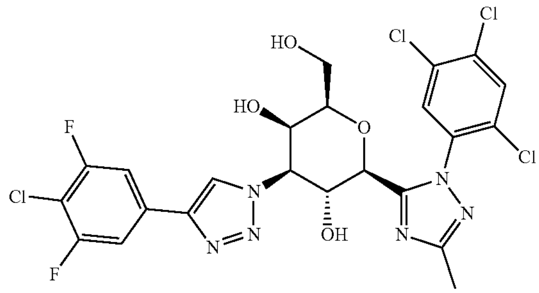 | A | MS (ESI) m/z: 622.8; 1H NMR (500 MHz, methanol-$d_4$) δ 8.58 (s, 1H), 7.96 (s, 1H), 7.87 (br s, 1H), 7.66 (s, 1H), 7.63-7.65 (m, 1H), 4.88 (br dd, J = 2.75, 10.73 Hz, 2H), 4.41 (br d, J = 9.08 Hz, 1H), 4.10 (d, J = 2.48 Hz, 1H), 3.76-3.81 (m, 1H), 3.63-3.73 (m, 2H), 2.45 (s, 3H) | 0.058 |
| A54 | 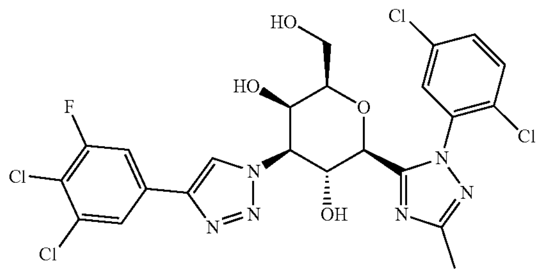 [SMILES: Cc1nc([C@@H]2O[C@H](CO)[C@H](O)[C@H](n3cc(-c4cc(F)c(Cl)c(Cl)c4)nn3)[C@H]2O)n(-c2cc(Cl)ccc2Cl)n1] | A | MS (ESI) m/z: 602.9; 1H NMR (400 MHz, methanol-$d_4$) δ 8.59 (s, 1H), 7.92 (t, J = 1.65 Hz, 1H), 7.75 (dd, J = 1.87, 9.79 Hz, 1H), 7.69 (s, 1H), 7.67 (s, 1H), 7.61-7.66 (m, 1H), 4.84-4.91 (m, 2H), 4.38 (d, J = 9.02 Hz, 1H), 4.11 (d, J = 1.98 Hz, 1H), 3.74-3.80 (m, 1H), 3.65-3.71 (m, 2H), 2.46 (s, 3H) | 0.048 |
| A55 | 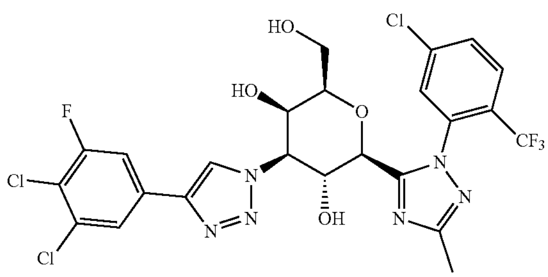 | A | MS (ESI) m/z: 636.9; 1H NMR (400 MHz, methanol-$d_4$) δ 8.62 (s, 1H), 7.92-7.99 (m, 2H), 7.84-7.89 (m, 1H), 7.76 (dd, J = 1.87, 9.79 Hz, 2H), 4.85-4.91 (m, 2H), 4.36 (br d, J = 8.58 Hz, 1H), 4.11 (s, 1H), 3.73 (q, J = 5.65 Hz, 1H), 3.64-3.69 (m, 2H), 2.45 (s, 3H) | 0.020 |
| A56 | 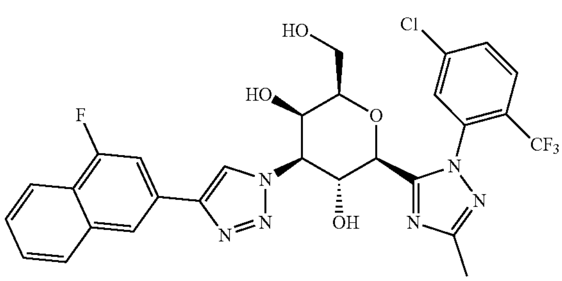 [SMILES: Cc1nc([C@@H]2O[C@H](CO)[C@H](O)[C@H](n3cc(-c4cc(F)c5ccccc5c4)nn3)[C@H]2O)n(-c2cc(Cl)ccc2C(F)(F)F)n1] | C | MS (ESI) m/z: 619.0; 1H NMR (400 MHz, methanol-$d_4$) δ 8.61 (s, 1H), 8.19 (s, 1H), 8.04-8.10 (m, 1H), 7.93-8.00 (m, 2H), 7.86 (dd, J = 1.32, 8.58 Hz, 1H), 7.77 (br s, 1H), 7.72 (dd, J = 1.32, 11.66 Hz, 1H), 7.59 (s, 2H), 4.88 (br s, 2H), 4.38 (s, 1H), 4.14 (s, 1H), 3.74 (d, J = 5.94 Hz, 1H), 3.65-3.70 (m, 2H), 2.45 (s, 3H) | 0.032 |
| A57 | 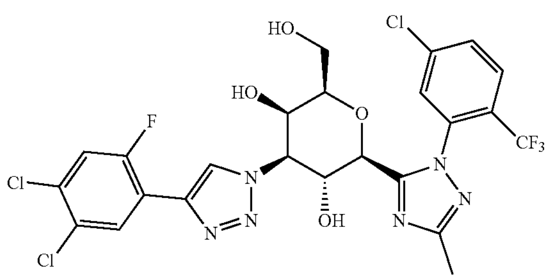 | A | MS (ESI) m/z: 621.0; 1H NMR (400 MHz, methanol-$d_4$) δ 8.45 (d, J = 3.74 Hz, 1H), 7.93-8.03 (m, 2H), 7.82-7.90 (m, 1H), 7.71-7.82 (m, 1H), 7.49 (dd, J = 6.05, 10.01 Hz, 1H), 4.86-4.94 (m, 2H), 4.36 (d, J = 9.02 Hz, 1H), 4.11 (d, J = 1.76 Hz, 1H), 3.73 (d, J = 5.94 Hz, 1H), 3.63-3.69 (m, 2H), 2.44 (s, 3H) | 0.046 |

-continued

| Ex. # | Structure | Method | LCMS (M + 1)+/1H NMR | hGal IC50 (μM) |
|---|---|---|---|---|
| A58 | 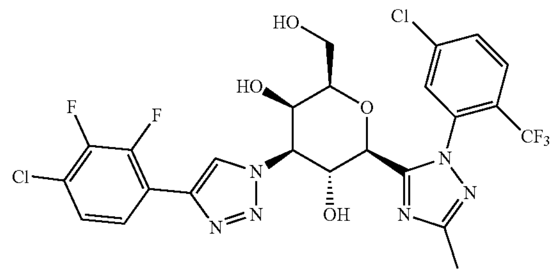 [SMILES: Cc1nc([C@@H]2O[C@H](CO)[C@H](O)[C@H](n3cc(-c4ccc(Cl)c(F)c4F)nn3)[C@H]2O)n(-c2cc(Cl)ccc2C(F)(F)F)n1] | A | MS (ESI) m/z: 621.2; 1H NMR (400 MHz, methanol-d4) δ 8.47 (d, J = 3.52 Hz, 1H), 7.90-7.99 (m, 2H), 7.83-7.89 (m, 1H), 7.77 (br s, 1H), 7.41 (ddd, J = 1.87, 6.82, 8.69 Hz, 1H), 4.87-4.95 (m, 2H), 4.37 (d, J = 9.02 Hz, 1H), 4.13 (d, J = 1.76 Hz, 1H), 3.71-3.77 (m, 1H), 3.63-3.71 (m, 2H), 2.45 (s, 3H) | 0.011 |
| A59 | 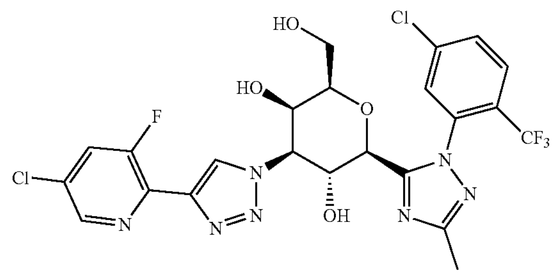 [SMILES: Cc1nc([C@@H]2O[C@H](CO)[C@H](O)[C@H](n3cc(-c4ncc(Cl)cc4F)nn3)[C@H]2O)n(-c2cc(Cl)ccc2C(F)(F)F)n1] | A | MS (ESI) m/z: 604.0; 1H NMR (500 MHz, methanol-d4) δ 8.61 (d, J = 2.48 Hz, 1H), 8.51-8.56 (m, 1H), 7.91-7.99 (m, 2H), 7.87 (dd, J = 1.38, 8.53 Hz, 1H), 7.71-7.84 (m, 1H), 4.94 (dd, J = 2.75, 10.73 Hz, 1H), 4.85-4.86 (m, 1H), 4.38 (d, J = 9.08 Hz, 1H), 4.14 (d, J = 1.93 Hz, 1H), 3.71-3.79 (m, 1H), 3.63-3.71 (m, 2H), 2.45 (s, 3H) | 0.158 |
| A60 | 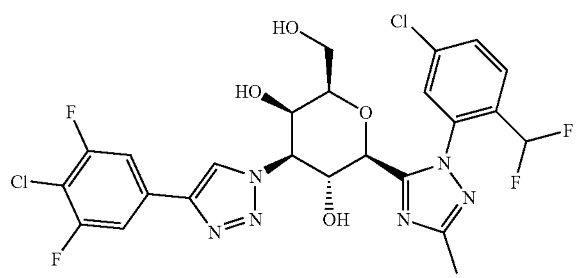 [SMILES: Cc1nc([C@@H]2O[C@H](CO)[C@H](O)[C@H](n3cc(-c4cc(F)c(Cl)c(F)c4)nn3)[C@H]2O)n(-c2cc(Cl)ccc2C(F)F)n1] | A | MS (ESI) m/z: 603.0; 1H NMR (400 MHz, methanol-d4) δ 8.59 (s, 1H), 7.83-7.90 (m, 1H), 7.76-7.82 (m, 2H), 7.62-7.68 (m, 2H), 6.53-6.83 (m, 1H), 4.86-4.90 (m, 2H), 4.38-4.45 (m, 1H), 4.12 (d, J = 1.76 Hz, 1H), 3.65-3.83 (m, 3H), 2.46 (s, 3H) | 0.036 |
| A61 | 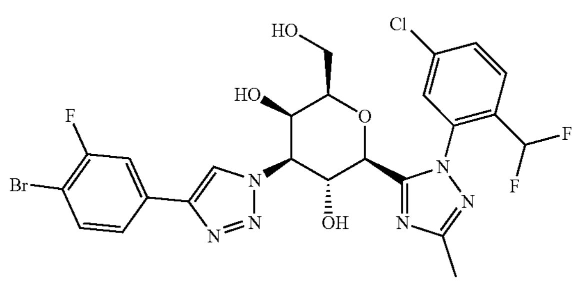 [SMILES: Cc1nc([C@@H]2O[C@H](CO)[C@H](O)[C@H](n3cc(-c4ccc(Br)c(F)c4)nn3)[C@H]2O)n(-c2cc(Cl)ccc2C(F)F)n1] | A | MS (ESI) m/z: 628.9; 1H NMR (400 MHz, methanol-d4) δ 8.53 (s, 1H), 7.87 (d, J = 9.02 Hz, 1H), 7.77-7.82 (m, 2H), 7.67-7.75 (m, 2H), 7.58-7.64 (m, 1H), 6.52-6.85 (m, 1H), 4.86-4.90 (m, 2H), 4.39-4.44 (m, 1H), 4.12 (d, J = 1.32 Hz, 1H), 3.79 (d, J = 5.50 Hz, 1H), 3.65-3.76 (m, 2H), 2.47 (s, 3H) | 0.049 |
| A62 | 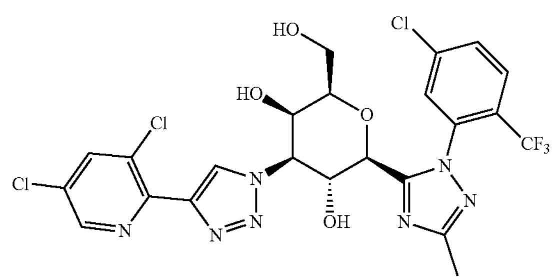 | C | MS (ESI) m/z: 620.0; 1H NMR (400 MHz, methanol-d4) δ 8.75-8.89 (m, 1H), 8.54-8.74 (m, 1H), 8.17 (br s, 1H), 7.96 (br d, J = 8.58 Hz, 1H), 7.86 (br d, J = 8.36 Hz, 1H), 7.77 (br s, 1H), 4.92 (br d, J = 11.66 Hz, 2H), 4.31-4.45 (m, 1H), 4.15 (br s, 1H), 3.71-3.79 (m, 1H), 3.60-3.71 (m, 2H), 2.45 (s, 3H) | 0.172 |

-continued

| Ex. # | Structure | Method | LCMS (M + 1)+/1H NMR | hGal IC50 (μM) |
|---|---|---|---|---|
| A63 | 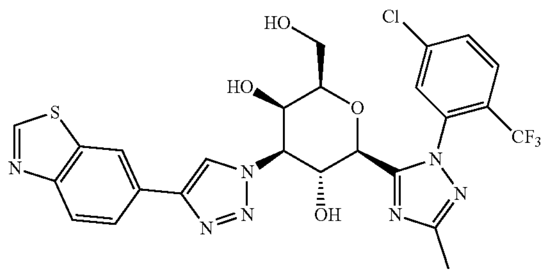 [SMILES: Cc1nc([C@@H]2O[C@H](CO)[C@H](O)[C@H](n3cc(-c4ccc5ncsc5c4)nn3)[C@H]2O)n(-c2cc(Cl)ccc2C(F)(F)F)n1] | C | MS (ESI) m/z: 608.0; 1H NMR (400 MHz, methanol-d4) δ 9.26 (s, 1H), 8.56-8.60 (m, 2H), 8.14 (d, J = 8.58 Hz, 1H), 8.03-8.09 (m, 1H), 7.96 (d, J = 8.58 Hz, 1H), 7.83-7.90 (m, 1H), 7.77 (br s, 1H), 4.88 (br s, 2H), 4.34-4.40 (m, 1H), 4.12-4.17 (m, 1H), 3.71-3.77 (m, 1H), 3.64-3.70 (m, 2H), 2.45 (s, 3H) | 0.291 |
| A64 | 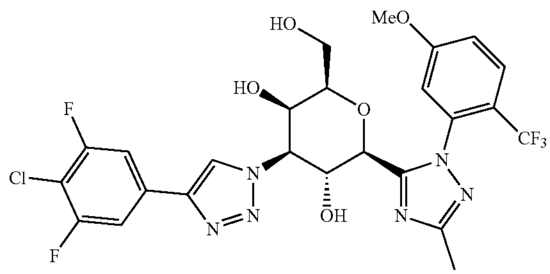 [SMILES: COc1ccc(C(F)(F)F)c(-n2nc(C)nc2[C@@H]2O[C@H](CO)[C@H](O)[C@H](n3cc(-c4cc(F)c(Cl)c(F)c4)nn3)[C@H]2O)c1] | A | MS (ESI) m/z: 617.1; 1H NMR (500 MHz, methanol-d4) δ 8.61 (s, 1H), 7.85 (d, J = 9.08 Hz, 1H), 7.62-7.68 (m, 2H), 7.31 (dd, J = 2.20, 8.80 Hz, 1H), 7.18 (br s, 1H), 4.84-4.88 (m, 2H), 4.34 (br d, J = 8.80 Hz, 1H), 4.11 (s, 1H), 3.91 (s, 3H), 3.71-3.76 (m, 1H), 3.65-3.71 (m, 2H), 2.45 (s, 3H) | 0.042 |
| A65 | 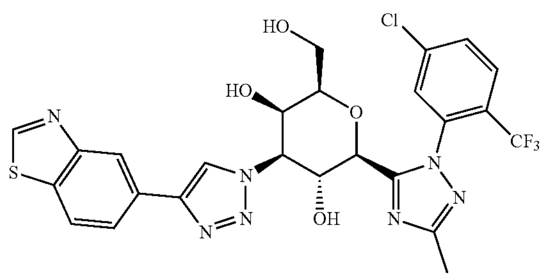 [SMILES: Cc1nc([C@@H]2O[C@H](CO)[C@H](O)[C@H](n3cc(-c4ccc5scnc5c4)nn3)[C@H]2O)n(-c2cc(Cl)ccc2C(F)(F)F)n1] | C | MS (ESI) m/z: 608.1; 1H NMR (400 MHz, methanol-d4) δ 9.28 (s, 1H), 8.59 (s, 1H), 8.54 (d, J = 1.10 Hz, 1H), 8.14 (d, J = 8.80 Hz, 1H), 8.00 (dd, J = 1.43, 8.47 Hz, 1H), 7.95 (d, J = 8.58 Hz, 1H), 7.82-7.89 (m, 1H), 7.77 (br s, 1H), 4.89 (br s, 2H), 4.34-4.42 (m, 1H), 4.15 (s, 1H), 3.74 (d, J = 6.38 Hz, 1H), 3.65-3.71 (m, 2H), 2.44 (s, 3H) | 0.087 |
| A66 | 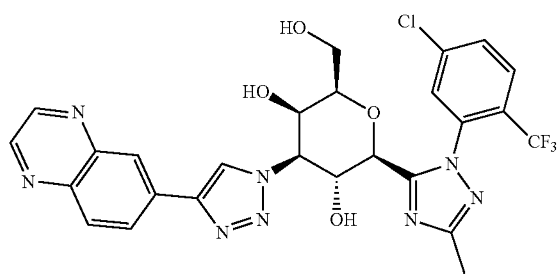 [SMILES: Cc1nc([C@@H]2O[C@H](CO)[C@H](O)[C@H](n3cc(-c4ccc5nccnc5c4)nn3)[C@H]2O)n(-c2cc(Cl)ccc2C(F)(F)F)n1] | C | MS (ESI) m/z: 603.2; 1H NMR (400 MHz, methanol-d4) δ 8.92 (d, J = 1.98 Hz, 1H), 8.86-8.90 (m, 1H), 8.75 (s, 1H), 8.58 (d, J = 1.76 Hz, 1H), 8.40 (dd, J = 1.98, 8.80 Hz, 1H), 8.19 (d, J = 8.80 Hz, 1H), 7.97 (d, J = 8.58 Hz, 1H), 7.84-7.91 (m, 1H), 7.79 (br s, 1H), 4.93 (br s, 2H), 4.40 (br d, J = 9.02 Hz, 1H), 4.15-4.20 (m, 1H), 3.73-3.82 (m, 1H), 3.70 (d, J = 5.50 Hz, 2H), 2.46 (s, 3H) | 0.208 |
| A67 | 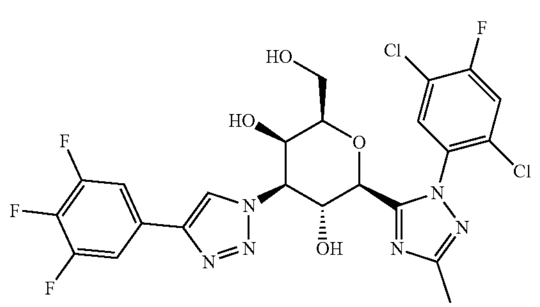 [SMILES: Cc1nc([C@@H]2O[C@H](CO)[C@H](O)[C@H](n3cc(-c4cc(F)c(F)c(F)c4)nn3)[C@H]2O)n(-c2cc(Cl)c(F)cc2Cl)n1] | A | MS (ESI) m/z: 588.9; 1H NMR (500 MHz, chloroform-d) δ 8.17 (s, 1H), 7.61 (br d, J = 6.88 Hz, 1H), 7.36-7.47 (m, 3H), 4.77-4.83 (m, 1H), 4.65 (dd, J = 2.34, 10.59 Hz, 1H), 4.55-4.62 (m, 2H), 4.38 (br s, 1H), 3.70 (br t, J = 4.81 Hz, 3H), 2.41 (s, 3H) | 0.039 |

| Ex. # | Structure | Method | LCMS (M + 1)⁺/¹H NMR | hGal IC50 (μM) |
|---|---|---|---|---|
| A68 | 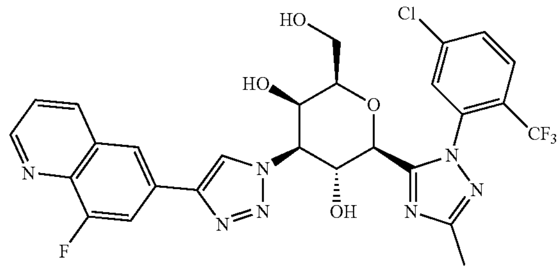 [SMILES: Cc1nc([C@@H]2O[C@H](CO)[C@H](O)[C@H](n3cc(-c4cc(F)c5ncccc5c4)nn3)[C@H]2O)n(-c2cc(Cl)ccc2C(F)(F)F)n1] | C | MS (ESI) m/z: 620.1; ¹H NMR (400 MHz, methanol-$d_4$) δ 8.89-8.94 (m, 1H), 8.71 (s, 1H), 8.56 (d, J = 8.80 Hz, 1H), 8.31 (s, 1H), 8.11 (dd, J = 1.43, 11.77 Hz, 1H), 7.97 (d, J = 8.58 Hz, 1H), 7.84-7.90 (m, 1H), 7.78 (br s, 1H), 7.71 (dd, J = 4.40, 8.36 Hz, 1H), 4.91 (br s, 2H), 4.38 (br d, J = 9.02 Hz, 1H), 4.16 (s, 1H), 3.76 (s, 1H), 3.65-3.72 (m, 2H), 2.46 (s, 3H) | 0.154 |
| A69 | 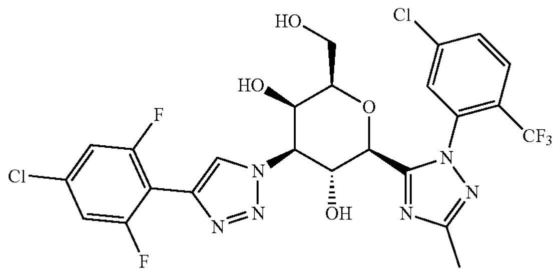 [SMILES: Cc1nc([C@@H]2O[C@H](CO)[C@H](O)[C@H](n3cc(-c4c(F)cc(Cl)cc4F)nn3)[C@H]2O)n(-c2cc(Cl)ccc2C(F)(F)F)n1] | C | MS (ESI) m/z: 621.0; ¹H NMR (400 MHz, methanol-$d_4$) δ 8.42 (s, 1H), 7.94 (s, 1H), 7.87 (s, 1H), 7.77 (br s, 1H), 7.28 (d, J = 8.14 Hz, 2H), 4.89-4.95 (m, 2H), 4.36 (d, J = 9.02 Hz, 1H), 4.12 (d, J = 1.98 Hz, 1H), 3.74 (s, 1H), 3.62-3.70 (m, 2H), 2.44 (s, 3H) | 0.056 |
| A70 | 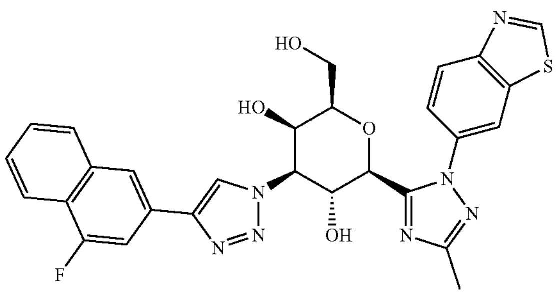 [SMILES: Cc1nc([C@@H]2O[C@H](CO)[C@H](O)[C@H](n3cc(-c4cc(F)c5ccccc5c4)nn3)[C@H]2O)n(-c2ccc3ncsc3c2)n1] | C | MS (ESI) m/z: 574.3; ¹H NMR (400 MHz, methanol-$d_4$) δ 9.42 (s, 1H), 8.64 (s, 1H), 8.54 (d, J =1.98 Hz, 1H), 8.28 (d, J = 8.80 Hz, 1H), 8.20 (s, 1H), 8.06-8.11 (m, 1H), 7.99 (br d, J = 7.70 Hz, 1H), 7.88 (dd, J = 2.09, 8.69 Hz, 1H), 7.73 (dd, J = 1.32, 11.66 Hz, 1H), 7.60 (br t, J = 2.75 Hz, 2H), 5.00-5.07 (m, 1H), 4.92-4.98 (m, 1H), 4.60 (d, J = 9.24 Hz, 1H), 4.17 (d, J = 2.20 Hz, 1H), 3.89-3.94 (m, 1H), 3.82-3.89 (m, 1H), 3.76 (d, J = 3.96 Hz, 1H), 2.50 (s, 3H) | 0.015 |
| A71 | 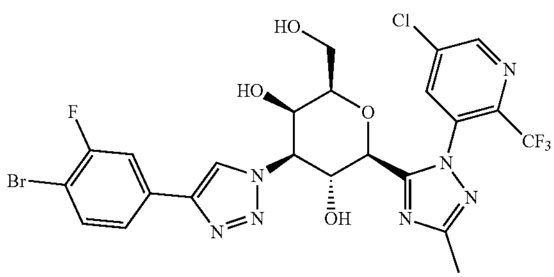 [SMILES: Cc1nc([C@@H]2O[C@H](CO)[C@H](O)[C@H](n3cc(-c4ccc(Br)c(F)c4)nn3)[C@H]2O)n(-c2cc(Cl)cnc2C(F)(F)F)n1] | A | MS (ESI) m/z: 648.0; ¹H NMR (400 MHz, methanol-$d_4$) δ 8.94 (d, J = 1.98 Hz, 1H), 8.52 (s, 1H), 8.31 (s, 1H), 7.66-7.74 (m, 2H), 7.60 (dd, J = 1.76, 8.36 Hz, 1H), 4.84-4.89 (m, 2H), 4.48 (d, J = 9.02 Hz, 1H), 4.09 (d, J = 2.20 Hz, 1H), 3.75 (s, 1H), 3.61 (dd, J = 3.52, 5.94 Hz, 2H), 2.44 (s, 3H) | 0.049 |
| A72 | 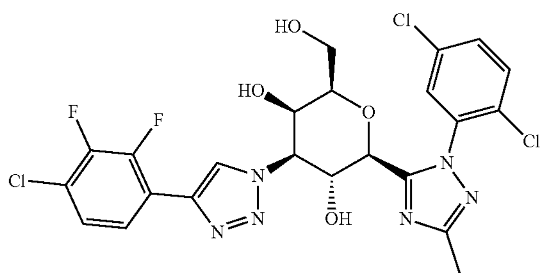 [SMILES: Cc1nc([C@@H]2O[C@H](CO)[C@H](O)[C@H](n3cc(-c4ccc(Cl)c(F)c4F)nn3)[C@H]2O)n(-c2cc(Cl)ccc2Cl)n1] | A | MS (ESI) m/z: 587.1; ¹H NMR (400 MHz, methanol-$d_4$) δ 8.45 (d, J = 3.30 Hz, 1H), 7.93 (ddd, J = 2.20, 6.99, 8.86 Hz, 1H), 7.62-7.74 (m, 3H), 7.41 (ddd, J = 1.98, 6.71, 8.69 Hz, 1H), 4.86-4.95 (m, 2H), 4.40 (br d, J = 9.02 Hz, 1H), 4.12 (d, J = 1.98 Hz, 1H), 3.77 (d, J = 5.94 Hz, 1H), 3.61-3.75 (m, 2H), 2.46 (s, 3H) | 0.011 |

| Ex. # | Structure | Method | LCMS (M + 1)+/1H NMR | hGal IC50 (μM) |
|---|---|---|---|---|
| A73 | 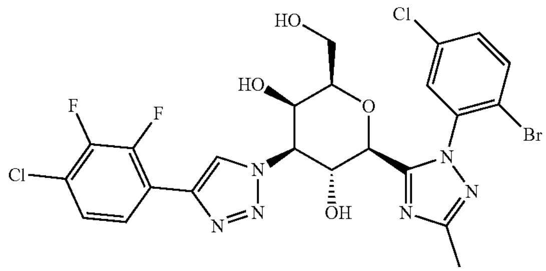 [SMILES: Cc1nc([C@@H]2O[C@H](CO)[C@H](O)[C@H](n3cc(-c4ccc(Cl)c(F)c4F)nn3)[C@H]2O)n(-c2cc(Cl)ccc2Br)n1] | A | MS (ESI) m/z: 631.0; 1H NMR (400 MHz, methanol-d4) δ 8.42-8.48 (m, 1H), 7.92 (ddd, J = 2.20, 6.99, 8.86 Hz, 1H), 7.84 (d, J = 8.80 Hz, 1H), 7.60-7.74 (m, 1H), 7.56 (dd, J = 2.53, 8.69 Hz, 1H), 7.41 (s, 1H), 4.85-4.94 (m, 2H), 4.38 (br d, J = 8.80 Hz, 1H), 4.12 (d, J = 1.76 Hz, 1H), 3.74-3.80 (m, 1H), 3.63-3.73 (m, 2H), 2.46 (s, 3H) | 0.010 |
| A74 | 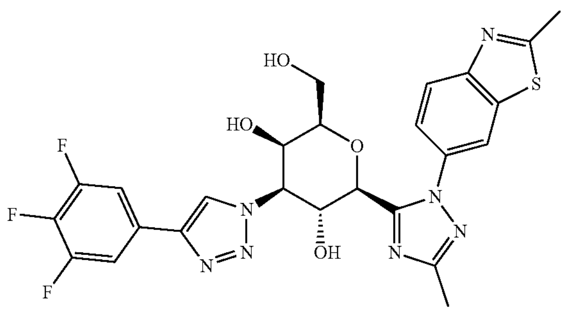 | | MS (ESI) m/z: 561.1; 1H NMR (400 MHz, methanol-d4) δ 8.58 (s, 1H), 8.51 (d, J = 2.1 Hz, 1H), 8.17 (d, J = 8.7 Hz, 1H), 7.89 (dd, J = 8.7, 2.2 Hz, 1H), 7.73-7.58 (m, 2H), 5.09 (dd, J = 10.7, 9.3 Hz, 1H), 4.98 (dd, J = 10.7, 2.9 Hz, 1H), 4.78 (d, J = 9.3 Hz, 1H), 4.17 (dd, J = 2.9, 1.0 Hz, 1H), 3.96 (ddd, J = 7.5, 4.1, 1.1 Hz, 1H), 3.84 (dd, J = 11.7, 7.5 Hz, 1H), 3.73 (dd, J = 11.7, 4.1 Hz, 1H), 2.94 (s, 3H). hGal-3 IC50 = 0.058 μM. | 0.058 |
| A75 | 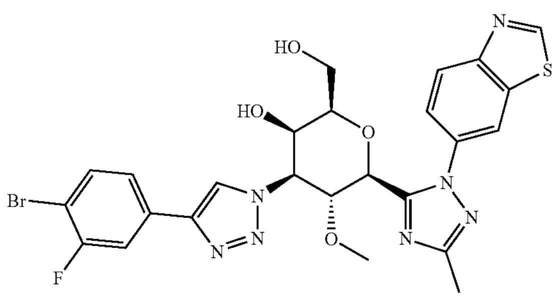 [SMILES: CO[C@@H]1[C@@H](n2cc(-c3ccc(Br)c(F)c3)nn2)[C@@H](O)[C@@H](CO)O[C@H]1c1nc(C)nn1-c1ccc2ncsc2c1] | E | MS (ESI) m/z: 615.9; 1H NMR (400 MHz, Methanol-d4) δ 9.43 (s, 1H), 8.74 (s, 1H), 8.53 (d, J = 2.1 Hz, 1H), 8.29 (d, J = 8.7 Hz, 1H), 7.86 (dd, J = 8.7, 2.1 Hz, 1H), 7.77 (dd, J = 9.9, 1.9 Hz, 1H), 7.72 (dd, J = 8.3, 7.0 Hz, 1H), 7.65 (dd, J = 8.4, 2.0 Hz, 1H), 5.00 (dd, J = 10.5, 2.9 Hz, 1H), 4.74 (dd, J = 10.5, 9.3 Hz, 1H), 4.60 (d, J = 9.4 Hz, 1H), 4.12 (d, J = 2.9 Hz, 1H), 3.96 -3.82 (m, 2H), 3.80-3.70 (m, 1H), 2.97 (s, 3H), 2.51 (s, 3H) | 0.34 |
| A76 | 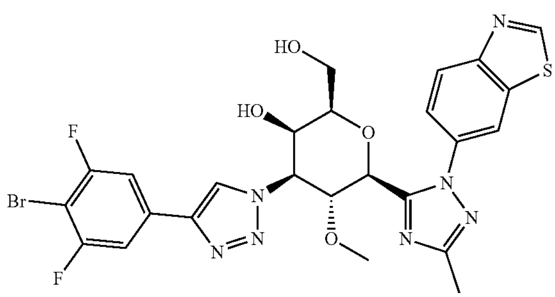 [SMILES: CO[C@@H]1[C@@H](n2cc(-c3cc(F)c(Br)c(F)c3)nn2)[C@@H](O)[C@@H](CO)O[C@H]1c1nc(C)nn1-c1ccc2ncsc2c1] | E | MS (ESI) m/z: 633.9; 1H NMR (400 MHz, Methanol-d4) δ 9.42 (s, 1H), 8.81 (s, 1H), 8.52 (d, J = 2.1 Hz, 1H), 8.28 (d, J = 8.7 Hz, 1H), 7.86 (dd, J = 8.7, 2.2 Hz, 1H), 7.72-7.55 (m, 2H), 5.02 (dd, J = 10.5, 2.9 Hz, 1H), 4.74 (dd, J = 10.6, 9.3 Hz, 1H), 4.61 (d, J = 9.3 Hz, 1H), 4.12 (d, J = 3.0 Hz, 1H), 3.94 - 3.81 (m, 2H), 3.81 -3.68 (m, 1H), 2.97 (s, 3H), 2.51 (s, 3H). | NA |
| A77 | 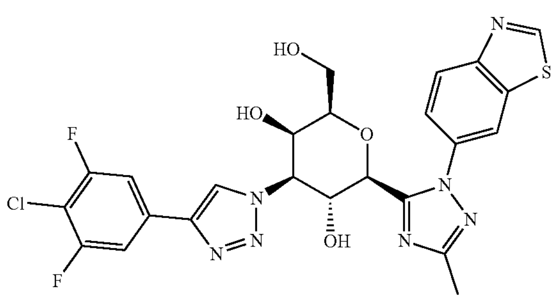 [SMILES: Cc1nc([C@@H]2O[C@H](CO)[C@H](O)[C@H](n3cc(-c4cc(F)c(Cl)c(F)c4)nn3)[C@H]2O)n(-c2ccc3ncsc3c2)n1] | A | MS (ESI) m/z: 576.0; 1H NMR (400 MHz, Methanol-d4) δ 9.42 (s, 1H), 8.64 (s, 1H), 8.54 (d, J = 2.0 Hz, 1H), 8.27 (d, J = 8.7 Hz, 1H), 7.88 (dd, J = 8.8, 2.2 Hz, 1H), 7.76-7.58 (m, 2H), 5.01 (dd, J = 10.7, 8.8 Hz, 1H), 4.95 (dd, J = 10.7, 2.8 Hz, 1H), 4.60 (d, J = 8.9 Hz, 1H), 4.15 (dd, J = 2.8, 1.0 Hz, 1H), 3.91 (ddd, J = 7.3, 3.9, 1.0 Hz, 1H), 3.85 (dd, J = 11.3, 7.4 Hz, 1H), 3.75 (dd, J = 11.4, 4.0 Hz, 1H), 2.50 (s, 3H). | NA |

| Ex. # | Structure | Method | LCMS (M + 1)$^+$/$^1$H NMR | hGal IC50 (μM) |
|---|---|---|---|---|
| A78 | 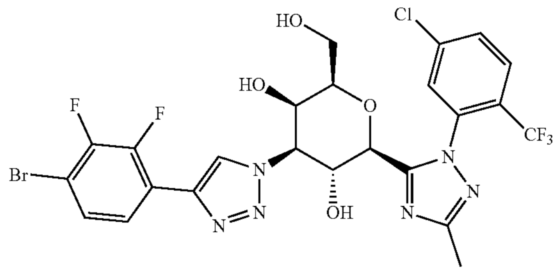 [SMILES: Cc1nc([C@@H]2O[C@H](CO)[C@H](O)[C@H](n3cc(-c4ccc(Br)c(F)c4F)nn3)[C@H]2O)n(-c2cc(Cl)ccc2C(F)(F)F)n1] | A | MS (ESI) m/z: 665.2; $^1$H NMR (400 MHz, Methanol-$d_4$) δ 8.48 (d, J = 3.30 Hz, 1H), 7.96 (d, J = 8.58 Hz, 1H), 7.84-7.91 (m, 2H), 7.77 (br s, 1H), 7.55 (ddd, J = 1.98,6.38, 8.58 Hz, 1H), 4.85-4.94 (m, 2H), 4.37 (d, J = 9.02 Hz, 1H), 4.12 (d, J = 1.54 Hz, 1H), 3.74 (d , J = 6.16 Hz, 1H), 3.64-3.70 (m, 2H), 2.45 (s, 3H) | 0.007 |
| A79 | 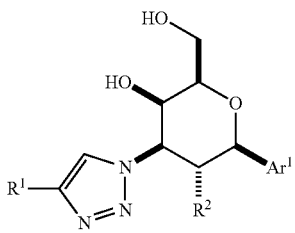 | C | MS (ESI) m/z: 615.2; $^1$H NMR (400 MHz, Methanol-$d_4$) δ 8.51(s, 1H), 7.96 (br d, J = 8.58 Hz, 1H), 7.86 (br d, J = 8.14 Hz, 1H), 7.68-7.81 (m, 1H), 7.58 (s, 1H), 7.31-7.50 (m, 2H), 4.85-4.89 (m, 2H), 4.24-4.47 (m, 1H), 4.13 (s, 1H), 3.89-4.05 (m, 3H), 3.71-3.76 (m, 1H), 3.62-3.71 (m, 2H), 2.45 (s, 3H) | 0.04 |

We claim:

1. A compound of formula I where:

$R^1$ is (($R^3$)($R^4$)N)carbonyl or $Ar^2$;

$R^2$ is hydrogen, halo, hydroxy, alkoxy, alkenyloxy, (halo)alkenyloxy, ((alkyl)$_2$(O)P)alkenyloxy (Ph$_2$(O)P)alkenyloxy, haloalkoxy, (hydroxy)alkoxy, (alkoxy)alkoxy, (alkoxycarbonyl)alkoxy, (carboxy)alkoxy, ((alkylSO$_2$)N(H)C(O))alkoxy, ((Ar$^4$SO$_2$)N(H)C(O))alkoxy, (tetrazolyl)alkoxy, (carboxy)alkyl, ($R^5$)($R^6$)NC(O)alkyl, or (carboxy)cycloalkyl;

$R^3$ is hydrogen, alkyl, cycloalkyl, benzyl, or halobenzyl;

$R^4$ is hydrogen or alkyl;

or ($R^3$)($R^4$)N taken together is azetidinyl, pyrrolidinyl, piperidinyl, piperazinyl, or morpholinyl, and is substituted with 0-3 substituents selected from halo, alkyl, and alkylcarbonyl;

$R^5$ is hydrogen or alkyl;

$R^6$ is hydrogen or alkyl;

or ($R^5$)($R^6$)N taken together is azetidinyl, pyrrolidinyl, piperidinyl, piperazinyl, morpholinyl, thiomorpholinyl, (oxo)thiomorpholinyl, (dioxo)thiomorpholinyl, homopiperidinyl, or homopiperazinyl;

$R^7$ is hydrogen or alkyl;

$R^8$ is hydrogen or alkyl;

or ($R^7$)($R^8$)N taken together is azetidinyl, pyrrolidinyl, piperidinyl, piperazinyl, or morpholinyl, and is substituted with 0-3 substituents selected from halo, alkyl, and hydroxy;

$R^9$ is hydrogen, alkyl, alkylcarbonyl, or alkylsulfonyl;

$R^{10}$ is hydrogen or alkyl;

or ($R^9$)($R^{10}$)N taken together is azetidinyl, pyrrolidinyl, piperidinyl, piperazinyl, or morpholinyl, and is substituted with 0-3 substituents selected from halo, alkyl, and alkylcarbonyl;

$R^{11}$ is cyano, halo, alkoxy, or ($R^{12}$)($R^{13}$)N;

$R^{12}$ is hydrogen or alkyl;

$R^{13}$ is hydrogen or alkyl;

or ($R^{12}$)($R^{13}$)N taken together is azetidinyl, pyrrolidinyl, piperidinyl, piperazinyl, or morpholinyl;

$R^{14}$ is hydrogen, alkyl, alkylcarbonyl, alkoxycarbonyl, or alkylsulfonyl;

$R^{15}$ is hydrogen or alkyl;

or ($R^{14}$)($R^{15}$)N taken together is azetidinyl, pyrrolidinyl, piperidinyl, piperazinyl, or morpholinyl, and is substituted with 0-3 substituents selected from halo, alkyl, and hydroxy;

$R^{16}$ is hydrogen, alkyl, alkylcarbonyl, or alkylsulfonyl;

$R^{17}$ is hydrogen or alkyl;

or ($R^{16}$)($R^{17}$)N taken together is azetidinyl, pyrrolidinyl, piperidinyl, piperazinyl, or morpholinyl, and is substituted with 0-3 substituents selected from halo, alkyl, and alkylcarbonyl;

$Ar^1$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from alkyl, haloalkyl, hydroxyalkyl, alkoxyalkyl, (carboxy)alkyl, (alkoxycarbonyl)alkyl, (H$_2$NCO)alkyl, (Ar$^3$)alkyl, cycloalkyl, hydroxycycloalkyl, alkenyl, alkoxy, alkylthio, alkylsulfonyl, carboxy, alkoxycarbonyl, (alkylNH)carbonyl, ((($R^7$)($R^8$)N)alkylNH)carbonyl, ((pyridinyl)alkylNH)carbonyl,) ($R^9$)($R^{10}$)N, and $Ar^3$;

Ar² is phenyl, pyridinyl, naphthyl, benzoxazolyl, benzothiazolyl, quinolinyl, or quinoxalinyl, and is substituted with 0-5 substituents selected from cyano, halo, alkyl, (R¹¹)alkyl, haloalkyl, cycloalkyl, (R¹¹)cycloalkyl, alkoxy, cycloalkoxy, haloalkoxy, and (R¹⁴)(R¹⁵)N;

Ar³ is phenyl, naphthalinyl, biphenyl, pyridinyl, pyridazinyl, pyrimidinyl, pyrazinyl, quinolinyl, isoquinolinyl, quinoxainyl, indolyl, indazolyl, benzimidazolyl, benzisoxazolyl, benzisothiazolyl, benzoxazolyl, benzothiazolyl, benzodioxolyl, dihydrobenzodioxinyl, dihydroquinolinonyl, or dihydrobenzothiophene-2,2-dioxide, and is substituted with 0-5 substituents selected from cyano, nitro, halo, alkyl, haloalkyl, cycloalkyl, alkoxy, haloalkoxy, alkylthio, carboxy, alkoxycarbonyl, CONH₂, and (R¹⁶)(R¹⁷)N;

or Ar³ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from cyano, nitro, halo, alkyl, haloalkyl, alkoxy, haloalkoxy, alkylthio, carboxy, alkoxycarbonyl, CONH₂, and (R¹⁶)(R¹⁷)N;

or Ar³ is (alkylSO₂)phenyl, (alkyl SO₂)(halo)phenyl, (aminoSO₂)phenyl, (dialkylaminoSO₂)phenyl, ((alkylNHSO₂)alkyl)phenyl, (pyrrolyl)phenyl, (imidazolyl)phenyl, (oxazolyl)phenyl, (tetrazolyl)phenyl, ((pyridinyl)methyl)phenyl, phenoxyphenyl, (benzyloxy)phenyl, ((methyl)thiazolyl)phenyl, (thiazolyl)benzenesulfamido, ((methyl)thiadiazolyl)benzenesulfamido, (methyl)benzothiazolonyl, or fluoropyrazolopyrimidinyl; and Ar⁴ is phenyl substituted with 0-5 substituents selected from cyano, halo, alkyl, haloalkyl, alkoxy, and haloalkoxy;

or a pharmaceutically acceptable salt thereof.

2. A compound of claim 1 where R¹ is Ar²; R² is hydroxy; Ar¹ is triazolyl substituted with 0-3 substituents selected from alkyl, haloalkyl, hydroxyalkyl, alkoxyalkyl, (carboxy)alkyl, (alkoxycarbonyl)alkyl, (H₂NCO)alkyl, (Ar³)alkyl, cycloalkyl, hydroxycycloalkyl, alkenyl, alkoxy, alkylthio, alkyl sulfonyl, carboxy, alkoxycarbonyl, (alkylNH)carbonyl, (((R⁷)(R⁸)N)alkylNH)carbonyl, ((pyridinyl)alkylNH)carbonyl,)(R⁹)(R¹⁰)N, and Ar³; Ar² is phenyl or pyridinyl and is substituted with 0-5 substituents selected from cyano, halo, alkyl, (R¹¹)alkyl, haloalkyl, cycloalkyl, (R¹¹)cycloalkyl, alkoxy, cycloalkoxy, haloalkoxy, and (R¹⁴)(R¹⁵)N; and Ar³ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, CONH₂, and (R¹⁶)(R¹⁷)N; or a pharmaceutically acceptable salt thereof.

3. A compound of claim 1 where R¹ is Ar²; R² is hydroxy; Ar¹ is triazolyl substituted with 0-2 substituents selected from alkyl, haloalkyl, and Ar³; Ar² is phenyl substituted with 0-5 halo substituents; and Ar³ is phenyl or benzothiazolyl and is substituted with 0-5 substituents selected from halo, alkyl, haloalkyl, cycloalkyl, alkoxy, and haloalkoxy; or a pharmaceutically acceptable salt thereof.

4. A compound of claim 2 where Ar¹ is triazolyl substituted with 0-3 substituents selected from alkyl, haloalkyl, hydroxyalkyl, alkoxyalkyl, (carboxy)alkyl, (alkoxycarbonyl)alkyl, (H₂NCO)alkyl, (Ar³)alkyl, cycloalkyl, hydroxycycloalkyl, alkenyl, alkoxy, alkylthio, alkyl sulfonyl, carboxy, alkoxycarbonyl, (alkylNH)carbonyl, (((R⁷)(R⁸)N)alkylNH)carbonyl, ((pyridinyl)alkylNH)carbonyl,)(R⁹)(R¹⁰)N, and Ar³.

5. A compound of claim 2 where Ar¹ is triazolyl substituted with 0-2 substituents selected from alkyl, haloalkyl, and Ar³.

6. A compound of claim 2 where Ar² is phenyl or pyridinyl and is substituted with 0-5 substituents selected from cyano, halo, alkyl, (R¹¹)alkyl, haloalkyl, cycloalkyl, (R¹¹)cycloalkyl, alkoxy, cycloalkoxy, haloalkoxy, and (R¹⁴)(R¹⁵)N.

7. A compound of claim 5 where Ar² is phenyl substituted with 0-5 halo substituents.

8. A compound of claim 2 where Ar³ is phenyl or benzothiazolyl and is substituted with 0-5 substituents selected from cyano, nitro, halo, alkyl, haloalkyl, cycloalkyl, alkoxy, haloalkoxy, alkylthio, carboxy, alkoxycarbonyl, CONH₂, and (R¹⁶)(R¹⁷)N; or a pharmaceutically acceptable salt thereof.

9. A compound of claim 8 where Ar³ is phenyl or benzothiazolyl and is substituted with 0-5 substituents selected from halo, alkyl, haloalkyl, cycloalkyl, alkoxy, and haloalkoxy.

10. A compound selected from the group consisting of

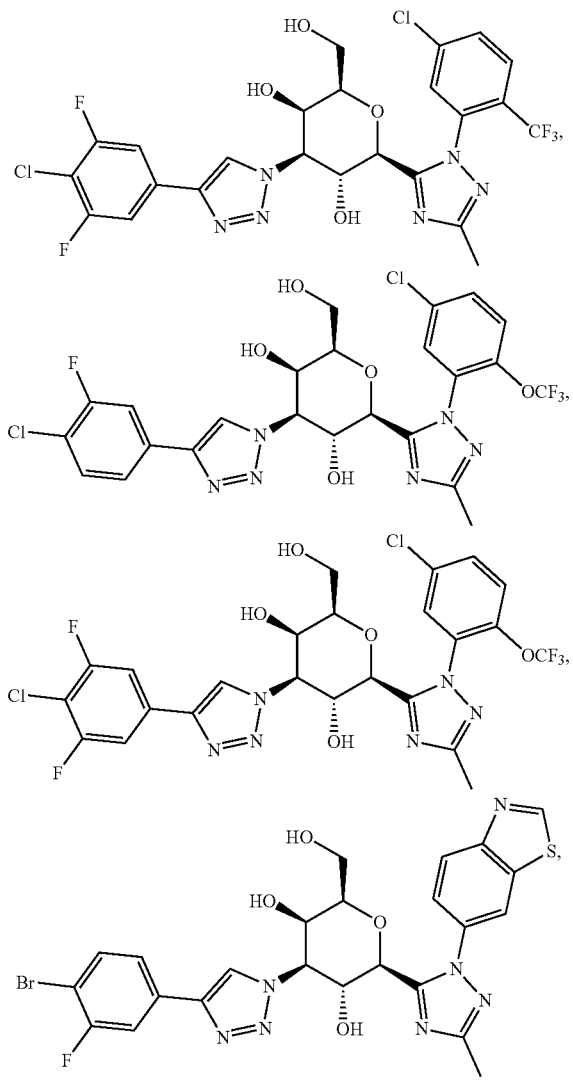

357
-continued
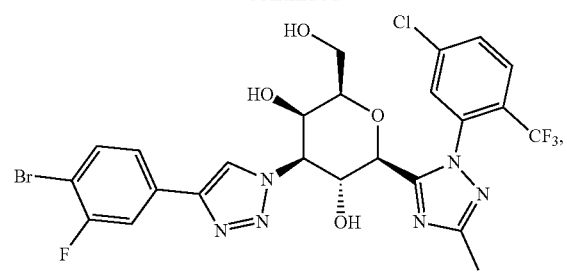
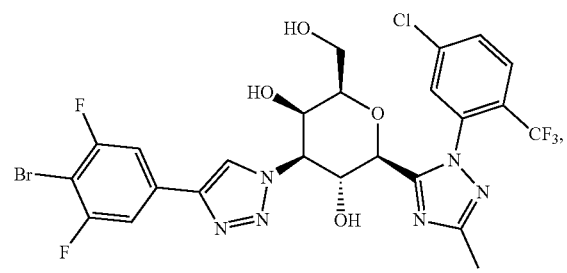
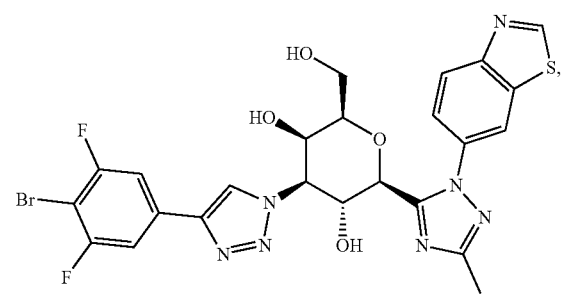
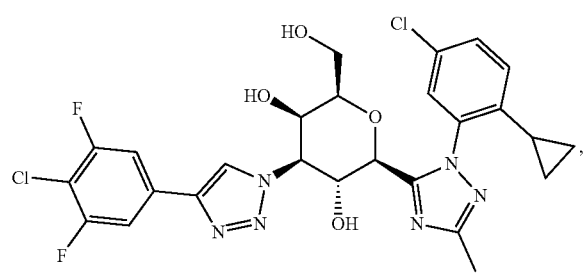
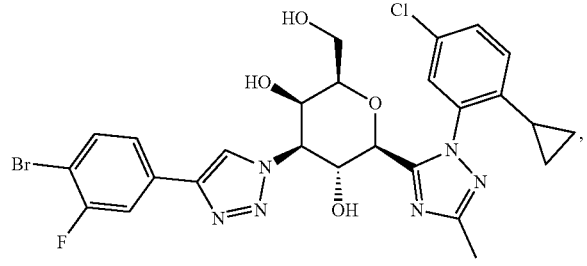
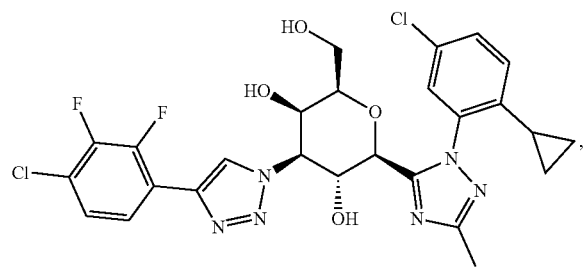
358
-continued
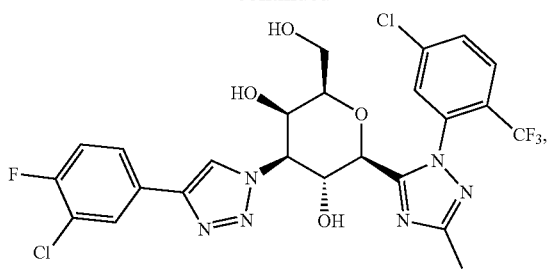
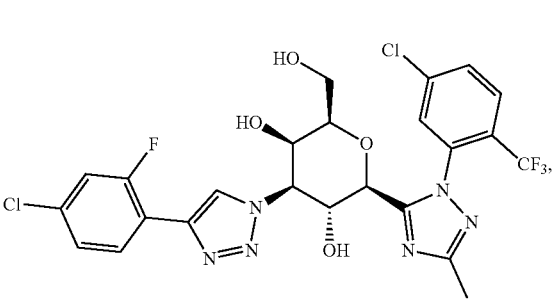
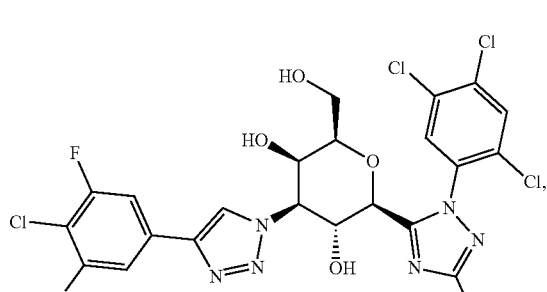
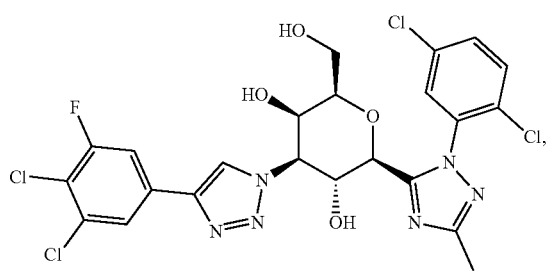
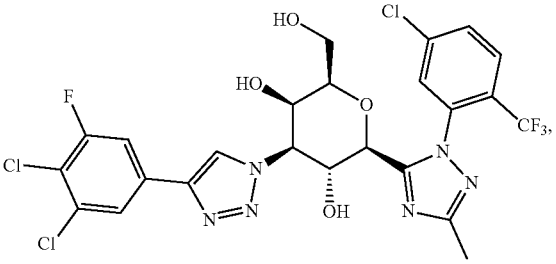
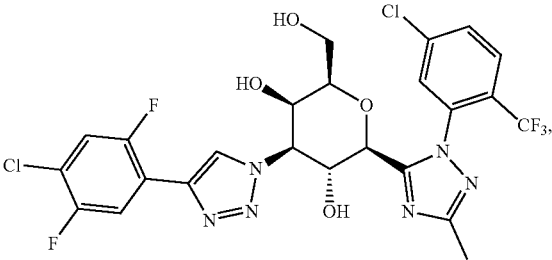

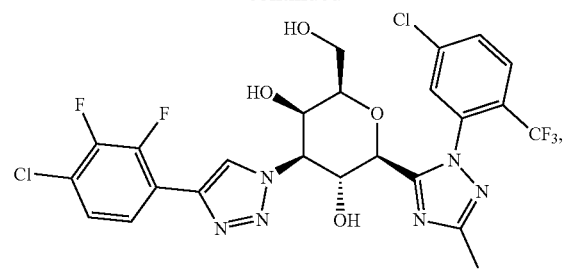
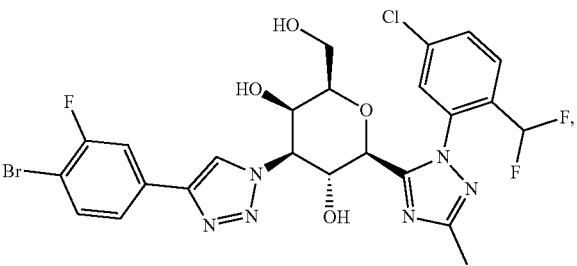
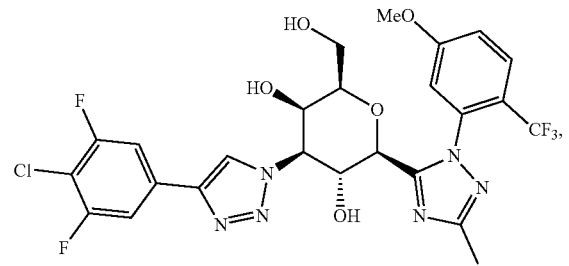
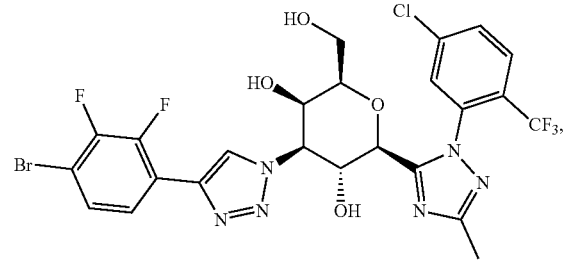
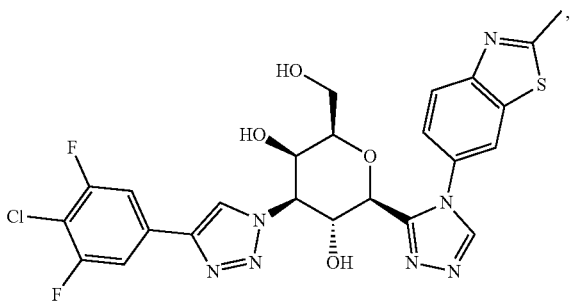
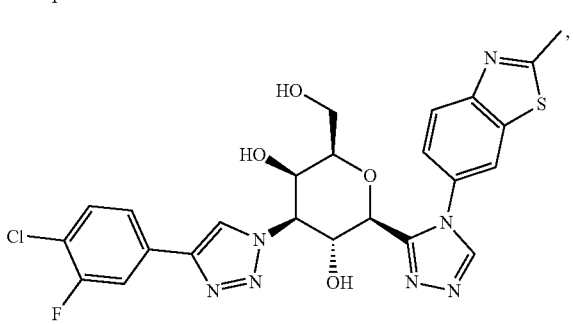
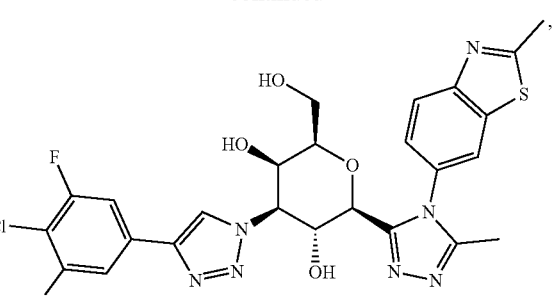
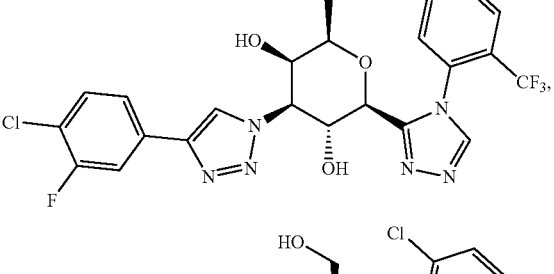
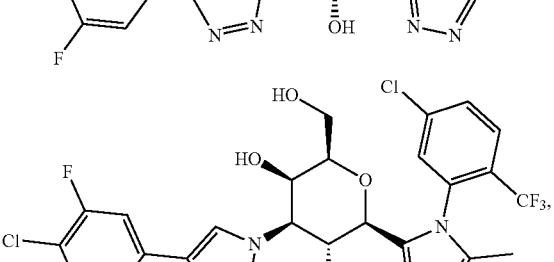
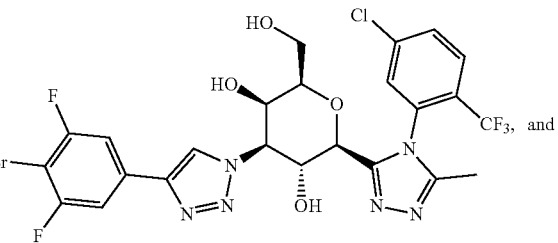
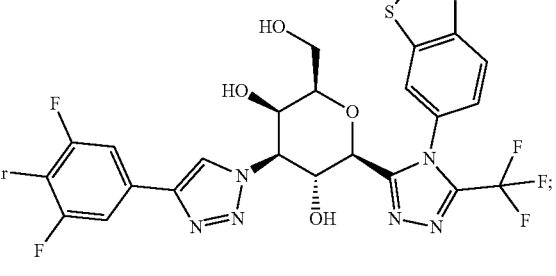
or a pharmaceutically acceptable salt thereof.

11. A composition comprising a therapeutically effective amount of a compound of claim 1, or a pharmaceutically acceptable salt thereof, and a pharmaceutically acceptable carrier.

12. A method for treating liver fibrosis, kidney fibrosis, lung fibrosis, heart fibrosis, skin fibrosis, acute hepatitis, chronic hepatitis, liver fibrosis, liver cirrhosis, portal hypertension, regenerative failure, non-alcoholic steatohepatitis, liver hypofunction, hepatic blood flow disorder, solid tumor, solid tumor metastasis, vascular fibroma, myeloma, multiple myeloma, Kaposi's sarcoma, leukemia, chronic lymphocytic leukemia, invasive metastasis of cancer cell, psoriasis, nephropathy, pneumonia, irritable bowel syndrome, inflammatory bowel disease, abnormal pancreatic secretion, neuropathic pain, peripheral neuropathy, age-related macular degeneration, diabetic retinopathy, comprising administering a therapeutically effective amount of a compound of claim 1, or a pharmaceutically acceptable salt thereof, to a patient.

13. A method for treating renal fibrosis, pulmonary fibrosis, hepatic fibrosis, arterial fibrosis, or systemic sclerosis, comprising administering a therapeutically effective amount of a compound of claim 1, or a pharmaceutically acceptable salt thereof, to a patient.

14. A composition comprising a therapeutically effective amount of a compound of claim 4, or a pharmaceutically acceptable salt thereof, and a pharmaceutically acceptable carrier.

15. A composition comprising a therapeutically effective amount of a compound of claim 5, or a pharmaceutically acceptable salt thereof, and a pharmaceutically acceptable carrier.

16. A composition comprising a therapeutically effective amount of a compound of claim 6, or a pharmaceutically acceptable salt thereof, and a pharmaceutically acceptable carrier.

17. A composition comprising a therapeutically effective amount of a compound of claim 7, or a pharmaceutically acceptable salt thereof, and a pharmaceutically acceptable carrier.

18. A composition comprising a therapeutically effective amount of a compound of claim 8, or a pharmaceutically acceptable salt thereof, and a pharmaceutically acceptable carrier.

19. A composition comprising a therapeutically effective amount of a compound of claim 9, or a pharmaceutically acceptable salt thereof, and a pharmaceutically acceptable carrier.

20. A composition comprising a therapeutically effective amount of a compound of claim 10, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 11,267,811 B2
APPLICATION NO. : 16/650403
DATED : March 8, 2022
INVENTOR(S) : Prasada Jalagam et al.

It is certified that error appears in the above-identified patent and that said Letters Patent is hereby corrected as shown below:

In the Claims

Column 354
Line 66-67, Claim 1, "carbonyl,)" should read -- carbonyl, --.

Column 355
Line 44, Claim 2, "carbonyl,)" should read -- carbonyl, --; and
Line 66, Claim 4, "carbonyl,)" should read -- carbonyl, --.

Column 356
Line 4-5, Claim 6, after "phenyl" delete "or pyridinyl".

Signed and Sealed this
Twelfth Day of July, 2022

Katherine Kelly Vidal
*Director of the United States Patent and Trademark Office*